US010925922B2

(12) United States Patent
Khaldi et al.

(10) Patent No.: US 10,925,922 B2
(45) Date of Patent: Feb. 23, 2021

(54) GROWTH PROMOTING PEPTIDES, AND USES THEREOF

(71) Applicant: NURITAS LIMITED, South Dublin (IE)

(72) Inventors: Nora Khaldi, Dublin (IE); Cyril Lopez, Dublin (IE); Alessandro Adelfio, Dublin (IE)

(73) Assignee: NURITAS LIMITED, South Dublin (IE)

( * ) Notice: Subject to any disclaimer, the term of this patent is extended or adjusted under 35 U.S.C. 154(b) by 0 days.

(21) Appl. No.: 16/504,872

(22) Filed: Jul. 8, 2019

(65) Prior Publication Data

US 2019/0321436 A1    Oct. 24, 2019

Related U.S. Application Data

(63) Continuation of application No. 15/744,390, filed as application No. PCT/EP2016/067097 on Jul. 18, 2016.

(30) Foreign Application Priority Data

Jul. 16, 2015   (EP) .................................. 15177017

(51) Int. Cl.
| | | |
|---|---|---|
| A61K 38/01 | (2006.01) | |
| C07K 14/415 | (2006.01) | |
| A61Q 19/08 | (2006.01) | |
| A61K 8/64 | (2006.01) | |
| A61P 35/00 | (2006.01) | |
| A61F 13/00 | (2006.01) | |
| A61K 9/00 | (2006.01) | |
| A61P 17/02 | (2006.01) | |
| C12N 9/02 | (2006.01) | |
| A61K 38/00 | (2006.01) | |

(52) U.S. Cl.
CPC ........ *A61K 38/01* (2013.01); *A61F 13/00063* (2013.01); *A61K 8/64* (2013.01); *A61K 9/0014* (2013.01); *A61K 38/011* (2013.01); *A61P 17/02* (2018.01); *A61P 35/00* (2018.01); *A61Q 19/08* (2013.01); *C07K 14/415* (2013.01); *C12N 9/0069* (2013.01); *C12Y 113/11012* (2013.01); *A61F 2013/00089* (2013.01); *A61F 2013/00361* (2013.01); *A61K 38/00* (2013.01)

(58) Field of Classification Search
CPC ........ A61K 38/01; A61K 38/011; A61K 8/64; A61K 9/0014; A61K 38/00; C07K 14/415; A61Q 19/08; C12N 9/0069; C12Y 113/11012; A61P 17/02; A61P 35/00; A61F 13/00063; A61F 2013/00089; A61F 2013/00361
See application file for complete search history.

(56) References Cited

U.S. PATENT DOCUMENTS

| | | | |
|---|---|---|---|
| 5,516,642 A | 5/1996 | Mapelli et al. | |
| 5,520,935 A | 5/1996 | Eriksen et al. | |
| 2004/0031072 A1 | 2/2004 | La Rosa et al. | |
| 2011/0214199 A1* | 9/2011 | Coffin | C12N 15/1079 800/275 |
| 2016/0158143 A1* | 6/2016 | Gan | A61K 8/042 424/62 |
| 2018/0291070 A1 | 10/2018 | Khaldi et al. | |

FOREIGN PATENT DOCUMENTS

| | | |
|---|---|---|
| EP | 2039366 A1 | 3/2009 |
| EP | 1896496 B1 | 1/2012 |
| JP | H07224093 A1 | 8/1995 |
| JP | 2001335596 A | 12/2001 |
| WO | 2002084250 A2 | 10/2002 |
| WO | 2004/042026 A2 | 5/2004 |
| WO | 2007/094570 A1 | 8/2007 |
| WO | 2008131008 A2 | 10/2008 |
| WO | 2009/026622 A1 | 3/2009 |
| WO | 2011122937 A1 | 10/2011 |
| WO | 2013092851 A1 | 6/2013 |

OTHER PUBLICATIONS

Geneseq Database Accession No. ANM73492, "Oryza sativa amino acid sequence SEQ ID No. 187493", (2007).
Geneseq Database Accession No. AWH80057, "Human PHLDA1 protein PH domain peptide, SEQ ID 414", (2009).
Geneseq Database Acession No. AFP68974 XP-002789557 "Glycline max protein SEQ ID No. 160152" (2007).
Geneseq Database Acession No. AD043092 XP-002756637 "Cashew nut major allergen Ana o 2 peptide fragment" (2004).
(Continued)

*Primary Examiner* — Li N Komatsu
(74) *Attorney, Agent, or Firm* — Nixon Peabody LLP; David S. Resnick; Ravinderjit S. Braich

(57) ABSTRACT

A natural peptide comprising a cellular growth promoting fragment of a protein selected from SEQ ID NOs: 1 to 13, and a composition comprising a plurality of growth promoting peptides, is described. Also disclosed is the use of the peptides and compositions in prevention of ageing of human skin, treatment of diseases or conditions characterised by damaged epithelial cells or tissue such as colon cancer and peripheral inflammatory disorders, and wound treatment. Specific pea and rice protein derived peptides are described in SEQ ID NOs: 15 to 505, and 546 to 704.

11 Claims, 42 Drawing Sheets

Specification includes a Sequence Listing.

(56) References Cited

OTHER PUBLICATIONS

Kipp et al., "Comparative studies of high M (r) subunits of rye and wheat. II. Partial amino acid sequences." Journal of Cereal Science 30:303-313 (1999).

Tong et al., "Rice α-globulin decreases serum cholesterol concentrations in rats fed a hypercholesterolemic diet and ameliorates atherosclerotic lesions in apolipoprotein E-deficient mice", Food Chemistry 132:194-200 (2012).

Uniprot Database Accession No. P29835 (1993).

Definition of Serum by Merriam-Webster, from https://merriam-webster.com/dictionary/serum, pp. 1-2 accessed May 8, 2019.

What is a humectant, from https://www.annmariegianni.com/what-is-a-humectant-and-which-natural-ones-to-look-for-in-anti-aging-products/, pp. 1-7 accessed May 8, 2019.

Water, from http://biology-online.org/dictionary/Water, pp. 1-3 accessed Apr. 24, 2014.

Human Ribosomal protein S6 kinase beta-1, from https://www.uniprot.org/uniprot/P23443, pp. 1-24 accessed May 2, 2019.

Wang et al., "Ana o 2, a Major Cashew (*Anacardium occidentale* L.) Nut Allergen of the Legumin Family" Int Arch Allergy Immunol 132(1): 27-39 (2003).

Definition of Comestible by Merriam-Webster, from https://merriam-webster.com/dictionary/comestible, 12 Pages, accessed Jun. 5, 2019.

Texas Health Resources Article "Pea is for Protein: What You Need to Know About Pea Protein Powder," Available online at https://areyouwellbeing.texashealth.org/pea-protein-need-know-pea-protein-powder/, 7 pages (2017).

Lammi et al., "Three Peptides from Soy Glycinin Modulate Glucose Metabolism in Human Hepatic HepG2 Cells", International Journal of Molecular Sciences 16:27362-27370 (2015).

Pak et al., "Design of a highly potent inhibitory peptide acting as a competitive inhibitor of HMG-CoA reductase", Amino Acids 43(5):2015-2025 (2012).

Shibata et al., "Dissection of GLUT4 Recycling Pathway into Exocytosis and Endocytosis in Rat Adipocytes: Evidence That GTP-Binding Proteins Are Involved in Both Processes", The Journal of Biological Chemistry 270(19):11489-11495 (1995).

Stagsted et al., "Amino acid residues essential for biological activity of a peptide derived from a major histocompatibility complex class I antigen", Proceedings of the National Academy of Sciences 90:7686-7690 (1993).

Uniprot Database Accession No. P13918 (1990).

Watson et al., "Isolation and expression of a pea vicilin cDNA in the yeast *Saccharomyces cerevisiae*", Biochemical Journal 251:857-864 (1988).

Hughes et al., "Characterization of authentic recombinant pea-seed lipoxygenases with distinct properties and reaction mechanisms", Biochemical Journal, 333, (1.), 33-43 (1998).

Sequence Listing XP-002794154 (2019).

\* cited by examiner

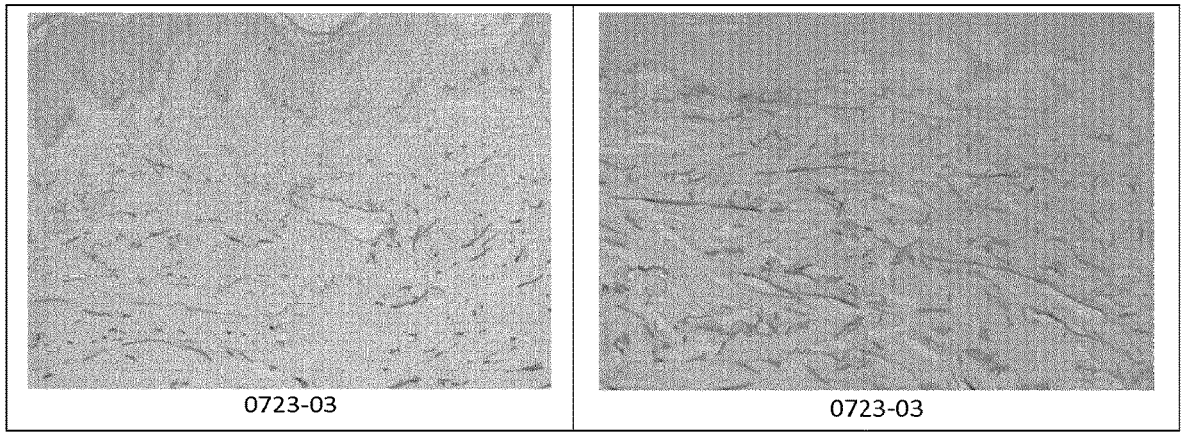
FIGURE 114 (CONTD.)

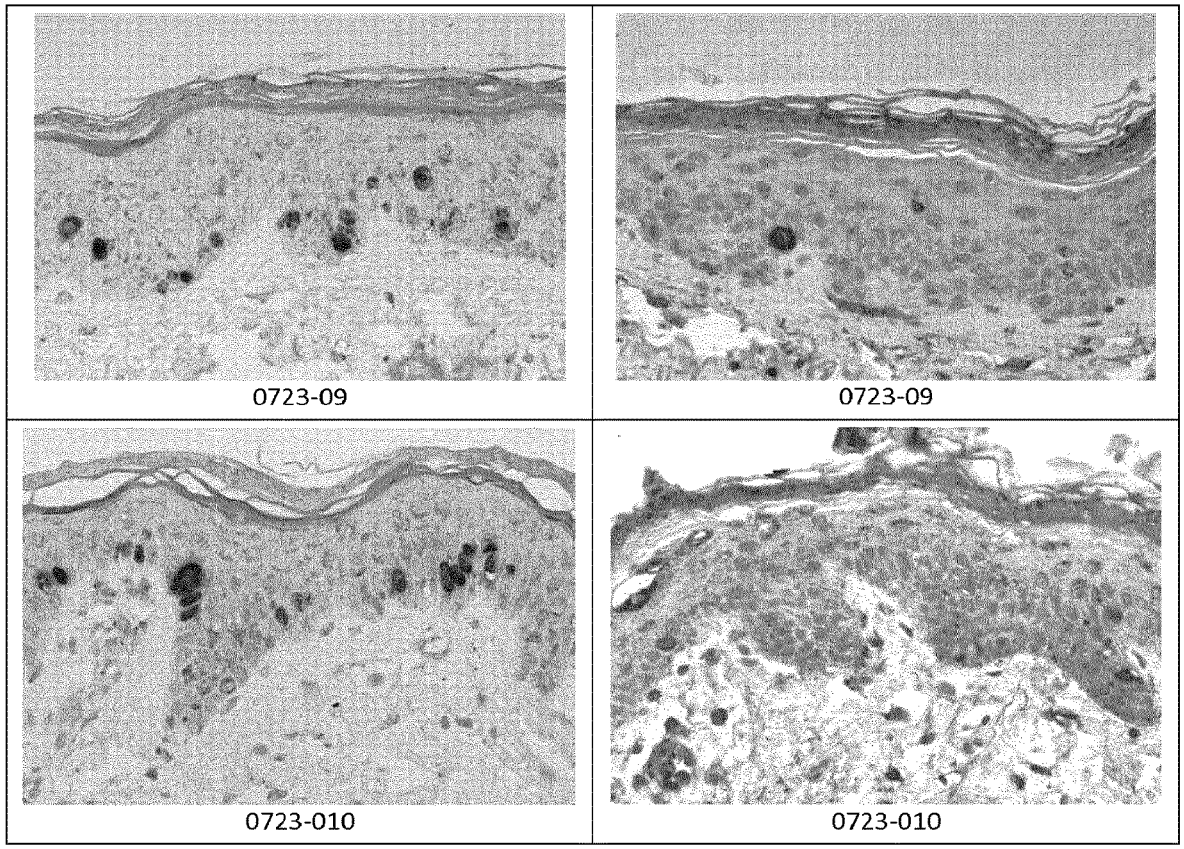
FIGURE 115 (CONTD)

SEQUENCE LISTING

```
<160> NUMBER OF SEQ ID NOS: 778

<210> SEQ ID NO 1
<211> LENGTH: 459
<212> TYPE: PRT
<213> ORGANISM: Pisum sativum

<400> SEQUENCE: 1

Met Ala Ala Thr Thr Met Lys Ala Ser Phe Pro Leu Leu Met Leu Met
1               5                   10                  15

Gly Ile Ser Phe Leu Ala Ser Val Cys Val Ser Ser Arg Ser Asp Pro
            20                  25                  30

Gln Asn Pro Phe Ile Phe Lys Ser Asn Lys Phe Gln Thr Leu Phe Glu
        35                  40                  45

Asn Glu Asn Gly His Ile Arg Leu Leu Gln Lys Phe Asp Gln Arg Ser
    50                  55                  60

Lys Ile Phe Glu Asn Leu Gln Asn Tyr Arg Leu Leu Glu Tyr Lys Ser
65                  70                  75                  80

Lys Pro His Thr Ile Phe Leu Pro Gln His Thr Asp Ala Asp Tyr Ile
                85                  90                  95

Leu Val Val Leu Ser Gly Lys Ala Ile Leu Thr Val Leu Lys Pro Asp
            100                 105                 110

Asp Arg Asn Ser Phe Asn Leu Glu Arg Gly Asp Thr Ile Lys Leu Pro
        115                 120                 125

Ala Gly Thr Ile Ala Tyr Leu Val Asn Arg Asp Asp Asn Glu Glu Leu
    130                 135                 140

Arg Val Leu Asp Leu Ala Ile Pro Val Asn Arg Pro Gly Gln Leu Gln
145                 150                 155                 160

Ser Phe Leu Leu Ser Gly Asn Gln Asn Gln Gln Asn Tyr Leu Ser Gly
                165                 170                 175

Phe Ser Lys Asn Ile Leu Glu Ala Ser Phe Asn Thr Asp Tyr Glu Glu
            180                 185                 190

Ile Glu Lys Val Leu Leu Glu Glu His Glu Lys Glu Thr Gln His Arg
        195                 200                 205

Arg Ser Leu Lys Asp Lys Arg Gln Gln Ser Gln Glu Glu Asn Val Ile
    210                 215                 220

Val Lys Leu Ser Arg Gly Gln Ile Glu Glu Leu Ser Lys Asn Ala Lys
225                 230                 235                 240

Ser Thr Ser Lys Lys Ser Val Ser Ser Glu Ser Glu Pro Phe Asn Leu
                245                 250                 255

Arg Ser Arg Gly Pro Ile Tyr Ser Asn Glu Phe Gly Lys Phe Phe Glu
            260                 265                 270

Ile Thr Pro Glu Lys Asn Pro Gln Leu Gln Asp Leu Asp Ile Phe Val
        275                 280                 285
```

-continued

```
Asn Ser Val Glu Ile Lys Glu Gly Ser Leu Leu Pro His Tyr Asn
        290                 295                 300

Ser Arg Ala Ile Val Ile Val Thr Val Asn Glu Gly Lys Gly Asp Phe
305                 310                 315                 320

Glu Leu Val Gly Gln Arg Asn Glu Asn Gln Gln Glu Gln Arg Lys Glu
                325                 330                 335

Asp Asp Glu Glu Glu Glu Gln Gly Glu Glu Ile Asn Lys Gln Val
            340                 345                 350

Gln Asn Tyr Lys Ala Lys Leu Ser Ser Gly Asp Val Phe Val Ile Pro
                355                 360                 365

Ala Gly His Pro Val Ala Val Lys Ala Ser Ser Asn Leu Asp Leu Leu
            370                 375                 380

Gly Phe Gly Ile Asn Ala Glu Asn Asn Gln Arg Asn Phe Leu Ala Gly
385                 390                 395                 400

Asp Glu Asp Asn Val Ile Ser Gln Ile Gln Arg Pro Val Lys Glu Leu
                405                 410                 415

Ala Phe Pro Gly Ser Ala Gln Glu Val Asp Arg Ile Leu Glu Asn Gln
            420                 425                 430

Lys Gln Ser His Phe Ala Asp Ala Gln Pro Gln Gln Arg Glu Arg Gly
            435                 440                 445

Ser Arg Glu Thr Arg Asp Arg Leu Ser Ser Val
450                 455
```

<210> SEQ ID NO 2
<211> LENGTH: 613
<212> TYPE: PRT
<213> ORGANISM: Pisum sativum

<400> SEQUENCE: 2

```
Met Ala Thr Thr Ile Lys Ser Arg Phe Pro Leu Leu Leu Leu Leu Gly
1               5                   10                  15

Ile Ile Phe Leu Ala Ser Val Val Cys Val Thr Tyr Ala Asn Tyr Asp
                20                  25                  30

Glu Gly Ser Glu Pro Arg Val Pro Ala Gln Arg Glu Arg Gly Arg Gln
            35                  40                  45

Glu Gly Glu Lys Glu Glu Lys Arg His Gly Glu Trp Arg Pro Ser Tyr
        50                  55                  60

Glu Lys Glu Glu Asp Glu Glu Gly Gln Arg Glu Arg Gly Arg Gln
65              70                  75                  80

Glu Gly Glu Lys Glu Glu Lys Arg His Gly Glu Trp Arg Pro Ser Tyr
                85                  90                  95

Glu Lys Gln Glu Asp Glu Glu Lys Gln Lys Tyr Arg Tyr Gln Arg
            100                 105                 110

Glu Lys Glu Asp Glu Glu Glu Lys Gln Lys Tyr Gln Tyr Gln Arg Glu
        115                 120                 125

Lys Lys Glu Gln Lys Glu Val Gln Pro Gly Arg Glu Arg Trp Glu Arg
    130                 135                 140

Glu Glu Asp Glu Glu Gln Val Asp Glu Glu Trp Arg Gly Ser Gln Arg
145                 150                 155                 160

Arg Glu Asp Pro Glu Glu Arg Ala Arg Leu Arg His Arg Glu Glu Arg
                165                 170                 175

Thr Lys Arg Asp Arg Arg His Gln Arg Glu Gly Glu Glu Glu Glu Arg
            180                 185                 190

Ser Ser Glu Ser Gln Glu Arg Arg Asn Pro Phe Leu Phe Lys Ser Asn
```

-continued

```
              195                 200                 205
Lys Phe Leu Thr Leu Phe Glu Asn Glu Asn Gly His Ile Arg Leu Leu
    210                 215                 220
Gln Arg Phe Asp Lys Arg Ser Asp Leu Phe Glu Asn Leu Gln Asn Tyr
225                 230                 235                 240
Arg Leu Val Glu Tyr Arg Ala Lys Pro His Thr Ile Phe Leu Pro Gln
            245                 250                 255
His Ile Asp Ala Asp Leu Ile Leu Val Val Leu Ser Gly Lys Ala Ile
                260                 265                 270
Leu Thr Val Leu Ser Pro Asn Asp Arg Asn Ser Tyr Asn Leu Glu Arg
            275                 280                 285
Gly Asp Thr Ile Lys Leu Pro Ala Gly Thr Thr Ser Tyr Leu Val Asn
    290                 295                 300
Gln Asp Asp Glu Glu Asp Leu Arg Leu Val Asp Leu Val Ile Pro Val
305                 310                 315                 320
Asn Gly Pro Gly Lys Phe Glu Ala Phe Asp Leu Ala Lys Asn Lys Asn
                325                 330                 335
Gln Tyr Leu Arg Gly Phe Ser Lys Asn Ile Leu Glu Ala Ser Tyr Asn
            340                 345                 350
Thr Arg Tyr Glu Thr Ile Glu Lys Val Leu Leu Glu Glu Gln Glu Lys
    355                 360                 365
Asp Arg Lys Arg Gln Gln Gly Glu Glu Thr Asp Ala Ile Val Lys
370                 375                 380
Val Ser Arg Glu Gln Ile Glu Glu Leu Lys Lys Leu Ala Lys Ser Ser
385                 390                 395                 400
Ser Lys Lys Ser Leu Pro Ser Glu Phe Glu Pro Ile Asn Leu Arg Ser
                405                 410                 415
His Lys Pro Glu Tyr Ser Asn Lys Phe Gly Lys Leu Phe Glu Ile Thr
            420                 425                 430
Pro Glu Lys Lys Tyr Pro Gln Leu Gln Asp Leu Asp Leu Phe Val Ser
    435                 440                 445
Cys Val Glu Ile Asn Glu Gly Ala Leu Met Leu Pro His Tyr Asn Ser
    450                 455                 460
Arg Ala Ile Val Val Leu Val Asn Glu Gly Lys Gly Asn Leu Glu
465                 470                 475                 480
Leu Leu Gly Leu Lys Asn Glu Gln Gln Glu Arg Glu Asp Arg Lys Glu
                485                 490                 495
Arg Asn Asn Glu Val Gln Arg Tyr Glu Ala Arg Leu Ser Pro Gly Asp
            500                 505                 510
Val Val Ile Ile Pro Ala Gly His Pro Val Ala Ile Thr Ala Ser Ser
    515                 520                 525
Asn Leu Asn Leu Leu Gly Phe Gly Ile Asn Ala Glu Asn Asn Glu Arg
    530                 535                 540
Asn Phe Leu Ser Gly Ser Asp Asp Asn Val Ile Ser Gln Ile Glu Asn
545                 550                 555                 560
Pro Val Lys Glu Leu Thr Phe Pro Gly Ser Val Gln Glu Ile Asn Arg
                565                 570                 575
Leu Ile Lys Asn Gln Lys Gln Ser His Phe Ala Asn Ala Glu Pro Glu
            580                 585                 590
Gln Lys Glu Gln Gly Ser Gln Gly Lys Arg Ser Pro Leu Ser Ser Ile
    595                 600                 605
Leu Gly Thr Phe Tyr
    610
```

<210> SEQ ID NO 3
<211> LENGTH: 609
<212> TYPE: PRT
<213> ORGANISM: Oryza sativa

<400> SEQUENCE: 3

```
Met Ser Ala Leu Thr Ser Gln Leu Ala Thr Ser Ala Thr Gly Phe
1               5                   10                  15

Gly Ile Ala Asp Arg Ser Ala Pro Ser Ser Leu Leu Arg His Gly Phe
            20                  25                  30

Gln Gly Leu Lys Pro Arg Ser Pro Ala Gly Gly Asp Ala Thr Ser Leu
        35                  40                  45

Ser Val Thr Thr Ser Ala Arg Ala Thr Pro Lys Gln Gln Arg Ser Val
    50                  55                  60

Gln Arg Gly Ser Arg Arg Phe Pro Ser Val Val Tyr Ala Thr Gly
65                  70                  75                  80

Ala Gly Met Asn Val Val Phe Val Gly Ala Glu Met Ala Pro Trp Ser
                85                  90                  95

Lys Thr Gly Gly Leu Gly Asp Val Leu Gly Gly Leu Pro Pro Ala Met
            100                 105                 110

Ala Ala Asn Gly His Arg Val Met Val Ile Ser Pro Arg Tyr Asp Gln
        115                 120                 125

Tyr Lys Asp Ala Trp Asp Thr Ser Val Val Ala Glu Ile Lys Val Ala
    130                 135                 140

Asp Arg Tyr Glu Arg Val Arg Phe Phe His Cys Tyr Lys Arg Gly Val
145                 150                 155                 160

Asp Arg Val Phe Ile Asp His Pro Ser Phe Leu Glu Lys Val Trp Gly
                165                 170                 175

Lys Thr Gly Glu Lys Ile Tyr Gly Pro Asp Thr Gly Val Asp Tyr Lys
            180                 185                 190

Asp Asn Gln Met Arg Phe Ser Leu Leu Cys Gln Ala Ala Leu Glu Ala
        195                 200                 205

Pro Arg Ile Leu Asn Leu Asn Asn Asn Pro Tyr Phe Lys Gly Thr Tyr
    210                 215                 220

Gly Glu Asp Val Val Phe Val Cys Asn Asp Trp His Thr Gly Pro Leu
225                 230                 235                 240

Ala Ser Tyr Leu Lys Asn Asn Tyr Gln Pro Asn Gly Ile Tyr Arg Asn
                245                 250                 255

Ala Lys Val Ala Phe Cys Ile His Asn Ile Ser Tyr Gln Gly Arg Phe
            260                 265                 270

Ala Phe Glu Asp Tyr Pro Glu Leu Asn Leu Ser Glu Arg Phe Arg Ser
        275                 280                 285

Ser Phe Asp Phe Ile Asp Gly Tyr Asp Thr Pro Val Glu Gly Arg Lys
    290                 295                 300

Ile Asn Trp Met Lys Ala Gly Ile Leu Glu Ala Asp Arg Val Leu Thr
305                 310                 315                 320

Val Ser Pro Tyr Tyr Ala Glu Glu Leu Ile Ser Gly Ile Ala Arg Gly
                325                 330                 335

Cys Glu Leu Asp Asn Ile Met Arg Leu Thr Gly Ile Thr Gly Ile Val
            340                 345                 350

Asn Gly Met Asp Val Ser Glu Trp Asp Pro Ser Lys Asp Lys Tyr Ile
        355                 360                 365

Thr Ala Lys Tyr Asp Ala Thr Thr Ala Ile Glu Ala Lys Ala Leu Asn
```

Lys Glu Ala Leu Gln Ala Glu Ala Gly Leu Pro Val Asp Arg Lys Ile
385                 390                 395                 400

Pro Leu Ile Ala Phe Ile Gly Arg Leu Glu Glu Gln Lys Gly Pro Asp
            405                 410                 415

Val Met Ala Ala Ala Ile Pro Glu Leu Met Gln Glu Asp Val Gln Ile
            420                 425                 430

Val Leu Leu Gly Thr Gly Lys Lys Lys Phe Glu Lys Leu Leu Lys Ser
            435                 440                 445

Met Glu Glu Lys Tyr Pro Gly Lys Val Arg Ala Val Lys Phe Asn
    450                 455                 460

Ala Pro Leu Ala His Leu Ile Met Ala Gly Ala Asp Val Leu Ala Val
465                 470                 475                 480

Pro Ser Arg Phe Glu Pro Cys Gly Leu Ile Gln Leu Gln Gly Met Arg
            485                 490                 495

Tyr Gly Thr Pro Cys Ala Cys Ala Ser Thr Gly Gly Leu Val Asp Thr
            500                 505                 510

Val Ile Glu Gly Lys Thr Gly Phe His Met Gly Arg Leu Ser Val Asp
            515                 520                 525

Cys Lys Val Val Glu Pro Ser Asp Val Lys Lys Val Ala Ala Thr Leu
530                 535                 540

Lys Arg Ala Ile Lys Val Val Gly Thr Pro Ala Tyr Glu Glu Met Val
545                 550                 555                 560

Arg Asn Cys Met Asn Gln Asp Leu Ser Trp Lys Gly Pro Ala Lys Asn
            565                 570                 575

Trp Glu Asn Val Leu Leu Gly Leu Gly Val Ala Gly Ser Ala Pro Gly
            580                 585                 590

Ile Glu Gly Asp Glu Ile Ala Pro Leu Ala Lys Glu Asn Val Ala Ala
            595                 600                 605

Pro

<210> SEQ ID NO 4
<211> LENGTH: 499
<212> TYPE: PRT
<213> ORGANISM: Oryza sativa

<400> SEQUENCE: 4

Met Ala Ser Ser Val Phe Ser Arg Phe Ser Ile Tyr Phe Cys Val Leu
1               5                   10                  15

Leu Leu Cys His Gly Ser Met Ala Gln Leu Phe Asn Pro Ser Thr Asn
            20                  25                  30

Pro Trp His Ser Pro Arg Gln Gly Ser Phe Arg Glu Cys Arg Phe Asp
            35                  40                  45

Arg Leu Gln Ala Phe Glu Pro Leu Arg Lys Val Arg Ser Glu Ala Gly
    50                  55                  60

Val Thr Glu Tyr Phe Asp Glu Lys Asn Glu Leu Phe Gln Cys Thr Gly
65              70                  75                  80

Thr Phe Val Ile Arg Arg Val Ile Gln Pro Gln Gly Leu Leu Val Pro
            85                  90                  95

Arg Tyr Thr Asn Ile Pro Gly Val Val Tyr Ile Ile Gln Gly Arg Gly
            100                 105                 110

Ser Met Gly Leu Thr Phe Pro Gly Cys Pro Ala Thr Tyr Gln Gln Gln
        115                 120                 125

Phe Gln Gln Phe Ser Ser Gln Gly Gln Ser Gln Lys Phe Arg

```
                    130                 135                 140
Asp Glu His Gln Lys Ile His Gln Phe Arg Gln Gly Asp Ile Val Ala
145                 150                 155                 160

Leu Pro Ala Gly Val Ala His Trp Phe Tyr Asn Asp Gly Asp Ala Pro
                165                 170                 175

Ile Val Ala Val Tyr Val Tyr Asp Val Asn Asn Ala Asn Gln Leu
                180                 185                 190

Glu Pro Arg Gln Lys Glu Phe Leu Ala Gly Asn Asn Asn Arg Ala
                195                 200                 205

Gln Gln Gln Gln Val Tyr Gly Ser Ser Ile Glu Gln His Ser Gly Gln
210                 215                 220

Asn Ile Phe Ser Gly Phe Gly Val Glu Met Leu Ser Glu Ala Leu Gly
225                 230                 235                 240

Ile Asn Ala Val Ala Ala Lys Arg Leu Gln Ser Gln Asn Asp Gln Arg
                245                 250                 255

Gly Glu Ile Ile His Val Lys Asn Gly Leu Gln Leu Leu Lys Pro Thr
                260                 265                 270

Leu Thr Gln Gln Gln Glu Gln Ala Gln Ala Gln Asp Gln Tyr Gln Gln
                275                 280                 285

Val Gln Tyr Ser Glu Arg Gln Gln Thr Ser Ser Arg Trp Asn Gly Leu
                290                 295                 300

Glu Glu Asn Phe Cys Thr Ile Lys Val Arg Val Asn Ile Glu Asn Pro
305                 310                 315                 320

Ser Arg Ala Asp Ser Tyr Asn Pro Arg Ala Gly Arg Ile Thr Ser Val
                325                 330                 335

Asn Ser Gln Lys Phe Pro Ile Leu Asn Leu Ile Gln Met Ser Ala Thr
                340                 345                 350

Arg Val Asn Leu Tyr Gln Asn Ala Ile Leu Ser Pro Phe Trp Asn Val
                355                 360                 365

Asn Ala His Ser Leu Val Tyr Met Ile Gln Gly Arg Ser Arg Val Gln
                370                 375                 380

Val Val Ser Asn Phe Gly Lys Thr Val Phe Asp Gly Val Leu Arg Pro
385                 390                 395                 400

Gly Gln Leu Leu Ile Ile Pro Gln His Tyr Ala Val Leu Lys Lys Ala
                405                 410                 415

Glu Arg Glu Gly Cys Gln Tyr Ile Ala Ile Lys Thr Asn Ala Asn Ala
                420                 425                 430

Phe Val Ser His Leu Ala Gly Lys Asn Ser Val Phe Arg Ala Leu Pro
                435                 440                 445

Val Asp Val Val Ala Asn Ala Tyr Arg Ile Ser Arg Glu Gln Ala Arg
450                 455                 460

Ser Leu Lys Asn Asn Arg Gly Glu Glu His Gly Ala Phe Thr Pro Arg
465                 470                 475                 480

Phe Gln Gln Gln Tyr Tyr Pro Gly Leu Ser Asn Glu Ser Glu Ser Glu
                485                 490                 495

Thr Ser Glu

<210> SEQ ID NO 5
<211> LENGTH: 186
<212> TYPE: PRT
<213> ORGANISM: Oryza sativa

<400> SEQUENCE: 5

Met Ala Ser Lys Val Val Phe Phe Ala Ala Ala Leu Met Ala Ala Met
```

```
1               5                   10                  15
Val Ala Ile Ser Gly Ala Gln Leu Ser Glu Ser Glu Met Arg Phe Arg
            20                  25                  30

Asp Arg Gln Cys Gln Arg Glu Val Gln Asp Ser Pro Leu Asp Ala Cys
            35                  40                  45

Arg Gln Val Leu Asp Arg Gln Leu Thr Gly Arg Glu Arg Phe Gln Pro
    50                  55                  60

Met Phe Arg Arg Pro Gly Ala Leu Gly Leu Arg Met Gln Cys Cys Gln
65                  70                  75                  80

Gln Leu Gln Asp Val Ser Arg Glu Cys Arg Cys Ala Ala Ile Arg Arg
                85                  90                  95

Met Val Arg Ser Tyr Glu Glu Ser Met Pro Met Pro Leu Glu Gln Gly
            100                 105                 110

Trp Ser Ser Ser Ser Glu Tyr Tyr Gly Gly Glu Gly Ser Ser Ser Ser
            115                 120                 125

Glu Gln Gly Tyr Tyr Gly Glu Gly Ser Ser Glu Glu Gly Tyr Tyr Gly
            130                 135                 140

Glu Gln Gln Gln Gln Pro Gly Met Thr Arg Val Arg Leu Thr Arg Ala
145                 150                 155                 160

Arg Gln Tyr Ala Ala Gln Leu Pro Ser Met Cys Arg Val Glu Pro Gln
                165                 170                 175

Gln Cys Ser Ile Phe Ala Ala Gly Gln Tyr
            180                 185

<210> SEQ ID NO 6
<211> LENGTH: 500
<212> TYPE: PRT
<213> ORGANISM: Oryza sativa

<400> SEQUENCE: 6

Met Ala Thr Ile Ala Phe Ser Arg Leu Ser Ile Tyr Phe Cys Val Leu
1               5                   10                  15

Leu Leu Cys His Gly Ser Met Ala Gln Leu Phe Gly Pro Asn Val Asn
            20                  25                  30

Pro Trp His Asn Pro Arg Gln Gly Gly Phe Arg Glu Cys Arg Phe Asp
            35                  40                  45

Arg Leu Gln Ala Phe Glu Pro Leu Arg Arg Val Arg Ser Glu Ala Gly
    50                  55                  60

Val Thr Glu Tyr Phe Asp Glu Lys Asn Glu Gln Phe Gln Cys Thr Gly
65                  70                  75                  80

Thr Phe Val Ile Arg Arg Val Ile Glu Pro Gln Gly Leu Leu Val Pro
                85                  90                  95

Arg Tyr Ser Asn Thr Pro Gly Met Val Tyr Ile Ile Gln Gly Arg Gly
            100                 105                 110

Ser Met Gly Leu Thr Phe Pro Gly Cys Pro Ala Thr Tyr Gln Gln Gln
            115                 120                 125

Phe Gln Gln Phe Leu Pro Glu Gly Gln Ser Gln Ser Gln Lys Phe Arg
            130                 135                 140

Asp Glu His Gln Lys Ile His Gln Phe Arg Gln Gly Asp Ile Val Ala
145                 150                 155                 160

Leu Pro Ala Gly Val Ala His Trp Phe Tyr Asn Glu Gly Asp Ala Pro
                165                 170                 175

Val Val Ala Leu Tyr Val Phe Asp Leu Asn Asn Asn Ala Asn Gln Leu
            180                 185                 190
```

```
Glu Pro Arg Gln Lys Glu Phe Leu Leu Ala Gly Asn Asn Asn Arg Glu
            195                 200                 205

Gln Gln Met Tyr Gly Arg Ser Ile Glu Gln His Ser Gly Gln Asn Ile
        210                 215                 220

Phe Ser Gly Phe Asn Asn Glu Leu Leu Ser Glu Ala Leu Gly Val Asn
225                 230                 235                 240

Ala Leu Val Ala Lys Arg Leu Gln Gly Gln Asn Asp Gln Arg Gly Glu
            245                 250                 255

Ile Ile Arg Val Lys Asn Gly Leu Lys Leu Leu Arg Pro Ala Phe Ala
            260                 265                 270

Gln Gln Gln Glu Gln Ala Gln Gln Glu Gln Ala Gln Ala Gln Tyr
        275                 280                 285

Gln Val Gln Tyr Ser Glu Glu Gln Gln Pro Ser Thr Arg Cys Asn Gly
        290                 295                 300

Leu Asp Glu Asn Phe Cys Thr Ile Lys Ala Arg Leu Asn Ile Glu Asn
305                 310                 315                 320

Pro Ser His Ala Asp Thr Tyr Asn Pro Arg Ala Gly Arg Ile Thr Arg
            325                 330                 335

Leu Asn Ser Gln Lys Phe Pro Ile Leu Asn Leu Val Gln Leu Ser Ala
        340                 345                 350

Thr Arg Val Asn Leu Tyr Gln Asn Ala Ile Leu Ser Pro Phe Trp Asn
        355                 360                 365

Val Asn Ala His Ser Leu Val Tyr Ile Val Gln Gly His Ala Arg Val
        370                 375                 380

Gln Val Val Ser Asn Leu Gly Lys Thr Val Phe Asn Gly Val Leu Arg
385                 390                 395                 400

Pro Gly Gln Leu Leu Ile Ile Pro Gln His Tyr Val Val Leu Lys Lys
            405                 410                 415

Ala Glu His Glu Gly Cys Gln Tyr Ile Ser Phe Lys Thr Asn Ala Asn
        420                 425                 430

Ser Met Val Ser His Leu Ala Gly Lys Asn Ser Ile Phe Arg Ala Met
        435                 440                 445

Pro Val Asp Val Ile Ala Asn Ala Tyr Arg Ile Ser Arg Glu Gln Ala
450                 455                 460

Arg Ser Leu Lys Asn Asn Arg Gly Glu Glu Leu Gly Ala Phe Thr Pro
465                 470                 475                 480

Arg Tyr Gln Gln Gln Thr Tyr Pro Gly Phe Ser Asn Glu Ser Glu Asn
            485                 490                 495

Glu Ala Leu Glu
        500

<210> SEQ ID NO 7
<211> LENGTH: 861
<212> TYPE: PRT
<213> ORGANISM: Pisum sativum

<400> SEQUENCE: 7

Met Phe Ser Gly Val Thr Gly Ile Leu Asn Arg Gly His Lys Ile Lys
1               5                   10                  15

Gly Thr Val Val Leu Met Arg Lys Asn Val Leu Asp Ile Asn Ser Leu
            20                  25                  30

Thr Thr Val Gly Gly Val Ile Gly Gln Gly Phe Asp Ile Leu Gly Ser
        35                  40                  45

Thr Val Asp Asn Leu Thr Ala Phe Leu Gly Arg Ser Val Ser Leu Gln
    50                  55                  60
```

```
Leu Ile Ser Ala Thr Lys Pro Asp Ala Thr Gly Lys Gly Lys Leu Gly
 65                  70                  75                  80

Lys Ala Thr Phe Leu Glu Gly Ile Ile Ser Ser Leu Pro Thr Leu Gly
                 85                  90                  95

Ala Gly Gln Ser Ala Phe Lys Ile His Phe Glu Trp Asp Asp Met
            100                 105                 110

Gly Ile Pro Gly Ala Phe Tyr Ile Lys Asn Phe Met Gln Thr Glu Phe
            115                 120                 125

Phe Leu Val Ser Leu Thr Leu Asp Asp Ile Pro Asn His Gly Ser Ile
130                 135                 140

Tyr Phe Val Cys Asn Ser Trp Ile Tyr Asn Ala Lys His His Lys Ile
145                 150                 155                 160

Asp Arg Ile Phe Phe Ala Asn Gln Thr Tyr Leu Pro Ser Glu Thr Pro
                165                 170                 175

Ala Pro Leu Val His Tyr Arg Glu Glu Glu Leu Asn Asn Leu Arg Gly
            180                 185                 190

Asp Gly Thr Gly Glu Arg Lys Glu Trp Glu Arg Ile Tyr Asp Tyr Asp
            195                 200                 205

Val Tyr Asn Asp Leu Gly Asn Pro Asp Ser Gly Glu Asn His Ala Arg
210                 215                 220

Pro Val Leu Gly Gly Ser Glu Thr Tyr Pro Tyr Pro Arg Arg Gly Arg
225                 230                 235                 240

Thr Gly Arg Lys Pro Thr Arg Lys Asp Pro Asn Ser Glu Ser Arg Ser
                245                 250                 255

Asp Tyr Val Tyr Leu Pro Arg Asp Glu Ala Phe Gly His Leu Lys Ser
            260                 265                 270

Ser Asp Phe Leu Thr Tyr Gly Leu Lys Ala Val Ser Gln Asn Val Val
            275                 280                 285

Pro Ala Leu Glu Ser Val Phe Phe Asp Leu Asn Phe Thr Pro Asn Glu
290                 295                 300

Phe Asp Ser Phe Asp Glu Val His Gly Leu Tyr Glu Gly Gly Ile Lys
305                 310                 315                 320

Leu Pro Thr Asn Ile Leu Ser Gln Ile Ser Pro Leu Pro Val Leu Lys
                325                 330                 335

Glu Ile Phe Arg Thr Asp Gly Glu Asn Thr Leu Lys Tyr Pro Pro Pro
            340                 345                 350

Lys Val Ile Gln Val Ser Arg Ser Gly Trp Met Thr Asp Glu Glu Phe
            355                 360                 365

Ala Arg Glu Met Leu Ala Gly Val Asn Pro Asn Val Ile Cys Cys Leu
            370                 375                 380

Gln Glu Phe Pro Pro Arg Ser Lys Leu Asp Ser Gln Ile Tyr Gly Asp
385                 390                 395                 400

His Thr Ser Lys Ile Ser Lys Glu His Leu Glu Pro Asn Leu Glu Gly
                405                 410                 415

Leu Thr Val Glu Glu Ala Ile Gln Asn Lys Lys Leu Phe Leu Leu Asp
            420                 425                 430

His His Asp Ser Ile Met Pro Tyr Leu Arg Arg Ile Asn Ser Thr Ser
            435                 440                 445

Thr Lys Ala Tyr Ala Thr Arg Thr Ile Leu Phe Leu Asn Asn Asn Gln
            450                 455                 460

Asn Leu Lys Pro Leu Ala Ile Glu Leu Ser Leu Pro His Pro Gln Gly
465                 470                 475                 480
```

Asp Glu His Gly Ala Val Ser Tyr Val Tyr Gln Pro Ala Leu Glu Gly
            485                 490                 495

Val Glu Ser Ser Ile Trp Leu Leu Ala Lys Ala Tyr Val Ile Val Asn
        500                 505                 510

Asp Ser Cys Tyr His Gln Leu Val Ser His Trp Leu Asn Thr His Ala
        515                 520                 525

Val Val Glu Pro Phe Val Ile Ala Thr Asn Arg His Leu Ser Cys Leu
    530                 535                 540

His Pro Ile Tyr Lys Leu Leu Tyr Pro His Tyr Arg Asp Thr Met Asn
545                 550                 555                 560

Ile Asn Ser Leu Ala Arg Leu Ser Leu Val Asn Asp Gly Gly Ile Ile
                565                 570                 575

Glu Lys Thr Phe Leu Trp Gly Arg Tyr Ser Met Glu Met Ser Ser Lys
            580                 585                 590

Val Tyr Lys Asn Trp Val Phe Thr Glu Gln Ala Leu Pro Ala Asp Leu
        595                 600                 605

Ile Lys Arg Gly Met Ala Ile Glu Asp Pro Ser Pro Cys Gly Val
        610                 615                 620

Lys Leu Val Val Glu Asp Tyr Pro Tyr Ala Val Asp Gly Leu Glu Ile
625                 630                 635                 640

Trp Ala Ile Ile Lys Thr Trp Val Gln Asp Tyr Val Ser Leu Tyr Tyr
                645                 650                 655

Thr Ser Asp Glu Lys Leu Arg Gln Asp Ser Glu Leu Gln Ala Trp Trp
            660                 665                 670

Lys Glu Leu Val Glu Val Gly His Gly Asp Lys Asn Glu Pro Trp
        675                 680                 685

Trp Pro Lys Met Gln Thr Arg Glu Asp Leu Ile Glu Val Cys Ser Ile
    690                 695                 700

Val Ile Trp Thr Ala Ser Ala Leu His Ala Ala Val Asn Phe Gly Gln
705                 710                 715                 720

Tyr Ser Tyr Gly Gly Leu Ile Leu Asn Arg Pro Thr Leu Ser Arg Arg
                725                 730                 735

Phe Met Pro Glu Lys Gly Ser Ala Glu Phe Glu Glu Leu Val Lys Ser
            740                 745                 750

Pro Gln Lys Ala Tyr Leu Lys Thr Ile Thr Pro Lys Phe Gln Thr Leu
        755                 760                 765

Ile Asp Leu Ser Val Ile Glu Ile Leu Ser Arg His Ala Ser Asp Glu
    770                 775                 780

Leu Tyr Leu Gly Glu Arg Asp Asn Pro Asn Trp Thr Ser Asp Lys Arg
785                 790                 795                 800

Ala Leu Glu Ala Phe Lys Lys Phe Gly Asn Lys Leu Ala Glu Ile Glu
                805                 810                 815

Lys Lys Leu Thr Gln Arg Asn Asn Asp Glu Lys Leu Arg Asn Arg His
            820                 825                 830

Gly Pro Val Glu Met Pro Tyr Thr Leu Leu Tyr Pro Ser Ser Lys Glu
        835                 840                 845

Gly Leu Thr Phe Arg Gly Ile Pro Asn Ser Ile Ser Ile
    850                 855                 860

<210> SEQ ID NO 8
<211> LENGTH: 517
<212> TYPE: PRT
<213> ORGANISM: Pisum sativum

<400> SEQUENCE: 8

```
Met Ala Lys Leu Leu Ala Leu Ser Leu Ser Phe Cys Phe Leu Leu Leu
 1               5                  10                  15
Gly Gly Cys Phe Ala Leu Arg Glu Gln Pro Gln Gln Asn Glu Cys Gln
             20                  25                  30
Leu Glu Arg Leu Asp Ala Leu Glu Pro Asp Asn Arg Ile Glu Ser Glu
                 35                  40                  45
Gly Gly Leu Ile Glu Thr Trp Asn Pro Asn Asn Lys Gln Phe Arg Cys
 50                  55                  60
Ala Gly Val Ala Leu Ser Arg Ala Thr Leu Gln Arg Asn Ala Leu Arg
 65                  70                  75                  80
Arg Pro Tyr Tyr Ser Asn Ala Pro Gln Glu Ile Phe Ile Gln Gln Gly
             85                  90                  95
Asn Gly Tyr Phe Gly Met Val Phe Pro Gly Cys Pro Glu Thr Phe Glu
             100                 105                 110
Glu Pro Gln Glu Ser Glu Gln Gly Glu Gly Arg Arg Tyr Arg Asp Arg
             115                 120                 125
His Gln Lys Val Asn Arg Phe Arg Glu Gly Asp Ile Ile Ala Val Pro
             130                 135                 140
Thr Gly Ile Val Phe Trp Met Tyr Asn Asp Gln Asp Thr Pro Val Ile
145                 150                 155                 160
Ala Val Ser Leu Thr Asp Ile Arg Ser Ser Asn Asn Gln Leu Asp Gln
                 165                 170                 175
Met Pro Arg Arg Phe Tyr Leu Ala Gly Asn His Glu Gln Glu Phe Leu
             180                 185                 190
Gln Tyr Gln His Gln Gly Gly Lys Gln Glu Gln Glu Asn Glu Gly
             195                 200                 205
Asn Asn Ile Phe Ser Gly Phe Lys Arg Asp Tyr Leu Glu Asp Ala Phe
             210                 215                 220
Asn Val Asn Arg His Ile Val Asp Arg Leu Gln Gly Arg Asn Glu Asp
225                 230                 235                 240
Glu Glu Lys Gly Ala Ile Val Lys Val Lys Gly Gly Leu Ser Ile Ile
                 245                 250                 255
Ser Pro Pro Glu Lys Gln Ala Arg His Gln Arg Gly Ser Arg Gln Glu
             260                 265                 270
Glu Asp Glu Asp Glu Glu Lys Gln Pro Arg His Gln Arg Gly Ser Arg
             275                 280                 285
Gln Glu Glu Glu Glu Asp Glu Asp Glu Glu Arg Gln Pro Arg His Gln
             290                 295                 300
Arg Arg Arg Gly Glu Glu Glu Glu Asp Lys Lys Glu Arg Gly Gly
305                 310                 315                 320
Ser Gln Lys Gly Lys Ser Arg Arg Gln Gly Asp Asn Gly Leu Glu Glu
                 325                 330                 335
Thr Val Cys Thr Ala Lys Leu Arg Leu Asn Ile Gly Pro Ser Ser Ser
             340                 345                 350
Pro Asp Ile Tyr Asn Pro Glu Ala Gly Arg Ile Lys Thr Val Thr Ser
             355                 360                 365
Leu Asp Leu Pro Val Leu Arg Trp Leu Lys Leu Ser Ala Glu His Gly
             370                 375                 380
Ser Leu His Lys Asn Ala Met Phe Val Pro His Tyr Asn Leu Asn Ala
385                 390                 395                 400
Asn Ser Ile Ile Tyr Ala Leu Lys Gly Arg Ala Arg Leu Gln Val Val
                 405                 410                 415
```

Asn Cys Asn Gly Asn Thr Val Phe Asp Gly Glu Leu Glu Ala Gly Arg
                420                 425                 430

Ala Leu Thr Val Pro Gln Asn Tyr Ala Val Ala Ala Lys Ser Leu Ser
            435                 440                 445

Asp Arg Phe Ser Tyr Val Ala Phe Lys Thr Asn Asp Arg Ala Gly Ile
        450                 455                 460

Ala Arg Leu Ala Gly Thr Ser Ser Val Ile Asn Asn Leu Pro Leu Asp
465                 470                 475                 480

Val Val Ala Ala Thr Phe Asn Leu Gln Arg Asn Glu Ala Arg Gln Leu
                485                 490                 495

Lys Ser Asn Asn Pro Phe Lys Phe Leu Val Pro Ala Arg Glu Ser Glu
            500                 505                 510

Asn Arg Ala Ser Ala
        515

<210> SEQ ID NO 9
<211> LENGTH: 275
<212> TYPE: PRT
<213> ORGANISM: Pisum sativum

<400> SEQUENCE: 9

Asp Asn Ala Glu Ile Glu Lys Ile Leu Leu Glu His Glu Lys Glu
1               5                   10                  15

Thr His His Arg Arg Gly Leu Arg Asp Lys Arg Gln Gln Ser Gln Glu
                20                  25                  30

Lys Asn Val Ile Val Lys Val Ser Lys Lys Gln Ile Glu Glu Leu Ser
            35                  40                  45

Lys Asn Ala Lys Ser Ser Ser Lys Lys Ser Val Ser Ser Arg Ser Glu
50                  55                  60

Pro Phe Asn Leu Lys Ser Ser Asp Pro Ile Tyr Ser Asn Gln Tyr Gly
65                  70                  75                  80

Lys Phe Phe Glu Ile Thr Pro Lys Lys Asn Pro Gln Leu Gln Asp Leu
                85                  90                  95

Asp Ile Phe Val Asn Tyr Val Glu Ile Lys Glu Gly Ser Leu Trp Leu
            100                 105                 110

Pro His Tyr Asn Ser Arg Ala Ile Val Ile Val Thr Val Asn Glu Gly
        115                 120                 125

Lys Gly Asp Phe Glu Leu Val Gly Gln Arg Asn Glu Asn Gln Gln Gly
130                 135                 140

Leu Arg Glu Glu Asp Asp Glu Glu Glu Glu Arg Glu Glu Glu Thr
145                 150                 155                 160

Lys Asn Gln Val Gln Ser Tyr Lys Ala Lys Leu Thr Pro Gly Asp Val
                165                 170                 175

Phe Val Ile Pro Ala Gly His Pro Val Ala Val Arg Ala Ser Ser Asn
            180                 185                 190

Leu Asn Leu Leu Gly Phe Gly Ile Asn Ala Glu Asn Asn Gln Arg Asn
        195                 200                 205

Phe Leu Ala Gly Glu Glu Asp Asn Val Ile Ser Gln Ile Gln Lys Gln
210                 215                 220

Val Lys Asp Leu Thr Phe Pro Gly Ser Ala Gln Glu Val Asp Arg Leu
225                 230                 235                 240

Leu Glu Asn Gln Lys Gln Ser Tyr Phe Ala Asn Ala Gln Pro Gln Gln
                245                 250                 255

Arg Glu Thr Arg Ser Gln Glu Ile Lys Glu His Leu Tyr Ser Ile Leu
            260                 265                 270

```
Gly Ala Phe
        275

<210> SEQ ID NO 10
<211> LENGTH: 438
<212> TYPE: PRT
<213> ORGANISM: Pisum sativum

<400> SEQUENCE: 10

Met Ala Ala Thr Pro Ile Lys Pro Leu Met Leu Leu Ala Ile Ala Phe
1               5                   10                  15

Leu Ala Ser Val Cys Val Ser Ser Arg Ser Asp Gln Glu Asn Pro Phe
            20                  25                  30

Ile Phe Lys Ser Asn Arg Phe Gln Thr Leu Tyr Glu Asn Glu Asn Gly
        35                  40                  45

His Ile Arg Leu Leu Gln Lys Phe Asp Lys Arg Ser Lys Ile Phe Glu
    50                  55                  60

Asn Leu Gln Asn Tyr Arg Leu Leu Glu Tyr Lys Ser Lys Pro Arg Thr
65                  70                  75                  80

Leu Phe Leu Pro Gln Tyr Thr Asp Ala Asp Phe Ile Leu Val Val Leu
                85                  90                  95

Ser Gly Lys Ala Thr Leu Thr Val Leu Lys Ser Asn Asp Arg Asn Ser
            100                 105                 110

Phe Asn Leu Glu Arg Gly Asp Thr Ile Lys Leu Pro Ala Gly Thr Ile
        115                 120                 125

Ala Tyr Leu Ala Asn Arg Asp Asp Asn Glu Asp Leu Arg Val Leu Asp
    130                 135                 140

Leu Thr Ile Pro Val Asn Lys Pro Gly Gln Leu Gln Ser Phe Leu Leu
145                 150                 155                 160

Ser Gly Thr Gln Asn Gln Pro Ser Leu Leu Ser Gly Phe Ser Lys Asn
                165                 170                 175

Ile Leu Glu Ala Ala Phe Asn Thr Asn Tyr Glu Glu Ile Glu Lys Val
            180                 185                 190

Leu Leu Glu Gln Gln Glu Gln Glu Pro Gln His Arg Arg Ser Leu Lys
        195                 200                 205

Asp Arg Arg Gln Glu Ile Asn Glu Glu Asn Val Ile Val Lys Val Ser
    210                 215                 220

Arg Glu Gln Ile Glu Glu Leu Ser Lys Asn Ala Lys Ser Ser Ser Lys
225                 230                 235                 240

Lys Ser Val Ser Ser Glu Ser Gly Pro Phe Asn Leu Arg Ser Arg Asn
                245                 250                 255

Pro Ile Tyr Ser Asn Lys Phe Gly Lys Phe Phe Glu Ile Thr Pro Glu
            260                 265                 270

Lys Asn Gln Gln Leu Gln Asp Leu Asp Ile Phe Val Asn Ser Val Asp
        275                 280                 285

Ile Lys Glu Gly Ser Leu Leu Leu Pro Asn Tyr Asn Ser Arg Ala Ile
    290                 295                 300

Val Ile Val Thr Val Thr Glu Gly Lys Gly Asp Phe Glu Leu Val Gly
305                 310                 315                 320

Gln Arg Asn Glu Asn Gly Lys Glu Asn Asp Lys Glu Glu Glu
                325                 330                 335

Glu Glu Glu Thr Ser Lys Gln Val Gln Leu Tyr Arg Ala Lys Leu Ser
            340                 345                 350

Pro Gly Asp Val Phe Val Ile Pro Ala Gly His Pro Val Ala Ile Asn
```

```
            355                 360                 365
Ala Ser Ser Asp Leu Asn Leu Ile Gly Phe Gly Ile Asn Ala Glu Asn
    370                 375                 380

Asn Glu Arg Asn Phe Leu Ala Gly Glu Glu Asp Asn Val Ile Ser Gln
385                 390                 395                 400

Val Glu Arg Pro Val Lys Glu Leu Ala Phe Pro Gly Ser Ser His Glu
                405                 410                 415

Val Asp Arg Leu Leu Lys Asn Gln Lys Gln Ser Tyr Phe Ala Asn Ala
            420                 425                 430

Gln Pro Leu Gln Arg Glu
        435

<210> SEQ ID NO 11
<211> LENGTH: 499
<212> TYPE: PRT
<213> ORGANISM: Oryza sativa

<400> SEQUENCE: 11

Met Ala Ser Ile Asn Arg Pro Ile Val Phe Thr Val Cys Leu Phe
1               5                  10                  15

Leu Leu Cys Asn Gly Ser Leu Ala Gln Gln Leu Leu Gly Gln Ser Thr
            20                  25                  30

Ser Gln Trp Gln Ser Ser Arg Arg Gly Ser Pro Arg Glu Cys Arg Phe
        35                  40                  45

Asp Arg Leu Gln Ala Phe Glu Pro Ile Arg Ser Val Arg Ser Gln Ala
    50                  55                  60

Gly Thr Thr Glu Phe Phe Asp Val Ser Asn Glu Gln Phe Gln Cys Thr
65                  70                  75                  80

Gly Val Ser Val Val Arg Arg Val Ile Glu Pro Arg Gly Leu Leu Leu
                85                  90                  95

Pro His Tyr Thr Asn Gly Ala Ser Leu Val Tyr Ile Ile Gln Gly Arg
            100                 105                 110

Gly Ile Thr Gly Pro Thr Phe Pro Gly Cys Pro Glu Ser Tyr Gln Gln
        115                 120                 125

Gln Phe Gln Gln Ser Gly Gln Ala Gln Leu Thr Glu Ser Gln Ser Gln
    130                 135                 140

Ser Gln Lys Phe Lys Asp Glu His Gln Lys Ile His Arg Phe Arg Gln
145                 150                 155                 160

Gly Asp Val Ile Ala Leu Pro Ala Gly Val Ala His Trp Cys Tyr Asn
                165                 170                 175

Asp Gly Glu Val Pro Val Val Ala Ile Tyr Val Thr Asp Leu Asn Asn
            180                 185                 190

Gly Ala Asn Gln Leu Asp Pro Arg Gln Arg Asp Phe Leu Leu Ala Gly
        195                 200                 205

Asn Lys Arg Asn Pro Gln Ala Tyr Arg Arg Glu Val Glu Glu Arg Ser
    210                 215                 220

Gln Asn Ile Phe Ser Gly Phe Ser Thr Glu Leu Leu Ser Glu Ala Leu
225                 230                 235                 240

Gly Val Ser Ser Gln Val Ala Arg Gln Leu Gln Cys Gln Asn Asp Gln
                245                 250                 255

Arg Gly Glu Ile Val Arg Val Glu His Gly Leu Ser Leu Leu Gln Pro
            260                 265                 270

Tyr Ala Ser Leu Gln Glu Gln Glu Gln Gly Gln Val Gln Ser Arg Glu
        275                 280                 285
```

```
Arg Tyr Gln Glu Gly Gln Tyr Gln Gln Ser Gln Tyr Gly Ser Gly Cys
    290                 295                 300

Ser Asn Gly Leu Asp Glu Thr Phe Cys Thr Leu Arg Val Arg Gln Asn
305                 310                 315                 320

Ile Asp Asn Pro Asn Arg Ala Asp Thr Tyr Asn Pro Arg Ala Gly Arg
                325                 330                 335

Val Thr Asn Leu Asn Thr Gln Asn Phe Pro Ile Leu Ser Leu Val Gln
            340                 345                 350

Met Ser Ala Val Lys Val Asn Leu Tyr Gln Asn Ala Leu Leu Ser Pro
        355                 360                 365

Phe Trp Asn Ile Asn Ala His Ser Val Val Tyr Ile Thr Gln Gly Arg
370                 375                 380

Ala Arg Val Gln Val Val Asn Asn Gly Lys Thr Val Phe Asn Gly
385                 390                 395                 400

Glu Leu Arg Arg Gly Gln Leu Leu Ile Ile Pro Gln His Tyr Ala Val
                405                 410                 415

Val Lys Lys Ala Gln Arg Glu Gly Cys Ala Tyr Ile Ala Phe Lys Thr
            420                 425                 430

Asn Pro Asn Ser Met Val Ser His Ile Ala Gly Lys Ser Ser Ile Phe
        435                 440                 445

Arg Ala Leu Pro Asn Asp Val Leu Ala Asn Ala Tyr Arg Ile Ser Arg
450                 455                 460

Glu Glu Ala Gln Arg Leu Lys His Asn Arg Gly Asp Glu Phe Gly Ala
465                 470                 475                 480

Phe Thr Pro Ile Gln Tyr Lys Ser Tyr Gln Asp Val Tyr Asn Ala Ala
                485                 490                 495

Glu Ser Ser

<210> SEQ ID NO 12
<211> LENGTH: 499
<212> TYPE: PRT
<213> ORGANISM: Oryza sativa

<400> SEQUENCE: 12

Met Ala Ser Ile Asn Arg Pro Ile Val Phe Thr Val Cys Leu Phe
1               5                   10                  15

Leu Leu Cys Asp Gly Ser Leu Ala Gln Gln Leu Leu Gly Gln Ser Thr
            20                  25                  30

Ser Gln Trp Gln Ser Ser Arg Arg Gly Ser Pro Arg Gly Cys Arg Phe
        35                  40                  45

Asp Arg Leu Gln Ala Phe Glu Pro Ile Arg Ser Val Arg Ser Gln Ala
50                  55                  60

Gly Thr Thr Glu Phe Phe Asp Val Ser Asn Glu Leu Phe Gln Cys Thr
65                  70                  75                  80

Gly Val Ser Val Val Arg Arg Val Ile Glu Pro Arg Gly Leu Leu Leu
                85                  90                  95

Pro His Tyr Thr Asn Gly Ala Ser Leu Val Tyr Ile Ile Gln Gly Arg
            100                 105                 110

Gly Ile Thr Gly Pro Thr Phe Pro Gly Cys Pro Glu Thr Tyr Gln Gln
        115                 120                 125

Gln Phe Gln Gln Ser Gly Gln Ala Gln Leu Thr Glu Ser Gln Ser Gln
    130                 135                 140

Ser His Lys Phe Lys Asp Glu His Gln Lys Ile His Arg Phe Arg Gln
145                 150                 155                 160
```

Gly Asp Val Ile Ala Leu Pro Ala Gly Val Ala His Trp Cys Tyr Asn
            165                 170                 175

Asp Gly Glu Val Pro Val Val Ala Ile Tyr Val Thr Asp Ile Asn Asn
        180                 185                 190

Gly Ala Asn Gln Leu Asp Pro Arg Gln Arg Asp Phe Leu Leu Ala Gly
    195                 200                 205

Asn Lys Arg Asn Pro Gln Ala Tyr Arg Arg Glu Val Glu Glu Trp Ser
210                 215                 220

Gln Asn Ile Phe Ser Gly Phe Ser Thr Glu Leu Leu Ser Glu Ala Phe
225                 230                 235                 240

Gly Ile Ser Asn Gln Val Ala Arg Gln Leu Gln Cys Gln Asn Asp Gln
            245                 250                 255

Arg Gly Glu Ile Val Arg Val Glu Arg Gly Leu Ser Leu Leu Gln Pro
        260                 265                 270

Tyr Ala Ser Leu Gln Glu Gln Glu Gln Gly Gln Met Gln Ser Arg Glu
    275                 280                 285

His Tyr Gln Glu Gly Gly Tyr Gln Gln Ser Gln Tyr Gly Ser Gly Cys
290                 295                 300

Pro Asn Gly Leu Asp Glu Thr Phe Cys Thr Met Arg Val Arg Gln Asn
305                 310                 315                 320

Ile Asp Asn Pro Asn Arg Ala Asp Thr Tyr Asn Pro Arg Ala Gly Arg
            325                 330                 335

Val Thr Asn Leu Asn Ser Gln Asn Phe Pro Ile Leu Asn Leu Val Gln
        340                 345                 350

Met Ser Ala Val Lys Val Asn Leu Tyr Gln Asn Ala Leu Leu Ser Pro
    355                 360                 365

Phe Trp Asn Ile Asn Ala His Ser Ile Val Tyr Ile Thr Gln Gly Arg
370                 375                 380

Ala Gln Val Gln Val Val Asn Asn Asn Gly Lys Thr Val Phe Asn Gly
385                 390                 395                 400

Glu Leu Arg Arg Gly Gln Leu Leu Ile Val Pro Gln His Tyr Val Val
            405                 410                 415

Val Lys Lys Ala Gln Arg Glu Gly Cys Ala Tyr Ile Ala Phe Lys Thr
        420                 425                 430

Asn Pro Asn Ser Met Val Ser His Ile Ala Gly Lys Ser Ser Ile Phe
    435                 440                 445

Arg Ala Leu Pro Thr Asp Val Leu Ala Asn Ala Tyr Arg Ile Ser Arg
450                 455                 460

Glu Glu Ala Gln Arg Leu Lys His Asn Arg Gly Asp Glu Phe Gly Ala
465                 470                 475                 480

Phe Thr Pro Leu Gln Tyr Lys Ser Tyr Gln Asp Val Tyr Asn Val Ala
            485                 490                 495

Glu Ser Ser

<210> SEQ ID NO 13
<211> LENGTH: 160
<212> TYPE: PRT
<213> ORGANISM: Oryza sativa

<400> SEQUENCE: 13

Met Ala Ser Asn Lys Val Val Phe Ser Val Leu Leu Ala Val Val
1               5                   10                  15

Ser Val Leu Ala Ala Thr Ala Thr Met Ala Glu Tyr His His Gln Asp
            20                  25                  30

Gln Val Val Tyr Thr Pro Gly Pro Leu Cys Gln Pro Gly Met Gly Tyr
            35                  40                  45

Pro Met Tyr Pro Leu Pro Arg Cys Arg Ala Leu Val Lys Arg Gln Cys
 50                  55                  60

Val Gly Arg Gly Thr Ala Ala Ala Glu Gln Val Arg Arg Asp Cys
 65                  70                  75                  80

Cys Arg Gln Leu Ala Ala Val Asp Asp Ser Trp Cys Arg Cys Glu Ala
            85                  90                  95

Ile Ser His Met Leu Gly Gly Ile Tyr Arg Glu Leu Gly Ala Pro Asp
            100                 105                 110

Val Gly His Pro Met Ser Glu Val Phe Arg Gly Cys Arg Arg Gly Asp
            115                 120                 125

Leu Glu Arg Ala Ala Ala Ser Leu Pro Ala Phe Cys Asn Val Asp Ile
            130                 135                 140

Pro Asn Gly Gly Gly Val Cys Tyr Trp Leu Ala Arg Ser Gly Tyr
145                 150                 155                 160

<210> SEQ ID NO 14
<211> LENGTH: 336
<212> TYPE: PRT
<213> ORGANISM: Staphylococcus aureus

<400> SEQUENCE: 14

Met Lys Gly Lys Phe Leu Lys Val Ser Ser Leu Phe Val Ala Thr Leu
 1               5                  10                  15

Thr Thr Ala Thr Leu Val Ser Ser Pro Ala Ala Asn Ala Leu Ser Ser
            20                  25                  30

Lys Ala Met Asp Asn His Pro Gln Gln Thr Gln Ser Ser Lys Gln Gln
            35                  40                  45

Thr Pro Lys Ile Gln Lys Gly Gly Asn Leu Lys Pro Leu Glu Gln Arg
 50                  55                  60

Glu His Ala Asn Val Ile Leu Pro Asn Asn Asp Arg His Gln Ile Thr
 65                  70                  75                  80

Asp Thr Thr Asn Gly His Tyr Ala Pro Val Thr Tyr Ile Gln Val Glu
            85                  90                  95

Ala Pro Thr Gly Thr Phe Ile Ala Ser Gly Val Val Gly Lys Asp
            100                 105                 110

Thr Leu Leu Thr Asn Lys His Val Val Asp Ala Thr His Gly Asp Pro
            115                 120                 125

His Ala Leu Lys Ala Phe Pro Ser Ala Ile Asn Gln Asp Asn Tyr Pro
            130                 135                 140

Asn Gly Gly Phe Thr Ala Glu Gln Ile Thr Lys Tyr Ser Gly Glu Gly
145                 150                 155                 160

Asp Leu Ala Ile Val Lys Phe Ser Pro Asn Glu Gln Asn Lys His Ile
            165                 170                 175

Gly Glu Val Val Lys Pro Ala Thr Met Ser Asn Asn Ala Glu Thr Gln
            180                 185                 190

Val Asn Gln Asn Ile Thr Val Thr Gly Tyr Pro Gly Asp Lys Pro Val
            195                 200                 205

Ala Thr Met Trp Glu Ser Lys Gly Lys Ile Thr Tyr Leu Lys Gly Glu
            210                 215                 220

Ala Met Gln Tyr Asp Leu Ser Thr Thr Gly Gly Asn Ser Gly Ser Pro
225                 230                 235                 240

Val Phe Asn Glu Lys Asn Glu Val Ile Gly Ile His Trp Gly Gly Val
            245                 250                 255

```
Pro Asn Glu Phe Asn Gly Ala Val Phe Ile Asn Glu Asn Val Arg Asn
                260                 265                 270

Phe Leu Lys Gln Asn Ile Glu Asp Ile His Phe Ala Asn Asp Asp Gln
            275                 280                 285

Pro Asn Asn Pro Asp Asn Pro Asp Asn Pro Asn Asn Pro Asp Asn Pro
        290                 295                 300

Asn Asn Pro Asp Glu Pro Asn Asn Pro Asp Asn Pro Asn Asn Pro Asp
305                 310                 315                 320

Asn Pro Asp Asn Gly Asp Asn Asn Ser Asp Asn Pro Asp Ala Ala
                325                 330                 335

<210> SEQ ID NO 15
<211> LENGTH: 13
<212> TYPE: PRT
<213> ORGANISM: Artificial Sequence
<220> FEATURE:
<223> OTHER INFORMATION: Synthetic peptide

<400> SEQUENCE: 15

Gln Asn Tyr Leu Ser Gly Phe Ser Lys Asn Ile Leu Glu
1               5                   10

<210> SEQ ID NO 16
<211> LENGTH: 20
<212> TYPE: PRT
<213> ORGANISM: Artificial Sequence
<220> FEATURE:
<223> OTHER INFORMATION: Synthetic peptide

<400> SEQUENCE: 16

Thr Ile Lys Leu Pro Ala Gly Thr Ile Ala Tyr Leu Val Asn Arg Asp
1               5                   10                  15

Asp Asn Glu Glu
            20

<210> SEQ ID NO 17
<211> LENGTH: 15
<212> TYPE: PRT
<213> ORGANISM: Artificial Sequence
<220> FEATURE:
<223> OTHER INFORMATION: Synthetic peptide

<400> SEQUENCE: 17

Leu Ala Ile Pro Val Asn Arg Pro Gly Gln Leu Gln Ser Phe Leu
1               5                   10                  15

<210> SEQ ID NO 18
<211> LENGTH: 11
<212> TYPE: PRT
<213> ORGANISM: Artificial Sequence
<220> FEATURE:
<223> OTHER INFORMATION: Synthetic peptide

<400> SEQUENCE: 18

Ala Ile Pro Val Asn Arg Pro Gly Gln Leu Gln
1               5                   10

<210> SEQ ID NO 19
<211> LENGTH: 9
<212> TYPE: PRT
<213> ORGANISM: Artificial Sequence
<220> FEATURE:
<223> OTHER INFORMATION: Synthetic peptide
```

```
<400> SEQUENCE: 19

Pro Ala Gly His Pro Val Ala Val Lys
1               5

<210> SEQ ID NO 20
<211> LENGTH: 19
<212> TYPE: PRT
<213> ORGANISM: Artificial Sequence
<220> FEATURE:
<223> OTHER INFORMATION: Synthetic peptide

<400> SEQUENCE: 20

Val Gln Asn Tyr Lys Ala Lys Leu Ser Ser Gly Asp Val Phe Val Ile
1               5                   10                  15

Pro Ala Gly

<210> SEQ ID NO 21
<211> LENGTH: 24
<212> TYPE: PRT
<213> ORGANISM: Artificial Sequence
<220> FEATURE:
<223> OTHER INFORMATION: Synthetic peptide

<400> SEQUENCE: 21

Asn Asn Gln Arg Asn Phe Leu Ala Gly Asp Glu Asp Asn Val Ile Ser
1               5                   10                  15

Gln Ile Gln Arg Pro Val Lys Glu
            20

<210> SEQ ID NO 22
<211> LENGTH: 23
<212> TYPE: PRT
<213> ORGANISM: Artificial Sequence
<220> FEATURE:
<223> OTHER INFORMATION: Synthetic peptide

<400> SEQUENCE: 22

Ile Asn Lys Gln Val Gln Asn Tyr Lys Ala Lys Leu Ser Ser Gly Asp
1               5                   10                  15

Val Phe Val Ile Pro Ala Gly
            20

<210> SEQ ID NO 23
<211> LENGTH: 10
<212> TYPE: PRT
<213> ORGANISM: Artificial Sequence
<220> FEATURE:
<223> OTHER INFORMATION: Synthetic peptide

<400> SEQUENCE: 23

Leu Ala Ile Pro Val Asn Arg Pro Gly Gln
1               5                   10

<210> SEQ ID NO 24
<211> LENGTH: 20
<212> TYPE: PRT
<213> ORGANISM: Artificial Sequence
<220> FEATURE:
<223> OTHER INFORMATION: Synthetic peptide

<400> SEQUENCE: 24

Asn Phe Leu Ala Gly Asp Glu Asp Asn Val Ile Ser Gln Ile Gln Arg
1               5                   10                  15

Pro Val Lys Glu
```

-continued

```
            20

<210> SEQ ID NO 25
<211> LENGTH: 15
<212> TYPE: PRT
<213> ORGANISM: Artificial Sequence
<220> FEATURE:
<223> OTHER INFORMATION: Synthetic peptide

<400> SEQUENCE: 25

Asp Leu Ala Ile Pro Val Asn Arg Pro Gly Gln Leu Gln Ser Phe
1               5                   10                  15

<210> SEQ ID NO 26
<211> LENGTH: 11
<212> TYPE: PRT
<213> ORGANISM: Artificial Sequence
<220> FEATURE:
<223> OTHER INFORMATION: Synthetic peptide

<400> SEQUENCE: 26

Val Ile Pro Ala Gly His Pro Val Ala Val Lys
1               5                   10

<210> SEQ ID NO 27
<211> LENGTH: 21
<212> TYPE: PRT
<213> ORGANISM: Artificial Sequence
<220> FEATURE:
<223> OTHER INFORMATION: Synthetic peptide

<400> SEQUENCE: 27

Asp Thr Ile Lys Leu Pro Ala Gly Thr Ile Ala Tyr Leu Val Asn Arg
1               5                   10                  15

Asp Asp Asn Glu Glu
            20

<210> SEQ ID NO 28
<211> LENGTH: 14
<212> TYPE: PRT
<213> ORGANISM: Artificial Sequence
<220> FEATURE:
<223> OTHER INFORMATION: Synthetic peptide

<400> SEQUENCE: 28

Leu Ala Ile Pro Val Asn Arg Pro Gly Gln Leu Gln Ser Phe
1               5                   10

<210> SEQ ID NO 29
<211> LENGTH: 21
<212> TYPE: PRT
<213> ORGANISM: Artificial Sequence
<220> FEATURE:
<223> OTHER INFORMATION: Synthetic peptide

<400> SEQUENCE: 29

Lys Gln Val Gln Asn Tyr Lys Ala Lys Leu Ser Ser Gly Asp Val Phe
1               5                   10                  15

Val Ile Pro Ala Gly
            20

<210> SEQ ID NO 30
<211> LENGTH: 23
<212> TYPE: PRT
<213> ORGANISM: Artificial Sequence
<220> FEATURE:
```

<223> OTHER INFORMATION: Synthetic peptide

<400> SEQUENCE: 30

Arg Gly Asp Thr Ile Lys Leu Pro Ala Gly Thr Ile Ala Tyr Leu Val
1               5                   10                  15

Asn Arg Asp Asp Asn Glu Glu
            20

<210> SEQ ID NO 31
<211> LENGTH: 19
<212> TYPE: PRT
<213> ORGANISM: Artificial Sequence
<220> FEATURE:
<223> OTHER INFORMATION: Synthetic peptide

<400> SEQUENCE: 31

Phe Leu Ala Gly Asp Glu Asp Asn Val Ile Ser Gln Ile Gln Arg Pro
1               5                   10                  15

Val Lys Glu

<210> SEQ ID NO 32
<211> LENGTH: 13
<212> TYPE: PRT
<213> ORGANISM: Artificial Sequence
<220> FEATURE:
<223> OTHER INFORMATION: Synthetic peptide

<400> SEQUENCE: 32

Leu Ala Ile Pro Val Asn Arg Pro Gly Gln Leu Gln Ser
1               5                   10

<210> SEQ ID NO 33
<211> LENGTH: 15
<212> TYPE: PRT
<213> ORGANISM: Artificial Sequence
<220> FEATURE:
<223> OTHER INFORMATION: Synthetic peptide

<400> SEQUENCE: 33

Val Leu Asp Leu Ala Ile Pro Val Asn Arg Pro Gly Gln Leu Gln
1               5                   10                  15

<210> SEQ ID NO 34
<211> LENGTH: 13
<212> TYPE: PRT
<213> ORGANISM: Artificial Sequence
<220> FEATURE:
<223> OTHER INFORMATION: Synthetic peptide

<400> SEQUENCE: 34

Asp Leu Ala Ile Pro Val Asn Arg Pro Gly Gln Leu Gln
1               5                   10

<210> SEQ ID NO 35
<211> LENGTH: 13
<212> TYPE: PRT
<213> ORGANISM: Artificial Sequence
<220> FEATURE:
<223> OTHER INFORMATION: Synthetic peptide

<400> SEQUENCE: 35

Val Phe Val Ile Pro Ala Gly His Pro Val Ala Val Lys
1               5                   10

<210> SEQ ID NO 36

```
<211> LENGTH: 20
<212> TYPE: PRT
<213> ORGANISM: Artificial Sequence
<220> FEATURE:
<223> OTHER INFORMATION: Synthetic peptide

<400> SEQUENCE: 36

Thr Ile Phe Leu Pro Gln His Thr Asp Ala Asp Tyr Ile Leu Val Val
1               5                   10                  15

Leu Ser Gly Lys
            20

<210> SEQ ID NO 37
<211> LENGTH: 23
<212> TYPE: PRT
<213> ORGANISM: Artificial Sequence
<220> FEATURE:
<223> OTHER INFORMATION: Synthetic peptide

<400> SEQUENCE: 37

Asn Gln Arg Asn Phe Leu Ala Gly Asp Glu Asp Asn Val Ile Ser Gln
1               5                   10                  15

Ile Gln Arg Pro Val Lys Glu
            20

<210> SEQ ID NO 38
<211> LENGTH: 12
<212> TYPE: PRT
<213> ORGANISM: Artificial Sequence
<220> FEATURE:
<223> OTHER INFORMATION: Synthetic peptide

<400> SEQUENCE: 38

Leu Ala Ile Pro Val Asn Arg Pro Gly Gln Leu Gln
1               5                   10

<210> SEQ ID NO 39
<211> LENGTH: 17
<212> TYPE: PRT
<213> ORGANISM: Artificial Sequence
<220> FEATURE:
<223> OTHER INFORMATION: Synthetic peptide

<400> SEQUENCE: 39

His Pro Val Ala Val Lys Ala Ser Ser Asn Leu Asp Leu Leu Gly Phe
1               5                   10                  15

Gly

<210> SEQ ID NO 40
<211> LENGTH: 11
<212> TYPE: PRT
<213> ORGANISM: Artificial Sequence
<220> FEATURE:
<223> OTHER INFORMATION: Synthetic peptide

<400> SEQUENCE: 40

Leu Ala Ile Pro Val Asn Arg Pro Gly Gln Leu
1               5                   10

<210> SEQ ID NO 41
<211> LENGTH: 12
<212> TYPE: PRT
<213> ORGANISM: Artificial Sequence
<220> FEATURE:
<223> OTHER INFORMATION: Synthetic peptide
```

```
<400> SEQUENCE: 41

Asp Leu Ala Ile Pro Val Asn Arg Pro Gly Gln Leu
1               5                   10

<210> SEQ ID NO 42
<211> LENGTH: 24
<212> TYPE: PRT
<213> ORGANISM: Artificial Sequence
<220> FEATURE:
<223> OTHER INFORMATION: Synthetic peptide

<400> SEQUENCE: 42

Ser Lys Pro His Thr Ile Phe Leu Pro Gln His Thr Asp Ala Asp Tyr
1               5                   10                  15

Ile Leu Val Val Leu Ser Gly Lys
                20

<210> SEQ ID NO 43
<211> LENGTH: 12
<212> TYPE: PRT
<213> ORGANISM: Artificial Sequence
<220> FEATURE:
<223> OTHER INFORMATION: Synthetic peptide

<400> SEQUENCE: 43

Phe Val Ile Pro Ala Gly His Pro Val Ala Val Lys
1               5                   10

<210> SEQ ID NO 44
<211> LENGTH: 14
<212> TYPE: PRT
<213> ORGANISM: Artificial Sequence
<220> FEATURE:
<223> OTHER INFORMATION: Synthetic peptide

<400> SEQUENCE: 44

Asp Leu Ala Ile Pro Val Asn Arg Pro Gly Gln Leu Gln Ser
1               5                   10

<210> SEQ ID NO 45
<211> LENGTH: 22
<212> TYPE: PRT
<213> ORGANISM: Artificial Sequence
<220> FEATURE:
<223> OTHER INFORMATION: Synthetic peptide

<400> SEQUENCE: 45

Ser Gly Asp Val Phe Val Ile Pro Ala Gly His Pro Val Ala Val Lys
1               5                   10                  15

Ala Ser Ser Asn Leu Asp
                20

<210> SEQ ID NO 46
<211> LENGTH: 13
<212> TYPE: PRT
<213> ORGANISM: Artificial Sequence
<220> FEATURE:
<223> OTHER INFORMATION: Synthetic peptide

<400> SEQUENCE: 46

Ala Ile Pro Val Asn Arg Pro Gly Gln Leu Gln Ser Phe
1               5                   10

<210> SEQ ID NO 47
<211> LENGTH: 13
```

```
<212> TYPE: PRT
<213> ORGANISM: Artificial Sequence
<220> FEATURE:
<223> OTHER INFORMATION: Synthetic peptide

<400> SEQUENCE: 47

Glu Leu Ala Phe Pro Gly Ser Ala Gln Glu Val Asp Arg
1               5                   10

<210> SEQ ID NO 48
<211> LENGTH: 18
<212> TYPE: PRT
<213> ORGANISM: Artificial Sequence
<220> FEATURE:
<223> OTHER INFORMATION: Synthetic peptide

<400> SEQUENCE: 48

Leu Ala Ile Pro Val Asn Arg Pro Gly Gln Leu Gln Ser Phe Leu Leu
1               5                   10                  15

Ser Gly

<210> SEQ ID NO 49
<211> LENGTH: 24
<212> TYPE: PRT
<213> ORGANISM: Artificial Sequence
<220> FEATURE:
<223> OTHER INFORMATION: Synthetic peptide

<400> SEQUENCE: 49

Val Phe Val Ile Pro Ala Gly His Pro Val Ala Val Lys Ala Ser Ser
1               5                   10                  15

Asn Leu Asp Leu Leu Gly Phe Gly
            20

<210> SEQ ID NO 50
<211> LENGTH: 8
<212> TYPE: PRT
<213> ORGANISM: Artificial Sequence
<220> FEATURE:
<223> OTHER INFORMATION: Synthetic peptide

<400> SEQUENCE: 50

Ala Gly His Pro Val Ala Val Lys
1               5

<210> SEQ ID NO 51
<211> LENGTH: 21
<212> TYPE: PRT
<213> ORGANISM: Artificial Sequence
<220> FEATURE:
<223> OTHER INFORMATION: Synthetic peptide

<400> SEQUENCE: 51

His Pro Val Ala Val Lys Ala Ser Ser Asn Leu Asp Leu Leu Gly Phe
1               5                   10                  15

Gly Ile Asn Ala Glu
            20

<210> SEQ ID NO 52
<211> LENGTH: 22
<212> TYPE: PRT
<213> ORGANISM: Artificial Sequence
<220> FEATURE:
<223> OTHER INFORMATION: Synthetic peptide

<400> SEQUENCE: 52
```

```
Leu Ala Ile Pro Val Asn Arg Pro Gly Gln Leu Gln Ser Phe Leu Leu
1               5                   10                  15

Ser Gly Asn Gln Asn Gln
            20

<210> SEQ ID NO 53
<211> LENGTH: 10
<212> TYPE: PRT
<213> ORGANISM: Artificial Sequence
<220> FEATURE:
<223> OTHER INFORMATION: Synthetic peptide

<400> SEQUENCE: 53

Ser Gly Asp Val Phe Val Ile Pro Ala Gly
1               5                   10

<210> SEQ ID NO 54
<211> LENGTH: 20
<212> TYPE: PRT
<213> ORGANISM: Artificial Sequence
<220> FEATURE:
<223> OTHER INFORMATION: Synthetic peptide

<400> SEQUENCE: 54

Gly Ser Leu Leu Leu Pro His Tyr Asn Ser Arg Ala Ile Val Ile Val
1               5                   10                  15

Thr Val Asn Glu
            20

<210> SEQ ID NO 55
<211> LENGTH: 19
<212> TYPE: PRT
<213> ORGANISM: Artificial Sequence
<220> FEATURE:
<223> OTHER INFORMATION: Synthetic peptide

<400> SEQUENCE: 55

Asn Phe Leu Ala Gly Asp Glu Asp Asn Val Ile Ser Gln Ile Gln Arg
1               5                   10                  15

Pro Val Lys

<210> SEQ ID NO 56
<211> LENGTH: 14
<212> TYPE: PRT
<213> ORGANISM: Artificial Sequence
<220> FEATURE:
<223> OTHER INFORMATION: Synthetic peptide

<400> SEQUENCE: 56

Ser Gly Asp Val Phe Val Ile Pro Ala Gly His Pro Val Ala
1               5                   10

<210> SEQ ID NO 57
<211> LENGTH: 16
<212> TYPE: PRT
<213> ORGANISM: Artificial Sequence
<220> FEATURE:
<223> OTHER INFORMATION: Synthetic peptide

<400> SEQUENCE: 57

Gly Ser Leu Leu Leu Pro His Tyr Asn Ser Arg Ala Ile Val Ile Val
1               5                   10                  15

<210> SEQ ID NO 58
```

```
<211> LENGTH: 20
<212> TYPE: PRT
<213> ORGANISM: Artificial Sequence
<220> FEATURE:
<223> OTHER INFORMATION: Synthetic peptide

<400> SEQUENCE: 58

Arg Gly Asp Thr Ile Lys Leu Pro Ala Gly Thr Ile Ala Tyr Leu Val
1               5                   10                  15

Asn Arg Asp Asp
            20

<210> SEQ ID NO 59
<211> LENGTH: 16
<212> TYPE: PRT
<213> ORGANISM: Artificial Sequence
<220> FEATURE:
<223> OTHER INFORMATION: Synthetic peptide

<400> SEQUENCE: 59

Ser Gly Asp Val Phe Val Ile Pro Ala Gly His Pro Val Ala Val Lys
1               5                   10                  15

<210> SEQ ID NO 60
<211> LENGTH: 18
<212> TYPE: PRT
<213> ORGANISM: Artificial Sequence
<220> FEATURE:
<223> OTHER INFORMATION: Synthetic peptide

<400> SEQUENCE: 60

Leu Ser Ser Gly Asp Val Phe Val Ile Pro Ala Gly His Pro Val Ala
1               5                   10                  15

Val Lys

<210> SEQ ID NO 61
<211> LENGTH: 13
<212> TYPE: PRT
<213> ORGANISM: Artificial Sequence
<220> FEATURE:
<223> OTHER INFORMATION: Synthetic peptide

<400> SEQUENCE: 61

Leu Asp Leu Ala Ile Pro Val Asn Arg Pro Gly Gln Leu
1               5                   10

<210> SEQ ID NO 62
<211> LENGTH: 10
<212> TYPE: PRT
<213> ORGANISM: Artificial Sequence
<220> FEATURE:
<223> OTHER INFORMATION: Synthetic peptide

<400> SEQUENCE: 62

Ala Ile Pro Val Asn Arg Pro Gly Gln Leu
1               5                   10

<210> SEQ ID NO 63
<211> LENGTH: 16
<212> TYPE: PRT
<213> ORGANISM: Artificial Sequence
<220> FEATURE:
<223> OTHER INFORMATION: Synthetic peptide

<400> SEQUENCE: 63

Leu Ala Ile Pro Val Asn Arg Pro Gly Gln Leu Gln Ser Phe Leu Leu
```

<210> SEQ ID NO 64
<211> LENGTH: 22
<212> TYPE: PRT
<213> ORGANISM: Artificial Sequence
<220> FEATURE:
<223> OTHER INFORMATION: Synthetic peptide

<400> SEQUENCE: 64

Pro His Thr Ile Phe Leu Pro Gln His Thr Asp Ala Asp Tyr Ile Leu
1               5                   10                  15

Val Val Leu Ser Gly Lys
            20

<210> SEQ ID NO 65
<211> LENGTH: 19
<212> TYPE: PRT
<213> ORGANISM: Artificial Sequence
<220> FEATURE:
<223> OTHER INFORMATION: Synthetic peptide

<400> SEQUENCE: 65

Val Phe Val Ile Pro Ala Gly His Pro Val Ala Val Lys Ala Ser Ser
1               5                   10                  15

Asn Leu Asp

<210> SEQ ID NO 66
<211> LENGTH: 17
<212> TYPE: PRT
<213> ORGANISM: Artificial Sequence
<220> FEATURE:
<223> OTHER INFORMATION: Synthetic peptide

<400> SEQUENCE: 66

Leu Ala Ile Pro Val Asn Arg Pro Gly Gln Leu Gln Ser Phe Leu Leu
1               5                   10                  15

Ser

<210> SEQ ID NO 67
<211> LENGTH: 17
<212> TYPE: PRT
<213> ORGANISM: Artificial Sequence
<220> FEATURE:
<223> OTHER INFORMATION: Synthetic peptide

<400> SEQUENCE: 67

Val Leu Asp Leu Ala Ile Pro Val Asn Arg Pro Gly Gln Leu Gln Ser
1               5                   10                  15

Phe

<210> SEQ ID NO 68
<211> LENGTH: 12
<212> TYPE: PRT
<213> ORGANISM: Artificial Sequence
<220> FEATURE:
<223> OTHER INFORMATION: Synthetic peptide

<400> SEQUENCE: 68

Ala Ile Pro Val Asn Arg Pro Gly Gln Leu Gln Ser
1               5                   10

<210> SEQ ID NO 69
<211> LENGTH: 20

<212> TYPE: PRT
<213> ORGANISM: Artificial Sequence
<220> FEATURE:
<223> OTHER INFORMATION: Synthetic peptide

<400> SEQUENCE: 69

Asp Thr Ile Lys Leu Pro Ala Gly Thr Ile Ala Tyr Leu Val Asn Arg
1               5                   10                  15

Asp Asp Asn Glu
            20

<210> SEQ ID NO 70
<211> LENGTH: 17
<212> TYPE: PRT
<213> ORGANISM: Artificial Sequence
<220> FEATURE:
<223> OTHER INFORMATION: Synthetic peptide

<400> SEQUENCE: 70

Asn Tyr Lys Ala Lys Leu Ser Ser Gly Asp Val Phe Val Ile Pro Ala
1               5                   10                  15

Gly

<210> SEQ ID NO 71
<211> LENGTH: 19
<212> TYPE: PRT
<213> ORGANISM: Artificial Sequence
<220> FEATURE:
<223> OTHER INFORMATION: Synthetic peptide

<400> SEQUENCE: 71

Gly Lys Ala Ile Leu Thr Val Leu Lys Pro Asp Asp Arg Asn Ser Phe
1               5                   10                  15

Asn Leu Glu

<210> SEQ ID NO 72
<211> LENGTH: 17
<212> TYPE: PRT
<213> ORGANISM: Artificial Sequence
<220> FEATURE:
<223> OTHER INFORMATION: Synthetic peptide

<400> SEQUENCE: 72

Tyr Lys Ser Lys Pro His Thr Ile Phe Leu Pro Gln His Thr Asp Ala
1               5                   10                  15

Asp

<210> SEQ ID NO 73
<211> LENGTH: 11
<212> TYPE: PRT
<213> ORGANISM: Artificial Sequence
<220> FEATURE:
<223> OTHER INFORMATION: Synthetic peptide

<400> SEQUENCE: 73

Ala Ser Ser Asn Leu Asp Leu Leu Gly Phe Gly
1               5                   10

<210> SEQ ID NO 74
<211> LENGTH: 13
<212> TYPE: PRT
<213> ORGANISM: Artificial Sequence
<220> FEATURE:
<223> OTHER INFORMATION: Synthetic peptide

```
<400> SEQUENCE: 74

Asp Glu Glu Glu Glu Gln Gly Glu Glu Glu Ile Asn Lys
1               5                   10

<210> SEQ ID NO 75
<211> LENGTH: 15
<212> TYPE: PRT
<213> ORGANISM: Artificial Sequence
<220> FEATURE:
<223> OTHER INFORMATION: Synthetic peptide

<400> SEQUENCE: 75

Tyr Lys Ser Lys Pro His Thr Ile Phe Leu Pro Gln His Thr Asp
1               5                   10                  15

<210> SEQ ID NO 76
<211> LENGTH: 10
<212> TYPE: PRT
<213> ORGANISM: Artificial Sequence
<220> FEATURE:
<223> OTHER INFORMATION: Synthetic peptide

<400> SEQUENCE: 76

Val Leu Asp Leu Ala Ile Pro Val Asn Arg
1               5                   10

<210> SEQ ID NO 77
<211> LENGTH: 25
<212> TYPE: PRT
<213> ORGANISM: Artificial Sequence
<220> FEATURE:
<223> OTHER INFORMATION: Synthetic peptide

<400> SEQUENCE: 77

Phe Phe Glu Ile Thr Pro Glu Lys Asn Pro Gln Leu Gln Asp Leu Asp
1               5                   10                  15

Ile Phe Val Asn Ser Val Glu Ile Lys
            20                  25

<210> SEQ ID NO 78
<211> LENGTH: 14
<212> TYPE: PRT
<213> ORGANISM: Artificial Sequence
<220> FEATURE:
<223> OTHER INFORMATION: Synthetic peptide

<400> SEQUENCE: 78

Thr Ile Phe Leu Pro Gln His Thr Asp Ala Asp Tyr Ile Leu
1               5                   10

<210> SEQ ID NO 79
<211> LENGTH: 16
<212> TYPE: PRT
<213> ORGANISM: Artificial Sequence
<220> FEATURE:
<223> OTHER INFORMATION: Synthetic peptide

<400> SEQUENCE: 79

Ser Phe Leu Leu Ser Gly Asn Gln Asn Gln Gln Asn Tyr Leu Ser Gly
1               5                   10                  15

<210> SEQ ID NO 80
<211> LENGTH: 18
<212> TYPE: PRT
<213> ORGANISM: Artificial Sequence
<220> FEATURE:
```

<223> OTHER INFORMATION: Synthetic peptide

<400> SEQUENCE: 80

Ser Phe Leu Leu Ser Gly Asn Gln Asn Gln Gln Asn Tyr Leu Ser Gly
1               5                   10                  15

Phe Ser

<210> SEQ ID NO 81
<211> LENGTH: 19
<212> TYPE: PRT
<213> ORGANISM: Artificial Sequence
<220> FEATURE:
<223> OTHER INFORMATION: Synthetic peptide

<400> SEQUENCE: 81

Asn Gln Gln Glu Gln Arg Lys Glu Asp Asp Glu Glu Glu Gln Gly
1               5                   10                  15

Glu Glu Glu

<210> SEQ ID NO 82
<211> LENGTH: 10
<212> TYPE: PRT
<213> ORGANISM: Artificial Sequence
<220> FEATURE:
<223> OTHER INFORMATION: Synthetic peptide

<400> SEQUENCE: 82

Glu Glu Gln Gly Glu Glu Glu Ile Asn Lys
1               5                   10

<210> SEQ ID NO 83
<211> LENGTH: 9
<212> TYPE: PRT
<213> ORGANISM: Artificial Sequence
<220> FEATURE:
<223> OTHER INFORMATION: Synthetic peptide

<400> SEQUENCE: 83

Ser Arg Gly Pro Ile Tyr Ser Asn Glu
1               5

<210> SEQ ID NO 84
<211> LENGTH: 15
<212> TYPE: PRT
<213> ORGANISM: Artificial Sequence
<220> FEATURE:
<223> OTHER INFORMATION: Synthetic peptide

<400> SEQUENCE: 84

Glu Asp Asp Glu Glu Glu Glu Gln Gly Glu Glu Glu Ile Asn Lys
1               5                   10                  15

<210> SEQ ID NO 85
<211> LENGTH: 14
<212> TYPE: PRT
<213> ORGANISM: Artificial Sequence
<220> FEATURE:
<223> OTHER INFORMATION: Synthetic peptide

<400> SEQUENCE: 85

Asp Asp Glu Glu Glu Glu Gln Gly Glu Glu Glu Ile Asn Lys
1               5                   10

<210> SEQ ID NO 86
<211> LENGTH: 15

<212> TYPE: PRT
<213> ORGANISM: Artificial Sequence
<220> FEATURE:
<223> OTHER INFORMATION: Synthetic peptide

<400> SEQUENCE: 86

Lys Glu Asp Asp Glu Glu Glu Gln Gly Glu Glu Glu Ile Asn
1               5                   10                  15

<210> SEQ ID NO 87
<211> LENGTH: 12
<212> TYPE: PRT
<213> ORGANISM: Artificial Sequence
<220> FEATURE:
<223> OTHER INFORMATION: Synthetic peptide

<400> SEQUENCE: 87

Lys Glu Asp Asp Glu Glu Glu Gln Gly Glu Glu
1               5                   10

<210> SEQ ID NO 88
<211> LENGTH: 15
<212> TYPE: PRT
<213> ORGANISM: Artificial Sequence
<220> FEATURE:
<223> OTHER INFORMATION: Synthetic peptide

<400> SEQUENCE: 88

Gln Arg Lys Glu Asp Asp Glu Glu Glu Gln Gly Glu Glu Glu
1               5                   10                  15

<210> SEQ ID NO 89
<211> LENGTH: 16
<212> TYPE: PRT
<213> ORGANISM: Artificial Sequence
<220> FEATURE:
<223> OTHER INFORMATION: Synthetic peptide

<400> SEQUENCE: 89

Lys Glu Asp Asp Glu Glu Glu Gln Gly Glu Glu Glu Ile Asn Lys
1               5                   10                  15

<210> SEQ ID NO 90
<211> LENGTH: 13
<212> TYPE: PRT
<213> ORGANISM: Artificial Sequence
<220> FEATURE:
<223> OTHER INFORMATION: Synthetic peptide

<400> SEQUENCE: 90

Lys Glu Asp Asp Glu Glu Glu Gln Gly Glu Glu Glu
1               5                   10

<210> SEQ ID NO 91
<211> LENGTH: 15
<212> TYPE: PRT
<213> ORGANISM: Artificial Sequence
<220> FEATURE:
<223> OTHER INFORMATION: Synthetic peptide

<400> SEQUENCE: 91

His Pro Val Ala Ile Thr Ala Ser Ser Asn Leu Asn Leu Leu Gly
1               5                   10                  15

<210> SEQ ID NO 92
<211> LENGTH: 11
<212> TYPE: PRT

<213> ORGANISM: Artificial Sequence
<220> FEATURE:
<223> OTHER INFORMATION: Synthetic peptide

<400> SEQUENCE: 92

Ala Ser Ser Asn Leu Asn Leu Leu Gly Phe Gly
1               5                   10

<210> SEQ ID NO 93
<211> LENGTH: 13
<212> TYPE: PRT
<213> ORGANISM: Artificial Sequence
<220> FEATURE:
<223> OTHER INFORMATION: Synthetic peptide

<400> SEQUENCE: 93

Ile Thr Ala Ser Ser Asn Leu Asn Leu Leu Gly Phe Gly
1               5                   10

<210> SEQ ID NO 94
<211> LENGTH: 17
<212> TYPE: PRT
<213> ORGANISM: Artificial Sequence
<220> FEATURE:
<223> OTHER INFORMATION: Synthetic peptide

<400> SEQUENCE: 94

Ile Thr Ala Ser Ser Asn Leu Asn Leu Leu Gly Phe Gly Ile Asn Ala
1               5                   10                  15
Glu

<210> SEQ ID NO 95
<211> LENGTH: 10
<212> TYPE: PRT
<213> ORGANISM: Artificial Sequence
<220> FEATURE:
<223> OTHER INFORMATION: Synthetic peptide

<400> SEQUENCE: 95

Ser Ser Asn Leu Asn Leu Leu Gly Phe Gly
1               5                   10

<210> SEQ ID NO 96
<211> LENGTH: 13
<212> TYPE: PRT
<213> ORGANISM: Artificial Sequence
<220> FEATURE:
<223> OTHER INFORMATION: Synthetic peptide

<400> SEQUENCE: 96

Val Asp Leu Val Ile Pro Val Asn Gly Pro Gly Lys Phe
1               5                   10

<210> SEQ ID NO 97
<211> LENGTH: 12
<212> TYPE: PRT
<213> ORGANISM: Artificial Sequence
<220> FEATURE:
<223> OTHER INFORMATION: Synthetic peptide

<400> SEQUENCE: 97

Leu Val Ile Pro Val Asn Gly Pro Gly Lys Phe Glu
1               5                   10

<210> SEQ ID NO 98
<211> LENGTH: 13

```
-continued

<212> TYPE: PRT
<213> ORGANISM: Artificial Sequence
<220> FEATURE:
<223> OTHER INFORMATION: Synthetic peptide

<400> SEQUENCE: 98

Leu Val Ile Pro Val Asn Gly Pro Gly Lys Phe Glu Ala
1               5                   10

<210> SEQ ID NO 99
<211> LENGTH: 17
<212> TYPE: PRT
<213> ORGANISM: Artificial Sequence
<220> FEATURE:
<223> OTHER INFORMATION: Synthetic peptide

<400> SEQUENCE: 99

Leu Arg Leu Val Asp Leu Val Ile Pro Val Asn Gly Pro Gly Lys Phe
1               5                   10                  15

Glu

<210> SEQ ID NO 100
<211> LENGTH: 17
<212> TYPE: PRT
<213> ORGANISM: Artificial Sequence
<220> FEATURE:
<223> OTHER INFORMATION: Synthetic peptide

<400> SEQUENCE: 100

Tyr Arg Ala Lys Pro His Thr Ile Phe Leu Pro Gln His Ile Asp Ala
1               5                   10                  15

Asp

<210> SEQ ID NO 101
<211> LENGTH: 21
<212> TYPE: PRT
<213> ORGANISM: Artificial Sequence
<220> FEATURE:
<223> OTHER INFORMATION: Synthetic peptide

<400> SEQUENCE: 101

His Pro Val Ala Ile Thr Ala Ser Ser Asn Leu Asn Leu Leu Gly Phe
1               5                   10                  15

Gly Ile Asn Ala Glu
            20

<210> SEQ ID NO 102
<211> LENGTH: 9
<212> TYPE: PRT
<213> ORGANISM: Artificial Sequence
<220> FEATURE:
<223> OTHER INFORMATION: Synthetic peptide

<400> SEQUENCE: 102

Ser Asn Leu Asn Leu Leu Gly Phe Gly
1               5

<210> SEQ ID NO 103
<211> LENGTH: 24
<212> TYPE: PRT
<213> ORGANISM: Artificial Sequence
<220> FEATURE:
<223> OTHER INFORMATION: Synthetic peptide

<400> SEQUENCE: 103
```

His Pro Val Ala Ile Thr Ala Ser Ser Asn Leu Asn Leu Leu Gly Phe
1               5                   10                  15

Gly Ile Asn Ala Glu Asn Asn Glu
            20

<210> SEQ ID NO 104
<211> LENGTH: 15
<212> TYPE: PRT
<213> ORGANISM: Artificial Sequence
<220> FEATURE:
<223> OTHER INFORMATION: Synthetic peptide

<400> SEQUENCE: 104

Leu Val Asp Leu Val Ile Pro Val Asn Gly Pro Gly Lys Phe Glu
1               5                   10                  15

<210> SEQ ID NO 105
<211> LENGTH: 11
<212> TYPE: PRT
<213> ORGANISM: Artificial Sequence
<220> FEATURE:
<223> OTHER INFORMATION: Synthetic peptide

<400> SEQUENCE: 105

Leu Val Ile Pro Val Asn Gly Pro Gly Lys Phe
1               5                   10

<210> SEQ ID NO 106
<211> LENGTH: 18
<212> TYPE: PRT
<213> ORGANISM: Artificial Sequence
<220> FEATURE:
<223> OTHER INFORMATION: Synthetic peptide

<400> SEQUENCE: 106

Thr Ile Lys Leu Pro Ala Gly Thr Thr Ser Tyr Leu Val Asn Gln Asp
1               5                   10                  15

Asp Glu

<210> SEQ ID NO 107
<211> LENGTH: 18
<212> TYPE: PRT
<213> ORGANISM: Artificial Sequence
<220> FEATURE:
<223> OTHER INFORMATION: Synthetic peptide

<400> SEQUENCE: 107

Asp Leu Arg Leu Val Asp Leu Val Ile Pro Val Asn Gly Pro Gly Lys
1               5                   10                  15

Phe Glu

<210> SEQ ID NO 108
<211> LENGTH: 19
<212> TYPE: PRT
<213> ORGANISM: Artificial Sequence
<220> FEATURE:
<223> OTHER INFORMATION: Synthetic peptide

<400> SEQUENCE: 108

Glu Asp Leu Arg Leu Val Asp Leu Val Ile Pro Val Asn Gly Pro Gly
1               5                   10                  15

Lys Phe Glu

<210> SEQ ID NO 109

```
<211> LENGTH: 17
<212> TYPE: PRT
<213> ORGANISM: Artificial Sequence
<220> FEATURE:
<223> OTHER INFORMATION: Synthetic peptide

<400> SEQUENCE: 109

His Pro Val Ala Ile Thr Ala Ser Ser Asn Leu Asn Leu Leu Gly Phe
1               5                   10                  15

Gly

<210> SEQ ID NO 110
<211> LENGTH: 21
<212> TYPE: PRT
<213> ORGANISM: Artificial Sequence
<220> FEATURE:
<223> OTHER INFORMATION: Synthetic peptide

<400> SEQUENCE: 110

Leu Val Asp Leu Val Ile Pro Val Asn Gly Pro Gly Lys Phe Glu Ala
1               5                   10                  15

Phe Asp Leu Ala Lys
            20

<210> SEQ ID NO 111
<211> LENGTH: 13
<212> TYPE: PRT
<213> ORGANISM: Artificial Sequence
<220> FEATURE:
<223> OTHER INFORMATION: Synthetic peptide

<400> SEQUENCE: 111

Asp Asn Val Ile Ser Gln Ile Glu Asn Pro Val Lys Glu
1               5                   10

<210> SEQ ID NO 112
<211> LENGTH: 24
<212> TYPE: PRT
<213> ORGANISM: Artificial Sequence
<220> FEATURE:
<223> OTHER INFORMATION: Synthetic peptide

<400> SEQUENCE: 112

Val Val Ile Ile Pro Ala Gly His Pro Val Ala Ile Thr Ala Ser Ser
1               5                   10                  15

Asn Leu Asn Leu Leu Gly Phe Gly
            20

<210> SEQ ID NO 113
<211> LENGTH: 17
<212> TYPE: PRT
<213> ORGANISM: Artificial Sequence
<220> FEATURE:
<223> OTHER INFORMATION: Synthetic peptide

<400> SEQUENCE: 113

Leu Val Asp Leu Val Ile Pro Val Asn Gly Pro Gly Lys Phe Glu Ala
1               5                   10                  15

Phe

<210> SEQ ID NO 114
<211> LENGTH: 9
<212> TYPE: PRT
<213> ORGANISM: Artificial Sequence
<220> FEATURE:
```

<223> OTHER INFORMATION: Synthetic peptide

<400> SEQUENCE: 114

Tyr Pro Gln Leu Gln Asp Leu Asp Leu
1               5

<210> SEQ ID NO 115
<211> LENGTH: 10
<212> TYPE: PRT
<213> ORGANISM: Artificial Sequence
<220> FEATURE:
<223> OTHER INFORMATION: Synthetic peptide

<400> SEQUENCE: 115

Val Ile Pro Val Asn Gly Pro Gly Lys Phe
1               5                   10

<210> SEQ ID NO 116
<211> LENGTH: 8
<212> TYPE: PRT
<213> ORGANISM: Artificial Sequence
<220> FEATURE:
<223> OTHER INFORMATION: Synthetic peptide

<400> SEQUENCE: 116

Ser Lys Lys Ser Leu Pro Ser Glu
1               5

<210> SEQ ID NO 117
<211> LENGTH: 17
<212> TYPE: PRT
<213> ORGANISM: Artificial Sequence
<220> FEATURE:
<223> OTHER INFORMATION: Synthetic peptide

<400> SEQUENCE: 117

Leu Pro Gln His Ile Asp Ala Asp Leu Ile Leu Val Val Leu Ser Gly
1               5                   10                  15

Lys

<210> SEQ ID NO 118
<211> LENGTH: 19
<212> TYPE: PRT
<213> ORGANISM: Artificial Sequence
<220> FEATURE:
<223> OTHER INFORMATION: Synthetic peptide

<400> SEQUENCE: 118

Arg Gly Asp Thr Ile Lys Leu Pro Ala Gly Thr Thr Ser Tyr Leu Val
1               5                   10                  15

Asn Gln Asp

<210> SEQ ID NO 119
<211> LENGTH: 9
<212> TYPE: PRT
<213> ORGANISM: Artificial Sequence
<220> FEATURE:
<223> OTHER INFORMATION: Synthetic peptide

<400> SEQUENCE: 119

Ile Pro Val Asn Gly Pro Gly Lys Phe
1               5

<210> SEQ ID NO 120
<211> LENGTH: 9

```
<212> TYPE: PRT
<213> ORGANISM: Artificial Sequence
<220> FEATURE:
<223> OTHER INFORMATION: Synthetic peptide

<400> SEQUENCE: 120

Leu Pro Gln His Ile Asp Ala Asp Leu
1               5

<210> SEQ ID NO 121
<211> LENGTH: 10
<212> TYPE: PRT
<213> ORGANISM: Artificial Sequence
<220> FEATURE:
<223> OTHER INFORMATION: Synthetic peptide

<400> SEQUENCE: 121

Leu Val Ile Pro Val Asn Gly Pro Gly Lys
1               5                   10

<210> SEQ ID NO 122
<211> LENGTH: 10
<212> TYPE: PRT
<213> ORGANISM: Artificial Sequence
<220> FEATURE:
<223> OTHER INFORMATION: Synthetic peptide

<400> SEQUENCE: 122

Ile Phe Leu Pro Gln His Ile Asp Ala Asp
1               5                   10

<210> SEQ ID NO 123
<211> LENGTH: 8
<212> TYPE: PRT
<213> ORGANISM: Artificial Sequence
<220> FEATURE:
<223> OTHER INFORMATION: Synthetic peptide

<400> SEQUENCE: 123

Leu Pro Gln His Ile Asp Ala Asp
1               5

<210> SEQ ID NO 124
<211> LENGTH: 9
<212> TYPE: PRT
<213> ORGANISM: Artificial Sequence
<220> FEATURE:
<223> OTHER INFORMATION: Synthetic peptide

<400> SEQUENCE: 124

Val Ile Pro Val Asn Gly Pro Gly Lys
1               5

<210> SEQ ID NO 125
<211> LENGTH: 9
<212> TYPE: PRT
<213> ORGANISM: Artificial Sequence
<220> FEATURE:
<223> OTHER INFORMATION: Synthetic peptide

<400> SEQUENCE: 125

Ile Phe Leu Pro Gln His Ile Asp Ala
1               5

<210> SEQ ID NO 126
<211> LENGTH: 19
<212> TYPE: PRT
```

```
<213> ORGANISM: Artificial Sequence
<220> FEATURE:
<223> OTHER INFORMATION: Synthetic peptide

<400> SEQUENCE: 126

Thr Ile Lys Leu Pro Ala Gly Thr Thr Ser Tyr Leu Val Asn Gln Asp
1               5                   10                  15

Asp Glu Glu

<210> SEQ ID NO 127
<211> LENGTH: 21
<212> TYPE: PRT
<213> ORGANISM: Artificial Sequence
<220> FEATURE:
<223> OTHER INFORMATION: Synthetic peptide

<400> SEQUENCE: 127

His Gly Glu Trp Arg Pro Ser Tyr Glu Lys Glu Glu Asp Glu Glu Glu
1               5                   10                  15

Gly Gln Arg Glu Arg
            20

<210> SEQ ID NO 128
<211> LENGTH: 23
<212> TYPE: PRT
<213> ORGANISM: Artificial Sequence
<220> FEATURE:
<223> OTHER INFORMATION: Synthetic peptide

<400> SEQUENCE: 128

Glu Lys Arg His Gly Glu Trp Arg Pro Ser Tyr Glu Lys Glu Glu Asp
1               5                   10                  15

Glu Glu Glu Gly Gln Arg Glu
            20

<210> SEQ ID NO 129
<211> LENGTH: 19
<212> TYPE: PRT
<213> ORGANISM: Artificial Sequence
<220> FEATURE:
<223> OTHER INFORMATION: Synthetic peptide

<400> SEQUENCE: 129

Leu Pro Ala Gly Thr Thr Ser Tyr Leu Val Asn Gln Asp Asp Glu Glu
1               5                   10                  15

Asp Leu Arg

<210> SEQ ID NO 130
<211> LENGTH: 16
<212> TYPE: PRT
<213> ORGANISM: Artificial Sequence
<220> FEATURE:
<223> OTHER INFORMATION: Synthetic peptide

<400> SEQUENCE: 130

Pro Ser Tyr Glu Lys Glu Glu Asp Glu Glu Gly Gln Arg Glu Arg
1               5                   10                  15

<210> SEQ ID NO 131
<211> LENGTH: 12
<212> TYPE: PRT
<213> ORGANISM: Artificial Sequence
<220> FEATURE:
<223> OTHER INFORMATION: Synthetic peptide
```

```
<400> SEQUENCE: 131

Glu Lys Arg His Gly Glu Trp Arg Pro Ser Tyr Glu
1               5                   10

<210> SEQ ID NO 132
<211> LENGTH: 20
<212> TYPE: PRT
<213> ORGANISM: Artificial Sequence
<220> FEATURE:
<223> OTHER INFORMATION: Synthetic peptide

<400> SEQUENCE: 132

Thr Ile Lys Leu Pro Ala Gly Thr Thr Ser Tyr Leu Val Asn Gln Asp
1               5                   10                  15

Asp Glu Glu Asp
            20

<210> SEQ ID NO 133
<211> LENGTH: 17
<212> TYPE: PRT
<213> ORGANISM: Artificial Sequence
<220> FEATURE:
<223> OTHER INFORMATION: Synthetic peptide

<400> SEQUENCE: 133

His Gly Glu Trp Arg Pro Ser Tyr Glu Lys Gln Glu Asp Glu Glu Glu
1               5                   10                  15

Lys

<210> SEQ ID NO 134
<211> LENGTH: 14
<212> TYPE: PRT
<213> ORGANISM: Artificial Sequence
<220> FEATURE:
<223> OTHER INFORMATION: Synthetic peptide

<400> SEQUENCE: 134

Glu Trp Arg Pro Ser Tyr Glu Lys Glu Glu Asp Glu Glu Glu
1               5                   10

<210> SEQ ID NO 135
<211> LENGTH: 14
<212> TYPE: PRT
<213> ORGANISM: Artificial Sequence
<220> FEATURE:
<223> OTHER INFORMATION: Synthetic peptide

<400> SEQUENCE: 135

Pro Ser Tyr Glu Lys Glu Glu Asp Glu Glu Glu Gly Gln Arg
1               5                   10

<210> SEQ ID NO 136
<211> LENGTH: 11
<212> TYPE: PRT
<213> ORGANISM: Artificial Sequence
<220> FEATURE:
<223> OTHER INFORMATION: Synthetic peptide

<400> SEQUENCE: 136

Glu Lys Glu Glu Asp Glu Glu Glu Gly Gln Arg
1               5                   10

<210> SEQ ID NO 137
<211> LENGTH: 18
<212> TYPE: PRT
```

<213> ORGANISM: Artificial Sequence
<220> FEATURE:
<223> OTHER INFORMATION: Synthetic peptide

<400> SEQUENCE: 137

Glu Trp Arg Pro Ser Tyr Glu Lys Glu Glu Asp Glu Glu Gly Gln
1               5                   10                  15

Arg Glu

<210> SEQ ID NO 138
<211> LENGTH: 10
<212> TYPE: PRT
<213> ORGANISM: Artificial Sequence
<220> FEATURE:
<223> OTHER INFORMATION: Synthetic peptide

<400> SEQUENCE: 138

Lys Glu Glu Asp Glu Glu Glu Gly Gln Arg
1               5                   10

<210> SEQ ID NO 139
<211> LENGTH: 19
<212> TYPE: PRT
<213> ORGANISM: Artificial Sequence
<220> FEATURE:
<223> OTHER INFORMATION: Synthetic peptide

<400> SEQUENCE: 139

Val Gln Pro Gly Arg Glu Arg Trp Glu Arg Glu Asp Glu Glu Gln
1               5                   10                  15

Val Asp Glu

<210> SEQ ID NO 140
<211> LENGTH: 12
<212> TYPE: PRT
<213> ORGANISM: Artificial Sequence
<220> FEATURE:
<223> OTHER INFORMATION: Synthetic peptide

<400> SEQUENCE: 140

Asp Val Val Ile Ile Pro Ala Gly His Pro Val Ala
1               5                   10

<210> SEQ ID NO 141
<211> LENGTH: 14
<212> TYPE: PRT
<213> ORGANISM: Artificial Sequence
<220> FEATURE:
<223> OTHER INFORMATION: Synthetic peptide

<400> SEQUENCE: 141

His Gly Glu Trp Arg Pro Ser Tyr Glu Lys Gln Glu Asp Glu
1               5                   10

<210> SEQ ID NO 142
<211> LENGTH: 9
<212> TYPE: PRT
<213> ORGANISM: Artificial Sequence
<220> FEATURE:
<223> OTHER INFORMATION: Synthetic peptide

<400> SEQUENCE: 142

Glu Glu Asp Glu Glu Glu Gly Gln Arg
1               5

<210> SEQ ID NO 143
<211> LENGTH: 19
<212> TYPE: PRT
<213> ORGANISM: Artificial Sequence
<220> FEATURE:
<223> OTHER INFORMATION: Synthetic peptide

<400> SEQUENCE: 143

His Gly Glu Trp Arg Pro Ser Tyr Glu Lys Glu Glu Asp Glu Glu
1               5                   10                  15

Gly Gln Arg

<210> SEQ ID NO 144
<211> LENGTH: 14
<212> TYPE: PRT
<213> ORGANISM: Artificial Sequence
<220> FEATURE:
<223> OTHER INFORMATION: Synthetic peptide

<400> SEQUENCE: 144

Glu Glu Trp Arg Gly Ser Gln Arg Arg Glu Asp Pro Glu Glu
1               5                   10

<210> SEQ ID NO 145
<211> LENGTH: 23
<212> TYPE: PRT
<213> ORGANISM: Artificial Sequence
<220> FEATURE:
<223> OTHER INFORMATION: Synthetic peptide

<400> SEQUENCE: 145

Arg Glu Glu Asp Glu Glu Gln Val Asp Glu Trp Arg Gly Ser Gln
1               5                   10                  15

Arg Arg Glu Asp Pro Glu Glu
            20

<210> SEQ ID NO 146
<211> LENGTH: 9
<212> TYPE: PRT
<213> ORGANISM: Artificial Sequence
<220> FEATURE:
<223> OTHER INFORMATION: Synthetic peptide

<400> SEQUENCE: 146

Arg His Gly Glu Trp Arg Pro Ser Tyr
1               5

<210> SEQ ID NO 147
<211> LENGTH: 15
<212> TYPE: PRT
<213> ORGANISM: Artificial Sequence
<220> FEATURE:
<223> OTHER INFORMATION: Synthetic peptide

<400> SEQUENCE: 147

His Gly Glu Trp Arg Pro Ser Tyr Glu Lys Gln Glu Asp Glu Glu
1               5                   10                  15

<210> SEQ ID NO 148
<211> LENGTH: 11
<212> TYPE: PRT
<213> ORGANISM: Artificial Sequence
<220> FEATURE:
<223> OTHER INFORMATION: Synthetic peptide

<400> SEQUENCE: 148

```
Val Val Ile Ile Pro Ala Gly His Pro Val Ala
1               5                   10
```

<210> SEQ ID NO 149
<211> LENGTH: 9
<212> TYPE: PRT
<213> ORGANISM: Artificial Sequence
<220> FEATURE:
<223> OTHER INFORMATION: Synthetic peptide

<400> SEQUENCE: 149

```
His Gly Glu Trp Arg Pro Ser Tyr Glu
1               5
```

<210> SEQ ID NO 150
<211> LENGTH: 12
<212> TYPE: PRT
<213> ORGANISM: Artificial Sequence
<220> FEATURE:
<223> OTHER INFORMATION: Synthetic peptide

<400> SEQUENCE: 150

```
Lys Glu Glu Asp Glu Glu Gly Gln Arg Glu Arg
1               5                   10
```

<210> SEQ ID NO 151
<211> LENGTH: 13
<212> TYPE: PRT
<213> ORGANISM: Artificial Sequence
<220> FEATURE:
<223> OTHER INFORMATION: Synthetic peptide

<400> SEQUENCE: 151

```
Val Val Ile Ile Pro Ala Gly His Pro Val Ala Ile Thr
1               5                   10
```

<210> SEQ ID NO 152
<211> LENGTH: 17
<212> TYPE: PRT
<213> ORGANISM: Artificial Sequence
<220> FEATURE:
<223> OTHER INFORMATION: Synthetic peptide

<400> SEQUENCE: 152

```
Glu Lys Arg His Gly Glu Trp Arg Pro Ser Tyr Glu Lys Glu Glu Asp
1               5                   10                  15

Glu
```

<210> SEQ ID NO 153
<211> LENGTH: 17
<212> TYPE: PRT
<213> ORGANISM: Artificial Sequence
<220> FEATURE:
<223> OTHER INFORMATION: Synthetic peptide

<400> SEQUENCE: 153

```
Gln Val Asp Glu Glu Trp Arg Gly Ser Gln Arg Arg Glu Asp Pro Glu
1               5                   10                  15

Glu
```

<210> SEQ ID NO 154
<211> LENGTH: 24
<212> TYPE: PRT
<213> ORGANISM: Artificial Sequence
<220> FEATURE:
<223> OTHER INFORMATION: Synthetic peptide

```
<400> SEQUENCE: 154

Gly Asp Thr Ile Lys Leu Pro Ala Gly Thr Thr Ser Tyr Leu Val Asn
1               5                   10                  15

Gln Asp Asp Glu Glu Asp Leu Arg
            20

<210> SEQ ID NO 155
<211> LENGTH: 11
<212> TYPE: PRT
<213> ORGANISM: Artificial Sequence
<220> FEATURE:
<223> OTHER INFORMATION: Synthetic peptide

<400> SEQUENCE: 155

Gly Ser Glu Pro Arg Val Pro Ala Gln Arg Glu
1               5                   10

<210> SEQ ID NO 156
<211> LENGTH: 15
<212> TYPE: PRT
<213> ORGANISM: Artificial Sequence
<220> FEATURE:
<223> OTHER INFORMATION: Synthetic peptide

<400> SEQUENCE: 156

Glu Glu Lys Arg His Gly Glu Trp Arg Pro Ser Tyr Glu Lys Glu
1               5                   10                  15

<210> SEQ ID NO 157
<211> LENGTH: 13
<212> TYPE: PRT
<213> ORGANISM: Artificial Sequence
<220> FEATURE:
<223> OTHER INFORMATION: Synthetic peptide

<400> SEQUENCE: 157

Glu Trp Arg Pro Ser Tyr Glu Lys Glu Glu Asp Glu Glu
1               5                   10

<210> SEQ ID NO 158
<211> LENGTH: 15
<212> TYPE: PRT
<213> ORGANISM: Artificial Sequence
<220> FEATURE:
<223> OTHER INFORMATION: Synthetic peptide

<400> SEQUENCE: 158

Asn Tyr Asp Glu Gly Ser Glu Pro Arg Val Pro Ala Gln Arg Glu
1               5                   10                  15

<210> SEQ ID NO 159
<211> LENGTH: 12
<212> TYPE: PRT
<213> ORGANISM: Artificial Sequence
<220> FEATURE:
<223> OTHER INFORMATION: Synthetic peptide

<400> SEQUENCE: 159

Val Ile Ile Pro Ala Gly His Pro Val Ala Ile Thr
1               5                   10

<210> SEQ ID NO 160
<211> LENGTH: 11
<212> TYPE: PRT
<213> ORGANISM: Artificial Sequence
```

```
<220> FEATURE:
<223> OTHER INFORMATION: Synthetic peptide

<400> SEQUENCE: 160

Arg His Gly Glu Trp Arg Pro Ser Tyr Glu Lys
1               5                   10

<210> SEQ ID NO 161
<211> LENGTH: 9
<212> TYPE: PRT
<213> ORGANISM: Artificial Sequence
<220> FEATURE:
<223> OTHER INFORMATION: Synthetic peptide

<400> SEQUENCE: 161

Asn Tyr Asp Glu Gly Ser Glu Pro Arg
1               5

<210> SEQ ID NO 162
<211> LENGTH: 12
<212> TYPE: PRT
<213> ORGANISM: Artificial Sequence
<220> FEATURE:
<223> OTHER INFORMATION: Synthetic peptide

<400> SEQUENCE: 162

Trp Arg Pro Ser Tyr Glu Lys Glu Glu Asp Glu Glu
1               5                   10

<210> SEQ ID NO 163
<211> LENGTH: 13
<212> TYPE: PRT
<213> ORGANISM: Artificial Sequence
<220> FEATURE:
<223> OTHER INFORMATION: Synthetic peptide

<400> SEQUENCE: 163

Trp Arg Pro Ser Tyr Glu Lys Gln Glu Asp Glu Glu Glu
1               5                   10

<210> SEQ ID NO 164
<211> LENGTH: 19
<212> TYPE: PRT
<213> ORGANISM: Artificial Sequence
<220> FEATURE:
<223> OTHER INFORMATION: Synthetic peptide

<400> SEQUENCE: 164

Glu Lys Arg His Gly Glu Trp Arg Pro Ser Tyr Glu Lys Gln Glu Asp
1               5                   10                  15

Glu Glu Glu

<210> SEQ ID NO 165
<211> LENGTH: 14
<212> TYPE: PRT
<213> ORGANISM: Artificial Sequence
<220> FEATURE:
<223> OTHER INFORMATION: Synthetic peptide

<400> SEQUENCE: 165

Val Val Ile Ile Pro Ala Gly His Pro Val Ala Ile Thr Ala
1               5                   10

<210> SEQ ID NO 166
<211> LENGTH: 11
<212> TYPE: PRT
```

```
<213> ORGANISM: Artificial Sequence
<220> FEATURE:
<223> OTHER INFORMATION: Synthetic peptide

<400> SEQUENCE: 166

Lys Arg His Gly Glu Trp Arg Pro Ser Tyr Glu
1               5                   10

<210> SEQ ID NO 167
<211> LENGTH: 16
<212> TYPE: PRT
<213> ORGANISM: Artificial Sequence
<220> FEATURE:
<223> OTHER INFORMATION: Synthetic peptide

<400> SEQUENCE: 167

Gly Ser Asp Asp Asn Val Ile Ser Gln Ile Glu Asn Pro Val Lys Glu
1               5                   10                  15

<210> SEQ ID NO 168
<211> LENGTH: 10
<212> TYPE: PRT
<213> ORGANISM: Artificial Sequence
<220> FEATURE:
<223> OTHER INFORMATION: Synthetic peptide

<400> SEQUENCE: 168

Val Val Ile Ile Pro Ala Gly His Pro Val
1               5                   10

<210> SEQ ID NO 169
<211> LENGTH: 8
<212> TYPE: PRT
<213> ORGANISM: Artificial Sequence
<220> FEATURE:
<223> OTHER INFORMATION: Synthetic peptide

<400> SEQUENCE: 169

His Gly Glu Trp Arg Pro Ser Tyr
1               5

<210> SEQ ID NO 170
<211> LENGTH: 15
<212> TYPE: PRT
<213> ORGANISM: Artificial Sequence
<220> FEATURE:
<223> OTHER INFORMATION: Synthetic peptide

<400> SEQUENCE: 170

Arg Pro Ser Tyr Glu Lys Glu Glu Asp Glu Glu Glu Gly Gln Arg
1               5                   10                  15

<210> SEQ ID NO 171
<211> LENGTH: 10
<212> TYPE: PRT
<213> ORGANISM: Artificial Sequence
<220> FEATURE:
<223> OTHER INFORMATION: Synthetic peptide

<400> SEQUENCE: 171

His Gly Glu Trp Arg Pro Ser Tyr Glu Lys
1               5                   10

<210> SEQ ID NO 172
<211> LENGTH: 14
<212> TYPE: PRT
<213> ORGANISM: Artificial Sequence
```

```
<220> FEATURE:
<223> OTHER INFORMATION: Synthetic peptide

<400> SEQUENCE: 172

Lys Arg His Gly Glu Trp Arg Pro Ser Tyr Glu Lys Glu Glu
1               5                   10

<210> SEQ ID NO 173
<211> LENGTH: 15
<212> TYPE: PRT
<213> ORGANISM: Artificial Sequence
<220> FEATURE:
<223> OTHER INFORMATION: Synthetic peptide

<400> SEQUENCE: 173

Val Val Ile Ile Pro Ala Gly His Pro Val Ala Ile Thr Ala Ser
1               5                   10                  15

<210> SEQ ID NO 174
<211> LENGTH: 23
<212> TYPE: PRT
<213> ORGANISM: Artificial Sequence
<220> FEATURE:
<223> OTHER INFORMATION: Synthetic peptide

<400> SEQUENCE: 174

Arg Gly Asp Thr Ile Lys Leu Pro Ala Gly Thr Thr Ser Tyr Leu Val
1               5                   10                  15

Asn Gln Asp Asp Glu Glu Asp
            20

<210> SEQ ID NO 175
<211> LENGTH: 18
<212> TYPE: PRT
<213> ORGANISM: Artificial Sequence
<220> FEATURE:
<223> OTHER INFORMATION: Synthetic peptide

<400> SEQUENCE: 175

Lys Arg His Gly Glu Trp Arg Pro Ser Tyr Glu Lys Gln Glu Asp Glu
1               5                   10                  15

Glu Glu

<210> SEQ ID NO 176
<211> LENGTH: 20
<212> TYPE: PRT
<213> ORGANISM: Artificial Sequence
<220> FEATURE:
<223> OTHER INFORMATION: Synthetic peptide

<400> SEQUENCE: 176

Asp Glu Glu Gln Val Asp Glu Glu Trp Arg Gly Ser Gln Arg Arg Glu
1               5                   10                  15

Asp Pro Glu Glu
            20

<210> SEQ ID NO 177
<211> LENGTH: 10
<212> TYPE: PRT
<213> ORGANISM: Artificial Sequence
<220> FEATURE:
<223> OTHER INFORMATION: Synthetic peptide

<400> SEQUENCE: 177

Arg His Gly Glu Trp Arg Pro Ser Tyr Glu
```

```
                           1               5                   10
```

<210> SEQ ID NO 178
<211> LENGTH: 11
<212> TYPE: PRT
<213> ORGANISM: Artificial Sequence
<220> FEATURE:
<223> OTHER INFORMATION: Synthetic peptide

<400> SEQUENCE: 178

```
His Gly Glu Trp Arg Pro Ser Tyr Glu Lys Glu
1               5                   10
```

<210> SEQ ID NO 179
<211> LENGTH: 18
<212> TYPE: PRT
<213> ORGANISM: Artificial Sequence
<220> FEATURE:
<223> OTHER INFORMATION: Synthetic peptide

<400> SEQUENCE: 179

```
Lys Arg His Gly Glu Trp Arg Pro Ser Tyr Glu Lys Glu Glu Asp Glu
1               5                   10                  15

Glu Glu
```

<210> SEQ ID NO 180
<211> LENGTH: 19
<212> TYPE: PRT
<213> ORGANISM: Artificial Sequence
<220> FEATURE:
<223> OTHER INFORMATION: Synthetic peptide

<400> SEQUENCE: 180

```
Glu Lys Arg His Gly Glu Trp Arg Pro Ser Tyr Glu Lys Glu Glu Asp
1               5                   10                  15

Glu Glu Glu
```

<210> SEQ ID NO 181
<211> LENGTH: 25
<212> TYPE: PRT
<213> ORGANISM: Artificial Sequence
<220> FEATURE:
<223> OTHER INFORMATION: Synthetic peptide

<400> SEQUENCE: 181

```
Thr Ile Lys Leu Pro Ala Gly Thr Thr Ser Tyr Leu Val Asn Gln Asp
1               5                   10                  15

Asp Glu Glu Asp Leu Arg Leu Val Asp
            20                  25
```

<210> SEQ ID NO 182
<211> LENGTH: 17
<212> TYPE: PRT
<213> ORGANISM: Artificial Sequence
<220> FEATURE:
<223> OTHER INFORMATION: Synthetic peptide

<400> SEQUENCE: 182

```
Trp Arg Pro Ser Tyr Glu Lys Glu Glu Asp Glu Glu Glu Gly Gln Arg
1               5                   10                  15

Glu
```

<210> SEQ ID NO 183
<211> LENGTH: 17

```
<212> TYPE: PRT
<213> ORGANISM: Artificial Sequence
<220> FEATURE:
<223> OTHER INFORMATION: Synthetic peptide

<400> SEQUENCE: 183

Lys Arg His Gly Glu Trp Arg Pro Ser Tyr Glu Lys Glu Glu Asp Glu
1               5                   10                  15

Glu

<210> SEQ ID NO 184
<211> LENGTH: 12
<212> TYPE: PRT
<213> ORGANISM: Artificial Sequence
<220> FEATURE:
<223> OTHER INFORMATION: Synthetic peptide

<400> SEQUENCE: 184

Val Val Ile Ile Pro Ala Gly His Pro Val Ala Ile
1               5                   10

<210> SEQ ID NO 185
<211> LENGTH: 13
<212> TYPE: PRT
<213> ORGANISM: Artificial Sequence
<220> FEATURE:
<223> OTHER INFORMATION: Synthetic peptide

<400> SEQUENCE: 185

Glu Trp Arg Gly Ser Gln Arg Arg Glu Asp Pro Glu Glu
1               5                   10

<210> SEQ ID NO 186
<211> LENGTH: 19
<212> TYPE: PRT
<213> ORGANISM: Artificial Sequence
<220> FEATURE:
<223> OTHER INFORMATION: Synthetic peptide

<400> SEQUENCE: 186

His Gly Glu Trp Arg Pro Ser Tyr Glu Lys Gln Glu Asp Glu Glu Glu
1               5                   10                  15

Lys Gln Lys

<210> SEQ ID NO 187
<211> LENGTH: 17
<212> TYPE: PRT
<213> ORGANISM: Artificial Sequence
<220> FEATURE:
<223> OTHER INFORMATION: Synthetic peptide

<400> SEQUENCE: 187

Ser Gly Ser Asp Asp Asn Val Ile Ser Gln Ile Glu Asn Pro Val Lys
1               5                   10                  15

Glu

<210> SEQ ID NO 188
<211> LENGTH: 17
<212> TYPE: PRT
<213> ORGANISM: Artificial Sequence
<220> FEATURE:
<223> OTHER INFORMATION: Synthetic peptide

<400> SEQUENCE: 188

Arg Pro Ser Tyr Glu Lys Glu Glu Asp Glu Glu Glu Gly Gln Arg Glu
```

```
1               5                   10                  15
Arg

<210> SEQ ID NO 189
<211> LENGTH: 13
<212> TYPE: PRT
<213> ORGANISM: Artificial Sequence
<220> FEATURE:
<223> OTHER INFORMATION: Synthetic peptide

<400> SEQUENCE: 189

Glu Lys Glu Glu Asp Glu Glu Glu Gly Gln Arg Glu Arg
1               5                   10

<210> SEQ ID NO 190
<211> LENGTH: 11
<212> TYPE: PRT
<213> ORGANISM: Artificial Sequence
<220> FEATURE:
<223> OTHER INFORMATION: Synthetic peptide

<400> SEQUENCE: 190

His Gly Glu Trp Arg Pro Ser Tyr Glu Lys Gln
1               5                   10

<210> SEQ ID NO 191
<211> LENGTH: 13
<212> TYPE: PRT
<213> ORGANISM: Artificial Sequence
<220> FEATURE:
<223> OTHER INFORMATION: Synthetic peptide

<400> SEQUENCE: 191

Trp Arg Pro Ser Tyr Glu Lys Glu Glu Asp Glu Glu Glu
1               5                   10

<210> SEQ ID NO 192
<211> LENGTH: 13
<212> TYPE: PRT
<213> ORGANISM: Artificial Sequence
<220> FEATURE:
<223> OTHER INFORMATION: Synthetic peptide

<400> SEQUENCE: 192

Leu Ala Lys Asn Lys Asn Gln Tyr Leu Arg Gly Phe Ser
1               5                   10

<210> SEQ ID NO 193
<211> LENGTH: 10
<212> TYPE: PRT
<213> ORGANISM: Artificial Sequence
<220> FEATURE:
<223> OTHER INFORMATION: Synthetic peptide

<400> SEQUENCE: 193

Asn Lys Asn Gln Tyr Leu Arg Gly Phe Ser
1               5                   10

<210> SEQ ID NO 194
<211> LENGTH: 10
<212> TYPE: PRT
<213> ORGANISM: Artificial Sequence
<220> FEATURE:
<223> OTHER INFORMATION: Synthetic peptide

<400> SEQUENCE: 194
```

```
Leu Arg Gly Phe Ser Lys Asn Ile Leu Glu
 1               5                  10
```

<210> SEQ ID NO 195
<211> LENGTH: 15
<212> TYPE: PRT
<213> ORGANISM: Artificial Sequence
<220> FEATURE:
<223> OTHER INFORMATION: Synthetic peptide

<400> SEQUENCE: 195

```
Leu Ala Lys Asn Lys Asn Gln Tyr Leu Arg Gly Phe Ser Lys Asn
 1               5                  10                  15
```

<210> SEQ ID NO 196
<211> LENGTH: 11
<212> TYPE: PRT
<213> ORGANISM: Artificial Sequence
<220> FEATURE:
<223> OTHER INFORMATION: Synthetic peptide

<400> SEQUENCE: 196

```
Thr Val Leu Ser Pro Asn Asp Arg Asn Ser Tyr
 1               5                  10
```

<210> SEQ ID NO 197
<211> LENGTH: 12
<212> TYPE: PRT
<213> ORGANISM: Artificial Sequence
<220> FEATURE:
<223> OTHER INFORMATION: Synthetic peptide

<400> SEQUENCE: 197

```
Gln Tyr Leu Arg Gly Phe Ser Lys Asn Ile Leu Glu
 1               5                  10
```

<210> SEQ ID NO 198
<211> LENGTH: 19
<212> TYPE: PRT
<213> ORGANISM: Artificial Sequence
<220> FEATURE:
<223> OTHER INFORMATION: Synthetic peptide

<400> SEQUENCE: 198

```
Gly Lys Ala Ile Leu Thr Val Leu Ser Pro Asn Asp Arg Asn Ser Tyr
 1               5                  10                  15

Asn Leu Glu
```

<210> SEQ ID NO 199
<211> LENGTH: 9
<212> TYPE: PRT
<213> ORGANISM: Artificial Sequence
<220> FEATURE:
<223> OTHER INFORMATION: Synthetic peptide

<400> SEQUENCE: 199

```
Arg Gly Phe Ser Lys Asn Ile Leu Glu
 1               5
```

<210> SEQ ID NO 200
<211> LENGTH: 15
<212> TYPE: PRT
<213> ORGANISM: Artificial Sequence
<220> FEATURE:
<223> OTHER INFORMATION: Synthetic peptide

<400> SEQUENCE: 200

```
Asn Lys Asn Gln Tyr Leu Arg Gly Phe Ser Lys Asn Ile Leu Glu
1               5                   10                  15

<210> SEQ ID NO 201
<211> LENGTH: 15
<212> TYPE: PRT
<213> ORGANISM: Artificial Sequence
<220> FEATURE:
<223> OTHER INFORMATION: Synthetic peptide

<400> SEQUENCE: 201

Ala Ser Ser Asn Leu Asn Leu Leu Gly Phe Gly Ile Asn Ala Glu
1               5                   10                  15

<210> SEQ ID NO 202
<211> LENGTH: 10
<212> TYPE: PRT
<213> ORGANISM: Artificial Sequence
<220> FEATURE:
<223> OTHER INFORMATION: Synthetic peptide

<400> SEQUENCE: 202

Ala Ser Ser Asn Leu Asn Leu Leu Gly Phe
1               5                   10

<210> SEQ ID NO 203
<211> LENGTH: 14
<212> TYPE: PRT
<213> ORGANISM: Artificial Sequence
<220> FEATURE:
<223> OTHER INFORMATION: Synthetic peptide

<400> SEQUENCE: 203

Leu Ala Lys Asn Lys Asn Gln Tyr Leu Arg Gly Phe Ser Lys
1               5                   10

<210> SEQ ID NO 204
<211> LENGTH: 22
<212> TYPE: PRT
<213> ORGANISM: Artificial Sequence
<220> FEATURE:
<223> OTHER INFORMATION: Synthetic peptide

<400> SEQUENCE: 204

Arg Gly Asp Thr Ile Lys Leu Pro Ala Gly Thr Thr Ser Tyr Leu Val
1               5                   10                  15

Asn Gln Asp Asp Glu Glu
            20

<210> SEQ ID NO 205
<211> LENGTH: 24
<212> TYPE: PRT
<213> ORGANISM: Artificial Sequence
<220> FEATURE:
<223> OTHER INFORMATION: Synthetic peptide

<400> SEQUENCE: 205

Ala Arg Leu Ser Pro Gly Asp Val Val Ile Ile Pro Ala Gly His Pro
1               5                   10                  15

Val Ala Ile Thr Ala Ser Ser Asn
            20

<210> SEQ ID NO 206
<211> LENGTH: 12
<212> TYPE: PRT
```

```
<213> ORGANISM: Artificial Sequence
<220> FEATURE:
<223> OTHER INFORMATION: Synthetic peptide

<400> SEQUENCE: 206

Val Gln Arg Tyr Glu Ala Arg Leu Ser Pro Gly Asp
1               5                   10

<210> SEQ ID NO 207
<211> LENGTH: 20
<212> TYPE: PRT
<213> ORGANISM: Artificial Sequence
<220> FEATURE:
<223> OTHER INFORMATION: Synthetic peptide

<400> SEQUENCE: 207

Ala Arg Leu Ser Pro Gly Asp Val Val Ile Ile Pro Ala Gly His Pro
1               5                   10                  15

Val Ala Ile Thr
            20

<210> SEQ ID NO 208
<211> LENGTH: 21
<212> TYPE: PRT
<213> ORGANISM: Artificial Sequence
<220> FEATURE:
<223> OTHER INFORMATION: Synthetic peptide

<400> SEQUENCE: 208

Arg Gly Asp Thr Ile Lys Leu Pro Ala Gly Thr Thr Ser Tyr Leu Val
1               5                   10                  15

Asn Gln Asp Asp Glu
            20

<210> SEQ ID NO 209
<211> LENGTH: 18
<212> TYPE: PRT
<213> ORGANISM: Artificial Sequence
<220> FEATURE:
<223> OTHER INFORMATION: Synthetic peptide

<400> SEQUENCE: 209

Ala Arg Leu Ser Pro Gly Asp Val Val Ile Ile Pro Ala Gly His Pro
1               5                   10                  15

Val Ala

<210> SEQ ID NO 210
<211> LENGTH: 20
<212> TYPE: PRT
<213> ORGANISM: Artificial Sequence
<220> FEATURE:
<223> OTHER INFORMATION: Synthetic peptide

<400> SEQUENCE: 210

Gly Ala Leu Met Leu Pro His Tyr Asn Ser Arg Ala Ile Val Val Leu
1               5                   10                  15

Leu Val Asn Glu
            20

<210> SEQ ID NO 211
<211> LENGTH: 23
<212> TYPE: PRT
<213> ORGANISM: Artificial Sequence
<220> FEATURE:
<223> OTHER INFORMATION: Synthetic peptide
```

-continued

<400> SEQUENCE: 211

Ala Arg Leu Ser Pro Gly Asp Val Val Ile Ile Pro Ala Gly His Pro
1               5                   10                  15

Val Ala Ile Thr Ala Ser Ser
            20

<210> SEQ ID NO 212
<211> LENGTH: 37
<212> TYPE: PRT
<213> ORGANISM: Artificial Sequence
<220> FEATURE:
<223> OTHER INFORMATION: Synthetic peptide

<400> SEQUENCE: 212

Leu Ser Pro Gly Asp Val Val Ile Ile Pro Ala Gly His Pro Val Ala
1               5                   10                  15

Ile Thr Ala Ser Ser Asn Leu Asn Leu Leu Gly Phe Gly Ile Asn Ala
            20                  25                  30

Glu Asn Asn Glu Arg
        35

<210> SEQ ID NO 213
<211> LENGTH: 22
<212> TYPE: PRT
<213> ORGANISM: Artificial Sequence
<220> FEATURE:
<223> OTHER INFORMATION: Synthetic peptide

<400> SEQUENCE: 213

Ala Arg Leu Ser Pro Gly Asp Val Val Ile Ile Pro Ala Gly His Pro
1               5                   10                  15

Val Ala Ile Thr Ala Ser
            20

<210> SEQ ID NO 214
<211> LENGTH: 23
<212> TYPE: PRT
<213> ORGANISM: Artificial Sequence
<220> FEATURE:
<223> OTHER INFORMATION: Synthetic peptide

<400> SEQUENCE: 214

Leu Ser Pro Gly Asp Val Val Ile Ile Pro Ala Gly His Pro Val Ala
1               5                   10                  15

Ile Thr Ala Ser Ser Asn Leu
            20

<210> SEQ ID NO 215
<211> LENGTH: 21
<212> TYPE: PRT
<213> ORGANISM: Artificial Sequence
<220> FEATURE:
<223> OTHER INFORMATION: Synthetic peptide

<400> SEQUENCE: 215

Ala Arg Leu Ser Pro Gly Asp Val Val Ile Ile Pro Ala Gly His Pro
1               5                   10                  15

Val Ala Ile Thr Ala
            20

<210> SEQ ID NO 216
<211> LENGTH: 28

```
<212> TYPE: PRT
<213> ORGANISM: Artificial Sequence
<220> FEATURE:
<223> OTHER INFORMATION: Synthetic peptide

<400> SEQUENCE: 216

Asn Trp Glu Asn Val Leu Leu Gly Leu Gly Val Ala Gly Ser Ala Pro
1               5                   10                  15

Gly Ile Glu Gly Asp Glu Ile Ala Pro Leu Ala Lys
            20                  25

<210> SEQ ID NO 217
<211> LENGTH: 17
<212> TYPE: PRT
<213> ORGANISM: Artificial Sequence
<220> FEATURE:
<223> OTHER INFORMATION: Synthetic peptide

<400> SEQUENCE: 217

Tyr Asp Gln Tyr Lys Asp Ala Trp Asp Thr Ser Val Val Ala Glu Ile
1               5                   10                  15

Lys

<210> SEQ ID NO 218
<211> LENGTH: 16
<212> TYPE: PRT
<213> ORGANISM: Artificial Sequence
<220> FEATURE:
<223> OTHER INFORMATION: Synthetic peptide

<400> SEQUENCE: 218

Ser Ser Phe Asp Phe Ile Asp Gly Tyr Asp Thr Pro Val Glu Gly Arg
1               5                   10                  15

<210> SEQ ID NO 219
<211> LENGTH: 13
<212> TYPE: PRT
<213> ORGANISM: Artificial Sequence
<220> FEATURE:
<223> OTHER INFORMATION: Synthetic peptide

<400> SEQUENCE: 219

Gly Pro Asp Thr Gly Val Asp Tyr Lys Asp Asn Gln Met
1               5                   10

<210> SEQ ID NO 220
<211> LENGTH: 11
<212> TYPE: PRT
<213> ORGANISM: Artificial Sequence
<220> FEATURE:
<223> OTHER INFORMATION: Synthetic peptide

<400> SEQUENCE: 220

Ile Leu Asn Leu Asn Asn Asn Pro Tyr Phe Lys
1               5                   10

<210> SEQ ID NO 221
<211> LENGTH: 9
<212> TYPE: PRT
<213> ORGANISM: Artificial Sequence
<220> FEATURE:
<223> OTHER INFORMATION: Synthetic peptide

<400> SEQUENCE: 221

Val Val Gly Thr Pro Ala Tyr Glu Glu
1               5
```

<210> SEQ ID NO 222
<211> LENGTH: 11
<212> TYPE: PRT
<213> ORGANISM: Artificial Sequence
<220> FEATURE:
<223> OTHER INFORMATION: Synthetic peptide

<400> SEQUENCE: 222

Ile Asp Gly Tyr Asp Thr Pro Val Glu Gly Arg
1               5                   10

<210> SEQ ID NO 223
<211> LENGTH: 8
<212> TYPE: PRT
<213> ORGANISM: Artificial Sequence
<220> FEATURE:
<223> OTHER INFORMATION: Synthetic peptide

<400> SEQUENCE: 223

Val Val Gly Thr Pro Ala Tyr Glu
1               5

<210> SEQ ID NO 224
<211> LENGTH: 11
<212> TYPE: PRT
<213> ORGANISM: Artificial Sequence
<220> FEATURE:
<223> OTHER INFORMATION: Synthetic peptide

<400> SEQUENCE: 224

Ile Tyr Gly Pro Asp Thr Gly Val Asp Tyr Lys
1               5                   10

<210> SEQ ID NO 225
<211> LENGTH: 12
<212> TYPE: PRT
<213> ORGANISM: Artificial Sequence
<220> FEATURE:
<223> OTHER INFORMATION: Synthetic peptide

<400> SEQUENCE: 225

Val Ala Gly Ser Ala Pro Gly Ile Glu Gly Asp Glu
1               5                   10

<210> SEQ ID NO 226
<211> LENGTH: 16
<212> TYPE: PRT
<213> ORGANISM: Artificial Sequence
<220> FEATURE:
<223> OTHER INFORMATION: Synthetic peptide

<400> SEQUENCE: 226

Ile Tyr Gly Pro Asp Thr Gly Val Asp Tyr Lys Asp Asn Gln Met Arg
1               5                   10                  15

<210> SEQ ID NO 227
<211> LENGTH: 12
<212> TYPE: PRT
<213> ORGANISM: Artificial Sequence
<220> FEATURE:
<223> OTHER INFORMATION: Synthetic peptide

<400> SEQUENCE: 227

Val Val Gly Thr Pro Ala Tyr Glu Glu Met Val Arg
1               5                   10

```
<210> SEQ ID NO 228
<211> LENGTH: 13
<212> TYPE: PRT
<213> ORGANISM: Artificial Sequence
<220> FEATURE:
<223> OTHER INFORMATION: Synthetic peptide

<400> SEQUENCE: 228

Asp Phe Ile Asp Gly Tyr Asp Thr Pro Val Glu Gly Arg
1               5                   10

<210> SEQ ID NO 229
<211> LENGTH: 22
<212> TYPE: PRT
<213> ORGANISM: Artificial Sequence
<220> FEATURE:
<223> OTHER INFORMATION: Synthetic peptide

<400> SEQUENCE: 229

Leu Gly Leu Gly Val Ala Gly Ser Ala Pro Gly Ile Glu Gly Asp Glu
1               5                   10                  15

Ile Ala Pro Leu Ala Lys
            20

<210> SEQ ID NO 230
<211> LENGTH: 21
<212> TYPE: PRT
<213> ORGANISM: Artificial Sequence
<220> FEATURE:
<223> OTHER INFORMATION: Synthetic peptide

<400> SEQUENCE: 230

Phe Asn Ala Pro Leu Ala His Leu Ile Met Ala Gly Ala Asp Val Leu
1               5                   10                  15

Ala Val Pro Ser Arg
            20

<210> SEQ ID NO 231
<211> LENGTH: 16
<212> TYPE: PRT
<213> ORGANISM: Artificial Sequence
<220> FEATURE:
<223> OTHER INFORMATION: Synthetic peptide

<400> SEQUENCE: 231

Leu Gly Leu Gly Val Ala Gly Ser Ala Pro Gly Ile Glu Gly Asp Glu
1               5                   10                  15

<210> SEQ ID NO 232
<211> LENGTH: 20
<212> TYPE: PRT
<213> ORGANISM: Artificial Sequence
<220> FEATURE:
<223> OTHER INFORMATION: Synthetic peptide

<400> SEQUENCE: 232

Leu Gly Leu Gly Val Ala Gly Ser Ala Pro Gly Ile Glu Gly Asp Glu
1               5                   10                  15

Ile Ala Pro Leu
            20

<210> SEQ ID NO 233
<211> LENGTH: 18
<212> TYPE: PRT
<213> ORGANISM: Artificial Sequence
```

```
<220> FEATURE:
<223> OTHER INFORMATION: Synthetic peptide

<400> SEQUENCE: 233

Val Leu Thr Val Ser Pro Tyr Tyr Ala Glu Glu Leu Ile Ser Gly Ile
1               5                   10                  15
Ala Arg

<210> SEQ ID NO 234
<211> LENGTH: 13
<212> TYPE: PRT
<213> ORGANISM: Artificial Sequence
<220> FEATURE:
<223> OTHER INFORMATION: Synthetic peptide

<400> SEQUENCE: 234

Glu Ala Leu Gln Ala Glu Ala Gly Leu Pro Val Asp Arg
1               5                   10

<210> SEQ ID NO 235
<211> LENGTH: 15
<212> TYPE: PRT
<213> ORGANISM: Artificial Sequence
<220> FEATURE:
<223> OTHER INFORMATION: Synthetic peptide

<400> SEQUENCE: 235

Leu Gly Leu Gly Val Ala Gly Ser Ala Pro Gly Ile Glu Gly Asp
1               5                   10                  15

<210> SEQ ID NO 236
<211> LENGTH: 13
<212> TYPE: PRT
<213> ORGANISM: Artificial Sequence
<220> FEATURE:
<223> OTHER INFORMATION: Synthetic peptide

<400> SEQUENCE: 236

Ile Met Ala Gly Ala Asp Val Leu Ala Val Pro Ser Arg
1               5                   10

<210> SEQ ID NO 237
<211> LENGTH: 15
<212> TYPE: PRT
<213> ORGANISM: Artificial Sequence
<220> FEATURE:
<223> OTHER INFORMATION: Synthetic peptide

<400> SEQUENCE: 237

Gly Leu Gly Val Ala Gly Ser Ala Pro Gly Ile Glu Gly Asp Glu
1               5                   10                  15

<210> SEQ ID NO 238
<211> LENGTH: 14
<212> TYPE: PRT
<213> ORGANISM: Artificial Sequence
<220> FEATURE:
<223> OTHER INFORMATION: Synthetic peptide

<400> SEQUENCE: 238

Glu Ala Leu Gln Ala Glu Ala Gly Leu Pro Val Asp Arg Lys
1               5                   10

<210> SEQ ID NO 239
<211> LENGTH: 21
<212> TYPE: PRT
```

```
<213> ORGANISM: Artificial Sequence
<220> FEATURE:
<223> OTHER INFORMATION: Synthetic peptide

<400> SEQUENCE: 239

Thr Gly Gly Leu Gly Asp Val Leu Gly Gly Leu Pro Pro Ala Met Ala
1               5                   10                  15

Ala Asn Gly His Arg
            20

<210> SEQ ID NO 240
<211> LENGTH: 11
<212> TYPE: PRT
<213> ORGANISM: Artificial Sequence
<220> FEATURE:
<223> OTHER INFORMATION: Synthetic peptide

<400> SEQUENCE: 240

Leu Glu Glu Gln Lys Gly Pro Asp Val Met Ala
1               5                   10

<210> SEQ ID NO 241
<211> LENGTH: 20
<212> TYPE: PRT
<213> ORGANISM: Artificial Sequence
<220> FEATURE:
<223> OTHER INFORMATION: Synthetic peptide

<400> SEQUENCE: 241

Leu Gly Val Ala Gly Ser Ala Pro Gly Ile Glu Gly Asp Glu Ile Ala
1               5                   10                  15

Pro Leu Ala Lys
            20

<210> SEQ ID NO 242
<211> LENGTH: 21
<212> TYPE: PRT
<213> ORGANISM: Artificial Sequence
<220> FEATURE:
<223> OTHER INFORMATION: Synthetic peptide

<400> SEQUENCE: 242

Gly Leu Gly Val Ala Gly Ser Ala Pro Gly Ile Glu Gly Asp Glu Ile
1               5                   10                  15

Ala Pro Leu Ala Lys
            20

<210> SEQ ID NO 243
<211> LENGTH: 15
<212> TYPE: PRT
<213> ORGANISM: Artificial Sequence
<220> FEATURE:
<223> OTHER INFORMATION: Synthetic peptide

<400> SEQUENCE: 243

Thr Gly Gly Leu Gly Asp Val Leu Gly Gly Leu Pro Pro Ala Met
1               5                   10                  15

<210> SEQ ID NO 244
<211> LENGTH: 19
<212> TYPE: PRT
<213> ORGANISM: Artificial Sequence
<220> FEATURE:
<223> OTHER INFORMATION: Synthetic peptide

<400> SEQUENCE: 244
```

```
Asn Val Leu Gly Leu Gly Val Ala Gly Ser Ala Pro Gly Ile Glu
1               5                   10                  15

Gly Asp Glu

<210> SEQ ID NO 245
<211> LENGTH: 12
<212> TYPE: PRT
<213> ORGANISM: Artificial Sequence
<220> FEATURE:
<223> OTHER INFORMATION: Synthetic peptide

<400> SEQUENCE: 245

Thr Val Phe Asp Gly Val Leu Arg Pro Gly Gln Leu
1               5                   10

<210> SEQ ID NO 246
<211> LENGTH: 16
<212> TYPE: PRT
<213> ORGANISM: Artificial Sequence
<220> FEATURE:
<223> OTHER INFORMATION: Synthetic peptide

<400> SEQUENCE: 246

Arg Leu Gln Ser Gln Asn Asp Gln Arg Gly Glu Ile Ile His Val Lys
1               5                   10                  15

<210> SEQ ID NO 247
<211> LENGTH: 15
<212> TYPE: PRT
<213> ORGANISM: Artificial Sequence
<220> FEATURE:
<223> OTHER INFORMATION: Synthetic peptide

<400> SEQUENCE: 247

Glu Gly Tyr Tyr Gly Glu Gln Gln Gln Pro Gly Met Thr Arg
1               5                   10                  15

<210> SEQ ID NO 248
<211> LENGTH: 14
<212> TYPE: PRT
<213> ORGANISM: Artificial Sequence
<220> FEATURE:
<223> OTHER INFORMATION: Synthetic peptide

<400> SEQUENCE: 248

Gly Tyr Tyr Gly Glu Gln Gln Gln Pro Gly Met Thr Arg
1               5                   10

<210> SEQ ID NO 249
<211> LENGTH: 16
<212> TYPE: PRT
<213> ORGANISM: Artificial Sequence
<220> FEATURE:
<223> OTHER INFORMATION: Synthetic peptide

<400> SEQUENCE: 249

Glu Glu Gly Tyr Tyr Gly Glu Gln Gln Gln Pro Gly Met Thr Arg
1               5                   10                  15

<210> SEQ ID NO 250
<211> LENGTH: 20
<212> TYPE: PRT
<213> ORGANISM: Artificial Sequence
<220> FEATURE:
<223> OTHER INFORMATION: Synthetic peptide
```

```
<400> SEQUENCE: 250

Tyr Tyr Gly Gly Glu Gly Ser Ser Glu Gln Gly Tyr Tyr Gly Glu
1               5                   10                  15

Gly Ser Ser Glu
            20

<210> SEQ ID NO 251
<211> LENGTH: 19
<212> TYPE: PRT
<213> ORGANISM: Artificial Sequence
<220> FEATURE:
<223> OTHER INFORMATION: Synthetic peptide

<400> SEQUENCE: 251

Tyr Gly Gly Glu Gly Ser Ser Glu Gln Gly Tyr Tyr Gly Glu Gly
1               5                   10                  15

Ser Ser Glu

<210> SEQ ID NO 252
<211> LENGTH: 18
<212> TYPE: PRT
<213> ORGANISM: Artificial Sequence
<220> FEATURE:
<223> OTHER INFORMATION: Synthetic peptide

<400> SEQUENCE: 252

Ser Ser Glu Glu Gly Tyr Tyr Gly Glu Gln Gln Gln Gln Pro Gly Met
1               5                   10                  15

Thr Arg

<210> SEQ ID NO 253
<211> LENGTH: 17
<212> TYPE: PRT
<213> ORGANISM: Artificial Sequence
<220> FEATURE:
<223> OTHER INFORMATION: Synthetic peptide

<400> SEQUENCE: 253

Ser Glu Glu Gly Tyr Tyr Gly Glu Gln Gln Gln Gln Pro Gly Met Thr
1               5                   10                  15

Arg

<210> SEQ ID NO 254
<211> LENGTH: 11
<212> TYPE: PRT
<213> ORGANISM: Artificial Sequence
<220> FEATURE:
<223> OTHER INFORMATION: Synthetic peptide

<400> SEQUENCE: 254

Gln Gly Tyr Tyr Gly Glu Gly Ser Ser Glu Glu
1               5                   10

<210> SEQ ID NO 255
<211> LENGTH: 22
<212> TYPE: PRT
<213> ORGANISM: Artificial Sequence
<220> FEATURE:
<223> OTHER INFORMATION: Synthetic peptide

<400> SEQUENCE: 255

Tyr Gly Gly Glu Gly Ser Ser Ser Glu Gln Gly Tyr Tyr Gly Glu Gly
1               5                   10                  15
```

```
Ser Ser Glu Glu Gly Tyr
            20

<210> SEQ ID NO 256
<211> LENGTH: 12
<212> TYPE: PRT
<213> ORGANISM: Artificial Sequence
<220> FEATURE:
<223> OTHER INFORMATION: Synthetic peptide

<400> SEQUENCE: 256

Tyr Gly Glu Gln Gln Gln Gln Pro Gly Met Thr Arg
1               5                   10

<210> SEQ ID NO 257
<211> LENGTH: 13
<212> TYPE: PRT
<213> ORGANISM: Artificial Sequence
<220> FEATURE:
<223> OTHER INFORMATION: Synthetic peptide

<400> SEQUENCE: 257

Tyr Tyr Gly Glu Gln Gln Gln Gln Pro Gly Met Thr Arg
1               5                   10

<210> SEQ ID NO 258
<211> LENGTH: 20
<212> TYPE: PRT
<213> ORGANISM: Artificial Sequence
<220> FEATURE:
<223> OTHER INFORMATION: Synthetic peptide

<400> SEQUENCE: 258

Ser Tyr Glu Glu Ser Met Pro Met Pro Leu Glu Gln Gly Trp Ser Ser
1               5                   10                  15

Ser Ser Ser Glu
            20

<210> SEQ ID NO 259
<211> LENGTH: 23
<212> TYPE: PRT
<213> ORGANISM: Artificial Sequence
<220> FEATURE:
<223> OTHER INFORMATION: Synthetic peptide

<400> SEQUENCE: 259

Tyr Tyr Gly Glu Gly Ser Ser Glu Glu Gly Tyr Tyr Gly Glu Gln Gln
1               5                   10                  15

Gln Gln Pro Gly Met Thr Arg
            20

<210> SEQ ID NO 260
<211> LENGTH: 10
<212> TYPE: PRT
<213> ORGANISM: Artificial Sequence
<220> FEATURE:
<223> OTHER INFORMATION: Synthetic peptide

<400> SEQUENCE: 260

Gln Gln Gln Gln Pro Gly Met Thr Arg Val
1               5                   10

<210> SEQ ID NO 261
<211> LENGTH: 11
<212> TYPE: PRT
<213> ORGANISM: Artificial Sequence
```

```
<220> FEATURE:
<223> OTHER INFORMATION: Synthetic peptide

<400> SEQUENCE: 261

Gly Glu Gln Gln Gln Gln Pro Gly Met Thr Arg
1               5                   10

<210> SEQ ID NO 262
<211> LENGTH: 21
<212> TYPE: PRT
<213> ORGANISM: Artificial Sequence
<220> FEATURE:
<223> OTHER INFORMATION: Synthetic peptide

<400> SEQUENCE: 262

Ser Tyr Glu Glu Ser Met Pro Met Pro Leu Glu Gln Gly Trp Ser Ser
1               5                   10                  15

Ser Ser Ser Glu Tyr
            20

<210> SEQ ID NO 263
<211> LENGTH: 23
<212> TYPE: PRT
<213> ORGANISM: Artificial Sequence
<220> FEATURE:
<223> OTHER INFORMATION: Synthetic peptide

<400> SEQUENCE: 263

Tyr Tyr Gly Gly Glu Gly Ser Ser Ser Glu Gln Gly Tyr Tyr Gly Glu
1               5                   10                  15

Gly Ser Ser Glu Glu Gly Tyr
            20

<210> SEQ ID NO 264
<211> LENGTH: 14
<212> TYPE: PRT
<213> ORGANISM: Artificial Sequence
<220> FEATURE:
<223> OTHER INFORMATION: Synthetic peptide

<400> SEQUENCE: 264

Tyr Gly Glu Gln Gln Gln Gln Pro Gly Met Thr Arg Val Arg
1               5                   10

<210> SEQ ID NO 265
<211> LENGTH: 21
<212> TYPE: PRT
<213> ORGANISM: Artificial Sequence
<220> FEATURE:
<223> OTHER INFORMATION: Synthetic peptide

<400> SEQUENCE: 265

Gly Glu Gly Ser Ser Glu Glu Gly Tyr Tyr Gly Glu Gln Gln Gln Gln
1               5                   10                  15

Pro Gly Met Thr Arg
            20

<210> SEQ ID NO 266
<211> LENGTH: 22
<212> TYPE: PRT
<213> ORGANISM: Artificial Sequence
<220> FEATURE:
<223> OTHER INFORMATION: Synthetic peptide

<400> SEQUENCE: 266
```

Tyr Gly Glu Gly Ser Ser Glu Glu Gly Tyr Tyr Gly Glu Gln Gln Gln
1               5                   10                  15

Gln Pro Gly Met Thr Arg
            20

<210> SEQ ID NO 267
<211> LENGTH: 11
<212> TYPE: PRT
<213> ORGANISM: Artificial Sequence
<220> FEATURE:
<223> OTHER INFORMATION: Synthetic peptide

<400> SEQUENCE: 267

Gln Gln Gln Gln Pro Gly Met Thr Arg Val Arg
1               5                   10

<210> SEQ ID NO 268
<211> LENGTH: 25
<212> TYPE: PRT
<213> ORGANISM: Artificial Sequence
<220> FEATURE:
<223> OTHER INFORMATION: Synthetic peptide

<400> SEQUENCE: 268

Gln Tyr Ala Ala Gln Leu Pro Ser Met Cys Arg Val Glu Pro Gln Gln
1               5                   10                  15

Cys Ser Ile Phe Ala Ala Gly Gln Tyr
            20                  25

<210> SEQ ID NO 269
<211> LENGTH: 12
<212> TYPE: PRT
<213> ORGANISM: Artificial Sequence
<220> FEATURE:
<223> OTHER INFORMATION: Synthetic peptide

<400> SEQUENCE: 269

Thr Val Phe Asn Gly Val Leu Arg Pro Gly Gln Leu
1               5                   10

<210> SEQ ID NO 270
<211> LENGTH: 13
<212> TYPE: PRT
<213> ORGANISM: Artificial Sequence
<220> FEATURE:
<223> OTHER INFORMATION: Synthetic peptide

<400> SEQUENCE: 270

Thr Val Phe Asn Gly Val Leu Arg Pro Gly Gln Leu Leu
1               5                   10

<210> SEQ ID NO 271
<211> LENGTH: 20
<212> TYPE: PRT
<213> ORGANISM: Artificial Sequence
<220> FEATURE:
<223> OTHER INFORMATION: Synthetic peptide

<400> SEQUENCE: 271

Ser Gly Phe Asn Asn Glu Leu Leu Ser Glu Ala Leu Gly Val Asn Ala
1               5                   10                  15

Leu Val Ala Lys
            20

<210> SEQ ID NO 272

```
<211> LENGTH: 9
<212> TYPE: PRT
<213> ORGANISM: Artificial Sequence
<220> FEATURE:
<223> OTHER INFORMATION: Synthetic peptide

<400> SEQUENCE: 272

Asn Gly Val Leu Arg Pro Gly Gln Leu
1               5

<210> SEQ ID NO 273
<211> LENGTH: 17
<212> TYPE: PRT
<213> ORGANISM: Artificial Sequence
<220> FEATURE:
<223> OTHER INFORMATION: Synthetic peptide

<400> SEQUENCE: 273

Ala Leu Val Ala Lys Arg Leu Gln Gly Gln Asn Asp Gln Arg Gly Glu
1               5                   10                  15

Ile

<210> SEQ ID NO 274
<211> LENGTH: 10
<212> TYPE: PRT
<213> ORGANISM: Artificial Sequence
<220> FEATURE:
<223> OTHER INFORMATION: Synthetic peptide

<400> SEQUENCE: 274

Val Pro Arg Tyr Ser Asn Thr Pro Gly Met
1               5                   10

<210> SEQ ID NO 275
<211> LENGTH: 10
<212> TYPE: PRT
<213> ORGANISM: Artificial Sequence
<220> FEATURE:
<223> OTHER INFORMATION: Synthetic peptide

<400> SEQUENCE: 275

Pro Arg Tyr Ser Asn Thr Pro Gly Met Val
1               5                   10

<210> SEQ ID NO 276
<211> LENGTH: 9
<212> TYPE: PRT
<213> ORGANISM: Artificial Sequence
<220> FEATURE:
<223> OTHER INFORMATION: Synthetic peptide

<400> SEQUENCE: 276

Tyr Ser Asn Thr Pro Gly Met Val Tyr
1               5

<210> SEQ ID NO 277
<211> LENGTH: 11
<212> TYPE: PRT
<213> ORGANISM: Artificial Sequence
<220> FEATURE:
<223> OTHER INFORMATION: Synthetic peptide

<400> SEQUENCE: 277

Leu Val Pro Arg Tyr Ser Asn Thr Pro Gly Met
1               5                   10
```

```
<210> SEQ ID NO 278
<211> LENGTH: 10
<212> TYPE: PRT
<213> ORGANISM: Artificial Sequence
<220> FEATURE:
<223> OTHER INFORMATION: Synthetic peptide

<400> SEQUENCE: 278

Phe Tyr Asn Glu Gly Asp Ala Pro Val Val
1               5                   10

<210> SEQ ID NO 279
<211> LENGTH: 12
<212> TYPE: PRT
<213> ORGANISM: Artificial Sequence
<220> FEATURE:
<223> OTHER INFORMATION: Synthetic peptide

<400> SEQUENCE: 279

Phe Tyr Asn Glu Gly Asp Ala Pro Val Val Ala Leu
1               5                   10

<210> SEQ ID NO 280
<211> LENGTH: 15
<212> TYPE: PRT
<213> ORGANISM: Artificial Sequence
<220> FEATURE:
<223> OTHER INFORMATION: Synthetic peptide

<400> SEQUENCE: 280

Phe Glu Pro Leu Arg Arg Val Arg Ser Glu Ala Gly Val Thr Glu
1               5                   10                  15

<210> SEQ ID NO 281
<211> LENGTH: 13
<212> TYPE: PRT
<213> ORGANISM: Artificial Sequence
<220> FEATURE:
<223> OTHER INFORMATION: Synthetic peptide

<400> SEQUENCE: 281

Phe Tyr Asn Glu Gly Asp Ala Pro Val Val Ala Leu Tyr
1               5                   10

<210> SEQ ID NO 282
<211> LENGTH: 11
<212> TYPE: PRT
<213> ORGANISM: Artificial Sequence
<220> FEATURE:
<223> OTHER INFORMATION: Synthetic peptide

<400> SEQUENCE: 282

Phe Tyr Asn Glu Gly Asp Ala Pro Val Val Ala
1               5                   10

<210> SEQ ID NO 283
<211> LENGTH: 16
<212> TYPE: PRT
<213> ORGANISM: Artificial Sequence
<220> FEATURE:
<223> OTHER INFORMATION: Synthetic peptide

<400> SEQUENCE: 283

His Gly Pro Val Glu Met Pro Tyr Thr Leu Leu Tyr Pro Ser Ser Lys
1               5                   10                  15

<210> SEQ ID NO 284
```

```
<211> LENGTH: 9
<212> TYPE: PRT
<213> ORGANISM: Artificial Sequence
<220> FEATURE:
<223> OTHER INFORMATION: Synthetic peptide

<400> SEQUENCE: 284

Leu Asp Ala Leu Glu Pro Asp Asn Arg
1               5

<210> SEQ ID NO 285
<211> LENGTH: 8
<212> TYPE: PRT
<213> ORGANISM: Artificial Sequence
<220> FEATURE:
<223> OTHER INFORMATION: Synthetic peptide

<400> SEQUENCE: 285

Asp Ala Leu Glu Pro Asp Asn Arg
1               5

<210> SEQ ID NO 286
<211> LENGTH: 24
<212> TYPE: PRT
<213> ORGANISM: Artificial Sequence
<220> FEATURE:
<223> OTHER INFORMATION: Synthetic peptide

<400> SEQUENCE: 286

His Gly Ser Leu His Lys Asn Ala Met Phe Val Pro His Tyr Asn Leu
1               5                   10                  15

Asn Ala Asn Ser Ile Ile Tyr Ala
            20

<210> SEQ ID NO 287
<211> LENGTH: 20
<212> TYPE: PRT
<213> ORGANISM: Artificial Sequence
<220> FEATURE:
<223> OTHER INFORMATION: Synthetic peptide

<400> SEQUENCE: 287

Leu Ala Gly Thr Ser Ser Val Ile Asn Asn Leu Pro Leu Asp Val Val
1               5                   10                  15

Ala Ala Thr Phe
            20

<210> SEQ ID NO 288
<211> LENGTH: 16
<212> TYPE: PRT
<213> ORGANISM: Artificial Sequence
<220> FEATURE:
<223> OTHER INFORMATION: Synthetic peptide

<400> SEQUENCE: 288

Phe Arg Glu Gly Asp Ile Ile Ala Val Pro Thr Gly Ile Val Phe Trp
1               5                   10                  15

<210> SEQ ID NO 289
<211> LENGTH: 24
<212> TYPE: PRT
<213> ORGANISM: Artificial Sequence
<220> FEATURE:
<223> OTHER INFORMATION: Synthetic peptide

<400> SEQUENCE: 289
```

Gly Thr Ser Ser Val Ile Asn Asn Leu Pro Leu Asp Val Val Ala Ala
1               5                   10                  15

Thr Phe Asn Leu Gln Arg Asn Glu
            20

<210> SEQ ID NO 290
<211> LENGTH: 18
<212> TYPE: PRT
<213> ORGANISM: Artificial Sequence
<220> FEATURE:
<223> OTHER INFORMATION: Synthetic peptide

<400> SEQUENCE: 290

Lys Gly Ala Ile Val Lys Val Lys Gly Gly Leu Ser Ile Ile Ser Pro
1               5                   10                  15

Pro Glu

<210> SEQ ID NO 291
<211> LENGTH: 15
<212> TYPE: PRT
<213> ORGANISM: Artificial Sequence
<220> FEATURE:
<223> OTHER INFORMATION: Synthetic peptide

<400> SEQUENCE: 291

Arg Leu Ala Gly Thr Ser Ser Val Ile Asn Asn Leu Pro Leu Asp
1               5                   10                  15

<210> SEQ ID NO 292
<211> LENGTH: 25
<212> TYPE: PRT
<213> ORGANISM: Artificial Sequence
<220> FEATURE:
<223> OTHER INFORMATION: Synthetic peptide

<400> SEQUENCE: 292

Ala Gly Thr Ser Ser Val Ile Asn Asn Leu Pro Leu Asp Val Val Ala
1               5                   10                  15

Ala Thr Phe Asn Leu Gln Arg Asn Glu
            20                  25

<210> SEQ ID NO 293
<211> LENGTH: 12
<212> TYPE: PRT
<213> ORGANISM: Artificial Sequence
<220> FEATURE:
<223> OTHER INFORMATION: Synthetic peptide

<400> SEQUENCE: 293

Ala Gly Thr Ser Ser Val Ile Asn Asn Leu Pro Leu
1               5                   10

<210> SEQ ID NO 294
<211> LENGTH: 17
<212> TYPE: PRT
<213> ORGANISM: Artificial Sequence
<220> FEATURE:
<223> OTHER INFORMATION: Synthetic peptide

<400> SEQUENCE: 294

Leu Ala Gly Thr Ser Ser Val Ile Asn Asn Leu Pro Leu Asp Val Val
1               5                   10                  15

Ala

```
<210> SEQ ID NO 295
<211> LENGTH: 14
<212> TYPE: PRT
<213> ORGANISM: Artificial Sequence
<220> FEATURE:
<223> OTHER INFORMATION: Synthetic peptide

<400> SEQUENCE: 295

Ala Gly Thr Ser Ser Val Ile Asn Asn Leu Pro Leu Asp Val
1               5                   10

<210> SEQ ID NO 296
<211> LENGTH: 17
<212> TYPE: PRT
<213> ORGANISM: Artificial Sequence
<220> FEATURE:
<223> OTHER INFORMATION: Synthetic peptide

<400> SEQUENCE: 296

Ala Gly Arg Ile Lys Thr Val Thr Ser Leu Asp Leu Pro Val Leu Arg
1               5                   10                  15

Trp

<210> SEQ ID NO 297
<211> LENGTH: 16
<212> TYPE: PRT
<213> ORGANISM: Artificial Sequence
<220> FEATURE:
<223> OTHER INFORMATION: Synthetic peptide

<400> SEQUENCE: 297

Ala Gly Arg Ile Lys Thr Val Thr Ser Leu Asp Leu Pro Val Leu Arg
1               5                   10                  15

<210> SEQ ID NO 298
<211> LENGTH: 15
<212> TYPE: PRT
<213> ORGANISM: Artificial Sequence
<220> FEATURE:
<223> OTHER INFORMATION: Synthetic peptide

<400> SEQUENCE: 298

Phe Arg Glu Gly Asp Ile Ile Ala Val Pro Thr Gly Ile Val Phe
1               5                   10                  15

<210> SEQ ID NO 299
<211> LENGTH: 13
<212> TYPE: PRT
<213> ORGANISM: Artificial Sequence
<220> FEATURE:
<223> OTHER INFORMATION: Synthetic peptide

<400> SEQUENCE: 299

Ala Gly Thr Ser Ser Val Ile Asn Asn Leu Pro Leu Asp
1               5                   10

<210> SEQ ID NO 300
<211> LENGTH: 13
<212> TYPE: PRT
<213> ORGANISM: Artificial Sequence
<220> FEATURE:
<223> OTHER INFORMATION: Synthetic peptide

<400> SEQUENCE: 300

Leu Ala Gly Thr Ser Ser Val Ile Asn Asn Leu Pro Leu
1               5                   10
```

```
<210> SEQ ID NO 301
<211> LENGTH: 16
<212> TYPE: PRT
<213> ORGANISM: Artificial Sequence
<220> FEATURE:
<223> OTHER INFORMATION: Synthetic peptide

<400> SEQUENCE: 301

Leu Ala Gly Thr Ser Ser Val Ile Asn Asn Leu Pro Leu Asp Val Val
1               5                   10                  15

<210> SEQ ID NO 302
<211> LENGTH: 13
<212> TYPE: PRT
<213> ORGANISM: Artificial Sequence
<220> FEATURE:
<223> OTHER INFORMATION: Synthetic peptide

<400> SEQUENCE: 302

Glu Gly Asp Ile Ile Ala Val Pro Thr Gly Ile Val Phe
1               5                   10

<210> SEQ ID NO 303
<211> LENGTH: 15
<212> TYPE: PRT
<213> ORGANISM: Artificial Sequence
<220> FEATURE:
<223> OTHER INFORMATION: Synthetic peptide

<400> SEQUENCE: 303

Leu Ala Gly Thr Ser Ser Val Ile Asn Asn Leu Pro Leu Asp Val
1               5                   10                  15

<210> SEQ ID NO 304
<211> LENGTH: 20
<212> TYPE: PRT
<213> ORGANISM: Artificial Sequence
<220> FEATURE:
<223> OTHER INFORMATION: Synthetic peptide

<400> SEQUENCE: 304

Ala Gly Arg Ala Leu Thr Val Pro Gln Asn Tyr Ala Val Ala Ala Lys
1               5                   10                  15
Ser Leu Ser Asp
            20

<210> SEQ ID NO 305
<211> LENGTH: 12
<212> TYPE: PRT
<213> ORGANISM: Artificial Sequence
<220> FEATURE:
<223> OTHER INFORMATION: Synthetic peptide

<400> SEQUENCE: 305

Ala Gly Arg Ala Leu Thr Val Pro Gln Asn Tyr Ala
1               5                   10

<210> SEQ ID NO 306
<211> LENGTH: 14
<212> TYPE: PRT
<213> ORGANISM: Artificial Sequence
<220> FEATURE:
<223> OTHER INFORMATION: Synthetic peptide

<400> SEQUENCE: 306

Leu Ala Gly Thr Ser Ser Val Ile Asn Asn Leu Pro Leu Asp
```

```
1               5                  10

<210> SEQ ID NO 307
<211> LENGTH: 23
<212> TYPE: PRT
<213> ORGANISM: Artificial Sequence
<220> FEATURE:
<223> OTHER INFORMATION: Synthetic peptide

<400> SEQUENCE: 307

Arg Ala Gly Ile Ala Arg Leu Ala Gly Thr Ser Ser Val Ile Asn Asn
1               5                  10                  15

Leu Pro Leu Asp Val Val Ala
            20

<210> SEQ ID NO 308
<211> LENGTH: 16
<212> TYPE: PRT
<213> ORGANISM: Artificial Sequence
<220> FEATURE:
<223> OTHER INFORMATION: Synthetic peptide

<400> SEQUENCE: 308

Arg Ala Ser Ser Asn Leu Asn Leu Leu Gly Phe Gly Ile Asn Ala Glu
1               5                  10                  15

<210> SEQ ID NO 309
<211> LENGTH: 12
<212> TYPE: PRT
<213> ORGANISM: Artificial Sequence
<220> FEATURE:
<223> OTHER INFORMATION: Synthetic peptide

<400> SEQUENCE: 309

Val Thr Val Asn Glu Gly Lys Gly Asp Phe Glu Leu
1               5                  10

<210> SEQ ID NO 310
<211> LENGTH: 17
<212> TYPE: PRT
<213> ORGANISM: Artificial Sequence
<220> FEATURE:
<223> OTHER INFORMATION: Synthetic peptide

<400> SEQUENCE: 310

Val Arg Ala Ser Ser Asn Leu Asn Leu Leu Gly Phe Gly Ile Asn Ala
1               5                  10                  15

Glu

<210> SEQ ID NO 311
<211> LENGTH: 13
<212> TYPE: PRT
<213> ORGANISM: Artificial Sequence
<220> FEATURE:
<223> OTHER INFORMATION: Synthetic peptide

<400> SEQUENCE: 311

Val Arg Ala Ser Ser Asn Leu Asn Leu Leu Gly Phe Gly
1               5                  10

<210> SEQ ID NO 312
<211> LENGTH: 17
<212> TYPE: PRT
<213> ORGANISM: Artificial Sequence
<220> FEATURE:
<223> OTHER INFORMATION: Synthetic peptide
```

<400> SEQUENCE: 312

His Pro Val Ala Val Arg Ala Ser Ser Asn Leu Asn Leu Leu Gly Phe
1               5                   10                  15

Gly

<210> SEQ ID NO 313
<211> LENGTH: 16
<212> TYPE: PRT
<213> ORGANISM: Artificial Sequence
<220> FEATURE:
<223> OTHER INFORMATION: Synthetic peptide

<400> SEQUENCE: 313

Thr Lys Asn Gln Val Gln Ser Tyr Lys Ala Lys Leu Thr Pro Gly Asp
1               5                   10                  15

<210> SEQ ID NO 314
<211> LENGTH: 15
<212> TYPE: PRT
<213> ORGANISM: Artificial Sequence
<220> FEATURE:
<223> OTHER INFORMATION: Synthetic peptide

<400> SEQUENCE: 314

His Pro Val Ala Val Arg Ala Ser Ser Asn Leu Asn Leu Leu Gly
1               5                   10                  15

<210> SEQ ID NO 315
<211> LENGTH: 15
<212> TYPE: PRT
<213> ORGANISM: Artificial Sequence
<220> FEATURE:
<223> OTHER INFORMATION: Synthetic peptide

<400> SEQUENCE: 315

Lys Ala Lys Leu Thr Pro Gly Asp Val Phe Val Ile Pro Ala Gly
1               5                   10                  15

<210> SEQ ID NO 316
<211> LENGTH: 19
<212> TYPE: PRT
<213> ORGANISM: Artificial Sequence
<220> FEATURE:
<223> OTHER INFORMATION: Synthetic peptide

<400> SEQUENCE: 316

Asp Leu Thr Phe Pro Gly Ser Ala Gln Glu Val Asp Arg Leu Leu Glu
1               5                   10                  15

Asn Gln Lys

<210> SEQ ID NO 317
<211> LENGTH: 9
<212> TYPE: PRT
<213> ORGANISM: Artificial Sequence
<220> FEATURE:
<223> OTHER INFORMATION: Synthetic peptide

<400> SEQUENCE: 317

Pro Ala Gly His Pro Val Ala Val Arg
1               5

<210> SEQ ID NO 318
<211> LENGTH: 18
<212> TYPE: PRT

<213> ORGANISM: Artificial Sequence
<220> FEATURE:
<223> OTHER INFORMATION: Synthetic peptide

<400> SEQUENCE: 318

Ala Lys Leu Thr Pro Gly Asp Val Phe Val Ile Pro Ala Gly His Pro
1               5                   10                  15

Val Ala

<210> SEQ ID NO 319
<211> LENGTH: 21
<212> TYPE: PRT
<213> ORGANISM: Artificial Sequence
<220> FEATURE:
<223> OTHER INFORMATION: Synthetic peptide

<400> SEQUENCE: 319

Ser Tyr Lys Ala Lys Leu Thr Pro Gly Asp Val Phe Val Ile Pro Ala
1               5                   10                  15

Gly His Pro Val Ala
            20

<210> SEQ ID NO 320
<211> LENGTH: 18
<212> TYPE: PRT
<213> ORGANISM: Artificial Sequence
<220> FEATURE:
<223> OTHER INFORMATION: Synthetic peptide

<400> SEQUENCE: 320

Leu Thr Pro Gly Asp Val Phe Val Ile Pro Ala Gly His Pro Val Ala
1               5                   10                  15

Val Arg

<210> SEQ ID NO 321
<211> LENGTH: 19
<212> TYPE: PRT
<213> ORGANISM: Artificial Sequence
<220> FEATURE:
<223> OTHER INFORMATION: Synthetic peptide

<400> SEQUENCE: 321

Val Gln Ser Tyr Lys Ala Lys Leu Thr Pro Gly Asp Val Phe Val Ile
1               5                   10                  15

Pro Ala Gly

<210> SEQ ID NO 322
<211> LENGTH: 20
<212> TYPE: PRT
<213> ORGANISM: Artificial Sequence
<220> FEATURE:
<223> OTHER INFORMATION: Synthetic peptide

<400> SEQUENCE: 322

Tyr Lys Ala Lys Leu Thr Pro Gly Asp Val Phe Val Ile Pro Ala Gly
1               5                   10                  15

His Pro Val Ala
            20

<210> SEQ ID NO 323
<211> LENGTH: 12
<212> TYPE: PRT
<213> ORGANISM: Artificial Sequence
<220> FEATURE:

<223> OTHER INFORMATION: Synthetic peptide

<400> SEQUENCE: 323

Phe Val Ile Pro Ala Gly His Pro Val Ala Val Arg
1               5                   10

<210> SEQ ID NO 324
<211> LENGTH: 16
<212> TYPE: PRT
<213> ORGANISM: Artificial Sequence
<220> FEATURE:
<223> OTHER INFORMATION: Synthetic peptide

<400> SEQUENCE: 324

Tyr Lys Ala Lys Leu Thr Pro Gly Asp Val Phe Val Ile Pro Ala Gly
1               5                   10                  15

<210> SEQ ID NO 325
<211> LENGTH: 13
<212> TYPE: PRT
<213> ORGANISM: Artificial Sequence
<220> FEATURE:
<223> OTHER INFORMATION: Synthetic peptide

<400> SEQUENCE: 325

Asp Leu Thr Phe Pro Gly Ser Ala Gln Glu Val Asp Arg
1               5                   10

<210> SEQ ID NO 326
<211> LENGTH: 20
<212> TYPE: PRT
<213> ORGANISM: Artificial Sequence
<220> FEATURE:
<223> OTHER INFORMATION: Synthetic peptide

<400> SEQUENCE: 326

Ala Lys Leu Thr Pro Gly Asp Val Phe Val Ile Pro Ala Gly His Pro
1               5                   10                  15

Val Ala Val Arg
            20

<210> SEQ ID NO 327
<211> LENGTH: 12
<212> TYPE: PRT
<213> ORGANISM: Artificial Sequence
<220> FEATURE:
<223> OTHER INFORMATION: Synthetic peptide

<400> SEQUENCE: 327

Leu Thr Pro Gly Asp Val Phe Val Ile Pro Ala Gly
1               5                   10

<210> SEQ ID NO 328
<211> LENGTH: 17
<212> TYPE: PRT
<213> ORGANISM: Artificial Sequence
<220> FEATURE:
<223> OTHER INFORMATION: Synthetic peptide

<400> SEQUENCE: 328

Ser Tyr Lys Ala Lys Leu Thr Pro Gly Asp Val Phe Val Ile Pro Ala
1               5                   10                  15

Gly

<210> SEQ ID NO 329

```
<211> LENGTH: 23
<212> TYPE: PRT
<213> ORGANISM: Artificial Sequence
<220> FEATURE:
<223> OTHER INFORMATION: Synthetic peptide

<400> SEQUENCE: 329

Ser Tyr Lys Ala Lys Leu Thr Pro Gly Asp Val Phe Val Ile Pro Ala
1               5                   10                  15

Gly His Pro Val Ala Val Arg
            20

<210> SEQ ID NO 330
<211> LENGTH: 11
<212> TYPE: PRT
<213> ORGANISM: Artificial Sequence
<220> FEATURE:
<223> OTHER INFORMATION: Synthetic peptide

<400> SEQUENCE: 330

Val Ile Pro Ala Gly His Pro Val Ala Val Arg
1               5                   10

<210> SEQ ID NO 331
<211> LENGTH: 20
<212> TYPE: PRT
<213> ORGANISM: Artificial Sequence
<220> FEATURE:
<223> OTHER INFORMATION: Synthetic peptide

<400> SEQUENCE: 331

Gln Val Gln Ser Tyr Lys Ala Lys Leu Thr Pro Gly Asp Val Phe Val
1               5                   10                  15

Ile Pro Ala Gly
            20

<210> SEQ ID NO 332
<211> LENGTH: 14
<212> TYPE: PRT
<213> ORGANISM: Artificial Sequence
<220> FEATURE:
<223> OTHER INFORMATION: Synthetic peptide

<400> SEQUENCE: 332

Ala Lys Leu Thr Pro Gly Asp Val Phe Val Ile Pro Ala Gly
1               5                   10

<210> SEQ ID NO 333
<211> LENGTH: 21
<212> TYPE: PRT
<213> ORGANISM: Artificial Sequence
<220> FEATURE:
<223> OTHER INFORMATION: Synthetic peptide

<400> SEQUENCE: 333

His Pro Val Ala Val Arg Ala Ser Ser Asn Leu Asn Leu Leu Gly Phe
1               5                   10                  15

Gly Ile Asn Ala Glu
            20

<210> SEQ ID NO 334
<211> LENGTH: 22
<212> TYPE: PRT
<213> ORGANISM: Artificial Sequence
<220> FEATURE:
<223> OTHER INFORMATION: Synthetic peptide
```

<400> SEQUENCE: 334

Tyr Lys Ala Lys Leu Thr Pro Gly Asp Val Phe Val Ile Pro Ala Gly
1               5                   10                  15

His Pro Val Ala Val Arg
            20

<210> SEQ ID NO 335
<211> LENGTH: 23
<212> TYPE: PRT
<213> ORGANISM: Artificial Sequence
<220> FEATURE:
<223> OTHER INFORMATION: Synthetic peptide

<400> SEQUENCE: 335

Thr Lys Asn Gln Val Gln Ser Tyr Lys Ala Lys Leu Thr Pro Gly Asp
1               5                   10                  15

Val Phe Val Ile Pro Ala Gly
            20

<210> SEQ ID NO 336
<211> LENGTH: 12
<212> TYPE: PRT
<213> ORGANISM: Artificial Sequence
<220> FEATURE:
<223> OTHER INFORMATION: Synthetic peptide

<400> SEQUENCE: 336

Pro Phe Asn Leu Lys Ser Ser Asp Pro Ile Tyr Ser
1               5                   10

<210> SEQ ID NO 337
<211> LENGTH: 8
<212> TYPE: PRT
<213> ORGANISM: Artificial Sequence
<220> FEATURE:
<223> OTHER INFORMATION: Synthetic peptide

<400> SEQUENCE: 337

Ile Glu Lys Ile Leu Leu Glu Glu
1               5

<210> SEQ ID NO 338
<211> LENGTH: 16
<212> TYPE: PRT
<213> ORGANISM: Artificial Sequence
<220> FEATURE:
<223> OTHER INFORMATION: Synthetic peptide

<400> SEQUENCE: 338

Ser Arg Ser Glu Pro Phe Asn Leu Lys Ser Ser Asp Pro Ile Tyr Ser
1               5                   10                  15

<210> SEQ ID NO 339
<211> LENGTH: 13
<212> TYPE: PRT
<213> ORGANISM: Artificial Sequence
<220> FEATURE:
<223> OTHER INFORMATION: Synthetic peptide

<400> SEQUENCE: 339

His Pro Val Ala Val Arg Ala Ser Ser Asn Leu Asn Leu
1               5                   10

<210> SEQ ID NO 340

```
<211> LENGTH: 20
<212> TYPE: PRT
<213> ORGANISM: Artificial Sequence
<220> FEATURE:
<223> OTHER INFORMATION: Synthetic peptide

<400> SEQUENCE: 340

Thr Leu Phe Leu Pro Gln Tyr Thr Asp Ala Asp Phe Ile Leu Val Val
1               5                   10                  15

Leu Ser Gly Lys
            20

<210> SEQ ID NO 341
<211> LENGTH: 10
<212> TYPE: PRT
<213> ORGANISM: Artificial Sequence
<220> FEATURE:
<223> OTHER INFORMATION: Synthetic peptide

<400> SEQUENCE: 341

Glu Val Glu Glu Arg Ser Gln Asn Ile Phe
1               5                   10

<210> SEQ ID NO 342
<211> LENGTH: 12
<212> TYPE: PRT
<213> ORGANISM: Artificial Sequence
<220> FEATURE:
<223> OTHER INFORMATION: Synthetic peptide

<400> SEQUENCE: 342

Val Glu Glu Arg Ser Gln Asn Ile Phe Ser Gly Phe
1               5                   10

<210> SEQ ID NO 343
<211> LENGTH: 12
<212> TYPE: PRT
<213> ORGANISM: Artificial Sequence
<220> FEATURE:
<223> OTHER INFORMATION: Synthetic peptide

<400> SEQUENCE: 343

Ala Ser Leu Gln Glu Gln Glu Gln Gly Gln Val Gln
1               5                   10

<210> SEQ ID NO 344
<211> LENGTH: 11
<212> TYPE: PRT
<213> ORGANISM: Artificial Sequence
<220> FEATURE:
<223> OTHER INFORMATION: Synthetic peptide

<400> SEQUENCE: 344

Gln Glu Gln Glu Gln Gly Gln Val Gln Ser Arg
1               5                   10

<210> SEQ ID NO 345
<211> LENGTH: 14
<212> TYPE: PRT
<213> ORGANISM: Artificial Sequence
<220> FEATURE:
<223> OTHER INFORMATION: Synthetic peptide

<400> SEQUENCE: 345

Ala Ser Leu Gln Glu Gln Glu Gln Gly Gln Val Gln Ser Arg
1               5                   10
```

<210> SEQ ID NO 346
<211> LENGTH: 13
<212> TYPE: PRT
<213> ORGANISM: Artificial Sequence
<220> FEATURE:
<223> OTHER INFORMATION: Synthetic peptide

<400> SEQUENCE: 346

Glu Val Glu Glu Arg Ser Gln Asn Ile Phe Ser Gly Phe
1               5                   10

<210> SEQ ID NO 347
<211> LENGTH: 17
<212> TYPE: PRT
<213> ORGANISM: Artificial Sequence
<220> FEATURE:
<223> OTHER INFORMATION: Synthetic peptide

<400> SEQUENCE: 347

Val Thr Asp Leu Asn Asn Gly Ala Asn Gln Leu Asp Pro Arg Gln Arg
1               5                   10                  15

Asp

<210> SEQ ID NO 348
<211> LENGTH: 14
<212> TYPE: PRT
<213> ORGANISM: Artificial Sequence
<220> FEATURE:
<223> OTHER INFORMATION: Synthetic peptide

<400> SEQUENCE: 348

Val Glu His Gly Leu Ser Leu Leu Gln Pro Tyr Ala Ser Leu
1               5                   10

<210> SEQ ID NO 349
<211> LENGTH: 21
<212> TYPE: PRT
<213> ORGANISM: Artificial Sequence
<220> FEATURE:
<223> OTHER INFORMATION: Synthetic peptide

<400> SEQUENCE: 349

Ile Tyr Val Thr Asp Leu Asn Asn Gly Ala Asn Gln Leu Asp Pro Arg
1               5                   10                  15

Gln Arg Asp Phe Leu
            20

<210> SEQ ID NO 350
<211> LENGTH: 19
<212> TYPE: PRT
<213> ORGANISM: Artificial Sequence
<220> FEATURE:
<223> OTHER INFORMATION: Synthetic peptide

<400> SEQUENCE: 350

Val Thr Asp Leu Asn Asn Gly Ala Asn Gln Leu Asp Pro Arg Gln Arg
1               5                   10                  15

Asp Phe Leu

<210> SEQ ID NO 351
<211> LENGTH: 25
<212> TYPE: PRT
<213> ORGANISM: Artificial Sequence
<220> FEATURE:
<223> OTHER INFORMATION: Synthetic peptide

<400> SEQUENCE: 351

Val Glu His Gly Leu Ser Leu Leu Gln Pro Tyr Ala Ser Leu Gln Glu
1               5                   10                  15

Gln Glu Gln Gly Gln Val Gln Ser Arg
            20                  25

<210> SEQ ID NO 352
<211> LENGTH: 14
<212> TYPE: PRT
<213> ORGANISM: Artificial Sequence
<220> FEATURE:
<223> OTHER INFORMATION: Synthetic peptide

<400> SEQUENCE: 352

Val Thr Asp Leu Asn Asn Gly Ala Asn Gln Leu Asp Pro Arg
1               5                   10

<210> SEQ ID NO 353
<211> LENGTH: 19
<212> TYPE: PRT
<213> ORGANISM: Artificial Sequence
<220> FEATURE:
<223> OTHER INFORMATION: Synthetic peptide

<400> SEQUENCE: 353

Ile Tyr Val Thr Asp Leu Asn Asn Gly Ala Asn Gln Leu Asp Pro Arg
1               5                   10                  15

Gln Arg Asp

<210> SEQ ID NO 354
<211> LENGTH: 20
<212> TYPE: PRT
<213> ORGANISM: Artificial Sequence
<220> FEATURE:
<223> OTHER INFORMATION: Synthetic peptide

<400> SEQUENCE: 354

Tyr Val Thr Asp Leu Asn Asn Gly Ala Asn Gln Leu Asp Pro Arg Gln
1               5                   10                  15

Arg Asp Phe Leu
            20

<210> SEQ ID NO 355
<211> LENGTH: 15
<212> TYPE: PRT
<213> ORGANISM: Artificial Sequence
<220> FEATURE:
<223> OTHER INFORMATION: Synthetic peptide

<400> SEQUENCE: 355

Tyr Val Thr Asp Leu Asn Asn Gly Ala Asn Gln Leu Asp Pro Arg
1               5                   10                  15

<210> SEQ ID NO 356
<211> LENGTH: 17
<212> TYPE: PRT
<213> ORGANISM: Artificial Sequence
<220> FEATURE:
<223> OTHER INFORMATION: Synthetic peptide

<400> SEQUENCE: 356

Ser Thr Glu Leu Leu Ser Glu Ala Leu Gly Val Ser Ser Gln Val Ala
1               5                   10                  15

Arg

<210> SEQ ID NO 357
<211> LENGTH: 16
<212> TYPE: PRT
<213> ORGANISM: Artificial Sequence
<220> FEATURE:
<223> OTHER INFORMATION: Synthetic peptide

<400> SEQUENCE: 357

His Gly Leu Ser Leu Leu Gln Pro Tyr Ala Ser Leu Gln Glu Gln Glu
1               5                   10                  15

<210> SEQ ID NO 358
<211> LENGTH: 20
<212> TYPE: PRT
<213> ORGANISM: Artificial Sequence
<220> FEATURE:
<223> OTHER INFORMATION: Synthetic peptide

<400> SEQUENCE: 358

Ser Gly Phe Ser Thr Glu Leu Leu Ser Glu Ala Leu Gly Val Ser Ser
1               5                   10                  15

Gln Val Ala Arg
            20

<210> SEQ ID NO 359
<211> LENGTH: 13
<212> TYPE: PRT
<213> ORGANISM: Artificial Sequence
<220> FEATURE:
<223> OTHER INFORMATION: Synthetic peptide

<400> SEQUENCE: 359

Gly Ala Phe Thr Pro Leu Gln Tyr Lys Ser Tyr Gln Asp
1               5                   10

<210> SEQ ID NO 360
<211> LENGTH: 15
<212> TYPE: PRT
<213> ORGANISM: Artificial Sequence
<220> FEATURE:
<223> OTHER INFORMATION: Synthetic peptide

<400> SEQUENCE: 360

Gly Leu Leu Leu Pro His Tyr Thr Asn Gly Ala Ser Leu Val Tyr
1               5                   10                  15

<210> SEQ ID NO 361
<211> LENGTH: 16
<212> TYPE: PRT
<213> ORGANISM: Artificial Sequence
<220> FEATURE:
<223> OTHER INFORMATION: Synthetic peptide

<400> SEQUENCE: 361

Phe Leu Leu Ala Gly Asn Lys Arg Asn Pro Gln Ala Tyr Arg Arg Glu
1               5                   10                  15

<210> SEQ ID NO 362
<211> LENGTH: 12
<212> TYPE: PRT
<213> ORGANISM: Artificial Sequence
<220> FEATURE:
<223> OTHER INFORMATION: Synthetic peptide

<400> SEQUENCE: 362

```
Ala Leu Pro Thr Asp Val Leu Ala Asn Ala Tyr Arg
1               5                   10
```

<210> SEQ ID NO 363
<211> LENGTH: 8
<212> TYPE: PRT
<213> ORGANISM: Artificial Sequence
<220> FEATURE:
<223> OTHER INFORMATION: Synthetic peptide

<400> SEQUENCE: 363

```
Asp Phe Leu Leu Ala Gly Asn Lys
1               5
```

<210> SEQ ID NO 364
<211> LENGTH: 8
<212> TYPE: PRT
<213> ORGANISM: Artificial Sequence
<220> FEATURE:
<223> OTHER INFORMATION: Synthetic peptide

<400> SEQUENCE: 364

```
Asp Val Leu Ala Asn Ala Tyr Arg
1               5
```

<210> SEQ ID NO 365
<211> LENGTH: 9
<212> TYPE: PRT
<213> ORGANISM: Artificial Sequence
<220> FEATURE:
<223> OTHER INFORMATION: Synthetic peptide

<400> SEQUENCE: 365

```
Gly Ala Phe Thr Pro Leu Gln Tyr Lys
1               5
```

<210> SEQ ID NO 366
<211> LENGTH: 14
<212> TYPE: PRT
<213> ORGANISM: Artificial Sequence
<220> FEATURE:
<223> OTHER INFORMATION: Synthetic peptide

<400> SEQUENCE: 366

```
Gln Gly Asp Val Ile Ala Leu Pro Ala Gly Val Ala His Trp
1               5                   10
```

<210> SEQ ID NO 367
<211> LENGTH: 12
<212> TYPE: PRT
<213> ORGANISM: Artificial Sequence
<220> FEATURE:
<223> OTHER INFORMATION: Synthetic peptide

<400> SEQUENCE: 367

```
Phe Gly Ala Phe Thr Pro Leu Gln Tyr Lys Ser Tyr
1               5                   10
```

<210> SEQ ID NO 368
<211> LENGTH: 14
<212> TYPE: PRT
<213> ORGANISM: Artificial Sequence
<220> FEATURE:
<223> OTHER INFORMATION: Synthetic peptide

<400> SEQUENCE: 368

Phe Leu Leu Ala Gly Asn Lys Arg Asn Pro Gln Ala Tyr Arg
1               5                   10

<210> SEQ ID NO 369
<211> LENGTH: 13
<212> TYPE: PRT
<213> ORGANISM: Artificial Sequence
<220> FEATURE:
<223> OTHER INFORMATION: Synthetic peptide

<400> SEQUENCE: 369

Phe Gly Ala Phe Thr Pro Leu Gln Tyr Lys Ser Tyr Gln
1               5                   10

<210> SEQ ID NO 370
<211> LENGTH: 15
<212> TYPE: PRT
<213> ORGANISM: Artificial Sequence
<220> FEATURE:
<223> OTHER INFORMATION: Synthetic peptide

<400> SEQUENCE: 370

Gly Leu Ser Leu Leu Gln Pro Tyr Ala Ser Leu Gln Glu Gln Glu
1               5                   10                  15

<210> SEQ ID NO 371
<211> LENGTH: 8
<212> TYPE: PRT
<213> ORGANISM: Artificial Sequence
<220> FEATURE:
<223> OTHER INFORMATION: Synthetic peptide

<400> SEQUENCE: 371

Ala Phe Thr Pro Leu Gln Tyr Lys
1               5

<210> SEQ ID NO 372
<211> LENGTH: 14
<212> TYPE: PRT
<213> ORGANISM: Artificial Sequence
<220> FEATURE:
<223> OTHER INFORMATION: Synthetic peptide

<400> SEQUENCE: 372

Phe Gly Ala Phe Thr Pro Leu Gln Tyr Lys Ser Tyr Gln Asp
1               5                   10

<210> SEQ ID NO 373
<211> LENGTH: 13
<212> TYPE: PRT
<213> ORGANISM: Artificial Sequence
<220> FEATURE:
<223> OTHER INFORMATION: Synthetic peptide

<400> SEQUENCE: 373

Gly Asp Glu Phe Gly Ala Phe Thr Pro Leu Gln Tyr Lys
1               5                   10

<210> SEQ ID NO 374
<211> LENGTH: 15
<212> TYPE: PRT
<213> ORGANISM: Artificial Sequence
<220> FEATURE:
<223> OTHER INFORMATION: Synthetic peptide

<400> SEQUENCE: 374

Phe Gly Ala Phe Thr Pro Leu Gln Tyr Lys Ser Tyr Gln Asp Val

```
1               5                  10                  15
```

<210> SEQ ID NO 375
<211> LENGTH: 10
<212> TYPE: PRT
<213> ORGANISM: Artificial Sequence
<220> FEATURE:
<223> OTHER INFORMATION: Synthetic peptide

<400> SEQUENCE: 375

```
Phe Gly Ala Phe Thr Pro Leu Gln Tyr Lys
1               5                   10
```

<210> SEQ ID NO 376
<211> LENGTH: 11
<212> TYPE: PRT
<213> ORGANISM: Artificial Sequence
<220> FEATURE:
<223> OTHER INFORMATION: Synthetic peptide

<400> SEQUENCE: 376

```
Phe Gly Ala Phe Thr Pro Leu Gln Tyr Lys Ser
1               5                   10
```

<210> SEQ ID NO 377
<211> LENGTH: 14
<212> TYPE: PRT
<213> ORGANISM: Artificial Sequence
<220> FEATURE:
<223> OTHER INFORMATION: Synthetic peptide

<400> SEQUENCE: 377

```
Val Tyr Ile Ile Gln Gly Arg Gly Ile Thr Gly Pro Thr Phe
1               5                   10
```

<210> SEQ ID NO 378
<211> LENGTH: 13
<212> TYPE: PRT
<213> ORGANISM: Artificial Sequence
<220> FEATURE:
<223> OTHER INFORMATION: Synthetic peptide

<400> SEQUENCE: 378

```
Tyr Ile Ile Gln Gly Arg Gly Ile Thr Gly Pro Thr Phe
1               5                   10
```

<210> SEQ ID NO 379
<211> LENGTH: 14
<212> TYPE: PRT
<213> ORGANISM: Artificial Sequence
<220> FEATURE:
<223> OTHER INFORMATION: Synthetic peptide

<400> SEQUENCE: 379

```
Lys Thr Asn Pro Asn Ser Met Val Ser His Ile Ala Gly Lys
1               5                   10
```

<210> SEQ ID NO 380
<211> LENGTH: 13
<212> TYPE: PRT
<213> ORGANISM: Artificial Sequence
<220> FEATURE:
<223> OTHER INFORMATION: Synthetic peptide

<400> SEQUENCE: 380

```
Thr Asn Pro Asn Ser Met Val Ser His Ile Ala Gly Lys
1               5                   10
```

```
<210> SEQ ID NO 381
<211> LENGTH: 12
<212> TYPE: PRT
<213> ORGANISM: Artificial Sequence
<220> FEATURE:
<223> OTHER INFORMATION: Synthetic peptide

<400> SEQUENCE: 381

Pro Asn Ser Met Val Ser His Ile Ala Gly Lys Ser
1               5                   10

<210> SEQ ID NO 382
<211> LENGTH: 20
<212> TYPE: PRT
<213> ORGANISM: Artificial Sequence
<220> FEATURE:
<223> OTHER INFORMATION: Synthetic peptide

<400> SEQUENCE: 382

Asn Ile Asp Asn Pro Asn Arg Ala Asp Thr Tyr Asn Pro Arg Ala Gly
1               5                   10                  15

Arg Val Thr Asn
            20

<210> SEQ ID NO 383
<211> LENGTH: 11
<212> TYPE: PRT
<213> ORGANISM: Artificial Sequence
<220> FEATURE:
<223> OTHER INFORMATION: Synthetic peptide

<400> SEQUENCE: 383

Gln Arg Asp Phe Leu Leu Ala Gly Asn Lys Arg
1               5                   10

<210> SEQ ID NO 384
<211> LENGTH: 12
<212> TYPE: PRT
<213> ORGANISM: Artificial Sequence
<220> FEATURE:
<223> OTHER INFORMATION: Synthetic peptide

<400> SEQUENCE: 384

Leu Leu Gln Pro Tyr Ala Ser Leu Gln Glu Gln Glu
1               5                   10

<210> SEQ ID NO 385
<211> LENGTH: 10
<212> TYPE: PRT
<213> ORGANISM: Artificial Sequence
<220> FEATURE:
<223> OTHER INFORMATION: Synthetic peptide

<400> SEQUENCE: 385

Gln Arg Asp Phe Leu Leu Ala Gly Asn Lys
1               5                   10

<210> SEQ ID NO 386
<211> LENGTH: 11
<212> TYPE: PRT
<213> ORGANISM: Artificial Sequence
<220> FEATURE:
<223> OTHER INFORMATION: Synthetic peptide

<400> SEQUENCE: 386
```

```
Gln Glu Gln Glu Gln Gly Gln Met Gln Ser Arg
1               5                   10
```

<210> SEQ ID NO 387
<211> LENGTH: 13
<212> TYPE: PRT
<213> ORGANISM: Artificial Sequence
<220> FEATURE:
<223> OTHER INFORMATION: Synthetic peptide

<400> SEQUENCE: 387

```
Ser Leu Leu Gln Pro Tyr Ala Ser Leu Gln Glu Gln Glu
1               5                   10
```

<210> SEQ ID NO 388
<211> LENGTH: 11
<212> TYPE: PRT
<213> ORGANISM: Artificial Sequence
<220> FEATURE:
<223> OTHER INFORMATION: Synthetic peptide

<400> SEQUENCE: 388

```
Ala Ser Leu Gln Glu Gln Glu Gln Gly Gln Met
1               5                   10
```

<210> SEQ ID NO 389
<211> LENGTH: 14
<212> TYPE: PRT
<213> ORGANISM: Artificial Sequence
<220> FEATURE:
<223> OTHER INFORMATION: Synthetic peptide

<400> SEQUENCE: 389

```
Ala Ser Leu Gln Glu Gln Glu Gln Gly Gln Met Gln Ser Arg
1               5                   10
```

<210> SEQ ID NO 390
<211> LENGTH: 9
<212> TYPE: PRT
<213> ORGANISM: Artificial Sequence
<220> FEATURE:
<223> OTHER INFORMATION: Synthetic peptide

<400> SEQUENCE: 390

```
Asp Phe Leu Leu Ala Gly Asn Lys Arg
1               5
```

<210> SEQ ID NO 391
<211> LENGTH: 18
<212> TYPE: PRT
<213> ORGANISM: Artificial Sequence
<220> FEATURE:
<223> OTHER INFORMATION: Synthetic peptide

<400> SEQUENCE: 391

```
Gln Ala Phe Glu Pro Ile Arg Ser Val Arg Ser Gln Ala Gly Thr Thr
1               5                   10                  15

Glu Phe
```

<210> SEQ ID NO 392
<211> LENGTH: 18
<212> TYPE: PRT
<213> ORGANISM: Artificial Sequence
<220> FEATURE:
<223> OTHER INFORMATION: Synthetic peptide

<400> SEQUENCE: 392

```
Lys Thr Asn Pro Asn Ser Met Val Ser His Ile Ala Gly Lys Ser Ser
1               5                   10                  15

Ile Phe

<210> SEQ ID NO 393
<211> LENGTH: 21
<212> TYPE: PRT
<213> ORGANISM: Artificial Sequence
<220> FEATURE:
<223> OTHER INFORMATION: Synthetic peptide

<400> SEQUENCE: 393

Val Arg Arg Val Ile Glu Pro Arg Gly Leu Leu Leu Pro His Tyr Thr
1               5                   10                  15

Asn Gly Ala Ser Leu
            20

<210> SEQ ID NO 394
<211> LENGTH: 17
<212> TYPE: PRT
<213> ORGANISM: Artificial Sequence
<220> FEATURE:
<223> OTHER INFORMATION: Synthetic peptide

<400> SEQUENCE: 394

Phe Gly Ala Phe Thr Pro Leu Gln Tyr Lys Ser Tyr Gln Asp Val Tyr
1               5                   10                  15

Asn

<210> SEQ ID NO 395
<211> LENGTH: 10
<212> TYPE: PRT
<213> ORGANISM: Artificial Sequence
<220> FEATURE:
<223> OTHER INFORMATION: Synthetic peptide

<400> SEQUENCE: 395

Ile Ala Leu Pro Ala Gly Val Ala His Trp
1               5                   10

<210> SEQ ID NO 396
<211> LENGTH: 25
<212> TYPE: PRT
<213> ORGANISM: Artificial Sequence
<220> FEATURE:
<223> OTHER INFORMATION: Synthetic peptide

<400> SEQUENCE: 396

Arg Val Arg Gln Asn Ile Asp Asn Pro Asn Arg Ala Asp Thr Tyr Asn
1               5                   10                  15

Pro Arg Ala Gly Arg Val Thr Asn Leu
            20                  25

<210> SEQ ID NO 397
<211> LENGTH: 21
<212> TYPE: PRT
<213> ORGANISM: Artificial Sequence
<220> FEATURE:
<223> OTHER INFORMATION: Synthetic peptide

<400> SEQUENCE: 397

Asn Ile Asp Asn Pro Asn Arg Ala Asp Thr Tyr Asn Pro Arg Ala Gly
1               5                   10                  15
```

Arg Val Thr Asn Leu
            20

<210> SEQ ID NO 398
<211> LENGTH: 16
<212> TYPE: PRT
<213> ORGANISM: Artificial Sequence
<220> FEATURE:
<223> OTHER INFORMATION: Synthetic peptide

<400> SEQUENCE: 398

Gly Ala Phe Thr Pro Leu Gln Tyr Lys Ser Tyr Gln Asp Val Tyr Asn
1               5                   10                  15

<210> SEQ ID NO 399
<211> LENGTH: 16
<212> TYPE: PRT
<213> ORGANISM: Artificial Sequence
<220> FEATURE:
<223> OTHER INFORMATION: Synthetic peptide

<400> SEQUENCE: 399

Pro Asn Ser Met Val Ser His Ile Ala Gly Lys Ser Ser Ile Phe Arg
1               5                   10                  15

<210> SEQ ID NO 400
<211> LENGTH: 19
<212> TYPE: PRT
<213> ORGANISM: Artificial Sequence
<220> FEATURE:
<223> OTHER INFORMATION: Synthetic peptide

<400> SEQUENCE: 400

Arg Leu Gln Ala Phe Glu Pro Ile Arg Ser Val Arg Ser Gln Ala Gly
1               5                   10                  15

Thr Thr Glu

<210> SEQ ID NO 401
<211> LENGTH: 18
<212> TYPE: PRT
<213> ORGANISM: Artificial Sequence
<220> FEATURE:
<223> OTHER INFORMATION: Synthetic peptide

<400> SEQUENCE: 401

Thr Asn Pro Asn Ser Met Val Ser His Ile Ala Gly Lys Ser Ser Ile
1               5                   10                  15

Phe Arg

<210> SEQ ID NO 402
<211> LENGTH: 11
<212> TYPE: PRT
<213> ORGANISM: Artificial Sequence
<220> FEATURE:
<223> OTHER INFORMATION: Synthetic peptide

<400> SEQUENCE: 402

Glu Leu Gly Ala Pro Asp Val Gly His Pro Met
1               5                   10

<210> SEQ ID NO 403
<211> LENGTH: 10
<212> TYPE: PRT
<213> ORGANISM: Artificial Sequence
<220> FEATURE:
<223> OTHER INFORMATION: Synthetic peptide

```
<400> SEQUENCE: 403

Leu Gly Ala Pro Asp Val Gly His Pro Met
1               5                   10

<210> SEQ ID NO 404
<211> LENGTH: 15
<212> TYPE: PRT
<213> ORGANISM: Artificial Sequence
<220> FEATURE:
<223> OTHER INFORMATION: Synthetic peptide

<400> SEQUENCE: 404

Glu Leu Gly Ala Pro Asp Val Gly His Pro Met Ser Glu Val Phe
1               5                   10                  15

<210> SEQ ID NO 405
<211> LENGTH: 12
<212> TYPE: PRT
<213> ORGANISM: Artificial Sequence
<220> FEATURE:
<223> OTHER INFORMATION: Synthetic peptide

<400> SEQUENCE: 405

Glu Leu Gly Ala Pro Asp Val Gly His Pro Met Ser
1               5                   10

<210> SEQ ID NO 406
<211> LENGTH: 16
<212> TYPE: PRT
<213> ORGANISM: Artificial Sequence
<220> FEATURE:
<223> OTHER INFORMATION: Synthetic peptide

<400> SEQUENCE: 406

Glu Leu Gly Ala Pro Asp Val Gly His Pro Met Ser Glu Val Phe Arg
1               5                   10                  15

<210> SEQ ID NO 407
<211> LENGTH: 14
<212> TYPE: PRT
<213> ORGANISM: Artificial Sequence
<220> FEATURE:
<223> OTHER INFORMATION: Synthetic peptide

<400> SEQUENCE: 407

Glu Leu Gly Ala Pro Asp Val Gly His Pro Met Ser Glu Val
1               5                   10

<210> SEQ ID NO 408
<211> LENGTH: 13
<212> TYPE: PRT
<213> ORGANISM: Artificial Sequence
<220> FEATURE:
<223> OTHER INFORMATION: Synthetic peptide

<400> SEQUENCE: 408

Glu Leu Gly Ala Pro Asp Val Gly His Pro Met Ser Glu
1               5                   10

<210> SEQ ID NO 409
<211> LENGTH: 12
<212> TYPE: PRT
<213> ORGANISM: Artificial Sequence
<220> FEATURE:
<223> OTHER INFORMATION: Synthetic peptide
```

```
<400> SEQUENCE: 409

Leu Gly Ala Pro Asp Val Gly His Pro Met Ser Glu
1               5                   10

<210> SEQ ID NO 410
<211> LENGTH: 15
<212> TYPE: PRT
<213> ORGANISM: Artificial Sequence
<220> FEATURE:
<223> OTHER INFORMATION: Synthetic peptide

<400> SEQUENCE: 410

Tyr Arg Glu Leu Gly Ala Pro Asp Val Gly His Pro Met Ser Glu
1               5                   10                  15

<210> SEQ ID NO 411
<211> LENGTH: 13
<212> TYPE: PRT
<213> ORGANISM: Artificial Sequence
<220> FEATURE:
<223> OTHER INFORMATION: Synthetic peptide

<400> SEQUENCE: 411

Leu Gly Ala Pro Asp Val Gly His Pro Met Ser Glu Val
1               5                   10

<210> SEQ ID NO 412
<211> LENGTH: 14
<212> TYPE: PRT
<213> ORGANISM: Artificial Sequence
<220> FEATURE:
<223> OTHER INFORMATION: Synthetic peptide

<400> SEQUENCE: 412

Arg Glu Leu Gly Ala Pro Asp Val Gly His Pro Met Ser Glu
1               5                   10

<210> SEQ ID NO 413
<211> LENGTH: 16
<212> TYPE: PRT
<213> ORGANISM: Artificial Sequence
<220> FEATURE:
<223> OTHER INFORMATION: Synthetic peptide

<400> SEQUENCE: 413

Ala Pro Thr Gly Thr Phe Ile Ala Ser Gly Val Val Gly Lys Asp
1               5                   10                  15

<210> SEQ ID NO 414
<211> LENGTH: 17
<212> TYPE: PRT
<213> ORGANISM: Artificial Sequence
<220> FEATURE:
<223> OTHER INFORMATION: Synthetic peptide

<400> SEQUENCE: 414

Leu Ala Ile Val Lys Phe Ser Pro Asn Glu Gln Asn Lys His Ile Gly
1               5                   10                  15

Glu

<210> SEQ ID NO 415
<211> LENGTH: 21
<212> TYPE: PRT
<213> ORGANISM: Artificial Sequence
<220> FEATURE:
<223> OTHER INFORMATION: Synthetic peptide
```

<400> SEQUENCE: 415

Arg His Gln Ile Thr Asp Thr Thr Asn Gly His Tyr Ala Pro Val Thr
1               5                   10                  15

Tyr Ile Gln Val Glu
            20

<210> SEQ ID NO 416
<211> LENGTH: 19
<212> TYPE: PRT
<213> ORGANISM: Artificial Sequence
<220> FEATURE:
<223> OTHER INFORMATION: Synthetic peptide

<400> SEQUENCE: 416

Gly Asp Leu Ala Ile Val Lys Phe Ser Pro Asn Glu Gln Asn Lys His
1               5                   10                  15

Ile Gly Glu

<210> SEQ ID NO 417
<211> LENGTH: 18
<212> TYPE: PRT
<213> ORGANISM: Artificial Sequence
<220> FEATURE:
<223> OTHER INFORMATION: Synthetic peptide

<400> SEQUENCE: 417

Asn Pro Asp Asn Pro Asp Asn Pro Asn Asn Pro Asp Asn Pro Asn Asn
1               5                   10                  15

Pro Asp

<210> SEQ ID NO 418
<211> LENGTH: 9
<212> TYPE: PRT
<213> ORGANISM: Artificial Sequence
<220> FEATURE:
<223> OTHER INFORMATION: Synthetic peptide

<400> SEQUENCE: 418

Gln Ser Phe Ile Leu Ser Gly Asn Glu
1               5

<210> SEQ ID NO 419
<211> LENGTH: 9
<212> TYPE: PRT
<213> ORGANISM: Artificial Sequence
<220> FEATURE:
<223> OTHER INFORMATION: Synthetic peptide

<400> SEQUENCE: 419

Glu Ser Phe Leu Leu Ser Gly Asn Gln
1               5

<210> SEQ ID NO 420
<211> LENGTH: 9
<212> TYPE: PRT
<213> ORGANISM: Artificial Sequence
<220> FEATURE:
<223> OTHER INFORMATION: Synthetic peptide

<400> SEQUENCE: 420

Gln Ser Tyr Leu Leu Ser Gly Asn Gln
1               5

```
<210> SEQ ID NO 421
<211> LENGTH: 9
<212> TYPE: PRT
<213> ORGANISM: Artificial Sequence
<220> FEATURE:
<223> OTHER INFORMATION: Synthetic peptide

<400> SEQUENCE: 421

Gln Ser Phe Leu Leu Ser Gly Asp Gln
1               5

<210> SEQ ID NO 422
<211> LENGTH: 9
<212> TYPE: PRT
<213> ORGANISM: Artificial Sequence
<220> FEATURE:
<223> OTHER INFORMATION: Synthetic peptide

<400> SEQUENCE: 422

Gln Ser Tyr Leu Leu Ser Gly Asn Glu
1               5

<210> SEQ ID NO 423
<211> LENGTH: 9
<212> TYPE: PRT
<213> ORGANISM: Artificial Sequence
<220> FEATURE:
<223> OTHER INFORMATION: Synthetic peptide

<400> SEQUENCE: 423

Glu Ser Phe Leu Leu Ser Gly Asn Glu
1               5

<210> SEQ ID NO 424
<211> LENGTH: 9
<212> TYPE: PRT
<213> ORGANISM: Artificial Sequence
<220> FEATURE:
<223> OTHER INFORMATION: Synthetic peptide

<400> SEQUENCE: 424

Glu Ser Tyr Leu Leu Ser Gly Asn Gln
1               5

<210> SEQ ID NO 425
<211> LENGTH: 9
<212> TYPE: PRT
<213> ORGANISM: Artificial Sequence
<220> FEATURE:
<223> OTHER INFORMATION: Synthetic peptide

<400> SEQUENCE: 425

Gln Ser Phe Leu Leu Ser Gly Asp Glu
1               5

<210> SEQ ID NO 426
<211> LENGTH: 9
<212> TYPE: PRT
<213> ORGANISM: Artificial Sequence
<220> FEATURE:
<223> OTHER INFORMATION: Synthetic peptide

<400> SEQUENCE: 426

Gln Ser Tyr Leu Leu Ser Gly Asp Gln
1               5

<210> SEQ ID NO 427
```

```
<211> LENGTH: 9
<212> TYPE: PRT
<213> ORGANISM: Artificial Sequence
<220> FEATURE:
<223> OTHER INFORMATION: Synthetic peptide

<400> SEQUENCE: 427

Gln Ser Phe Arg Leu Ser Gly Asn Gln
1               5

<210> SEQ ID NO 428
<211> LENGTH: 9
<212> TYPE: PRT
<213> ORGANISM: Artificial Sequence
<220> FEATURE:
<223> OTHER INFORMATION: Synthetic peptide

<400> SEQUENCE: 428

Gln Ser Phe Leu Leu Ser Tyr Asn Gln
1               5

<210> SEQ ID NO 429
<211> LENGTH: 9
<212> TYPE: PRT
<213> ORGANISM: Artificial Sequence
<220> FEATURE:
<223> OTHER INFORMATION: Synthetic peptide

<400> SEQUENCE: 429

Gln Phe Phe Leu Leu Ser Gly Asn Gln
1               5

<210> SEQ ID NO 430
<211> LENGTH: 9
<212> TYPE: PRT
<213> ORGANISM: Artificial Sequence
<220> FEATURE:
<223> OTHER INFORMATION: Synthetic peptide

<400> SEQUENCE: 430

Gln Ser Phe Leu Leu Ser Gly Ala Gln
1               5

<210> SEQ ID NO 431
<211> LENGTH: 9
<212> TYPE: PRT
<213> ORGANISM: Artificial Sequence
<220> FEATURE:
<223> OTHER INFORMATION: Synthetic peptide

<400> SEQUENCE: 431

Gln Ser Phe Leu Leu Ser Gly Asn Pro
1               5

<210> SEQ ID NO 432
<211> LENGTH: 9
<212> TYPE: PRT
<213> ORGANISM: Artificial Sequence
<220> FEATURE:
<223> OTHER INFORMATION: Synthetic peptide

<400> SEQUENCE: 432

Gln Ser Phe Arg Arg Ser Gly Asn Gln
1               5

<210> SEQ ID NO 433
<211> LENGTH: 9
```

```
<212> TYPE: PRT
<213> ORGANISM: Artificial Sequence
<220> FEATURE:
<223> OTHER INFORMATION: Synthetic peptide

<400> SEQUENCE: 433

Gln Ser Phe Leu Leu Ser Tyr Ile Gln
1               5

<210> SEQ ID NO 434
<211> LENGTH: 9
<212> TYPE: PRT
<213> ORGANISM: Artificial Sequence
<220> FEATURE:
<223> OTHER INFORMATION: Synthetic peptide

<400> SEQUENCE: 434

Gln Phe Phe Leu Leu Ser Gly Asn Leu
1               5

<210> SEQ ID NO 435
<211> LENGTH: 10
<212> TYPE: PRT
<213> ORGANISM: Artificial Sequence
<220> FEATURE:
<223> OTHER INFORMATION: Synthetic peptide

<400> SEQUENCE: 435

Gln Ser Phe Leu Leu Ser Gly Ala Gln Ala
1               5                   10

<210> SEQ ID NO 436
<211> LENGTH: 9
<212> TYPE: PRT
<213> ORGANISM: Artificial Sequence
<220> FEATURE:
<223> OTHER INFORMATION: Synthetic peptide

<400> SEQUENCE: 436

Gln Ser Phe Leu Leu Ser Gly Asn Pro
1               5

<210> SEQ ID NO 437
<211> LENGTH: 10
<212> TYPE: PRT
<213> ORGANISM: Artificial Sequence
<220> FEATURE:
<223> OTHER INFORMATION: Synthetic peptide

<400> SEQUENCE: 437

Gln Ser Phe Leu Leu Ser Gly Asn Gln Gln
1               5                   10

<210> SEQ ID NO 438
<211> LENGTH: 10
<212> TYPE: PRT
<213> ORGANISM: Artificial Sequence
<220> FEATURE:
<223> OTHER INFORMATION: Synthetic peptide

<400> SEQUENCE: 438

Gln Ser Phe Leu Leu Leu Ser Gly Asn Gln
1               5                   10

<210> SEQ ID NO 439
<211> LENGTH: 11
<212> TYPE: PRT
```

```
<213> ORGANISM: Artificial Sequence
<220> FEATURE:
<223> OTHER INFORMATION: Synthetic peptide

<400> SEQUENCE: 439

Ala Gln Ser Phe Gly Leu Leu Ser Gly Asn Gln
1               5                   10

<210> SEQ ID NO 440
<211> LENGTH: 11
<212> TYPE: PRT
<213> ORGANISM: Artificial Sequence
<220> FEATURE:
<223> OTHER INFORMATION: Synthetic peptide

<400> SEQUENCE: 440

Arg Gln Ser Phe Leu Leu Ile Ser Gly Asn Gln
1               5                   10

<210> SEQ ID NO 441
<211> LENGTH: 10
<212> TYPE: PRT
<213> ORGANISM: Artificial Sequence
<220> FEATURE:
<223> OTHER INFORMATION: Synthetic peptide

<400> SEQUENCE: 441

Gln Ser Phe Leu Leu Ser Gly Asn Gln Lys
1               5                   10

<210> SEQ ID NO 442
<211> LENGTH: 8
<212> TYPE: PRT
<213> ORGANISM: Artificial Sequence
<220> FEATURE:
<223> OTHER INFORMATION: Synthetic peptide

<400> SEQUENCE: 442

Gln Phe Leu Leu Ser Gly Asn Gln
1               5

<210> SEQ ID NO 443
<211> LENGTH: 8
<212> TYPE: PRT
<213> ORGANISM: Artificial Sequence
<220> FEATURE:
<223> OTHER INFORMATION: Synthetic peptide

<400> SEQUENCE: 443

Ser Phe Leu Leu Ser Gly Asn Gln
1               5

<210> SEQ ID NO 444
<211> LENGTH: 8
<212> TYPE: PRT
<213> ORGANISM: Artificial Sequence
<220> FEATURE:
<223> OTHER INFORMATION: Synthetic peptide

<400> SEQUENCE: 444

Gln Ser Phe Leu Leu Ser Gly Asn
1               5

<210> SEQ ID NO 445
<211> LENGTH: 9
<212> TYPE: PRT
<213> ORGANISM: Artificial Sequence
```

```
<220> FEATURE:
<223> OTHER INFORMATION: Synthetic peptide

<400> SEQUENCE: 445

Gln Ser Phe Leu Leu Ser Gly Asn Gln
1               5

<210> SEQ ID NO 446
<211> LENGTH: 8
<212> TYPE: PRT
<213> ORGANISM: Artificial Sequence
<220> FEATURE:
<223> OTHER INFORMATION: Synthetic peptide

<400> SEQUENCE: 446

Gln Ser Phe Leu Ser Gly Asn Gln
1               5

<210> SEQ ID NO 447
<211> LENGTH: 8
<212> TYPE: PRT
<213> ORGANISM: Artificial Sequence
<220> FEATURE:
<223> OTHER INFORMATION: Synthetic peptide

<400> SEQUENCE: 447

Gln Ser Leu Leu Ser Gly Asn Gln
1               5

<210> SEQ ID NO 448
<211> LENGTH: 8
<212> TYPE: PRT
<213> ORGANISM: Artificial Sequence
<220> FEATURE:
<223> OTHER INFORMATION: Synthetic peptide

<400> SEQUENCE: 448

Ser Phe Leu Leu Ser Gly Asn Gln
1               5

<210> SEQ ID NO 449
<211> LENGTH: 8
<212> TYPE: PRT
<213> ORGANISM: Artificial Sequence
<220> FEATURE:
<223> OTHER INFORMATION: Synthetic peptide

<400> SEQUENCE: 449

Gln Ser Phe Leu Leu Ser Gly Asn
1               5

<210> SEQ ID NO 450
<211> LENGTH: 7
<212> TYPE: PRT
<213> ORGANISM: Artificial Sequence
<220> FEATURE:
<223> OTHER INFORMATION: Synthetic peptide

<400> SEQUENCE: 450

Ser Phe Leu Leu Ser Gly Asn
1               5

<210> SEQ ID NO 451
<211> LENGTH: 7
<212> TYPE: PRT
<213> ORGANISM: Artificial Sequence
<220> FEATURE:
```

<223> OTHER INFORMATION: Synthetic peptide

<400> SEQUENCE: 451

Gln Ser Phe Ser Gly Asn Gln
1               5

<210> SEQ ID NO 452
<211> LENGTH: 11
<212> TYPE: PRT
<213> ORGANISM: Artificial Sequence
<220> FEATURE:
<223> OTHER INFORMATION: Synthetic peptide

<400> SEQUENCE: 452

His Pro Arg Pro Pro Lys Pro Asp Ala Pro Arg
1               5                   10

<210> SEQ ID NO 453
<211> LENGTH: 10
<212> TYPE: PRT
<213> ORGANISM: Artificial Sequence
<220> FEATURE:
<223> OTHER INFORMATION: Synthetic peptide

<400> SEQUENCE: 453

Leu Gln Gln Ala Pro Pro Pro Pro Gln Arg
1               5                   10

<210> SEQ ID NO 454
<211> LENGTH: 11
<212> TYPE: PRT
<213> ORGANISM: Artificial Sequence
<220> FEATURE:
<223> OTHER INFORMATION: Synthetic peptide

<400> SEQUENCE: 454

Val Gly Trp Gly Glu Gln Pro Trp Ser Pro Tyr
1               5                   10

<210> SEQ ID NO 455
<211> LENGTH: 5
<212> TYPE: PRT
<213> ORGANISM: Artificial Sequence
<220> FEATURE:
<223> OTHER INFORMATION: Synthetic peptide

<400> SEQUENCE: 455

Phe His Met Pro Pro
1               5

<210> SEQ ID NO 456
<211> LENGTH: 4
<212> TYPE: PRT
<213> ORGANISM: Artificial Sequence
<220> FEATURE:
<223> OTHER INFORMATION: Synthetic peptide

<400> SEQUENCE: 456

Phe Arg Arg Pro
1

<210> SEQ ID NO 457
<211> LENGTH: 4
<212> TYPE: PRT
<213> ORGANISM: Artificial Sequence
<220> FEATURE:
<223> OTHER INFORMATION: Synthetic peptide

<400> SEQUENCE: 457

Phe Trp Met Ala
1

<210> SEQ ID NO 458
<211> LENGTH: 5
<212> TYPE: PRT
<213> ORGANISM: Artificial Sequence
<220> FEATURE:
<223> OTHER INFORMATION: Synthetic peptide

<400> SEQUENCE: 458

His Met Pro Pro Ser
1               5

<210> SEQ ID NO 459
<211> LENGTH: 11
<212> TYPE: PRT
<213> ORGANISM: Artificial Sequence
<220> FEATURE:
<223> OTHER INFORMATION: Synthetic peptide

<400> SEQUENCE: 459

Pro Val Glu Met Pro Thr Leu Leu Tyr Pro Ser
1               5                   10

<210> SEQ ID NO 460
<211> LENGTH: 5
<212> TYPE: PRT
<213> ORGANISM: Artificial Sequence
<220> FEATURE:
<223> OTHER INFORMATION: Synthetic peptide

<400> SEQUENCE: 460

His Met Pro Ser Ser
1               5

<210> SEQ ID NO 461
<211> LENGTH: 4
<212> TYPE: PRT
<213> ORGANISM: Artificial Sequence
<220> FEATURE:
<223> OTHER INFORMATION: Synthetic peptide

<400> SEQUENCE: 461

His Arg Phe Arg
1

<210> SEQ ID NO 462
<211> LENGTH: 4
<212> TYPE: PRT
<213> ORGANISM: Artificial Sequence
<220> FEATURE:
<223> OTHER INFORMATION: Synthetic peptide

<400> SEQUENCE: 462

His Arg Arg Ser
1

<210> SEQ ID NO 463
<211> LENGTH: 4
<212> TYPE: PRT
<213> ORGANISM: Artificial Sequence
<220> FEATURE:
<223> OTHER INFORMATION: Synthetic peptide

```
<400> SEQUENCE: 463

His Ser Pro Arg
1

<210> SEQ ID NO 464
<211> LENGTH: 4
<212> TYPE: PRT
<213> ORGANISM: Artificial Sequence
<220> FEATURE:
<223> OTHER INFORMATION: Synthetic peptide

<400> SEQUENCE: 464

His Trp Phe Ala
1

<210> SEQ ID NO 465
<211> LENGTH: 4
<212> TYPE: PRT
<213> ORGANISM: Artificial Sequence
<220> FEATURE:
<223> OTHER INFORMATION: Synthetic peptide

<400> SEQUENCE: 465

Met Phe Arg Arg
1

<210> SEQ ID NO 466
<211> LENGTH: 5
<212> TYPE: PRT
<213> ORGANISM: Artificial Sequence
<220> FEATURE:
<223> OTHER INFORMATION: Synthetic peptide

<400> SEQUENCE: 466

Met Phe Arg Arg Pro
1               5

<210> SEQ ID NO 467
<211> LENGTH: 4
<212> TYPE: PRT
<213> ORGANISM: Artificial Sequence
<220> FEATURE:
<223> OTHER INFORMATION: Synthetic peptide

<400> SEQUENCE: 467

Met Pro Pro Ser
1

<210> SEQ ID NO 468
<211> LENGTH: 4
<212> TYPE: PRT
<213> ORGANISM: Artificial Sequence
<220> FEATURE:
<223> OTHER INFORMATION: Synthetic peptide

<400> SEQUENCE: 468

Met Pro Arg Arg
1

<210> SEQ ID NO 469
<211> LENGTH: 4
<212> TYPE: PRT
<213> ORGANISM: Artificial Sequence
<220> FEATURE:
<223> OTHER INFORMATION: Synthetic peptide

<400> SEQUENCE: 469
```

```
Asn Met Pro Ser
1

<210> SEQ ID NO 470
<211> LENGTH: 4
<212> TYPE: PRT
<213> ORGANISM: Artificial Sequence
<220> FEATURE:
<223> OTHER INFORMATION: Synthetic peptide

<400> SEQUENCE: 470

Pro His Met Pro
1

<210> SEQ ID NO 471
<211> LENGTH: 5
<212> TYPE: PRT
<213> ORGANISM: Artificial Sequence
<220> FEATURE:
<223> OTHER INFORMATION: Synthetic peptide

<400> SEQUENCE: 471

Pro His Met Pro Ser
1               5

<210> SEQ ID NO 472
<211> LENGTH: 4
<212> TYPE: PRT
<213> ORGANISM: Artificial Sequence
<220> FEATURE:
<223> OTHER INFORMATION: Synthetic peptide

<400> SEQUENCE: 472

Pro Arg Arg Phe
1

<210> SEQ ID NO 473
<211> LENGTH: 4
<212> TYPE: PRT
<213> ORGANISM: Artificial Sequence
<220> FEATURE:
<223> OTHER INFORMATION: Synthetic peptide

<400> SEQUENCE: 473

Trp Met Lys Ala
1

<210> SEQ ID NO 474
<211> LENGTH: 11
<212> TYPE: PRT
<213> ORGANISM: Artificial Sequence
<220> FEATURE:
<223> OTHER INFORMATION: Synthetic peptide

<400> SEQUENCE: 474

Asp Ser Ile Asn Ala Leu Glu Pro Asp His Arg
1               5                   10

<210> SEQ ID NO 475
<211> LENGTH: 9
<212> TYPE: PRT
<213> ORGANISM: Artificial Sequence
<220> FEATURE:
<223> OTHER INFORMATION: Synthetic peptide

<400> SEQUENCE: 475
```

Glu Leu Thr Phe Pro Gly Ser Val Gln
1               5

<210> SEQ ID NO 476
<211> LENGTH: 10
<212> TYPE: PRT
<213> ORGANISM: Artificial Sequence
<220> FEATURE:
<223> OTHER INFORMATION: Synthetic peptide

<400> SEQUENCE: 476

Glu Leu Thr Phe Pro Gly Ser Val Gln Glu
1               5                   10

<210> SEQ ID NO 477
<211> LENGTH: 11
<212> TYPE: PRT
<213> ORGANISM: Artificial Sequence
<220> FEATURE:
<223> OTHER INFORMATION: Synthetic peptide

<400> SEQUENCE: 477

Ile Phe Glu Asp Ala Ile Thr Ile Pro Gly Arg
1               5                   10

<210> SEQ ID NO 478
<211> LENGTH: 13
<212> TYPE: PRT
<213> ORGANISM: Artificial Sequence
<220> FEATURE:
<223> OTHER INFORMATION: Synthetic peptide

<400> SEQUENCE: 478

Leu Asp Ala Leu Glu Pro Asp Asn Arg Ile Glu Ser Glu
1               5                   10

<210> SEQ ID NO 479
<211> LENGTH: 10
<212> TYPE: PRT
<213> ORGANISM: Artificial Sequence
<220> FEATURE:
<223> OTHER INFORMATION: Synthetic peptide

<400> SEQUENCE: 479

Lys Thr Leu Asp Tyr Trp Pro Ser Leu Arg
1               5                   10

<210> SEQ ID NO 480
<211> LENGTH: 9
<212> TYPE: PRT
<213> ORGANISM: Artificial Sequence
<220> FEATURE:
<223> OTHER INFORMATION: Synthetic peptide

<400> SEQUENCE: 480

Arg His Gly Glu Trp Gly Pro Ser Tyr
1               5

<210> SEQ ID NO 481
<211> LENGTH: 11
<212> TYPE: PRT
<213> ORGANISM: Artificial Sequence
<220> FEATURE:
<223> OTHER INFORMATION: Synthetic peptide

<400> SEQUENCE: 481

Ile Leu Val Asp Gly Ser His Asp Ile Glu Arg

```
1               5              10
```

<210> SEQ ID NO 482
<211> LENGTH: 11
<212> TYPE: PRT
<213> ORGANISM: Artificial Sequence
<220> FEATURE:
<223> OTHER INFORMATION: Synthetic peptide

<400> SEQUENCE: 482

```
Ile Leu Val Asp Gly Ser His Asp Ile Glu Arg
1               5                   10
```

<210> SEQ ID NO 483
<211> LENGTH: 11
<212> TYPE: PRT
<213> ORGANISM: Artificial Sequence
<220> FEATURE:
<223> OTHER INFORMATION: Synthetic peptide

<400> SEQUENCE: 483

```
Asn Leu Ala Gln Ala Pro Ala Gln Ala Leu Leu
1               5                   10
```

<210> SEQ ID NO 484
<211> LENGTH: 7
<212> TYPE: PRT
<213> ORGANISM: Artificial Sequence
<220> FEATURE:
<223> OTHER INFORMATION: Synthetic peptide

<400> SEQUENCE: 484

```
Phe Leu Pro Gln His Thr Asp
1               5
```

<210> SEQ ID NO 485
<211> LENGTH: 6
<212> TYPE: PRT
<213> ORGANISM: Artificial Sequence
<220> FEATURE:
<223> OTHER INFORMATION: Synthetic peptide

<400> SEQUENCE: 485

```
Leu Glu Pro Asp Asn Arg
1               5
```

<210> SEQ ID NO 486
<211> LENGTH: 6
<212> TYPE: PRT
<213> ORGANISM: Artificial Sequence
<220> FEATURE:
<223> OTHER INFORMATION: Synthetic peptide

<400> SEQUENCE: 486

```
Leu Gln Ser Gln Asn Asp
1               5
```

<210> SEQ ID NO 487
<211> LENGTH: 11
<212> TYPE: PRT
<213> ORGANISM: Artificial Sequence
<220> FEATURE:
<223> OTHER INFORMATION: Synthetic peptide

<400> SEQUENCE: 487

```
Leu Gln Ser Gln Asn Asp Gln Arg Gly Glu Ile
1               5                   10
```

<210> SEQ ID NO 488
<211> LENGTH: 14
<212> TYPE: PRT
<213> ORGANISM: Artificial Sequence
<220> FEATURE:
<223> OTHER INFORMATION: Synthetic peptide

<400> SEQUENCE: 488

Gln Ser Gln Asn Asp Gln Arg Gly Glu Ile Ile His Val Lys
1               5                   10

<210> SEQ ID NO 489
<211> LENGTH: 8
<212> TYPE: PRT
<213> ORGANISM: Artificial Sequence
<220> FEATURE:
<223> OTHER INFORMATION: Synthetic peptide

<400> SEQUENCE: 489

Arg Gly Glu Ile Ile His Val Lys
1               5

<210> SEQ ID NO 490
<211> LENGTH: 8
<212> TYPE: PRT
<213> ORGANISM: Artificial Sequence
<220> FEATURE:
<223> OTHER INFORMATION: Synthetic peptide

<400> SEQUENCE: 490

Arg Leu Gln Ser Gln Asn Asp Gln
1               5

<210> SEQ ID NO 491
<211> LENGTH: 10
<212> TYPE: PRT
<213> ORGANISM: Artificial Sequence
<220> FEATURE:
<223> OTHER INFORMATION: Synthetic peptide

<400> SEQUENCE: 491

Arg Leu Gln Ser Gln Asn Asp Gln Arg Gly
1               5                   10

<210> SEQ ID NO 492
<211> LENGTH: 14
<212> TYPE: PRT
<213> ORGANISM: Artificial Sequence
<220> FEATURE:
<223> OTHER INFORMATION: Synthetic peptide

<400> SEQUENCE: 492

Arg Leu Gln Ser Gln Asn Asp Gln Arg Gly Glu Ile Ile His
1               5                   10

<210> SEQ ID NO 493
<211> LENGTH: 9
<212> TYPE: PRT
<213> ORGANISM: Artificial Sequence
<220> FEATURE:
<223> OTHER INFORMATION: Synthetic peptide

<400> SEQUENCE: 493

Val Phe Asp Gly Val Leu Arg Pro Gly
1               5

```
<210> SEQ ID NO 494
<211> LENGTH: 4
<212> TYPE: PRT
<213> ORGANISM: Artificial Sequence
<220> FEATURE:
<223> OTHER INFORMATION: Synthetic peptide

<400> SEQUENCE: 494

His Asn Pro Arg
1

<210> SEQ ID NO 495
<211> LENGTH: 4
<212> TYPE: PRT
<213> ORGANISM: Artificial Sequence
<220> FEATURE:
<223> OTHER INFORMATION: Synthetic peptide

<400> SEQUENCE: 495

His Pro Met Ser
1

<210> SEQ ID NO 496
<211> LENGTH: 4
<212> TYPE: PRT
<213> ORGANISM: Artificial Sequence
<220> FEATURE:
<223> OTHER INFORMATION: Synthetic peptide

<400> SEQUENCE: 496

His Pro Ser Phe
1

<210> SEQ ID NO 497
<211> LENGTH: 4
<212> TYPE: PRT
<213> ORGANISM: Artificial Sequence
<220> FEATURE:
<223> OTHER INFORMATION: Synthetic peptide

<400> SEQUENCE: 497

Met Pro Met Pro
1

<210> SEQ ID NO 498
<211> LENGTH: 4
<212> TYPE: PRT
<213> ORGANISM: Artificial Sequence
<220> FEATURE:
<223> OTHER INFORMATION: Synthetic peptide

<400> SEQUENCE: 498

Pro Met Pro Leu
1

<210> SEQ ID NO 499
<211> LENGTH: 4
<212> TYPE: PRT
<213> ORGANISM: Artificial Sequence
<220> FEATURE:
<223> OTHER INFORMATION: Synthetic peptide

<400> SEQUENCE: 499

Pro Asn Ser Met
1
```

```
<210> SEQ ID NO 500
<211> LENGTH: 4
<212> TYPE: PRT
<213> ORGANISM: Artificial Sequence
<220> FEATURE:
<223> OTHER INFORMATION: Synthetic peptide

<400> SEQUENCE: 500

Trp Asp Pro Ala
1

<210> SEQ ID NO 501
<211> LENGTH: 6
<212> TYPE: PRT
<213> ORGANISM: Artificial Sequence
<220> FEATURE:
<223> OTHER INFORMATION: Synthetic peptide

<400> SEQUENCE: 501

Leu Arg Gly Phe Ser Lys
1               5

<210> SEQ ID NO 502
<211> LENGTH: 6
<212> TYPE: PRT
<213> ORGANISM: Artificial Sequence
<220> FEATURE:
<223> OTHER INFORMATION: Synthetic peptide

<400> SEQUENCE: 502

Arg Ser Gln Asn Ile Phe
1               5

<210> SEQ ID NO 503
<211> LENGTH: 6
<212> TYPE: PRT
<213> ORGANISM: Artificial Sequence
<220> FEATURE:
<223> OTHER INFORMATION: Synthetic peptide

<400> SEQUENCE: 503

Tyr Leu Arg Gly Phe Ser
1               5

<210> SEQ ID NO 504
<211> LENGTH: 9
<212> TYPE: PRT
<213> ORGANISM: Artificial Sequence
<220> FEATURE:
<223> OTHER INFORMATION: Synthetic peptide

<400> SEQUENCE: 504

Gly Ala Leu Met Leu Pro His Tyr Asn
1               5

<210> SEQ ID NO 505
<211> LENGTH: 11
<212> TYPE: PRT
<213> ORGANISM: Artificial Sequence
<220> FEATURE:
<223> OTHER INFORMATION: Synthetic peptide

<400> SEQUENCE: 505

Gly Ala Leu Met Leu Pro His Tyr Asn Ser Arg
1               5                   10

<210> SEQ ID NO 506
```

```
<211> LENGTH: 463
<212> TYPE: PRT
<213> ORGANISM: Vicia faba

<400> SEQUENCE: 506
```

| | | | | | | | | | | | | | | |
|---|---|---|---|---|---|---|---|---|---|---|---|---|---|---|
|Met|Ala|Ala|Thr|Thr|Leu|Lys|Asp|Ser|Phe|Pro|Leu|Leu|Thr|Leu|Leu|
|1| | | |5| | | | |10| | | | |15| |

| | | | | | | | | | | | | | | |
|---|---|---|---|---|---|---|---|---|---|---|---|---|---|---|
|Gly|Ile|Ala|Phe|Leu|Ala|Ser|Val|Cys|Leu|Ser|Ser|Arg|Ser|Asp|Gln|
| | | |20| | | | |25| | | | |30| | |

Asp Asn Pro Phe Val Phe Glu Ser Asn Arg Phe Gln Thr Leu Phe Glu
            35                  40                  45

Asn Glu Asn Gly His Ile Arg Leu Leu Gln Lys Phe Asp Gln His Ser
    50                  55                  60

Lys Leu Leu Glu Asn Leu Gln Asn Tyr Arg Leu Leu Glu Tyr Lys Ser
65                  70                  75                  80

Lys Pro His Thr Ile Phe Leu Pro Gln Gln Thr Asp Ala Asp Phe Ile
                85                  90                  95

Leu Val Val Leu Ser Gly Lys Ala Ile Leu Thr Val Leu Leu Pro Asn
            100                 105                 110

Asp Arg Asn Ser Phe Ser Leu Glu Arg Gly Asp Thr Ile Lys Leu Pro
        115                 120                 125

Ala Gly Thr Ile Gly Tyr Leu Val Asn Arg Asp Asp Glu Glu Asp Leu
    130                 135                 140

Arg Val Leu Asp Leu Val Ile Pro Val Asn Arg Pro Gly Glu Pro Gln
145                 150                 155                 160

Ser Phe Leu Leu Ser Gly Asn Gln Asn Gln Pro Ser Ile Leu Ser Gly
                165                 170                 175

Phe Ser Lys Asn Ile Leu Glu Ala Ser Phe Asn Thr Asp Tyr Lys Glu
            180                 185                 190

Ile Glu Lys Val Leu Leu Glu His Gly Lys Glu Lys Tyr His Arg
        195                 200                 205

Arg Gly Leu Lys Asp Arg Arg Gln Arg Gly Gln Glu Glu Asn Val Ile
    210                 215                 220

Val Lys Ile Ser Arg Lys Gln Ile Glu Glu Leu Asn Lys Asn Ala Lys
225                 230                 235                 240

Ser Ser Ser Lys Lys Ser Thr Ser Ser Glu Ser Glu Pro Phe Asn Leu
                245                 250                 255

Arg Ser Arg Glu Pro Ile Tyr Ser Asn Lys Phe Gly Lys Phe Phe Glu
            260                 265                 270

Ile Thr Pro Lys Arg Asn Pro Gln Leu Gln Asp Leu Asn Ile Phe Val
        275                 280                 285

Asn Tyr Val Glu Ile Asn Glu Gly Ser Leu Leu Pro His Tyr Asn
    290                 295                 300

Ser Arg Ala Ile Val Ile Val Thr Val Asn Glu Gly Lys Gly Asp Phe
305                 310                 315                 320

Glu Leu Val Gly Gln Arg Asn Glu Asn Gln Gly Leu Arg Glu Glu
                325                 330                 335

Tyr Asp Glu Glu Lys Glu Gln Gly Glu Glu Ile Arg Lys Gln Val
            340                 345                 350

Gln Asn Tyr Lys Ala Lys Leu Ser Pro Gly Asp Val Leu Val Ile Pro
        355                 360                 365

Ala Gly Tyr Pro Val Ala Ile Lys Ala Ser Ser Asn Leu Asn Leu Val
    370                 375                 380

Gly Phe Gly Ile Asn Ala Glu Asn Asn Gln Arg Tyr Phe Leu Ala Gly

```
               385                 390                 395                 400
Glu Glu Asp Asn Val Ile Ser Gln Ile His Lys Pro Val Lys Glu Leu
                405                 410                 415

Ala Phe Pro Gly Ser Ala Gln Glu Val Asp Thr Leu Leu Glu Asn Gln
                420                 425                 430

Lys Gln Ser His Phe Ala Asn Ala Gln Pro Arg Glu Arg Glu Arg Gly
                435                 440                 445

Ser Gln Glu Ile Lys Asp His Leu Tyr Ser Ile Leu Gly Ser Phe
                450                 455                 460

<210> SEQ ID NO 507
<211> LENGTH: 446
<212> TYPE: PRT
<213> ORGANISM: Cicer arietinum

<400> SEQUENCE: 507

Met Ala Ile Lys Ala Arg Phe Pro Leu Leu Val Leu Leu Gly Ile Val
1               5                   10                  15

Phe Leu Ala Ser Val Cys Ala Lys Ser Asp Lys Glu Asn Pro Phe Phe
                20                  25                  30

Phe Lys Ser Asn Asn Cys Gln Thr Leu Phe Glu Asn Glu Asn Gly His
                35                  40                  45

Val Arg Leu Leu Gln Arg Phe Asp Lys Arg Ser Gln Leu Phe Glu Asn
        50                  55                  60

Leu Gln Asn Tyr Arg Leu Met Glu Tyr Asn Ser Lys Pro His Thr Leu
65              70                  75                  80

Phe Leu Pro Gln His Asn Asp Ala Asp Phe Ile Leu Val Val Leu Arg
                85                  90                  95

Gly Arg Ala Ile Leu Thr Val Leu Asn Pro Asn Asp Arg Asn Thr Phe
                100                 105                 110

Lys Leu Glu Arg Gly Asp Thr Ile Lys Leu Pro Ala Gly Thr Ile Ala
                115                 120                 125

Tyr Leu Ala Asn Arg Asp Asp Asn Glu Asp Leu Arg Val Leu Asp Leu
        130                 135                 140

Ala Ile Pro Val Asn Arg Pro Gly Gln Phe Gln Ser Phe Ser Leu Ser
145                 150                 155                 160

Gly Asn Glu Asn Gln Gln Ser Tyr Phe Gln Gly Phe Ser Lys Lys Ile
                165                 170                 175

Leu Glu Ala Ser Phe Asn Ser Asp Tyr Glu Glu Ile Glu Arg Val Leu
                180                 185                 190

Leu Glu Glu Gln Glu Gln Lys Pro Glu Gln Arg Arg Gly His Lys Gly
                195                 200                 205

Arg Gln Gln Ser Gln Glu Thr Asp Val Ile Val Lys Ile Ser Arg Glu
        210                 215                 220

Gln Ile Glu Glu Leu Ser Lys Asn Ala Lys Ser Asn Cys Lys Lys Ser
225                 230                 235                 240

Val Ser Ser Glu Ser Glu Pro Phe Asn Leu Arg Ser Arg Ser Pro Ile
                245                 250                 255

Tyr Ser Asn Arg Phe Gly Asn Phe Phe Glu Ile Thr Pro Glu Lys Asn
                260                 265                 270

Pro Gln Leu Lys Asp Leu Asp Ile Phe Val Asn Ser Val Glu Ile Lys
                275                 280                 285

Glu Gly Ser Leu Leu Leu Pro His Phe Asn Ser Arg Ala Thr Val Ile
        290                 295                 300
```

Leu Val Val Asn Glu Gly Lys Gly Glu Val Glu Leu Val Gly Leu Arg
305                 310                 315                 320

Asn Glu Asn Glu Gln Glu Asn Lys Lys Glu Asp Glu Glu Glu Glu Glu
                325                 330                 335

Asp Arg Asn Val Gln Val Gln Arg Phe Gln Ser Lys Leu Ser Ser Gly
                340                 345                 350

Asp Val Val Ile Pro Ala Ser His Pro Phe Ser Ile Asn Ala Ser
        355                 360                 365

Ser Asp Leu Phe Leu Leu Gly Phe Gly Ile Asn Ala Gln Asn Asn Gln
    370                 375                 380

Arg Asn Phe Leu Ala Gly Glu Glu Asp Asn Val Ile Ser Gln Ile Gln
385                 390                 395                 400

Arg Pro Val Lys Glu Val Ala Phe Pro Gly Ser Ala Glu Glu Val Asp
                405                 410                 415

Arg Leu Leu Lys Asn Gln Arg Gln Ser His Phe Ala Asn Ala Gln Pro
                420                 425                 430

Gln Gln Lys Arg Lys Gly Ser Gln Arg Ile Arg Ser Pro Phe
                435                 440                 445

<210> SEQ ID NO 508
<211> LENGTH: 418
<212> TYPE: PRT
<213> ORGANISM: Lens culinaris

<400> SEQUENCE: 508

Ser Arg Ser Asp Gln Glu Asn Pro Phe Ile Phe Lys Ser Asn Arg Phe
1               5                   10                  15

Gln Thr Ile Tyr Glu Asn Glu Asn Gly His Ile Arg Leu Leu Gln Arg
                20                  25                  30

Phe Asp Lys Arg Ser Lys Ile Phe Glu Asn Leu Gln Asn Tyr Arg Leu
            35                  40                  45

Leu Glu Tyr Lys Ser Lys Pro His Thr Ile Phe Leu Pro Gln Phe Thr
50                  55                  60

Asp Ala Asp Phe Ile Leu Val Val Leu Ser Gly Lys Ala Ile Leu Thr
65                  70                  75                  80

Val Leu Asn Ser Asn Asp Arg Asn Ser Phe Asn Leu Glu Arg Gly Asp
                85                  90                  95

Thr Ile Lys Leu Pro Ala Gly Thr Ile Ala Tyr Leu Ala Asn Arg Asp
                100                 105                 110

Asp Asn Glu Asp Leu Arg Val Leu Asp Leu Ala Ile Pro Val Asn Arg
            115                 120                 125

Pro Gly Gln Leu Gln Ser Phe Leu Leu Ser Gly Thr Gln Asn Gln Pro
130                 135                 140

Ser Phe Leu Ser Gly Phe Ser Lys Asn Ile Leu Glu Ala Ala Phe Asn
145                 150                 155                 160

Thr Glu Tyr Glu Glu Ile Glu Lys Val Leu Leu Glu Glu Gln Glu Gln
                165                 170                 175

Lys Ser Gln His Arg Arg Ser Leu Arg Asp Lys Arg Gln Glu Ile Thr
            180                 185                 190

Asn Glu Asp Val Ile Val Lys Val Ser Arg Glu Gln Ile Glu Glu Leu
        195                 200                 205

Ser Lys Asn Ala Lys Ser Ser Ser Lys Ser Val Ser Ser Glu Ser
210                 215                 220

Glu Pro Phe Asn Leu Arg Ser Arg Asn Pro Ile Tyr Ser Asn Lys Phe
225                 230                 235                 240

```
Gly Lys Phe Phe Glu Ile Thr Pro Glu Lys Asn Pro Gln Leu Gln Asp
                245                 250                 255

Leu Asp Ile Phe Val Asn Ser Val Glu Ile Lys Glu Gly Ser Leu Leu
            260                 265                 270

Leu Pro Asn Tyr Asn Ser Arg Ala Ile Val Ile Val Thr Val Asn Glu
        275                 280                 285

Gly Lys Gly Asp Phe Glu Leu Val Gly Gln Arg Asn Glu Asn Gln Gln
    290                 295                 300

Glu Gln Arg Glu Glu Asn Asp Glu Glu Gly Gln Glu Glu Glu Thr
305                 310                 315                 320

Thr Lys Gln Val Gln Arg Tyr Arg Ala Arg Leu Ser Pro Gly Asp Val
                325                 330                 335

Leu Val Ile Pro Ala Gly His Pro Val Ala Ile Asn Ala Ser Ser Asp
            340                 345                 350

Leu Asn Leu Ile Gly Phe Gly Ile Asn Ala Lys Asn Asn Gln Arg Asn
        355                 360                 365

Phe Leu Ala Gly Glu Glu Asp Asn Val Ile Ser Gln Ile Gln Arg Pro
370                 375                 380

Val Lys Glu Leu Ala Phe Pro Gly Ser Ser Arg Glu Val Asp Arg Leu
385                 390                 395                 400

Leu Thr Asn Gln Lys Gln Ser His Phe Ala Asn Ala Gln Pro Leu Gln
                405                 410                 415

Ile Glu

<210> SEQ ID NO 509
<211> LENGTH: 526
<212> TYPE: PRT
<213> ORGANISM: Pisum elatius

<400> SEQUENCE: 509

Met Ala Thr Thr Val Glu Ser Arg Phe Pro Leu Leu Leu Phe Pro Gly
1               5                   10                  15

Ile Ile Phe Leu Ala Ser Val Cys Val Thr Tyr Ala Asn Tyr Asp Glu
                20                  25                  30

Gly Ser Glu Thr Arg Val Pro Gly Gln Arg Glu Arg Gly Arg Gln Glu
            35                  40                  45

Gly Glu Lys Glu Glu Lys Arg His Gly Glu Trp Arg Pro Ser Tyr Glu
        50                  55                  60

Lys Glu Glu Asp Glu Glu Glu Lys Gln Lys Tyr Arg Tyr Gln Arg Glu
65                  70                  75                  80

Lys Glu Asp Glu Glu Glu Lys Gln Lys Tyr Arg Tyr Gln Arg Glu Lys
                85                  90                  95

Lys Glu Glu Lys Glu Val Gln Pro Gly Arg Glu Arg Trp Glu Arg Glu
            100                 105                 110

Glu Asp Glu Glu Gln Val Asp Glu Glu Trp Arg Gly Ser Gln Arg Arg
        115                 120                 125

Gln Asp Pro Glu Glu Arg Ala Arg Leu Arg His Arg Glu Glu Arg Thr
130                 135                 140

Lys Arg Asp Arg Arg His Lys Arg Glu Gly Glu Glu Glu Arg Ser
145                 150                 155                 160

Ser Glu Ser Gln Glu Gln Arg Asn Pro Phe Leu Phe Lys Ser Asn Lys
                165                 170                 175

Phe Leu Thr Leu Phe Glu Asn Glu Asn Gly His Ile Arg Arg Leu Gln
            180                 185                 190
```

Arg Phe Asp Lys Arg Ser Asp Leu Phe Glu Asn Leu Gln Asn Tyr Arg
            195                 200                 205

Leu Val Glu Tyr Arg Ala Lys Pro His Thr Ile Phe Leu Pro Gln His
        210                 215                 220

Ile Asp Ala Asp Leu Ile Leu Val Val Leu Asn Gly Lys Ala Ile Leu
225                 230                 235                 240

Thr Val Leu Ser Pro Asn Asp Arg Asn Ser Tyr Asn Leu Glu Arg Gly
                245                 250                 255

Asp Thr Ile Lys Ile Pro Ala Gly Thr Thr Ser Tyr Leu Val Asn Gln
            260                 265                 270

Asp Asp Glu Glu Asp Leu Arg Val Val Asp Phe Val Ile Pro Val Asn
        275                 280                 285

Arg Pro Gly Lys Phe Glu Ala Phe Gly Leu Ser Glu Asn Lys Asn Gln
        290                 295                 300

Tyr Leu Arg Gly Phe Ser Lys Asn Ile Leu Glu Ala Ser Leu Asn Thr
305                 310                 315                 320

Lys Tyr Glu Thr Ile Glu Lys Val Leu Leu Glu Gln Glu Lys Lys
                325                 330                 335

Pro Gln Gln Leu Arg Asp Arg Lys Arg Arg Gln Gln Gly Gly Glu Arg
            340                 345                 350

Asp Ala Ile Ile Lys Val Ser Arg Glu Gln Ile Glu Glu Leu Arg Lys
            355                 360                 365

Leu Ala Lys Ser Ser Ser Lys Lys Ser Leu Pro Ser Glu Phe Glu Pro
        370                 375                 380

Phe Asn Leu Arg Ser His Lys Pro Glu Tyr Ser Asn Lys Phe Gly Lys
385                 390                 395                 400

Leu Phe Glu Ile Thr Pro Glu Lys Lys Tyr Pro Gln Leu Gln Asp Leu
                405                 410                 415

Asp Ile Leu Val Ser Cys Val Glu Ile Asn Lys Gly Ala Leu Met Leu
            420                 425                 430

Pro His Tyr Asn Ser Arg Ala Ile Val Val Leu Leu Val Asn Glu Gly
        435                 440                 445

Lys Gly Asn Leu Glu Leu Leu Gly Leu Lys Asn Glu Gln Gln Glu Arg
        450                 455                 460

Glu Asp Arg Lys Glu Arg Asn Asn Glu Val Gln Arg Tyr Glu Ala Arg
465                 470                 475                 480

Leu Ser Pro Gly Asp Val Val Ile Ile Pro Ala Gly His Pro Val Ala
                485                 490                 495

Ile Ser Ala Ser Ser Asn Leu Asn Leu Leu Gly Phe Gly Thr Asn Ala
            500                 505                 510

Glu Asn Asn Gln Arg Asn Phe Leu Ser Gly Ser Asp Asp Asn
            515                 520                 525

<210> SEQ ID NO 510
<211> LENGTH: 541
<212> TYPE: PRT
<213> ORGANISM: Lathyrus aphaca

<400> SEQUENCE: 510

Met Ala Thr Thr Ile Lys Ser Arg Phe Pro Leu Leu Leu Leu Leu Gly
1               5                   10                  15

Ile Ile Phe Leu Ala Ser Val Cys Val Thr Trp Ala Asn Tyr Asp Glu
            20                  25                  30

Gly Ser Glu Pro Arg Val Pro Gly Gln Arg Glu Arg Gly Arg Gln Glu

```
                35                  40                  45
Gly Glu Lys Glu Glu Lys Arg His Gly Glu Trp Arg Pro Ser Tyr Glu
 50                  55                  60
Glu Glu Tyr Asp Glu Gly Leu Glu Pro Lys Val Pro Gly Lys Arg Glu
65                  70                  75                  80
Arg Gly Arg Gln Glu Gly Lys Glu Lys Arg His Glu Glu Trp
                85                  90                  95
Arg Pro Ser Tyr Glu Lys Glu Glu Asp Glu Glu Lys Gln Lys Tyr
                100                 105                 110
Asn Tyr Gln Arg Glu Lys Lys Glu His Lys Glu Val Gln Pro Gly Arg
                115                 120                 125
Glu Arg Trp Glu Arg Lys Gln Asp Glu Lys Gln Val Glu Glu Asp Glu
                130                 135                 140
Glu Pro Gly Glu Glu Gln Trp Arg Gly Ser Lys Arg His Glu Asp Pro
145                 150                 155                 160
Glu Glu Arg Ala Arg Leu Arg His Arg Glu Glu Lys Thr Lys Ser Tyr
                165                 170                 175
Val Glu Asp Asn Glu Glu Thr Ser Ser Lys Glu Gly Arg Asn Pro Phe
                180                 185                 190
Leu Phe Lys Ser Asn Lys Phe Leu Thr Leu Phe Glu Asn Glu Asn Gly
                195                 200                 205
His Ile Arg Arg Leu Gln Arg Phe Asp Glu Arg Ser Asp Ile Phe Glu
210                 215                 220
Asn Leu Gln Asn Tyr Arg Leu Val Glu Tyr Arg Ala Lys Pro His Thr
225                 230                 235                 240
Met Phe Leu Pro Gln His Ile Asp Ala Asp Leu Ile Leu Val Val Leu
                245                 250                 255
Asn Gly Lys Ala Ile Leu Thr Val Leu Ser Pro Asn Asp Arg Asn Ser
                260                 265                 270
Tyr Asn Leu Glu Arg Gly Asp Thr Val Lys Leu Pro Ala Gly Thr Thr
                275                 280                 285
Ser Tyr Leu Val Asn Gln Asp Asp Glu Glu Asp Leu Arg Val Val Asp
                290                 295                 300
Leu Ala Ile Pro Val Asn Arg Pro Gly Lys Phe Glu Ala Phe Gly Leu
305                 310                 315                 320
Ser Ala Asn Lys Asn Gln Tyr Leu Arg Gly Phe Ser Lys Asn Ile Leu
                325                 330                 335
Glu Ala Ser Leu Asn Thr Lys Tyr Glu Thr Ile Glu Lys Val Leu Leu
                340                 345                 350
Glu Glu Arg Arg Asp Gln Lys Gly Arg Gln Gln Gly Gln Glu Thr Asn
                355                 360                 365
Ala Ile Val Lys Val Ser Arg Glu Gln Ile Glu Glu Leu Arg Lys Leu
                370                 375                 380
Ala Lys Ser Ser Ser Lys Lys Ser Leu Leu Ser Glu Ser Glu Pro Leu
385                 390                 395                 400
Asn Leu Arg Ser Gln Asn Pro Lys Tyr Ser Asn Lys Phe Gly Lys Phe
                405                 410                 415
Phe Glu Ile Thr Pro Gln Lys Lys Tyr Pro Gln Leu Gln Asp Leu Asp
                420                 425                 430
Val Ser Ile Ser Cys Val Glu Ile Asn Lys Gly Ala Leu Leu Leu Pro
                435                 440                 445
His Tyr Asn Ser Arg Ser Ile Gly Ile Leu Leu Val Asn Glu Gly Lys
                450                 455                 460
```

```
Gly Asn Leu Glu Leu Val Gly Phe Lys Asn Glu Gln Gln Arg Gln Arg
465                 470                 475                 480

Glu Asn Glu Glu Thr Asn Lys Lys Leu Gln Arg Tyr Glu Ala Arg Leu
            485                 490                 495

Ser Ser Gly Asp Val Val Ile Pro Glu Gly His Pro Val Ala Ile
        500                 505                 510

Ser Ala Ser Ser Asn Leu Asn Leu Leu Gly Phe Gly Ile Asn Ala Ala
        515                 520                 525

Asn Asn Gln Arg Asn Phe Leu Thr Gly Ser Asp Asp Asn
530                 535                 540

<210> SEQ ID NO 511
<211> LENGTH: 589
<212> TYPE: PRT
<213> ORGANISM: Vicia villosa

<400> SEQUENCE: 511

Met Ala Thr Thr Ile Lys Ser Arg Phe Pro Val Leu Leu Leu Leu Gly
1               5                   10                  15

Ile Ile Phe Leu Thr Ser Val Cys Val Thr Tyr Ala Asn Tyr Asp Glu
            20                  25                  30

Gly Arg Glu Pro Ser Val Pro Gly Gln Arg Glu Arg Gly Arg Gln Glu
        35                  40                  45

Gly Glu Lys Glu Glu Lys Arg His Gly Glu Trp Arg Pro Ser Glu Glu
50                  55                  60

Asp Glu Glu Glu Lys Tyr Lys Tyr Glu Glu Gly Arg Val Pro Gly Gln
65                  70                  75                  80

Arg Glu Arg Gly Arg Gln Glu Gly Glu Lys Glu Glu Lys Arg His Gly
                85                  90                  95

Lys Trp Arg Pro Ser Glu Glu Glu Asp Glu Glu Glu Lys Tyr Arg Tyr
            100                 105                 110

Glu Glu Gly Ser Glu Pro Arg Gly Pro Gly Gln Arg Glu Thr Gly Arg
        115                 120                 125

Gln Glu Gly Glu Lys Glu Lys Gln Arg Pro Glu Arg Glu Pro Ser Tyr
130                 135                 140

Glu Lys Glu Glu Asp Glu Glu Glu Lys Gln Lys Tyr Gln Tyr His Arg
145                 150                 155                 160

Glu Lys Lys Glu Gln Arg Glu Val Arg Pro Gly Arg Glu Arg Phe Glu
                165                 170                 175

Arg His Glu Asp Glu Glu Gln Trp Arg Gly Ile Gln Arg His Glu Asp
            180                 185                 190

Pro Glu Glu Arg Ala Arg Glu Arg Tyr Arg Ala Glu Ile Ala Lys Arg
        195                 200                 205

Gln Val Glu Glu Glu Arg Glu Glu Arg Asp Ile Pro His Glu Arg Glu
210                 215                 220

Gln Arg Asn Pro Phe Leu Phe Lys Ser Asn Lys Phe Gln Thr Leu Phe
225                 230                 235                 240

Gln Asn Glu Asn Gly Tyr Ile Arg Arg Leu Gln Arg Phe Asp Lys Arg
                245                 250                 255

Ser Asp Leu Phe Glu Asn Leu Gln Asn Tyr Arg Leu Val Glu Tyr Arg
            260                 265                 270

Ala Lys Pro His Thr Ile Phe Leu Pro Gln His Ile Asp Ala Asp Leu
        275                 280                 285

Ile Ile Val Val Leu Ser Gly Arg Ala Ile Leu Thr Val Leu Ser Pro
```

```
            290                 295                 300

Asp Asp Arg Asn Ser Tyr Asn Leu Glu Arg Gly Asp Thr Ile Lys Leu
305                 310                 315                 320

Pro Ala Gly Thr Thr Ser Tyr Leu Val Asn Gln Asp Asp Glu Glu Asp
                325                 330                 335

Leu Arg Val Val Asp Leu Ala Ile Pro Val Asn Arg Pro Gly Lys Val
                340                 345                 350

Glu Ser Phe Leu Leu Ser Gly Asn Lys Asn Gln Tyr Leu Arg Gly Phe
            355                 360                 365

Ser Lys Asn Ile Leu Glu Ala Ser Phe Asn Thr Asn Tyr Glu Thr Ile
        370                 375                 380

Glu Arg Val Leu Leu Glu Gln Asp Lys Glu Ser Gln Gln Ser Ile
385                 390                 395                 400

Gly Gln Lys Arg Arg Ser Gln Arg Gln Glu Thr Asn Ala Leu Val Lys
                405                 410                 415

Val Ser Arg Glu Gln Leu Glu Asp Leu Lys Arg Leu Ala Lys Ser Ser
                420                 425                 430

Ser Gln Glu Gly Leu Ser Ser Gln Phe Glu Pro Ile Asn Leu Arg Ser
            435                 440                 445

Gln Asn Pro Lys Tyr Ser Asn Lys Phe Gly Lys Val Phe Glu Ile Thr
        450                 455                 460

Pro Glu Lys Lys Tyr Pro Gln Leu Gln Asp Leu Asp Leu Phe Val Ser
465                 470                 475                 480

Ser Val Asp Ile Lys Glu Gly Ala Leu Met Leu Pro His Tyr Asn Ser
                485                 490                 495

Arg Ala Ile Val Val Leu Leu Val Asn Glu Gly Arg Gly Asn Leu Glu
                500                 505                 510

Leu Val Gly Leu Lys Asn Glu Gln Glu Gln Arg Glu Lys Glu Asp
            515                 520                 525

Glu Gln Gln Glu Arg Asn Asn Gln Val Gln Arg Tyr Glu Ala Arg Leu
        530                 535                 540

Ser Pro Gly Asp Val Val Ile Ile Pro Ala Gly His Pro Val Ala Val
545                 550                 555                 560

Arg Ala Ser Ser Asp Leu Asn Leu Leu Ala Phe Gly Ile Asn Ala Glu
                565                 570                 575

Asn Asn Gln Arg Asn Phe Leu Ala Gly Ser Asp Asp Asn
                580                 585

<210> SEQ ID NO 512
<211> LENGTH: 861
<212> TYPE: PRT
<213> ORGANISM: Medicago truncatula

<400> SEQUENCE: 512

Met Phe Ser Gly Val Thr Gly Ile Leu Asn Arg Gly His Lys Ile Lys
1               5                   10                  15

Gly Thr Val Val Leu Met Arg Lys Asn Val Leu Asp Ile Asn Ser Leu
                20                  25                  30

Thr Ser Val Gly Val Ile Gly Gln Gly Phe Asp Ile Leu Gly Ser
            35                  40                  45

Thr Leu Asp Asn Leu Thr Ala Phe Leu Gly Arg Ser Val Ser Leu Gln
        50                  55                  60

Leu Ile Ser Ala Thr Lys Pro Asp Ala Asn Gly Lys Gly Lys Leu Gly
65                  70                  75                  80
```

-continued

```
Lys Ala Thr Phe Leu Glu Gly Ile Ile Thr Ser Leu Pro Thr Leu Gly
                85                  90                  95
Ala Gly Gln Ser Ala Phe Lys Ile His Phe Glu Trp Asp Asp Met
            100                 105                 110
Gly Ile Pro Gly Ala Phe Tyr Ile Lys Asn Phe Met Gln Thr Glu Phe
            115                 120                 125
Phe Leu Val Ser Leu Thr Leu Glu Asp Ile Pro Asn His Gly Ser Ile
        130                 135                 140
Tyr Phe Val Cys Asn Ser Trp Ile Tyr Asn Ala Lys His His Lys Leu
145                 150                 155                 160
Asp Arg Ile Phe Phe Ala Asn Lys Ala Tyr Leu Pro Ser Glu Thr Pro
                165                 170                 175
Ala Pro Leu Val His Tyr Arg Glu Glu Leu Asn Asn Leu Arg Gly
            180                 185                 190
Asp Gly Thr Gly Glu Arg Lys Glu Trp Glu Arg Ile Tyr Asp Tyr Asp
            195                 200                 205
Val Tyr Asn Asp Leu Gly Asn Pro Glu Lys Gly Asp Asn His Ala Arg
    210                 215                 220
Pro Val Leu Gly Gly Ser Asp Thr Tyr Pro Tyr Pro Arg Arg Gly Arg
225                 230                 235                 240
Thr Gly Arg Lys Pro Asn Pro Lys Asp Pro Lys Ser Glu Ser Arg Ser
                245                 250                 255
Asp Phe Val Tyr Leu Pro Arg Asp Glu Ala Phe Gly His Leu Lys Ser
            260                 265                 270
Ser Asp Phe Leu Thr Tyr Gly Leu Lys Ala Val Ser Gln Asn Val Val
        275                 280                 285
Pro Ala Leu Glu Ser Val Ile Phe Asp Leu Asn Phe Thr Pro Asn Glu
    290                 295                 300
Phe Asp Ser Phe Asp Glu Val His Gly Leu Tyr Glu Gly Gly Ile Lys
305                 310                 315                 320
Leu Pro Thr Asp Val Leu Ser Lys Ile Ser Pro Leu Pro Val Leu Lys
                325                 330                 335
Glu Ile Phe Arg Thr Asp Gly Glu Gln Phe Leu Lys Tyr Pro Pro Pro
            340                 345                 350
Lys Val Leu Gln Val Ser Arg Ser Ala Trp Met Thr Asp Glu Glu Phe
        355                 360                 365
Ala Arg Glu Met Leu Ala Gly Val Asn Pro Asn Val Ile Cys Cys Leu
    370                 375                 380
Gln Glu Phe Pro Pro Arg Ser Lys Leu Asp Ser Gln Val Tyr Gly Asp
385                 390                 395                 400
His Thr Ser Lys Ile Thr Lys Glu His Leu Glu Pro Asn Leu Glu Gly
                405                 410                 415
Leu Thr Val Glu Glu Ala Ile Gln Asn Lys Lys Leu Phe Leu Leu Asp
            420                 425                 430
His His Asp Ser Ile Met Pro Tyr Leu Arg Arg Ile Asn Ser Thr Pro
        435                 440                 445
Thr Lys Ala Tyr Ala Thr Arg Thr Ile Leu Phe Leu Ser Ser Asp Lys
    450                 455                 460
Thr Leu Lys Pro Leu Ala Ile Glu Leu Ser Leu Pro His Pro Asp Gly
465                 470                 475                 480
Asp Glu His Gly Ala Val Ser His Val Tyr Gln Pro Ala Leu Glu Gly
                485                 490                 495
Val Glu Ser Thr Ile Trp Leu Leu Ala Lys Ala Tyr Val Val Val Asn
```

```
            500                 505                 510
Asp Ser Cys Tyr His Gln Leu Val Ser His Trp Leu Asn Thr His Ala
        515                 520                 525

Val Val Glu Pro Phe Val Ile Ala Thr Asn Arg His Leu Ser Tyr Leu
    530                 535                 540

His Pro Ile Tyr Lys Leu Leu Tyr Pro His Tyr Arg Asp Thr Met Asn
545                 550                 555                 560

Ile Asn Ser Leu Ala Arg Gln Ser Leu Val Asn Asp Gly Gly Ile Ile
                565                 570                 575

Glu Lys Thr Phe Leu Trp Gly Arg Tyr Ser Met Glu Met Ser Ser Lys
            580                 585                 590

Val Tyr Lys Asn Trp Thr Leu Pro Gly Gln Ala Leu Pro Ala Asp Leu
        595                 600                 605

Ile Lys Arg Gly Met Ala Ile Glu Glu Pro Ser Pro Cys Gly Val
    610                 615                 620

Lys Leu Val Val Glu Asp Tyr Pro Tyr Ala His Asp Gly Leu Glu Ile
625                 630                 635                 640

Trp Ala Ala Ile Lys Thr Trp Val Gln Asp Tyr Val Ser Leu Tyr Tyr
                645                 650                 655

Thr Thr Asp Asp Ile Leu Arg Gln Asp Ser Glu Leu Gln Ala Trp Trp
            660                 665                 670

Lys Glu Leu Val Glu Val Gly His Gly Asp Lys Lys Asn Glu Pro Trp
        675                 680                 685

Trp Pro Lys Met Gln Ala Arg Glu Glu Leu Val Glu Val Cys Thr Thr
    690                 695                 700

Val Ile Trp Ile Ala Ser Ala Leu His Ala Ala Val Asn Phe Gly Gln
705                 710                 715                 720

Tyr Ser Tyr Gly Gly Leu Ile Leu Asn Arg Pro Thr Leu Ser Arg Arg
                725                 730                 735

Phe Met Pro Glu Lys Gly Ser Ala Glu Tyr Asn Glu Leu Val Lys Ser
            740                 745                 750

Pro Gln Lys Ala Tyr Leu Lys Thr Ile Thr Pro Lys Phe Gln Thr Leu
        755                 760                 765

Ile Asp Leu Ser Val Ile Glu Ile Leu Ser Arg His Ala Ser Asp Glu
    770                 775                 780

Val Tyr Leu Gly Glu Arg Asp Asn Pro Asn Trp Thr Ser Asp Thr Arg
785                 790                 795                 800

Ala Leu Glu Ala Phe Lys Lys Phe Gly Asn Lys Leu Ala Glu Ile Glu
                805                 810                 815

Lys Asn Leu Ala Gln Arg Asn Asn Asp Glu Lys Leu Arg His Arg Leu
            820                 825                 830

Gly Pro Val Gln Met Pro Tyr Thr Leu Leu His Pro Ser Ser Glu Glu
        835                 840                 845

Gly Leu Thr Phe Arg Gly Ile Pro Asn Ser Ile Ser Ile
    850                 855                 860

<210> SEQ ID NO 513
<211> LENGTH: 857
<212> TYPE: PRT
<213> ORGANISM: Glycine soja

<400> SEQUENCE: 513

Met Leu Gly Gly Leu Leu His Arg Gly His Lys Ile Lys Gly Thr Val
1               5                   10                  15
```

Val Leu Met Arg Lys Asn Val Leu Asp Val Asn Ser Val Thr Ser Val
            20                  25                  30

Gly Gly Ile Ile Gly Gln Gly Leu Asp Leu Val Gly Ser Thr Leu Asp
        35                  40                  45

Thr Leu Thr Ala Phe Leu Gly Arg Ser Val Ser Leu Gln Leu Ile Ser
50                  55                  60

Ala Thr Lys Ala Asp Ala Asn Gly Lys Gly Lys Leu Gly Lys Ala Thr
65                  70                  75                  80

Phe Leu Glu Gly Ile Ile Thr Ser Leu Pro Thr Leu Gly Ala Gly Gln
                85                  90                  95

Ser Ala Phe Lys Ile Asn Phe Glu Trp Asp Asp Gly Ser Gly Ile Pro
                100                 105                 110

Gly Ala Phe Tyr Ile Lys Asn Phe Met Gln Thr Glu Phe Phe Leu Val
                115                 120                 125

Ser Leu Thr Leu Glu Asp Ile Pro Asn His Gly Ser Ile His Phe Val
130                 135                 140

Cys Asn Ser Trp Ile Tyr Asn Ala Lys Leu Phe Lys Ser Asp Arg Ile
145                 150                 155                 160

Phe Phe Ala Asn Gln Thr Tyr Leu Pro Ser Glu Thr Pro Ala Pro Leu
                165                 170                 175

Val Lys Tyr Arg Glu Glu Leu His Asn Leu Arg Gly Asp Gly Thr
                180                 185                 190

Gly Glu Arg Lys Glu Trp Glu Arg Ile Tyr Asp Tyr Asp Val Tyr Asn
                195                 200                 205

Asp Leu Gly Asp Pro Asp Lys Gly Glu Asn His Ala Arg Pro Val Leu
210                 215                 220

Gly Gly Asn Asp Thr Phe Pro Tyr Pro Arg Arg Gly Arg Thr Gly Arg
225                 230                 235                 240

Lys Pro Thr Arg Lys Asp Pro Asn Ser Glu Ser Arg Ser Asn Asp Val
                245                 250                 255

Tyr Leu Pro Arg Asp Glu Ala Phe Gly His Leu Lys Ser Ser Asp Phe
                260                 265                 270

Leu Thr Tyr Gly Leu Lys Ser Val Ser Gln Asn Val Leu Pro Leu Leu
                275                 280                 285

Gln Ser Ala Phe Asp Leu Asn Phe Thr Pro Arg Glu Phe Asp Ser Phe
290                 295                 300

Asp Glu Val His Gly Leu Tyr Ser Gly Gly Ile Lys Leu Pro Thr Asp
305                 310                 315                 320

Ile Ile Ser Lys Ile Ser Pro Leu Pro Val Leu Lys Glu Ile Phe Arg
                325                 330                 335

Thr Asp Gly Glu Gln Ala Leu Lys Phe Pro Pro Lys Val Ile Gln
                340                 345                 350

Val Ser Lys Ser Ala Trp Met Thr Asp Glu Glu Phe Ala Arg Glu Met
        355                 360                 365

Leu Ala Gly Val Asn Pro Asn Leu Ile Arg Cys Leu Lys Asp Phe Pro
        370                 375                 380

Pro Arg Ser Lys Leu Asp Ser Gln Val Tyr Gly Asp His Thr Ser Gln
385                 390                 395                 400

Ile Thr Lys Glu His Leu Glu Pro Asn Leu Glu Gly Leu Thr Val Asp
                405                 410                 415

Glu Ala Ile Gln Asn Lys Arg Leu Phe Leu Leu Asp His His Asp Pro
        420                 425                 430

Ile Met Pro Tyr Leu Arg Arg Ile Asn Ala Thr Ser Thr Lys Ala Tyr

```
                435                 440                 445
Ala Thr Arg Thr Ile Leu Phe Leu Lys Asn Asp Gly Thr Leu Arg Pro
450                 455                 460

Leu Ala Ile Glu Leu Ser Leu Pro His Pro Gln Gly Asp Gln Ser Gly
465                 470                 475                 480

Ala Phe Ser Gln Val Phe Leu Pro Ala Asp Glu Gly Val Glu Ser Ser
                485                 490                 495

Ile Trp Leu Leu Ala Lys Ala Tyr Val Val Asn Asp Ser Cys Tyr
            500                 505                 510

His Gln Leu Val Ser His Trp Leu Asn Thr His Ala Val Val Glu Pro
            515                 520                 525

Phe Ile Ile Ala Thr Asn Arg His Leu Ser Val Val His Pro Ile Tyr
530                 535                 540

Lys Leu Leu His Pro His Tyr Arg Asp Thr Met Asn Ile Asn Gly Leu
545                 550                 555                 560

Ala Arg Leu Ser Leu Val Asn Asp Gly Gly Val Ile Glu Gln Thr Phe
                565                 570                 575

Leu Trp Gly Arg Tyr Ser Val Glu Met Ser Ala Val Val Tyr Lys Asp
            580                 585                 590

Trp Val Phe Thr Asp Gln Ala Leu Pro Ala Asp Leu Ile Lys Arg Gly
            595                 600                 605

Met Ala Ile Glu Asp Pro Ser Cys Pro His Gly Ile Arg Leu Val Ile
610                 615                 620

Glu Asp Tyr Pro Tyr Ala Val Asp Gly Leu Glu Ile Trp Asp Ala Ile
625                 630                 635                 640

Lys Thr Trp Val His Glu Tyr Val Phe Leu Tyr Tyr Lys Ser Asp Asp
                645                 650                 655

Thr Leu Arg Glu Asp Pro Glu Leu Gln Ala Cys Trp Lys Glu Leu Val
            660                 665                 670

Glu Val Gly His Gly Asp Lys Lys Asn Glu Pro Trp Trp Pro Lys Met
            675                 680                 685

Gln Thr Arg Glu Glu Leu Val Glu Ser Cys Ala Ile Ile Ile Trp Thr
690                 695                 700

Ala Ser Ala Leu His Ala Ala Val Asn Phe Gly Gln Tyr Pro Tyr Gly
705                 710                 715                 720

Gly Leu Ile Leu Asn Arg Pro Thr Leu Ser Arg Arg Phe Met Pro Glu
                725                 730                 735

Lys Gly Ser Ala Glu Tyr Glu Glu Leu Arg Lys Asn Pro Gln Lys Ala
            740                 745                 750

Tyr Leu Lys Thr Ile Thr Pro Lys Phe Gln Thr Leu Ile Asp Leu Ser
            755                 760                 765

Val Ile Glu Ile Leu Ser Arg His Ala Ser Asp Glu Val Tyr Leu Gly
770                 775                 780

Glu Arg Asp Asn Pro Asn Trp Thr Ser Asp Thr Arg Ala Leu Glu Ala
785                 790                 795                 800

Phe Lys Arg Phe Gly Asn Lys Leu Ala Gln Ile Glu Asn Lys Leu Ser
                805                 810                 815

Glu Arg Asn Asn Asp Glu Lys Leu Arg Asn Arg Cys Gly Pro Val Gln
            820                 825                 830

Met Pro Tyr Thr Leu Leu Leu Pro Ser Ser Lys Glu Gly Leu Thr Phe
            835                 840                 845

Arg Gly Ile Pro Asn Ser Ile Ser Ile
850                 855
```

<210> SEQ ID NO 514
<211> LENGTH: 860
<212> TYPE: PRT
<213> ORGANISM: Phaseolus vulgaris

<400> SEQUENCE: 514

```
Met Phe Ser Gly Val Ser Gly Leu Ile Asn Arg Gly His Lys Leu Lys
1               5                   10                  15

Gly Thr Val Val Leu Met Arg Lys Asn Val Leu Asp Val Asn Ser Val
            20                  25                  30

Thr Ser Val Gly Gly Ile Val Gly Gln Gly Leu Asp Ile Leu Gly Ser
        35                  40                  45

Thr Val Asp Asn Leu Thr Ala Phe Leu Gly Arg Ser Val Ser Leu Gln
50                  55                  60

Leu Ile Ser Ala Thr Lys Pro Asp Ala Asn Gly Lys Gly Lys Leu Gly
65                  70                  75                  80

Lys Ala Thr Phe Leu Glu Gly Ile Ile Thr Ser Leu Pro Thr Leu Gly
                85                  90                  95

Ala Gly Gln Ser Ala Phe Lys Ile His Phe Glu Trp Asp Asp Glu Met
            100                 105                 110

Gly Ile Pro Gly Ala Phe Tyr Ile Lys Asn Phe Met Gln Thr Glu Phe
        115                 120                 125

Tyr Leu Val Ser Leu Thr Leu Glu Asp Ile Pro Asn His Gly Ser Leu
130                 135                 140

His Phe Leu Cys Asn Ser Trp Ile Tyr Asn Ala Lys His Phe Lys Asn
145                 150                 155                 160

Asp Arg Ile Phe Phe Val Asn Gln Ile Tyr Leu Pro Ser Glu Thr Pro
                165                 170                 175

Ala Pro Leu Val Lys Tyr Arg Glu Glu Glu Leu Val Asn Met Arg Gly
            180                 185                 190

Asp Gly Thr Gly Glu Arg Lys Glu Trp Asp Arg Ile Tyr Asp Tyr Asp
        195                 200                 205

Val Tyr Asn Asp Leu Gly Asp Pro Asp Lys Gly Glu Asn Asn Ala Arg
210                 215                 220

Pro Ile Leu Gly Gly Ser Asp Thr Leu Pro Tyr Pro Arg Arg Gly Arg
225                 230                 235                 240

Thr Gly Arg Arg Pro Thr Arg Lys Asp Pro Lys Ser Glu Ser Arg Ser
                245                 250                 255

Ser Asp Ile Tyr Leu Pro Arg Asp Glu Ala Phe Gly His Leu Lys Ser
            260                 265                 270

Ser Asp Phe Leu Thr Tyr Gly Leu Lys Ser Val Ser Gln Asn Phe Leu
        275                 280                 285

Pro Ala Leu Gln Ser Ala Phe Asp Leu Asn Phe Thr Pro Asn Glu Phe
290                 295                 300

Asp Ser Phe Glu Glu Val His Gly Leu Tyr Ser Gly Gly Ile Lys Leu
305                 310                 315                 320

Pro Thr Asp Val Leu Ser Lys Ile Ser Pro Leu Pro Val Leu Lys Glu
                325                 330                 335

Ile Phe Arg Thr Asp Gly Glu Gln Thr Leu Lys Phe Pro Pro Pro Lys
            340                 345                 350

Val Val Gln Asp Ser Lys Ser Ala Trp Met Thr Asp Glu Glu Phe Ala
        355                 360                 365

Arg Glu Met Ile Cys Gly Val Asn Pro Asn Leu Ile Arg Leu Leu Gln
```

```
              370                 375                 380
Asp Phe Pro Pro Gln Ser Lys Leu Asp Ser Gln Val Tyr Gly Asp His
385                 390                 395                 400

Thr Ser Gln Ile Thr Lys Glu Asn Leu Glu Pro Asn Leu Glu Gly Leu
                405                 410                 415

Thr Val Asp Glu Ala Ile Gln Ser Lys Arg Leu Phe Leu Leu Asp His
                420                 425                 430

His Asp Ser Ile Met Pro Tyr Leu Arg Arg Ile Asn Ala Thr Ser Ser
                435                 440                 445

Lys Ala Tyr Ala Thr Arg Thr Ile Leu Phe Leu Lys Lys Asp Arg Thr
                450                 455                 460

Leu Lys Pro Leu Ala Ile Glu Leu Ser Leu Pro His Pro Gly Gly Asp
465                 470                 475                 480

Lys Ser Gly Val Val Ser Gln Val Phe Leu Pro Ala Asp Glu Gly Val
                485                 490                 495

Glu Ser Ser Val Trp Leu Leu Ala Lys Ser Tyr Val Ile Val Asn Asp
                500                 505                 510

Ser Ser Tyr His Gln Leu Val Ser His Trp Leu Asn Thr His Ala Val
                515                 520                 525

Val Glu Pro Phe Val Ile Ala Thr Asn Arg His Leu Ser Val Val His
                530                 535                 540

Pro Ile Tyr Lys Leu Leu His Pro His Tyr Arg Asp Thr Met Asn Ile
545                 550                 555                 560

Asn Ala Leu Ala Arg Gly Asp Leu Val Asn His Gly Gly Ile Ile Glu
                565                 570                 575

Lys Thr Phe Val Trp Gly Arg Tyr Ser Met Glu Met Ser Ala Val Ile
                580                 585                 590

Tyr Lys Asp Trp Val Phe Thr Asp Gln Ala Leu Pro Ala Asp Leu Ile
                595                 600                 605

Lys Arg Gly Ile Ala Thr Glu Asp Pro Glu Cys Pro His Gly Leu Arg
610                 615                 620

Leu Phe Ile Glu Asp Tyr Pro Tyr Ala Val Asp Gly Leu Glu Ile Trp
625                 630                 635                 640

Asp Ala Ile Lys Thr Trp Val His Glu Tyr Val Phe Leu Tyr Tyr Lys
                645                 650                 655

Ser Asp Asp Thr Leu Lys Glu Asp Pro Glu Leu Gln Ala Trp Trp Lys
                660                 665                 670

Glu Leu Val Glu Val Gly His Gly Asp Lys Lys Asn Glu Pro Trp Trp
                675                 680                 685

Pro Lys Met Gln Thr Arg Glu Glu Leu Val Glu Ala Cys Ser Ile Val
690                 695                 700

Ile Trp Thr Ala Ser Ala Leu His Ala Ala Val Asn Phe Gly Gln Tyr
705                 710                 715                 720

Pro Tyr Gly Gly Leu Ile Leu Asn Arg Pro Thr Leu Ser Arg Arg Phe
                725                 730                 735

Met Pro Glu Glu Gly Ser Ala Glu Tyr Glu Glu Leu Lys Lys Ser Pro
                740                 745                 750

Gln Lys Ala Leu Leu Lys Thr Ile Thr Pro Lys Phe Gln Thr Leu Val
                755                 760                 765

Asp Leu Ser Val Ile Glu Ile Leu Ser Arg His Ala Ser Asp Glu Val
                770                 775                 780

Tyr Leu Gly Glu Arg Asp Asn Pro Asn Trp Thr Ser Asp Thr Arg Ala
785                 790                 795                 800
```

```
Leu Glu Ala Phe Lys Arg Phe Gly Lys Lys Leu Ser Glu Ile Glu Lys
            805                 810                 815

Lys Leu Ser Gln Arg Asn Asn Asp Glu Lys Leu Arg Asn Arg Tyr Gly
            820                 825                 830

Pro Val Met Met Pro Tyr Thr Leu Leu Phe Pro Ser Ser Asp Glu Gly
            835                 840                 845

Leu Thr Phe Arg Gly Ile Pro Asn Ser Ile Ser Ile
            850                 855                 860

<210> SEQ ID NO 515
<211> LENGTH: 498
<212> TYPE: PRT
<213> ORGANISM: Vicia sativa

<400> SEQUENCE: 515

Met Ala Lys Leu Leu Ala Leu Ser Leu Ser Phe Cys Phe Leu Leu Phe
1               5                   10                  15

Ser Ser Cys Phe Ala Leu Arg Glu Gln Ser Gln Gln Asn Glu Cys Gln
            20                  25                  30

Leu Glu Arg Ile Asn Ala Leu Glu Pro Asp Asn Arg Ile Glu Ser Glu
        35                  40                  45

Gly Gly Leu Ile Glu Thr Trp Asn Pro Asn Asn Arg Gln Phe Arg Cys
50                  55                  60

Ala Arg Val Ala Leu Ser Arg Ala Thr Leu Gln Arg Asn Ala Leu Arg
65                  70                  75                  80

Arg Pro Tyr Tyr Ser Asn Ala Pro Gln Glu Ile Tyr Ile Gln Gln Gly
            85                  90                  95

Asn Gly Tyr Phe Gly Met Val Phe Pro Gly Cys Pro Glu Thr His Glu
            100                 105                 110

Glu Pro Gln Gln Ser Glu Gln Gly Glu Gly Arg Arg Tyr Arg Asp Ser
        115                 120                 125

His Gln Lys Val Asn Arg Phe Arg Glu Gly Asp Ile Ile Ala Val Pro
    130                 135                 140

Thr Gly Ile Ala Phe Trp Met Tyr Asn Asp Gln Asp Thr Pro Val Ile
145                 150                 155                 160

Ala Ile Ser Leu Thr Asp Thr Gly Ser Ser Asn Asn Gln Leu Asp Gln
                165                 170                 175

Met Pro Arg Arg Phe Tyr Leu Ala Gly Asn Gln Glu Gln Glu Phe Leu
            180                 185                 190

Arg Tyr Gln His Gln Gln Gly Gly Lys Gln Glu Gln Asp Asn Asp Gly
        195                 200                 205

Asn Asn Ile Phe Ser Gly Phe Lys Arg Asp Phe Leu Glu Asp Ala Phe
    210                 215                 220

Asn Val Asn Arg His Ile Val Asp Arg Leu Gln Gly Arg Asn Glu Asp
225                 230                 235                 240

Glu Glu Lys Gly Ala Ile Val Lys Val Lys Gly Gly Leu Ser Ile Ile
                245                 250                 255

Ala Pro Pro Glu Arg Gln Ala Arg His Glu Arg Gly Ser Arg Gln Glu
            260                 265                 270

Glu Asp Glu Asp Glu Lys Glu Arg Gln Pro Ser His His Lys Ser
        275                 280                 285

Arg Arg Asp Glu Asp Glu Asp Lys Glu Lys Arg His Ser Gln Lys
    290                 295                 300

Gly Gln Ser Arg Arg Gln Gly Asp Asn Gly Leu Glu Glu Thr Val Cys
```

```
        305                 310                 315                 320
    Thr Ala Lys Leu Arg Ala Asn Ile Gly Ser Ser Pro Ser Pro Asp Ile
                    325                 330                 335

Tyr Asn Pro Gln Ala Gly Arg Ile Lys Thr Val Thr Ser Leu Asp Leu
                    340                 345                 350

Pro Val Leu Arg Trp Leu Lys Leu Ser Ala Glu His Gly Ser Leu His
                    355                 360                 365

Lys Asn Ala Met Phe Val Pro His Tyr Asn Leu Asn Ala Asn Ser Val
                    370                 375                 380

Ile Tyr Ala Leu Lys Gly Arg Ala Arg Leu Gln Val Val Asn Cys Asn
    385                 390                 395                 400

Gly Asn Thr Val Phe Asp Gly Glu Leu Glu Ala Gly Arg Ala Leu Thr
                    405                 410                 415

Val Pro Gln Asn Tyr Ala Val Ala Lys Ser Leu Ser Glu Arg Phe
                    420                 425                 430

Thr Tyr Val Ala Phe Lys Thr Asp Asp Arg Ala Ser Ile Ala Arg Leu
                    435                 440                 445

Ala Gly Thr Ser Ser Val Ile Asp Asp Leu Pro Leu Asp Val Val Ala
                    450                 455                 460

Ala Thr Phe Asn Met Gln Arg Asn Glu Ala Arg Gln Leu Lys Ser Asn
    465                 470                 475                 480

Asn Pro Phe Lys Phe Leu Val Pro Pro Arg Gln Ser Glu Met Arg Ala
                    485                 490                 495

Ser Ala

<210> SEQ ID NO 516
<211> LENGTH: 482
<212> TYPE: PRT
<213> ORGANISM: Vicia narbonensis

<400> SEQUENCE: 516

Met Ala Lys Leu Leu Ala Leu Ser Leu Ser Leu Cys Phe Leu Leu Phe
    1               5                   10                  15

Ser Asn Ser Phe Ala Leu Arg Glu Gln Ser Gln Gln Asn Glu Cys Gln
                    20                  25                  30

Leu Glu Arg Leu Asp Ala Leu Glu Pro Asp Asn Arg Ile Glu Ser Glu
                    35                  40                  45

Gly Gly Leu Ile Glu Thr Trp Asn Pro Asn Asn Arg Gln Phe Arg Cys
                    50                  55                  60

Ala Gly Val Ala Leu Ser Arg Val Thr Leu Gln Arg Asn Ala Leu Arg
    65                  70                  75                  80

Arg Pro Tyr Tyr Ser Asn Ala Pro Gln Glu Ile Tyr Ile Gln Gln Gly
                    85                  90                  95

Asn Gly Tyr Phe Gly Val Val Phe Pro Gly Cys Pro Glu Thr Phe Glu
                    100                 105                 110

Glu Pro Gln Glu Ser Glu Gln Arg Glu Arg Arg Tyr Arg Asp Ser
                    115                 120                 125

His Gln Lys Val Asn Arg Phe Arg Glu Gly Asp Ile Ile Ala Val Pro
                    130                 135                 140

Thr Gly Asn Val Leu Trp Met Tyr Asn Asp Gln Asp Thr Pro Val Ile
    145                 150                 155                 160

Ala Ile Ser Leu Thr Asp Thr Gly Ser Ser Asn Asn Gln Leu Asp Gln
                    165                 170                 175

Ile Pro Arg Arg Phe Tyr Leu Ala Gly Asn Gln Glu Gln Glu Phe Leu
```

```
            180                 185                 190
Arg Tyr Gln Arg Glu Gln Gly Gly Lys Gln Glu Gln Glu Asn Asp Gly
            195                 200                 205

Asn Asn Ile Phe Ser Gly Phe Lys Arg Asp Phe Leu Glu Asp Ala Leu
            210                 215                 220

Asn Val Asn Arg His Ile Val Asp Arg Leu Gln Gly Arg Asn Glu Asp
225                 230                 235                 240

Glu Glu Lys Gly Ala Ile Val Lys Val Lys Gly Gly Leu Ser Ile Ile
                245                 250                 255

Thr Pro Pro Glu Arg Gln Arg Gly Ser Arg Gln Glu Glu Asp Glu Asp
                260                 265                 270

Glu Lys Glu Glu Arg Gln Pro Ser Arg Arg Asp Glu Ser Gln Lys
            275                 280                 285

Gly Glu Ser Arg Arg His Gly Asp Asn Gly Leu Glu Glu Thr Val Cys
            290                 295                 300

Thr Ala Lys Leu Arg Val Asn Ile Gly Ser Ser Pro Ser Pro Asp Ile
305                 310                 315                 320

Tyr Asn Pro Gln Ala Gly Arg Ile Asn Thr Val Thr Ser Leu Asp Leu
                325                 330                 335

Pro Val Leu Arg Trp Leu Lys Leu Ser Ala Glu His Gly Ser Leu Arg
                340                 345                 350

Lys Asn Ala Leu Ile Val Pro His Tyr Asn Arg Asn Ala Asn Ser Val
            355                 360                 365

Ile Tyr Ala Leu Lys Gly Arg Ala Arg Leu Gln Val Val Asn Cys Asn
            370                 375                 380

Gly Asn Thr Val Phe Asp Gly Glu Leu Glu Ala Gly Arg Ala Leu Thr
385                 390                 395                 400

Val Pro Gln Asn Tyr Ala Val Ala Ala Lys Ser Leu Ser Glu Arg Phe
                405                 410                 415

Thr Tyr Val Ala Phe Lys Thr Asn Asp Arg Asp Gly Ile Ala Arg Leu
                420                 425                 430

Ala Gly Thr Ser Ser Val Ile Asn Asp Leu Pro Leu Asp Val Val Ala
            435                 440                 445

Ala Thr Phe Asn Leu Gln Arg Asn Glu Ala Arg Gln Leu Lys Ser Asn
            450                 455                 460

Asn Pro Phe Lys Leu Leu Val Pro Pro Arg Glu Ser Glu Lys Arg Ala
465                 470                 475                 480

Ser Ala

<210> SEQ ID NO 517
<211> LENGTH: 499
<212> TYPE: PRT
<213> ORGANISM: Cicer arietinum
<220> FEATURE:
<221> NAME/KEY: MISC_FEATURE
<222> LOCATION: (189)..(196)
<223> OTHER INFORMATION: Xaa can be any naturally occurring amino acid

<400> SEQUENCE: 517

Met Ala Lys Leu Leu Ala Leu Ser Leu Ser Phe Cys Phe Leu Leu Phe
1               5                   10                  15

Gly Ser Cys Phe Ala Leu Arg Asp Gln Pro Glu Gln Asn Glu Cys Gln
                20                  25                  30

Leu Glu His Leu Asn Ala Leu Glu Pro Asp Asn Arg Ile Lys Ser Glu
            35                  40                  45
```

```
Gly Gly Leu Ile Glu Thr Trp Asn Pro Ser Asn Lys Gln Phe Arg Cys
         50                  55                  60

Ala Gly Val Ala Leu Ser Arg Ala Thr Leu Gln Pro Asn Ser Leu Arg
 65                  70                  75                  80

Arg Pro Phe Tyr Thr Asn Ala Pro Gln Glu Ile Phe Ile Gln Gln Gly
                     85                  90                  95

Asn Gly Tyr Phe Gly Met Val Phe Pro Gly Cys Val Glu Thr Phe Glu
                100                 105                 110

Glu Pro Arg Glu Ser Glu Gln Gly Glu Gly Ser Lys Phe Arg Asp Ser
            115                 120                 125

His Gln Lys Val Asn Arg Phe Arg Glu Gly Asp Ile Ile Ala Val Pro
130                 135                 140

Thr Gly Val Val Phe Trp Met Phe Asn Asp Gln Asp Thr Pro Val Ile
145                 150                 155                 160

Ala Val Ser Leu Ile Asp Thr Ser Ser Phe Gln Asn Gln Leu Asp Gln
                165                 170                 175

Met Pro Arg Arg Phe Tyr Leu Ala Gly Asn His Glu Xaa Xaa Xaa Xaa
            180                 185                 190

Xaa Xaa Xaa Xaa Gln Gln Glu Gly Ser Glu Glu Glu Asn Glu Gly
        195                 200                 205

Gly Asn Ile Phe Ser Gly Phe Lys Arg Asp Phe Leu Glu Asp Ala Leu
        210                 215                 220

Asn Val Asn Arg Arg Ile Val Asn Lys Leu Gln Gly Arg Asn Glu Asp
225                 230                 235                 240

Glu Glu Lys Gly Ala Ile Val Lys Val Lys Gly Gly Leu Ser Ile Ile
                245                 250                 255

Thr Pro Pro Glu Lys Glu Pro Arg Gln Lys Arg Gly Ser Arg Gln Glu
            260                 265                 270

Glu Asp Glu Asp Glu Asp Lys Arg Gln Pro His Arg His Ser Arg
        275                 280                 285

Gln Asp Glu Asp Glu Asp Lys Arg Gln Pro Arg Arg His Ser Arg
        290                 295                 300

Gly Gly Ser Lys Ser Gln Arg Asp Asn Gly Phe Glu Glu Thr Ile Cys
305                 310                 315                 320

Thr Ala Arg Leu His Gln Asn Ile Gly Ser Ser Ser Pro Asp Ile
                325                 330                 335

Tyr Asn Pro Gln Ala Gly Arg Ile Lys Thr Val Thr Ser Phe Asp Leu
                340                 345                 350

Pro Ala Leu Arg Phe Leu Lys Leu Ser Ala Glu Phe Gly Ser Leu His
            355                 360                 365

Lys Asn Ala Met Phe Val Pro His Tyr Asn Leu Asn Ala Asn Ser Ile
370                 375                 380

Leu Tyr Ala Leu Lys Gly Arg Ala Arg Leu Gln Ile Val Asn Cys Lys
385                 390                 395                 400

Gly Asn Ser Val Phe Asp Gly Glu Leu Glu Ala Gly Arg Ala Leu Ile
                405                 410                 415

Val Pro Gln Asn Phe Ala Ile Ala Ala Lys Ser Leu Ser Asp Arg Phe
            420                 425                 430

Ser Tyr Val Ala Phe Lys Thr Asn Asp Arg Ala Ala Ile Gly Arg Leu
        435                 440                 445

Leu Gly Ala Ser Ser Leu Ile Asn Gly Met Pro Glu Glu Val Val Ala
450                 455                 460

Ala Ala Phe Asn Met Glu Arg Asn Glu Ala Arg Gln Leu Lys Phe Asn
```

```
                465                 470                 475                 480
Ser Pro Phe Ser Phe Leu Val Pro Pro Arg Ser Asp Ser Asp Asn Lys
                    485                 490                 495

Ala Ala Ala

<210> SEQ ID NO 518
<211> LENGTH: 576
<212> TYPE: PRT
<213> ORGANISM: Lathyrus hirsutus

<400> SEQUENCE: 518

Met Ala Ile Ile Ile Lys Ser Arg Phe Pro Leu Leu Leu Leu Leu Gly
1               5                   10                  15

Ile Ile Phe Leu Ala Ser Val Cys Ala Thr Trp Ala Asn Tyr Asp Glu
            20                  25                  30

Gly Ser Glu Pro Arg Val Pro Gly Gln Arg Glu Arg Gly Arg Gln Glu
        35                  40                  45

Gly Glu Lys Ala Glu Lys Ser His Glu Lys Trp Arg Pro Ser Tyr Glu
    50                  55                  60

Glu Glu Tyr Asp Glu Gly Ser Glu Pro Arg Val Pro Gly Lys Arg Glu
65                  70                  75                  80

Arg Gly Arg Gln Glu Gly Glu Lys Glu Lys Arg His Gly Glu Trp
                85                  90                  95

Arg Pro Ser His Glu Glu Glu Tyr Asp Gly Ser Glu Pro Arg Val
                    100                 105                 110

Pro Thr His Gly Glu Arg Gly Arg Gln Glu Gly Glu Lys Glu Glu Lys
            115                 120                 125

Arg His Glu Glu Trp Arg Pro Ser Tyr Glu Lys Glu Asp Glu Glu
    130                 135                 140

Glu Lys Glu Lys Tyr Lys Tyr Gln Arg Glu Lys Lys Glu Gln Lys Glu
145                 150                 155                 160

Val Gln Pro Gly Arg Glu Lys Trp Glu Arg Lys Gln Asp Glu Lys His
                165                 170                 175

Val Glu Glu Asp Glu Asp Gln Glu Glu Glu Gln Trp Arg Gly Ser Lys
                    180                 185                 190

Arg Arg Glu Asp Pro Glu Glu Arg Ala Arg Leu Arg Tyr Arg Glu Glu
            195                 200                 205

Arg Thr Lys Ser Asn Val Glu Glu Thr Glu Glu Arg Arg Asn Pro
    210                 215                 220

Phe Leu Phe Lys Ser Asn Lys Phe Leu Thr Leu Phe Glu Asn Glu Asn
225                 230                 235                 240

Gly His Ile Arg Arg Leu Gln Arg Phe Asp Glu Arg Ser Asp Ile Phe
                245                 250                 255

Glu Asn Leu Gln Asn Tyr Arg Leu Val Glu Tyr Lys Ala Lys Pro His
                    260                 265                 270

Thr Met Phe Leu Pro Gln His Ile Asp Ala Asp Leu Ile Ile Val Val
            275                 280                 285

Leu Asn Gly Lys Ala Ile Leu Thr Val Leu Ser Pro Asn Asp Arg Asn
    290                 295                 300

Ser Tyr Asn Leu Glu Arg Gly Asp Thr Ile Lys Leu Pro Ala Gly Thr
305                 310                 315                 320

Thr Ser Tyr Leu Val Asn Gln Asp Asp Glu Glu Asp Leu Arg Val Val
                325                 330                 335

Asp Leu Ala Ile Pro Val Asn Arg Pro Gly Lys Phe Glu Ala Phe Gly
```

```
              340                 345                 350
Leu Ser Ala Asn Lys Asn Gln Tyr Leu Arg Gly Phe Ser Lys Asn Ile
            355                 360                 365

Leu Glu Ala Phe Leu Asn Thr Lys Tyr Glu Thr Ile Glu Lys Val Leu
        370                 375                 380

Leu Glu Glu Gln Glu Arg Asp Arg Lys Gly Arg Gln Gln Gly Gln
385                 390                 395                 400

Glu Thr Asn Ala Ile Val Lys Val Ser Arg Glu Gln Ile Glu Glu Leu
                405                 410                 415

Arg Lys Leu Ala Lys Ser Ser Lys Lys Ser Leu Leu Ser Glu Ser
            420                 425                 430

Glu Pro Ile Asn Leu Arg Ser Gln Asn Pro Lys Tyr Ser Asn Lys Phe
        435                 440                 445

Gly Lys Leu Phe Glu Ile Thr Pro Glu Lys Lys Tyr Pro Gln Leu Gln
    450                 455                 460

Asp Leu Asp Val Ser Ile Ser Cys Val Glu Ile Asn Glu Gly Ala Pro
465                 470                 475                 480

Leu Leu Pro His Tyr Asn Ser Arg Ala Ile Val Leu Leu Leu Val Asn
                485                 490                 495

Glu Gly Lys Gly Asn Leu Glu Leu Val Gly Phe Lys Asn Glu Gln Gln
            500                 505                 510

Arg Gln Arg Glu Asn Glu Glu Arg Asn Lys Lys Val Gln Arg Tyr Glu
        515                 520                 525

Ala Arg Leu Ser Pro Gly Asp Val Val Ile Pro Ala Gly His Pro
    530                 535                 540

Val Ala Ile Ser Ala Ser Leu Asn Leu Asn Leu Val Gly Phe Gly Val
545                 550                 555                 560

Asn Ala Glu Asn Asn Gln Arg Asn Phe Leu Thr Gly Ser Asp Asp Asn
                565                 570                 575

<210> SEQ ID NO 519
<211> LENGTH: 564
<212> TYPE: PRT
<213> ORGANISM: Lathyrus cicera

<400> SEQUENCE: 519

Met Ala Thr Ile Ile Lys Ser Arg Phe Pro Leu Leu Leu Leu Leu Gly
1               5                   10                  15

Ile Ile Phe Leu Ala Ser Val Cys Val Thr Leu Ala Asn Tyr Asp Glu
            20                  25                  30

Gly Ser Glu Pro Arg Val Pro Ala Gln Arg Glu Arg Gly Arg Gln Glu
        35                  40                  45

Gly Glu Lys Glu Glu Lys Arg His Gly Glu Trp Arg Pro Ser His Glu
    50                  55                  60

Lys Glu Tyr Asp Glu Gly Ser Glu Pro Arg Val Pro Gly Arg Arg Glu
65                  70                  75                  80

Arg Gly Arg Gln Glu Gly Glu Lys Glu Glu Lys Arg His Gly Glu Trp
                85                  90                  95

Arg Pro Ser Tyr Glu Lys Glu Tyr Asp Glu Gly Ser Glu Pro Arg Val
            100                 105                 110

Pro Gly Arg Arg Glu Arg Gly Arg Gln Glu Gly Glu Lys Glu Glu Lys
        115                 120                 125

Arg His Gly Glu Trp Arg Pro Ser Tyr Glu Lys Glu Tyr Asp Glu Glu
    130                 135                 140
```

```
Glu Lys Gln Lys Tyr Gln Tyr Glu Arg Glu Lys Glu Gln Lys Glu
145                 150                 155                 160

Val Gln Pro Gly Arg Glu Arg Trp Glu Arg Lys Glu Asp Glu Lys
            165                 170                 175

Glu Glu Asp Gln Trp Arg Gly Ser Gln Arg His Glu Asp Pro Glu Glu
            180                 185                 190

Arg Ala Arg Leu Arg Tyr Arg Lys Glu Arg Thr Lys Lys Tyr Val Glu
            195                 200                 205

Glu Asp Thr Glu Glu Thr Ser Ser Glu Ser Gln Gly Arg Arg Asn Pro
        210                 215                 220

Phe Leu Phe Lys Ser Asn Lys Phe Leu Thr Leu Phe Glu Asn Glu Asn
225                 230                 235                 240

Gly Tyr Ile Arg Arg Leu Gln Arg Phe Asp Glu Arg Ser Asp Ile Phe
                245                 250                 255

Glu Asn Leu Gln Asn Tyr Arg Leu Val Glu Tyr Arg Ala Lys Pro His
            260                 265                 270

Thr Ile Phe Leu Pro Gln His Ile Asp Ala Asp Leu Ile Leu Val Ile
        275                 280                 285

Leu Asn Gly Lys Ala Ile Leu Thr Val Leu Ser Pro Asn Asp Arg Asn
290                 295                 300

Ser Tyr Asn Leu Glu Arg Gly Asp Thr Ile Lys Leu Pro Ala Gly Thr
305                 310                 315                 320

Thr Ser Tyr Leu Val Asn Glu Asp Glu Asp Leu Arg Val Val
            325                 330                 335

Asp Leu Val Ile Pro Val Asn Arg Pro Gly Lys Phe Glu Ala Phe Asp
            340                 345                 350

Leu Asn Gln Tyr Leu Gly Gly Phe Ser Lys Ser Val Leu Glu Ala Ser
            355                 360                 365

Leu Asn Thr Lys Tyr Glu Thr Ile Glu Lys Val Leu Leu Glu Glu Gln
        370                 375                 380

Gln Lys Gln Gly Gln Glu Thr Asn Ala Ile Val Lys Val Ser Arg Glu
385                 390                 395                 400

Gln Ile Glu Glu Leu Arg Lys Leu Ala Lys Ser Ser Ser Lys Lys Ser
                405                 410                 415

Leu Leu Ser Glu Leu Glu Pro Val Asn Leu Arg Ser His Ser Pro Lys
            420                 425                 430

Tyr Ser Asn Lys Phe Gly Lys Phe Phe Glu Ile Thr Pro Glu Lys Lys
            435                 440                 445

Tyr Pro Gln Leu Gln Asp Leu Asp Val Ser Ile Ser Cys Val Glu Ile
450                 455                 460

Asn Glu Gly Ala Leu Leu Leu Pro His Tyr Asn Ser Arg Ala Ile Val
465                 470                 475                 480

Val Val Leu Val Asn Glu Gly Lys Gly Asn Leu Glu Leu Leu Gly Val
            485                 490                 495

Gln Asn Glu Asp Glu Gln Glu Arg Lys Arg Asn Lys Glu Val
            500                 505                 510

Gln Arg Tyr Glu Ala Arg Leu Ser Pro Gly Asp Val Val Ile Ile Pro
            515                 520                 525

Ser Gly His Pro Val Ala Val Ser Ala Ser Ser Asn Leu Asn Leu Leu
            530                 535                 540

Gly Phe Gly Ile Asn Ala Glu Asn Asn Gln Arg Asn Phe Leu Ser Gly
545                 550                 555                 560

Ser Asp Asp Asn
```

<210> SEQ ID NO 520
<211> LENGTH: 527
<212> TYPE: PRT
<213> ORGANISM: Lathyrus sativus

<400> SEQUENCE: 520

```
Met Ala Thr Ile Ile Lys Ser Arg Phe Pro Leu Leu Leu Leu Leu Gly
1               5                   10                  15

Ile Ile Phe Leu Ala Ser Val Cys Val Thr Tyr Ala Asn Tyr Asp Glu
            20                  25                  30

Gly Ser Glu Pro Arg Val Pro Ala Gln Arg Glu Arg Gly Arg Gln Glu
        35                  40                  45

Gly Glu Lys Glu Glu Lys Arg His Gly Glu Trp Arg Pro Ser Ser Glu
    50                  55                  60

Lys Glu Tyr Asp Glu Gly Ser Glu Pro Arg Val Pro Gly Arg Arg Glu
65                  70                  75                  80

Arg Gly Arg Gln Glu Gly Glu Lys Glu Glu Lys Arg His Gly Glu Trp
                85                  90                  95

Arg Pro Ser Tyr Glu Lys Glu Tyr Asp Glu Glu Lys Gln Lys Tyr
            100                 105                 110

Gln Tyr Glu Arg Glu Lys Lys Glu Gln Lys Glu Val Glu Pro Gly Arg
        115                 120                 125

Glu Arg Trp Glu Arg Lys Glu Asp Glu Lys Glu Glu Asp Gln Trp
    130                 135                 140

Arg Gly Ser Gln Arg His Glu Asp Pro Glu Glu Arg Ala Arg Leu Arg
145                 150                 155                 160

Tyr Arg Lys Glu Arg Thr Lys Lys Tyr Val Glu Glu Asp Thr Glu Glu
                165                 170                 175

Thr Ser Ser Glu Ser Gln Gly Arg Arg Asn Pro Phe Leu Phe Lys Ser
            180                 185                 190

Asn Lys Phe Leu Thr Leu Phe Glu Asn Glu Asn Gly Tyr Ile Arg Arg
        195                 200                 205

Leu Gln Arg Phe Asp Glu Arg Ser Asp Leu Phe Glu Asn Leu Gln Asn
    210                 215                 220

Tyr Arg Leu Val Glu Tyr Arg Ala Lys Pro His Thr Ile Phe Leu Pro
225                 230                 235                 240

Gln His Ile Asp Ala Asp Leu Ile Leu Val Ile Leu Asn Gly Lys Ala
                245                 250                 255

Ile Leu Thr Val Leu Ser Pro Asn Asp Arg Asn Ser Tyr Asn Leu Glu
            260                 265                 270

Arg Gly Asp Thr Ile Lys Leu Pro Ala Gly Thr Thr Ser Tyr Leu Val
        275                 280                 285

Asn Glu Asp Asp Glu Glu Asp Leu Arg Val Val Asp Leu Val Ile Pro
    290                 295                 300

Val Asn Arg Pro Gly Lys Phe Glu Ala Phe Asp Leu Asn Gln Tyr Leu
305                 310                 315                 320

Gly Gly Phe Ser Lys Ser Val Leu Lys Ala Ser Leu Asn Thr Lys Tyr
                325                 330                 335

Glu Thr Ile Glu Lys Val Leu Leu Glu Gln Gln Lys Gln Gly Gln
            340                 345                 350

Glu Thr Asn Ala Ile Val Lys Val Ser Arg Glu Gln Ile Glu Glu Leu
        355                 360                 365

Arg Lys Leu Ala Lys Ser Ser Ser Lys Lys Ser Leu Leu Ser Glu Leu
```

```
                   370                 375                 380
Glu Pro Val Asn Leu Arg Ser His Ser Pro Lys Tyr Ser Asn Lys Phe
385                 390                 395                 400

Gly Lys Phe Phe Glu Ile Thr Pro Glu Lys Lys Tyr Pro Gln Leu Gln
                405                 410                 415

Asp Leu Asp Val Ser Ile Ser Cys Val Glu Ile Asn Glu Gly Ala Leu
                420                 425                 430

Leu Leu Pro His Tyr Asn Ser Arg Ala Ile Val Val Leu Leu Val Asn
                435                 440                 445

Glu Gly Lys Gly Asn Leu Glu Leu Leu Gly Val Gln Asp Glu Asp Glu
                450                 455                 460

Gln Gln Glu Arg Lys Arg Asn Lys Glu Val Gln Arg Tyr Glu Ala
465                 470                 475                 480

Arg Leu Ser Pro Ser Asp Val Val Ile Ile Pro Ala Gly His Pro Val
                485                 490                 495

Ala Val Ser Ala Ser Ser Asn Leu Asn Leu Leu Gly Phe Gly Ile Asn
                500                 505                 510

Ala Glu Asn Asn Glu Arg Asn Phe Leu Ser Gly Ser Asp Asn
                515                 520                 525

<210> SEQ ID NO 521
<211> LENGTH: 463
<212> TYPE: PRT
<213> ORGANISM: Medicago truncatula

<400> SEQUENCE: 521

Met Ala Ile Lys Ala Pro Phe Gln Leu Leu Met Leu Leu Gly Ile Phe
1               5                   10                  15

Phe Leu Ala Ser Val Cys Val Ser Ser Arg Asp Asp Arg His Asp Gln
                20                  25                  30

Glu Asn Pro Phe Phe Phe Asn Ala Asn His Phe Gln Thr Leu Phe Glu
                35                  40                  45

Asn Glu Asn Gly His Ile Arg Leu Leu Gln Arg Phe Asp Lys Arg Ser
    50                  55                  60

Lys Ile Phe Glu Asn Leu Gln Asn Tyr Arg Leu Leu Glu Tyr His Ser
65                  70                  75                  80

Lys Pro His Thr Leu Phe Leu Pro Gln His Asn Asp Ala Asp Phe Ile
                85                  90                  95

Leu Ala Val Leu Ser Gly Lys Ala Ile Leu Thr Val Leu Asn Pro Asp
                100                 105                 110

Asn Arg Asn Ser Phe Asn Leu Glu Arg Gly Asp Thr Ile Lys Leu Pro
                115                 120                 125

Ala Gly Ser Ile Ala Tyr Leu Ala Asn Arg Asp Asn Glu Asp Leu
                130                 135                 140

Arg Val Leu Asp Leu Ala Ile Pro Val Asn Arg Pro Gly Lys Phe Gln
145                 150                 155                 160

Ser Phe Ser Leu Ser Gly Ser Gln Asn Gln Gln Ser Phe Phe Ser Gly
                165                 170                 175

Phe Ser Lys Asn Ile Leu Glu Ala Ala Phe Asn Ala Asn Tyr Glu Glu
                180                 185                 190

Ile Glu Arg Val Leu Ile Glu Glu His Glu Gln Glu Pro Gln His Arg
                195                 200                 205

Arg Gly Leu Arg Lys Asp Arg Arg Gln Gln Ser Gln Asp Ser Asn Val
                210                 215                 220
```

```
Ile Val Lys Val Ser Arg Glu Gln Ile Glu Glu Leu Ser Arg His Ala
225                 230                 235                 240

Lys Ser Ser Ser Arg Arg Ser Gly Ser Ser Glu Ser Ala Pro Phe Asn
            245                 250                 255

Leu Arg Ser Arg Glu Pro Ile Tyr Ser Asn Glu Phe Gly Asn Phe Phe
            260                 265                 270

Glu Ile Thr Pro Glu Lys Asn Pro Gln Leu Lys Asp Leu Asp Ile Leu
            275                 280                 285

Val Asn Tyr Ala Glu Ile Arg Glu Gly Ser Leu Leu Pro His Phe
            290                 295                 300

Asn Ser Arg Ala Thr Val Ile Val Val Asp Glu Gly Lys Gly Glu
305                 310                 315                 320

Phe Glu Leu Val Gly Gln Arg Asn Glu Asn Gln Gln Glu Gln Arg Glu
            325                 330                 335

Glu Asp Glu Gln Gln Glu Glu Arg Ser Gln Gln Val Gln Arg Tyr
            340                 345                 350

Arg Ala Arg Leu Ser Pro Gly Asp Val Tyr Val Ile Pro Ala Gly His
            355                 360                 365

Pro Thr Val Val Ser Ala Ser Ser Asp Leu Ser Leu Leu Gly Phe Gly
370                 375                 380

Ile Asn Ala Glu Asn Asn Glu Arg Asn Phe Leu Ala Gly Glu Glu Asp
385                 390                 395                 400

Asn Val Ile Ser Gln Ile Glu Arg Pro Val Lys Glu Val Ala Phe Pro
            405                 410                 415

Gly Ser Ala Gln Asp Val Glu Ser Leu Leu Lys Asn Gln Arg Gln Ser
            420                 425                 430

Tyr Phe Ala Asn Ala Gln Pro Gln Gln Arg Glu Arg Glu Glu Gly Arg
            435                 440                 445

Ser Gln Arg Gln Arg Glu Leu Ile Ser Ser Ile Leu Gly Val Phe
            450                 455                 460

<210> SEQ ID NO 522
<211> LENGTH: 499
<212> TYPE: PRT
<213> ORGANISM: Vicia pannonica

<400> SEQUENCE: 522

Met Ala Thr Thr Phe Lys Ser Arg Phe Ser Leu Leu Leu Leu Leu Gly
1               5                   10                  15

Ile Ile Phe Leu Ala Phe Val Cys Val Thr Cys Ala Asn Tyr Asp Glu
            20                  25                  30

Gly Ser Glu Pro Arg Val Pro Gly Gln Arg Glu Arg Gly Arg Gln Glu
            35                  40                  45

Gly Glu Lys Glu Glu Gln Ser Arg Glu Arg His Pro Gln Arg Glu Pro
50                  55                  60

Ser Arg Glu Lys Glu Glu Asp Glu Glu Lys Gln Lys Tyr Asp Glu
65                  70                  75                  80

Gly Thr Glu Pro Arg Val Pro Gly Gln Arg Glu Arg Gly Arg Gln Glu
            85                  90                  95

Gly Glu Lys Glu Glu Gln Arg Glu Arg His Pro Gly Gln Arg Glu
            100                 105                 110

Pro Ser Gln Glu Glu Asp Glu Glu Arg Glu Glu Ser Asp Arg Arg Gln
            115                 120                 125

Glu Gly Ser Ser Lys Ser Glu Glu Gln Arg Asn Pro Phe Leu Phe Lys
130                 135                 140
```

```
Ser Asn Lys Phe Leu Thr Leu Phe Gln Asn Gly Asn Gly His Ile Arg
145                 150                 155                 160

Leu Leu Gln Arg Phe Asp Lys Arg Ser Asp Leu Phe Glu Asn Leu Gln
            165                 170                 175

Asn Tyr Arg Leu Leu Glu Tyr Arg Ala Lys Pro His Thr Ile Phe Leu
            180                 185                 190

Pro Gln His Ile Asp Ala Asp Leu Ile Leu Val Val Leu Ser Gly Arg
            195                 200                 205

Ala Ile Leu Thr Val Leu Ser Pro Asp Asp Arg Asn Ser Tyr Asn Leu
210                 215                 220

Glu Arg Gly Asp Thr Ile Lys Leu Pro Ala Gly Thr Thr Ser Tyr Pro
225                 230                 235                 240

Leu Asn Gln Asp Asp Glu Glu Asp Leu Arg Val Val Asp Leu Ala Ile
            245                 250                 255

Ser Val Asn Arg Pro Gly Lys Val Glu Ser Phe Asn Leu Ser Gly Asn
            260                 265                 270

Lys Asn Gln Tyr Leu Arg Gly Phe Ser Glu Asn Ile Leu Glu Ala Ser
            275                 280                 285

Phe Asn Thr Lys Tyr Glu Thr Ile Glu Lys Val Leu Leu Glu Glu Gln
290                 295                 300

Asp Lys Glu Ser Gln Gln Pro Arg Gly Gln Arg Leu Gln Arg Gln Glu
305                 310                 315                 320

Thr Asn Ala Leu Val Lys Val Ser Arg Glu Gln Val Glu Leu Lys
            325                 330                 335

Arg Leu Ala Arg Thr Ser Ser Lys Lys Gly Val Ser Glu Phe Glu
            340                 345                 350

Pro Phe Asn Leu Arg Ser His Gly Pro Lys Tyr Ser Asn Lys Phe Gly
            355                 360                 365

Lys Phe Phe Glu Ile Thr Pro Glu Lys Lys Tyr Pro Gln Leu Gln Asp
370                 375                 380

Leu Asp Ile Ser Val Ser Ser Val Glu Ile Asn Glu Gly Ala Leu Phe
385                 390                 395                 400

Leu Pro His Tyr Asn Ser Arg Ala Ile Val Val Val Leu Val Asp Glu
            405                 410                 415

Gly Lys Gly Asn Leu Glu Leu Val Gly Phe Lys Asn Glu Gln Gln Glu
            420                 425                 430

Gln Arg Glu Lys Glu Asp Glu Gln Glu Arg Asn Lys Gln Val Gln
            435                 440                 445

Arg Tyr Glu Ala Lys Leu Ser Pro Gly Asp Val Val Ile Ile Pro Ala
            450                 455                 460

Gly His Pro Val Ala Val Ser Ala Ser Ser Asn Leu Asn Leu Leu Gly
465                 470                 475                 480

Phe Gly Ile Asn Ala Glu Asn Asn Gln Arg Asn Phe Leu Thr Gly Ser
            485                 490                 495

Asp Asp Asn

<210> SEQ ID NO 523
<211> LENGTH: 515
<212> TYPE: PRT
<213> ORGANISM: Vicia ludoviciana

<400> SEQUENCE: 523

Met Ala Thr Thr Ile Lys Leu Arg Phe Pro Leu Leu Leu Leu Leu Gly
1               5                   10                  15
```

```
Val Ile Leu Leu Ala Ser Val Cys Val Thr Cys Ala Asn Tyr Asp Glu
             20                  25                  30

Gly Ser Glu Pro Arg Val Pro Gly Arg Pro Glu Gly Glu Lys Glu Glu
         35                  40                  45

Lys His Arg Gly Lys Leu Arg Pro Ser Tyr Glu Lys Glu Glu Asp Glu
 50                  55                  60

Gly Glu Lys Gln Arg Tyr His Tyr Glu Lys Lys Glu Gln Lys Glu Ala
 65                  70                  75                  80

Gln Pro Arg Arg Glu Lys Lys Glu Gln Lys Glu Glu Lys Gln Val
             85                  90                  95

Glu Glu Glu Ser Arg Glu Ser Gln Arg Tyr Glu Asp Pro Gly Glu Arg
             100                 105                 110

Ala Arg Glu Arg Tyr Arg Ala Glu Ile Ile Lys Arg Gln Val Glu Lys
             115                 120                 125

Glu Arg Glu Glu Arg Asp Arg Arg His Gln Arg Glu Gly Glu Glu Glu
     130                 135                 140

Glu Gly Ser Ser Lys Ser Arg Asn Pro Phe Leu Phe Lys Ser Asn Asn
145                 150                 155                 160

Phe Leu Thr Leu Phe Glu Asn Glu Asn Gly His Ile Arg Leu Leu Gln
                 165                 170                 175

Arg Phe Asp Lys Arg Ser Asp Leu Phe Glu Asn Leu Gln Asn Tyr Arg
             180                 185                 190

Leu Val Glu Tyr Arg Ala Lys Pro His Thr Ile Phe Leu Pro Gln His
             195                 200                 205

Ile Asp Ala Asp Leu Ile Leu Val Val Leu Ser Gly Lys Ala Ile Leu
     210                 215                 220

Thr Val Leu Ser Pro Asn Asn Arg Asn Ser Tyr Asn Leu Lys Arg Gly
225                 230                 235                 240

Asp Thr Ile Lys Leu Pro Ala Gly Thr Thr Ser Tyr Leu Leu Asn Ser
             245                 250                 255

Asp Asp Glu Glu Asp Leu Arg Met Val Asp Leu Ala Ile Ser Val Asn
             260                 265                 270

Arg Pro Gly Lys Val Glu Ser Phe Asn Leu Ser Gly Asn Lys Asn Gln
             275                 280                 285

Tyr Leu Arg Gly Phe Ser Lys Asn Ile Leu Glu Ala Ser Phe Asn Thr
             290                 295                 300

Lys Tyr Glu Thr Ile Glu Lys Val Leu Leu Glu Glu Gln Asp Lys Glu
305                 310                 315                 320

Ser Gln Gln Ser Ile Gly Gln Lys Arg Ile Ser Gln Arg Gln Glu Thr
                 325                 330                 335

Asn Ala Leu Val Lys Val Ser Arg Glu Gln Ile Glu Glu Pro Lys Arg
             340                 345                 350

Leu Ala Arg Ser Ser Ser Arg Lys Gly Val Ser Ser Glu Phe Glu Pro
             355                 360                 365

Ile Asn Leu Arg Ser Gln Arg Pro Lys Tyr Ser Asn Lys Phe Gly Lys
             370                 375                 380

Phe Tyr Glu Ile Ser Pro Glu Lys Lys Tyr Pro Gln Leu Gln Asp Leu
385                 390                 395                 400

Asp Val Ser Val Ser Ser Val Glu Ile Asn Glu Gly Ala Leu Leu Leu
                 405                 410                 415

Pro His Tyr Asn Ser Arg Ala Ile Val Thr Val Leu Val Asn Glu Gly
             420                 425                 430
```

```
Lys Gly Asn Leu Glu Leu Ile Gly Phe Gln Asn Glu Gln Gln Gly Gln
            435                 440                 445

Arg Glu Lys Glu Asp Glu Gln Gln His Glu Arg Asn Lys Gln Val Gln
450                 455                 460

Arg Tyr Asp Ala Arg Leu Ser Ser Gly Asp Val Val Ile Ile Pro Ala
465                 470                 475                 480

Gly His Pro Val Ala Val Ser Ala Ser Ser Asn Leu Asp Leu Leu Gly
                    485                 490                 495

Phe Gly Ile Asn Ala Glu Asn Ser Gln Arg Asn Phe Leu Thr Gly Ser
                500                 505                 510

Asp Asp Asn
       515

<210> SEQ ID NO 524
<211> LENGTH: 454
<212> TYPE: PRT
<213> ORGANISM: Oryza sativa

<400> SEQUENCE: 524

Cys Arg Phe Asp Arg Leu Gln Ala Phe Glu Pro Ile Arg Ser Val Arg
1               5                   10                  15

Ser Gln Ala Gly Thr Thr Glu Phe Phe Asp Val Ser Asn Glu Gln Phe
            20                  25                  30

Gln Cys Thr Gly Val Ser Ala Val Arg Arg Val Ile Glu Pro Arg Gly
        35                  40                  45

Leu Leu Leu Pro His Tyr Thr Asn Gly Ala Ser Leu Val Tyr Ile Ile
50                  55                  60

Gln Gly Arg Gly Ile Thr Gly Pro Thr Phe Pro Gly Cys Pro Glu Ser
65                  70                  75                  80

Tyr Gln Gln Gln Phe Gln Gln Ser Gly Gln Ala Gln Leu Thr Glu Ser
                85                  90                  95

Gln Ser Gln Ser His Lys Phe Lys Asp Glu His Gln Lys Ile His Arg
            100                 105                 110

Phe Arg Gln Gly Asp Val Ile Ala Leu Pro Ala Gly Val Ala His Trp
        115                 120                 125

Cys Tyr Asn Asp Gly Glu Val Pro Val Val Ala Ile Tyr Val Thr Asp
130                 135                 140

Leu Asn Asn Gly Ala Asn Gln Leu Asp Pro Arg Gln Arg Asp Phe Leu
145                 150                 155                 160

Leu Ala Gly Asn Lys Arg Asn Pro Gln Ala Tyr Arg Arg Glu Val Glu
                165                 170                 175

Glu Arg Ser Gln Asn Ile Phe Ser Gly Phe Ser Thr Glu Leu Leu Ser
            180                 185                 190

Glu Ala Leu Gly Val Ser Ser Gln Val Ala Arg Gln Leu Gln Cys Gln
        195                 200                 205

Asn Asp Gln Arg Gly Glu Ile Val Arg Val Glu His Gly Leu Ser Leu
210                 215                 220

Leu Gln Pro Tyr Ala Ser Leu Gln Glu Gln Glu Gly Gln Val Gln
225                 230                 235                 240

Ser Arg Glu Arg Tyr Gln Glu Gly Gln Tyr Gln Gln Ser Gln Tyr Gly
                245                 250                 255

Ser Gly Cys Ser Asn Gly Leu Asp Glu Thr Phe Cys Thr Met Lys Val
            260                 265                 270

Arg Gln Asn Ile Asp Asn Pro Asn Arg Ala Asp Thr Tyr Asn Pro Arg
        275                 280                 285
```

Ala Gly Arg Val Thr Asn Leu Asn Thr Gln Asn Phe Pro Ile Leu Asn
290                 295                 300

Leu Val Gln Met Ser Ala Val Lys Val Asn Leu Tyr Gln Asn Ala Leu
305                 310                 315                 320

Leu Ser Pro Phe Trp Asn Ile Asn Ala His Ser Val Val Tyr Ile Thr
                325                 330                 335

Gln Gly Arg Ala Arg Val Gln Val Val Asn Asn Asn Gly Lys Thr Val
                340                 345                 350

Phe Asn Gly Glu Leu Arg Arg Gly Gln Leu Leu Ile Ile Pro Gln His
                355                 360                 365

Tyr Ala Val Val Lys Lys Ala Gln Arg Glu Gly Cys Ala Tyr Ile Ala
    370                 375                 380

Phe Lys Thr Asn Pro Asn Ser Met Val Ser His Ile Ala Gly Lys Ser
385                 390                 395                 400

Ser Ile Phe Arg Ala Leu Pro Asn Asp Val Leu Ala Asn Ala Tyr Arg
                405                 410                 415

Ile Ser Arg Glu Glu Ala Gln Arg Leu Lys His Asn Arg Gly Asp Glu
                420                 425                 430

Phe Gly Ala Phe Thr Pro Ile Gln Tyr Lys Ser Tyr Gln Asp Val Tyr
                435                 440                 445

Asn Ala Ala Glu Ser Ser
    450

<210> SEQ ID NO 525
<211> LENGTH: 500
<212> TYPE: PRT
<213> ORGANISM: Zizania latifolia

<400> SEQUENCE: 525

Met Asn Met Ala Thr Ile Asn Gly Pro Thr Ile Phe Phe Thr Val Cys
1               5                   10                  15

Leu Phe Leu Leu Cys His Gly Ser Leu Ala Gln Leu Leu Gly Gln Ser
                20                  25                  30

Thr Ser Gln Trp Gln Ser Ser His Arg Gly Ser Ser Arg Gln Cys Arg
                35                  40                  45

Phe Asp Arg Leu Gln Ala Phe Glu Pro Val Arg Ser Val Arg Ser Gln
50                  55                  60

Ala Gly Thr Thr Glu Phe Asp Ala Ser Asn Glu Leu Phe Gln Cys
65                  70                  75                  80

Ala Gly Val Ser Ile Val Arg Arg Ile Ile Glu Pro Arg Gly Leu Leu
                85                  90                  95

Leu Pro Gln Tyr Thr Asn Gly Ala Thr Ile Met Tyr Ile Ile Gln Gly
                100                 105                 110

Arg Gly Ile Thr Gly Gln Thr Phe Pro Gly Cys Pro Glu Ser Tyr Gln
                115                 120                 125

Gln Gln Phe Gln Gln Ser Met Gln Ala Gln Leu Thr Gly Ser Gln Ser
130                 135                 140

Gln Ser Gln Lys Phe Lys Asp Glu His Gln Lys Ile Asn Arg Phe Arg
145                 150                 155                 160

Gln Gly Asp Val Ile Ala Leu Pro Ala Gly Val Ala His Trp Cys Tyr
                165                 170                 175

Asn Asp Gly Glu Val Pro Val Val Ala Ile Tyr Val Ile Asp Ile Asn
                180                 185                 190

Asn Ala Ala Asn Gln Leu Asp Pro Arg Gln Arg Asp Phe Leu Leu Ala

```
                195                 200                 205
Gly Asn Met Arg Ser Pro Gln Ala Tyr Arg Arg Glu Val Glu Asn Gln
210                 215                 220

Ser Gln Asn Ile Phe Ser Gly Phe Ser Ala Glu Leu Leu Ser Glu Ala
225                 230                 235                 240

Leu Gly Ile Ser Thr Gly Val Ala Arg Gln Leu Gln Cys Gln Asn Asp
                245                 250                 255

Gln Arg Gly Glu Ile Val Arg Val Glu His Gly Leu Ser Leu Leu Gln
            260                 265                 270

Pro Tyr Ala Ser Leu Gln Glu Gln Gln Lys Gln Glu Gln Pro Arg
        275                 280                 285

Glu Arg Tyr Gln Val Thr Gln His Gln Gln Ser Gln Tyr Gly Gly Gly
290                 295                 300

Cys Ser Asn Gly Leu Asp Glu Thr Phe Cys Ala Met Arg Ile Trp Gln
305                 310                 315                 320

Asn Ile Asp Asn Pro Asn Leu Ala Asp Thr Tyr Asn Pro Arg Ala Gly
                325                 330                 335

Arg Val Thr Asn Leu Asn Ser Gln Lys Phe Pro Ile Leu Asn Leu Ile
            340                 345                 350

Gln Met Ser Ala Val Lys Val Asn Leu Tyr Gln Asn Ala Leu Leu Ser
        355                 360                 365

Pro Phe Trp Asn Ile Asn Ser His Ser Val Val Tyr Val Thr Gln Gly
370                 375                 380

Cys Ala Arg Val Gln Val Val Asn Asn Asn Gly Lys Thr Val Phe Asn
385                 390                 395                 400

Gly Glu Leu Arg Arg Gly Gln Leu Leu Ile Ile Pro Gln His Tyr Val
                405                 410                 415

Val Val Lys Lys Ala Gln Arg Glu Gly Cys Ala Tyr Ile Ala Phe Lys
            420                 425                 430

Thr Asn Pro Asn Ser Met Val Ser His Ile Val Gly Lys Ser Ser Ile
        435                 440                 445

Phe Arg Ala Leu Pro Thr Asp Val Leu Ala Asn Ala Tyr Arg Ile Ser
450                 455                 460

Arg Glu Asp Ala Gln Arg Leu Lys His Asn Arg Gly Asp Glu Leu Gly
465                 470                 475                 480

Ala Phe Thr Pro Leu Gln Tyr Lys Ser Tyr Gln Asp Val Ser Ser Val
                485                 490                 495

Ala Ala Ser Ser
        500

<210> SEQ ID NO 526
<211> LENGTH: 527
<212> TYPE: PRT
<213> ORGANISM: Avena sativa

<400> SEQUENCE: 526

Met Ala Thr Thr Ser Phe Pro Ser Met Leu Phe Tyr Phe Cys Ile Phe
1               5                   10                  15

Leu Leu Phe His Gly Ser Met Ala Gln Leu Phe Gly Gln Ser Ser Thr
                20                  25                  30

Pro Trp Gln Ser Ser Arg Gln Gly Gly Leu Arg Gly Cys Arg Phe Asp
            35                  40                  45

Arg Leu Gln Ala Phe Glu Pro Leu Arg Gln Val Arg Ser Gln Ala Gly
        50                  55                  60
```

-continued

```
Ile Thr Glu Tyr Phe Asp Glu Gln Asn Glu Gln Phe Arg Cys Thr Gly
 65                  70                  75                  80

Val Ser Val Ile Arg Arg Val Ile Glu Pro Gln Gly Leu Val Leu Pro
                 85                  90                  95

Gln Tyr His Asn Ala Pro Ala Leu Val Tyr Ile Leu Gln Gly Arg Gly
            100                 105                 110

Phe Thr Gly Leu Thr Phe Pro Gly Cys Pro Ala Thr Phe Gln Gln Gln
        115                 120                 125

Phe Gln Pro Phe Asp Gln Ser Gln Phe Ala Gln Gly Gln Arg Gln Ser
130                 135                 140

Gln Thr Ile Lys Asp Glu His Gln Arg Val Gln Arg Phe Lys Gln Gly
145                 150                 155                 160

Asp Val Val Ala Leu Pro Ala Gly Ile Val His Trp Cys Tyr Asn Asp
                165                 170                 175

Gly Asp Ala Pro Ile Val Ala Ile Tyr Val Phe Asp Val Asn Asn Asn
            180                 185                 190

Ala Asn Gln Leu Glu Pro Arg Gln Lys Glu Phe Leu Leu Ala Gly Asn
        195                 200                 205

Asn Lys Arg Glu Gln Gln Ser Gly Asn Asn Ile Phe Ser Gly Leu Ser
210                 215                 220

Val Gln Leu Leu Ser Glu Ala Leu Gly Ile Ser Gln Gln Ala Ala Gln
225                 230                 235                 240

Arg Ile Gln Ser Gln Asn Asp Gln Arg Gly Glu Ile Ile Arg Val Ser
                245                 250                 255

Gln Gly Leu Gln Phe Leu Lys Pro Ile Val Ser Gln Gln Val Pro Gly
            260                 265                 270

Glu Gln Gln Val Tyr Gln Pro Ile Gln Thr Gln Glu Gly Gln Ala Thr
        275                 280                 285

Gln Tyr Gln Val Gly Gln Ser Thr Gln Tyr Gln Val Gly Lys Ser Thr
290                 295                 300

Pro Tyr Gln Gly Gly Gln Ser Ser Gln Tyr Gln Ala Gly Gln Ser Trp
305                 310                 315                 320

Asp Gln Ser Phe Asn Gly Leu Glu Glu Asn Phe Cys Ser Leu Glu Ala
                325                 330                 335

Arg Lys Asn Ile Glu Asn Pro Gln His Ala Asp Thr Tyr Asn Pro Arg
            340                 345                 350

Ala Gly Arg Ile Thr Arg Leu Asn Ser Lys Asn Phe Pro Ile Leu Asn
        355                 360                 365

Ile Val Gln Met Ser Ala Thr Arg Val Asn Leu Tyr Gln Asn Ala Ile
370                 375                 380

Leu Ser Pro Phe Trp Asn Ile Asn Ala His Ser Val Ile Tyr Met Ile
385                 390                 395                 400

Gln Gly His Ala Arg Val Gln Val Val Asn Asn Asn Gly Gln Thr Val
                405                 410                 415

Phe Asn Asp Ile Leu Arg Arg Gly Gln Leu Leu Ile Val Pro Gln His
            420                 425                 430

Phe Val Val Leu Lys Lys Ala Glu Arg Glu Gly Cys Gln Tyr Ile Ser
        435                 440                 445

Phe Lys Thr Asn Pro Asn Ser Met Val Ser His Ile Ala Gly Lys Ser
450                 455                 460

Ser Ile Leu Arg Ala Leu Pro Ile Asp Val Leu Ala Asn Ala Tyr Arg
465                 470                 475                 480

Ile Ser Arg Gln Glu Ala Arg Asn Leu Lys Asn Asn Arg Gly Glu Glu
```

```
                        485                 490                 495
Phe Gly Ala Phe Thr Pro Lys Leu Thr Gln Lys Gly Phe Gln Ser Tyr
                500                 505                 510
Gln Asp Ile Glu Glu Gly Ser Ser Pro Val Arg Ala Ser Glu
            515                 520                 525

<210> SEQ ID NO 527
<211> LENGTH: 495
<212> TYPE: PRT
<213> ORGANISM: Oryza sativa

<400> SEQUENCE: 527

Met Thr Ile Ser Val Phe Ser Arg Phe Ser Ile Tyr Phe Cys Val Leu
1               5                   10                  15

Leu Leu Cys Asn Gly Ser Met Ala Gln Leu Phe Asp Pro Ala Thr Asn
                20                  25                  30

Gln Trp Gln Thr His Arg Gln Gly Ser Phe Arg Glu Cys Arg Phe Glu
            35                  40                  45

Arg Leu Gln Ala Phe Glu Pro Leu Gln Asn Val Arg Ser Glu Ala Gly
    50                  55                  60

Val Thr Glu Tyr Phe Asp Glu Thr Asn Glu Leu Phe Gln Cys Thr Gly
65                  70                  75                  80

Thr Phe Val Ile Arg Arg Val Ile Gln Pro Gln Gly Leu Leu Ile Pro
                85                  90                  95

Arg Tyr Ala Asn Thr Pro Gly Met Val Tyr Ile Ile Gln Gly Arg Gly
            100                 105                 110

Ser Met Gly Leu Thr Phe Pro Gly Cys Pro Ala Thr Tyr Gln Gln Gln
    115                 120                 125

Ser Gln Gln Phe Leu Phe Gln Gly Glu Ser Gln Ser Gln Lys Phe Ile
130                 135                 140

Asp Glu His Gln Lys Ile His Gln Phe Arg Gln Gly Asp Ile Val Val
145                 150                 155                 160

Leu Pro Thr Gly Val Ala His Trp Phe Tyr Asn Asp Gly Asp Thr Pro
                165                 170                 175

Val Val Ala Leu Tyr Val Tyr Asp Ile Asn Asn Ser Ala Asn Gln Leu
            180                 185                 190

Glu Pro Arg His Arg Glu Phe Leu Leu Ala Gly Lys Asn Asn Arg Val
    195                 200                 205

Gln Gln Val Tyr Gly Arg Ser Ile Gln Gln His Ser Gly Gln Asn Ile
210                 215                 220

Phe Asn Gly Phe Ser Val Glu Pro Leu Ser Glu Ala Leu Asn Ile Asn
225                 230                 235                 240

Thr Val Thr Thr Lys Arg Leu Gln Ser Gln Asn Asp Gln Arg Gly Glu
                245                 250                 255

Ile Ile His Val Lys Asn Gly Leu Gln Leu Leu Lys Pro Thr Leu Thr
            260                 265                 270

Gln Arg Gln Glu Gln Glu Gln Ala Gln Tyr Gln Glu Val Gln Tyr Ser
    275                 280                 285

Glu Lys Pro Gln Thr Ser Ser Arg Trp Asn Gly Leu Glu Glu Asn Leu
290                 295                 300

Cys Thr Ile Lys Thr Arg Leu Asn Ile Glu Asn Pro Ser Arg Ala Asp
305                 310                 315                 320

Ser Tyr Asp Pro Arg Ala Gly Arg Ile Thr Ser Leu Asp Ser Gln Lys
                325                 330                 335
```

```
Phe Pro Ile Leu Asn Ile Ile Gln Met Ser Ala Thr Arg Val Asn Leu
                340                 345                 350

Tyr Gln Asn Ala Ile Leu Thr Pro Phe Trp Asn Val Asn Ala His Ser
            355                 360                 365

Leu Met Tyr Val Ile Arg Gly Arg Ala Arg Val Gln Val Val Ser Asn
        370                 375                 380

Phe Gly Lys Thr Val Phe Asp Gly Val Leu Arg Pro Glu Gln Leu Leu
385                 390                 395                 400

Ile Ile Pro Gln Asn Tyr Val Val Leu Lys Lys Ala Gln His Glu Gly
                405                 410                 415

Cys Gln Tyr Ile Ala Ile Asn Thr Asn Ala Asn Ala Phe Val Ser His
            420                 425                 430

Leu Ala Gly Val Asp Ser Val Phe His Ala Leu Pro Val Asp Val Ile
        435                 440                 445

Ala Asn Ala Tyr Cys Ile Ser Arg Glu Glu Ala Arg Arg Leu Lys Asn
    450                 455                 460

Asn Arg Gly Asp Glu Tyr Gly Pro Phe Pro Arg Leu Gln Gln Gln
465                 470                 475                 480

Ile Tyr Pro Glu Phe Ser Asn Glu Ser Lys Gly Glu Thr Ser Glu
                485                 490                 495

<210> SEQ ID NO 528
<211> LENGTH: 480
<212> TYPE: PRT
<213> ORGANISM: Oryza sativa

<400> SEQUENCE: 528

Leu Leu Cys His Gly Ser Met Ala Gln Ile Phe Ser Leu Gly Ile Asn
1               5                   10                  15

Pro Trp Gln Asn Pro Arg Gln Gly Gly Ser Arg Glu Cys Arg Phe Asp
                20                  25                  30

Arg Leu Gln Ala Phe Glu Pro Leu Arg Lys Val Arg His Glu Ala Gly
            35                  40                  45

Val Thr Glu Tyr Phe Asp Glu Lys Asn Glu Gln Phe Gln Cys Thr Gly
        50                  55                  60

Thr Leu Val Ile Arg Arg Ile Ile Glu Pro Gln Gly Leu Leu Pro
65                  70                  75                  80

Arg Tyr Ser Asn Thr Pro Gly Leu Val Tyr Ile Ile Gln Gly Thr Gly
                85                  90                  95

Val Leu Gly Leu Thr Phe Pro Gly Cys Pro Ala Thr Tyr Gln Lys Gln
            100                 105                 110

Phe Arg His Phe Gly Leu Glu Gly Gly Ser Gln Arg Gln Gly Lys Lys
        115                 120                 125

Leu Arg Asp Glu Asn Gln Lys Ile His Gln Phe Arg Gln Gly Asp Val
    130                 135                 140

Val Ala Leu Pro Ser Gly Ile Pro His Trp Phe Tyr Asn Glu Gly Asp
145                 150                 155                 160

Thr Pro Val Val Ala Leu Phe Val Phe Asp Val Asn Asn Asn Ala Asn
                165                 170                 175

Gln Leu Glu Pro Arg Gln Lys Glu Phe Leu Leu Ala Gly Asn Asn Ile
            180                 185                 190

Glu Gln Gln Val Ser Asn Pro Ser Ile Asn Lys His Ser Gly Gln Asn
        195                 200                 205

Ile Phe Asn Gly Phe Asn Thr Lys Leu Leu Ser Glu Ala Leu Gly Val
    210                 215                 220
```

Asn Ile Glu Val Thr Arg Arg Leu Gln Ser Gln Asn Asp Arg Gly
225                 230                 235                 240

Asp Ile Ile Arg Val Lys Asn Gly Leu Arg Leu Ile Lys Pro Thr Ile
            245                 250                 255

Thr Gln Gln Gln Glu Gln Thr Gln Asp Gln Tyr Gln Gln Ile Gln Tyr
        260                 265                 270

His Arg Glu Gln Arg Ser Thr Ser Lys Tyr Asn Gly Leu Asp Glu Asn
    275                 280                 285

Phe Cys Ala Ile Arg Ala Arg Leu Asn Ile Glu Asn Pro Asn His Ala
290                 295                 300

Asp Thr Tyr Asn Pro Arg Ala Gly Arg Ile Thr Asn Leu Asn Ser Gln
305                 310                 315                 320

Lys Phe Ser Ile Leu Asn Leu Val Gln Met Ser Ala Thr Arg Val Asn
                325                 330                 335

Leu Tyr Gln Asn Ala Ile Leu Ser Pro Phe Trp Asn Ile Asn Ala His
            340                 345                 350

Ser Leu Val Tyr Thr Ile Gln Gly Arg Ala Arg Val Gln Val Val Ser
        355                 360                 365

Asn His Gly Lys Ala Val Phe Asn Gly Val Leu Arg Pro Gly Gln Leu
    370                 375                 380

Leu Ile Ile Pro Gln Asn Tyr Val Val Met Lys Lys Ala Glu Leu Glu
385                 390                 395                 400

Gly Phe Gln Phe Ile Ala Phe Lys Thr Asn Pro Asn Ala Met Val Asn
                405                 410                 415

His Ile Ala Gly Lys Asn Ser Val Leu Arg Ala Met Pro Val Asp Val
            420                 425                 430

Ile Ala Asn Ala Tyr Arg Ile Ser Arg Gln Glu Ala Arg Ser Leu Lys
        435                 440                 445

Asn Asn Arg Gly Glu Glu Ile Gly Ala Phe Thr Pro Arg Tyr Gln Gln
    450                 455                 460

Gln Lys Ile His Gln Glu Tyr Ser Asn Pro Asn Glu Ser Glu Thr Gln
465                 470                 475                 480

<210> SEQ ID NO 529
<211> LENGTH: 518
<212> TYPE: PRT
<213> ORGANISM: Oryza sativa

<400> SEQUENCE: 529

Met Ala Thr Thr Arg Phe Pro Ser Leu Leu Phe Tyr Ser Cys Ile Phe
1               5                   10                  15

Leu Leu Cys Asn Gly Ser Met Ala Gln Leu Phe Gly Gln Ser Phe Thr
            20                  25                  30

Pro Trp Gln Ser Ser Arg Gln Gly Gly Leu Arg Gly Cys Arg Phe Asp
        35                  40                  45

Arg Leu Gln Ala Phe Glu Pro Leu Arg Gln Val Arg Ser Gln Ala Gly
    50                  55                  60

Ile Thr Glu Tyr Phe Asp Glu Gln Asn Glu Gln Phe Arg Cys Ala Gly
65                  70                  75                  80

Val Ser Val Ile Arg Arg Val Ile Glu Pro Gly Leu Leu Leu Pro
                85                  90                  95

Gln Tyr His Asn Ala Pro Gly Leu Val Tyr Ile Leu Gln Gly Arg Gly
            100                 105                 110

Phe Thr Gly Leu Thr Phe Pro Gly Cys Pro Ala Thr Phe Gln Gln Gln

```
            115                 120                 125
Phe Gln Pro Phe Asp Gln Ala Arg Phe Ala Gln Gly Gln Ser Lys Ser
            130                 135                 140
Gln Asn Leu Lys Asp Glu His Gln Arg Val His His Ile Lys Gln Gly
145                 150                 155                 160
Asp Val Val Ala Leu Pro Ala Gly Ile Val His Trp Cys Tyr Asn Asp
            165                 170                 175
Gly Asp Ala Pro Ile Val Ala Val Tyr Val Phe Asp Val Asn Asn Asn
            180                 185                 190
Ala Asn Gln Leu Glu Pro Arg Gln Lys Glu Phe Leu Leu Ala Gly Asn
            195                 200                 205
Asn Lys Arg Glu Gln Gln Phe Gly Gln Asn Ile Phe Ser Gly Phe Ser
210                 215                 220
Val Gln Leu Leu Ser Glu Ala Leu Gly Ile Ser Gln Gln Ala Ala Gln
225                 230                 235                 240
Lys Ile Gln Ser Gln Asn Asp Gln Arg Gly Glu Ile Ile Arg Val Ser
            245                 250                 255
Gln Gly Leu Gln Phe Leu Lys Pro Phe Val Ser Gln Gln Gly Pro Val
            260                 265                 270
Glu His Gln Ala Tyr Gln Pro Ile Gln Ser Gln Gln Glu Gln Ser Thr
            275                 280                 285
Gln Tyr Gln Val Gly Gln Ser Pro Gln Tyr Gln Glu Gly Gln Ser Thr
            290                 295                 300
Gln Tyr Gln Ser Gly Gln Ser Trp Asp Gln Ser Phe Asn Gly Leu Glu
305                 310                 315                 320
Glu Asn Phe Cys Ser Leu Glu Ala Arg Gln Asn Ile Glu Asn Pro Lys
            325                 330                 335
Arg Ala Asp Thr Tyr Asn Pro Arg Ala Gly Arg Ile Thr His Leu Asn
            340                 345                 350
Ser Lys Asn Phe Pro Thr Leu Asn Leu Val Gln Met Ser Ala Thr Arg
            355                 360                 365
Val Asn Leu Tyr Gln Asn Ala Ile Leu Ser Pro Tyr Trp Asn Ile Asn
370                 375                 380
Ala His Ser Val Met His Met Ile Gln Gly Arg Ala Arg Val Gln Val
385                 390                 395                 400
Val Asn Asn His Gly Gln Thr Val Phe Asn Asp Ile Leu Arg Arg Gly
            405                 410                 415
Gln Leu Leu Ile Ile Pro Gln His Tyr Val Val Leu Lys Lys Ala Glu
            420                 425                 430
Arg Glu Gly Cys Gln Tyr Ile Ser Phe Lys Thr Thr Pro Asn Ser Met
            435                 440                 445
Val Ser Tyr Ile Ala Gly Lys Thr Ser Ile Leu Arg Ala Leu Pro Val
            450                 455                 460
Asp Val Leu Ala Asn Ala Tyr Arg Ile Ser Arg Gln Glu Ser Gln Asn
465                 470                 475                 480
Leu Lys Asn Asn Arg Gly Glu Glu Phe Gly Ala Phe Thr Pro Lys Phe
            485                 490                 495
Ala Gln Thr Gly Ser Gln Ser Tyr Gln Asp Glu Gly Glu Ser Ser Ser
            500                 505                 510
Thr Glu Lys Ala Ser Glu
            515

<210> SEQ ID NO 530
```

-continued

```
<211> LENGTH: 498
<212> TYPE: PRT
<213> ORGANISM: Oryza sativa

<400> SEQUENCE: 530
```

| | | | | | | | | | | | | | | |
|---|---|---|---|---|---|---|---|---|---|---|---|---|---|---|
| Met | Ala | Ser | Thr | Asn | Arg | Pro | Ile | Val | Phe | Thr | Val | Cys | Leu | Phe |
| 1 | | | | 5 | | | | | 10 | | | | | 15 |
| Leu | Leu | Cys | Asp | Gly | Ser | Leu | Ala | Gln | Gln | Leu | Leu | Gly | Gln | Ser | Thr |
| | | | 20 | | | | | 25 | | | | | 30 | |
| Ser | Gln | Trp | Gln | Ser | Ser | Arg | Arg | Gly | Ser | Pro | Arg | Gly | Cys | Arg | Phe |
| | | | 35 | | | | | 40 | | | | | 45 | |
| Asp | Arg | Leu | Gln | Ala | Phe | Glu | Pro | Ile | Arg | Ser | Val | Arg | Ser | Gln | Ala |
| | 50 | | | | | 55 | | | | | 60 | | | | |
| Gly | Thr | Thr | Glu | Phe | Phe | Asp | Val | Ser | Asn | Glu | Leu | Phe | Gln | Cys | Thr |
| 65 | | | | | 70 | | | | | 75 | | | | | 80 |
| Gly | Val | Ser | Val | Val | Arg | Arg | Val | Ile | Glu | Pro | Arg | Gly | Leu | Leu | Leu |
| | | | | 85 | | | | | 90 | | | | | 95 | |
| Pro | His | Tyr | Thr | Asn | Gly | Ala | Ser | Leu | Val | Tyr | Ile | Ile | Gln | Gly | Arg |
| | | | 100 | | | | | 105 | | | | | 110 | | |
| Gly | Ile | Thr | Gly | Pro | Thr | Phe | Pro | Gly | Cys | Pro | Glu | Thr | Tyr | Gln | Gln |
| | | | 115 | | | | | 120 | | | | | 125 | | |
| Gln | Phe | Gln | Gln | Ser | Gly | Gln | Ala | Gly | Leu | Thr | Glu | Ser | Gln | Ser | Gln |
| | 130 | | | | | 135 | | | | | 140 | | | | |
| Ser | His | Lys | Phe | Lys | Asp | Glu | His | Gln | Lys | Ile | His | Arg | Phe | Arg | Gln |
| 145 | | | | | 150 | | | | | 155 | | | | | 160 |
| Gly | Asp | Val | Ile | Ala | Leu | Pro | Ala | Gly | Val | Ala | His | Trp | Cys | Tyr | Asn |
| | | | | 165 | | | | | 170 | | | | | 175 | |
| Asp | Cys | Glu | Val | Pro | Val | Val | Ala | Ile | Tyr | Val | Thr | Asp | Ile | Asn | Asn |
| | | | 180 | | | | | 185 | | | | | 190 | | |
| Gly | Ala | Asn | Gln | Leu | Asp | Pro | Arg | Gln | Arg | Asp | Phe | Leu | Leu | Ala | Gly |
| | | | 195 | | | | | 200 | | | | | 205 | | |
| Asn | Lys | Arg | Asn | Pro | Gln | Ala | Tyr | Arg | Arg | Glu | Val | Glu | Glu | Trp | Ser |
| | 210 | | | | | 215 | | | | | 220 | | | | |
| Gln | Asn | Ile | Phe | Ser | Gly | Phe | Ser | Thr | Glu | Leu | Leu | Ser | Glu | Ala | Phe |
| 225 | | | | | 230 | | | | | 235 | | | | | 240 |
| Gly | Ile | Ser | Asn | Gln | Val | Ala | Arg | Gln | Leu | Gln | Cys | Gln | Asn | Asp | Gln |
| | | | | 245 | | | | | 250 | | | | | 255 | |
| Lys | Gly | Glu | Ile | Val | Arg | Val | Glu | Arg | Gly | Leu | Ser | Leu | Leu | Gln | Pro |
| | | | 260 | | | | | 265 | | | | | 270 | | |
| Tyr | Ala | Ser | Leu | Gln | Glu | Gln | Glu | Gln | Gly | Gln | Met | Gln | Ser | Arg | Glu |
| | | | 275 | | | | | 280 | | | | | 285 | | |
| His | Tyr | Gln | Glu | Gly | Gly | Tyr | Gln | Gln | Ser | Gln | Tyr | Gly | Ser | Gly | Cys |
| | 290 | | | | | 295 | | | | | 300 | | | | |
| Pro | Asn | Gly | Leu | Asp | Glu | Thr | Phe | Cys | Val | Asn | Lys | Val | Arg | Gln | Asn |
| 305 | | | | | 310 | | | | | 315 | | | | | 320 |
| Ile | Asp | Asn | Pro | Asn | Arg | Ala | Asp | Thr | Tyr | Asn | Pro | Arg | Ala | Gly | Arg |
| | | | | 325 | | | | | 330 | | | | | 335 | |
| Val | Thr | Asn | Leu | Ser | Gln | Asn | Phe | Pro | Ile | Leu | Asn | Leu | Val | Gln | Met |
| | | | 340 | | | | | 345 | | | | | 350 | | |
| Ser | Ala | Val | Lys | Val | Asn | Leu | Tyr | Gln | Asn | Thr | Asp | Thr | Trp | Ile | Ser |
| | | | 355 | | | | | 360 | | | | | 365 | | |
| Met | Gly | Gln | Glu | Glu | Asn | Ala | Leu | Leu | Ser | Pro | Phe | Trp | Asn | Ile | Asn |
| | 370 | | | | | 375 | | | | | 380 | | | | |
| Ala | His | Ser | Ile | Val | Tyr | Ile | Thr | Gln | Gly | Arg | Ala | Gln | Val | Gln | Val |

```
                385                 390                 395                 400
Leu Arg Arg Gly Gln Leu Leu Ile Val Pro Gln His Tyr Val Val
                405                 410                 415
Lys Lys Ala Gln Arg Glu Gly Cys Ala Tyr Ile Ala Phe Lys Thr Asn
                420                 425                 430
Pro Asn Ser Met Val Ser His Ile Ala Gly Lys Ser Ile Phe Arg
                435                 440                 445
Ala Leu Pro Thr Asp Val Leu Ala Asn Ala Tyr Arg Ile Ser Arg Glu
450                 455                 460
Glu Ala Gln Arg Leu Lys His Asn Arg Gly Asp Glu Phe Gly Ala Phe
465                 470                 475                 480
Thr Pro Leu Gln Tyr Lys Ser Tyr Gln Asp Val Tyr Asn Val Ala Glu
                485                 490                 495
Ser Ser

<210> SEQ ID NO 531
<211> LENGTH: 491
<212> TYPE: PRT
<213> ORGANISM: Oryza brachyantha

<400> SEQUENCE: 531

Met Lys Ser Ser Ile Val Phe Ser Thr Ile Cys Leu Val Leu Leu Cys
1               5                   10                  15

His Gly Ser Leu Ala Gln Leu Leu Ser Gln Ser Thr Ser Gln Trp Gln
                20                  25                  30

Ser Ser Arg Arg Gly Ser Pro Arg Gln Cys Arg Phe Asp Gln Leu Gln
                35                  40                  45

Ala Phe Glu Pro Ile Arg Thr Val Arg Ser Gln Ala Gly Val Thr Glu
            50                  55                  60

Phe Tyr Asp Val Ser Asn Glu Leu Phe Gln Cys Thr Gly Val Ser Val
65              70                  75                  80

Val Arg Arg Val Ile Glu Pro Arg Gly Leu Leu Pro His Tyr Ser
                85                  90                  95

Asn Gly Ala Thr Leu Val Tyr Ile Ile Gln Gly Arg Gly Ile Thr Gly
                100                 105                 110

Pro Thr Phe Pro Gly Cys Pro Glu Thr Tyr Gln Gln Gln Phe Gln Gln
            115                 120                 125

Ser Gly Glu Ala Gln Pro Phe Glu Gly Gln Ser His Lys Phe Arg Asp
130                 135                 140

Glu His Gln Lys Ile His Arg Phe Arg Gln Gly Asp Val Val Ala Leu
145                 150                 155                 160

Pro Ala Gly Val Ala His Trp Cys Tyr Asn Asp Gly Glu Val Pro Ile
                165                 170                 175

Val Ala Ile Tyr Val Thr Asp Ile Tyr Asn Ser Ala Asn Gln Leu Asp
                180                 185                 190

Pro Arg His Arg Asp Phe Phe Leu Ala Gly Asn Asn Lys Val Ala Gln
            195                 200                 205

Gln Leu Tyr Arg Ser Glu Ala Arg Glu Asn Ser Lys Asn Ile Phe Gly
210                 215                 220

Gly Phe Ser Val Glu Leu Leu Ser Glu Ala Leu Gly Ile Ser Arg Gly
225                 230                 235                 240

Val Ala Arg Gln Leu Gln Cys Gln Asn Asp Gln Arg Gly Glu Ile Val
                245                 250                 255

Arg Val Glu His Gly Leu Ala Leu Leu Gln Pro Tyr Ala Ser Val Gln
```

```
            260                 265                 270
Glu Gln Gln Gln Glu Gln Val Gln Ser Arg Asp Tyr Glu Gln Thr Gln
            275                 280                 285

Tyr Gln Gln Lys Gln Pro Gln Gly Ser Cys Ser Asn Gly Leu Asp Glu
            290                 295                 300

Thr Phe Cys Thr Met Arg Leu Arg Gln Asn Ile Asp Asn Pro Asn Leu
305                 310                 315                 320

Ala Asp Thr Tyr Asn Pro Lys Ala Gly Arg Ile Thr Tyr Leu Asn Gly
                325                 330                 335

Gln Lys Phe Pro Ile Leu Asn Leu Val Gln Met Ser Ala Val Lys Val
            340                 345                 350

Asn Leu Tyr Gln Asn Ala Val Leu Ser Pro Phe Trp Asn Ile Asn Ala
            355                 360                 365

His Ser Val Val Tyr Ile Thr Gln Gly Arg Ala Arg Val Gln Val Val
            370                 375                 380

Asn Asn Asn Gly Lys Thr Val Phe Asp Gly Glu Leu Arg Gln Gly Gln
385                 390                 395                 400

Leu Leu Ile Ile Pro Gln His His Val Val Leu Lys Lys Ala Gln Arg
                405                 410                 415

Glu Gly Cys Ser Tyr Ile Ala Leu Lys Thr Asn Pro Asn Ser Ile Val
                420                 425                 430

Ser His Ile Ala Gly Lys Asn Ser Ile Phe Arg Ala Leu Pro Gly Asp
            435                 440                 445

Val Val Thr Asn Ala Tyr Arg Ile Ser Arg Glu Glu Ala Lys Arg Ile
450                 455                 460

Lys His Asn Arg Gly Asp Glu Ser Gly Val Phe Ala Pro Ser His Ala
465                 470                 475                 480

Tyr Arg Ser Tyr Gln Asp Met Ser Val Ala Ala
                485                 490

<210> SEQ ID NO 532
<211> LENGTH: 492
<212> TYPE: PRT
<213> ORGANISM: Brachypodium distachyon

<400> SEQUENCE: 532

Met Ala His Thr Ser Phe Ser Ser Phe Leu Ser Tyr Phe Cys Leu Phe
1               5                   10                  15

Leu Leu Phe His Gly Ser Met Ala Gln Val Leu Gly Gln Val Ser Thr
            20                  25                  30

Trp Gln Ser Ser Arg Gln Gly Gly Ser Arg Asp Cys Ser Phe Asp Arg
            35                  40                  45

Leu Gln Ala Ile Glu Pro Val Thr Gln Val Arg Ser Gln Ala Gly Leu
        50                  55                  60

Thr Glu Tyr Phe Asp Glu Gln Asn Glu Gln Phe Arg Cys Ala Gly Val
65                  70                  75                  80

Phe Val Ile Arg Arg Val Ile Glu Pro Arg Gly Leu Leu Leu Pro Arg
                85                  90                  95

Tyr His Asn Thr Pro Gly Leu Val Tyr Ile Leu Gln Gly Asn Gly Phe
            100                 105                 110

Val Gly Leu Thr Phe Pro Gly Cys Pro Glu Thr Phe Arg Glu Gln Phe
        115                 120                 125

Gln Gln Phe Arg Gln Thr Gln Ser Thr Leu Gly Gln Ser Gln Cys Gln
    130                 135                 140
```

```
Ser Gln Lys Leu Gly Asp Val His Gln Arg Val His Gln Phe Thr Gln
145                 150                 155                 160

Gly Asp Val Val Ala Leu Pro Thr Gly Val Ala His Trp Ile Tyr Asn
                165                 170                 175

Gly Gly Asp Ala Pro Val Val Ile Val Tyr Val Phe Asp Val Asn Asn
            180                 185                 190

Asn Ala Asn Gln Leu Glu Pro Arg Gln Lys Glu Phe Leu Leu Gly Gly
        195                 200                 205

Asn Tyr Asn Gly Val Leu Gln Tyr Gly Gln Asn Ile Phe Ser Gly Phe
    210                 215                 220

Asn Ala Gln Leu Leu Ser Gln Ala Phe Gly Ile Asn Glu Gln Thr Ser
225                 230                 235                 240

Gln Arg Ile Gln Asn Gln Asn Asp Gly Arg Gly Asp Ile Ile Arg Val
                245                 250                 255

Asp Asn Gly Leu Gln Phe Leu Lys Pro Val Thr Gln Gln Gln Pro
                260                 265                 270

Glu Gln Pro Phe Met Pro Ile Gln His Gln Thr Gly Gln Ser Ser Arg
                275                 280                 285

Asn Gly Leu Glu Glu Asn Phe Cys Ser Leu Glu Pro Arg Gln Asn Ile
        290                 295                 300

Glu Asp Pro Asn Arg Ala Asp Thr Tyr Asn Pro Arg Ala Gly Ser Ile
305                 310                 315                 320

Thr Arg Leu Asn Gly Gln Asn Phe Pro Ile Leu Asn Leu Val Gln Met
                325                 330                 335

Ser Ala Thr Arg Val Asn Leu Gln Lys Asn Ala Ile Leu Ser Pro Phe
                340                 345                 350

Trp Asn Ile Asn Ala His Ser Val Val Tyr Val Ile Gln Gly His Ala
                355                 360                 365

Leu Val Gln Val Val Asn Asn Gln Gly His Asn Val Phe Asn Gly Leu
        370                 375                 380

Leu His Arg Gly Gln Leu Leu Ile Ile Pro Gln Asn Tyr Val Val Leu
385                 390                 395                 400

Lys Lys Ala Glu Ser Glu Gly Tyr Gln Tyr Ile Ala Phe Lys Thr Asn
                405                 410                 415

Ala Asn Ser Met Val Ser His Ile Ala Gly Lys Asn Ser Ile Leu Arg
                420                 425                 430

Ala Leu Pro Val Asp Val Ile Ala Asn Ala Tyr Arg Ile Ser Arg Gln
                435                 440                 445

Glu Ala Gln Asn Leu Lys Asn Asn Arg Gly Glu Glu Thr Gly Val Leu
        450                 455                 460

Thr Pro Asn Phe Ser Gln Ser Thr Cys Gln Ser Tyr Gln Thr Glu Asp
465                 470                 475                 480

Val Gln Ser Leu Arg Pro Met Ser His Trp Ser Glu
                485                 490

<210> SEQ ID NO 533
<211> LENGTH: 166
<212> TYPE: PRT
<213> ORGANISM: Oryza sativa
<220> FEATURE:
<221> NAME/KEY: MISC_FEATURE
<222> LOCATION: (120)..(120)
<223> OTHER INFORMATION: Xaa can be any naturally occurring amino acid

<400> SEQUENCE: 533

Met Ala Ser Asn Lys Val Val Phe Ser Ala Leu Leu Leu Ile Ile Val
```

```
                1               5                   10                  15
            Ser Val Leu Ala Ala Thr Ala Thr Met Ala Asp His His Lys Asp Gln
                            20                  25                  30
            Val Val Tyr Ser Leu Gly Glu Arg Cys Gln Pro Gly Met Gly Tyr Pro
                            35                  40                  45
            Met Tyr Ser Leu Pro Arg Cys Arg Ala Val Val Lys Arg Gln Cys Val
                        50                  55                      60
            Gly His Gly Ala Pro Gly Ala Val Asp Glu Gln Leu Arg Gln Asp
             65                     70                  75                  80
            Cys Cys Arg Gln Leu Ala Ala Val Asp Asp Ser Trp Cys Arg Cys Ser
                                85                  90                  95
            Ala Leu Asn His Met Val Gly Gly Ile Tyr Arg Glu Leu Gly Ala Thr
                            100                 105                 110
            Asp Val Gly His Pro Met Ala Xaa Val Phe Pro Gly Cys Arg Arg Gly
                            115                 120                 125
            Asp Leu Glu Arg Ala Ala Ala Ser Leu Pro Ala Phe Cys Asn Val Asp
                            130                 135                 140
            Ile Pro Asn Gly Thr Gly Gly Val Cys Tyr Trp Leu Gly Tyr Pro Arg
            145                 150                 155                 160
            Thr Pro Arg Thr Gly His
                            165
```

<210> SEQ ID NO 534
<211> LENGTH: 165
<212> TYPE: PRT
<213> ORGANISM: Oryza sativa

<400> SEQUENCE: 534

```
            Met Ala Ser Asn Lys Val Val Phe Ser Ala Leu Leu Ile Ile Val
             1               5                   10                  15
            Ser Val Leu Arg Arg Asp Gly Thr Met Ala Asp His His Lys Asp Gln
                            20                  25                  30
            Val Val Tyr Ser Leu Gly Glu Arg Cys Gln Pro Gly Met Gly Tyr Pro
                            35                  40                  45
            Met Tyr Ser Leu Pro Arg Cys Arg Ala Val Val Lys Arg Gln Cys Val
                        50                  55                      60
            Gly His Gly Ala Pro Gly Ala Val Asp Glu Gln Leu Arg Gln Asp Cys
             65                     70                  75                  80
            Cys Arg Gln Leu Ala Ala Val Asp Asp Ser Trp Cys Arg Cys Ser Ala
                                85                  90                  95
            Leu Asn His Met Val Gly Gly Ile Tyr Arg Glu Leu Gly Ala Thr Asp
                            100                 105                 110
            Val Gly His Pro Met Ala Glu Val Phe Pro Gly Cys Arg Arg Gly Asp
                            115                 120                 125
            Leu Glu Arg Ala Ala Ala Ser Leu Pro Ala Phe Cys Asn Val Asp Ile
                            130                 135                 140
            Pro Asn Gly Thr Gly Gly Val Cys Tyr Trp Leu Gly Tyr Pro Arg Thr
            145                 150                 155                 160
            Pro Arg Thr Gly His
                            165
```

<210> SEQ ID NO 535
<211> LENGTH: 157
<212> TYPE: PRT
<213> ORGANISM: Oryza sativa

<400> SEQUENCE: 535

```
Met Ala Ser Asn Lys Val Val Ile Ser Ala Leu Leu Val Val Val
1               5                   10                  15

Ser Val Leu Ala Ala Thr Thr Thr Met Ala Asp His His Gln Glu Gln
            20                  25                  30

Val Val Tyr Thr Pro Gly Gln Leu Cys Gln Pro Gly Ile Gly Tyr Pro
        35                  40                  45

Thr Tyr Pro Leu Pro Arg Cys Arg Ala Phe Val Lys Arg Gln Cys Val
    50                  55                  60

Ala Pro Gly Thr Val Asp Glu Gln Val Arg Arg Gly Cys Cys Arg Gln
65                  70                  75                  80

Leu Ala Ala Ile Asp Ser Ser Trp Cys Arg Cys Asp Ala Leu Asn His
                85                  90                  95

Met Leu Arg Ile Ile Tyr Arg Glu Ser Gly Ala Ala Asp Ala Gly His
            100                 105                 110

Pro Met Ala Glu Val Phe Arg Gly Cys Arg Arg Gly Asp Ile Glu Arg
        115                 120                 125

Ala Ala Ala Ser Leu Pro Ala Phe Cys Asn Val Asp Ile Pro Asn Gly
    130                 135                 140

Val Gly Gly Val Cys Tyr Trp Leu Pro Gly Thr Gly Tyr
145                 150                 155
```

<210> SEQ ID NO 536
<211> LENGTH: 605
<212> TYPE: PRT
<213> ORGANISM: Oryza rufipogon

<400> SEQUENCE: 536

```
Met Ser Ala Leu Thr Thr Ser Gln Leu Ala Thr Ser Ala Thr Gly Phe
1               5                   10                  15

Gly Ile Ala Asp Arg Ser Ala Pro Ser Ser Leu Leu Arg His Gly Phe
            20                  25                  30

Gln Gly Leu Lys Pro Arg Ser Pro Ala Gly Gly Asp Ala Thr Ser Leu
        35                  40                  45

Ser Val Thr Thr Ser Ala Arg Ala Thr Pro Lys Gln Gln Arg Ser Val
    50                  55                  60

Gln Arg Gly Ser Arg Arg Phe Pro Ser Val Val Tyr Ala Thr Gly
65                  70                  75                  80

Ala Gly Met Asn Val Val Phe Val Gly Ala Glu Met Ala Pro Trp Ser
                85                  90                  95

Lys Thr Gly Gly Leu Gly Asp Val Leu Gly Gly Leu Pro Pro Ala Met
            100                 105                 110

Ala Ala Asn Gly His Arg Val Met Val Ile Ser Pro Arg Tyr Asp Gln
        115                 120                 125

Tyr Lys Asp Ala Trp Asp Thr Ser Val Ala Glu Ile Lys Val Ala
    130                 135                 140

Asp Arg Tyr Glu Arg Val Arg Phe Phe His Cys Tyr Lys Arg Gly Val
145                 150                 155                 160

Asp Arg Val Phe Val Asp His Pro Ser Phe Leu Glu Lys Val Trp Gly
                165                 170                 175

Lys Thr Gly Glu Lys Ile Tyr Gly Pro Asp Thr Gly Val Asp Tyr Lys
            180                 185                 190

Asp Asn Gln Met Arg Phe Ser Leu Leu Cys Gln Ala Pro Arg Ile Leu
        195                 200                 205
```

Asn Leu Asn Asn Pro Tyr Phe Lys Gly Thr Tyr Gly Glu Asp Val
210                 215                 220

Val Phe Val Cys Asn Asp Trp His Thr Gly Pro Leu Ala Ser Tyr Leu
225                 230                 235                 240

Lys Asn Asn Tyr Gln Pro Asn Gly Ile Tyr Arg Asn Ala Lys Val Ala
            245                 250                 255

Phe Cys Ile His Asn Ile Ser Tyr Gln Gly Arg Phe Ala Phe Glu Asp
            260                 265                 270

Tyr Pro Glu Leu Asn Leu Ser Glu Arg Phe Arg Ser Ser Phe Asp Phe
            275                 280                 285

Ile Asp Gly Tyr Asp Thr Pro Val Glu Gly Arg Lys Ile Asn Trp Met
290                 295                 300

Lys Ala Gly Ile Leu Glu Ala Asp Arg Val Leu Thr Val Ser Pro Tyr
305                 310                 315                 320

Tyr Ala Glu Glu Leu Ile Ser Gly Ile Ala Arg Gly Cys Glu Leu Asp
            325                 330                 335

Asn Ile Met Arg Leu Thr Gly Ile Thr Gly Ile Val Asn Gly Met Asp
            340                 345                 350

Val Ser Glu Trp Asp Pro Ser Lys Asp Lys Tyr Ile Thr Ala Lys Tyr
355                 360                 365

Asp Ala Thr Thr Ala Ile Glu Ala Lys Ala Leu Asn Lys Glu Ala Leu
370                 375                 380

Gln Ala Glu Ala Gly Leu Pro Val Asp Arg Lys Ile Pro Leu Ile Ala
385                 390                 395                 400

Phe Ile Gly Arg Leu Glu Glu Gln Lys Gly Pro Asp Val Met Ala Ala
            405                 410                 415

Ala Ile Pro Glu Leu Met Gln Glu Asp Val Gln Ile Val Leu Leu Gly
            420                 425                 430

Thr Gly Lys Lys Lys Phe Glu Lys Leu Leu Lys Ser Met Glu Glu Lys
            435                 440                 445

Tyr Pro Gly Lys Val Arg Ala Val Val Lys Phe Asn Ala Pro Leu Ala
450                 455                 460

His Leu Ile Met Ala Gly Ala Asp Val Leu Ala Val Pro Ser Arg Phe
465                 470                 475                 480

Glu Pro Cys Gly Leu Ile Gln Leu Gln Gly Met Arg Tyr Gly Thr Pro
            485                 490                 495

Cys Ala Cys Ala Ser Thr Gly Gly Leu Val Asp Thr Val Ile Glu Gly
            500                 505                 510

Lys Thr Gly Phe His Met Gly Arg Leu Ser Val Asp Cys Lys Val Val
            515                 520                 525

Glu Pro Ser Asp Val Lys Lys Val Ala Ala Thr Leu Lys Arg Ala Ile
530                 535                 540

Lys Val Val Gly Thr Pro Ala Tyr Glu Glu Met Val Arg Asn Cys Met
545                 550                 555                 560

Asn Gln Asp Leu Ser Trp Lys Gly Pro Ala Lys Asn Trp Glu Asn Val
            565                 570                 575

Leu Leu Gly Leu Gly Val Ala Gly Ser Ala Pro Gly Ile Glu Gly Asp
            580                 585                 590

Glu Ile Ala Pro Leu Ala Lys Glu Asn Val Ala Ala Pro
595                 600                 605

<210> SEQ ID NO 537
<211> LENGTH: 609
<212> TYPE: PRT

<213> ORGANISM: Oryza nivarra

<400> SEQUENCE: 537

```
Met Ser Ala Leu Thr Thr Ser Gln Leu Ala Thr Ser Ala Thr Gly Phe
 1               5                  10                  15

Gly Ile Ala Asp Arg Ser Ala Pro Ser Ser Leu Leu Arg His Gly Phe
             20                  25                  30

Gln Gly Leu Lys Pro Arg Ser Pro Ala Gly Gly Asp Ala Ser Ser Leu
         35                  40                  45

Ser Val Thr Thr Ser Ala Arg Ala Thr Pro Lys Gln Gln Arg Ser Val
     50                  55                  60

Gln Arg Gly Ser Arg Arg Phe Pro Ser Val Val Tyr Ala Thr Gly
 65                  70                  75                  80

Ala Gly Met Asn Val Val Phe Val Gly Ala Glu Met Ala Pro Trp Ser
                 85                  90                  95

Lys Thr Gly Gly Leu Gly Asp Val Leu Gly Gly Leu Pro Pro Ala Met
             100                 105                 110

Ala Ala Asn Gly His Arg Val Met Val Ile Ser Pro Arg His Asp Gln
         115                 120                 125

Tyr Lys Asp Ala Trp Asp Thr Ser Val Val Ala Glu Ile Lys Val Ala
    130                 135                 140

Asp Arg Tyr Glu Arg Val Arg Phe Phe His Cys Tyr Lys Arg Gly Val
145                 150                 155                 160

Asp Arg Val Phe Ile Asp His Pro Ser Phe Leu Glu Lys Val Trp Gly
                165                 170                 175

Lys Thr Gly Glu Lys Ile Tyr Gly Pro Asp Thr Gly Val Asp Tyr Lys
            180                 185                 190

Asp Asn Gln Met Arg Phe Ser Leu Leu Cys Gln Ala Ala Leu Glu Ala
        195                 200                 205

Pro Arg Ile Leu Asn Leu Asn Asn Pro Tyr Phe Lys Gly Thr Tyr
    210                 215                 220

Gly Glu Asp Val Val Phe Val Cys Asn Asp Trp His Thr Gly Pro Leu
225                 230                 235                 240

Pro Ser Tyr Leu Lys Asn Asn Tyr Gln Pro Asn Gly Ile Tyr Arg Asn
                245                 250                 255

Ala Lys Val Ala Phe Cys Ile His Asn Ile Ser Tyr Gln Gly Arg Phe
            260                 265                 270

Ala Phe Glu Asp Tyr Pro Glu Leu Asn Leu Ser Glu Arg Phe Arg Ser
        275                 280                 285

Ser Phe Asp Phe Ile Asp Gly Tyr Asp Thr Pro Val Glu Gly Arg Lys
    290                 295                 300

Ile Asn Trp Met Lys Ala Gly Ile Leu Glu Ser Asp Arg Val Leu Thr
305                 310                 315                 320

Val Ser Pro Tyr Tyr Ala Glu Glu Leu Ile Ser Gly Ile Ala Arg Gly
                325                 330                 335

Cys Glu Leu Asp Asn Ile Met Arg Leu Thr Gly Ile Thr Gly Ile Val
            340                 345                 350

Asn Gly Met Asp Val Ser Glu Trp Asp Pro Ser Lys Asp Lys Tyr Ile
        355                 360                 365

Ala Ala Lys Tyr Asp Ala Thr Thr Ala Ile Glu Ala Lys Ala Leu Asn
    370                 375                 380

Lys Glu Ala Leu Gln Ala Glu Ala Gly Leu Pro Val Asp Arg Lys Ile
385                 390                 395                 400
```

```
Pro Leu Ile Ala Phe Ile Gly Arg Leu Glu Glu Gln Lys Gly Pro Asp
                405                 410                 415

Val Met Ala Ala Ala Ile Pro Glu Leu Met Gln Glu Asn Val Gln Ile
            420                 425                 430

Val Leu Leu Gly Thr Gly Lys Lys Lys Phe Glu Lys Leu Leu Lys Ser
        435                 440                 445

Met Glu Glu Lys Tyr Pro Gly Lys Val Arg Ala Val Lys Phe Asn
    450                 455                 460

Ala Pro Leu Ala His Leu Ile Met Ala Gly Ala Asp Val Leu Ala Val
465                 470                 475                 480

Pro Ser Arg Phe Glu Pro Cys Gly Leu Ile Gln Leu Gln Gly Met Arg
                485                 490                 495

Tyr Gly Thr Pro Cys Ala Cys Ala Ser Thr Gly Gly Leu Val Asp Thr
            500                 505                 510

Val Ile Glu Gly Lys Thr Gly Phe His Met Gly Arg Leu Ser Val Asp
        515                 520                 525

Cys Lys Val Val Glu Pro Ser Asp Val Gln Lys Val Ala Thr Thr Leu
    530                 535                 540

Lys Arg Ala Ile Lys Ile Val Gly Thr Pro Ala Tyr Asn Glu Met Val
545                 550                 555                 560

Arg Asn Cys Met Asn Gln Asp Leu Ser Trp Lys Gly Pro Ala Lys Asn
                565                 570                 575

Trp Glu Asn Val Leu Leu Gly Leu Gly Val Ala Gly Ser Ala Pro Gly
            580                 585                 590

Val Glu Gly Glu Glu Ile Ala Pro Leu Ala Lys Glu Asn Val Ala Ala
        595                 600                 605

Pro

<210> SEQ ID NO 538
<211> LENGTH: 603
<212> TYPE: PRT
<213> ORGANISM: Hordeum vulgare

<400> SEQUENCE: 538

Met Ala Ala Leu Ala Thr Ser Gln Leu Ala Thr Ser Gly Thr Val Leu
1               5                   10                  15

Gly Val Thr Asp Arg Phe Arg Arg Pro Gly Phe Gln Gly Leu Arg Pro
                20                  25                  30

Arg Asn Pro Ala Asp Ala Ala Leu Gly Met Arg Thr Ile Gly Ala Ser
            35                  40                  45

Ala Ala Pro Lys Gln Ser Arg Lys Ala His Arg Gly Ser Arg Arg Cys
        50                  55                  60

Leu Ser Val Val Arg Ala Thr Gly Ser Gly Met Asn Leu Val Phe
65                  70                  75                  80

Val Gly Ala Glu Met Ala Pro Trp Ser Lys Thr Gly Gly Leu Gly Asp
                85                  90                  95

Val Leu Gly Gly Leu Pro Pro Ala Met Ala Ala Asn Gly His Arg Val
            100                 105                 110

Met Val Val Ser Pro Arg Tyr Asp Gln Tyr Lys Asp Ala Trp Asp Thr
        115                 120                 125

Ser Val Ile Ser Glu Ile Lys Val Ala Asp Glu Tyr Glu Arg Val Arg
    130                 135                 140

Phe Phe His Cys Tyr Lys Arg Gly Val Asp Arg Val Phe Ile Asp His
145                 150                 155                 160
```

```
Pro Trp Phe Leu Glu Lys Val Arg Gly Lys Thr Lys Glu Lys Ile Tyr
                165                 170                 175
Gly Pro Asp Ala Gly Thr Asp Tyr Glu Asp Asn Gln Gln Arg Phe Ser
            180                 185                 190
Leu Leu Cys Gln Ala Ala Leu Glu Ala Pro Arg Ile Leu Asn Leu Asn
        195                 200                 205
Asn Asn Pro Tyr Phe Ser Gly Pro Tyr Gly Glu Asp Val Val Phe Val
    210                 215                 220
Cys Asn Asp Trp His Thr Gly Leu Leu Ala Cys Tyr Leu Lys Ser Asn
225                 230                 235                 240
Tyr Gln Ser Asn Gly Ile Tyr Arg Thr Ala Lys Val Ala Phe Cys Ile
                245                 250                 255
His Asn Ile Ser Tyr Gln Gly Arg Phe Ser Phe Asp Asp Phe Ala Gln
            260                 265                 270
Leu Asn Leu Pro Asp Arg Phe Lys Ser Ser Phe Asp Phe Ile Asp Gly
        275                 280                 285
Tyr Asp Lys Pro Val Glu Gly Arg Lys Ile Asn Trp Met Lys Ala Gly
    290                 295                 300
Ile Leu Gln Ala Asp Lys Val Leu Thr Val Ser Pro Tyr Tyr Ala Glu
305                 310                 315                 320
Glu Leu Ile Ser Asp Glu Ala Arg Gly Cys Glu Leu Asp Asn Ile Met
                325                 330                 335
Arg Leu Thr Gly Ile Thr Gly Ile Val Asn Gly Met Asp Val Ser Glu
            340                 345                 350
Trp Asp Pro Thr Lys Asp Lys Phe Leu Ala Val Asn Tyr Asp Ile Thr
        355                 360                 365
Thr Ala Leu Glu Ala Lys Ala Leu Asn Lys Glu Ala Leu Gln Ala Glu
    370                 375                 380
Val Gly Leu Pro Val Asp Arg Lys Val Pro Leu Val Ala Phe Ile Gly
385                 390                 395                 400
Arg Leu Glu Glu Gln Lys Gly Pro Asp Val Met Ile Ala Ala Ile Pro
                405                 410                 415
Glu Ile Leu Lys Glu Glu Asp Val Gln Ile Ile Leu Leu Gly Thr Gly
            420                 425                 430
Lys Lys Lys Phe Glu Lys Leu Leu Lys Ser Met Glu Glu Lys Phe Pro
        435                 440                 445
Gly Lys Val Arg Ala Val Val Arg Phe Asn Ala Pro Leu Ala His Gln
    450                 455                 460
Met Met Ala Gly Ala Asp Leu Leu Ala Val Thr Ser Arg Phe Glu Pro
465                 470                 475                 480
Cys Gly Leu Ile Gln Leu Gln Gly Met Arg Tyr Gly Thr Pro Cys Val
                485                 490                 495
Cys Ala Ser Thr Gly Gly Leu Val Asp Thr Ile Val Glu Gly Lys Thr
            500                 505                 510
Gly Phe His Met Gly Arg Leu Ser Val Asp Cys Asn Val Val Glu Pro
        515                 520                 525
Ala Asp Val Lys Lys Val Ala Thr Thr Leu Lys Arg Ala Val Lys Val
    530                 535                 540
Val Gly Thr Pro Ala Tyr Gln Glu Met Val Lys Asn Cys Met Ile Gln
545                 550                 555                 560
Asp Leu Ser Trp Lys Gly Pro Ala Lys Asn Trp Glu Asp Val Leu Leu
                565                 570                 575
Glu Leu Gly Val Glu Gly Ser Glu Pro Gly Ile Val Gly Glu Glu Ile
```

-continued

```
                580                 585                 590
Ala Pro Leu Ala Met Glu Asn Val Ala Ala Pro
            595                 600

<210> SEQ ID NO 539
<211> LENGTH: 495
<212> TYPE: PRT
<213> ORGANISM: Oryza brachyantha

<400> SEQUENCE: 539

Met Ala Thr Thr Val Phe Ser Arg Phe Ser Thr Tyr Phe Cys Val Leu
1               5                   10                  15

Leu Leu Cys His Gly Ser Met Ala Gln Leu Phe Asn Pro Ser Thr Asn
            20                  25                  30

Pro Trp His Asn Pro Arg Gln Gly Ser Ser Arg Glu Cys Arg Phe Asp
        35                  40                  45

Arg Leu Gln Pro Phe Glu Pro Leu Arg Lys Val Arg Ser Glu Ala Gly
    50                  55                  60

Val Thr Glu Tyr Phe Asp Glu Lys Asn Glu Leu Phe Gln Cys Thr Gly
65                  70                  75                  80

Thr Phe Val Ile Arg Arg Val Ile Gln Pro Gln Gly Leu Leu Val Pro
                85                  90                  95

Arg Tyr Thr Asn Ala Pro Gly Leu Val Tyr Ile Ile Gln Gly Arg Gly
            100                 105                 110

Ser Ile Gly Leu Thr Phe Pro Gly Cys Pro Ala Thr Tyr Gln Gln Gln
        115                 120                 125

Phe Gln Gln Phe Leu Pro Gln Glu Ser Gln Ser Gln Lys Phe Arg
    130                 135                 140

Asp Glu His Gln Lys Ile His Gln Phe Arg Gln Gly Asp Ile Val Ala
145                 150                 155                 160

Leu Pro Ala Gly Val Ala His Trp Phe Tyr Asn Asp Gly Asp Ala Pro
                165                 170                 175

Val Val Ala Val Tyr Val Tyr Asp Val Lys Asn Ser Ala Asn Gln Leu
            180                 185                 190

Glu Pro Arg Gln Arg Glu Phe Leu Leu Gly Gly Asn Asn Met Arg Ala
        195                 200                 205

Gln Gln Val Tyr Gly Ser Ser Ala Glu Gln His Ser Arg Gln Asn Ile
    210                 215                 220

Phe Ser Gly Phe Gly Val Glu Ile Leu Ser Glu Ala Leu Gly Ile Ser
225                 230                 235                 240

Thr Val Thr Thr Lys Arg Leu Gln Ser Gln Asn Asp Gln Arg Gly Glu
                245                 250                 255

Ile Ile His Val Lys Asn Gly Leu Gln Phe Leu Lys Pro Thr Leu Thr
            260                 265                 270

Gln Gln Gln Glu Gln Ala Gln Ala Gln Tyr Gln Glu Val Gln Tyr Ser
        275                 280                 285

Glu Gln Gln Gln Thr Ser Ser Arg Trp Asn Gly Leu Asp Glu Asn Phe
    290                 295                 300

Cys Thr Ile Lys Ala Arg Met Asn Ile Glu Asn Thr Ser Arg Ala Asp
305                 310                 315                 320

Thr Tyr Asn Pro Arg Ala Gly Arg Thr Thr Ser Leu Asn Ser Gln Lys
                325                 330                 335

Phe Pro Ile Leu Asn Leu Val Gln Met Ser Ala Thr Arg Val Asn Leu
            340                 345                 350
```

```
Tyr Gln Asn Ala Ile Leu Ser Thr Phe Trp Asn Val Asn Ala His Ser
                355                 360                 365

Leu Val Tyr Thr Ile Gln Gly Arg Ala Arg Val Gln Val Val Ser Asn
    370                 375                 380

Phe Gly Lys Thr Val Phe Asp Gly Glu Leu Arg Pro Gly Gln Leu Leu
385                 390                 395                 400

Ile Ile Pro Gln His Tyr Val Val Leu Lys Lys Ala Gln Arg Glu Gly
                405                 410                 415

Phe Arg Tyr Ile Ala Ile Lys Thr Asn Ala Asn Ala Phe Val Ser Gln
                420                 425                 430

Leu Val Gly Lys Asn Ser Val Phe Arg Ser Leu Pro Val Asp Val Ile
                435                 440                 445

Ala Asn Val Tyr Arg Ile Ser Arg Glu Gln Ala Arg Ser Leu Lys Asn
450                 455                 460

Asn Arg Gly Glu Glu His Gly Ala Phe Ala Pro Arg Ser Gln Gln Gln
465                 470                 475                 480

Ser Tyr Pro Gly Phe Ser Asn Gln Ser Glu Ser Glu Thr Ser Glu
                485                 490                 495

<210> SEQ ID NO 540
<211> LENGTH: 494
<212> TYPE: PRT
<213> ORGANISM: Oryza brachyantha

<400> SEQUENCE: 540

Met Ala Thr Thr Thr Phe Ser Arg Phe Ser Ile Tyr Phe Cys Val Leu
1               5                   10                  15

Leu Leu Cys His Gly Ser Met Ala Gln Leu Phe Ser Pro Thr Leu Asn
                20                  25                  30

Pro Trp His Ser Arg Arg Gly Gly Ser Arg Asp Cys Arg Phe Asp
                35                  40                  45

Arg Leu Gln Ala Phe Glu Pro Leu Arg Arg Val Arg Ser Glu Ala Gly
    50                  55                  60

Val Thr Glu Tyr Phe Asp Glu Arg Asn Glu Gln Phe Gln Cys Thr Gly
65                  70                  75                  80

Thr Phe Val Ile Arg Arg Val Ile Glu Pro Gln Gly Leu Leu Val Pro
                85                  90                  95

Arg Tyr Thr Asn Thr Pro Gly Val Val Tyr Ile Met Gln Gly Arg Gly
                100                 105                 110

Ser Met Gly Leu Thr Phe Pro Gly Cys Pro Ala Thr Tyr Gln Gln Gln
            115                 120                 125

Phe Gln Gln Phe Leu Pro Glu Gly Gln Ser Gln Ser Gln Lys Phe Arg
    130                 135                 140

Asp Glu His Gln Lys Ile His Gln Phe Arg Gln Gly Asp Ile Val Ala
145                 150                 155                 160

Leu Pro Ala Gly Val Ala His Trp Phe Tyr Asn Glu Gly Asp Thr Pro
                165                 170                 175

Val Val Ala Leu Tyr Val Phe Asp Ile Asn Asn Ser Ala Asn Gln Leu
                180                 185                 190

Glu Pro Arg Gln Lys Asp Phe Leu Leu Ala Gly Asn Asn Asn Arg Glu
            195                 200                 205

Gln Gln Val Tyr Gly Arg Ser Ile Glu Lys His Ser Gly Gln Asn Ile
    210                 215                 220

Phe Ser Gly Phe Asn His Glu Leu Leu Ser Glu Ala Leu Gly Ile Ser
225                 230                 235                 240
```

```
Thr Leu Ala Ala Lys Arg Leu Gln Gly Gln Asn Asp His Arg Gly Glu
            245                 250                 255

Ile Ile Arg Val Arg Asn Gly Leu Gln Leu Leu Lys Pro Thr Phe Thr
        260                 265                 270

Gln Gln Gln Glu Gln Ala Gln Ser Gln Tyr Gln Val Gln Tyr Ser Glu
    275                 280                 285

Lys Gln Gln Glu Ser Thr Arg Cys Asn Gly Leu Asp Glu Asn Phe Cys
290                 295                 300

Thr Ile Asn Ala Arg Leu Asn Ile Glu Asn Pro Ser Arg Ala Asp Thr
305                 310                 315                 320

Tyr Asn Pro Arg Ala Gly Arg Ile Thr His Leu Asn Asn Gln Lys Phe
                325                 330                 335

Pro Ile Leu Asn Leu Val Gln Met Ser Ala Thr Arg Val Asn Leu Tyr
            340                 345                 350

Gln Asn Ala Ile Leu Ser Pro Tyr Trp Asn Val Asn Ala His Ser Leu
        355                 360                 365

Val Tyr Met Val Gln Gly His Ala Arg Val Gln Val Val Ser Asn Leu
    370                 375                 380

Gly Lys Thr Val Phe Asn Ser Val Leu Arg Pro Gly Gln Leu Leu Ile
385                 390                 395                 400

Ile Pro Gln His Tyr Val Val Leu Lys Lys Ala Glu Arg Glu Gly Cys
                405                 410                 415

Gln Tyr Ile Ala Phe Lys Thr Asn Ala Asn Ser Ile Val Ser Gln Leu
            420                 425                 430

Ala Gly Lys Asn Ser Ile Leu Arg Ala Met Pro Val Asp Val Val Ala
        435                 440                 445

Asn Ala Tyr Arg Ile Ser Arg Glu Gln Ala Arg Asp Leu Lys Asn Asn
    450                 455                 460

Arg Gly Glu Glu Leu Gly Ala Phe Thr Pro Lys Phe Glu Gln Gln Ser
465                 470                 475                 480

Tyr Pro Gly Leu Ser Asn Glu Ser Glu Ser Glu Ala Ser Glu
                485                 490

<210> SEQ ID NO 541
<211> LENGTH: 500
<212> TYPE: PRT
<213> ORGANISM: Zizania latifolia

<400> SEQUENCE: 541

Met Asn Met Ala Thr Ile Asn Gly Pro Thr Ile Phe Phe Thr Val Cys
1               5                   10                  15

Leu Phe Leu Leu Cys His Gly Ser Leu Ala Gln Leu Leu Gly Gln Ser
            20                  25                  30

Thr Ser Gln Trp Gln Ser Ser His Arg Gly Ser Ser Arg Gln Cys Arg
        35                  40                  45

Phe Asp Arg Leu Gln Ala Phe Glu Pro Val Arg Ser Val Arg Ser Gln
    50                  55                  60

Ala Gly Thr Thr Glu Phe Phe Asp Ala Ser Asn Glu Leu Phe Gln Cys
65                  70                  75                  80

Ala Gly Val Ser Ile Val Arg Arg Ile Ile Glu Pro Arg Gly Leu Leu
                85                  90                  95

Leu Pro Gln Tyr Thr Asn Gly Ala Thr Ile Met Tyr Ile Ile Gln Gly
            100                 105                 110

Arg Gly Ile Thr Gly Gln Thr Phe Pro Gly Cys Pro Glu Ser Tyr Gln
```

```
            115                 120                 125
Gln Gln Phe Gln Gln Ser Met Gln Ala Gln Leu Thr Gly Ser Gln Ser
130                 135                 140
Gln Ser Gln Lys Phe Lys Asp Glu His Gln Lys Ile Asn Arg Phe Arg
145                 150                 155                 160
Gln Gly Asp Val Ile Ala Leu Pro Ala Gly Val Ala His Trp Cys Tyr
                165                 170                 175
Asn Asp Gly Glu Val Pro Val Ala Ile Tyr Val Ile Asp Ile Asn
            180                 185                 190
Asn Ala Ala Asn Gln Leu Asp Pro Arg Gln Arg Asp Phe Leu Leu Ala
            195                 200                 205
Gly Asn Met Arg Ser Pro Gln Ala Tyr Arg Arg Glu Val Glu Asn Gln
            210                 215                 220
Ser Gln Asn Ile Phe Ser Gly Phe Ser Ala Glu Leu Leu Ser Glu Ala
225                 230                 235                 240
Leu Gly Ile Ser Thr Gly Val Ala Arg Gln Leu Gln Cys Gln Asn Asp
                245                 250                 255
Gln Arg Gly Glu Ile Val Arg Val Glu His Gly Leu Ser Leu Leu Gln
            260                 265                 270
Pro Tyr Ala Ser Leu Gln Glu Gln Glu Lys Gln Glu Gln Pro Arg
            275                 280                 285
Glu Arg Tyr Gln Val Thr Gln His Gln Gln Ser Gln Tyr Gly Gly Gly
            290                 295                 300
Cys Ser Asn Gly Leu Asp Glu Thr Phe Cys Ala Met Arg Ile Trp Gln
305                 310                 315                 320
Asn Ile Asp Asn Pro Asn Leu Ala Asp Thr Tyr Asn Pro Arg Ala Gly
                325                 330                 335
Arg Val Thr Asn Leu Asn Ser Gln Lys Phe Pro Ile Leu Asn Leu Ile
            340                 345                 350
Gln Met Ser Ala Val Lys Val Asn Leu Tyr Gln Asn Ala Leu Leu Ser
            355                 360                 365
Pro Phe Trp Asn Ile Asn Ser His Ser Val Val Tyr Val Thr Gln Gly
            370                 375                 380
Cys Ala Arg Val Gln Val Val Asn Asn Asn Gly Lys Thr Val Phe Asn
385                 390                 395                 400
Gly Glu Leu Arg Arg Gly Gln Leu Leu Ile Ile Pro Gln His Tyr Val
                405                 410                 415
Val Val Lys Lys Ala Gln Arg Glu Gly Cys Ala Tyr Ile Ala Phe Lys
            420                 425                 430
Thr Asn Pro Asn Ser Met Val Ser His Ile Val Gly Lys Ser Ser Ile
            435                 440                 445
Phe Arg Ala Leu Pro Thr Asp Val Leu Ala Asn Ala Tyr Arg Ile Ser
            450                 455                 460
Arg Glu Asp Ala Gln Arg Leu Lys His Asn Arg Gly Asp Glu Leu Gly
465                 470                 475                 480
Ala Phe Thr Pro Leu Gln Tyr Lys Ser Tyr Gln Asp Val Ser Ser Val
                485                 490                 495
Ala Ala Ser Ser
            500

<210> SEQ ID NO 542
<211> LENGTH: 197
<212> TYPE: PRT
<213> ORGANISM: Zea mays
```

<400> SEQUENCE: 542

```
Met Ala Lys Ile Ala Ala Ala Ala Ala Ala Ala Leu Cys Phe
1               5                   10                  15

Ala Ala Leu Val Ala Val Ala Val Cys Gln Gly Glu Val Glu Arg Gln
            20                  25                  30

Arg Leu Arg Asp Leu Gln Cys Trp Gln Glu Val Gln Glu Ser Pro Leu
        35                  40                  45

Asp Ala Cys Arg Gln Val Leu Asp Arg Gln Leu Thr Gly Gly Gly Val
    50                  55                  60

Gly Gly Pro Phe Arg Trp Gly Thr Gly Leu Arg Met Arg Cys Cys Gln
65                  70                  75                  80

Gln Leu Gln Asp Val Ser Arg Glu Cys Arg Cys Ala Ala Ile Arg Ser
                85                  90                  95

Met Val Arg Gly Tyr Glu Glu Ala Met Pro Pro Leu Glu Lys Gly Trp
            100                 105                 110

Trp Pro Trp Gly Arg Gln Gln Pro Pro Gln Gly Gly Gly Gly
        115                 120                 125

Gly Gln Gly Gly Tyr Tyr Tyr Pro Cys Ser Arg Ala Gly Glu Gly Tyr
    130                 135                 140

Gln Thr Gln Met Tyr Pro Pro Cys Arg Pro Gly Thr Thr Gly Pro Arg
145                 150                 155                 160

Ile Gly Arg Val Arg Leu Thr Lys Ala Arg Glu Tyr Ala Ala Gly Leu
                165                 170                 175

Pro Met Met Cys Arg Leu Ser Glu Pro Gln Glu Cys Ser Ile Phe Ser
            180                 185                 190

Gly Gly Asp Gln Tyr
        195
```

<210> SEQ ID NO 543
<211> LENGTH: 192
<212> TYPE: PRT
<213> ORGANISM: Sorghum bicolor

<400> SEQUENCE: 543

```
Met Ala Lys Ile Ala Ala Val Ala Ala Thr Ala Ala Leu Cys Leu Ala
1               5                   10                  15

Ala Leu Val Ala Val Ala Val Gly Gln Gly Val Val Glu Arg Gln Arg
            20                  25                  30

Leu Lys Asp Leu Gln Cys Trp Gln Glu Val Gln Glu Asn Pro Leu Gly
        35                  40                  45

Ala Cys Arg Gln Val Leu Asp Arg Gln Leu Thr Gly Gly Met Arg Tyr
    50                  55                  60

Gly Ile Gly Pro Phe Arg Trp Gly Thr Gly Leu Arg Met Arg Cys Cys
65                  70                  75                  80

Gln Gln Leu Gln Asp Val Ser Arg Glu Cys Arg Cys Ala Ala Ile Arg
                85                  90                  95

Ser Met Val Arg Gly Tyr Glu Glu Thr Met Pro Pro Leu Glu Lys Gly
            100                 105                 110

Trp Trp Gly Gln Gln Pro Gln Pro Gly Tyr Asp Tyr Pro Cys Ser Gln
        115                 120                 125

Ala Gly Glu Gly Tyr Gly Tyr Gly Glu Ser Gly Gln Gln Gln Met Tyr
    130                 135                 140

Pro Pro Cys Arg Pro Gly Thr Gly Gln Lys Ile Ala Arg Val Lys Leu
145                 150                 155                 160
```

```
Thr Lys Ala Arg Gln Tyr Ala Ala Gly Met Pro Met Met Cys Arg Leu
                165                 170                 175

Ser Glu Pro Gln Glu Cys Ser Val Phe Ser Gly Gly Asp Gln Tyr Tyr
            180                 185                 190
```

<210> SEQ ID NO 544
<211> LENGTH: 177
<212> TYPE: PRT
<213> ORGANISM: Setaria italica

<400> SEQUENCE: 544

```
Met Ala Lys Phe Val Val Ala Ala Ala Thr Ala Leu Cys Leu Ala
1               5                   10                  15

Ala Leu Val Ala Met Ala Ala Gly Gln Ser Gly Phe Glu Arg Gln Arg
                20                  25                  30

Leu Arg Asp Leu Arg Cys Gln Arg Glu Val Glu Glu Asn Pro Leu Trp
            35                  40                  45

Ala Cys Arg Gln Val Leu Asp Arg Gln Leu Thr Gly Gly Met Arg Tyr
        50                  55                  60

Gly Val Gly Pro Phe Arg Trp Gly Thr Gly Leu Arg Met Arg Cys Cys
65                  70                  75                  80

Gln Gln Leu Gln Asp Val Ser Arg Glu Cys Arg Cys Ser Ala Val Arg
                85                  90                  95

Arg Met Val Arg Gly Tyr Glu Glu Ala Met Pro Pro Leu Glu Glu Gly
            100                 105                 110

Pro Tyr Gly Tyr Gly Gly Glu Gln Gly Glu Tyr Tyr Gly Gly Gly
        115                 120                 125

Glu Gly Gly Glu Gly Tyr Leu Pro Phe Pro Pro Arg Arg Ile Gly Arg
130                 135                 140

Val Arg Leu Thr Lys Ala Arg Gln Tyr Ala Ala Gly Leu Pro Met Met
145                 150                 155                 160

Cys Arg Leu Glu Pro Gln Glu Cys Ser Val Phe Ser Gly Asp Gln Tyr
                165                 170                 175

Lys
```

<210> SEQ ID NO 545
<211> LENGTH: 336
<212> TYPE: PRT
<213> ORGANISM: Staphylococcus aureus

<400> SEQUENCE: 545

```
Met Lys Gly Lys Phe Leu Lys Val Ser Ser Leu Phe Val Ala Thr Leu
1               5                   10                  15

Thr Thr Ala Thr Leu Val Ser Ser Pro Ala Ala Asn Ala Leu Ser Ser
                20                  25                  30

Lys Ala Met Asp Asn His Pro Gln Gln Ser Gln Ser Ser Lys Gln Gln
            35                  40                  45

Thr Pro Lys Ile Gln Lys Gly Gly Asn Leu Lys Pro Leu Glu Gln Arg
        50                  55                  60

Glu His Ala Asn Val Ile Leu Pro Asn Asn Asp Arg His Gln Ile Thr
65                  70                  75                  80

Asp Thr Thr Asn Gly His Tyr Ala Pro Val Thr Tyr Ile Gln Val Glu
                85                  90                  95

Ala Pro Thr Gly Thr Phe Ile Ala Ser Gly Val Val Val Gly Lys Asp
            100                 105                 110
```

-continued

```
Thr Leu Leu Thr Asn Lys His Val Asp Ala Thr His Gly Asp Pro
            115                 120                 125

His Ala Leu Lys Ala Phe Pro Ser Ala Ile Asn Gln Asp Asn Tyr Pro
130                 135                 140

Asn Gly Gly Phe Thr Ala Glu Gln Ile Thr Lys Tyr Ser Gly Glu Gly
145                 150                 155                 160

Asp Leu Ala Ile Val Lys Phe Ser Pro Asn Glu Gln Asn Lys His Ile
                165                 170                 175

Gly Glu Val Val Lys Pro Ala Thr Met Ser Asn Ala Glu Thr Gln
            180                 185                 190

Val Asn Gln Asn Ile Thr Val Thr Gly Tyr Pro Gly Asp Lys Pro Val
        195                 200                 205

Ala Thr Met Trp Glu Ser Lys Gly Lys Ile Thr Tyr Leu Lys Gly Glu
    210                 215                 220

Ala Met Gln Tyr Asp Leu Ser Thr Thr Gly Gly Asn Ser Gly Ser Pro
225                 230                 235                 240

Val Phe Asn Glu Lys Asn Glu Val Ile Gly Ile His Trp Gly Gly Val
                245                 250                 255

Pro Asn Glu Phe Asn Gly Ala Val Phe Ile Asn Glu Asn Val Arg Asn
            260                 265                 270

Phe Leu Lys Gln Asn Ile Glu Asp Ile His Phe Ala Asn Asp Asp Gln
        275                 280                 285

Pro Asn Asn Pro Asp Asn Pro Asp Asn Pro Asn Asn Pro Asp Asn Pro
    290                 295                 300

Asn Asn Pro Asp Glu Pro Asn Asn Pro Asp Asn Pro Asn Asn Pro Asp
305                 310                 315                 320

Asn Pro Asp Asn Gly Asp Asn Asn Asn Ser Asp Asn Pro Asp Ala Ala
                325                 330                 335
```

<210> SEQ ID NO 546
<211> LENGTH: 11
<212> TYPE: PRT
<213> ORGANISM: Artificial Sequence
<220> FEATURE:
<223> OTHER INFORMATION: Synthetic peptide

<400> SEQUENCE: 546

```
Ser Arg Ala Ile Val Ile Val Thr Val Asn Glu
1               5                   10
```

<210> SEQ ID NO 547
<211> LENGTH: 8
<212> TYPE: PRT
<213> ORGANISM: Artificial Sequence
<220> FEATURE:
<223> OTHER INFORMATION: Synthetic peptide

<400> SEQUENCE: 547

```
Ala Lys Leu Thr Pro Gly Asp Val
1               5
```

<210> SEQ ID NO 548
<211> LENGTH: 10
<212> TYPE: PRT
<213> ORGANISM: Artificial Sequence
<220> FEATURE:
<223> OTHER INFORMATION: Synthetic peptide

<400> SEQUENCE: 548

```
Ile Val Ile Val Thr Val Asn Glu Gly Lys
```

<210> SEQ ID NO 549
<211> LENGTH: 16
<212> TYPE: PRT
<213> ORGANISM: Artificial Sequence
<220> FEATURE:
<223> OTHER INFORMATION: Synthetic peptide

<400> SEQUENCE: 549

Leu Asp Ala Leu Glu Pro Asp Asn Arg Ile Glu Ser Glu Gly Gly Leu
1               5                   10                  15

<210> SEQ ID NO 550
<211> LENGTH: 10
<212> TYPE: PRT
<213> ORGANISM: Artificial Sequence
<220> FEATURE:
<223> OTHER INFORMATION: Synthetic peptide

<400> SEQUENCE: 550

Arg Pro Tyr Tyr Ser Asn Ala Pro Gln Glu
1               5                   10

<210> SEQ ID NO 551
<211> LENGTH: 25
<212> TYPE: PRT
<213> ORGANISM: Artificial Sequence
<220> FEATURE:
<223> OTHER INFORMATION: Synthetic peptide

<400> SEQUENCE: 551

Leu Asp Ala Leu Glu Pro Asp Asn Arg Ile Glu Ser Glu Gly Gly Leu
1               5                   10                  15

Ile Glu Thr Trp Asn Pro Asn Asn Lys
            20                  25

<210> SEQ ID NO 552
<211> LENGTH: 11
<212> TYPE: PRT
<213> ORGANISM: Artificial Sequence
<220> FEATURE:
<223> OTHER INFORMATION: Synthetic peptide

<400> SEQUENCE: 552

Ala Ile Val Ile Val Thr Val Asn Glu Gly Lys
1               5                   10

<210> SEQ ID NO 553
<211> LENGTH: 16
<212> TYPE: PRT
<213> ORGANISM: Artificial Sequence
<220> FEATURE:
<223> OTHER INFORMATION: Synthetic peptide

<400> SEQUENCE: 553

Leu Gln Val Val Asn Cys Asn Gly Asn Thr Val Phe Asp Gly Glu Leu
1               5                   10                  15

<210> SEQ ID NO 554
<211> LENGTH: 15
<212> TYPE: PRT
<213> ORGANISM: Artificial Sequence
<220> FEATURE:
<223> OTHER INFORMATION: Synthetic peptide

<400> SEQUENCE: 554

Gln Val Val Asn Cys Asn Gly Asn Thr Val Phe Asp Gly Glu Leu
1               5                   10                  15

<210> SEQ ID NO 555
<211> LENGTH: 10
<212> TYPE: PRT
<213> ORGANISM: Artificial Sequence
<220> FEATURE:
<223> OTHER INFORMATION: Synthetic peptide

<400> SEQUENCE: 555

Ile Ile Ala Val Pro Thr Gly Ile Val Phe
1               5                   10

<210> SEQ ID NO 556
<211> LENGTH: 16
<212> TYPE: PRT
<213> ORGANISM: Artificial Sequence
<220> FEATURE:
<223> OTHER INFORMATION: Synthetic peptide

<400> SEQUENCE: 556

Gly Arg Arg Tyr Arg Asp Arg His Gln Lys Val Asn Arg Phe Arg Glu
1               5                   10                  15

<210> SEQ ID NO 557
<211> LENGTH: 11
<212> TYPE: PRT
<213> ORGANISM: Artificial Sequence
<220> FEATURE:
<223> OTHER INFORMATION: Synthetic peptide

<400> SEQUENCE: 557

Arg Pro Tyr Tyr Ser Asn Ala Pro Gln Glu Ile
1               5                   10

<210> SEQ ID NO 558
<211> LENGTH: 12
<212> TYPE: PRT
<213> ORGANISM: Artificial Sequence
<220> FEATURE:
<223> OTHER INFORMATION: Synthetic peptide

<400> SEQUENCE: 558

Arg Leu Asp Ala Leu Glu Pro Asp Asn Arg Ile Glu
1               5                   10

<210> SEQ ID NO 559
<211> LENGTH: 14
<212> TYPE: PRT
<213> ORGANISM: Artificial Sequence
<220> FEATURE:
<223> OTHER INFORMATION: Synthetic peptide

<400> SEQUENCE: 559

Arg Leu Asp Ala Leu Glu Pro Asp Asn Arg Ile Glu Ser Glu
1               5                   10

<210> SEQ ID NO 560
<211> LENGTH: 20
<212> TYPE: PRT
<213> ORGANISM: Artificial Sequence
<220> FEATURE:
<223> OTHER INFORMATION: Synthetic peptide

<400> SEQUENCE: 560

```
Leu Asp Ala Leu Glu Pro Asp Asn Arg Ile Glu Ser Glu Gly Gly Leu
1               5                   10                  15

Ile Glu Thr Trp
            20
```

<210> SEQ ID NO 561
<211> LENGTH: 11
<212> TYPE: PRT
<213> ORGANISM: Artificial Sequence
<220> FEATURE:
<223> OTHER INFORMATION: Synthetic peptide

<400> SEQUENCE: 561

```
Leu Asp Ala Leu Glu Pro Asp Asn Arg Ile Glu
1               5                   10
```

<210> SEQ ID NO 562
<211> LENGTH: 18
<212> TYPE: PRT
<213> ORGANISM: Artificial Sequence
<220> FEATURE:
<223> OTHER INFORMATION: Synthetic peptide

<400> SEQUENCE: 562

```
Leu Asp Ala Leu Glu Pro Asp Asn Arg Ile Glu Ser Glu Gly Gly Leu
1               5                   10                  15

Ile Glu
```

<210> SEQ ID NO 563
<211> LENGTH: 16
<212> TYPE: PRT
<213> ORGANISM: Artificial Sequence
<220> FEATURE:
<223> OTHER INFORMATION: Synthetic peptide

<400> SEQUENCE: 563

```
Leu Asp Ala Leu Glu Pro Asp Asn Arg Ile Glu Ser Glu Gly Gly Leu
1               5                   10                  15
```

<210> SEQ ID NO 564
<211> LENGTH: 10
<212> TYPE: PRT
<213> ORGANISM: Artificial Sequence
<220> FEATURE:
<223> OTHER INFORMATION: Synthetic peptide

<400> SEQUENCE: 564

```
Arg Pro Tyr Tyr Ser Asn Ala Pro Gln Glu
1               5                   10
```

<210> SEQ ID NO 565
<211> LENGTH: 25
<212> TYPE: PRT
<213> ORGANISM: Artificial Sequence
<220> FEATURE:
<223> OTHER INFORMATION: Synthetic peptide

<400> SEQUENCE: 565

```
Leu Asp Ala Leu Glu Pro Asp Asn Arg Ile Glu Ser Glu Gly Gly Leu
1               5                   10                  15

Ile Glu Thr Trp Asn Pro Asn Asn Lys
            20                  25
```

<210> SEQ ID NO 566
<211> LENGTH: 27

```
<212> TYPE: PRT
<213> ORGANISM: Artificial Sequence
<220> FEATURE:
<223> OTHER INFORMATION: Synthetic peptide

<400> SEQUENCE: 566

Val Glu His Gly Leu Ser Leu Leu Gln Pro Tyr Ala Ser Leu Gln Glu
1               5                   10                  15

Gln Glu Gln Gly Gln Val Gln Ser Arg Glu Arg
            20                  25

<210> SEQ ID NO 567
<211> LENGTH: 9
<212> TYPE: PRT
<213> ORGANISM: Artificial Sequence
<220> FEATURE:
<223> OTHER INFORMATION: Synthetic peptide

<400> SEQUENCE: 567

Arg Ser Gln Asn Ile Phe Ser Gly Phe
1               5

<210> SEQ ID NO 568
<211> LENGTH: 14
<212> TYPE: PRT
<213> ORGANISM: Artificial Sequence
<220> FEATURE:
<223> OTHER INFORMATION: Synthetic peptide

<400> SEQUENCE: 568

Gly Ile Thr Gly Pro Thr Phe Pro Gly Cys Pro Glu Ser Tyr
1               5                   10

<210> SEQ ID NO 569
<211> LENGTH: 4
<212> TYPE: PRT
<213> ORGANISM: Artificial Sequence
<220> FEATURE:
<223> OTHER INFORMATION: Synthetic peptide

<400> SEQUENCE: 569

Cys Asn Gly Ser
1

<210> SEQ ID NO 570
<211> LENGTH: 5
<212> TYPE: PRT
<213> ORGANISM: Artificial Sequence
<220> FEATURE:
<223> OTHER INFORMATION: Synthetic peptide

<400> SEQUENCE: 570

Ser Pro Arg Glu Cys
1               5

<210> SEQ ID NO 571
<211> LENGTH: 4
<212> TYPE: PRT
<213> ORGANISM: Artificial Sequence
<220> FEATURE:
<223> OTHER INFORMATION: Synthetic peptide

<400> SEQUENCE: 571

Pro Arg Glu Cys
1
```

```
<210> SEQ ID NO 572
<211> LENGTH: 5
<212> TYPE: PRT
<213> ORGANISM: Artificial Sequence
<220> FEATURE:
<223> OTHER INFORMATION: Synthetic peptide

<400> SEQUENCE: 572

Pro Arg Glu Cys Arg
1               5

<210> SEQ ID NO 573
<211> LENGTH: 4
<212> TYPE: PRT
<213> ORGANISM: Artificial Sequence
<220> FEATURE:
<223> OTHER INFORMATION: Synthetic peptide

<400> SEQUENCE: 573

Cys Pro Glu Ser
1

<210> SEQ ID NO 574
<211> LENGTH: 4
<212> TYPE: PRT
<213> ORGANISM: Artificial Sequence
<220> FEATURE:
<223> OTHER INFORMATION: Synthetic peptide

<400> SEQUENCE: 574

Ser Gly Cys Ser
1

<210> SEQ ID NO 575
<211> LENGTH: 4
<212> TYPE: PRT
<213> ORGANISM: Artificial Sequence
<220> FEATURE:
<223> OTHER INFORMATION: Synthetic peptide

<400> SEQUENCE: 575

Cys Ser Asn Gly
1

<210> SEQ ID NO 576
<211> LENGTH: 12
<212> TYPE: PRT
<213> ORGANISM: Artificial Sequence
<220> FEATURE:
<223> OTHER INFORMATION: Synthetic peptide

<400> SEQUENCE: 576

Arg Ser Gln Asn Ile Phe Ser Gly Phe Ser Thr Glu
1               5                   10

<210> SEQ ID NO 577
<211> LENGTH: 14
<212> TYPE: PRT
<213> ORGANISM: Artificial Sequence
<220> FEATURE:
<223> OTHER INFORMATION: Synthetic peptide

<400> SEQUENCE: 577

Val Glu Glu Trp Ser Gln Asn Ile Phe Ser Gly Phe Ser Thr
1               5                   10

<210> SEQ ID NO 578
```

```
<211> LENGTH: 13
<212> TYPE: PRT
<213> ORGANISM: Artificial Sequence
<220> FEATURE:
<223> OTHER INFORMATION: Synthetic peptide

<400> SEQUENCE: 578

Trp Ser Gln Asn Ile Phe Ser Gly Phe Ser Thr Glu Leu
1               5                   10

<210> SEQ ID NO 579
<211> LENGTH: 12
<212> TYPE: PRT
<213> ORGANISM: Artificial Sequence
<220> FEATURE:
<223> OTHER INFORMATION: Synthetic peptide

<400> SEQUENCE: 579

Trp Ser Gln Asn Ile Phe Ser Gly Phe Ser Thr Glu
1               5                   10

<210> SEQ ID NO 580
<211> LENGTH: 10
<212> TYPE: PRT
<213> ORGANISM: Artificial Sequence
<220> FEATURE:
<223> OTHER INFORMATION: Synthetic peptide

<400> SEQUENCE: 580

Ser Thr Ser Gln Trp Gln Ser Ser Arg Arg
1               5                   10

<210> SEQ ID NO 581
<211> LENGTH: 4
<212> TYPE: PRT
<213> ORGANISM: Artificial Sequence
<220> FEATURE:
<223> OTHER INFORMATION: Synthetic peptide

<400> SEQUENCE: 581

Asn Arg Pro Ile
1

<210> SEQ ID NO 582
<211> LENGTH: 4
<212> TYPE: PRT
<213> ORGANISM: Artificial Sequence
<220> FEATURE:
<223> OTHER INFORMATION: Synthetic peptide

<400> SEQUENCE: 582

Cys Asp Gly Ser
1

<210> SEQ ID NO 583
<211> LENGTH: 4
<212> TYPE: PRT
<213> ORGANISM: Artificial Sequence
<220> FEATURE:
<223> OTHER INFORMATION: Synthetic peptide

<400> SEQUENCE: 583

Pro Arg Gly Cys
1

<210> SEQ ID NO 584
<211> LENGTH: 5
```

```
<212> TYPE: PRT
<213> ORGANISM: Artificial Sequence
<220> FEATURE:
<223> OTHER INFORMATION: Synthetic peptide

<400> SEQUENCE: 584

Pro Arg Gly Cys Arg
1               5

<210> SEQ ID NO 585
<211> LENGTH: 4
<212> TYPE: PRT
<213> ORGANISM: Artificial Sequence
<220> FEATURE:
<223> OTHER INFORMATION: Synthetic peptide

<400> SEQUENCE: 585

Arg Gly Cys Arg
1

<210> SEQ ID NO 586
<211> LENGTH: 4
<212> TYPE: PRT
<213> ORGANISM: Artificial Sequence
<220> FEATURE:
<223> OTHER INFORMATION: Synthetic peptide

<400> SEQUENCE: 586

Gly Cys Arg Phe
1

<210> SEQ ID NO 587
<211> LENGTH: 4
<212> TYPE: PRT
<213> ORGANISM: Artificial Sequence
<220> FEATURE:
<223> OTHER INFORMATION: Synthetic peptide

<400> SEQUENCE: 587

Pro Thr Phe Pro
1

<210> SEQ ID NO 588
<211> LENGTH: 5
<212> TYPE: PRT
<213> ORGANISM: Artificial Sequence
<220> FEATURE:
<223> OTHER INFORMATION: Synthetic peptide

<400> SEQUENCE: 588

Pro Gly Cys Pro Glu
1               5

<210> SEQ ID NO 589
<211> LENGTH: 4
<212> TYPE: PRT
<213> ORGANISM: Artificial Sequence
<220> FEATURE:
<223> OTHER INFORMATION: Synthetic peptide

<400> SEQUENCE: 589

Gly Cys Pro Glu
1

<210> SEQ ID NO 590
<211> LENGTH: 4
<212> TYPE: PRT
```

```
<213> ORGANISM: Artificial Sequence
<220> FEATURE:
<223> OTHER INFORMATION: Synthetic peptide

<400> SEQUENCE: 590

Cys Pro Glu Thr
1

<210> SEQ ID NO 591
<211> LENGTH: 4
<212> TYPE: PRT
<213> ORGANISM: Artificial Sequence
<220> FEATURE:
<223> OTHER INFORMATION: Synthetic peptide

<400> SEQUENCE: 591

Ala His Trp Cys
1

<210> SEQ ID NO 592
<211> LENGTH: 4
<212> TYPE: PRT
<213> ORGANISM: Artificial Sequence
<220> FEATURE:
<223> OTHER INFORMATION: Synthetic peptide

<400> SEQUENCE: 592

His Trp Cys Tyr
1

<210> SEQ ID NO 593
<211> LENGTH: 4
<212> TYPE: PRT
<213> ORGANISM: Artificial Sequence
<220> FEATURE:
<223> OTHER INFORMATION: Synthetic peptide

<400> SEQUENCE: 593

Ser Gly Cys Pro
1

<210> SEQ ID NO 594
<211> LENGTH: 5
<212> TYPE: PRT
<213> ORGANISM: Artificial Sequence
<220> FEATURE:
<223> OTHER INFORMATION: Synthetic peptide

<400> SEQUENCE: 594

Ser Gly Cys Pro Asn
1               5

<210> SEQ ID NO 595
<211> LENGTH: 4
<212> TYPE: PRT
<213> ORGANISM: Artificial Sequence
<220> FEATURE:
<223> OTHER INFORMATION: Synthetic peptide

<400> SEQUENCE: 595

Gly Cys Pro Asn
1

<210> SEQ ID NO 596
<211> LENGTH: 4
<212> TYPE: PRT
<213> ORGANISM: Artificial Sequence
```

```
<220> FEATURE:
<223> OTHER INFORMATION: Synthetic peptide

<400> SEQUENCE: 596

Cys Pro Asn Gly
1

<210> SEQ ID NO 597
<211> LENGTH: 5
<212> TYPE: PRT
<213> ORGANISM: Artificial Sequence
<220> FEATURE:
<223> OTHER INFORMATION: Synthetic peptide

<400> SEQUENCE: 597

Thr Phe Cys Thr Met
1               5

<210> SEQ ID NO 598
<211> LENGTH: 4
<212> TYPE: PRT
<213> ORGANISM: Artificial Sequence
<220> FEATURE:
<223> OTHER INFORMATION: Synthetic peptide

<400> SEQUENCE: 598

Phe Cys Thr Met
1

<210> SEQ ID NO 599
<211> LENGTH: 5
<212> TYPE: PRT
<213> ORGANISM: Artificial Sequence
<220> FEATURE:
<223> OTHER INFORMATION: Synthetic peptide

<400> SEQUENCE: 599

Phe Cys Thr Met Arg
1               5

<210> SEQ ID NO 600
<211> LENGTH: 4
<212> TYPE: PRT
<213> ORGANISM: Artificial Sequence
<220> FEATURE:
<223> OTHER INFORMATION: Synthetic peptide

<400> SEQUENCE: 600

Cys Thr Met Arg
1

<210> SEQ ID NO 601
<211> LENGTH: 4
<212> TYPE: PRT
<213> ORGANISM: Artificial Sequence
<220> FEATURE:
<223> OTHER INFORMATION: Synthetic peptide

<400> SEQUENCE: 601

Glu Gly Cys Ala
1

<210> SEQ ID NO 602
<211> LENGTH: 13
<212> TYPE: PRT
<213> ORGANISM: Artificial Sequence
<220> FEATURE:
```

<223> OTHER INFORMATION: Synthetic peptide

<400> SEQUENCE: 602

Ser Gln Asn Ile Phe Ser Gly Phe Ser Thr Glu Leu Leu
1               5                   10

<210> SEQ ID NO 603
<211> LENGTH: 11
<212> TYPE: PRT
<213> ORGANISM: Artificial Sequence
<220> FEATURE:
<223> OTHER INFORMATION: Synthetic peptide

<400> SEQUENCE: 603

Ser Gln Asn Ile Phe Ser Gly Phe Ser Thr Glu
1               5                   10

<210> SEQ ID NO 604
<211> LENGTH: 10
<212> TYPE: PRT
<213> ORGANISM: Artificial Sequence
<220> FEATURE:
<223> OTHER INFORMATION: Synthetic peptide

<400> SEQUENCE: 604

Gln Asn Asp Gln Arg Gly Glu Ile Val Arg
1               5                   10

<210> SEQ ID NO 605
<211> LENGTH: 12
<212> TYPE: PRT
<213> ORGANISM: Artificial Sequence
<220> FEATURE:
<223> OTHER INFORMATION: Synthetic peptide

<400> SEQUENCE: 605

Ser Gln Asn Ile Phe Ser Gly Phe Ser Thr Glu Leu
1               5                   10

<210> SEQ ID NO 606
<211> LENGTH: 12
<212> TYPE: PRT
<213> ORGANISM: Artificial Sequence
<220> FEATURE:
<223> OTHER INFORMATION: Synthetic peptide

<400> SEQUENCE: 606

Gln Leu Gln Cys Gln Asn Asp Gln Arg Gly Glu Ile
1               5                   10

<210> SEQ ID NO 607
<211> LENGTH: 12
<212> TYPE: PRT
<213> ORGANISM: Artificial Sequence
<220> FEATURE:
<223> OTHER INFORMATION: Synthetic peptide

<400> SEQUENCE: 607

Leu Gly Gln Ser Thr Ser Gln Trp Gln Ser Ser Arg
1               5                   10

<210> SEQ ID NO 608
<211> LENGTH: 15
<212> TYPE: PRT
<213> ORGANISM: Artificial Sequence
<220> FEATURE:
<223> OTHER INFORMATION: Synthetic peptide

<400> SEQUENCE: 608

Gln Gln Leu Leu Gly Gln Ser Thr Ser Gln Trp Gln Ser Ser Arg
1               5                   10                  15

<210> SEQ ID NO 609
<211> LENGTH: 13
<212> TYPE: PRT
<213> ORGANISM: Artificial Sequence
<220> FEATURE:
<223> OTHER INFORMATION: Synthetic peptide

<400> SEQUENCE: 609

Leu Leu Gly Gln Ser Thr Ser Gln Trp Gln Ser Ser Arg
1               5                   10

<210> SEQ ID NO 610
<211> LENGTH: 9
<212> TYPE: PRT
<213> ORGANISM: Artificial Sequence
<220> FEATURE:
<223> OTHER INFORMATION: Synthetic peptide

<400> SEQUENCE: 610

Asn Asp Gln Arg Gly Glu Ile Val Arg
1               5

<210> SEQ ID NO 611
<211> LENGTH: 11
<212> TYPE: PRT
<213> ORGANISM: Artificial Sequence
<220> FEATURE:
<223> OTHER INFORMATION: Synthetic peptide

<400> SEQUENCE: 611

Gly Gln Ser Thr Ser Gln Trp Gln Ser Ser Arg
1               5                   10

<210> SEQ ID NO 612
<211> LENGTH: 9
<212> TYPE: PRT
<213> ORGANISM: Artificial Sequence
<220> FEATURE:
<223> OTHER INFORMATION: Synthetic peptide

<400> SEQUENCE: 612

Ser Thr Ser Gln Trp Gln Ser Ser Arg
1               5

<210> SEQ ID NO 613
<211> LENGTH: 13
<212> TYPE: PRT
<213> ORGANISM: Artificial Sequence
<220> FEATURE:
<223> OTHER INFORMATION: Synthetic peptide

<400> SEQUENCE: 613

Gly Ile Thr Gly Pro Thr Phe Pro Gly Cys Pro Glu Thr
1               5                   10

<210> SEQ ID NO 614
<211> LENGTH: 14
<212> TYPE: PRT
<213> ORGANISM: Artificial Sequence
<220> FEATURE:
<223> OTHER INFORMATION: Synthetic peptide

<400> SEQUENCE: 614

Gly Ile Thr Gly Pro Thr Phe Pro Gly Cys Pro Glu Thr Tyr
1               5                   10

<210> SEQ ID NO 615
<211> LENGTH: 12
<212> TYPE: PRT
<213> ORGANISM: Artificial Sequence
<220> FEATURE:
<223> OTHER INFORMATION: Synthetic peptide

<400> SEQUENCE: 615

Ser Gln Asn Ile Phe Ser Gly Phe Ser Thr Glu Leu
1               5                   10

<210> SEQ ID NO 616
<211> LENGTH: 12
<212> TYPE: PRT
<213> ORGANISM: Artificial Sequence
<220> FEATURE:
<223> OTHER INFORMATION: Synthetic peptide

<400> SEQUENCE: 616

Gln Leu Gln Cys Gln Asn Asp Gln Arg Gly Glu Ile
1               5                   10

<210> SEQ ID NO 617
<211> LENGTH: 12
<212> TYPE: PRT
<213> ORGANISM: Artificial Sequence
<220> FEATURE:
<223> OTHER INFORMATION: Synthetic peptide

<400> SEQUENCE: 617

Leu Gly Gln Ser Thr Ser Gln Trp Gln Ser Ser Arg
1               5                   10

<210> SEQ ID NO 618
<211> LENGTH: 15
<212> TYPE: PRT
<213> ORGANISM: Artificial Sequence
<220> FEATURE:
<223> OTHER INFORMATION: Synthetic peptide

<400> SEQUENCE: 618

Gln Gln Leu Leu Gly Gln Ser Thr Ser Gln Trp Gln Ser Ser Arg
1               5                   10                  15

<210> SEQ ID NO 619
<211> LENGTH: 13
<212> TYPE: PRT
<213> ORGANISM: Artificial Sequence
<220> FEATURE:
<223> OTHER INFORMATION: Synthetic peptide

<400> SEQUENCE: 619

Leu Leu Gly Gln Ser Thr Ser Gln Trp Gln Ser Ser Arg
1               5                   10

<210> SEQ ID NO 620
<211> LENGTH: 9
<212> TYPE: PRT
<213> ORGANISM: Artificial Sequence
<220> FEATURE:
<223> OTHER INFORMATION: Synthetic peptide

<400> SEQUENCE: 620

```
Ile Phe Phe Ala Asn Gln Thr Tyr Leu
1               5
```

<210> SEQ ID NO 621
<211> LENGTH: 14
<212> TYPE: PRT
<213> ORGANISM: Artificial Sequence
<220> FEATURE:
<223> OTHER INFORMATION: Synthetic peptide

<400> SEQUENCE: 621

```
Glu His Leu Glu Pro Asn Leu Glu Gly Leu Thr Val Glu Glu
1               5                   10
```

<210> SEQ ID NO 622
<211> LENGTH: 36
<212> TYPE: PRT
<213> ORGANISM: Artificial Sequence
<220> FEATURE:
<223> OTHER INFORMATION: Synthetic peptide

<400> SEQUENCE: 622

```
Ile Phe Phe Ala Asn Gln Thr Tyr Leu Pro Ser Glu Thr Pro Ala Pro
1               5                   10                  15

Leu Val His Tyr Arg Glu Glu Glu Leu Asn Asn Leu Arg Gly Asp Gly
            20                  25                  30

Thr Gly Glu Arg
        35
```

<210> SEQ ID NO 623
<211> LENGTH: 18
<212> TYPE: PRT
<213> ORGANISM: Artificial Sequence
<220> FEATURE:
<223> OTHER INFORMATION: Synthetic peptide

<400> SEQUENCE: 623

```
Ile His Phe Glu Trp Asp Asp Asp Met Gly Ile Pro Gly Ala Phe Tyr
1               5                   10                  15

Ile Lys
```

<210> SEQ ID NO 624
<211> LENGTH: 29
<212> TYPE: PRT
<213> ORGANISM: Artificial Sequence
<220> FEATURE:
<223> OTHER INFORMATION: Synthetic peptide

<400> SEQUENCE: 624

```
Ile Phe Phe Ala Asn Gln Thr Tyr Leu Pro Ser Glu Thr Pro Ala Pro
1               5                   10                  15

Leu Val His Tyr Arg Glu Glu Glu Leu Asn Asn Leu Arg
            20                  25
```

<210> SEQ ID NO 625
<211> LENGTH: 11
<212> TYPE: PRT
<213> ORGANISM: Artificial Sequence
<220> FEATURE:
<223> OTHER INFORMATION: Synthetic peptide

<400> SEQUENCE: 625

```
Thr Glu Gln Ala Leu Pro Ala Asp Leu Ile Lys
1               5                   10
```

```
<210> SEQ ID NO 626
<211> LENGTH: 20
<212> TYPE: PRT
<213> ORGANISM: Artificial Sequence
<220> FEATURE:
<223> OTHER INFORMATION: Synthetic peptide

<400> SEQUENCE: 626

Glu His Leu Glu Pro Asn Leu Glu Gly Leu Thr Val Glu Glu Ala Ile
1               5                   10                  15

Gln Asn Lys Lys
            20

<210> SEQ ID NO 627
<211> LENGTH: 23
<212> TYPE: PRT
<213> ORGANISM: Artificial Sequence
<220> FEATURE:
<223> OTHER INFORMATION: Synthetic peptide

<400> SEQUENCE: 627

Ile Ser Lys Glu His Leu Glu Pro Asn Leu Glu Gly Leu Thr Val Glu
1               5                   10                  15

Glu Ala Ile Gln Asn Lys Lys
            20

<210> SEQ ID NO 628
<211> LENGTH: 16
<212> TYPE: PRT
<213> ORGANISM: Artificial Sequence
<220> FEATURE:
<223> OTHER INFORMATION: Synthetic peptide

<400> SEQUENCE: 628

Leu Ser Leu Pro His Pro Gln Gly Asp Glu His Gly Ala Val Ser Tyr
1               5                   10                  15

<210> SEQ ID NO 629
<211> LENGTH: 22
<212> TYPE: PRT
<213> ORGANISM: Artificial Sequence
<220> FEATURE:
<223> OTHER INFORMATION: Synthetic peptide

<400> SEQUENCE: 629

Ile Ser Lys Glu His Leu Glu Pro Asn Leu Glu Gly Leu Thr Val Glu
1               5                   10                  15

Glu Ala Ile Gln Asn Lys
            20

<210> SEQ ID NO 630
<211> LENGTH: 19
<212> TYPE: PRT
<213> ORGANISM: Artificial Sequence
<220> FEATURE:
<223> OTHER INFORMATION: Synthetic peptide

<400> SEQUENCE: 630

Glu His Leu Glu Pro Asn Leu Glu Gly Leu Thr Val Glu Glu Ala Ile
1               5                   10                  15

Gln Asn Lys

<210> SEQ ID NO 631
```

```
<211> LENGTH: 18
<212> TYPE: PRT
<213> ORGANISM: Artificial Sequence
<220> FEATURE:
<223> OTHER INFORMATION: Synthetic peptide

<400> SEQUENCE: 631

Leu Ser Thr Thr Gly Gly Asn Ser Gly Ser Pro Val Phe Asn Glu Lys
1               5                   10                  15

Asn Glu

<210> SEQ ID NO 632
<211> LENGTH: 17
<212> TYPE: PRT
<213> ORGANISM: Artificial Sequence
<220> FEATURE:
<223> OTHER INFORMATION: Synthetic peptide

<400> SEQUENCE: 632

Gln Ser Phe Leu Leu Ser Gly Asn Gln Asn Gln Gln Asn Tyr Leu Ser
1               5                   10                  15

Gly

<210> SEQ ID NO 633
<211> LENGTH: 16
<212> TYPE: PRT
<213> ORGANISM: Artificial Sequence
<220> FEATURE:
<223> OTHER INFORMATION: Synthetic peptide

<400> SEQUENCE: 633

Val Leu Asp Leu Ala Ile Pro Val Asn Arg Pro Gly Gln Leu Gln Ser
1               5                   10                  15

<210> SEQ ID NO 634
<211> LENGTH: 18
<212> TYPE: PRT
<213> ORGANISM: Artificial Sequence
<220> FEATURE:
<223> OTHER INFORMATION: Synthetic peptide

<400> SEQUENCE: 634

Val Leu Asp Leu Ala Ile Pro Val Asn Arg Pro Gly Gln Leu Gln Ser
1               5                   10                  15

Phe Leu

<210> SEQ ID NO 635
<211> LENGTH: 15
<212> TYPE: PRT
<213> ORGANISM: Artificial Sequence
<220> FEATURE:
<223> OTHER INFORMATION: Synthetic peptide

<400> SEQUENCE: 635

Phe Leu Leu Ser Gly Asn Gln Asn Gln Gln Asn Tyr Leu Ser Gly
1               5                   10                  15

<210> SEQ ID NO 636
<211> LENGTH: 18
<212> TYPE: PRT
<213> ORGANISM: Artificial Sequence
<220> FEATURE:
<223> OTHER INFORMATION: Synthetic peptide

<400> SEQUENCE: 636
```

```
Phe Leu Leu Ser Gly Asn Gln Asn Gln Gln Asn Tyr Leu Ser Gly Phe
1               5                   10                  15

Ser Lys
```

<210> SEQ ID NO 637
<211> LENGTH: 18
<212> TYPE: PRT
<213> ORGANISM: Artificial Sequence
<220> FEATURE:
<223> OTHER INFORMATION: Synthetic peptide

<400> SEQUENCE: 637

```
Asp Pro Gln Asn Pro Phe Ile Phe Lys Ser Asn Lys Phe Gln Thr Leu
1               5                   10                  15

Phe Glu
```

<210> SEQ ID NO 638
<211> LENGTH: 19
<212> TYPE: PRT
<213> ORGANISM: Artificial Sequence
<220> FEATURE:
<223> OTHER INFORMATION: Synthetic peptide

<400> SEQUENCE: 638

```
Glu Leu Ala Phe Pro Gly Ser Ala Gln Glu Val Asp Arg Ile Leu Glu
1               5                   10                  15

Asn Gln Lys
```

<210> SEQ ID NO 639
<211> LENGTH: 11
<212> TYPE: PRT
<213> ORGANISM: Artificial Sequence
<220> FEATURE:
<223> OTHER INFORMATION: Synthetic peptide

<400> SEQUENCE: 639

```
Ala Ile Val Ile Val Thr Val Asn Glu Gly Lys
1               5                   10
```

<210> SEQ ID NO 640
<211> LENGTH: 18
<212> TYPE: PRT
<213> ORGANISM: Artificial Sequence
<220> FEATURE:
<223> OTHER INFORMATION: Synthetic peptide

<400> SEQUENCE: 640

```
Ile Asn Ala Val Ala Ala Lys Arg Leu Gln Ser Gln Asn Asp Gln Arg
1               5                   10                  15

Gly Glu
```

<210> SEQ ID NO 641
<211> LENGTH: 14
<212> TYPE: PRT
<213> ORGANISM: Artificial Sequence
<220> FEATURE:
<223> OTHER INFORMATION: Synthetic peptide

<400> SEQUENCE: 641

```
Asn Arg Ala Gln Gln Gln Gln Val Tyr Gly Ser Ser Ile Glu
1               5                   10
```

<210> SEQ ID NO 642
<211> LENGTH: 10

<212> TYPE: PRT
<213> ORGANISM: Artificial Sequence
<220> FEATURE:
<223> OTHER INFORMATION: Synthetic peptide

<400> SEQUENCE: 642

Pro Ser Thr Asn Pro Trp His Ser Pro Arg
1               5                   10

<210> SEQ ID NO 643
<211> LENGTH: 4
<212> TYPE: PRT
<213> ORGANISM: Artificial Sequence
<220> FEATURE:
<223> OTHER INFORMATION: Synthetic peptide

<400> SEQUENCE: 643

Cys His Gly Ser
1

<210> SEQ ID NO 644
<211> LENGTH: 5
<212> TYPE: PRT
<213> ORGANISM: Artificial Sequence
<220> FEATURE:
<223> OTHER INFORMATION: Synthetic peptide

<400> SEQUENCE: 644

Cys His Gly Ser Met
1               5

<210> SEQ ID NO 645
<211> LENGTH: 4
<212> TYPE: PRT
<213> ORGANISM: Artificial Sequence
<220> FEATURE:
<223> OTHER INFORMATION: Synthetic peptide

<400> SEQUENCE: 645

Pro Trp His Ser
1

<210> SEQ ID NO 646
<211> LENGTH: 4
<212> TYPE: PRT
<213> ORGANISM: Artificial Sequence
<220> FEATURE:
<223> OTHER INFORMATION: Synthetic peptide

<400> SEQUENCE: 646

Phe Arg Glu Cys
1

<210> SEQ ID NO 647
<211> LENGTH: 4
<212> TYPE: PRT
<213> ORGANISM: Artificial Sequence
<220> FEATURE:
<223> OTHER INFORMATION: Synthetic peptide

<400> SEQUENCE: 647

Arg Glu Cys Arg
1

<210> SEQ ID NO 648
<211> LENGTH: 4
<212> TYPE: PRT

```
<213> ORGANISM: Artificial Sequence
<220> FEATURE:
<223> OTHER INFORMATION: Synthetic peptide

<400> SEQUENCE: 648

Glu Cys Arg Phe
1

<210> SEQ ID NO 649
<211> LENGTH: 4
<212> TYPE: PRT
<213> ORGANISM: Artificial Sequence
<220> FEATURE:
<223> OTHER INFORMATION: Synthetic peptide

<400> SEQUENCE: 649

Cys Arg Phe Asp
1

<210> SEQ ID NO 650
<211> LENGTH: 5
<212> TYPE: PRT
<213> ORGANISM: Artificial Sequence
<220> FEATURE:
<223> OTHER INFORMATION: Synthetic peptide

<400> SEQUENCE: 650

Cys Arg Phe Asp Arg
1               5

<210> SEQ ID NO 651
<211> LENGTH: 4
<212> TYPE: PRT
<213> ORGANISM: Artificial Sequence
<220> FEATURE:
<223> OTHER INFORMATION: Synthetic peptide

<400> SEQUENCE: 651

Cys Thr Gly Thr
1

<210> SEQ ID NO 652
<211> LENGTH: 4
<212> TYPE: PRT
<213> ORGANISM: Artificial Sequence
<220> FEATURE:
<223> OTHER INFORMATION: Synthetic peptide

<400> SEQUENCE: 652

Phe Pro Gly Cys
1

<210> SEQ ID NO 653
<211> LENGTH: 5
<212> TYPE: PRT
<213> ORGANISM: Artificial Sequence
<220> FEATURE:
<223> OTHER INFORMATION: Synthetic peptide

<400> SEQUENCE: 653

Phe Pro Gly Cys Pro
1               5

<210> SEQ ID NO 654
<211> LENGTH: 4
<212> TYPE: PRT
<213> ORGANISM: Artificial Sequence
```

```
<220> FEATURE:
<223> OTHER INFORMATION: Synthetic peptide

<400> SEQUENCE: 654

Pro Gly Cys Pro
1

<210> SEQ ID NO 655
<211> LENGTH: 5
<212> TYPE: PRT
<213> ORGANISM: Artificial Sequence
<220> FEATURE:
<223> OTHER INFORMATION: Synthetic peptide

<400> SEQUENCE: 655

Pro Gly Cys Pro Ala
1               5

<210> SEQ ID NO 656
<211> LENGTH: 6
<212> TYPE: PRT
<213> ORGANISM: Artificial Sequence
<220> FEATURE:
<223> OTHER INFORMATION: Synthetic peptide

<400> SEQUENCE: 656

Pro Gly Cys Pro Ala Thr
1               5

<210> SEQ ID NO 657
<211> LENGTH: 4
<212> TYPE: PRT
<213> ORGANISM: Artificial Sequence
<220> FEATURE:
<223> OTHER INFORMATION: Synthetic peptide

<400> SEQUENCE: 657

Gly Cys Pro Ala
1

<210> SEQ ID NO 658
<211> LENGTH: 4
<212> TYPE: PRT
<213> ORGANISM: Artificial Sequence
<220> FEATURE:
<223> OTHER INFORMATION: Synthetic peptide

<400> SEQUENCE: 658

Cys Pro Ala Thr
1

<210> SEQ ID NO 659
<211> LENGTH: 4
<212> TYPE: PRT
<213> ORGANISM: Artificial Sequence
<220> FEATURE:
<223> OTHER INFORMATION: Synthetic peptide

<400> SEQUENCE: 659

Glu Asn Phe Cys
1

<210> SEQ ID NO 660
<211> LENGTH: 4
<212> TYPE: PRT
<213> ORGANISM: Artificial Sequence
<220> FEATURE:
```

<223> OTHER INFORMATION: Synthetic peptide

<400> SEQUENCE: 660

Asn Phe Cys Thr
1

<210> SEQ ID NO 661
<211> LENGTH: 5
<212> TYPE: PRT
<213> ORGANISM: Artificial Sequence
<220> FEATURE:
<223> OTHER INFORMATION: Synthetic peptide

<400> SEQUENCE: 661

Asn Phe Cys Thr Ile
1               5

<210> SEQ ID NO 662
<211> LENGTH: 4
<212> TYPE: PRT
<213> ORGANISM: Artificial Sequence
<220> FEATURE:
<223> OTHER INFORMATION: Synthetic peptide

<400> SEQUENCE: 662

Phe Cys Thr Ile
1

<210> SEQ ID NO 663
<211> LENGTH: 14
<212> TYPE: PRT
<213> ORGANISM: Artificial Sequence
<220> FEATURE:
<223> OTHER INFORMATION: Synthetic peptide

<400> SEQUENCE: 663

Ala Gln Gln Gln Gln Val Tyr Gly Ser Ser Ile Glu Gln His
1               5                   10

<210> SEQ ID NO 664
<211> LENGTH: 23
<212> TYPE: PRT
<213> ORGANISM: Artificial Sequence
<220> FEATURE:
<223> OTHER INFORMATION: Synthetic peptide

<400> SEQUENCE: 664

Ala Gln Gln Gln Gln Val Tyr Gly Ser Ser Ile Glu Gln His Ser Gly
1               5                   10                  15

Gln Asn Ile Phe Ser Gly Phe
            20

<210> SEQ ID NO 665
<211> LENGTH: 14
<212> TYPE: PRT
<213> ORGANISM: Artificial Sequence
<220> FEATURE:
<223> OTHER INFORMATION: Synthetic peptide

<400> SEQUENCE: 665

Ala Ala Lys Arg Leu Gln Ser Gln Asn Asp Gln Arg Gly Glu
1               5                   10

<210> SEQ ID NO 666
<211> LENGTH: 12
<212> TYPE: PRT

<213> ORGANISM: Artificial Sequence
<220> FEATURE:
<223> OTHER INFORMATION: Synthetic peptide

<400> SEQUENCE: 666

Gln Ala Arg Ser Leu Lys Asn Asn Arg Gly Glu Glu
1               5                   10

<210> SEQ ID NO 667
<211> LENGTH: 15
<212> TYPE: PRT
<213> ORGANISM: Artificial Sequence
<220> FEATURE:
<223> OTHER INFORMATION: Synthetic peptide

<400> SEQUENCE: 667

Phe Asn Pro Ser Thr Asn Pro Trp His Ser Pro Arg Gln Gly Ser
1               5                   10                  15

<210> SEQ ID NO 668
<211> LENGTH: 12
<212> TYPE: PRT
<213> ORGANISM: Artificial Sequence
<220> FEATURE:
<223> OTHER INFORMATION: Synthetic peptide

<400> SEQUENCE: 668

Gln Ala Arg Ser Leu Lys Asn Asn Arg Gly Glu Glu
1               5                   10

<210> SEQ ID NO 669
<211> LENGTH: 26
<212> TYPE: PRT
<213> ORGANISM: Artificial Sequence
<220> FEATURE:
<223> OTHER INFORMATION: Synthetic peptide

<400> SEQUENCE: 669

Ala Ala Ala Ser Leu Pro Ala Phe Cys Asn Val Asp Ile Pro Asn Gly
1               5                   10                  15

Gly Gly Gly Val Cys Tyr Trp Leu Ala Arg
            20                  25

<210> SEQ ID NO 670
<211> LENGTH: 18
<212> TYPE: PRT
<213> ORGANISM: Artificial Sequence
<220> FEATURE:
<223> OTHER INFORMATION: Synthetic peptide

<400> SEQUENCE: 670

Val Ala Gly Ser Ala Pro Gly Ile Glu Gly Asp Glu Ile Ala Pro Leu
1               5                   10                  15

Ala Lys

<210> SEQ ID NO 671
<211> LENGTH: 22
<212> TYPE: PRT
<213> ORGANISM: Artificial Sequence
<220> FEATURE:
<223> OTHER INFORMATION: Synthetic peptide

<400> SEQUENCE: 671

Leu Gly Val Ala Gly Ser Ala Pro Gly Ile Glu Gly Asp Glu Ile Ala
1               5                   10                  15

Pro Leu Ala Lys Glu Asn
            20

<210> SEQ ID NO 672
<211> LENGTH: 17
<212> TYPE: PRT
<213> ORGANISM: Artificial Sequence
<220> FEATURE:
<223> OTHER INFORMATION: Synthetic peptide

<400> SEQUENCE: 672

Gly Ser Ala Pro Gly Ile Glu Gly Asp Glu Ile Ala Pro Leu Ala Lys
1               5                   10                  15

Glu

<210> SEQ ID NO 673
<211> LENGTH: 15
<212> TYPE: PRT
<213> ORGANISM: Artificial Sequence
<220> FEATURE:
<223> OTHER INFORMATION: Synthetic peptide

<400> SEQUENCE: 673

Val Ala Gly Ser Ala Pro Gly Ile Glu Gly Asp Glu Ile Ala Pro
1               5                   10                  15

<210> SEQ ID NO 674
<211> LENGTH: 19
<212> TYPE: PRT
<213> ORGANISM: Artificial Sequence
<220> FEATURE:
<223> OTHER INFORMATION: Synthetic peptide

<400> SEQUENCE: 674

Gly Val Ala Gly Ser Ala Pro Gly Ile Glu Gly Asp Glu Ile Ala Pro
1               5                   10                  15

Leu Ala Lys

<210> SEQ ID NO 675
<211> LENGTH: 21
<212> TYPE: PRT
<213> ORGANISM: Artificial Sequence
<220> FEATURE:
<223> OTHER INFORMATION: Synthetic peptide

<400> SEQUENCE: 675

Gly Val Ala Gly Ser Ala Pro Gly Ile Glu Gly Asp Glu Ile Ala Pro
1               5                   10                  15

Leu Ala Lys Glu Asn
            20

<210> SEQ ID NO 676
<211> LENGTH: 20
<212> TYPE: PRT
<213> ORGANISM: Artificial Sequence
<220> FEATURE:
<223> OTHER INFORMATION: Synthetic peptide

<400> SEQUENCE: 676

Val Ala Gly Ser Ala Pro Gly Ile Glu Gly Asp Glu Ile Ala Pro Leu
1               5                   10                  15

Ala Lys Glu Asn
            20

```
<210> SEQ ID NO 677
<211> LENGTH: 15
<212> TYPE: PRT
<213> ORGANISM: Artificial Sequence
<220> FEATURE:
<223> OTHER INFORMATION: Synthetic peptide

<400> SEQUENCE: 677

Ser Ala Pro Gly Ile Glu Gly Asp Glu Ile Ala Pro Leu Ala Lys
1               5                   10                  15

<210> SEQ ID NO 678
<211> LENGTH: 16
<212> TYPE: PRT
<213> ORGANISM: Artificial Sequence
<220> FEATURE:
<223> OTHER INFORMATION: Synthetic peptide

<400> SEQUENCE: 678

Gly Ser Ala Pro Gly Ile Glu Gly Asp Glu Ile Ala Pro Leu Ala Lys
1               5                   10                  15

<210> SEQ ID NO 679
<211> LENGTH: 17
<212> TYPE: PRT
<213> ORGANISM: Artificial Sequence
<220> FEATURE:
<223> OTHER INFORMATION: Synthetic peptide

<400> SEQUENCE: 679

Ser Ala Pro Gly Ile Glu Gly Asp Glu Ile Ala Pro Leu Ala Lys Glu
1               5                   10                  15

Asn

<210> SEQ ID NO 680
<211> LENGTH: 15
<212> TYPE: PRT
<213> ORGANISM: Artificial Sequence
<220> FEATURE:
<223> OTHER INFORMATION: Synthetic peptide

<400> SEQUENCE: 680

Phe Asn Pro Ser Thr Asn Pro Trp His Ser Pro Arg Gln Gly Ser
1               5                   10                  15

<210> SEQ ID NO 681
<211> LENGTH: 12
<212> TYPE: PRT
<213> ORGANISM: Artificial Sequence
<220> FEATURE:
<223> OTHER INFORMATION: Synthetic peptide

<400> SEQUENCE: 681

Val Asp Leu Val Ile Pro Val Asn Gly Pro Gly Lys
1               5                   10

<210> SEQ ID NO 682
<211> LENGTH: 13
<212> TYPE: PRT
<213> ORGANISM: Artificial Sequence
<220> FEATURE:
<223> OTHER INFORMATION: Synthetic peptide

<400> SEQUENCE: 682

Leu Val Asp Leu Val Ile Pro Val Asn Gly Pro Gly Lys
1               5                   10
```

<210> SEQ ID NO 683
<211> LENGTH: 10
<212> TYPE: PRT
<213> ORGANISM: Artificial Sequence
<220> FEATURE:
<223> OTHER INFORMATION: Synthetic peptide

<400> SEQUENCE: 683

Ile Lys Leu Pro Ala Gly Thr Thr Ser Tyr
1               5                   10

<210> SEQ ID NO 684
<211> LENGTH: 11
<212> TYPE: PRT
<213> ORGANISM: Artificial Sequence
<220> FEATURE:
<223> OTHER INFORMATION: Synthetic peptide

<400> SEQUENCE: 684

Ile Lys Leu Pro Ala Gly Thr Thr Ser Tyr Leu
1               5                   10

<210> SEQ ID NO 685
<211> LENGTH: 12
<212> TYPE: PRT
<213> ORGANISM: Artificial Sequence
<220> FEATURE:
<223> OTHER INFORMATION: Synthetic peptide

<400> SEQUENCE: 685

Arg Arg Asn Pro Phe Leu Phe Lys Ser Asn Lys Phe
1               5                   10

<210> SEQ ID NO 686
<211> LENGTH: 19
<212> TYPE: PRT
<213> ORGANISM: Artificial Sequence
<220> FEATURE:
<223> OTHER INFORMATION: Synthetic peptide

<400> SEQUENCE: 686

Ile Glu Asn Pro Val Lys Glu Leu Thr Phe Pro Gly Ser Val Gln Glu
1               5                   10                  15

Ile Asn Arg

<210> SEQ ID NO 687
<211> LENGTH: 14
<212> TYPE: PRT
<213> ORGANISM: Artificial Sequence
<220> FEATURE:
<223> OTHER INFORMATION: Synthetic peptide

<400> SEQUENCE: 687

Arg Arg Asn Pro Phe Leu Phe Lys Ser Asn Lys Phe Leu Thr
1               5                   10

<210> SEQ ID NO 688
<211> LENGTH: 14
<212> TYPE: PRT
<213> ORGANISM: Artificial Sequence
<220> FEATURE:
<223> OTHER INFORMATION: Synthetic peptide

<400> SEQUENCE: 688

Ala Lys Pro His Thr Ile Phe Leu Pro Gln His Ile Asp Ala
1               5                   10

<210> SEQ ID NO 689
<211> LENGTH: 15
<212> TYPE: PRT
<213> ORGANISM: Artificial Sequence
<220> FEATURE:
<223> OTHER INFORMATION: Synthetic peptide

<400> SEQUENCE: 689

Ala Lys Pro His Thr Ile Phe Leu Pro Gln His Ile Asp Ala Asp
1               5                   10                  15

<210> SEQ ID NO 690
<211> LENGTH: 9
<212> TYPE: PRT
<213> ORGANISM: Artificial Sequence
<220> FEATURE:
<223> OTHER INFORMATION: Synthetic peptide

<400> SEQUENCE: 690

Lys Gln Lys Tyr Arg Tyr Gln Arg Glu
1               5

<210> SEQ ID NO 691
<211> LENGTH: 9
<212> TYPE: PRT
<213> ORGANISM: Artificial Sequence
<220> FEATURE:
<223> OTHER INFORMATION: Synthetic peptide

<400> SEQUENCE: 691

Lys Gln Lys Tyr Gln Tyr Gln Arg Glu
1               5

<210> SEQ ID NO 692
<211> LENGTH: 4
<212> TYPE: PRT
<213> ORGANISM: Artificial Sequence
<220> FEATURE:
<223> OTHER INFORMATION: Synthetic peptide

<400> SEQUENCE: 692

Met Leu Pro His
1

<210> SEQ ID NO 693
<211> LENGTH: 19
<212> TYPE: PRT
<213> ORGANISM: Artificial Sequence
<220> FEATURE:
<223> OTHER INFORMATION: Synthetic peptide

<400> SEQUENCE: 693

Arg Arg Asn Pro Phe Leu Phe Lys Ser Asn Lys Phe Leu Thr Leu Phe
1               5                   10                  15

Glu Asn Glu

<210> SEQ ID NO 694
<211> LENGTH: 14
<212> TYPE: PRT
<213> ORGANISM: Artificial Sequence
<220> FEATURE:
<223> OTHER INFORMATION: Synthetic peptide

<400> SEQUENCE: 694

Pro Phe Leu Phe Lys Ser Asn Lys Phe Leu Thr Leu Phe Glu

```
1               5                   10

<210> SEQ ID NO 695
<211> LENGTH: 20
<212> TYPE: PRT
<213> ORGANISM: Artificial Sequence
<220> FEATURE:
<223> OTHER INFORMATION: Synthetic peptide

<400> SEQUENCE: 695

Ser Gln Glu Arg Arg Asn Pro Phe Leu Phe Lys Ser Asn Lys Phe Leu
1               5                   10                  15

Thr Leu Phe Glu
            20

<210> SEQ ID NO 696
<211> LENGTH: 17
<212> TYPE: PRT
<213> ORGANISM: Artificial Sequence
<220> FEATURE:
<223> OTHER INFORMATION: Synthetic peptide

<400> SEQUENCE: 696

Arg Arg Asn Pro Phe Leu Phe Lys Ser Asn Lys Phe Leu Thr Leu Phe
1               5                   10                  15

Glu

<210> SEQ ID NO 697
<211> LENGTH: 22
<212> TYPE: PRT
<213> ORGANISM: Artificial Sequence
<220> FEATURE:
<223> OTHER INFORMATION: Synthetic peptide

<400> SEQUENCE: 697

Ser Gln Glu Arg Arg Asn Pro Phe Leu Phe Lys Ser Asn Lys Phe Leu
1               5                   10                  15

Thr Leu Phe Glu Asn Glu
            20

<210> SEQ ID NO 698
<211> LENGTH: 9
<212> TYPE: PRT
<213> ORGANISM: Artificial Sequence
<220> FEATURE:
<223> OTHER INFORMATION: Synthetic peptide

<400> SEQUENCE: 698

Leu Thr Phe Pro Gly Ser Val Gln Glu
1               5

<210> SEQ ID NO 699
<211> LENGTH: 13
<212> TYPE: PRT
<213> ORGANISM: Artificial Sequence
<220> FEATURE:
<223> OTHER INFORMATION: Synthetic peptide

<400> SEQUENCE: 699

Glu Leu Thr Phe Pro Gly Ser Val Gln Glu Ile Asn Arg
1               5                   10

<210> SEQ ID NO 700
<211> LENGTH: 18
<212> TYPE: PRT
```

-continued

```
<213> ORGANISM: Artificial Sequence
<220> FEATURE:
<223> OTHER INFORMATION: Synthetic peptide

<400> SEQUENCE: 700

Lys Asn Pro Gln Leu Gln Asp Leu Asp Ile Phe Val Asn Tyr Val Glu
1               5                   10                  15

Ile Lys

<210> SEQ ID NO 701
<211> LENGTH: 24
<212> TYPE: PRT
<213> ORGANISM: Artificial Sequence
<220> FEATURE:
<223> OTHER INFORMATION: Synthetic peptide

<400> SEQUENCE: 701

Pro Gly Gln Leu Gln Ser Phe Leu Leu Ser Gly Asn Gln Asn Gln Gln
1               5                   10                  15

Asn Tyr Leu Ser Gly Phe Ser Lys
            20

<210> SEQ ID NO 702
<211> LENGTH: 14
<212> TYPE: PRT
<213> ORGANISM: Artificial Sequence
<220> FEATURE:
<223> OTHER INFORMATION: Synthetic peptide

<400> SEQUENCE: 702

Arg Gly Pro Gln Gln Tyr Ala Glu Trp Gln Ile Asn Glu Lys
1               5                   10

<210> SEQ ID NO 703
<211> LENGTH: 14
<212> TYPE: PRT
<213> ORGANISM: Artificial Sequence
<220> FEATURE:
<223> OTHER INFORMATION: Synthetic peptide

<400> SEQUENCE: 703

Val Leu Asp Leu Ala Ile Pro Val Asn Arg Pro Gly Gln Leu
1               5                   10

<210> SEQ ID NO 704
<211> LENGTH: 24
<212> TYPE: PRT
<213> ORGANISM: Artificial Sequence
<220> FEATURE:
<223> OTHER INFORMATION: Synthetic peptide

<400> SEQUENCE: 704

Gly Tyr Val Gly Leu Thr Phe Pro Gly Cys Pro Ala Thr His Gln Gln
1               5                   10                  15

Gln Phe Gln Leu Phe Glu Gln Arg
            20

<210> SEQ ID NO 705
<211> LENGTH: 820
<212> TYPE: PRT
<213> ORGANISM: Oryza sativa

<400> SEQUENCE: 705

Met Leu Cys Leu Thr Ser Ser Ser Ser Ala Pro Ala Pro Leu Leu
1               5                   10                  15
```

```
Pro Ser Leu Ala Asp Arg Pro Ser Gly Ile Ala Gly Gly Gly
         20                  25                  30

Asn Val Arg Leu Ser Val Val Ser Pro Arg Arg Ser Trp Pro Gly
         35                  40                  45

Lys Val Lys Thr Asn Phe Ser Val Pro Ala Thr Ala Arg Lys Asn Lys
 50                  55                  60

Thr Met Val Thr Val Val Glu Glu Val Asp His Leu Pro Ile Tyr Asp
 65                  70                  75                  80

Leu Asp Pro Lys Leu Glu Glu Phe Lys Asp His Phe Asn Tyr Arg Ile
                 85                  90                  95

Lys Arg Tyr Leu Asp Gln Lys Cys Leu Ile Glu Lys His Glu Gly Gly
                100                 105                 110

Leu Glu Glu Phe Ser Lys Gly Tyr Leu Lys Phe Gly Ile Asn Thr Val
                115                 120                 125

Asp Gly Ala Thr Ile Tyr Arg Glu Trp Ala Pro Ala Ala Gln Glu Ala
130                 135                 140

Gln Leu Ile Gly Glu Phe Asn Asn Trp Asn Gly Ala Lys His Lys Met
145                 150                 155                 160

Glu Lys Asp Lys Phe Gly Ile Trp Ser Ile Lys Ile Ser His Val Asn
                165                 170                 175

Gly Lys Pro Ala Ile Pro His Asn Ser Lys Val Lys Phe Arg Phe Arg
                180                 185                 190

His Gly Gly Gly Ala Trp Val Asp Arg Ile Pro Ala Trp Ile Arg Tyr
                195                 200                 205

Ala Thr Phe Asp Ala Ser Lys Phe Gly Ala Pro Tyr Asp Gly Val His
                210                 215                 220

Trp Asp Pro Pro Ala Cys Glu Arg Tyr Val Phe Lys His Pro Arg Pro
225                 230                 235                 240

Pro Lys Pro Asp Ala Pro Arg Ile Tyr Glu Ala His Val Gly Met Ser
                245                 250                 255

Gly Glu Glu Pro Glu Val Ser Thr Tyr Arg Glu Phe Ala Asp Asn Val
                260                 265                 270

Leu Pro Arg Ile Arg Ala Asn Asn Tyr Asn Thr Val Gln Leu Met Ala
                275                 280                 285

Ile Met Glu His Ser Tyr Tyr Ala Ser Phe Gly Tyr His Val Thr Asn
290                 295                 300

Phe Phe Ala Val Ser Ser Arg Ser Gly Thr Pro Glu Asp Leu Lys Tyr
305                 310                 315                 320

Leu Val Asp Lys Ala His Ser Leu Gly Leu Arg Val Leu Met Asp Val
                325                 330                 335

Val His Ser His Ala Ser Asn Asn Val Thr Asp Gly Leu Asn Gly Tyr
                340                 345                 350

Asp Val Gly Gln Asn Thr His Glu Ser Tyr Phe His Thr Gly Asp Arg
                355                 360                 365

Gly Tyr His Lys Leu Trp Asp Ser Arg Leu Phe Asn Tyr Ala Asn Trp
                370                 375                 380

Glu Val Leu Arg Phe Leu Leu Ser Asn Leu Arg Tyr Trp Met Asp Glu
385                 390                 395                 400

Phe Met Phe Asp Gly Phe Arg Phe Asp Gly Val Thr Ser Met Leu Tyr
                405                 410                 415

His His His Gly Ile Asn Lys Gly Phe Thr Gly Asn Tyr Lys Glu Tyr
                420                 425                 430
```

Phe Ser Leu Asp Thr Asp Val Asp Ala Ile Val Tyr Met Met Leu Ala
            435                 440                 445

Asn His Leu Met His Lys Leu Leu Pro Glu Ala Thr Ile Val Ala Glu
450                 455                 460

Asp Val Ser Gly Met Pro Val Leu Cys Arg Pro Val Asp Glu Gly Gly
465                 470                 475                 480

Val Gly Phe Asp Phe Arg Leu Ala Met Ala Ile Pro Asp Arg Trp Ile
            485                 490                 495

Asp Tyr Leu Lys Asn Lys Glu Asp Arg Lys Trp Ser Met Ser Glu Ile
            500                 505                 510

Val Gln Thr Leu Thr Asn Arg Arg Tyr Thr Glu Lys Cys Ile Ala Tyr
            515                 520                 525

Ala Glu Ser His Asp Gln Ser Ile Val Gly Asp Lys Thr Ile Ala Phe
530                 535                 540

Leu Leu Met Asp Lys Glu Met Tyr Thr Gly Met Ser Asp Leu Gln Pro
545                 550                 555                 560

Ala Ser Pro Thr Ile Asn Arg Gly Ile Ala Leu Gln Lys Met Ile His
            565                 570                 575

Phe Ile Thr Met Ala Leu Gly Gly Asp Gly Tyr Leu Asn Phe Met Gly
            580                 585                 590

Asn Glu Phe Gly His Pro Glu Trp Ile Asp Phe Pro Arg Glu Gly Asn
            595                 600                 605

Asn Trp Ser Tyr Asp Lys Cys Arg Arg Gln Trp Ser Leu Val Asp Thr
            610                 615                 620

Asp His Leu Arg Tyr Lys Tyr Met Asn Ala Phe Asp Gln Ala Met Asn
625                 630                 635                 640

Ala Leu Glu Glu Glu Phe Ser Phe Leu Ser Ser Lys Gln Ile Val
            645                 650                 655

Ser Asp Met Asn Glu Lys Asp Lys Val Ile Val Phe Glu Arg Gly Asp
            660                 665                 670

Leu Val Phe Val Phe Asn Phe His Pro Asn Lys Thr Tyr Lys Gly Tyr
            675                 680                 685

Lys Val Gly Cys Asp Leu Pro Gly Lys Tyr Arg Val Ala Leu Asp Ser
690                 695                 700

Asp Ala Leu Val Phe Gly Gly His Gly Arg Val Gly His Asp Val Asp
705                 710                 715                 720

His Phe Thr Ser Pro Glu Gly Met Pro Gly Val Pro Glu Thr Asn Phe
            725                 730                 735

Asn Asn Arg Pro Asn Ser Phe Lys Val Leu Ser Pro Arg Thr Cys
            740                 745                 750

Val Ala Tyr Tyr Arg Val Asp Glu Asp Arg Glu Glu Leu Arg Arg Gly
            755                 760                 765

Gly Ala Val Ala Ser Gly Lys Ile Val Thr Glu Tyr Ile Asp Val Glu
770                 775                 780

Ala Thr Ser Gly Glu Thr Ile Ser Gly Gly Trp Lys Gly Ser Glu Lys
785                 790                 795                 800

Asp Asp Cys Gly Lys Lys Gly Met Lys Phe Val Phe Arg Ser Ser Asp
            805                 810                 815

Glu Asp Cys Lys
            820

<210> SEQ ID NO 706
<211> LENGTH: 296
<212> TYPE: PRT

<213> ORGANISM: Oryza sativa

<400> SEQUENCE: 706

Met Asp Arg Tyr Gln Arg Val Glu Arg Pro Arg Glu Ser Ala Ile
1               5                   10                  15

Glu Glu Asn Glu Ile Arg Ile Thr Ala Gln Gly Leu Ile Arg Asn Tyr
            20                  25                  30

Val Ser Tyr Ala Thr Ser Leu Leu Gln Asp Arg Arg Ile Lys Glu Ile
        35                  40                  45

Val Leu Lys Ala Met Gly Gln Ala Ile Ser Lys Ser Val Ala Val Ala
    50                  55                  60

Glu Ile Ile Lys Lys Arg Val Pro Gly Leu Tyr Gln Asp Thr Asn Ile
65                  70                  75                  80

Ser Ser Val Ser Ile Thr Asp Val Trp Glu Pro Ile Glu Glu Gly Leu
                85                  90                  95

Val Pro Leu Glu Met Thr Arg His Val Ser Met Ile Ser Ile Thr Leu
            100                 105                 110

Ser Pro Arg Asp Leu Asp Lys Asn Ser Pro Gly Tyr Gln Thr Pro Val
        115                 120                 125

Tyr Val Glu Gln Pro Arg Gln Gln Pro Arg Leu Gln Gln Ala Pro Pro
    130                 135                 140

Pro Pro Gln Arg Gln Val Arg Gln Pro Pro Asp Tyr Glu Asp Ser
145                 150                 155                 160

Tyr Val Arg Gly Arg Gly Arg Gly Arg Gly Arg Gly Arg Gly Arg Gly
                165                 170                 175

Trp Gly Arg Gly Gly Tyr Gly Gly Tyr Gly Gly Tyr Gly Asn Asn Gln
            180                 185                 190

Gly Gly Tyr Asn Gln Gly Gly Tyr Tyr Asp Asn Gln Gly Gly Tyr
        195                 200                 205

Gly Gly Tyr Asp Asn Gln Gly Gly Tyr Gly Tyr Asp Asn Gln Gly
    210                 215                 220

Gly Tyr Gly Gly Gly Tyr Gly Tyr Asn Gln Gly Arg Tyr Gly Asn
225                 230                 235                 240

Tyr Gln Glu Asn Gly Gly Tyr Asn Arg Gly Arg Gly Gly Met Arg Gly
                245                 250                 255

Arg Gly Asn Trp Asn Tyr Arg Gly Gly Tyr Glu Arg Gly Arg Gly Gly
            260                 265                 270

Gly Phe Pro Gly Gly Arg Gly Tyr Gly Gly Arg Gly Arg Gly Arg Met
        275                 280                 285

Gly Gly Arg Gly Gly Arg Gly Asn
    290                 295

<210> SEQ ID NO 707
<211> LENGTH: 184
<212> TYPE: PRT
<213> ORGANISM: Oryza sativa

<400> SEQUENCE: 707

Met Ala Leu Glu His Leu Gly Arg Arg Asn Val Ala Gly Ser Leu Leu
1               5                   10                  15

Leu Leu Asn Leu Leu Met Tyr Val Phe Leu Leu Gly Phe Ala Gly Trp
            20                  25                  30

Ala Leu Asn Ser Ser Ile Lys Asn Ala Gly Ala Asp Val Gly Val Gly
        35                  40                  45

Trp Gly Glu Gln Pro Trp Ser Pro Tyr Tyr Arg Gln Ser Ala Trp Phe

Ala Ser Arg Phe His Leu Ala Thr Phe Ala Ala Leu Ala Gly Ala Leu
65                  70                  75                  80

Gly Val Ala Ala Lys Ala Ser Ala Ala Tyr His Gly Gly Arg Ser Gly
                85                  90                  95

Ala Ser Trp Arg Pro Gln Gly Leu Ala Ala Ala Ser Leu Gly Thr
            100                 105                 110

Ala Ala Trp Ala Ala Thr Ala Leu Ala Phe Gly Val Ala Cys Arg Glu
            115                 120                 125

Ile His Asp Ala Ala Ala Gly Pro Ala Gly Ala Ala Arg Gly Trp
        130                 135                 140

Arg Met Arg Ala Leu Glu Gly Leu Thr Val Thr Leu Ala Phe Thr Gln
145                 150                 155                 160

Leu Leu Tyr Val Leu Leu Leu His Ala Ala Val Ala Gly Glu Arg Cys
                165                 170                 175

Gly Leu Ala Cys Ala Ala Asp Ala
            180

<210> SEQ ID NO 708
<211> LENGTH: 483
<212> TYPE: PRT
<213> ORGANISM: Pisum sativum

<400> SEQUENCE: 708

Met Ala Ile Lys Thr Lys Leu Ser Leu Thr Ile Phe Leu Phe Phe Leu
1               5                   10                  15

Leu Ala Leu Leu Cys Ser Asn Leu Ala Val Gly Arg Lys Glu Lys Asp
                20                  25                  30

Pro Glu Leu Thr Thr Cys Lys Asp Gln Cys Asp Met Gln Arg Gln Tyr
            35                  40                  45

Asp Glu Glu Asp Lys Arg Ile Cys Met Glu Arg Cys Asp Asp Tyr Ile
        50                  55                  60

Lys Lys Lys Gln Glu Arg Gln Lys His Lys Glu His Glu Glu Glu Glu
65                  70                  75                  80

Glu Gln Glu Gln Glu Glu Asp Glu Asn Pro Tyr Val Phe Glu Asp Asn
                85                  90                  95

Asp Phe Glu Thr Lys Ile Asp Thr Lys Asp Gly Arg Val Leu Ile Leu
            100                 105                 110

Asn Lys Phe Asn Glu Lys Ser Lys Leu Leu Lys Asn Ile Glu Asn Tyr
        115                 120                 125

Gly Leu Ala Val Leu Glu Ile Lys Ala Asn Ala Phe Leu Ser Pro His
        130                 135                 140

His Tyr Asp Ser Glu Ala Ile Leu Phe Asn Ile Lys Gly Arg Gly Ile
145                 150                 155                 160

Ile Gly Leu Val Ala Glu Asp Arg Thr Glu Arg Phe Asn Leu Glu Glu
                165                 170                 175

Gly Asp Ile Met Arg Val Pro Ala Gly Thr Pro Met Tyr Leu Val Asn
            180                 185                 190

Arg Asp Glu Asn Glu Lys Leu Tyr Ile Ala Ala Phe His Met Pro Pro
        195                 200                 205

Ser Ser Gly Ser Ala Pro Val Asn Leu Glu Pro Phe Phe Glu Ser Ala
        210                 215                 220

Gly Arg Lys Pro Glu Ser Val Leu Asn Thr Phe Ser Ser Lys Val Leu
225                 230                 235                 240

```
Gln Ala Ala Leu Lys Ser Ser Lys Gly Glu Leu Glu Thr Val Leu Asp
                245                 250                 255

Glu Gln Lys Lys Gly Arg Ile Phe Lys Ile Glu Lys Glu Asp Val Arg
            260                 265                 270

Gly Leu Ala Pro Lys Lys Ser Leu Trp Pro Phe Gly Pro Phe Lys
        275                 280                 285

Ser Pro Phe Asn Ile Phe Ser Asn Asn Pro Ala Phe Ser Asn Lys Phe
    290                 295                 300

Gly Ser Leu Phe Glu Val Gly Pro Ser Gln Lys Ser Gly Leu Glu
305                 310                 315                 320

Gly Leu Asn Leu Met Leu Thr Leu Ala Asn Ile Thr Lys Gly Ser Met
                325                 330                 335

Ser Thr Ile His Tyr Asn Thr Asn Ala Asn Lys Ile Ala Leu Val Ile
                340                 345                 350

Asp Gly Glu Gly Glu Leu Glu Met Ala Cys Pro His Met Pro Ser Ser
            355                 360                 365

Ser Ser Asn Ser Arg Gln Lys Lys Ser Ser Ile Ser Tyr His Asn Ile
        370                 375                 380

Asn Ala Lys Leu Arg Pro Gly Val Met Phe Val Val Pro Ala Gly His
385                 390                 395                 400

Pro Phe Val Asn Ile Ala Ser Lys Lys Lys Asn Leu Ile Val Val Cys
                405                 410                 415

Phe Glu Val Asn Ala Gln Arg Asn Lys Lys Leu Ala Leu Ala Gly Lys
            420                 425                 430

Lys Asn Ile Val Ser Ala Leu Asp Lys Ala Ala Lys Glu Val Ala Phe
        435                 440                 445

Asp Ile Ala Ala Glu Lys Val Asp Glu Val Phe Glu Arg Lys Glu Glu
    450                 455                 460

Phe Phe Phe Pro Tyr Asp Asn Glu Glu Arg Lys Glu His Gly Arg
465                 470                 475                 480

Ala Val Val

<210> SEQ ID NO 709
<211> LENGTH: 197
<212> TYPE: PRT
<213> ORGANISM: Pisum sativum

<400> SEQUENCE: 709

Met Phe Arg Arg Ala Thr Ser Thr Phe Leu Ser Arg Ala Ser Ala Thr
1               5                   10                  15

Arg Arg Phe Ser Thr Asp Val Ala Pro Ala Thr Asn Ser Ser Phe
            20                  25                  30

Val Glu Ala Trp Arg Lys Val Ser Pro Asn Ile Asp Pro Pro Lys Thr
        35                  40                  45

Pro Leu Glu Phe Leu Lys Thr Arg Pro Pro Val Pro Ser Thr Ile Pro
    50                  55                  60

Thr Lys Leu Thr Val Asn Phe Val Leu Pro Tyr Ser Ser Gln Leu Ala
65                  70                  75                  80

Ala Lys Glu Val Asp Ser Val Ile Ile Pro Ala Thr Thr Gly Glu Met
                85                  90                  95

Gly Val Leu Pro Gly His Val Ala Thr Ile Ala Glu Leu Lys Pro Gly
            100                 105                 110

Val Leu Thr Val Gln Glu Gly Thr Asp Thr Lys Tyr Phe Val Ser
        115                 120                 125
```

```
Ser Gly Phe Arg Phe Ile His Ala Asn Ser Val Ala Asp Ile Ile Ala
    130                 135                 140

Val Glu Ala Val Pro Val Asn Gln Leu Asp Arg Asp Leu Val Gln Lys
145                 150                 155                 160

Gly Leu Gln Glu Phe Thr Gln Lys Leu Asn Ser Ala Thr Thr Asp Leu
                165                 170                 175

Glu Lys Arg Glu Ala Gln Ile Gly Ile Asp Val Asp Ser Ala Leu Asn
            180                 185                 190

Ser Ala Leu Thr Gly
        195

<210> SEQ ID NO 710
<211> LENGTH: 156
<212> TYPE: PRT
<213> ORGANISM: Oryza sativa

<400> SEQUENCE: 710

Met Lys Ile Ile Phe Phe Phe Ala Leu Leu Ala Ile Ala Ala Cys Ser
1               5                   10                  15

Ala Ser Ala Gln Phe Asp Ala Val Thr Gln Val Tyr Arg Gln Tyr Gln
            20                  25                  30

Leu Gln Pro His Leu Met Leu Gln Gln Met Leu Ser Pro Cys Gly
        35                  40                  45

Glu Phe Val Arg Gln Gln Cys Ser Thr Val Ala Thr Pro Phe Phe Gln
    50                  55                  60

Ser Pro Val Phe Gln Leu Arg Asn Cys Gln Val Met Gln Gln Gln Cys
65                  70                  75                  80

Cys Gln Gln Leu Arg Met Ile Ala Gln Ser His Cys Gln Ala Ile
                85                  90                  95

Ser Ser Val Gln Ala Ile Val Gln Gln Leu Arg Leu Gln Gln Phe Ala
            100                 105                 110

Ser Val Tyr Phe Asp Gln Ser Gln Ala Gln Ala Gln Ala Met Leu Ala
        115                 120                 125

Leu Asn Met Pro Ser Ile Cys Gly Ile Tyr Pro Ser Tyr Asn Thr Ala
130                 135                 140

Pro Cys Ser Ile Pro Thr Val Gly Gly Ile Trp Tyr
145                 150                 155

<210> SEQ ID NO 711
<211> LENGTH: 704
<212> TYPE: PRT
<213> ORGANISM: Pisum sativum

<400> SEQUENCE: 711

Met Gln Asp Ser Ser Thr Met Lys Phe Ser Pro Leu Asp Leu Met Thr
1               5                   10                  15

Ala Ile Ile Lys Gly Lys Phe Asn Pro Ser Asn Asp Ser Ser Gln Ala
            20                  25                  30

Pro Ala Ser Ile Ile Phe Glu Asn Arg Glu Phe Val Met Ile Leu Thr
        35                  40                  45

Thr Ser Ile Ala Val Leu Ile Gly Cys Val Val Leu Ile Trp Arg
    50                  55                  60

Arg Ser Asn Ser Asn Lys Ser Lys Gln Ile Glu Val Pro Lys Leu Val
65                  70                  75                  80

Ile Lys Lys Leu Pro Glu Leu Asp Val Asp Asp Gly Lys Lys Val
                85                  90                  95
```

```
Thr Val Phe Phe Gly Thr Gln Thr Gly Thr Ala Glu Gly Phe Ala Lys
                100                 105                 110

Ala Ile Ala Glu Glu Ala Lys Ala Arg Tyr Glu Lys Ala Lys Phe Arg
            115                 120                 125

Val Val Asp Met Asp Asp Tyr Ala Ala Asp Asp Glu Tyr Leu Glu
130                 135                 140

Lys Leu Lys Arg Glu Thr Met Ala Leu Phe Phe Leu Ala Thr Tyr Gly
145                 150                 155                 160

Asp Gly Glu Pro Thr Asp Asn Ala Ala Arg Phe Tyr Lys Trp Phe Thr
                165                 170                 175

Glu Glu Tyr Glu Gly Glu Glu Asp Ser Phe Lys Asn Leu Ser Tyr Gly
                180                 185                 190

Val Phe Gly Leu Gly Asn Arg Gln Tyr Glu His Phe Asn Lys Val Ala
                195                 200                 205

Lys Val Val Asp Asp Lys Leu Leu Glu Gln Gly Gly Lys Arg Leu Val
            210                 215                 220

Pro Val Gly Leu Gly Asp Asp Gln Cys Ile Glu Asp Asp Phe Thr
225                 230                 235                 240

Ala Trp Lys Glu Glu Leu Trp Pro Ala Leu Asp Gln Leu Leu Arg Asp
                245                 250                 255

Glu Asp Asp Thr Pro Val Ala Thr Pro Tyr Thr Ala Ala Val Ser Glu
                260                 265                 270

Tyr Arg Val Val Ile His Asp Pro Leu Asp Ala Thr Val Asp Glu Lys
            275                 280                 285

Lys Arg His Asn Val Asn Gly His Ala Val Val Asp Ala Gln His Pro
            290                 295                 300

Val Arg Ala Asn Val Ala Val Arg Arg Glu Leu His Thr Pro Ala Ser
305                 310                 315                 320

Asp Arg Ser Cys Thr His Leu Glu Phe Asp Ile Ser Gly Thr Gly Val
                325                 330                 335

Val Tyr Glu Thr Gly Asp His Val Gly Val Tyr Cys Glu Asn Leu Ser
            340                 345                 350

Asp Thr Val Glu Glu Ala Glu Arg Ile Leu Gly Leu Ser Pro Asp Thr
            355                 360                 365

Tyr Leu Ser Ile His Thr Asp Asp Glu Glu Gly Lys Pro Leu Gly Gly
            370                 375                 380

Ser Ser Leu Pro Pro Pro Phe Pro Pro Cys Thr Leu Arg Thr Ala Leu
385                 390                 395                 400

Thr Lys Tyr Ala Asp Leu Leu Ser Ser Pro Lys Lys Ser Ala Leu Val
                405                 410                 415

Ala Leu Ala Ala His Ala Ser Asp Pro Ser Glu Ala Asp Arg Leu Arg
            420                 425                 430

His Leu Ala Ser Pro Ala Gly Lys Asp Glu Tyr Ala Glu Trp Val Ile
            435                 440                 445

Ser Ser Gln Arg Ser Leu Leu Glu Val Met Ala Glu Phe Ser Ser Ala
450                 455                 460

Lys Pro Pro Ile Gly Val Phe Phe Ala Ala Val Ala Pro Arg Leu Gln
465                 470                 475                 480

Pro Arg Tyr Tyr Ser Ile Ser Ser Ser Pro Arg Met Ala Pro Ser Arg
                485                 490                 495

Ile His Val Thr Cys Ala Leu Val His Asp Lys Met Pro Thr Gly Arg
            500                 505                 510

Ile His Lys Gly Val Cys Ser Thr Trp Met Lys Asn Ser Val Pro Leu
```

|       |       |       |
|-------|-------|-------|
| 515   | 520   | 525   |

Glu Lys Asn Gln Asp Cys Ser Trp Ala Pro Ile Phe Val Arg Gln Ser
530                 535                 540

Asn Phe Arg Leu Pro Ala Asp Asn Lys Val Pro Val Ile Met Ile Gly
545                 550                 555                 560

Pro Gly Thr Gly Leu Ala Pro Phe Arg Gly Phe Leu Gln Glu Arg Leu
                565                 570                 575

Ala Leu Lys Glu Asp Gly Ala Glu Leu Gly Pro Ser Val Leu Phe Phe
            580                 585                 590

Gly Cys Arg Asn Arg Gln Val Asp Tyr Ile Tyr Glu Asp Glu Leu Asn
        595                 600                 605

His Phe Val Asn Gly Gly Ala Leu Ser Glu Leu Ile Val Ala Phe Ser
    610                 615                 620

Arg Asp Gly Pro Thr Lys Glu Tyr Val Gln His Lys Met Met Glu Lys
625                 630                 635                 640

Ala Ser Asp Ile Trp Asn Met Ile Ser Gln Gly Ala Tyr Val Tyr Val
                645                 650                 655

Cys Gly Asp Ala Lys Gly Met Ala Arg Asp Val His Arg Thr Leu His
                660                 665                 670

Thr Ile Leu Gln Glu Gln Gly Ser Leu Asp Ser Ser Lys Thr Glu Ser
            675                 680                 685

Met Val Lys Asn Leu Gln Met Thr Gly Arg Tyr Leu Arg Asp Val Trp
690                 695                 700

<210> SEQ ID NO 712
<211> LENGTH: 358
<212> TYPE: PRT
<213> ORGANISM: Oryza sativa

<400> SEQUENCE: 712

Met Ser Ala Tyr Cys Gly Lys Tyr Lys Asp Glu Leu Ile Lys Asn Ala
1               5                   10                  15

Ala Tyr Ile Gly Thr Pro Gly Lys Gly Ile Leu Ala Ala Asp Glu Ser
            20                  25                  30

Thr Gly Thr Ile Gly Lys Arg Phe Ala Ser Ile Asn Val Glu Asn Val
        35                  40                  45

Glu Glu Asn Arg Arg Ser Leu Arg Glu Leu Leu Phe Thr Thr Pro Gly
    50                  55                  60

Ala Leu Gln His Leu Ser Gly Val Ile Leu Phe Glu Glu Thr Leu Tyr
65                  70                  75                  80

Gln Lys Thr Lys Asp Gly Lys Pro Phe Val Asp Val Leu Lys Glu Gly
                85                  90                  95

Gly Val Leu Pro Gly Ile Lys Val Asp Lys Gly Thr Val Glu Val Ala
            100                 105                 110

Gly Thr Asn Lys Glu Thr Thr Thr Gln Gly His Asp Asp Leu Gly Lys
        115                 120                 125

Arg Cys Ala Lys Tyr Tyr Glu Ala Gly Ala Arg Phe Ala Lys Trp Arg
    130                 135                 140

Ala Val Leu Lys Ile Gly Pro Asn Glu Pro Ser Gln Leu Ser Ile Asp
145                 150                 155                 160

Leu Asn Ala Gln Gly Leu Ala Arg Tyr Ala Ile Ile Cys Gln Glu Asn
                165                 170                 175

Gly Leu Val Pro Ile Val Glu Pro Glu Ile Leu Val Asp Gly Ser His
            180                 185                 190

```
Asp Ile Glu Arg Cys Ala Tyr Val Thr Glu Lys Val Leu Ala Ala Cys
            195                 200                 205

Tyr Lys Ala Leu Asn Glu His His Val Leu Leu Glu Gly Ser Leu Leu
            210                 215                 220

Lys Pro Asn Met Val Thr Pro Gly Ser Glu Ser Lys Lys Val Ser Pro
225                 230                 235                 240

Gln Leu Ile Ala Glu Tyr Thr Val Arg Ala Leu Gln Arg Thr Val Pro
            245                 250                 255

Ala Ala Val Pro Ala Ile Val Phe Leu Ser Gly Gly Gln Ser Glu Glu
            260                 265                 270

Glu Ala Thr Val Asn Leu Asn Ala Met Asn Lys Leu Ser Thr Lys Lys
            275                 280                 285

Pro Trp Ala Leu Ser Phe Ser Phe Gly Arg Ala Leu Gln Gln Ser Thr
            290                 295                 300

Leu Lys Ala Trp Gly Gly Lys Thr Glu Asn Val Val Lys Ala Gln Lys
305                 310                 315                 320

Ala Phe Ile Thr Arg Cys Lys Ala Asn Ser Glu Ala Thr Leu Gly Thr
            325                 330                 335

Tyr Gln Gly Asp Ala Val Leu Gly Glu Gly Ala Ser Glu Ser Leu His
            340                 345                 350

Val Lys Asp Tyr Lys Tyr
            355

<210> SEQ ID NO 713
<211> LENGTH: 275
<212> TYPE: PRT
<213> ORGANISM: Pisum sativum

<400> SEQUENCE: 713

Met Ala Ser Leu Gln Thr Gln Met Ile Ser Phe Tyr Ala Ile Phe Leu
1               5                   10                  15

Ser Ile Leu Leu Thr Thr Ile Leu Phe Phe Lys Val Asn Ser Thr Glu
            20                  25                  30

Thr Thr Ser Phe Leu Ile Thr Lys Phe Ser Pro Asp Gln Gln Asn Leu
            35                  40                  45

Ile Phe Gln Gly Asp Gly Tyr Thr Thr Lys Glu Lys Leu Thr Leu Thr
    50                  55                  60

Lys Ala Val Lys Asn Thr Val Gly Arg Ala Leu Tyr Ser Ser Pro Ile
65                  70                  75                  80

His Ile Trp Asp Arg Glu Thr Gly Asn Val Ala Asn Phe Val Thr Ser
            85                  90                  95

Phe Thr Phe Val Ile Asn Ala Pro Asn Ser Tyr Asn Val Ala Asp Gly
            100                 105                 110

Phe Thr Phe Phe Ile Ala Pro Val Asp Thr Lys Pro Gln Thr Gly Gly
            115                 120                 125

Gly Tyr Leu Gly Val Phe Asn Ser Ala Glu Tyr Asp Lys Thr Thr Gln
            130                 135                 140

Thr Val Ala Val Glu Phe Asp Thr Phe Tyr Asn Ala Ala Trp Asp Pro
145                 150                 155                 160

Ser Asn Arg Asp Arg His Ile Gly Ile Asp Val Asn Ser Ile Lys Ser
            165                 170                 175

Val Asn Thr Lys Ser Trp Lys Leu Gln Asn Gly Glu Glu Ala Asn Val
            180                 185                 190

Val Ile Ala Phe Asn Ala Ala Thr Asn Val Leu Thr Val Ser Leu Thr
            195                 200                 205
```

Tyr Pro Asn Ser Leu Glu Glu Glu Asn Val Thr Ser Tyr Thr Leu Ser
            210                 215                 220

Asp Val Val Ser Leu Lys Asp Val Val Pro Glu Trp Val Arg Ile Gly
225                 230                 235                 240

Phe Ser Ala Thr Thr Gly Ala Glu Tyr Ala Ala His Glu Val Leu Ser
                245                 250                 255

Trp Ser Phe His Ser Glu Leu Ser Gly Thr Ser Ser Ser Lys Gln Ala
                260                 265                 270

Ala Asp Ala
        275

<210> SEQ ID NO 714
<211> LENGTH: 484
<212> TYPE: PRT
<213> ORGANISM: Oryza sativa

<400> SEQUENCE: 714

Met Ala Thr Thr Thr Ser Leu Leu Ser Ser Cys Leu Cys Ala Leu Leu
1               5                   10                  15

Leu Ala Pro Leu Phe Ser Gln Gly Val Asp Ala Trp Glu Ser Arg Gln
                20                  25                  30

Gly Ala Ser Arg Gln Cys Arg Phe Asp Arg Leu Gln Ala Phe Glu Pro
            35                  40                  45

Leu Arg Lys Val Arg Ser Glu Ala Gly Asp Thr Glu Tyr Phe Asp Glu
        50                  55                  60

Arg Asn Glu Gln Phe Arg Cys Ala Gly Val Phe Val Ile Arg Arg Val
65                  70                  75                  80

Ile Glu Pro Gln Gly Leu Val Val Pro Arg Tyr Ser Asn Thr Pro Ala
                85                  90                  95

Leu Ala Tyr Ile Ile Gln Gly Lys Gly Tyr Val Gly Leu Thr Phe Pro
                100                 105                 110

Gly Cys Pro Ala Thr His Gln Gln Gln Phe Gln Leu Phe Glu Gln Arg
            115                 120                 125

Gln Ser Asp Gln Ala His Lys Phe Arg Asp Glu His Gln Lys Ile His
        130                 135                 140

Glu Phe Arg Gln Gly Asp Val Val Ala Leu Pro Ala Ser Val Ala His
145                 150                 155                 160

Trp Phe Tyr Asn Gly Asp Thr Pro Ala Val Val Tyr Val Tyr
                165                 170                 175

Asp Ile Lys Ser Phe Ala Asn Gln Leu Glu Pro Arg Gln Lys Glu Phe
                180                 185                 190

Leu Leu Ala Gly Asn Asn Gln Arg Gly Gln Gln Ile Phe Glu His Ser
            195                 200                 205

Ile Phe Gln His Ser Gly Gln Asn Ile Phe Ser Gly Phe Asn Thr Glu
        210                 215                 220

Val Leu Ser Glu Ala Leu Gly Ile Asn Thr Glu Ala Ser Lys Arg Leu
225                 230                 235                 240

Gln Ser Gln Asn Asp Gln Arg Gly Asp Ile Ile Arg Val Lys His Gly
                245                 250                 255

Leu Gln Leu Leu Lys Pro Thr Leu Thr Gln Arg Gln Glu His Arg
                260                 265                 270

Gln Tyr Gln Gln Val Gln Tyr Arg Glu Gly Gln Tyr Asn Gly Leu Asp
        275                 280                 285

Glu Asn Phe Cys Thr Ile Lys Ala Arg Val Asn Ile Glu Asn Pro Ser

```
                290                 295                 300
Arg Ala Asp Tyr Tyr Asn Pro Arg Ala Gly Arg Ile Thr Leu Leu Asn
305                 310                 315                 320

Asn Gln Lys Phe Pro Ile Leu Asn Leu Ile Gly Met Gly Ala Ala Arg
                325                 330                 335

Val Asn Leu Tyr Gln Asn Ala Leu Leu Ser Pro Phe Trp Asn Ile Asn
            340                 345                 350

Ala His Ser Val Val Tyr Ile Ile Gln Gly Ser Val Arg Val Gln Val
        355                 360                 365

Ala Asn Asn Gln Gly Arg Ser Val Phe Asn Gly Val Leu His Gln Gly
    370                 375                 380

Gln Leu Leu Ile Ile Pro Gln Asn His Ala Val Ile Lys Lys Ala Glu
385                 390                 395                 400

His Asn Gly Cys Gln Tyr Val Ala Ile Lys Thr Ile Ser Asp Pro Thr
                405                 410                 415

Val Ser Trp Val Ala Gly Lys Asn Ser Ile Leu Arg Ala Leu Pro Val
            420                 425                 430

Asp Val Ile Ala Asn Ala Tyr Arg Ile Ser Arg Asp Glu Ala Arg Arg
        435                 440                 445

Leu Lys Asn Asn Arg Ala Asp Glu Ile Gly Pro Phe Thr Pro Arg Phe
    450                 455                 460

Pro Gln Lys Ser Gln Arg Gly Tyr Gln Phe Leu Thr Glu Gly Leu Ser
465                 470                 475                 480

Leu Ile Gly Met

<210> SEQ ID NO 715
<211> LENGTH: 123
<212> TYPE: PRT
<213> ORGANISM: Pisum sativum

<400> SEQUENCE: 715

Gln Lys Ala Pro Arg Lys Gln Leu Ala Thr Lys Ala Ala Arg Lys Ser
1               5                   10                  15

Ala Pro Ala Thr Gly Gly Val Lys Lys Pro His Arg Phe Arg Pro Gly
            20                  25                  30

Thr Val Ala Leu Arg Glu Ile Arg Lys Tyr Gln Lys Ser Thr Glu Leu
        35                  40                  45

Leu Ile Arg Lys Leu Pro Phe Gln Arg Leu Val Arg Glu Ile Ala Gln
    50                  55                  60

Asp Phe Lys Thr Asp Leu Arg Phe Gln Ser Ser Ala Val Ser Ala Leu
65                  70                  75                  80

Gln Glu Ala Ala Glu Ala Tyr Leu Val Gly Leu Phe Glu Asp Thr Asn
                85                  90                  95

Leu Cys Ala Ile His Ala Lys Arg Val Thr Ile Met Pro Lys Asp Ile
            100                 105                 110

Gln Leu Ala Arg Arg Ile Arg Gly Glu Arg Ala
        115                 120

<210> SEQ ID NO 716
<211> LENGTH: 232
<212> TYPE: PRT
<213> ORGANISM: Pisum sativum

<400> SEQUENCE: 716

Met Ala Gln Ser Val Ser Leu Ser Thr Ile Ala Ser Pro Ile Leu Ser
1               5                   10                  15
```

-continued

```
Gln Lys Pro Gly Ser Ser Val Lys Ser Thr Pro Pro Cys Met Ala Ser
         20                  25                  30

Phe Pro Leu Arg Arg Gln Leu Pro Arg Leu Gly Leu Arg Asn Val Arg
             35                  40                  45

Ala Gln Ala Gly Gly Asp Gly Asp Asn Lys Asp Asn Ser Val Glu Val
 50                  55                  60

His Arg Val Asn Lys Asp Asp Gln Gly Thr Ala Val Glu Arg Lys Pro
 65                  70                  75                  80

Arg Arg Ser Ser Ile Asp Ile Ser Pro Phe Gly Leu Leu Asp Pro Trp
                 85                  90                  95

Ser Pro Met Arg Ser Met Arg Gln Met Leu Asp Thr Met Asp Arg Ile
            100                 105                 110

Phe Glu Asp Ala Ile Thr Ile Pro Gly Arg Asn Ile Gly Gly Gly Glu
            115                 120                 125

Ile Arg Val Pro Trp Glu Ile Lys Asp Glu Glu His Glu Ile Arg Met
130                 135                 140

Arg Phe Asp Met Pro Gly Val Ser Lys Glu Asp Val Lys Val Ser Val
145                 150                 155                 160

Glu Asp Asp Val Leu Val Ile Lys Ser Asp His Arg Glu Glu Asn Gly
                165                 170                 175

Gly Glu Asp Cys Trp Ser Arg Lys Ser Tyr Ser Cys Tyr Asp Thr Arg
            180                 185                 190

Leu Lys Leu Pro Asp Asn Cys Glu Lys Glu Lys Val Lys Ala Glu Leu
        195                 200                 205

Lys Asp Gly Val Leu Tyr Ile Thr Ile Pro Lys Thr Lys Ile Glu Arg
    210                 215                 220

Thr Val Ile Asp Val Gln Ile Gln
225                 230

<210> SEQ ID NO 717
<211> LENGTH: 10
<212> TYPE: PRT
<213> ORGANISM: Artificial Sequence
<220> FEATURE:
<223> OTHER INFORMATION: Synthetic peptide

<400> SEQUENCE: 717

Leu Asp Val Thr Pro Leu Ser Leu Gly Leu
1               5                   10

<210> SEQ ID NO 718
<211> LENGTH: 12
<212> TYPE: PRT
<213> ORGANISM: Artificial Sequence
<220> FEATURE:
<223> OTHER INFORMATION: Synthetic peptide

<400> SEQUENCE: 718

Glu Glu Gly Ile Gln Leu Val Ala Glu Ala Ile Arg
1               5                   10

<210> SEQ ID NO 719
<211> LENGTH: 9
<212> TYPE: PRT
<213> ORGANISM: Artificial Sequence
<220> FEATURE:
<223> OTHER INFORMATION: Synthetic peptide

<400> SEQUENCE: 719
```

```
Tyr Ser Leu Lys Pro Leu Val Pro Arg
1               5
```

<210> SEQ ID NO 720
<211> LENGTH: 4
<212> TYPE: PRT
<213> ORGANISM: Artificial Sequence
<220> FEATURE:
<223> OTHER INFORMATION: Synthetic peptide

<400> SEQUENCE: 720

```
Trp His Thr Ala
1
```

<210> SEQ ID NO 721
<211> LENGTH: 4
<212> TYPE: PRT
<213> ORGANISM: Artificial Sequence
<220> FEATURE:
<223> OTHER INFORMATION: Synthetic peptide

<400> SEQUENCE: 721

```
Trp His Asn Ala
1
```

<210> SEQ ID NO 722
<211> LENGTH: 4
<212> TYPE: PRT
<213> ORGANISM: Artificial Sequence
<220> FEATURE:
<223> OTHER INFORMATION: Synthetic peptide

<400> SEQUENCE: 722

```
Asn Asn Pro Phe
1
```

<210> SEQ ID NO 723
<211> LENGTH: 4
<212> TYPE: PRT
<213> ORGANISM: Artificial Sequence
<220> FEATURE:
<223> OTHER INFORMATION: Synthetic peptide

<400> SEQUENCE: 723

```
Met Arg Phe Arg
1
```

<210> SEQ ID NO 724
<211> LENGTH: 5
<212> TYPE: PRT
<213> ORGANISM: Artificial Sequence
<220> FEATURE:
<223> OTHER INFORMATION: Synthetic peptide

<400> SEQUENCE: 724

```
Met Pro Pro Ser Ser
1               5
```

<210> SEQ ID NO 725
<211> LENGTH: 4
<212> TYPE: PRT
<213> ORGANISM: Artificial Sequence
<220> FEATURE:
<223> OTHER INFORMATION: Synthetic peptide

<400> SEQUENCE: 725

```
His Met Pro Ser
```

```
<210> SEQ ID NO 726
<211> LENGTH: 5
<212> TYPE: PRT
<213> ORGANISM: Artificial Sequence
<220> FEATURE:
<223> OTHER INFORMATION: Synthetic peptide

<400> SEQUENCE: 726

His Met Pro Pro Ser
1               5

<210> SEQ ID NO 727
<211> LENGTH: 4
<212> TYPE: PRT
<213> ORGANISM: Artificial Sequence
<220> FEATURE:
<223> OTHER INFORMATION: Synthetic peptide

<400> SEQUENCE: 727

Gly His Pro Met
1

<210> SEQ ID NO 728
<211> LENGTH: 4
<212> TYPE: PRT
<213> ORGANISM: Artificial Sequence
<220> FEATURE:
<223> OTHER INFORMATION: Synthetic peptide

<400> SEQUENCE: 728

Phe Trp Asn Ala
1

<210> SEQ ID NO 729
<211> LENGTH: 4
<212> TYPE: PRT
<213> ORGANISM: Artificial Sequence
<220> FEATURE:
<223> OTHER INFORMATION: Synthetic peptide

<400> SEQUENCE: 729

Phe His Met Pro
1

<210> SEQ ID NO 730
<211> LENGTH: 11
<212> TYPE: PRT
<213> ORGANISM: Artificial Sequence
<220> FEATURE:
<223> OTHER INFORMATION: Synthetic peptide

<400> SEQUENCE: 730

Trp Thr Ile Val Gln Gly Leu Pro Ile Asp Glu
1               5                   10

<210> SEQ ID NO 731
<211> LENGTH: 9
<212> TYPE: PRT
<213> ORGANISM: Artificial Sequence
<220> FEATURE:
<223> OTHER INFORMATION: Synthetic peptide

<400> SEQUENCE: 731

Gly Tyr Pro Met Tyr Pro Leu Pro Arg
1               5
```

<210> SEQ ID NO 732
<211> LENGTH: 9
<212> TYPE: PRT
<213> ORGANISM: Artificial Sequence
<220> FEATURE:
<223> OTHER INFORMATION: Synthetic peptide

<400> SEQUENCE: 732

His Gly Gly Glu Gly Gly Arg Pro Tyr
1               5

<210> SEQ ID NO 733
<211> LENGTH: 6
<212> TYPE: PRT
<213> ORGANISM: Artificial Sequence
<220> FEATURE:
<223> OTHER INFORMATION: Synthetic peptide

<400> SEQUENCE: 733

Leu Arg Gly Phe Ser Lys
1               5

<210> SEQ ID NO 734
<211> LENGTH: 9
<212> TYPE: PRT
<213> ORGANISM: Artificial Sequence
<220> FEATURE:
<223> OTHER INFORMATION: Synthetic peptide

<400> SEQUENCE: 734

Gly Ala Leu Met Leu Pro His Tyr Asn
1               5

<210> SEQ ID NO 735
<211> LENGTH: 11
<212> TYPE: PRT
<213> ORGANISM: Artificial Sequence
<220> FEATURE:
<223> OTHER INFORMATION: Synthetic peptide

<400> SEQUENCE: 735

Gly Ala Leu Met Leu Pro His Tyr Asn Ser Arg
1               5                   10

<210> SEQ ID NO 736
<211> LENGTH: 9
<212> TYPE: PRT
<213> ORGANISM: Artificial Sequence
<220> FEATURE:
<223> OTHER INFORMATION: Synthetic peptide

<400> SEQUENCE: 736

Val Phe Asp Gly Val Leu Arg Pro Gly
1               5

<210> SEQ ID NO 737
<211> LENGTH: 6
<212> TYPE: PRT
<213> ORGANISM: Artificial Sequence
<220> FEATURE:
<223> OTHER INFORMATION: Synthetic peptide

<400> SEQUENCE: 737

Leu Gln Ser Gln Asn Asp
1               5

```
<210> SEQ ID NO 738
<211> LENGTH: 11
<212> TYPE: PRT
<213> ORGANISM: Artificial Sequence
<220> FEATURE:
<223> OTHER INFORMATION: Synthetic peptide

<400> SEQUENCE: 738

Leu Gln Ser Gln Asn Asp Gln Arg Gly Glu Ile
1               5                   10

<210> SEQ ID NO 739
<211> LENGTH: 14
<212> TYPE: PRT
<213> ORGANISM: Artificial Sequence
<220> FEATURE:
<223> OTHER INFORMATION: Synthetic peptide

<400> SEQUENCE: 739

Gln Ser Gln Asn Asp Gln Arg Gly Glu Ile Ile His Val Lys
1               5                   10

<210> SEQ ID NO 740
<211> LENGTH: 8
<212> TYPE: PRT
<213> ORGANISM: Artificial Sequence
<220> FEATURE:
<223> OTHER INFORMATION: Synthetic peptide

<400> SEQUENCE: 740

Arg Gly Glu Ile Ile His Val Lys
1               5

<210> SEQ ID NO 741
<211> LENGTH: 8
<212> TYPE: PRT
<213> ORGANISM: Artificial Sequence
<220> FEATURE:
<223> OTHER INFORMATION: Synthetic peptide

<400> SEQUENCE: 741

Arg Leu Gln Ser Gln Asn Asp Gln
1               5

<210> SEQ ID NO 742
<211> LENGTH: 10
<212> TYPE: PRT
<213> ORGANISM: Artificial Sequence
<220> FEATURE:
<223> OTHER INFORMATION: Synthetic peptide

<400> SEQUENCE: 742

Arg Leu Gln Ser Gln Asn Asp Gln Arg Gly
1               5                   10

<210> SEQ ID NO 743
<211> LENGTH: 14
<212> TYPE: PRT
<213> ORGANISM: Artificial Sequence
<220> FEATURE:
<223> OTHER INFORMATION: Synthetic peptide

<400> SEQUENCE: 743

Arg Leu Gln Ser Gln Asn Asp Gln Arg Gly Glu Ile Ile His
1               5                   10
```

-continued

```
<210> SEQ ID NO 744
<211> LENGTH: 4
<212> TYPE: PRT
<213> ORGANISM: Artificial Sequence
<220> FEATURE:
<223> OTHER INFORMATION: Synthetic peptide

<400> SEQUENCE: 744

Met Pro Met Pro
1

<210> SEQ ID NO 745
<211> LENGTH: 4
<212> TYPE: PRT
<213> ORGANISM: Artificial Sequence
<220> FEATURE:
<223> OTHER INFORMATION: Synthetic peptide

<400> SEQUENCE: 745

Pro Met Pro Leu
1

<210> SEQ ID NO 746
<211> LENGTH: 6
<212> TYPE: PRT
<213> ORGANISM: Artificial Sequence
<220> FEATURE:
<223> OTHER INFORMATION: Synthetic peptide

<400> SEQUENCE: 746

Leu Glu Pro Asp Asn Arg
1               5

<210> SEQ ID NO 747
<211> LENGTH: 13
<212> TYPE: PRT
<213> ORGANISM: Artificial Sequence
<220> FEATURE:
<223> OTHER INFORMATION: Synthetic peptide

<400> SEQUENCE: 747

Gly Ile Ala Arg Leu Ala Gly Thr Ser Ser Val Ile Asn
1               5                   10

<210> SEQ ID NO 748
<211> LENGTH: 6
<212> TYPE: PRT
<213> ORGANISM: Artificial Sequence
<220> FEATURE:
<223> OTHER INFORMATION: Synthetic peptide

<400> SEQUENCE: 748

Arg Ser Gln Asn Ile Phe
1               5

<210> SEQ ID NO 749
<211> LENGTH: 4
<212> TYPE: PRT
<213> ORGANISM: Artificial Sequence
<220> FEATURE:
<223> OTHER INFORMATION: Synthetic peptide

<400> SEQUENCE: 749

Pro Asn Ser Met
1

<210> SEQ ID NO 750
```

```
<211> LENGTH: 4
<212> TYPE: PRT
<213> ORGANISM: Artificial Sequence
<220> FEATURE:
<223> OTHER INFORMATION: Synthetic peptide

<400> SEQUENCE: 750

Gly His Pro Met
1

<210> SEQ ID NO 751
<211> LENGTH: 4
<212> TYPE: PRT
<213> ORGANISM: Artificial Sequence
<220> FEATURE:
<223> OTHER INFORMATION: Synthetic peptide

<400> SEQUENCE: 751

His Pro Met Ser
1

<210> SEQ ID NO 752
<211> LENGTH: 7
<212> TYPE: PRT
<213> ORGANISM: Artificial Sequence
<220> FEATURE:
<223> OTHER INFORMATION: Synthetic peptide

<400> SEQUENCE: 752

Phe Leu Pro Gln His Thr Asp
1               5

<210> SEQ ID NO 753
<211> LENGTH: 7
<212> TYPE: PRT
<213> ORGANISM: Artificial Sequence
<220> FEATURE:
<223> OTHER INFORMATION: Synthetic peptide

<400> SEQUENCE: 753

Glu Trp Gln Ile Asn Glu Lys
1               5

<210> SEQ ID NO 754
<211> LENGTH: 13
<212> TYPE: PRT
<213> ORGANISM: Artificial Sequence
<220> FEATURE:
<223> OTHER INFORMATION: Synthetic peptide

<400> SEQUENCE: 754

Gly Pro Gln Gln Tyr Ala Glu Trp Gln Ile Asn Glu Lys
1               5                   10

<210> SEQ ID NO 755
<211> LENGTH: 8
<212> TYPE: PRT
<213> ORGANISM: Artificial Sequence
<220> FEATURE:
<223> OTHER INFORMATION: Synthetic peptide

<400> SEQUENCE: 755

Pro Gln Gln Tyr Ala Glu Trp Gln
1               5

<210> SEQ ID NO 756
<211> LENGTH: 7
```

```
<212> TYPE: PRT
<213> ORGANISM: Artificial Sequence
<220> FEATURE:
<223> OTHER INFORMATION: Synthetic peptide

<400> SEQUENCE: 756

Arg Gly Pro Gln Gln Tyr Ala
1               5

<210> SEQ ID NO 757
<211> LENGTH: 4
<212> TYPE: PRT
<213> ORGANISM: Artificial Sequence
<220> FEATURE:
<223> OTHER INFORMATION: Synthetic peptide

<400> SEQUENCE: 757

His Asn Pro Arg
1

<210> SEQ ID NO 758
<211> LENGTH: 4
<212> TYPE: PRT
<213> ORGANISM: Artificial Sequence
<220> FEATURE:
<223> OTHER INFORMATION: Synthetic peptide

<400> SEQUENCE: 758

Trp His Asn Arg
1

<210> SEQ ID NO 759
<211> LENGTH: 4
<212> TYPE: PRT
<213> ORGANISM: Artificial Sequence
<220> FEATURE:
<223> OTHER INFORMATION: Synthetic peptide

<400> SEQUENCE: 759

Trp Asp Pro Ala
1

<210> SEQ ID NO 760
<211> LENGTH: 4
<212> TYPE: PRT
<213> ORGANISM: Artificial Sequence
<220> FEATURE:
<223> OTHER INFORMATION: Synthetic peptide

<400> SEQUENCE: 760

His Pro Ser Phe
1

<210> SEQ ID NO 761
<211> LENGTH: 22
<212> TYPE: PRT
<213> ORGANISM: Artificial Sequence
<220> FEATURE:
<223> OTHER INFORMATION: Synthetic peptide

<400> SEQUENCE: 761

Pro Gly Gln Leu Gln Ser Phe Leu Leu Ser Gly Asn Gln Asn Gln Gln
1               5                   10                  15

Asn Tyr Leu Ser Gly Phe
            20
```

```
<210> SEQ ID NO 762
<211> LENGTH: 22
<212> TYPE: PRT
<213> ORGANISM: Artificial Sequence
<220> FEATURE:
<223> OTHER INFORMATION: Synthetic peptide

<400> SEQUENCE: 762

Gln Leu Gln Ser Phe Leu Leu Ser Gly Asn Gln Asn Gln Gln Asn Tyr
1               5                   10                  15

Leu Ser Gly Phe Ser Lys
            20

<210> SEQ ID NO 763
<211> LENGTH: 12
<212> TYPE: PRT
<213> ORGANISM: Artificial Sequence
<220> FEATURE:
<223> OTHER INFORMATION: Synthetic peptide

<400> SEQUENCE: 763

Gln Ser Phe Leu Leu Ser Gly Asn Gln Asn Gln Gln
1               5                   10

<210> SEQ ID NO 764
<211> LENGTH: 12
<212> TYPE: PRT
<213> ORGANISM: Artificial Sequence
<220> FEATURE:
<223> OTHER INFORMATION: Synthetic peptide

<400> SEQUENCE: 764

Pro Gly Gln Leu Gln Ser Phe Leu Leu Ser Gly Asn
1               5                   10

<210> SEQ ID NO 765
<211> LENGTH: 9
<212> TYPE: PRT
<213> ORGANISM: Artificial Sequence
<220> FEATURE:
<223> OTHER INFORMATION: Synthetic peptide

<400> SEQUENCE: 765

Gln Ser Phe Leu Leu Ser Gly Asn Gln
1               5

<210> SEQ ID NO 766
<211> LENGTH: 12
<212> TYPE: PRT
<213> ORGANISM: Artificial Sequence
<220> FEATURE:
<223> OTHER INFORMATION: Synthetic peptide

<400> SEQUENCE: 766

Gln Asn Gln Gln Asn Tyr Leu Ser Gly Phe Ser Lys
1               5                   10

<210> SEQ ID NO 767
<211> LENGTH: 6
<212> TYPE: PRT
<213> ORGANISM: Artificial Sequence
<220> FEATURE:
<223> OTHER INFORMATION: Synthetic peptide

<400> SEQUENCE: 767

Tyr Leu Arg Gly Phe Ser
1               5
```

<210> SEQ ID NO 768
<211> LENGTH: 11
<212> TYPE: PRT
<213> ORGANISM: Artificial Sequence
<220> FEATURE:
<223> OTHER INFORMATION: Synthetic peptide

<400> SEQUENCE: 768

Pro Val Glu Met Pro Thr Leu Leu Tyr Pro Ser
1               5                   10

<210> SEQ ID NO 769
<211> LENGTH: 13
<212> TYPE: PRT
<213> ORGANISM: Artificial Sequence
<220> FEATURE:
<223> OTHER INFORMATION: Synthetic peptide

<400> SEQUENCE: 769

Arg Gly Pro Gln Gln Tyr Ala Glu Trp Gln Ile Asn Glu
1               5                   10

<210> SEQ ID NO 770
<211> LENGTH: 24
<212> TYPE: PRT
<213> ORGANISM: Artificial Sequence
<220> FEATURE:
<223> OTHER INFORMATION: Synthetic peptide

<400> SEQUENCE: 770

Gly Tyr Val Gly Leu Thr Phe Pro Gly Cys Pro Ala Thr His Gln Gln
1               5                   10                  15

Gln Phe Gln Leu Phe Glu Gln Arg
            20

<210> SEQ ID NO 771
<211> LENGTH: 18
<212> TYPE: PRT
<213> ORGANISM: Artificial Sequence
<220> FEATURE:
<223> OTHER INFORMATION: Synthetic peptide

<400> SEQUENCE: 771

Lys Asn Pro Gln Leu Gln Asp Leu Asp Ile Phe Val Asn Tyr Val Glu
1               5                   10                  15

Ile Lys

<210> SEQ ID NO 772
<211> LENGTH: 24
<212> TYPE: PRT
<213> ORGANISM: Artificial Sequence
<220> FEATURE:
<223> OTHER INFORMATION: Synthetic peptide

<400> SEQUENCE: 772

Pro Gly Gln Leu Gln Ser Phe Leu Leu Ser Gly Asn Gln Asn Gln Gln
1               5                   10                  15

Asn Tyr Leu Ser Gly Phe Ser Lys
            20

<210> SEQ ID NO 773
<211> LENGTH: 14
<212> TYPE: PRT
<213> ORGANISM: Artificial Sequence

```
<220> FEATURE:
<223> OTHER INFORMATION: Synthetic peptide

<400> SEQUENCE: 773

Arg Gly Pro Gln Gln Tyr Ala Glu Trp Gln Ile Asn Glu Lys
1               5                   10

<210> SEQ ID NO 774
<211> LENGTH: 14
<212> TYPE: PRT
<213> ORGANISM: Artificial Sequence
<220> FEATURE:
<223> OTHER INFORMATION: Synthetic peptide

<400> SEQUENCE: 774

Val Leu Asp Leu Ala Ile Pro Val Asn Arg Pro Gly Gln Leu
1               5                   10

<210> SEQ ID NO 775
<211> LENGTH: 14
<212> TYPE: PRT
<213> ORGANISM: Artificial Sequence
<220> FEATURE:
<223> OTHER INFORMATION: Synthetic peptide

<400> SEQUENCE: 775

Arg Gly Pro Gln Gln Tyr Ala Glu Trp Gln Ile Asn Glu Lys
1               5                   10

<210> SEQ ID NO 776
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 776

Arg Pro Tyr Tyr Ser Asn Ala Pro Gln Glu Ile Phe
1               5                   10

<210> SEQ ID NO 777
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 777

Val Leu Leu Glu Gln Gln Glu Gln Glu Pro Gln His
1               5                   10

<210> SEQ ID NO 778
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 778

Gln Gln Tyr Gly Ile Ala Ala Ser Pro Phe Leu Gln Ser Ala Ala
1               5                   10                  15
```

GROWTH PROMOTING PEPTIDES, AND USES THEREOF

CROSS REFERENCE TO RELATED APPLICATION

This application is a continuation under 35 U.S.C. § 120 of co-pending U.S. application Ser. No. 15/744,390 filed on Jan. 12, 2018, which is a 35 U.S.C. § 371 National Phase Entry of the International Application No. PCT/EP2016/067097 filed on Jul. 18, 2016, which designates the U.S. and which claims benefit under 35 U.S.C. § 119(b) of European Patent Application No. 15177017.9 filed Jul. 16, 2015, the contents of which are incorporated herein by reference in their entirety.

SEQUENCE LISTING

The sequence listing of the present application has been submitted electronically via EFS-Web as an ASCII formatted sequence listing with a file name "048262-091340-US_SL.txt", creation date of Oct. 30, 2019 and a size of 420,014 bytes. The sequence listing submitted via EFS-Web is part of the specification and is herein incorporated by reference in its entirety.

BACKGROUND TO THE INVENTION

The growing will of maintaining a youthful appearance is leading to more and more research of new dermatological procedures for treatment of skin aging, especially when people keeps living longer and healthier. With age, structural and functional changes are be observed in human skin (Calleja-Agius J. et al. 2013) and many factors are responsible for them like environmental factors such as UV radiation from sunlight or internal factors such as changes in hormones due menopause (Affinito P. et al. 1999).

The alterations of connective tissue in the dermis and epidermis, especially the reduction of the extracellular matrix is highly responsible for skin wrinkling and sagging since they induce important changes in its mechanical properties. Furthermore, metabolism and synthesis of the extra-cellular matrix are affected by the ageing process through enzymatic activities.

There are mainly four solutions to fight against ageing process at the moment:

Diet and hormones management: fighting the ageing process by managing our diet by using supplements. This method is still controverted at the moment. Some studies suggest that antioxidant supplements like Vitamin C or lipoic acid for example could have anti-ageing properties.

Hormone treatment: a risky and controverted solution for anti-ageing purpose. One have to be really careful with anything related to hormones since it can have a broad spectrum of adverse effects. This solution isn't widely used and most of the studies are still on the animal stage.

Surgical anti-aging solutions: they are very effective on the short term but they are costly and can require long period of healing. Like in every surgical operation, there are risks but also side effects. For example, during surgical anti-aging solutions like eyelifts and facelifts, where an incision is made at the hairline, there are some risks of bruising, swelling, drooping eyelids, and secondary infections can occur.

Recently, there has been an increasing enthusiasm on minimally invasive treatments and techniques designed to deal with problems like wrinkles, volume loss and other skin damages. The most common topical anti-ageing solutions are creams and serums. Their active ingredients can be divided in several families:

Moisturiser ingredients will keep the skin hydrated. It's mostly big polar molecules that will make bonds with water like glycosaminoglycan (hyaluronic acid for instance).

Collagen and other extra-cellular matrix related ingredients will contribute to maintain a well organised skin structure by stimulating biosynthesis if they can trigger the right receptors.

Cell proliferation ingredients are important as well since they help to regenerate skin cells which will synthesise the component the skin needs like extra-cellular matrix and growth factors.

It is an object of the invention to provide an alternative minimally invasive treatment of skin ageing.

STATEMENTS OF INVENTION

The pea genome codes for over 70,000 different proteins. The Applicant has identified six of these proteins, each of which contains one or more peptides capable of promoting cellular growth and/or proliferation (hereafter "growth promoting peptide" or "growth promoting fragment"). Likewise, out of the more than 60,000 proteins encoded by the rice genome, the Applicant has identified seven proteins, each of which contains one or more peptides that are bioactive, typically capable of promoting cellular growth and/or proliferation. Cellular growth promoting fragments of the fourteen identified proteins have been shown to have an effect on elastin and collagen production and cell proliferation (FIGS. 1 to 109). The specific plant proteins from which the natural peptides are derived are provided in SEQ ID NOs: 1-14 and 705 to 716. The specific pea proteins from which the peptides are derived include SEQ ID NOs: 1-2 and 7-10, and the specific rice proteins from which the peptides are derived include SEQ ID NOs: 3-6 and 11-13. Homologs of these proteins are described in SEQ ID NOs: 525 to 564. The specific peptides initially identified in the pea proteins are shown in SEQ ID NOs: 15-215 and 283-340. The specific peptides initially identified in the rice proteins are shown in SEQ ID NOs: 216-282 and 341-412. Additional peptides identified in the pea and rice proteins disclosed herein, and variants thereof, are provided in SEQ ID NOs: 418 to 515 and 546 to 704 and 717-775.

In a first aspect, the invention provides a peptide, typically 5 to 50 amino acids in length, and comprising (a) a fragment of a pea or rice protein, for example the pea and rice protein disclosed herein such as one selected from SEQ ID NOs: 1 to 14 and 705 to 716 and 717-732, or a homolog thereof, or (b) a variant of the fragment, or (c) a fragment of the peptide (hereafter "peptide of the invention"). In one embodiment the peptide is bioactive. In one embodiment, the peptide has cellular growth or proliferation promotion activity.

In one embodiment, the peptide of the invention comprises a sequence selected from SEQ ID NOs: 15-505 and 546-704 and 717-775.

In one embodiment, the peptide of the invention consists essentially of a sequence selected from SEQ ID NOs: 15-505 and 546-704 and 717-775.

In one embodiment, the peptide of the invention consists of about 3-50 amino acids. In one embodiment, the peptide of the invention consists of about 4-50 amino acids. In one embodiment, the peptide of the invention consists of about 5-50 amino acids. In one embodiment, the peptide of the invention consists of about 6-50 amino acids. In one embodiment, the peptide of the invention consists of about 7-50 amino acids.

In one embodiment, the fragment has 8 to 37 amino acids. In one embodiment, the fragment has a charge of between −10 and +4.

Preferably, the c-terminal amino acid is not cysteine (C) or methionine (M).

Preferably, the n-terminal amino acid is not cysteine (C), histidine (H), or proline (P).

Preferably, the c-terminal domain of the fragment does not contain cysteine (C).

Preferably, the n-terminal domain of the fragment does not contain cysteine (C).

Preferably, the fragment does not contain cysteine (C).

Preferably, the peptide does not contain cysteine (C).

In one embodiment of the invention, the peptide comprises a sequence selected from SEQ ID NOs: 15 to 505.

In one embodiment of the invention, the peptide consists essentially of a sequence selected from SEQ ID NOs: 15 to 505.

Preferably, the fragment is selected from SEQ ID NOs: 15-215 and 283-340, or a bioactive variant of the fragment.

Preferably, the fragment is selected from SEQ ID NOs: 216-282 and 341-412, or a bioactive variant of the fragment.

Preferably, the peptide consists of a fragment selected from SEQ ID NOs: 15 to 417, or a bioactive variant of the fragment.

Preferably, the peptide consists of a sequence selected from SEQ ID NOs: 15 to 417.

Preferably, the fragment is selected from SEQ ID NOs: 413-417, or a bioactive variant of the fragment.

In one embodiment, the peptide comprises or consists of a fragment selected from SEQ ID NOs: 246, 283, 284, 245 and 42, or a bioactive variant of the fragment.

In one embodiment, the peptide comprises a fragment selected from SEQ ID NOs: 247 to 268.

In one embodiment, the peptide of the invention is modified. In one embodiment the peptide is modified with a protecting group. In one embodiment, the peptide is modified to increase its lipophilicity. In none embodiment, the peptide is modified to increase its half-life. In one embodiment, an N or C-terminal amino acid of the peptide is modified. In one embodiment, the N or C-terminal amino acid of the peptide is modified with a protecting group.

[SEQ ID NO: 1 (Pea Protein 1—P13918)]

Preferably, the peptide comprises a bioactive fragment of the protein of SEQ ID NO: 1 or a homolog thereof, or a bioactive variant of the fragment.

Preferably, the peptide comprises a bioactive fragment selected from SEQ ID NOs: 15 to 90, or a bioactive variant of the fragment.

The invention also provides a composition comprising at least 1, preferably at least 2, preferably at least 3, preferably at least 4, preferably at least 5, preferably at least 6, preferably at least 7, preferably at least 8, preferably at least 9, or preferably at least 10 bioactive peptides of the invention, each of which typically comprises a different a bioactive fragment of SEQ ID NO: 1 or a homolog thereof. Preferably, the composition comprises a first bioactive peptide comprising a first a bioactive fragment selected from SEQ ID NOs: 15 to 90 (or a bioactive variant of the fragment), and a second bioactive peptide comprising a second a bioactive fragment selected from SEQ ID NOs: 15-90 (or a bioactive variant of the fragment).

In one embodiment, the bioactive peptide, variant or fragment is a cellular growth or proliferation promoting peptide, variant or fragment, respectively.

Homologs of Pea Protein 1 (SEQ ID NO: 1) include *Vicia fabia, Cicer arietinum* and *Lens culinaris* homologs (SEQ ID NOs: 525 to 527).

[SEQ ID NO: 2 (Pea Protein 2—Q9M3X6)]

Preferably, the peptide comprises a bioactive fragment of the protein of SEQ ID NO: 2, or a homolog thereof, or a bioactive variant of the fragment.

Preferably, the peptide comprises a bioactive fragment selected from SEQ ID NOs: 91 to 215, or a bioactive variant of the fragment.

The invention also provides a composition comprising at least 1, preferably at least 2, preferably at least 3, preferably at least 4, preferably at least 5, preferably at least 6, preferably at least 7, preferably at least 8, preferably at least 9, or preferably at least 10 bioactive peptides of the invention, each of which comprises a different a bioactive fragment of SEQ ID NO: 2 or a homolog thereof. Preferably, the composition comprises a first bioactive peptide comprising a bioactive fragment selected from SEQ ID NOs: 91-215, and a second bioactive peptide comprising a bioactive fragment selected from SEQ ID NOs: 91-215.

In one embodiment, the bioactive peptide, variant or fragment is a cellular growth or proliferation promoting peptide, variant or fragment, respectively.

Homologs of Pea Protein 2 (SEQ ID NO: 2) include *Pisum abyssinicum, Lathyrus annuus,* and *Vicia villosa* (SEQ ID NOs: 528 to 530).

[SEQ ID NO: 3 (Rice Protein 1—Q0DEV5)]

Preferably, the peptide comprises a bioactive fragment of the protein of SEQ ID NO: 3, or a homolog thereof, or a bioactive variant of the fragment.

Preferably, the peptide comprises a bioactive fragment selected from SEQ ID NOs: 216-244, or a bioactive variant of the fragment.

The invention also provides a composition comprising at least 1, preferably at least 2, preferably at least 3, preferably at least 4, preferably at least 5, preferably at least 6, preferably at least 7, preferably at least 8, preferably at least 9, or preferably at least 10 bioactive peptides of the invention, each of which comprises a different bioactive fragment of SEQ ID NO: 3 or a homolog thereof. Preferably, the composition comprises a first bioactive peptide comprising a bioactive fragment selected from SEQ ID NOs: 216-244, and a second bioactive peptide comprising a bioactive fragment selected from SEQ ID NO 216-244.

In one embodiment, the bioactive peptide, variant or fragment is a cellular growth or proliferation promoting peptide, variant or fragment, respectively.

Homologs of Rice Protein 1 (SEQ ID NO: 15) include *Oryza rufipogon, Oryza officinalis, Hordeum vulgare* subsp. *vulgare* (SEQ ID NOs: 531 to 533).

[SEQ ID NO: 4 (Rice Protein 2—P14323)]

Preferably, the peptide comprises a bioactive fragment of the protein of SEQ ID NO: 4, or a homolog thereof, or a bioactive variant of the fragment.

Preferably, the peptide comprises a bioactive fragment selected from SEQ ID NOs: 245-246, or a bioactive variant of the fragment.

The invention also provides a composition comprising at least one or more peptides of the invention that comprise different bioactive fragments of SEQ ID NO: 4 or a homolog thereof. Preferably, the composition comprises a first peptide comprising the bioactive fragment SEQ ID NO: 245 and a second peptide comprising the bioactive fragment SEQ ID NO: 246.

In one embodiment, the bioactive peptide, variant or fragment is a cellular growth or proliferation promoting peptide, variant or fragment, respectively.

Homologs of Rice Protein 2 (SEQ ID NO: 4) include *Oryza brachyantha*, and *Zizania latifolia* (SEQ ID NOs: 534 to 536).

[SEQ ID NO: 5 (Rice Protein 3—P29835)]

Preferably, the peptide comprises a bioactive fragment of the protein of SEQ ID NO: 5, or a homolog thereof, or a bioactive variant of the fragment.

Preferably, the peptide comprises a bioactive fragment selected from SEQ ID NOs: 247-268, or a bioactive variant of the fragment.

The invention also provides a composition comprising at least 1, preferably at least 2, preferably at least 3, preferably at least 4, preferably at least 5, preferably at least 6, preferably at least 7, preferably at least 8, preferably at least 9, or preferably at least 10 bioactive peptides of the invention, each of which comprises a different bioactive fragment of SEQ ID NO: 5 or a homolog thereof. Preferably, the composition comprises a first bioactive peptide comprising a bioactive fragment selected from SEQ ID NOs: 247-268, and a second bioactive peptide comprising a bioactive fragment selected from SEQ ID NOs: 247-268.

In one embodiment, the bioactive peptide, variant or fragment is a cellular growth or proliferation promoting peptide, variant or fragment, respectively.

Homologs of Rice Protein 3 (SEQ ID NO: 5) include *Zea Mays, Sorghum bicolor* and *Setaria italica* (SEQ ID NOs: 537 to 539).

[SEQ ID NO: 6 (Rice Protein 4—P14614)]

Preferably, the peptide comprises a bioactive fragment of the protein of SEQ ID NO: 6 or a homolog thereof, or a bioactive variant of the fragment.

Preferably, the peptide comprises a bioactive fragment selected from SEQ ID NOs: 269-282, or a bioactive variant of the fragment.

The invention also provides a composition comprising at least 1, preferably at least 2, preferably at least 3, preferably at least 4, preferably at least 5, preferably at least 6, preferably at least 7, preferably at least 8, preferably at least 9, or preferably at least 10 bioactive peptides of the invention, each of which comprises a different bioactive fragment of SEQ ID NO: 6 or a homolog thereof. Preferably, the composition comprises a first bioactive peptide comprising a bioactive fragment selected from SEQ ID NOs: 269-282, and a second bioactive peptide comprising a bioactive fragment selected from SEQ ID NOs: 269-282.

In one embodiment, the bioactive peptide, variant or fragment is a cellular growth or proliferation promoting peptide, variant or fragment, respectively.

Homologs of Rice Protein 4 (SEQ ID NO: 6) include *Oryza sativa Japonica* Group, *Brachipodium distachyon* (SEQ ID NOs: 540 to 542).

[SEQ ID NO: 7 (Pea Protein 3—P09918)]

Preferably, the peptide comprises a bioactive fragment of the protein of SEQ ID NO: 7 or a homolog thereof, or a bioactive variant of the fragment.

Preferably, the peptide comprises a bioactive fragment of SEQ ID NO: 283, or a bioactive variant of the fragment.

The invention also provides a composition comprising at least 1, preferably at least 2, preferably at least 3, preferably at least 4, preferably at least 5, preferably at least 6, preferably at least 7, preferably at least 8, preferably at least 9, or preferably at least 10 bioactive peptides of the invention, each of which comprises a different bioactive fragment of SEQ ID NO: 7 or a homolog thereof. Preferably, the composition comprises a bioactive fragment SEQ ID NO: 283, or a bioactive variant of the fragment.

In one embodiment, the bioactive peptide, variant or fragment is a cellular growth or proliferation promoting peptide, variant or fragment, respectively.

Homologs of Pea Protein 3 (SEQ ID NO: 7) include *Medicago truncatula, Glycine soja*, and *Phaseolus vulgaris* (SEQ ID NOs: 543 to 545).

[SEQ ID NO: 8 (Pea Protein 4—P02857)]

Preferably, the peptide comprises a bioactive fragment of the protein of SEQ ID NO: 8 or a homolog thereof, or a bioactive variant of the fragment.

Preferably, the peptide comprises a bioactive fragment selected from SEQ ID NOs: 284-307, or a bioactive variant of the fragment.

The invention also provides a composition comprising at least 1, preferably at least 2, preferably at least 3, preferably at least 4, preferably at least 5, preferably at least 6, preferably at least 7, preferably at least 8, preferably at least 9, or preferably at least 10 bioactive peptides of the invention, each of which comprises a different bioactive fragment of SEQ ID NO: 8 or a homolog thereof. Preferably, the composition comprises a first bioactive peptide comprising a bioactive fragment selected from SEQ ID NOs: 284-307, and a second bioactive peptide comprising a bioactive fragment selected from SEQ ID NOs: 284-307.

In one embodiment, the bioactive peptide, variant or fragment is a cellular growth or proliferation promoting peptide, variant or fragment, respectively.

Homologs of Pea Protein 4 (SEQ ID NO: 8) include *Vicia sativa, Vicia narbonesis* and *Cicer arietinum* (SEQ ID NOs: 546 to 548).

[SEQ ID NO: 9 (Pea Protein 5—P02855)]

Preferably, the peptide comprises a bioactive fragment of the protein of SEQ ID NO: 9 or a homolog thereof, or a bioactive variant of the fragment.

Preferably, the peptide comprises a bioactive fragment selected from SEQ ID NOs: 308-339, or a bioactive variant of the fragment.

The invention also provides a composition comprising at least 1, preferably at least 2, preferably at least 3, preferably at least 4, preferably at least 5, preferably at least 6, preferably at least 7, preferably at least 8, preferably at least 9, or preferably at least 10 bioactive peptides of the invention, each of which comprises a different bioactive fragment of SEQ ID NO: 9 or a homolog thereof. Preferably, the composition comprises a first bioactive peptide comprising a bioactive fragment selected from SEQ ID NOs: 308-339, and a second bioactive peptide comprising a bioactive fragment selected from SEQ ID NOs: 308-339.

In one embodiment, the bioactive peptide, variant or fragment is a cellular growth or proliferation promoting peptide, variant or fragment, respectively.

Homologs of Pea Protein 5 (SEQ ID NO: 9) include *Lathyrus hirsutus, Lathyrus cicero, Lathyrus sativus* (SEQ ID NOs: 549 to 551).

[SEQ ID NO: 10 (Pea Protein 6—D3VNE1)]

Preferably, the peptide comprises a bioactive fragment of the protein of SEQ ID NO: 10 or a homolog thereof, or a bioactive variant of the fragment.

Preferably, the peptide comprises the bioactive fragment SEQ ID NO: 340, or a bioactive variant of the fragment.

The invention also provides a composition comprising at least 1, preferably at least 2, preferably at least 3, preferably at least 4, preferably at least 5, preferably at least 6, preferably at least 7, preferably at least 8, preferably at least 9, or preferably at least 10 bioactive peptides of the invention, each of which comprises a different bioactive fragment of SEQ ID NO: 10 or a homolog thereof. Preferably, the composition comprises a first bioactive peptide comprising the bioactive fragment SEQ ID NO: 340.

In one embodiment, the bioactive peptide, variant or fragment is a cellular growth or proliferation promoting peptide, variant or fragment, respectively.

Homologs of Pea Protein 6 (SEQ ID NO: 10) include *Medicago truncatula, Vicia peregrine*, and *Vicia lutea* (SEQ ID NOs: 552 to 554).

[SEQ ID NO: 11 (Rice Protein 5—P07728)]

Preferably, the peptide comprises a bioactive fragment of the protein of SEQ ID NO: 11 or a homolog thereof, or a bioactive variant of the fragment.

Preferably, the peptide comprises a bioactive fragment selected from SEQ ID NOs: 341-358, or a bioactive variant of the fragment.

The invention also provides a composition comprising at least 1, preferably at least 2, preferably at least 3, preferably at least 4, preferably at least 5, preferably at least 6, preferably at least 7, preferably at least 8, preferably at least 9, or preferably at least 10 bioactive peptides of the invention, each of which comprises a different bioactive fragment of SEQ ID NO: 11 or a homolog thereof. Preferably, the composition comprises a first bioactive peptide comprising a bioactive fragment selected from SEQ ID NOs: 341-358, and a second bioactive peptide comprising a bioactive fragment selected from SEQ ID NOs: 341-358.

In one embodiment, the bioactive peptide, variant or fragment is a cellular growth or proliferation promoting peptide, variant or fragment, respectively.

Homologs of Rice Protein 5 (SEQ ID NO: 11) include *Oryza sativa* Indica Group, *Zizania latifolia, Avena sativa* (SEQ ID NOs: 555 to 557).

[SEQ ID NO: 12 (Rice Protein 6—P07730)]

Preferably, the peptide comprises a bioactive fragment of the protein of SEQ ID NO: 12 or a homolog thereof, or a bioactive variant of the fragment.

Preferably, the peptide comprises a bioactive fragment selected from SEQ ID NOs: 359-401, or a bioactive variant of the fragment.

The invention also provides a composition comprising at least 1, preferably at least 2, preferably at least 3, preferably at least 4, preferably at least 5, preferably at least 6, preferably at least 7, preferably at least 8, preferably at least 9, or preferably at least 10 bioactive peptides of the invention, each of which comprises a different bioactive fragment of SEQ ID NO: 12 or a homolog thereof. Preferably, the composition comprises a first bioactive peptide comprising a bioactive fragment selected from SEQ ID NOs: 359-401, and a second bioactive peptide comprising a bioactive fragment selected from SEQ ID NOs: 359-401.

In one embodiment, the bioactive peptide, variant or fragment is a cellular growth or proliferation promoting peptide, variant or fragment, respectively.

Homologs of Rice Protein 6 (SEQ ID NO: 12) include *Oryza brachyantha, Brachypodium distachyon* (SEQ ID NOs: 558 to 560).

[SEQ ID NO: 13 (Rice Protein 7—Q0D7S0)]

Preferably, the peptide comprises a bioactive fragment of the protein of SEQ ID NO: 13 or a homolog thereof, or a bioactive variant of the fragment.

Preferably, the peptide comprises a bioactive fragment selected from SEQ ID NOs: 402-412, or a bioactive variant of the fragment.

The invention also provides a composition comprising at least 1, preferably at least 2, preferably at least 3, preferably at least 4, preferably at least 5, preferably at least 6, preferably at least 7, preferably at least 8, preferably at least 9, or preferably at least 10 bioactive peptides of the invention, each of which comprises a different bioactive fragment of SEQ ID NO: 13 or a homolog thereof. Preferably, the composition comprises a first bioactive peptide comprising a bioactive fragment selected from SEQ ID NOs: 402-412, and a second bioactive peptide comprising a bioactive fragment selected from SEQ ID NOs: 402-412.

In one embodiment, the bioactive peptide, variant or fragment is a cellular growth or proliferation promoting peptide, variant or fragment, respectively.

Homologs of Rice Protein 7 (SEQ ID NO: 13) include *Oryza sativa* Indica Group, *Zizania latifolia, Avena sativa* (SEQ ID NOs: 561 to 564).

[SEQ ID NO: 14 (*Staphylococcus Aureus* Protein 1—P0C1U8)]

Preferably, the peptide comprises a fragment of the protein of SEQ ID NO: 14 or a homolog thereof.

Preferably, the peptide comprises a bioactive fragment selected from SEQ ID NOs: 413-417, or a bioactive variant of the fragment.

The invention also provides a composition comprising at least 1, preferably at least 2, preferably at least 3, preferably at least 4, preferably at least 5, preferably at least 6, preferably at least 7, preferably at least 8, preferably at least 9, or preferably at least 10 bioactive peptides of the invention, each of which comprises a different bioactive fragment of SEQ ID NO: 14 or a homolog thereof. Preferably, the composition comprises a first bioactive peptide comprising a bioactive fragment selected from SEQ ID NOs: 413-417, and a second bioactive peptide comprising a bioactive fragment selected from SEQ ID NOs: 413-417.

In one embodiment, the bioactive peptide, variant or fragment is a cellular growth or proliferation promoting peptide, variant or fragment, respectively.

Homologs of *Staphylococcus Aureus* Protein 1 (SEQ ID NO: 14) include:

```
>gi|580560623|gb|EVF84961.1|glutamyl endopeptidase [Staphylococcus aureus COAS6020]
>gi|580687002|gb|EVH10169.1|glutamyl endopeptidase [Staphylococcus aureus UCIM6080]
>gi|751815683|gb|KIN24957.1|glutamyl endopeptidase [Staphylococcus aureus MRSA_CVM43477]
>gi|781884797|dbj|BAR08486.1|glutamyl endopeptidase precursor [Staphylococcus aureus subsp. aureus]
>gi|781887762|dbj|BAR11210.1|glutamyl endopeptidase precursor [Staphylococcus aureus subsp. aureus]
```

The invention also provides a composition comprising at least one and preferably a plurality of peptides of the invention, wherein each of the peptides of the invention comprises a bioactive fragment of a protein disclosed herein, for example selected from SEQ ID NO: 1 to 14 or a homolog thereof, or a bioactive variant of the fragment.

Typically, the or each peptide of the invention comprises, a bioactive fragment selected from, SEQ ID NOs: 15-505 and 546 to 704 and 717-775, or a bioactive variant of the fragment.

Typically, the or each peptide of the invention is selected from a bioactive fragment selected from, SEQ ID NOs: 15-505 and 546 to 704 and 717-775, or a bioactive variant of the fragment.

The invention also provides a composition comprising at least one and preferably a plurality of peptides of the invention, wherein the or each of the peptides of the invention comprise a bioactive fragment of a pea or rice protein disclosed herein, typically selected from SEQ ID NOs: 1-2 and 7-10. Typically, the or each peptide of the invention is selected from, or comprises a bioactive fragment selected from, SEQ ID NOs: 15-215 and 283 to 340, or a bioactive variant of the fragment.

The invention also provides a composition comprising at least one and preferably a plurality of peptides of the invention, wherein the or each of the peptides of the invention comprise a bioactive fragment of a protein disclosed herein typically selected from SEQ ID NOs: 3-6 and 11-13. Typically, the or each peptide of the invention is selected from, or comprises a bioactive fragment selected from, SEQ ID NOs: 216-282 and 341-412, or a bioactive variant of the fragment.

Preferably, the composition comprises at least two distinct growth promoting peptides of the invention.

Preferably, the composition comprises at least three distinct growth promoting peptides of the invention.

Preferably, the composition comprises at least four distinct growth promoting peptides of the invention.

Preferably, the composition comprises at least five distinct growth promoting peptides of the invention.

Preferably, the composition comprises at least six distinct growth promoting peptides of the invention.

Preferably, the composition comprises at least seven distinct growth promoting peptides of the invention.

Preferably, the composition comprises at least eight distinct growth promoting peptides of the invention.

Preferably, the composition comprises at least nine distinct growth promoting peptides of the invention.

Preferably, the composition comprises at least ten distinct growth promoting peptides of the invention.

In one embodiment, the composition comprises one or more of SEQ ID NOs: 247 to 268.

In one embodiment, the composition comprises one or more of SEQ ID NOs: 248, 249, 252, 253 and 257.

In one embodiment, the invention comprises a composition comprising substantially all of fragments SEQ ID NOs: 15-215 and 283-340, or growth promoting variants of the fragments, or a mixture of the growth promoting fragments and variants.

In one embodiment, the invention comprises a composition comprising substantially all of fragments SEQ ID NOs: 216-282 and 341-412, or growth promoting variants of the fragments, or a mixture of the growth promoting fragments and variants.

In one embodiment, the composition is enriched in peptides having a molecular weight of less than 10 KD.

In one embodiment, the composition is a powder.

The invention also relates to a plaster, bandage or dressing suitable for application to a wound and comprising a peptide or composition of the invention.

The invention also relates to a man-made cell culture media comprising a peptide of the invention. The invention also relates to a man-made cell culture media comprising a composition of the invention. In one embodiment, the cell culture media is formulated for culture of eukaryotic cells. In one embodiment, the cell culture media is formulated for culture of prokaryotic cells.

The invention also relates to a plaster, bandage or dressing suitable for application to a wound and comprising a peptide or composition of the invention.

The invention also relates to a comestible product comprising a growth promoting peptide of the invention. Preferably the comestible product is man-made.

The invention also relates to a comestible product comprising a composition of peptides of the invention. Preferably the comestible product is man-made.

Preferably, the comestible product is a food product for human or animal (mammalian) or cellular consumption.

In one embodiment the man-made comestible product is a beverage, In one embodiment the man-made comestible product is a bakery product. In one embodiment the man-made comestible product is a dairy product. In one embodiment the man-made comestible product is a snack product. In one embodiment the man-made comestible product is a baked extruded food product. In one embodiment the man-made comestible product is powdered milk. In one embodiment the man-made comestible product is an infant formula product. In one embodiment the man-made comestible product is a confectionary product. In one embodiment the man-made comestible product is a yoghurt. In one embodiment the man-made comestible product is a yoghurt drink. In one embodiment the man-made comestible product is an ice cream product. In one embodiment the man-made comestible product is a frozen food product. In one embodiment the man-made comestible product is a breakfast cereal. In one embodiment the man-made comestible product is a bread. In one embodiment the man-made comestible product is a flavoured milk drink. In one embodiment the man-made comestible product is a confectionary bar. In one embodiment the man-made comestible product is a tea or tea product. In one embodiment the man-made comestible product is a based extruded snack product. In one embodiment the man-made comestible product is a fried snack product. In one embodiment the man-made comestible product is a nutritional supplement. In one embodiment the man-made comestible product is a sports nutritional product. In one embodiment the man-made comestible product is a baby food product. In one embodiment the man-made comestible product is a specialty food product for immunocompromised individuals. In one embodiment the man-made comestible product is a food for geriatric patients.

The invention also relates to a peptide of the invention for use in promoting growth of a cell.

The invention also relates to a peptide of the invention for use in promoting growth of a cell culture.

The invention also relates to a peptide of the invention for use in promoting growth of a tissue.

The invention also relates to a peptide of the invention for use in promoting growth of dermal or epithelial tissue.

The invention also relates to a peptide of the invention for use in promoting growth of skin.

The invention also relates to a peptide of the invention for use in promoting growth of an organ.

The invention also relates to a peptide of the invention for use in promoting growth of an organism.

The invention also relates to a composition of the invention for use in promoting growth of a cell.

The invention also relates to a composition of the invention for use in promoting growth of a cell culture.

The invention also relates to a composition of the invention for use in promoting growth of a tissue.

The invention also relates to a composition of the invention for use in promoting growth of epithelial tissue.

The invention also relates to a composition of the invention for use in promoting growth of skin.

The invention also relates to a composition of the invention for use in promoting growth of an organ.

The invention also relates to a composition of the invention for use in promoting growth of an organism.

In one embodiment, the cell, tissue or organism has a normal pathology (for example ageing skin). In one embodiment of the invention, the cell, tissue or skin has abnormal pathology (for example tissue damaged due to trauma, drug use, or epithelial tissue in the GI tract damaged due to an inflammatory disorder).

The growth promoting uses may be in-vivo or in-vitro uses. The growth promoting uses may involve administration to mammal externally (i.e. to the skin) or internally (i.e. to the GI tract).

The invention also relates to a peptide of the invention for use in slowing or inhibiting ageing of human skin.

The invention also relates to a method of slowing or inhibiting ageing of human skin comprising a step of administering a peptide of the invention to the human skin. Typically, the peptide of the invention is administered topically to the skin. Administration may be by means of a plaster or patch or a formulation suitable for topical application.

The invention also relates to a composition of the invention for use in slowing or inhibiting ageing of human skin. The invention also relates to a peptide of the invention for use in preventing or slowing ageing of the human skin.

The invention also relates to a method of slowing or inhibiting ageing of human skin comprising a step of administering a composition of the invention to the human skin. Typically, the composition of the invention is administered topically to the skin.

The invention also relates to a peptide of the invention for use in treatment of a wound in a mammal.

The invention also relates to a composition of peptides of the invention for use in treatment of a wound in a mammal.

The invention also relates to a wound treatment composition or product of the invention for use in treatment of a wound in a mammal.

The invention also relates to a peptide of the invention for use in treatment or prevention of a disease or condition characterised by damaged epithelial cells or tissue.

The invention also relates to a composition of peptides of the invention for use in treatment or prevention of a disease or condition characterised by damaged dermal or epithelial cells or tissue.

In one embodiment, the disease or condition characterised by damaged dermal or epithelial cells or tissue is selected from cancer, trauma The invention also relates to a peptide of the invention for use in maintaining or restoring gut health in a mammal.

The invention also relates to a composition of peptides of the invention for use in maintaining or restoring gut health in in a mammal.

The invention also relates to a peptide of the invention for use in maintaining or restoring muscle health (for example lean tissue mass) in a mammal.

The invention also relates to a composition of peptides of the invention for use in maintaining or restoring muscle health (for example lean tissue mass) in in a mammal.

The invention also relates to a pharmaceutical composition comprising a peptide of the invention in combination with a pharmaceutically acceptable carrier.

The invention also relates to a pharmaceutical composition comprising a composition of peptides of the invention in combination with a pharmaceutically acceptable carrier.

The invention also relates to a peptide of the invention for use in treatment or prevention of an inflammatory disorder in a mammal.

The invention also relates to a composition of the invention for use in treatment or prevention of an inflammatory disorder in a mammal.

The invention also relates to a comestible product, for example a food product comprising a peptide or composition of the invention, for example a dairy or non-dairy product, a solid food or a beverage, a food additive or supplement. The dairy product may be a milk, a cheese, or yoghurt. In one embodiment, the food product is a snack bar. The food product may comprise any amount of the composition of the invention, for example from 0.1% to 30% (w/w).

The peptides of the invention are used in the topical cosmetic or pharmaceutical composition of this invention at cosmetically or pharmaceutically effective concentrations to achieve the desired effect; in a preferred form with regards to the total weight of the composition, between 0.00000001% (in weight) and 20% (in weight); preferably between 0.000001% (in weight) and 15% (in weight), more preferably between 0.0001% (in weight) and 10% (in weight) and even more preferably between 0.0001% (in weight) and 5% (in weight). Ideally, the peptides of the present invention are preferably used from about 0.00001% w/w to about 0.5% w/w [0.1 to 5000 ppm], and more preferably from 0.00005 w/w to about 0.05 w/w [0.5 to 500 ppm], and most preferably from about 0.0001 w/w to about 0.01 w/w of the composition [1 to 100 ppm]. Ideally, the peptides of the present invention are preferably used from about 0.0001% w/w to about 0.004% w/w of the composition.

For compositions of peptides of the invention, a typical daily dosage may be 0.2 g to 100 g. However, when administered as a food for special medicinal purpose, or medical food, the daily dosage may be 50-500 g per day.

The dosage of compositions of the invention for use in food products and food supplements (i.e. comestible compositions) will be broadly in the 0.2-100 g/day range. In one embodiment, the daily dosage is 1-10 g/day, ideally about 3-8 g/day. In one embodiment, the daily dosage is 10-20 g/day. In one embodiment, the daily dosage is 20-30 g/day. In one embodiment, the daily dosage is 30-40 g/day. In one embodiment, the daily dosage is 10-100 g/day. In one embodiment, the daily dosage is about 5 g/day, ideally about 3-8 g/day. In one embodiment, the dosage is 2-1000 mg/day/kg body weight. In one embodiment, the dosage is 10-500 mg/day/kg body weight. In one embodiment, the dosage is 10-100 mg/day/kg body weight. In one embodiment, the dosage is 30-70 mg/day/kg body weight. The dosage of peptides of the invention for food supplements may be 0.00001 mg-0.01 mg per day or dose.

The food product may be a Food for Specific Medicinal Purposes (FSMP) which is defined as foods that are specifically formulated, processed and intended for the dietary management of diseases, disorders or medical conditions of individuals who are being treated under medical supervision. These foods are intended for the exclusive or partial feeding of people whose nutritional requirements cannot be met by normal foods.

The invention also relates to a man-made personal care composition comprising a peptide of the invention.

The invention also relates to a man-made personal care composition comprising a composition of peptides of the invention.

In one embodiment the personal care composition is a skincare product. In one embodiment the personal care composition is a product formulated for topical application to the skin of a human. In one embodiment the personal care composition is an anti-aging product. In one embodiment the personal care composition is a dentrifice product. In one embodiment the personal care composition is a perfumery product. In one embodiment the personal care composition is a deodorant product. In one embodiment the personal care composition is an anti-perspirant product. In one embodiment the personal care composition is a soap. In one embodiment the personal care composition is a liquid soap. In one embodiment the personal care composition is a cream. In one embodiment the personal care composition is a lotion. In one embodiment the personal care composition is a gel. In one embodiment the personal care composition is a powder.

The invention also relates to a man-made wound treatment composition comprising a peptide of the invention. The invention also relates to a man-made wound treatment composition comprising a composition of the invention. Typically, the wound treatment composition is formulated for topical application to a wound. In one embodiment, the composition comprises a cream, gel, lotion, powder.

The invention also provides topical composition comprising a peptide of the invention. It will be appreciated that the topical composition may comprise a plurality of peptides, fragments and/or variants. In one embodiment, the topical composition comprises substantially all the peptides. In one embodiment, the topical composition comprises substantially all the variants. The topical composition of the invention may be presented in a formulation selected from the group comprising creams, multiple emulsions, anhydrous compositions, aqueous dispersions, oils, milks, balsams, foams, lotions, gels, cream gels, hydro-alcoholic solutions, hydro-glycolic solutions, cosmetic, personal care product, hydrogels, liniments, sera, soaps, dusting powder, paste, semi solid formulations, liniments, serums, shampoo, conditioner, ointments, any rinse off formulation, talc, mousses, powders, sprays, aerosols, solutions, suspensions, emulsions, syrups, elixirs, polysaccharide films, patches, gel patches, bandages, an adhesive system, water-in-oil emulsions, oil-in-water emulsions, and silicone emulsions.

In an embodiment of the current invention, the emulsion contains a lipid or oil. The emulsion may be, but is not limited to, oil-in-water, water-in-oil, water-in-oil-in-water and oil-in-water-in-silcone emulsions. The emulsion may contain a humectant. The emulsion may contain an anti-foaming agent, such as silicone. The emulsion may have any suitable viscosity. Emulsions may further contain an emulsifier and/or an anti-foaming agent. Methods of preparing an emulsion are known to a person skilled in the art.

The topical composition of the invention may be incorporated into a medical device for administration. Such a device can include but is not limited to a fabric, patch, bandage, gauge, sock, tight, underwear, dressing, glove, mask, adhesive patches, non-adhesive patches, occlusive patches and microelectric patches or suitable adhesive system. In such an embodiment, the device is in direct contact with the keratinous layer such as the skin, thus releasing the peptides of the invention. It will be understood that the topical composition may be incorporated in any suitable form as detailed herein. For example, the topical composition or peptides of the invention can be incorporated into the device or be present on the surface of the device or can be in a cream, gel or wax formulation or any suitable formulation defined herein and incorporated into the device or on the surface of the device. The device may be adapted for adhesion or attachment to the skin.

In one embodiment the device is adapted to release a constant quantity of the composition or the peptides of the invention. It will be understood that the amount of the composition contained in the sustained release system will depend, for example, on where the composition is to be administered, the kinetics and duration of the release of the composition of the invention, as well as the nature of the condition, disorder and/or disease to be treated and/or cared for. The device may be such that the composition is released by biodegradation of the device, or by friction between the device and the body, due to bodily moisture, the skin's pH or body temperature.

In an embodiment of the invention the topical composition may further comprise at least one cosmetically or pharmaceutically acceptable excipient. Excipient may be used interchangeably with functional ingredient or additive. It will be understood that although the topical compositions of the current invention can be administered alone, they will generally be administered in admixture with a cosmetic or pharmaceutical excipient. Cosmetically or pharmaceutically acceptable excipient are well known in the art and any known excipient, may be used provided that it is suitable for topical administration and is dermatologically acceptable without undue toxicity, incompatibility and/or allergic reaction.

Preferably any excipient included is present in trace amounts. The amount of excipient included will depend on numerous factors, including the type of excipient used, the nature of the excipient, the component(s) of the topical composition, the amount of active or peptide in the topical composition and/or the intended use of the topical composition. The nature and amount of any excipient should not unacceptably alter the benefits of the peptides of this invention.

In an embodiment of the invention the excipient may be a suitable diluent, carrier, binder, lubricant, suspending agent, coating agent, preservative, stabilisers, dyes, vehicle, solubilising agent, base, emollient, emulsifying agent, fragrance, humectant, and/or surfactants.

Examples of suitable diluents include, but are not limited to, any diluent disclosed in disclosed in US2014120131 or US2004132667. Examples include ethanol, glycerol and water.

Examples of suitable carriers include, but are not limited to, lactose, starch, glucose, methyl cellulose, magnesium stearate, mannitol, sorbitol and any suitable carrier disclosed in US2014120131 or US2004132667.

Examples of suitable binders include, but are not limited to, starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol and any suitable binder disclosed in US2014120131 or US2004132667.

Examples of suitable lubricants include, but are not limited to, sodium oleate, sodium stearate, magnesium stearate, sodium benzoate, sodium acetate, and sodium chloride and any suitable lubricant disclosed in US2014120131 or US2004132667.

The carrier may be any suitable carried known in the art or disclosed in US2014120131 or US2004132667. In some embodiments, the carrier may include, but is not limited to, a liquid, such as water, oils or surfactants, including those of petroleum, animal, plant or synthetic origin, polymer, oil, such as peanut oil, mineral oil, castor oil, soybean oil, alcohol, polysorbates, sorbitan esters, ether sulfates, sulfates, betaines, glycosides, maltosides, fatty alcohols, non-oxynols, poloxamers, polyoxyethylenes, polyethylene glycols, dextrose, glycerol, or digitonin. It will be understood that the carrier will be dermatologically acceptable. Preferred carriers contain an emulsion such as oil-in-water, water-in-oil, water-in-oil-in-water and oil-in-water-in-silicone emulsions. Emulsions may further contain an emulsifier and/or an anti-foaming agent.

In an embodiment of the invention, the topical composition may further comprise one or more additional ingredients. The topical composition of the invention may be administered consecutively, simultaneously or sequentially with the one or more other additional agents. Such additional ingredients may be those of benefit to include in a topical composition, or of benefit depending on the intended use of the topical composition. The additional ingredient may be active or functional or both.

Examples of such additional ingredients include, but are not limited to, one or more of cleaning agents, conditioning agents, sunscreen, pigment, moisturiser, thickening agents, gelling agents, essential oil, astringents, pigments, anti-caking agent, anti-foaming agent, binders, additives, buffers, chelating agents, external analgesics, film formers or materials, bulking agents, polymers, opacifying agents, pH adjusters, propellants, reducing agents, sequestrants, skin bleaching and lightening agents, skin conditioning agents, aloe vera, healing agents, soothing agents, smoothing agents, pantothenic acid, treating agents, thickeners, vitamins. colourants, pharmaceuticals, antiseptic agents, antifoaming agents, buffering agents, astringents, polymers, pH adjuster, deodorant or any other dermatologically acceptable carrier or surfactant.

It is to be understood that additional ingredients listed may provide more than one benefit. The classification given herein is for clarity and convenience only and not intended to limit the additional ingredient to that particular application or category listed.

Any additional ingredients should be suitable for application to the skin without undue toxicity, incompatibility and/or allergic reaction.

In some embodiments, the additional ingredient has glucose transport activity or aids glucose transport activity. In some embodiments, the additional ingredient has anti-inflammatory activity or aids anti-inflammatory activity. In some embodiments, the additional ingredient has anti-aging activity or aids anti-aging activity. In some embodiments, the additional ingredient is for keratinous layer health and/or development, skin health and/or development, and/or muscle health, recovery and/or development. The active agent may be a pharmacological enhancer. Such active agents are known and available on the market. In such cases, the topical composition of the invention may be administered consecutively, simultaneously or sequentially with the one or more other active agents.

In some embodiments, the additional ingredient may be farnesol ([2E, 6E],-3, 7, 11,-trimethyl-2, 6, 10, dodecatrien-1-ol), phytantriol (3, 7, 11, 15, tetramethylhexadecane-1, 2, 3,-triol), desquamation actives, enzymes, enzyme inhibitors, enzyme activators, botanical extracts and marine extracts, anti-acne actives, anti-wrinkle or anti atrophy actives, anti-oxidant/radical scavengers, chelators, flavonoids, anti-inflammatory agents, anti-cellulite agents, topical anaesthetics, tanning actives, skin lightening agents, skin healing agents, bisabolol, antimicrobial or antifungal active, sunscreen actives, particulate material, conditioning agents, structuring agents, thickening agent, The desquamation active may be any suitable agent that enhances the skin appearance or texture of the skin and is as disclosed in US2014120131 or US2004132667.

Examples of anti-acne actives are as disclosed in US2014120131 or US2004132667 and include, resorcinol, salicylic acid, erythromycin, zine, sulfur, benzoyl peroxides.

Examples of thickening agents are as disclosed in US2014120131 or US2004132667 and include carboxylic acid polymers, crosslinked polyacrylate polymers, polyacrylamide polymers, polysaccharides.

Examples of conditioning agents are as disclosed in US2014120131 or US2004132667 and include humectants, moisturiser or skin conditioner.

Examples of structuring agents are as disclosed in US2014120131 or US2004132667 and include any agent that provide rheological characteristics to the composition and contributes to the stability of the composition.

Any suitable antimicrobial or antifungal active may be used and examples are as disclosed in US2014120131 or US2004132667. Such actives are capable of destroying microbes, preventing growth or action of microbes. Examples include but are not limited to β-lactam drugs, quinolone drugs, tetracycline, erythromycin, streptomycin sulfate, salicylic acid, benzoyl peroxide.

Examples of a particulate material include metallic oxide. Examples of anti-cellulite agents include xanthine agents. Examples of tanning actives includes 1, 3-dihydroxy-2-propanone and those disclosed in US2014120131 or US2004132667. Examples of topical anaesthetics include benzocaine, lidocaine and bupivacaine and those disclosed in US2014120131 or US2004132667.

Examples of skin lightening agents include any agent known in the art such as kojic acid, ascorbic acid and those disclosed in US2014120131 or US2004132667.

Examples of sunscreen actives include any suitable organic or inorganic sunscreen active.

Examples include metallic oxides, 2-ethylhexyl-p-methoxycinnamate and those disclosed in US2014120131 or US2004132667.

Examples of skin healing agents includes panthenoic acid as disclosed in US2014120131 or US2004132667.

Examples of anti-inflammatory agents include any agent that enhances the skin appearance, tone or colour and include but are not limited to corticosteroids, hydrocortisone, non-steroidal agents such as ibuprofen and aspirin and those disclosed in US2014120131 or US2004132667.

Examples of flavonoids includes flavanones, methoxy flavonones, unsubstituted chalcone and mixtures thereof and those disclosed in US2014120131 or US2004132667.

Examples of enzymes include lipases, proteases, catalase, super oxide-dismutase, amylase, peroxidase, glucuronidase, ceramidases, hyaluronidases. Examples of enzyme inhibitors include trypsine inhibitors, Bowmann Birk inhibitors, chymotrypsin inhibitors, botanical extracts, flavonoids, quercetin chalcone and those disclosed in US2014120131 or US2004132667 and mixtures thereof. Examples of enzyme activators include coenzyme A, Q10 (ubiquinone), glycyrrhizin, berberine, chrysin and those disclosed in US2014120131 or US2004132667 and mixtures thereof Examples of anti-wrinkle or anti atrophy actives include sulfur containing D and L amino acids, particular, N-acyl derivatives such as N-acetyl-L-cysteine, hydroxyl acids, phytic acid, lipoic acid, lysophosphatidic acid, skin peel agents, vitamin $B_3$, retinoids and those disclosed in US2014120131 or US2004132667 and mixtures thereof.

The anti-oxidant/radical scavenger agent may be any agent that is useful for providing protection against UV radiation or other environmental agents which may cause skin damage such as those disclosed in US2014120131 or US2004132667. Examples of anti-oxidant/radical scavengers include ascorbic acid, its salts and derivatives (vitamin C), tocopherol its salts and derivatives (vitamin E), butylated hydroxyl benzoic acids and their salts, peroxides, gallic acids and alkyl esters, sorbic acid, lipoic acid, amines, lycine pidolate, arginine pilolate, nordihydroguaiaretic acid, bioflavonoids, curcumin, lysine, methionine, proline, superoxide dismutase, silymarin, tea extracts and mixtures thereof.

Examples of chelators include EDTA, NTA, hydoxamic acids, phytic acid, lactoferrin and those disclosed in US2014120131 or US2004132667 and mixtures thereof. A chelator means an agent capable of removing a metal ion by forming a complex so that the metal ion cannot participate in or catalyse chemical reactions. A chelator is useful for protection against UV radiation or other environmental agents that can cause skin damage.

It will be appreciated that a plurality of additional ingredients may be added. The amount of the additional ingredient may be from about 0.001% to about 50% weight of the composition, preferably, about 0.01% to about 20%, preferably about 0.1% to about 10%, about 0.5% to about 10%, about 1% to about 5%, preferably 2% weight of the composition. The amount of additional ingredient included will depend on numerous factors, including the type of additional ingredient used, the nature of the additional ingredient, the component(s) of the topical composition, the amount of active or peptide in the topical composition and/or the intended use of the topical composition. The nature and amount of any additional ingredient should not unacceptably alter the benefits of the peptides of this invention.

The topical composition may be alcohol free.

In some embodiments of the invention, the composition further comprises one or more additional active agents, in addition to the peptide of the invention (also known as the active of the composition). In addition, or alternatively, the composition may be administered with one or more other additional active agents. Typical said additional active agent is present in trace amounts only. In some embodiments, there may be no additional active agent present in the composition. The amount of additional active agent included will depend on numerous factors, including the type of additional active agent used, the nature of the additional active agent, the component(s) of the topical composition, the amount of active or peptide in the topical composition and/or the intended use of the topical composition. The nature and amount of any additional active agent should not unacceptably alter the benefits of the peptides of this invention.

It is to be understood that an ingredient that is considered to be an "active" ingredient in one product may be a "functional" or "excipient" ingredient in another and vice versa. It will also be appreciated that some ingredients play a dual role as both an active ingredient and as a functional or excipient ingredient.

Examples of the additional active agents include glucose transport promoting drugs, skin supplement, agent for treatment and/or care of the skin, anti-inflammatory agent, an anti-aging agent, a cellular growth promoting agent and pharmacological enhancers. Such agents are well known in the art and it will be appreciated that any suitable additional active agent may be used. Additional active agents for treatment and/or care of the skin may include collagen synthesis agents, retinoids, exfoliating agents, anti-cellulite agents, elastase inhibiting agents, melanin synthesis stimulating or inhibiting agents, self-tanning agents, antiaging agents, antimicrobial agents, antifungal agents, fungistatic agents, bactericidal agents, and healing agents. Active agents also include anti-inflammatory agents.

Any additional active agent should be suitable for application to the skin without undue toxicity, incompatibility and/or allergic reaction.

It will be understood that the classification given herein is for clarity and convenience only and not intended to limit the additional ingredient, excipient, or active to that particular application or category listed.

In a particularly preferred embodiment, the methods and uses of the invention involve administration of a peptide or composition of the invention in combination with one or more other active agents, for example, existing growth promoting drugs or pharmacological enhancers available on the market. In such cases, the compounds of the invention may be administered consecutively, simultaneously or sequentially with the one or more other active agents.

The effect of the current invention is accomplished by topical application or administration of the topical composition of the invention described herein to a person, animal or a patient in need of treatment or care. Topical delivery preferably means delivery to a keratinous layer such as the skin, hair and/or nails, but can also mean delivery to a body lumen lined with epithelial cells, for example the lungs or airways, the gastrointestinal tract, the buccal cavity. The effect may be confined to the surface of the skin or may be within the skin or a combination of both.

The topical composition of the invention is administered in a cosmetically or pharmaceutically effective amount. In other words, in an amount that is non-toxic but sufficient amount to provide the desired effect. It will be appreciated that a person skilled in the art would be capable of determining an appropriate dose of the topical compositions of the invention to administer without undue experimentation. Alternatively, a physician will determine the actual dose that is most suitable for a patient depending on the particular condition, disease or disorder to be treated or cared for and the age, body weight and/or health of the person. It will depend on a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy. There can, of course, be individual instances where higher or lower dosage ranges are merited, and such are within the scope of this invention. For example, the composition may be administered at a dose of from 0.01 to 50 mg/kg body weight, such as from 0.1 to 30 mg/kg, more preferably from 0.1 to 20 mg/kg body weight, more preferably from 0.1 to 10 mg/kg body weight, preferably 0.1 to 5 mg/kg body weight. In an exemplary embodiment, one or more doses of 10 to 300 mg/day or more preferably, 10 to 150 mg/day, will be administered to the patient. The amount and the frequency is as best suited to the purpose. The frequency of application or administration can vary greatly, depending on the needs of each subject, with a recommendation of an application or administration range from once a month to ten times a day, preferably from once a week to four times a day, more preferably from three times a week to three times a day, even more preferably once or twice a day.

In preferred embodiments, repeated use of the topical composition is provided. The topical composition may be applied by, but not limited to, rubbing, or massaging into the keratinous tissue, skin or area of the body to be treated or cared for. In some embodiments, the composition is left on or not removed from the area of the body. In other embodiments, the composition is removed after a period of time, such as, but not limited to, from about 2 minutes to 60 minutes, from about 5 minutes to about 30 minutes, preferably from about 10 minutes to about 20 minutes. The composition may be removed immediately after application. In some embodiments of the current invention, the composition of the invention may be applied to an area to be treated by means to achieve a greater penetration of the composition and/or peptide of the invention, such as, but not limited to, iontophoresis, sonophoresis, electroporation, microelectric patches, mechanical pressure, osmotic pressure gradient, occlusive cure, microinjections or needle-free injections by means of pressure, such as injections by oxygen pressure, or any combination thereof.

The peptides of the invention are used in the topical cosmetic or pharmaceutical composition of this invention at cosmetically or pharmaceutically effective concentrations to achieve the desired effect; in a preferred form with regards to the total weight of the composition, between 0.00000001% (in weight) and 20% (in weight); preferably between 0.000001% (in weight) and 15% (in weight), more preferably between 0.0001% (in weight) and 10% (in weight) and even more preferably between 0.0001% (in weight) and 5% (in weight).

In some embodiments of the current invention, the composition may be delivered via any one of liposomes, mixed liposomes, oleosomes, niosomes, ethosomes, millicapsules, capsules, macrocapsules, nanocapsules, nanostructured lipid carriers, sponges, cyclodextrins, vesicles, micelles, mixed micelles of surfactants, surfactant-phospholipid mixed micelles, milli spheres, spheres, liposphoeres, particles, nanospheres, nanoparticles, milliparticles, solid nanopartciles as well as microemulsions including water-in-oil microemulsions with an internal structure of reverse micelle and nanoemulsions microspheres, microparticles.

A variety of methods are available for preparing liposomes. See, e.g., Szoka et al., Ann. Rev. Biophys. Bioeng. 9:467 (1980), U.S. Pat. Nos. 4,186,183, 4,217,344, 4,235,871, 4,261,975, 4,485,054, 4,501,728, 4,774,085, 4,837,028, 4,235,871, 4,261,975, 4,485,054, 4,501,728, 4,774,085, 4,837,028, 4,946,787, PCT Publication No. WO 91/17424, Deamer & Bangham, Biochim. Biophys. Acta 443:629-634 (1976); Fraley, et al., PNAS 76:3348-3352 (1979); Hope et al., Biochim. Biophys. Acta 812:55-65 (1985); Mayer et al., Biochim. Biophys. Acta 858:161-168 (1986); Williams et al., PNAS 85:242-246 (1988); Liposomes (Ostro (ed.), 1983, Chapter 1); Hope et al., Chem. Phys. Lip. 40:89 (1986); Gregoriadis, Liposome Technology (1984) and Lasic, Liposomes: from Physics to Applications (1993)). Suitable methods include, for example, sonication, extrusion, high pressure/homogenization, microfluidization, detergent dialysis, calcium-induced fusion of small liposome vehicles and ether fusion methods, all of which are well known in the art.

These delivery systems may be adapted to achieve a greater penetration of the compound and/or peptides of the invention. This may improve pharmacokinetic and pharmacodynamics properties. The delivery system may be a sustained release system wherein the compound or peptide of the invention is gradually released during a period of time and preferably with a constant release rate over a period of time. The delivery systems are prepared by methods known in the art. The amount of peptide contained in the sustained release system will depend on where the composition is to be delivered and the duration of the release as well as the type of the condition, disease and/or disorder to be treated or cared for.

The topical composition of the invention may be for human or animal usage in human and veterinary medicine.

The topical composition of the invention may be used for pharmaceutical, personal care and/or cosmetic uses.

The composition can be used to treat or care for any disease, disorder or condition of the skin, including but not limited to, psoriasis, dermatitis, allergic dermatitis, eczema, spongiosis, edema, skin cancer, ulcers, acne, scars, cellulitis, elastosis, keratosis, rosacea, varicose veins, inflammatory disorders.

The topical composition may be used to for treating or caring for visible signs of aging including but not limited to wrinkles, stretch marks and dark circles, dryness, fine lines, age spots, red blotches, sagging skin, and conditions caused by sun exposure including sunburn, stress, pollution and/ diet. The topical composition may also be used for delaying, slowing or inhibiting the skins or the onset of aging. The composition may be administered by a medical device, such as a plaster or a patch as described herein.

The topical composition may be used to treat or care for a wound in a mammal. In another embodiment, the topical composition is for use in the treatment or prevention of a disease or condition characterised by damaged epithelial cells or tissue, and/or damaged dermal or epithelial cells or tissue. The disease may be but is not limited to cancer and trauma.

The topical composition may be used to treat or care for any muscle condition, to improve, muscle status in a mammal, to promote recovery of muscle, typically following exercise, to maintain or restore muscle health (for example lean tissue mass) in a mammal, to enhance physical performance, in treatment or prevention of a disease or condition characterised by lethargy or low energy levels.

The topical composition may be used to promote growth of a tissue, promote growth of epithelial tissue, promote growth of skin, promote growth of an organ, promote growth of an organism. The skin can have a normal pathology and/or an abnormal pathology.

The topical composition may also be used to treat or care for any inflammatory disorder.

A further aspect of the invention relates to a pharmaceutical composition comprising a peptide of the invention or a composition of peptides of the invention, admixed with one or more pharmaceutically acceptable diluents, excipients or carriers. Even though the peptides and compositions of the present invention can be administered alone, they will generally be administered in admixture with a pharmaceutical carrier, excipient or diluent, particularly for human therapy. The pharmaceutical compositions may be for human or animal usage in human and veterinary medicine. Examples of such suitable excipients for the various different forms of pharmaceutical compositions described herein may be found in the "Handbook of Pharmaceutical Excipients, $2^{nd}$ Edition, (1994), Edited by A Wade and PJ Weller. In particular, formulations for topical delivery are described in Topical drug delivery formulations edited by David Osborne and Antonio Aman, Taylor & Francis, the complete contents of which are incorporated herein by reference. Acceptable carriers or diluents for therapeutic use are well known in the pharmaceutical art, and are described, for example, in Remington's Pharmaceutical Sciences, Mack Publishing Co. (A. R. Gennaro edit. 1985). Examples of suitable carriers include lactose, starch, glucose, methyl cellulose, magnesium stearate, mannitol, sorbitol and the like. Examples of suitable diluents include ethanol, glycerol and water. The choice of pharmaceutical carrier, excipient or diluent can be selected with regard to the intended route of administration and standard pharmaceutical practice. The pharmaceutical compositions may comprise as, or in addition to, the carrier, excipient or diluent any suitable binder (s), lubricant(s), suspending agent(s), coating agent(s), solubilising agent(s). Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol. Examples of suitable lubricants include sodium oleate, sodium stearate, magnesium stearate, sodium benzoate, sodium acetate, sodium chloride and the like. Preservatives, stabilizers, dyes and even flavouring agents may be provided in the pharmaceutical composition. Examples of preservatives include sodium benzoate, sorbic acid and esters of p-hydroxybenzoic acid. Antioxidants and suspending agents may be also used.

The peptide or composition of the invention may be adapted for topical, oral, rectal, parenteral, intramuscular, intraperitoneal, intra-arterial, intrabronchial, subcutaneous, intradermal, intravenous, nasal, vaginal, buccal or sublingual routes of administration. For oral administration, particular use is made of compressed tablets, pills, tablets, gellules, drops, and capsules. Preferably, these compositions contain from 1 to 250 mg and more preferably from 10-100 mg, of active ingredient per dose. Other forms of administration comprise solutions or emulsions which may be injected intravenously, intra-arterial, subcutaneously, intradermally, intraperitoneally or intramuscularly, and which are prepared from sterile or sterilisable solutions. The pharmaceutical compositions of the present invention may also be in form of suppositories, vaginal rings, pessaries, suspensions, emulsions, lotions, ointments, creams, gels, sprays, solutions or dusting powders. The composition of the invention may be formulated for topical delivery. Topical delivery generally means delivery to the skin, but can also mean delivery to a body lumen lined with epithelial cells, for example the lungs or airways, the gastrointestinal tract, the buccal cavity. In particular, formulations for topical delivery are described in Topical drug delivery formulations edited by David Osborne and Antonio Aman, Taylor & Francis, the complete contents of which are incorporated herein by reference. Compositions or formulations for delivery to the airways are described in O'Riordan et al (Respir Care, 2002, November 47), EP2050437, WO2005023290, US2010098660, and US20070053845. Composition and formulations for delivering active agents to the iluem, especially the proximal iluem, include microparticles and microencapsulates where the active agent is encapsulated within a protecting matrix formed of polymer or dairy protein that is acid resistant but prone to dissolution in the more alkaline environment of the ileum. Examples of such delivery systems are described in EP1072600.2 and EP13171757.1. An alternative means of transdermal administration is by use of a skin patch. For example, the active ingredient can be incorporated into a cream consisting of an aqueous emulsion of polyethylene glycols or liquid paraffin. The active ingredient can also be incorporated, at a concentration of between 1 and 10% by weight, into an ointment consisting of a white wax or white soft paraffin base together with such stabilisers and preservatives as may be required.

Injectable forms may contain between 10-1000 mg, preferably between 10-250 mg, of active ingredient per dose.

Compositions may be formulated in unit dosage form, i.e., in the form of discrete portions containing a unit dose, or a multiple or sub-unit of a unit dose.

A person of ordinary skill in the art can easily determine an appropriate dose of one of the instant compositions to administer to a subject without undue experimentation. Typically, a physician will determine the actual dosage which will be most suitable for an individual patient and it will depend on a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy. The dosages disclosed herein are exemplary of the average case. There can of course be individual instances where higher or lower dosage ranges are merited, and such are within the scope of this invention. Depending upon the need, the agent may be administered at a dose of from 0.01 to 30 mg/kg body weight, such as from 0.1 to 10 mg/kg, more preferably from 0.1 to 1 mg/kg body weight. In an exemplary embodiment, one or more doses of 10 to 300 mg/day or more preferably, 10 to 150 mg/day, will be administered to the patient for the treatment of an inflammatory disorder.

In a particularly preferred embodiment, the methods and uses of the invention involve administration of a peptide or composition of the invention in combination with one or more other active agents, for example, existing anti-inflammatory drugs or pharmacological enhancers available on the market. In such cases, the compounds of the invention may be administered consecutively, simultaneously or sequentially with the one or more other active agents.

In one embodiment of the invention, the peptide of the invention may be administered in the form of a conjugate comprising the peptide, and may optionally include a linker, and a partner molecule, for example a protein such as an antibody molecule intended to increase the half-life of the conjugate in-vivo. In one embodiment, the peptide may be modified to substitute one or more amino acids with amino acids employed to attach partner molecules. For example, an amino acid may be substituted with a lysine residue for the purpose of conjugating a partner molecule such as a PEG molecule.

Definitions

All publications, patents, patent applications and other references mentioned herein are hereby incorporated by reference in their entireties for all purposes as if each individual publication, patent or patent application were specifically and individually indicated to be incorporated by reference and the content thereof recited in full.

Where used herein and unless specifically indicated otherwise, the following terms are intended to have the following meanings in addition to any broader (or narrower) meanings the terms might enjoy in the art:

Unless otherwise required by context, the use herein of the singular is to be read to include the plural and vice versa. The term "a" or "an" used in relation to an entity is to be read to refer to one or more of that entity. As such, the terms "a" (or "an"), "one or more," and "at least one" are used interchangeably herein.

As used herein, the term "comprise," or variations thereof such as "comprises" or "comprising," are to be read to indicate the inclusion of any recited integer (e.g. a feature, element, characteristic, property, method/process step or limitation) or group of integers (e.g. features, element, characteristics, properties, method/process steps or limitations) but not the exclusion of any other integer or group of integers. Thus, as used herein the term "comprising" is inclusive or open-ended and does not exclude additional, unrecited integers or method/process steps.

As used herein, the term "disease" is used to define any abnormal condition that impairs physiological function and is associated with specific symptoms. The term is used broadly to encompass any disorder, illness, abnormality, pathology, sickness, condition or syndrome in which physiological function is impaired irrespective of the nature of the aetiology (or indeed whether the aetiological basis for the disease is established). It therefore encompasses conditions arising from infection, trauma, injury, surgery, radiological ablation, poisoning or nutritional deficiencies.

As used herein, the term "treatment" or "treating" refers to an intervention (e.g. the administration of an agent to a subject) which cures, ameliorates or lessens the symptoms of a disease or removes (or lessens the impact of) its cause(s) (for example, the reduction in accumulation of pathological levels of lysosomal enzymes). In this case, the term is used synonymously with the term "therapy".

Additionally, the terms "treatment" or "treating" refers to an intervention (e.g. the administration of an agent to a subject) which prevents or delays the onset or progression of a disease or reduces (or eradicates) its incidence within a treated population. In this case, the term treatment is used synonymously with the term "prophylaxis".

As used herein, an effective amount or a therapeutically effective amount of an agent defines an amount that can be administered to a subject without excessive toxicity, irritation, allergic response, or other problem or complication, commensurate with a reasonable benefit/risk ratio, but one that is sufficient to provide the desired effect, e.g. the treatment or prophylaxis manifested by a permanent or temporary improvement in the subject's condition. The amount will vary from subject to subject, depending on the age and general condition of the individual, mode of administration and other factors. Thus, while it is not possible to specify an exact effective amount, those skilled in the art will be able to determine an appropriate "effective" amount in any individual case using routine experimentation and background general knowledge. A therapeutic result in this context includes eradication or lessening of symptoms, reduced pain or discomfort, prolonged survival, improved mobility and other markers of clinical improvement. A therapeutic result need not be a complete cure.

The term "human or animal" should be understood to means humans or mammalian or non-mammalian animals such as fish.

The term "composition" should be understood to mean a composition of matter made by the hand of man and not occurring in nature. Exemplary compositions include food compositions, beverage compositions, pharmaceutical compositions, nutritional supplement compositions, personal care compositions and healthcare compositions.

The term "peptide" used herein refers to a polymer composed of 5 to 50 amino acid monomers typically via peptide bond linkage. Peptides (including fragments and variants thereof) of and for use in the invention may be generated wholly or partly by chemical synthesis or by expression from nucleic acid. For example, the peptides of and for use in the present invention can be readily prepared according to well-established, standard liquid or, preferably, solid-phase peptide synthesis methods known in the art (see, for example, J. M. Stewart and J. D. Young, Solid Phase Peptide Synthesis, 2nd edition, Pierce Chemical Company, Rockford, Ill. (1984), in M. Bodanzsky and A. Bodanzsky, The Practice of Peptide Synthesis, Springer Verlag, New York (1984). When necessary, any of the peptides employed in the invention can be chemically modified to increase their stability. A chemically modified peptide or a peptide analog includes any functional chemical equivalent of the peptide characterized by its increased stability and/or efficacy in vivo or in vitro in respect of the practice of the invention. The term peptide analog also refers to any amino acid derivative of a peptide as described herein. A peptide analog can be produced by procedures that include, but are not limited to, modifications to side chains, incorporation of unnatural amino acids and/or their derivatives during peptide synthesis and the use of cross-linkers and other methods that impose conformational constraint on the peptides or their analogs. Examples of side chain modifications include modification of amino groups, such as by reductive alkylation by reaction with an aldehyde followed by reduction with $NaBH_4$; amidation with methylacetimidate; acetylation with acetic anhydride; carbamylation of amino groups with cyanate; trinitrobenzylation of amino groups with 2, 4, 6, trinitrobenzene sulfonic acid (TNBS); alkylation of amino groups with succinic anhydride and tetrahydrophthalic anhydride; and pyridoxylation of lysine with pyridoxa-5'-phosphate followed by reduction with $NABH_4$. The guanidino group of arginine residues may be modified by the formation of heterocyclic condensation products with reagents such as 2,3-butanedione, phenylglyoxal and glyoxal. The carboxyl group may be modified by carbodiimide activation via o-acylisourea formation followed by subsequent derivatization, for example, to a corresponding amide. Sulfhydryl groups may be modified by methods, such as carboxymethylation with iodoacetic acid or iodoacetamide; performic acid oxidation to cysteic acid; formation of mixed disulphides with other thiol compounds; reaction with maleimide; maleic anhydride or other substituted maleimide; formation of mercurial derivatives using 4-chloromercuribenzoate, 4-chloromercuriphenylsulfonic acid, phenylmercury chloride, 2-chloromercuric-4-nitrophenol and other mercurials; carbamylation with cyanate at alkaline pH. Tryptophan residues may be modified by, for example, oxidation with N-bromosuccinimide or alkylation of the indole ring with 2-hydroxy-5-nitrobenzyl bromide or sulphonyl halides. Tryosine residues may be altered by nitration with tetranitromethane to form a 3-nitrotyrosine derivative. Modification of the imidazole ring of a histidine residue may be accomplished by alkylation with iodoacetic acid derivatives or N-carbethoxylation with diethylpyrocarbonate. Examples of incorporating unnatural amino acids and derivatives during peptide synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids. Peptide structure modification includes the generation of retro-inverso peptides comprising the reversed sequence encoded by D-amino acids.

The term "modified peptide" is used interchangeably with the term derivative of the peptide. The modified peptide includes a peptide which has been substituted with one or more groups as defined herein. The modification may be any modified that provides the peptides and or the composition of the invention with an increased ability to penetrate a cell. The modification may be any modification that increases the half-life of the composition or peptides of the invention. In one embodiment, the group is a protecting group. The protecting group may be an N-terminal protecting group, a C-terminal protecting group or a side-chain protecting group. The peptide may have one or more of these protecting groups. The person skilled in the art is aware of suitable techniques to react amino acids with these protecting groups. These groups can be added by preparation methods known in the art, for example the methods as outlined in paragraphs [0104] to [0107] of US2014120141. The groups may remain on the peptide or may be removed. The protecting group may be added during synthesis. In an embodiment of the invention the peptides may be substituted with a group selected from one or more straight chain or branched chain, long or short chain, saturated, or unsaturated, substituted with a hydroxyl, amino, amino acyl, sulfate or sulphide group or unsubstituted having from 1 to 29 carbon atoms. N-acyl derivatives include acyl groups derived from acetic acid, capric acid, lauric acid, myristic acid, octanoic acid, palmitic acid, stearic acid, behenic acid, linoleic acid, linolenic acid, lipoic acid, oleic acid, isosteric acid, elaidoic acid, 2-ethylhexaneic acid, coconut oil fatty acid, tallow fatty acid, hardened tallow fatty acid, palm kernel fatty acid, lanolin fatty acid or similar acids. These may be substituted or unsubstituted. When substituted they are preferably substituted with hydroxyl, or sulphur containing groups such as but not limited to $SO_3H$, SH, or S—S. In an embodiment of the current invention, the peptide is $R_1$—X—$R_2$. $R_1$ and/or $R_2$ groups respectively bound to the amino-terminal (N-terminal) and carboxyl-terminal (C-terminal) of the peptide sequence. In one embodiment, the peptide is $R_1$—X. Alternatively, the peptide is X—$R_2$. Preferably, $R_1$ is H, $C_{1-4}$ alkyl, acetyl, benzoyl or trifluoroacetyl; X is the peptide of the invention; $R_2$ is OH or $NH_2$. In an embodiment, $R_1$ is selected from the group formed by H, a non-cyclic substituted or unsubstituted aliphatic group, substituted or unsubstituted alicyclyl, substituted or unsubstituted heterocyclyl, substituted or unsubstituted heteroarylalkyl, substituted or unsubstituted aryl, substituted or unsubstituted aralkyl, Tert-butyloxycarbonyl, 9-fluorenylmethyloxycarbonyl (Fmoc) and $R_5$—CO—, wherein $R_5$ is selected from the group formed by H, a non-cyclic substituted or unsubstituted aliphatic group, substituted or unsubstituted alicyclyl, substituted or unsubstituted aryl, substituted or unsubstituted aralkyl, substituted or unsubstituted heterocyclyl and substituted or unsubstituted heteroarylalkyl; $R_2$ is selected from the group formed by —$NR_3R_4$, —$OR_3$ and —$SR_3$, wherein $R_3$ and $R_4$ are independently selected from the group formed by H, a non-cyclic substituted or unsubstituted aliphatic group, substituted or unsubstituted alicyclyl, substituted or unsubstituted heterocyclyl, substituted or unsubstituted heteroarylalkyl, substituted or unsubstituted aryl, and substituted or unsubstituted aralkyl; and with the condition that $R_1$ and $R_2$ are not α-amino acids. In accordance with another preferred embodiment, $R_2$ is —$NR_3R_4$, —$OR_3$ or —$SR_3$ wherein $R_3$ and $R_4$ are independently selected from the group formed by H, substituted or unsubstituted $C_1$-$C_{24}$ alkyl, substituted or unsubstituted $C_2$-$C_{24}$ alkenyl, Tert-butyloxycarbonyl, 9-fluorenylmethyloxycarbonyl (Fmoc), substituted or unsubstituted $C_2$-$C_{24}$ alkynyl, substituted or unsubstituted $C_3$-$C_{24}$ cycloalkyl, substituted or unsubstituted $C_5$-$C_{24}$ cycloalkenyl, substituted or unsubstituted $C_8$-$C_{24}$ cycloalkynyl, substituted or unsubstituted $C_6$-$C_{30}$ aryl, substituted or unsubstituted $C_7$-$C_{24}$ aralkyl, substituted or unsubstituted heterocyclyl ring of 3-10 members, and substituted or unsubstituted heteroarylalkyl of 2 to 24 carbon atoms and 1 to 3 atoms other than carbon wherein the alkyl chain is of 1 to 6 carbon atoms. Optionally, $R_3$ and $R_4$ can be bound by a saturated or unsaturated carbon-carbon bond, forming a cycle with the nitrogen atom. More preferably $R_2$ is —$NR_3R_4$ or —$OR_3$, wherein $R_3$ and $R_4$ are independently selected from the group formed by H, substituted or unsubstituted $C_1$-$C_{24}$ alkyl, substituted or unsubstituted $C_2$-$C_{24}$ alkenyl, substituted or unsubstituted $C_2$-$C_{24}$ alkynyl, substituted or unsubstituted $C_3$-$C_{10}$ cycloalkyl, substituted or unsubstituted $C_6$-$C_{15}$ aryl and substituted or unsubstituted heterocyclyl of 3-10 members, substituted or unsubstituted heteroarylalkyl with a ring of 3 to 10 members and an alkyl chain of 1 to 6 carbon atoms. More preferably $R_3$ and $R_4$ are selected from the group formed by H, methyl, ethyl, hexyl, dodecyl, or hexadecyl. Even more preferably $R_3$ is H and $R_4$ is selected from the group formed by H, methyl, ethyl, hexyl, dodecyl, or hexadecyl. In accordance with an even more preferred embodiment, $R_2$ is selected from —OH and —$NH_2$.

In accordance with another embodiment of this invention $R_1$ is selected from the group formed by H, acetyl, lauroyl, myristoyl or palmitoyl, and $R_2$ is —$NR_3R_4$ or —$OR_3$ wherein $R_3$ and $R_4$ are independently selected from H, methyl, ethyl, hexyl, dodecyl and hexadecyl, preferably $R_2$ is —OH or —$NH_2$. More preferably, $R_1$ is acetyl or palmitoyl and $R_2$ is —$NH_2$. In a preferred embodiment, the acyl group is bound to the N-terminal end of at least one amino acid of the peptide. In an embodiment of the invention, the peptide is modified to comprise a side chain protecting group. The side chain protecting group may be one or more of the group comprising benzyl or benzyl based groups, t-butyl-based groups, benzyloxy-carbonyl (Z) group, and allyloxycarbonyl (alloc) protecting group. The side chain protecting group may be derived from an achiral amino acid such as achiral glycine. The use of an achiral amino acid helps to stabilise the resultant peptide and also facilitate the facile synthesis route of the present invention. Preferably, the peptide further comprises a modified C-terminus, preferably an amidated C-terminus. The achiral residue may be alpha-aminoisobutyric acid (methylalaine). It will be appreciated that the specific side chain protecting groups used will depend on the sequence of the peptide and the type of N-terminal protecting group used.

"Conjugate": In one embodiment of the invention the peptide is conjugated, linked or fused to a binding partner, for example one or more polyethylene glycol polymers or other compounds, such as molecular weight increasing compounds or lipophilic groups. The molecular weight increasing compound is any compound that will increase the molecular weight, typically by 10% to 90%, or 20% to 50% of the resulting conjugate and may have a molecular weight of between 200 and 20, 000, preferably between 500 and 10, 000. The molecular weight increasing compound may be PEG, any water-soluble (amphiphilic or hydrophilic) polymer moiety, homo or co-polymers of PEG, a monomethyl-substituted polymer of PEG (mPEG) and polyoxyethylene glycerol (POG), polyamino acids such as poly-lysine, poly-glutamic acid, poly-aspartic acid, particular those of L conformation, pharmacologically inactive proteins such as albumin, gelatin, a fatty acid, olysaccharide, a lipid amino acid and dextran. The polymer moiety may be straight chained or branched and it may have a molecular weight of 500 to 40000 Da, 5000 to 10000 Da, 10000 to 5000, Da. The compound (binding partner) may be any suitable cell penetrating compound, such as tat peptide, penetratin, pep-1. The compound (binding partner) may be an antibody molecule. The compound (binding partner) may be a lipophilic moiety or a polymeric moiety. The lipophilic substituent and polymeric substituents are known in the art. The lipophilic substituent includes an acyl group, a sulphonyl group, an N atom, an O atom or an S atom which forms part of the ester, sulphonyl ester, thioester, amide or sulphonamide. The lipophilic moiety may include a hydrocarbon chain having 4 to 30 C atoms, preferably between 8 and 12 C atoms. It may be linear or branched, saturated or unsaturated. The hydrocarbon chain may be further substituted. It may be cycloalkane or heterocycloalkane. The peptide may be modified at the N-terminal, C-terminal or both. The polymer or compound (binding partner) is preferably linked to an amino, carboxyl or thio group and may be linked by N-termini or C-termini of side chains of any amino acid residue. The polymer or compound (binding partner) may be conjugated to the side chain of any suitable residue. The polymer or compound (binding partner) may be conjugated via a spacer. The spacer may be a natural or unnatural amino acid, succinic acid, lysyl, glutamyl, asparagyl, glycyl, beta-alanyl, gamma-amino butanoyl. The polymer or compound (binding partner) may be conjugated via an ester, a sulphonyl ester, a thioester, an amide, a carbamate, a urea, a sulphonamide. A person skilled in the art is aware of suitable means to prepare the described conjugate.

"Fragment" means a segment of a protein selected from SEQ ID NOs: 1 to 14, the fragment typically being 7 to 37 contiguous amino acids in length, and generally having a charge of between −9 and +3; a c-terminal amino acid that typically is not cysteine (C) or methionine (M); and an n-terminal amino acid that typically is not cysteine (C), histidine (H), proline (P) or threonine (T). The charge of a peptide, fragment or region is determined using the method of Cameselle, J. C., Ribeiro, J. M., and Sillero, A. (1986). Derivation and use of a formula to calculate the net charge of acid-base compounds. Its application to amino acids, proteins and nucleotides. Biochem. Educ. 14, 131-136.

The term "natural" as applied to a peptide means a peptide that includes (a) a fragment of a plant protein, typically rice or pea protein, or variants of pea protein including lentil, sweet pea, or chick pea or variants of rice protein including oat, grass, corn, wild rice and bananas, or (b) a variant of the fragment of a plant protein, for example a fragment of a homolog of the plant protein. The peptides or fragments of the invention may be isolated from plant proteins or made synthetically using methods known to a person skilled in the art and described herein.

"C-terminal domain" as applied to a fragment means the first three amino acids at the c-terminus of the fragment.

"N-terminal domain" as applied to a fragment means the last three amino acids at the n-terminus of the fragment.

"Bioactive" as applied to a peptide or fragment means having a health promoting effect when administered a mammal, for example one or more of glucose transport promoting, anti-bacterial, anti-inflammatory, or cellular growth or proliferation promoting. In one embodiment, the term "bioactive" means cellular growth promoting.

"Growth promoting" or "growth promoting activity" as applied to a peptide or fragment means a peptide or fragment that is capable of increasing elastin production or cellular proliferation of human skin treated with a 20 μM solution of peptide or fragment as described in the assay below.

"Glucose transport promoting" or "glucose transport promoting activity" as applied to a peptide or variant or fragment means a peptide, variant or fragment that is capable of increasing GLUT4 translocation into skeletal muscle compared with an untreated control when employed at a concentration of 2 μM in the following in-vitro assay. L6-GLUT4myc cells were grown in 10% FBS and 2 μg/ml blasticidin. Cells were grown for 48-72 hours before being seeded in 24-well plates at 15,000 cells per well in 2% FBS and allowed to differentiate for 6 to 8 days prior to experimentation. L6-GLUT4myc cells were serum-starved for three hours prior to incubation with 100 nM of insulin for 30 mins, or 200, 20, 2.0 and 0.2 μM of SP, and 2, 1, 0.5 and 0.25 mg/ml of peptide/peptide composition for 3 hours respectively. A 3-hour incubation period was selected based on previous findings identifying that incubation with branch chain amino acid containing di-peptides for 3 hours increases glucose uptake in L6 myotubes 1. Treatments were staggered in order to determine GLUT4myc translocation at the same time point. The quantity of myc-tagged GLUT4 at the cell surface was measured by antibody-coupled colorimetric assay. Briefly, after incubation with either insulin for 30 mins or synthetic peptide or peptide composition for 3 hours respectively, L6-GLUT4myc cells were fixed via incubation with 3% paraformaldehyde (PFA). A 0.1 M glycine solution was then added to quench PFA and cells were blocked with 5% goat serum. The myotube monolayer was exposed to anti-myc antibody and then incubated with peroxidase conjugated donkey anti-mouse IgG. 1 mL of o-phenylenediamine dihydrochloride (OPD) reagent was added to each well and this reaction was stopped by adding 250 μl/well of 3 M HCL. To determine GLUT4 translocation to cell surface, a measured aliquot of each condition was determined spectrophotometrically on a plate reader using absorbance at 492 nm. Preferably the peptide or fragment is capable of increasing GLUT4 translocation compared with an untreated control by at least 50% (i.e a relative unit increase in GLUT4 translocation of 1% to 1.5%).

"Antibacterial" or "antibacterial activity" as applied to a peptide or fragment means a peptide or fragment that is capable of visibly inhibiting the growth of a bacteria in the following agar-plate based growth inhibition assay: Peptide stock=5 mg/mL dissolved in DMSO. Bacterial inoculums were adjusted to McFarland 0.5 standard and MHA plates swabbed. Blank disks were placed in the plates and 10 μL of each compound (at 64 μg/mL—maximum concentration tested) added. Plates were incubated at 37° C. for 16-18 hours. Appropriate controls (DMSO; Mueller-Hinton media alone; and two antibiotic discs—ciprofloxacin and tetracycline) were also performed.

"Anti-inflammatory" as applied to a peptide or fragment means a peptide or fragment that is capable of significantly reducing the secretion of TNFα by LPS-stimulated J774.2 macrophages (compared with untreated LPS-stimulated J774.2 macrophages) when the macrophages are treated with 100 μM of the peptide or fragment. J774.2 macrophages were treated with 100 μM of synthetic peptide for 24 hours and then stimulated with (A) LPS (long/ml) for five hours or (B) LPS (long/ml) for 5 hours followed by ATP (5 mM) for one hour. Supernatant was collected and levels of TNFα were determined by ELISA.

"Enriched in peptides having a molecular weight of less than 10 KD" as applied to a composition of the invention means that the dry weight % of peptides in the composition having a molecular weight of less than 10 KD is greater than the dry weight % of polypeptide/protein in the composition having a molecular weight of 10 KD or greater.

"Homolog" of a reference protein should be understood to mean a protein from a different species of plant having at least 60%, 70%, 80%, 90%, 91%, 92%, 93%, 94%, 95%, 96%, 97%, 98%, 99% sequence homology with the reference protein. Thus, for example, homologs of pea protein P13918 include:

```
>gi|137584|sp|P08438.1|VCL_VICFA RecName: Full = Vicilin; Flags: Precursor [Vicia faba]
>gi|22057|emb|CAA68559.1|vicilin [Vicia faba var. minor] >gi|383931031|gb|AFH56916.1|vicilin
[Vicia faba]
>gi|502105533|ref|XP_004492829.1|PREDICTED: vicilin-like isoform X1 [Cicer arietinum] ChickPea
>gi|29539109|emb|CAD87730.1|allergen Len c 1.0101 [Lens culinaris] Lentil
```

A "variant" of a growth promoting fragment shall be taken to mean a fragment having an amino acid sequence that is substantially identical to the reference growth promoting fragment, and which has growth promoting activity as defined above. Thus, for example, the term should be taken to include fragments that are altered in respect of one or more amino acid residues. Preferably such alterations involve the insertion, addition, deletion and/or substitution of 5 or fewer amino acids, more preferably of 4 or fewer, even more preferably of 3 or fewer, most preferably of 1 or 2 amino acids only. Insertion, addition and substitution with natural and modified amino acids is envisaged. The variant may have conservative amino acid changes, wherein the amino acid being introduced is similar structurally, chemically, or functionally to that being substituted. Generally, the variant will have at least 70% amino acid sequence homology, preferably at least 80% sequence homology, more preferably at least 90% sequence homology, and ideally at least 95%, 96%, 97%, 98% or 99% sequence homology with the reference growth promoting fragment.

In this specification, the term "sequence identity" should be understand to comprise both sequence identity and similarity, i.e. a variant (or homolog) that shares 70% sequence identity with a reference sequence is one in which any 70% of aligned residues of the variant (or homolog) are identical to or conservative substitutions of the corresponding residues in the reference sequence across the entire length of the sequence. Sequence identity is the amount of characters which match exactly between two different sequences. Hereby, gaps are not counted and the measurement is relational to the shorter of the two sequences. In terms of "sequence homology", the term should be understood to mean that a variant (or homolog) which shares a defined percent similarity or identity with a reference sequence when the percentage of aligned residues of the variant (or homolog) are either identical to, or conservative substitutions of, the corresponding residues in the reference sequence and where the variant (or homolog) shares the same function as the reference sequence. This alignment and the percent homology or sequence identity can be determined using software programs known in the art, for example, one alignment program is BLAST, using default parameters. Details of these programs can be found at the following Internet address: <www.ncbi.nlm.nih.goviblast/Blast.cgi>.

Variants of SEQ ID NO: 448 (QSFLLSGNQ)

Variants of SEQ ID NO: 448 (QSFLLSGNQ) including variants having 1 or 2 conservative amino acid substitutions, 1, 2 to 3 non-conservative amino acid substitutions, 1-2 amino acid additions, 1, 2 or 3 amino acid deletions, are provided below:

One conservative amino acid substitution:

QSFILSGNE,  (SEQ ID NO: 418)

ESFLLSGNQ,  (SEQ ID NO: 419)

QSYLLSGNQ,  (SEQ ID NO: 420)

QSFLLSGDQ  (SEQ ID NO: 421)

Two conservative amino acid substitutions:

QSYLLSGNE,  (SEQ ID NO: 422)

ESFLLSGNE,  (SEQ ID NO: 423)

ESYLLSGNQ,  (SEQ ID NO: 424)

QSFLLSGDE,  (SEQ ID NO: 425)

QSYLLSGDQ  (SEQ ID NO: 426)

One non-conservative amino acid substitution

QSFRLSGNQ,  (SEQ ID NO: 427)

QSFLLSYNQ,  (SEQ ID NO: 428)

QFFLLSGNQ,  (SEQ ID NO: 429)

QSFLLSGAQ,  (SEQ ID NO: 430)

QSFLLSGNP  (SEQ ID NO: 431)

Two non-conservative amino acid substitution

QSFRRSGNQ,  (SEQ ID NO: 432)

QSFLLSYIQ,  (SEQ ID NO: 433)

QFFLLSGNL,  (SEQ ID NO: 434)

QSFLLSGAQ,  (SEQ ID NO: 435)

QSFLLSGNP  (SEQ ID NO: 436)

One or two amino acid additions

QSFLLSGNQQ,  (SEQ ID NO: 437)

QSFLLLSGNQ,  (SEQ ID NO: 438)

```
                                   (SEQ ID NO: 439)
AQSFGLLSGNQ, (SEQ ID NO: 440)
RQSFLLISGNQ, (SEQ ID NO: 441)
QSFLLSGNQK
```

One, two or three amino acid deletions

```
                                   (SEQ ID NO: 442)
QFLLSGNQ, (SEQ ID NO: 443)
SFLLSGNQ, (SEQ ID NO: 444)
QSFLLSGN, (SEQ ID NO: 445)
QSFLLGNQ, (SEQ ID NO: 446)
QSFLSGNQ, (SEQ ID NO: 447)
QSLLSGNQ, (SEQ ID NO: 448)
SFLLSGNQ, (SEQ ID NO: 449)
QSFLLSGN, (SEQ ID NO: 450)
SFLLSGN, (SEQ ID NO: 451)
QSFSGNQ
```

The term "variant" also includes fragment of peptides of the invention. "Fragment of a peptide of the invention" or "peptide fragment" means a fragment of one of the peptides of the invention having at least 3, 4, 5, 6, 7, 8, 9, 10, 11, 12, 13, 14, 15, 16, 17, 18, 19, 20, 21 or 22 amino acids and that typically has a bioactivity, for example anti-inflammatory activity, anti-ageing activity, glucose transport promoting activity, or anti-bacterial activity. In one embodiment, the fragment consists of at least 30%, 40%, 50%, 60%, 70%, 80%, or 90% of the reference sequence. Thus, the invention also provides bioactive fragments of the peptides of the invention, and peptides comprising one or more of these fragments. In one embodiment, the fragments are bioactive. In one embodiment, the fragments are cellular growth or proliferation promoting fragments. Examples of fragments of peptides of the invention are provide in SEQ ID NOs: 494 to 524.

"Anti-ageing" means inhibiting or slowing the appearance of ageing of a human skin and/or reversing the appearance of ageing. "Slowing or inhibiting ageing of the skin" means slowing or inhibiting the ageing process in the skin, and/or reversing the appearance of ageing.

"Disease or condition characterised by damaged dermal or epithelial cells or tissue" means any condition or disease that results in damaged dermal or epithelial tissue or cells or organs. One example is trauma which often results in damaged skin. Another example is an inflammatory skin condition such as psoriasis or eczema which often results in damaged skin. Another example is an inflammatory disorder of the lower intestines which can result in damaged epithelial cells/tissue lining the lower intestines. Another example is damaged epithelial cells/tissue lining the lower intestines caused by ingestion of a toxic or damaging substance, for example toxic chemicals or drugs. Another example is cancer, for example bowel cancer, which can result in damaged epithelial tissue in the bowel. Another condition is a peripheral inflammatory disorder such as atopic dermatitis which can result in damage to the skin in humans.

"Inflammatory disorder" means an immune-mediated inflammatory condition that affects humans and is generally characterised by dysregulated expression of one or more cytokines. Examples of inflammatory disorders include skin inflammatory disorders, inflammatory disorders of the joints, inflammatory disorders of the cardiovascular system, certain autoimmune diseases, lung and airway inflammatory disorders, intestinal inflammatory disorders. Examples of skin inflammatory disorders include dermatitis, for example atopic dermatitis and contact dermatitis, acne vulgaris, and psoriasis. Examples of inflammatory disorders of the joints include rheumatoid arthritis. Examples of inflammatory disorders of the cardiovascular system are cardiovascular disease and atherosclerosis. Examples of autoimmune diseases include Type 1 diabetes, Graves disease, Guillain-Barre disease, Lupus, Psoriatic arthritis, and Ulcerative colitis. Examples of lung and airway inflammatory disorders include asthma, cystic fibrosis, COPD, emphysema, and acute respiratory distress syndrome. Examples of intestinal inflammatory disorders include colitis and inflammatory bowel disease. Other inflammatory disorders include cancer, hay fever, periodontitis, allergies, hypersensitivity, ischemia, depression, systemic diseases, post infection inflammation and bronchitis. The invention also relates to a peptide or composition of the invention for use in treating an inflammatory disorder in a mammal.

"Metabolic disorder" should be understood to include pre-diabetes, diabetes; Type-1 diabetes; Type-2 diabetes; metabolic syndrome; obesity; diabetic dyslipidemia; hyperlipidemia; hypertension; hypertriglyceridemia; hyperfattyacidemia; hypercholerterolemia; hyperinsulinemia, and MODY. The invention also relates to a peptide or composition of the invention for use in treating a metabolic disorder in a mammal.

"Disease or condition characterised by damaged dermal or epithelial cells or tissue" means any condition or disease that results in damaged dermal or epithelial tissue or cells or organs. One example is trauma which often results in damaged skin. Another example is an inflammatory skin condition such as psoriasis or eczema which often results in damaged skin. Another example is an inflammatory disorder of the lower intestines which can result in damaged epithelial cells/tissue lining the lower intestines. Another example is damaged epithelial cells/tissue lining the lower intestines caused by ingestion of a toxic or damaging substance, for example toxic chemicals or drugs. Another example is cancer, for example bowel cancer, which can result in damaged epithelial tissue in the bowel. Another condition is a peripheral inflammatory disorder such as atopic dermatitis which can result in damage to the skin in humans.

"Disease or condition characterised by bacterial infection" means any condition or disease characterised having a pathology caused by growth of bacteria or by bacterial infection, including for example MRSA, *salmonella, listeria*, bacterial pneumonia, Staphylococcal food poisoning, bacterial meningitis. Specific examples are provided in <en.wikipedia.org/wiki/List_of_infectious_diseases>.

"Man-made" as applied to comestible products should be understood to mean made by a human being and not existing in nature.

"Maintaining or restoring gut health" means reducing and/or regulating the pro-inflammatory response in the gut and more specifically the epithelial cells. The healthy microbiome offers some protection against pathogenic viruses and bacteria, and their presence is needed to guide the development of our immune system. It has been shown that these bacteria can react to human signals of stress, sickness, or age which can be manifested by inflammation and as a consequence switch on their virulence genes and cause or contribute to disease. Having the ability to reduce and maintain at healthy levels the inflammatory response can help maintain the healthy bacteria. Digestive problems, which comprise the number one health problem in North America, appear to be occurring with more frequency in recent years. One way to maintain digestive health is to maintain proper inflammation and intestinal flora.

"Improving muscle status" means improving the muscle health, for example promoting skeletal muscle protein synthesis, skeletal glucose absorption, improving lean tissue mass in therapeutic or non-therapeutic context, promoting muscle recovery generally after activity exercise, or improving muscle performance. The methods or uses may be therapeutic or non-therapeutic. The term "improving lean tissue mass status" should be understood to mean increasing lean tissue mass, or inhibiting or preventing the rate of lean tissue mass degradation.

"Promoting muscle recovery" means causing an increase in absorption of glucose in skeletal muscle compared with untreated skeletal muscle.

"Disease or condition characterised by lethargy or low energy levels" means any condition or disease characterised by a feeling or tiredness or low energy. Examples include allergies, asthma, anaemia, cancer and its treatments, chronic pain, heart disease, infection, depression, eating disorders, grief, sleeping disorders, thyroid problems, medication side effects, alcohol use, or drug use.

"Maintaining or restoring muscle health" means helping retain or restore mammalian muscle health resulting from damage incurred during exercise. By promoting glucose transport in skeletal muscle the peptides promote recovery from exercise, and relieve muscle soreness/pain and injury connected with exercise. They can also be used to decrease and prevent muscle cramping, and to allow a faster recovery from muscle cramping. Cramping can result from physical stress, mental stress, and or Repetitive Strain Injury stress. By promoting glucose transport the peptides help reduce Myopathy of the muscle, and help prevent Sarcopenia in mammals, promote recovery from injuries during exercise, and relieve muscle soreness/pain and injury connected with exercise. The invention also relates to a peptide or composition of the invention for use in maintaining or restoring muscle health in a mammal.

In this specification, the term "substantially all" as applied to a list of peptides should be understood to mean at least 60%, 70%, 80%, 90% or 95% of the peptides.

"Man-made" as applied to comestible products should be understood to mean made by a human being and not existing in nature.

DETAILED DESCRIPTION OF THE INVENTION

Example 1—Cell Proliferation Assay

BrDu is incorporated into newly synthesised DNA strands of actively proliferating cells. Following partial denaturation of double stranded DNA, Brdu is detected immunochemically allowing the assessment of the population of cells which are synthesizing DNA.

Human Dermal Fibroblasts (HDF—Sigma 10605a) were seeded in a 96 well plate at 10,000 cells per well in DMEM containing 10% fetal calf serum (FCS), 1% Pen/strep, 1% L-glutamine and allowed to adhere for 24 h.

Following the initial 24 h incubation the cells were incubated with 5 µg/ml, 0.5 µg/ml or 0.05 µg/ml synthetic peptide for 24 h respectively.

After 18 h incubation with synthetic peptides 20 µl BrDu reagent was added to each well.

At 24 h incubation the cell were fixed and the amount of 2-DG6P was measured using the BrdU Cell Proliferation Assay, all steps were carried out according to the manufacturer's instructions.

Results were calculated as a percentage of the untreated control. An increase in optical density reading indicates greatER incorporation of BrDu and increase cell proliferation.

Figure 1:
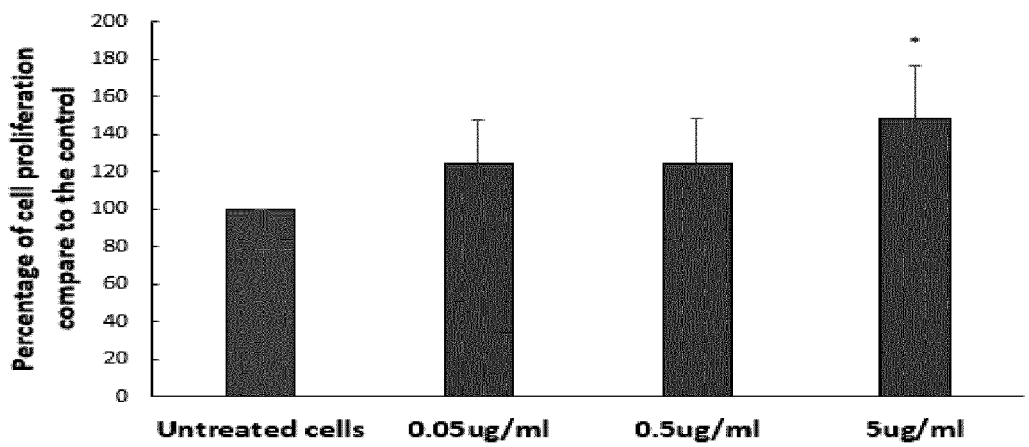
FIGS. 1 to 100: Effect of synthetic peptides of the invention on proliferation of Human Dermal Fibroblasts (HDF).
Figure 100:
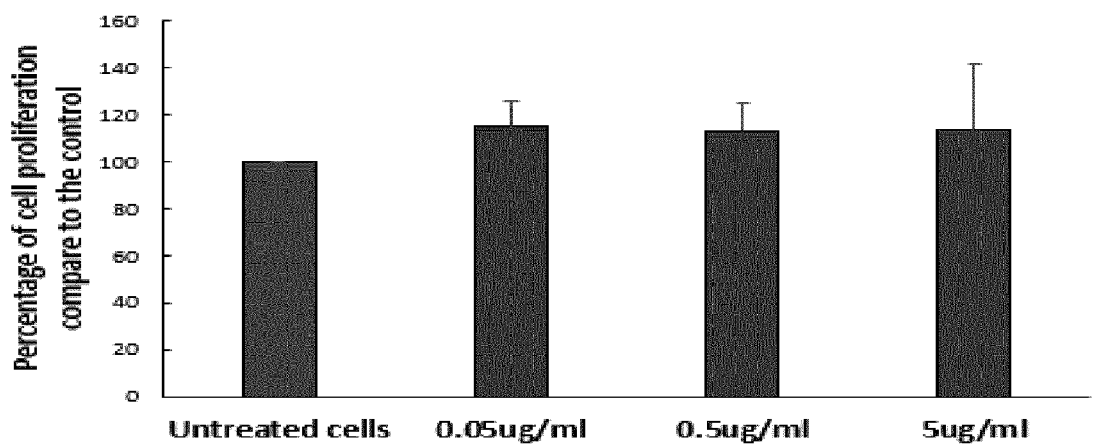
Figure 101:
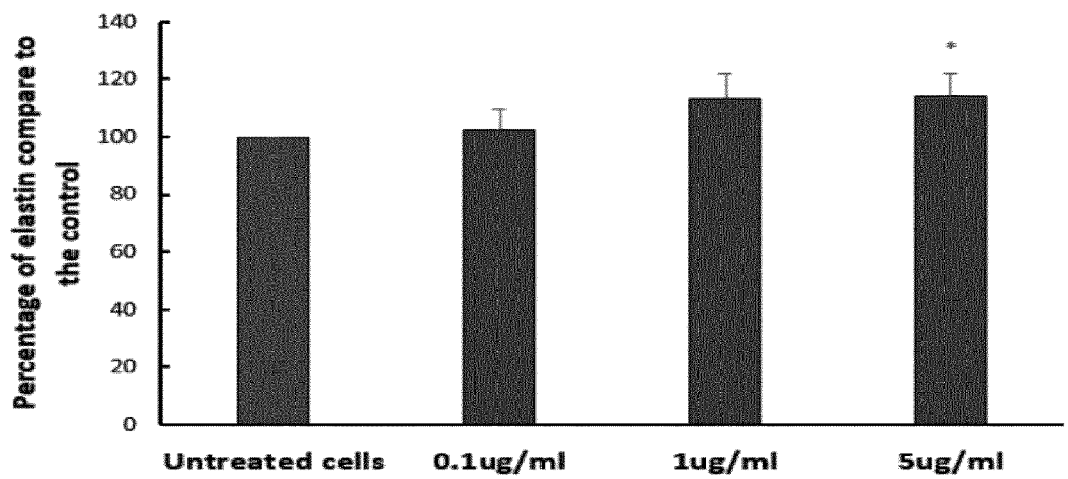
FIG. 101: Effect of synthetic peptide of the invention (SEQ ID NO: 42) on elastin synthesis of Human Dermal Fibroblasts (HDF).
Figure 102:
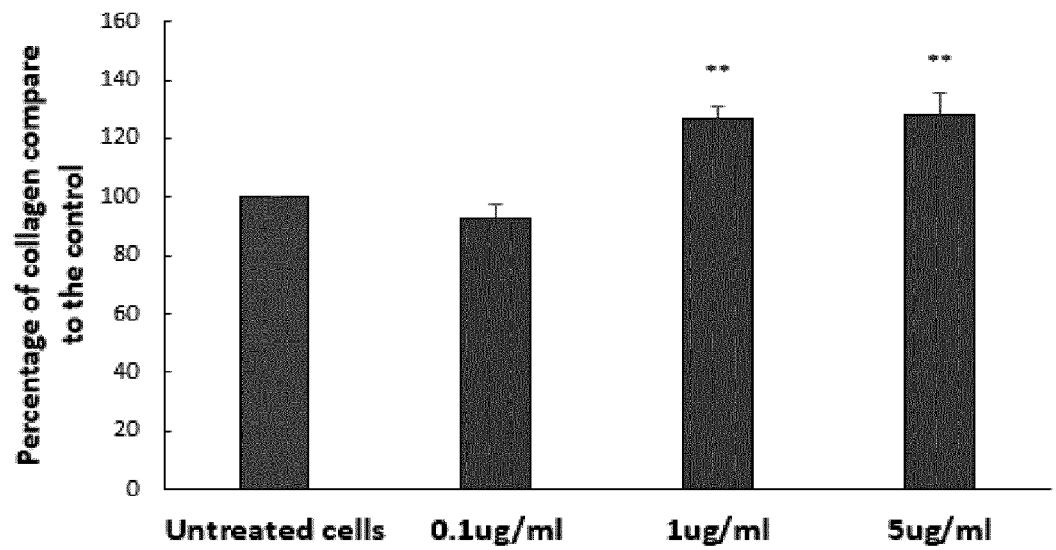
FIG. 102: Effect of synthetic peptide of the invention (SEQ ID NO: 42) on collagen synthesis of Human Dermal Fibroblasts (HDF).
Figure 103:
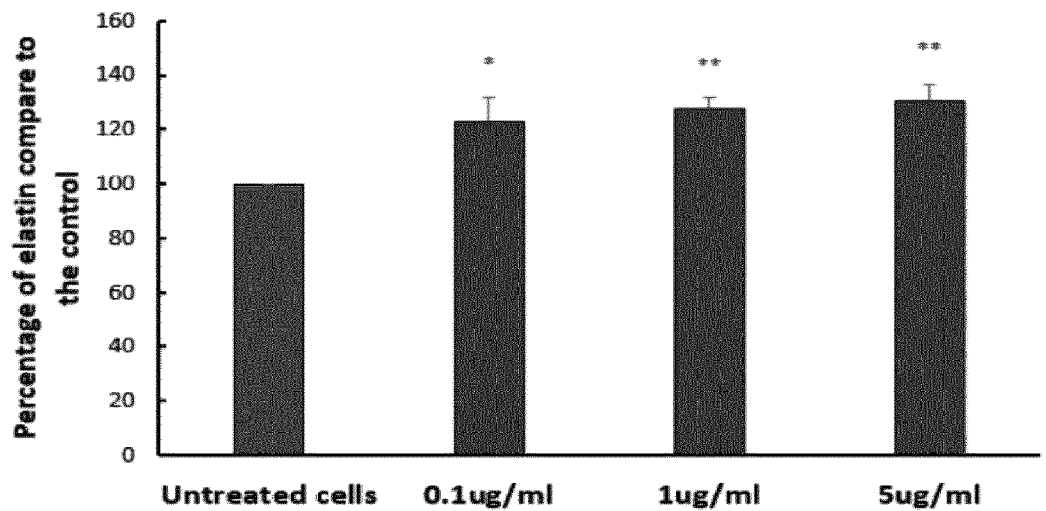
FIG. 103: Effect of synthetic peptide of the invention (SEQ ID NO: 701) on elastin synthesis of Human Dermal Fibroblasts (HDF).
Figure 104:
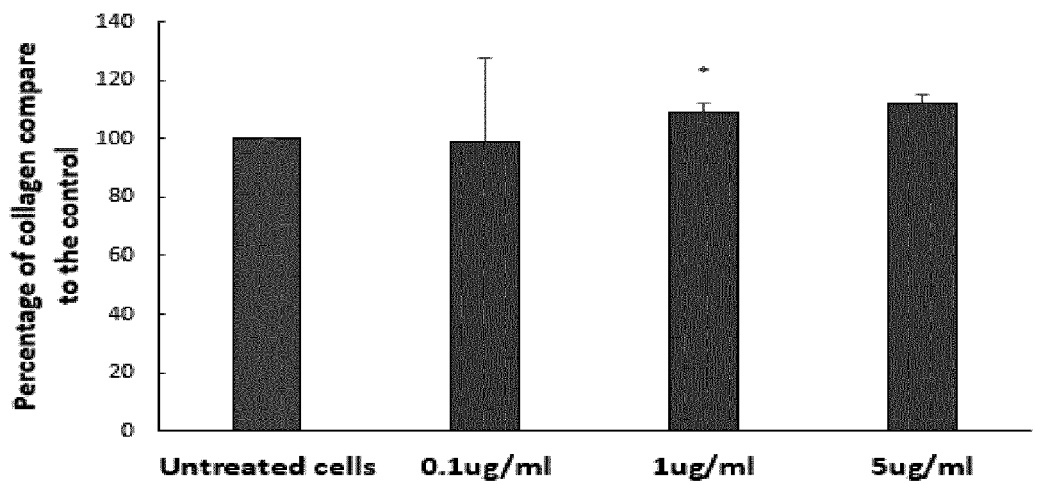
FIG. 104: Effect of synthetic peptide of the invention (SEQ ID NO: 701) on collagen synthesis of Human Dermal Fibroblasts (HDF).
Figure 105:
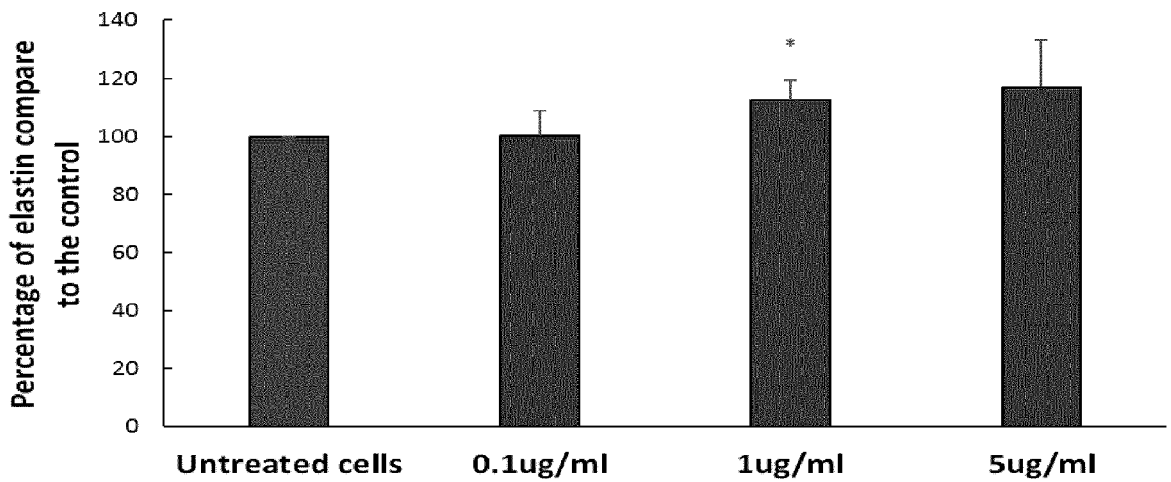
FIG. 105: Effect of synthetic peptide of the invention (SEQ ID NO: 246) on elastin synthesis of Human Dermal Fibroblasts (HDF).
Figure 106:
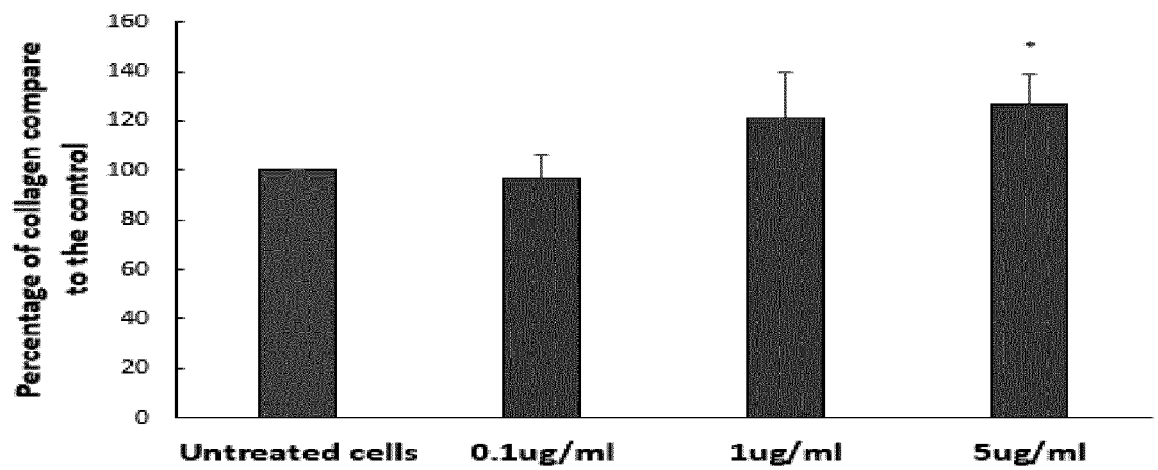
FIG. 106: Effect of synthetic peptide of the invention (SEQ ID NO: 246) on collagen synthesis of Human Dermal Fibroblasts (HDF).
Figure 107:
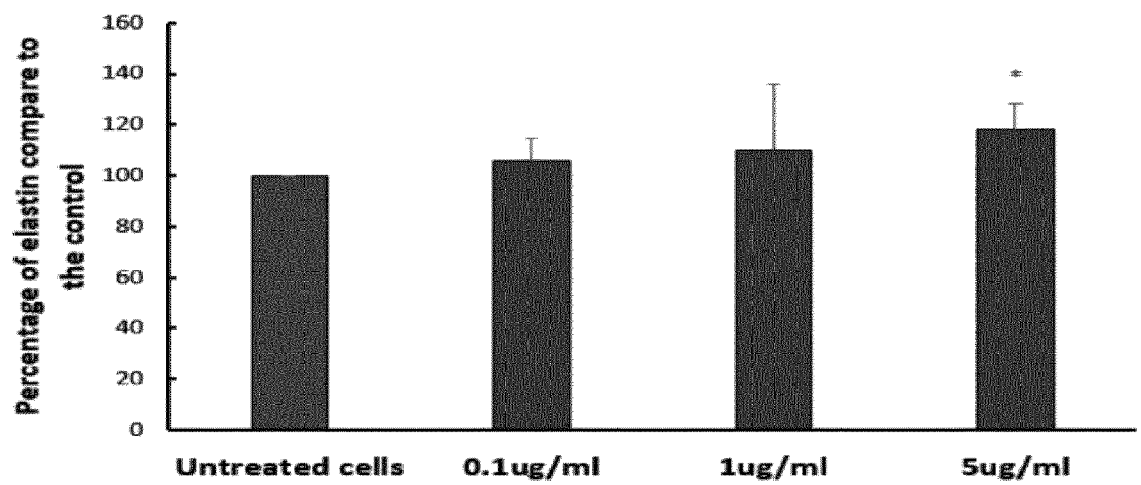
FIG. 107: Effect of synthetic peptide of the invention (SEQ ID NO: 284) on elastin synthesis of Human Dermal Fibroblasts (HDF).
Figure 108:
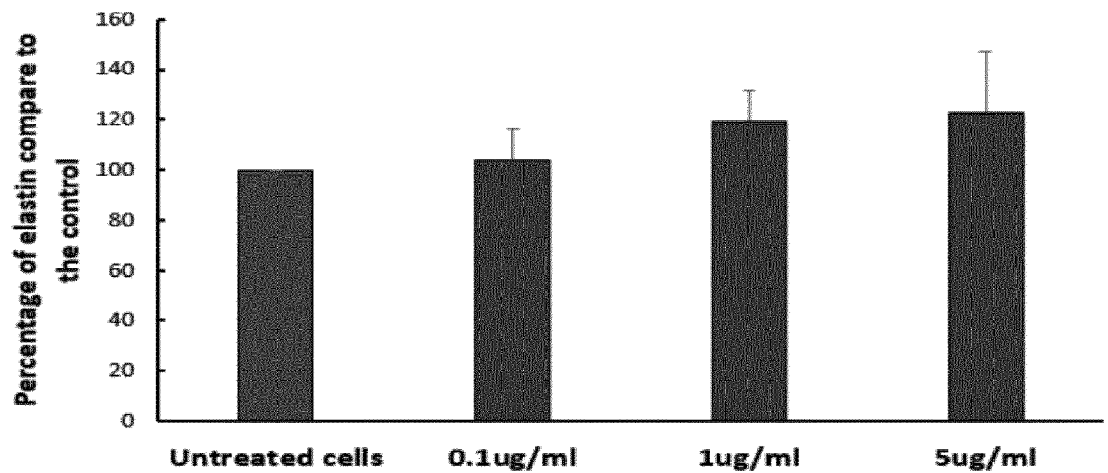
FIG. 108: Effect of synthetic peptide of the invention (SEQ ID NO: 245) on elastin synthesis of Human Dermal Fibroblasts (HDF).
Figure 109:
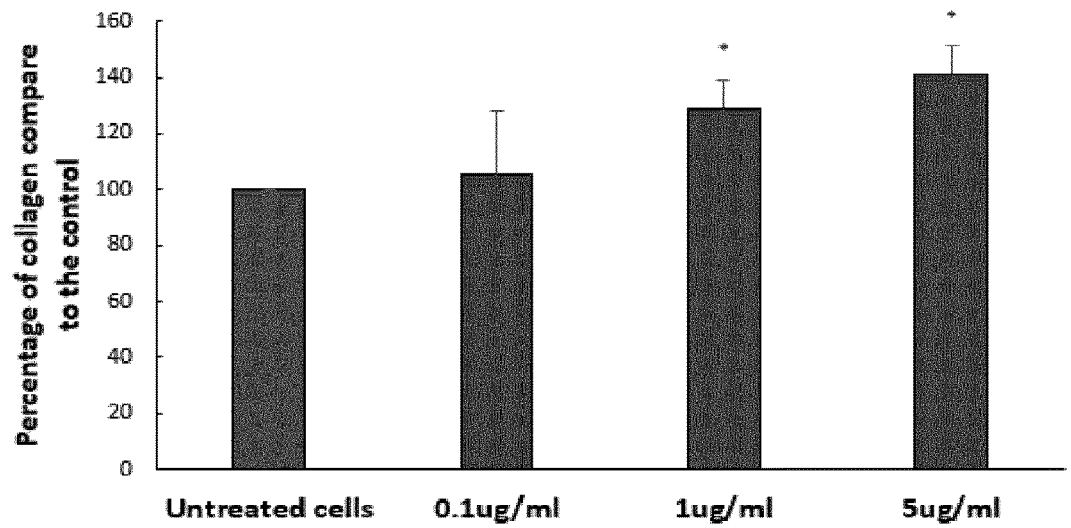
FIG. 109: Effect of synthetic peptide of the invention (SEQ ID NO: 245) on collagen synthesis of Human Dermal Fibroblasts (HDF).
Figure 110:
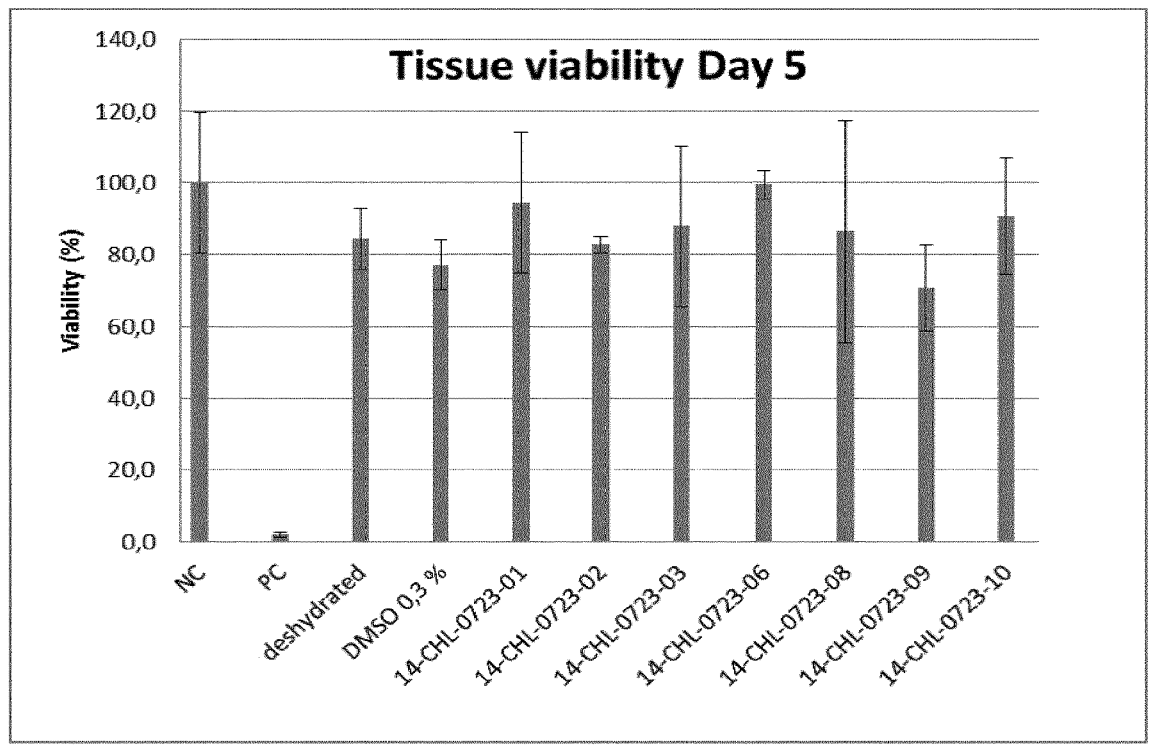
FIG. 110. shows the integrity controls and viability controls for the assay system.
Figure 111:
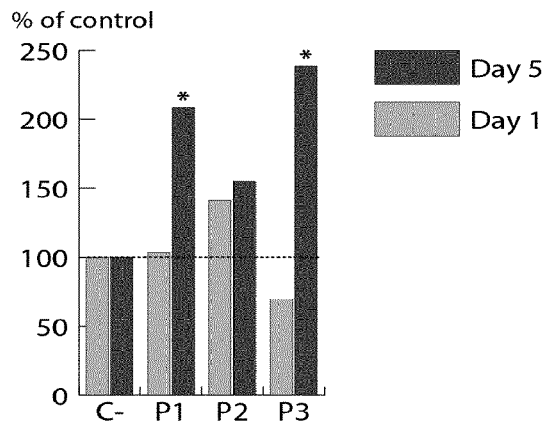
FIG. 111. % of elastin expression in superficial dermis compared to control (water or DMSO) for peptides P1, P2 and P3
*shows significant increases of elastin expression in superficial AND middle dermis.
Figure 112:
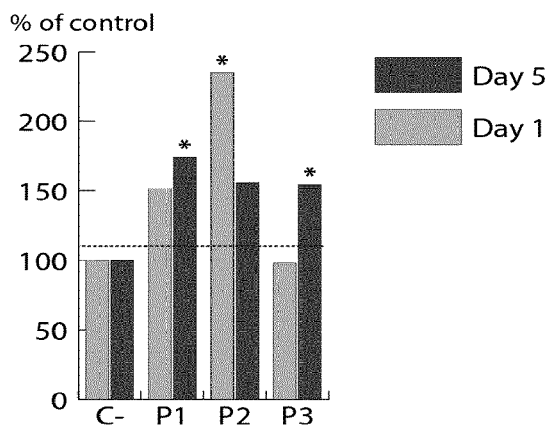
FIG. 112. % of elastin expression in middle dermis compared to control (water or DMSO) for peptides P1, P2 and P3.
*shows significant increases of elastin expression in superficial AND middle dermis.
Figure 113:
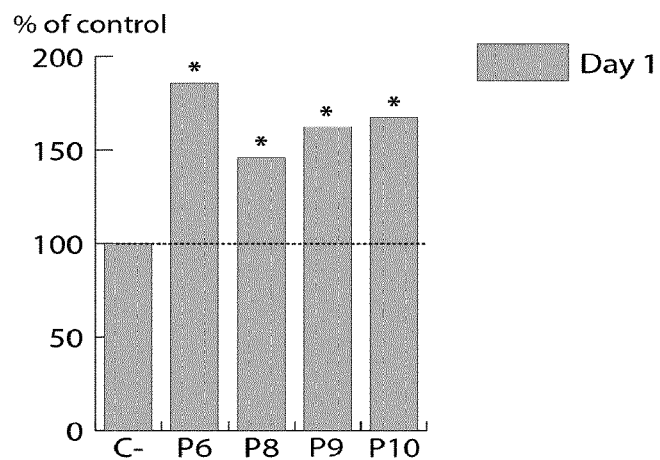
FIG. 113. % of cell proliferation in the basal layer of epidermis compared to control (water or DMSO) for peptides P6 and P8, and peptide compositions P9 and P10
*shows significant increases.
Figure 114:
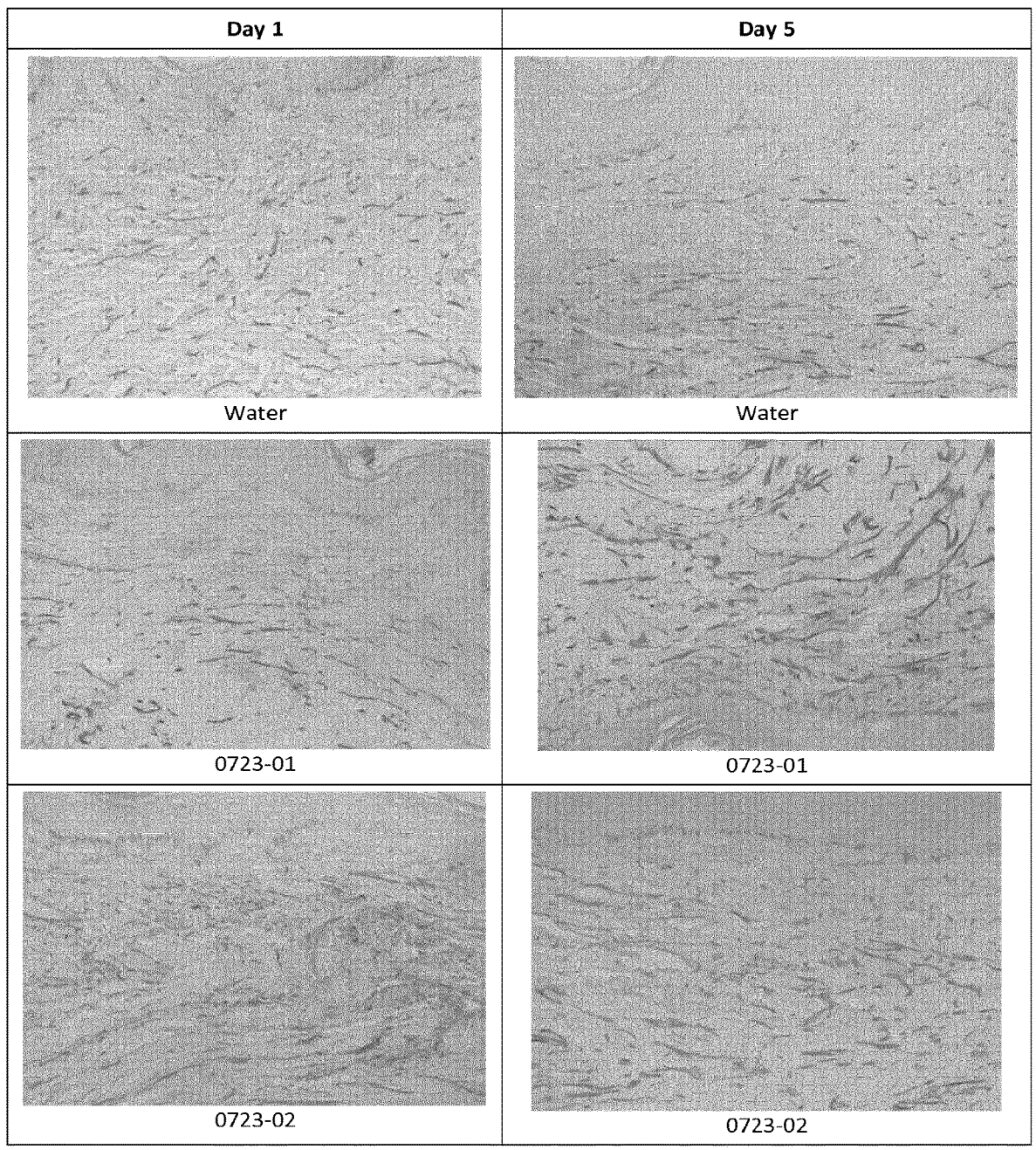
FIG. 114. Histological analysis of the elastic fibers (+catechin, ×200) FIG. 115. Immunohistochemical evaluation of the mitotic index (Ki67, ×400)

The results are shown in FIGS. 1-100 and Table 1 below.

TABLE 1

| FIG. NO | SEQ ID NO: | INCREASE IN PROLIFERATION |
| --- | --- | --- |
| 1 | 121 | 48% |
| 2 | 105 | 40% |
| 3 | 249 | 30% |
| 4 | 226 | 30% |
| 5 | 84 | 20% |
| 6 | 330 | 18% |
| 7 | 181 | 33% |
| 8 | 83 | 32% |
| 9 | 247 | 28% |
| 10 | 97 | 26% |
| 11 | 74 | 29% |
| 12 | | |
| 13 | 168 | |
| 14 | 151 | |
| 15 | 470 | 119% |
| 16 | 257 | 118% |
| 17 | 256 | 117% |
| 18 | 457 | 114% |
| 19 | 499 | 113% |
| 20 | 253 | 112% |
| 21 | 222 | 110% |
| 22 | 272 | 97% |
| 23 | 252 | 111% |
| 24 | 248 | 86% |
| 25 | 472 | 77% |
| 26 | 365 | 58% |
| 27 | 502 | 68% |
| 28 | 496 | 51% |
| 29 | 98 | 49% |
| 30 | 454 | 38% |
| 31 | 85 | 35% |
| 32 | 453 | 25% |
| 33 | 158 | 21% |
| 34 | 464 | 18% |
| 35 | 73 | 16% |
| 36 | 359 | 15% |
| 37 | 124 | 15% |
| 38 | 112 | 15% |
| 39 | 733 | |
| 40 | 728 | |
| 41 | 727 | |
| 42 | 730 | |
| 43 | 731 | |
| 44 | 148 | |
| 45 | 343 | |
| 46 | 345 | |
| 47 | 484 | |
| 48 | 729 | |
| 49 | 456 | |
| 50 | 494 | |
| 51 | 723 | |
| 52 | 722 | |
| 53 | 498 | |
| 54 | 475 | 13% |
| 55 | 718 | |
| 56 | 337 | 8% |
| 57 | 500 | 6% |
| 58 | 717 | |
| 59 | 297 | |
| 60 | 340 | |
| 61 | 719 | |
| 62 | 726 | |
| 63 | 725 | |
| 64 | 724 | |
| 65 | 720 | |
| 66 | 721 | |
| 67 | 503 | 125% |
| 68 | 474 | 121% |
| 69 | 504 | 119% |
| 70 | 114 | 119% |
| 71 | 505 | 118% |
| 72 | 482 | 113% |
| 73 | 479 | 106% |
| 74 | 477 | 81% |
| 75 | 410 | 73% |
| 76 | 475 | 69% |
| 77 | 497 | 58% |
| 78 | 480 | 102% |
| 79 | 463 | 100% |
| 80 | 465 | 96% |
| 81 | 467 | 90% |
| 82 | 461 | 85% |
| 83 | 341 | 83% |
| 84 | 468 | 82% |
| 85 | 285 | 81% |
| 86 | 496 | 81% |
| 87 | 146 | 80% |
| 88 | 478 | 76% |
| 89 | 452 | 76% |
| 90 | 495 | 68% |
| 91 | 403 | 51% |
| 92 | 455 | 47% |
| 93 | 270 | 47% |
| 94 | 501 | 43% |
| 95 | 473 | 41% |
| 96 | | 39% |
| 97 | 471 | 38% |
| 98 | 460 | 38% |
| 99 | 93 | 26% |
| 100 | 462 | 15% |

FIG. 1 shows an increase in HGF cell proliferation of 48% when incubated with SEQ ID 121.

Figure 2:
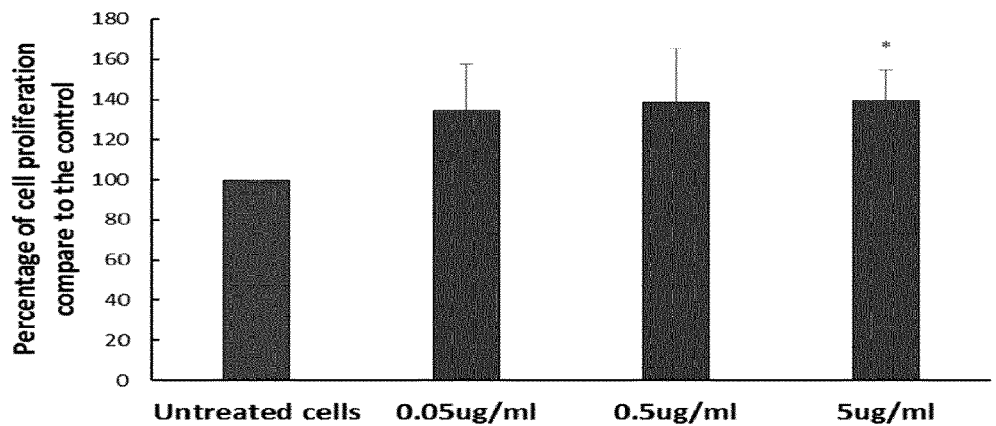

FIG. 2 shows an increase in HGF cell proliferation of 40% when incubated with SEQ ID 105.

Figure 3:
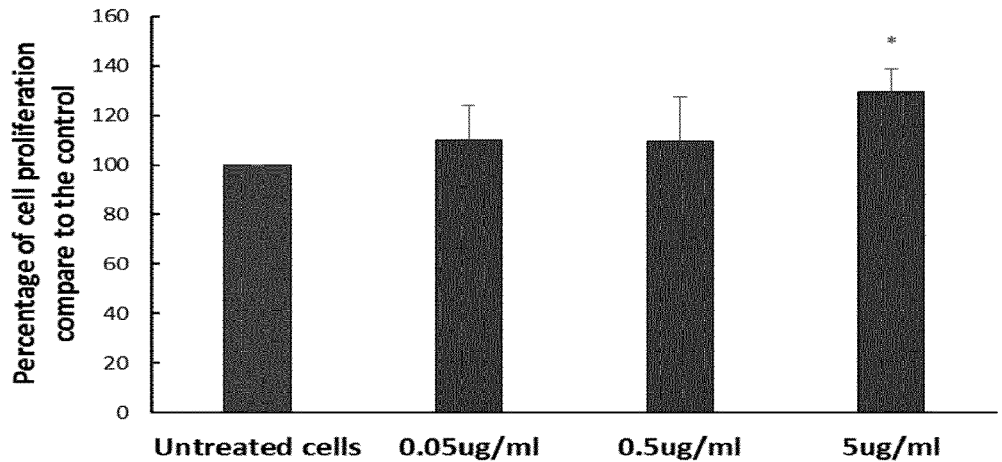

FIG. 3 shows an increase in HGF cell proliferation of 30% when incubated with SEQ ID 249.

Figure 4:
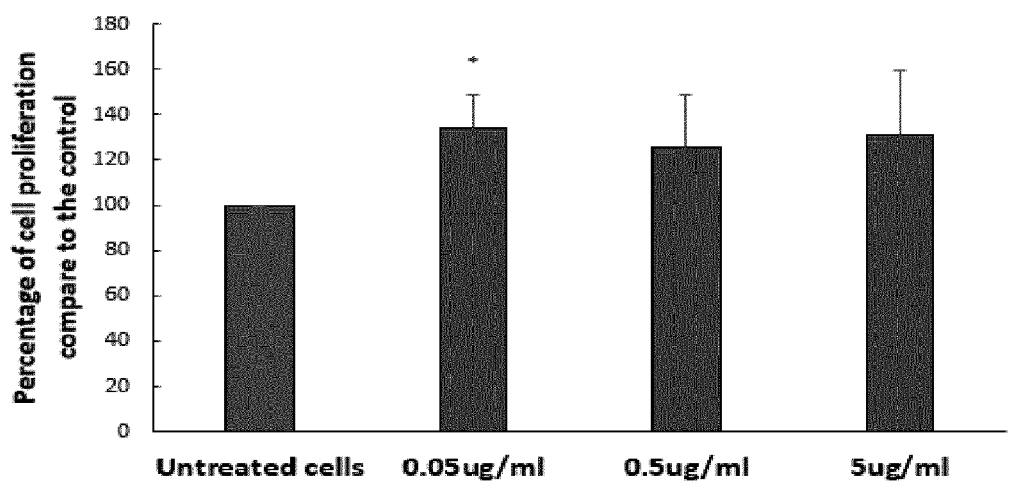

FIG. 4 shows an increase in HGF cell proliferation of 30% when incubated with SEQ ID 226.

Figure 5:
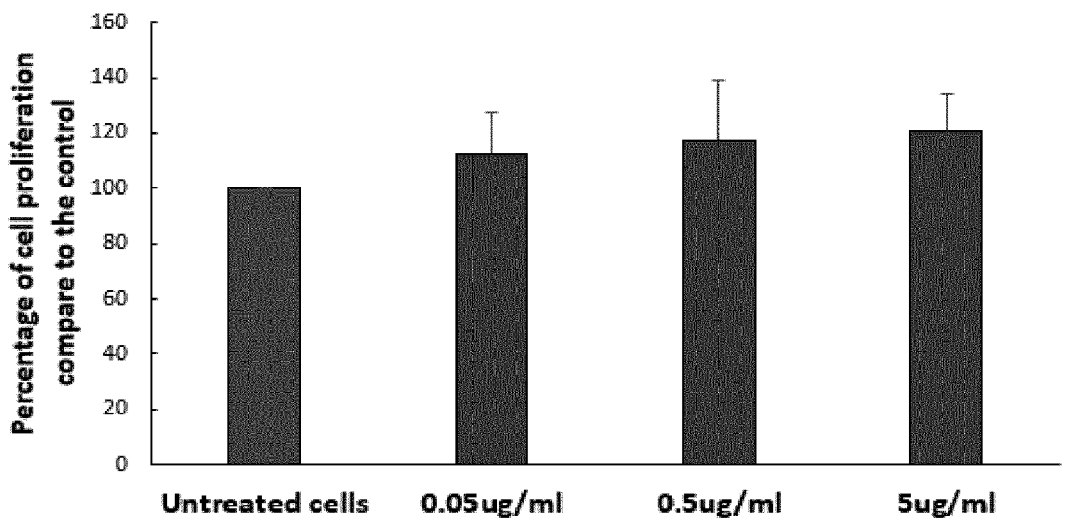

FIG. 5 shows an increase in HGF cell proliferation of 20% when incubated with SEQ ID 84.

Figure 6:
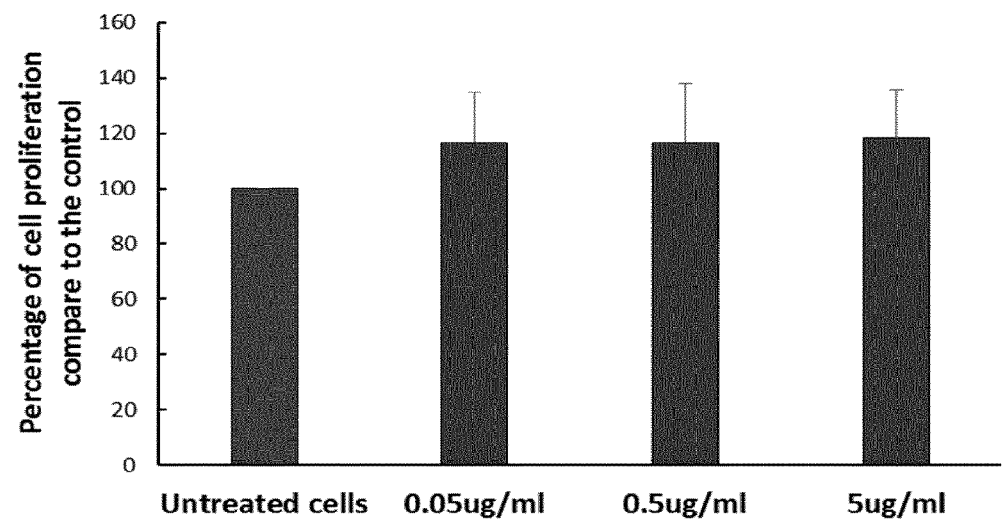

FIG. 6 shows an increase in HGF cell proliferation of 18% when incubated with SEQ ID 330.

Figure 7:
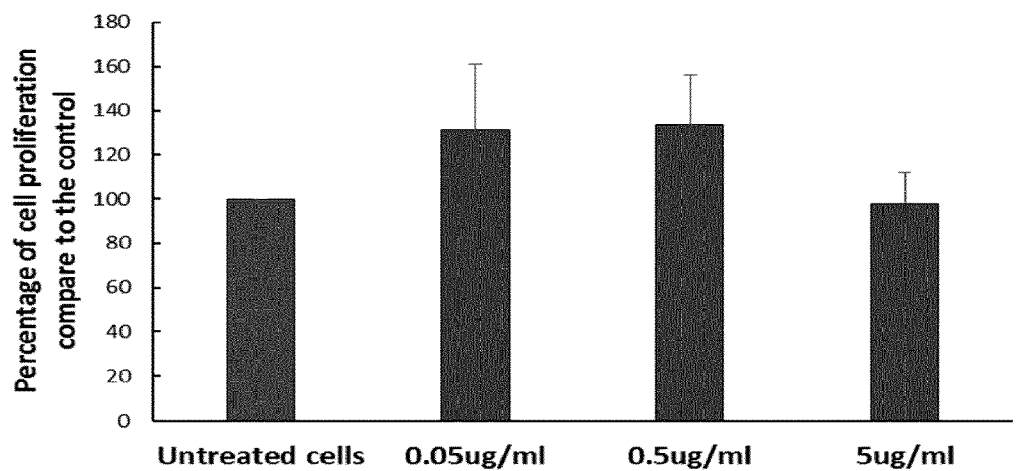

FIG. 7 shows an increase in HGF cell proliferation of 33% when incubated with SEQ ID 181.

Figure 8:
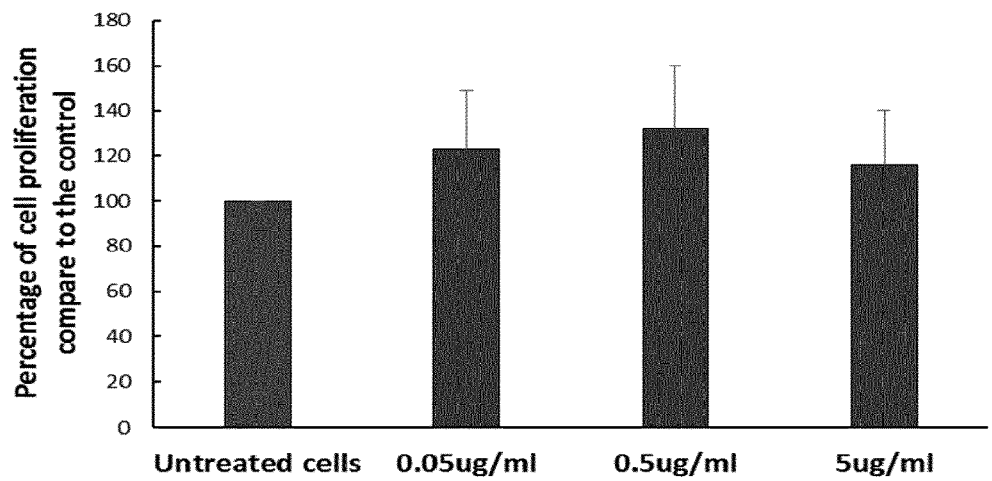

FIG. 8 shows an increase in HGF cell proliferation of 32% when incubated with SEQ ID 83.

Figure 9:
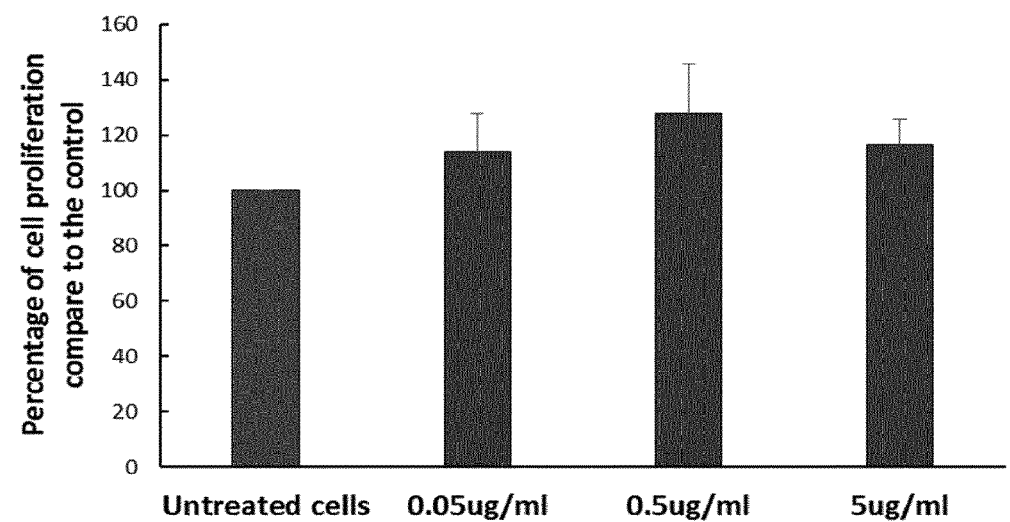

FIG. 9 shows an increase in HGF cell proliferation of 28% when incubated with SEQ ID 247.

Figure 10:
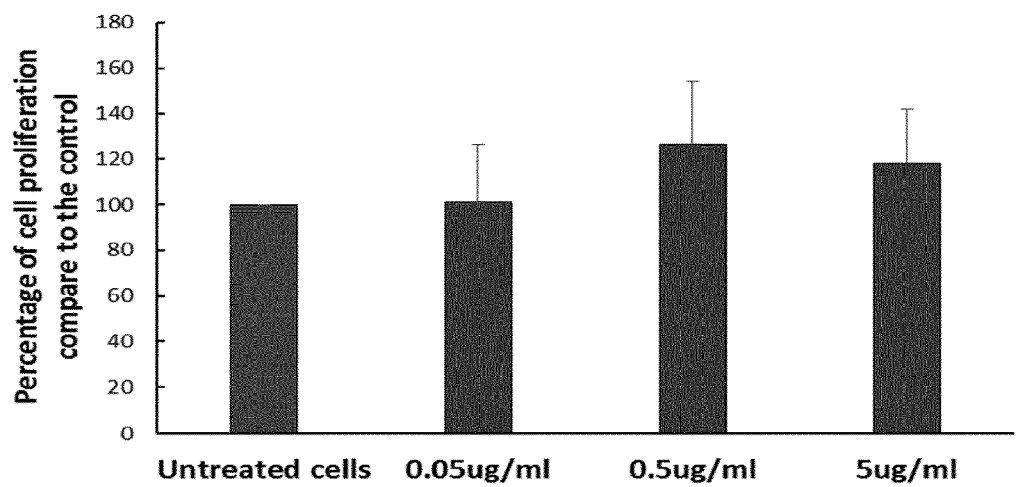

FIG. 10 shows an increase in HGF cell proliferation of 26% when incubated with SEQ ID 97.

Figure 11:
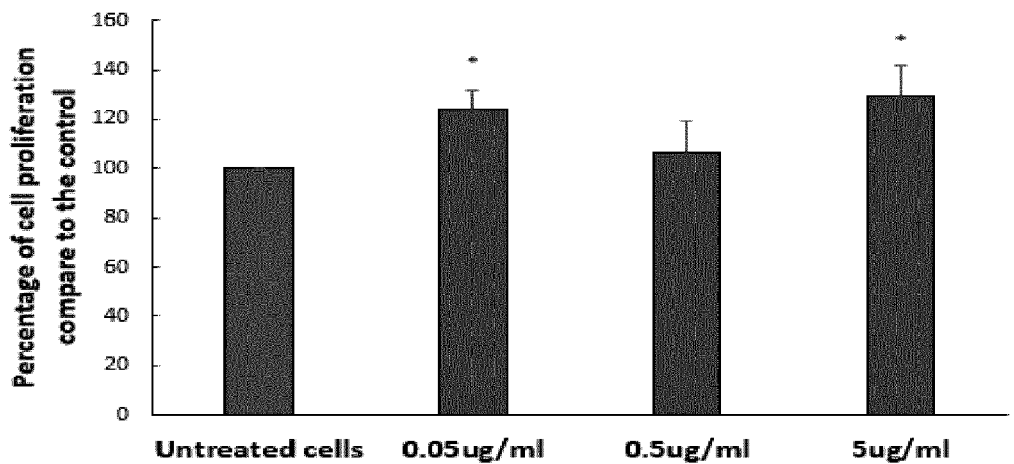
Figure 12:
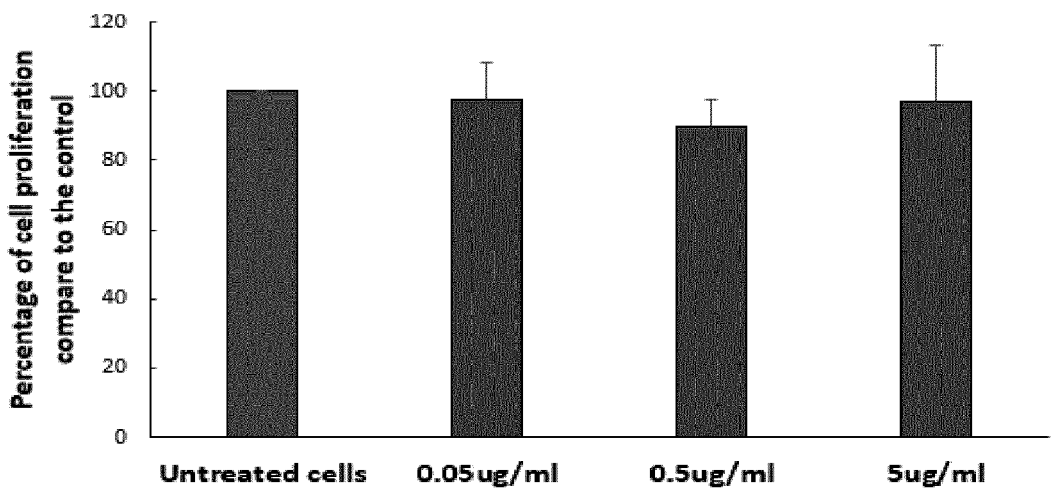
Figure 13:
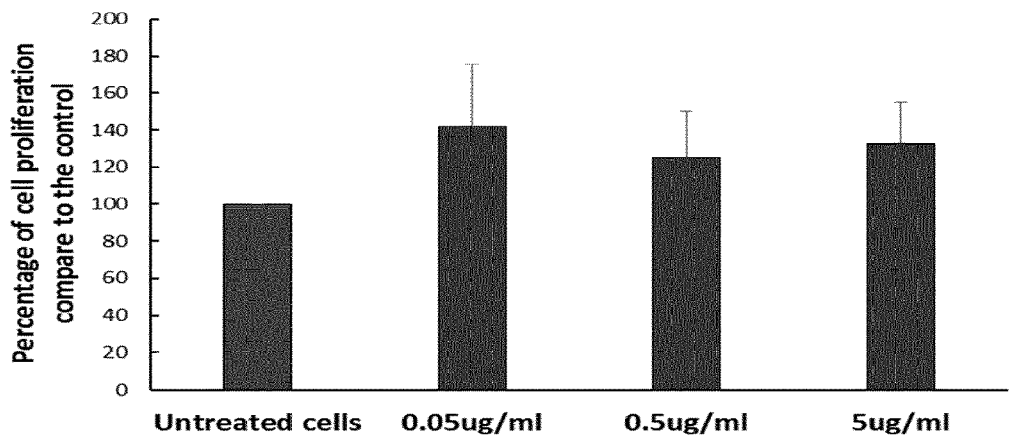
Figure 14:
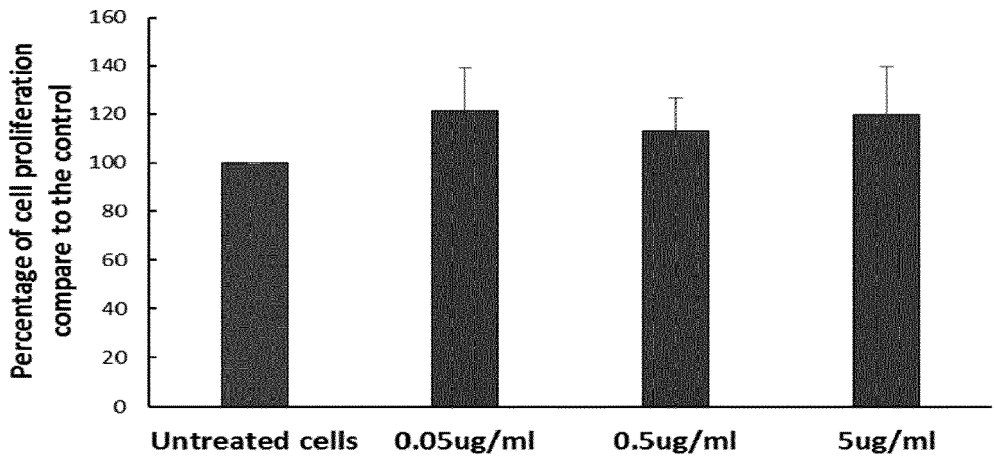

FIG. 11 shows an increase in HGF cell proliferation of 29% when incubated with SEQ ID 74.

Figure 15:
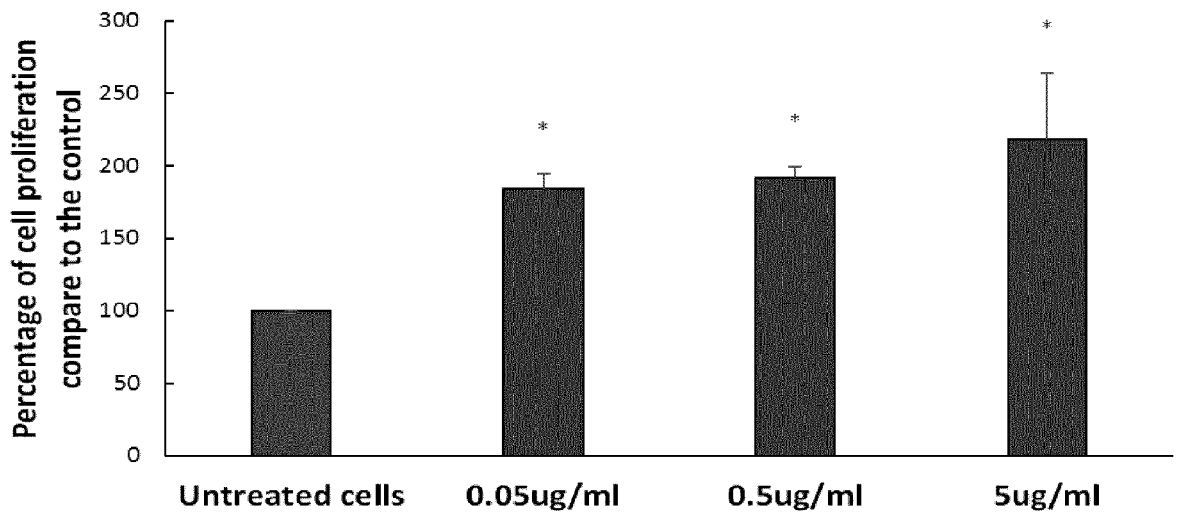

FIG. 15 shows an increase in HGF cell proliferation of 119% when incubated with SEQ ID 470.

Figure 16:
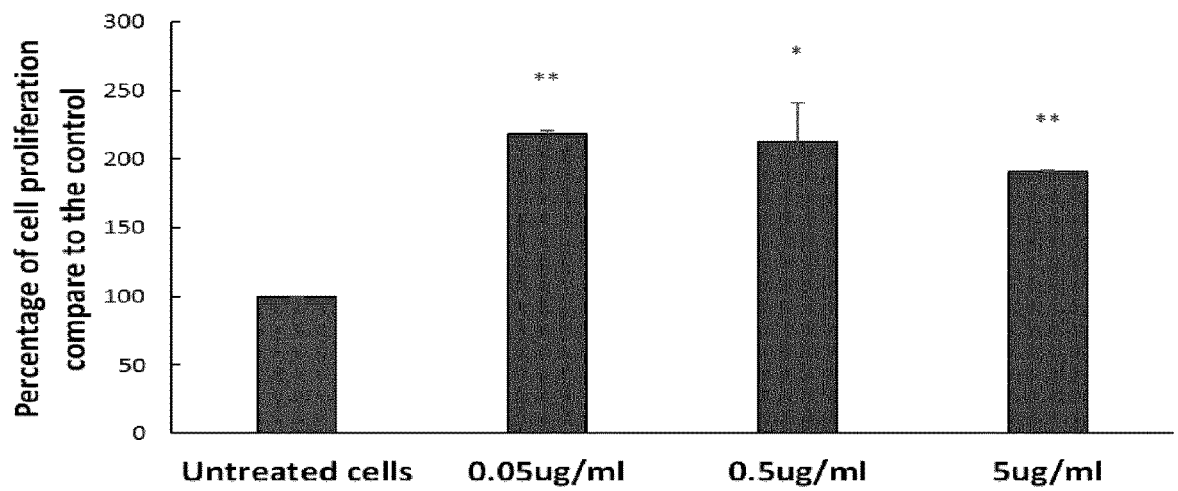

FIG. 16 shows an increase in HGF cell proliferation of 118% when incubated with SEQ ID 257.

Figure 17:
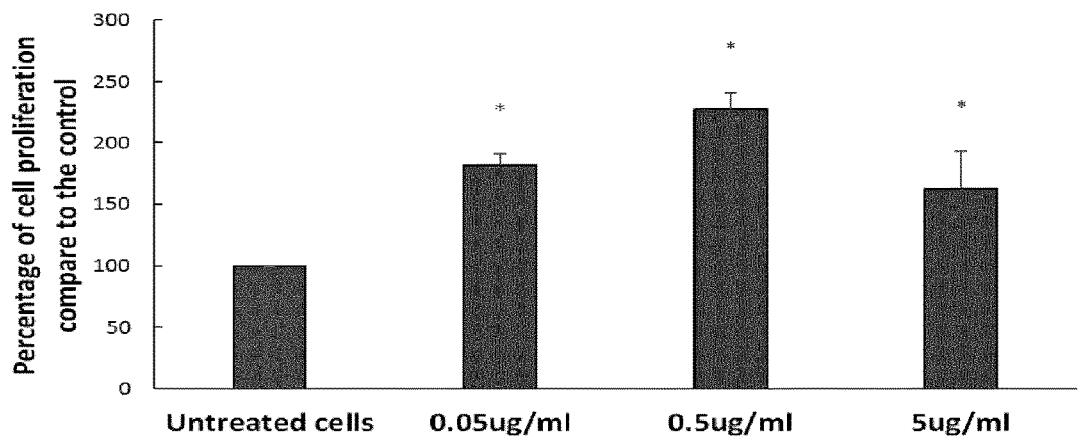

FIG. 17 shows an increase in HGF cell proliferation of 117% when incubated with SEQ ID 256.

Figure 18:
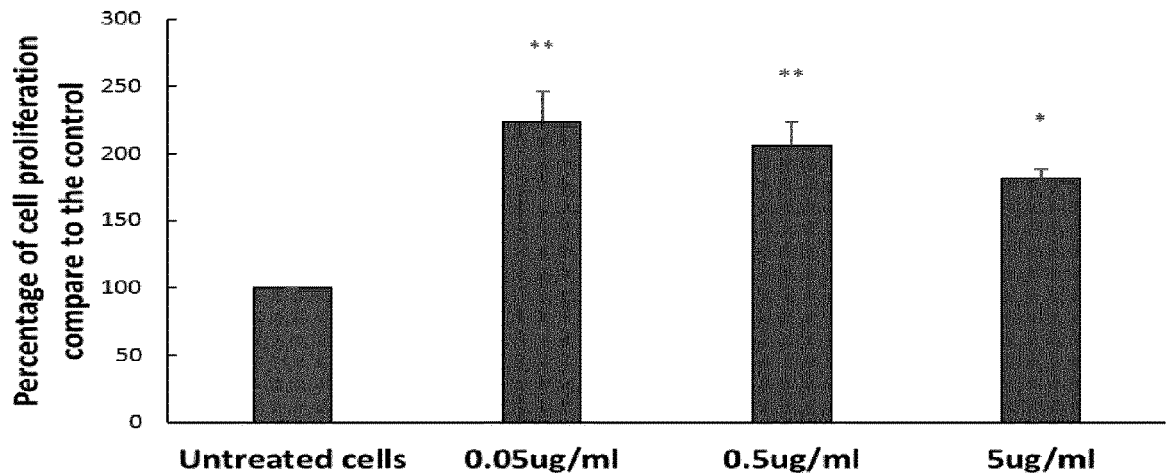

FIG. 18 shows an increase in HGF cell proliferation of 114% when incubated with SEQ ID 457.

Figure 19:
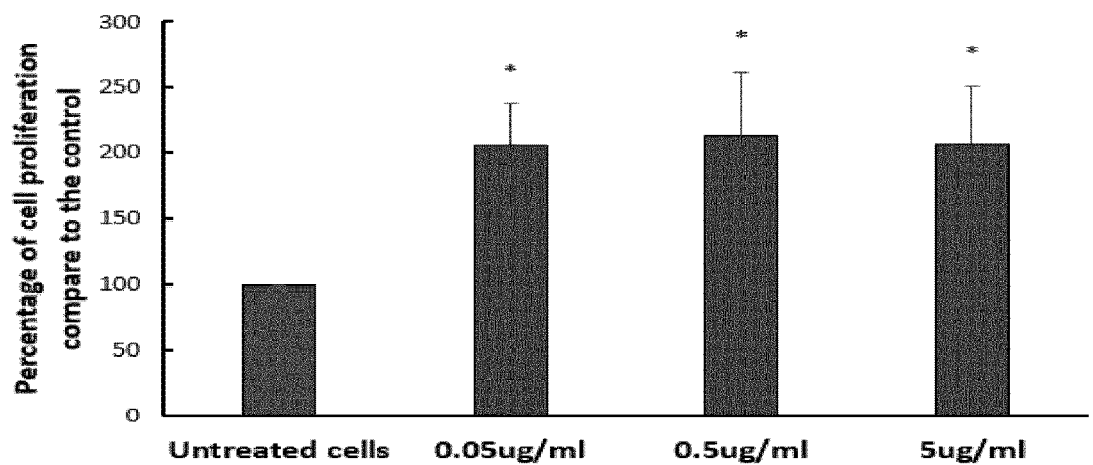

FIG. 19 shows an increase in HGF cell proliferation of 113% when incubated with SEQ ID 499.

Figure 20:
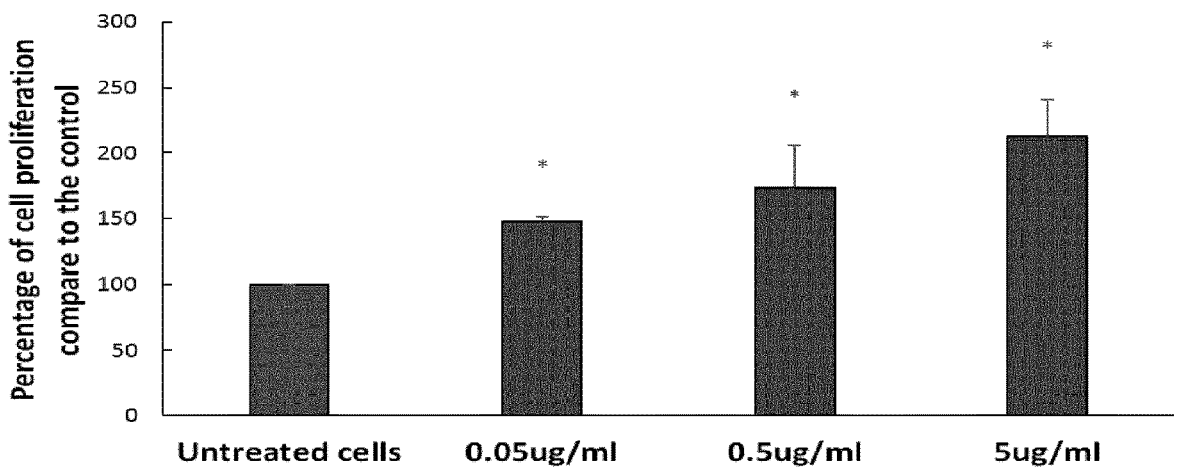

FIG. 20 shows an increase in HGF cell proliferation of 112% when incubated with SEQ ID 253.

Figure 21:
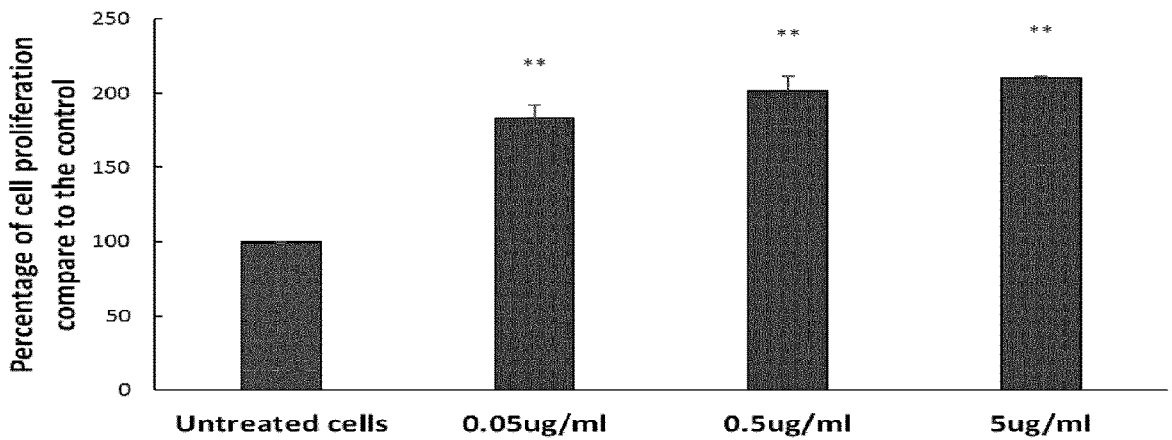

FIG. 21 shows an increase in HGF cell proliferation of 110% when incubated with SEQ ID 222.

Figure 22:
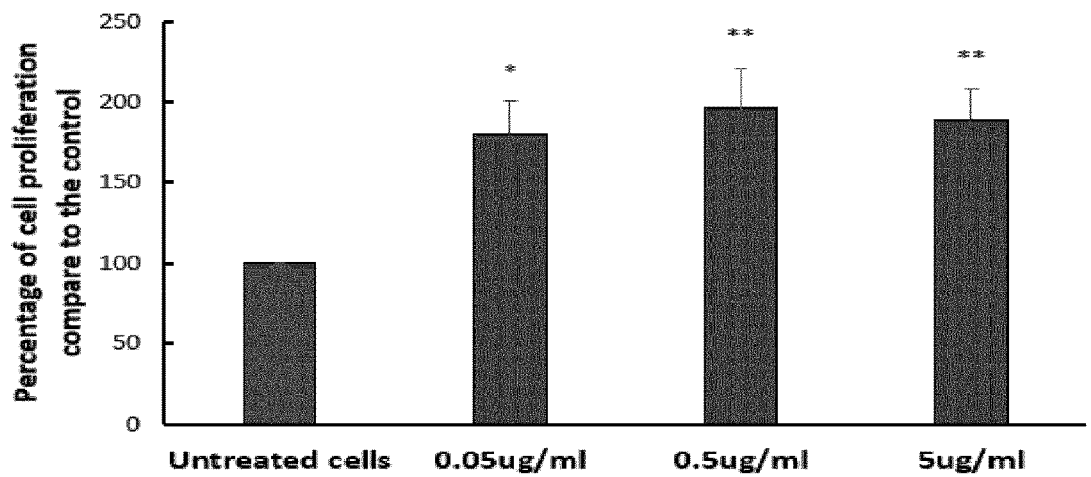

FIG. 22 shows an increase in HGF cell proliferation of 97% when incubated with SEQ ID 272.

Figure 23:
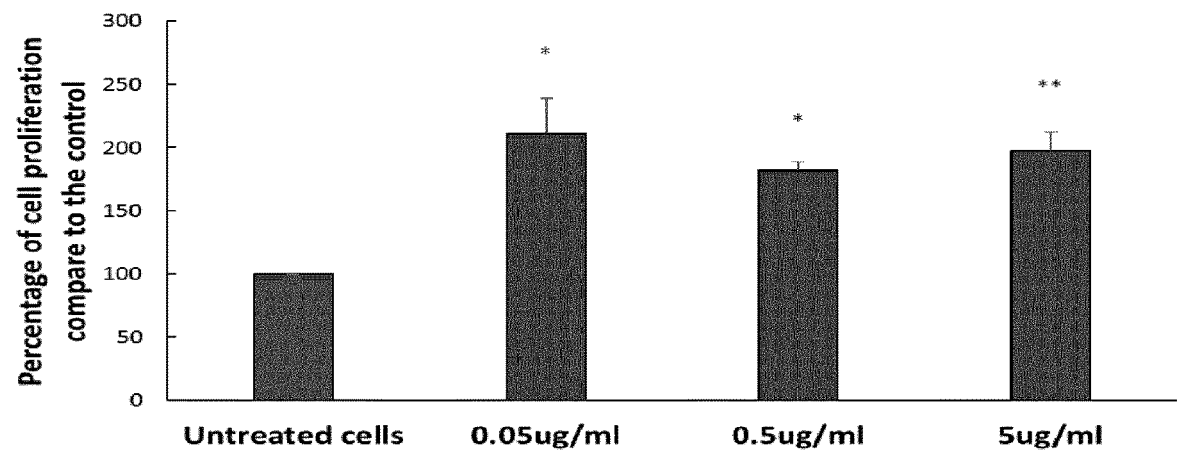

FIG. 23 shows an increase in HGF cell proliferation of 111% when incubated with SEQ ID 252.

Figure 24:
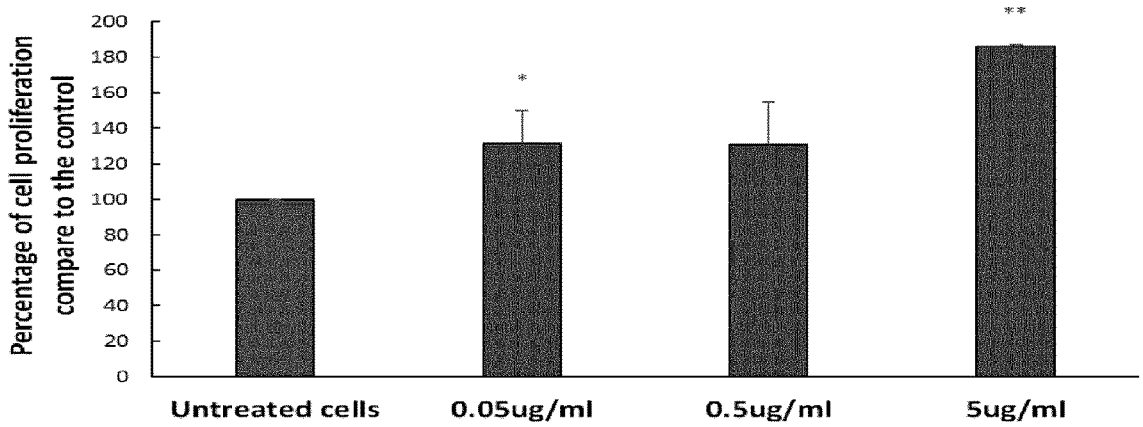

FIG. 24 shows an increase in HGF cell proliferation of 86% when incubated with SEQ ID 248.

Figure 25:
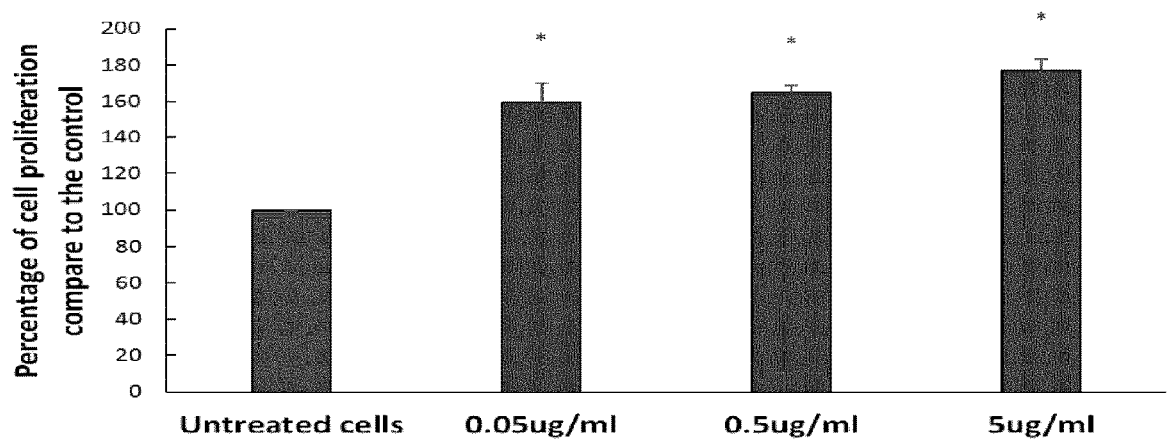

FIG. 25 shows an increase in HGF cell proliferation of 77% when incubated with SEQ ID 472.

Figure 26:
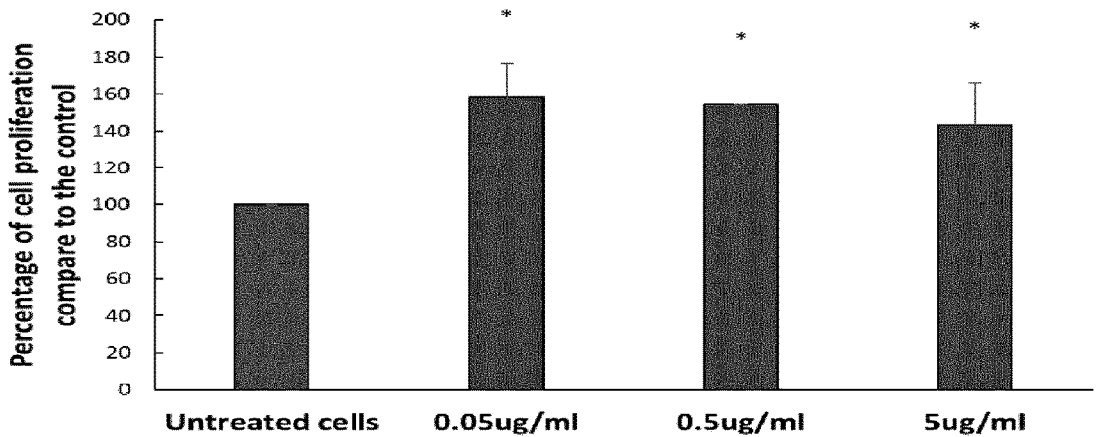

FIG. 26 shows an increase in HGF cell proliferation of 58% when incubated with SEQ ID 365.

Figure 27:
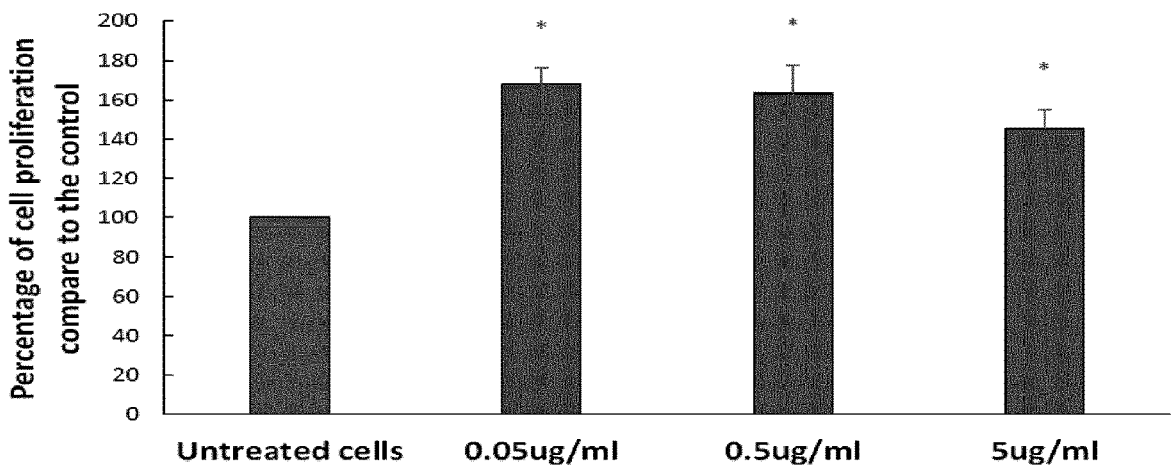

FIG. 27 shows an increase in HGF cell proliferation of 68% when incubated with SEQ ID 502.

Figure 28:
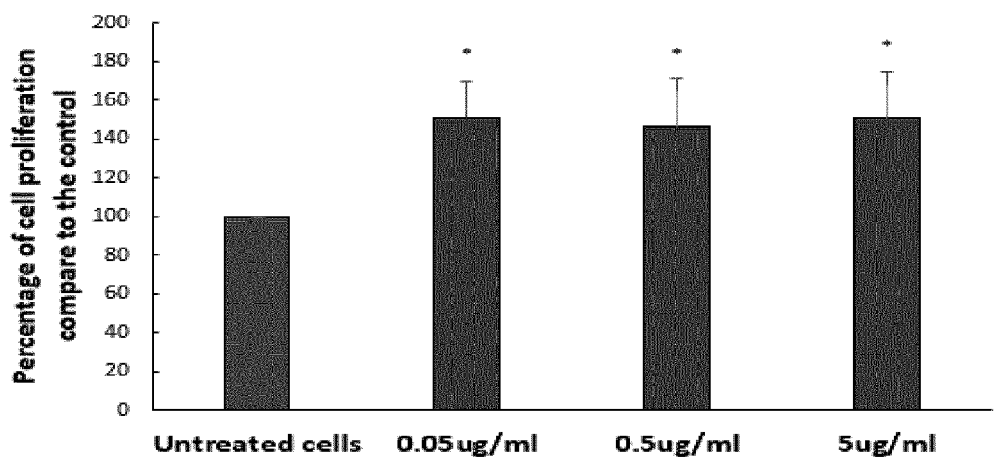

FIG. 28 shows an increase in HGF cell proliferation of 51% when incubated with SEQ ID 496.

Figure 29:
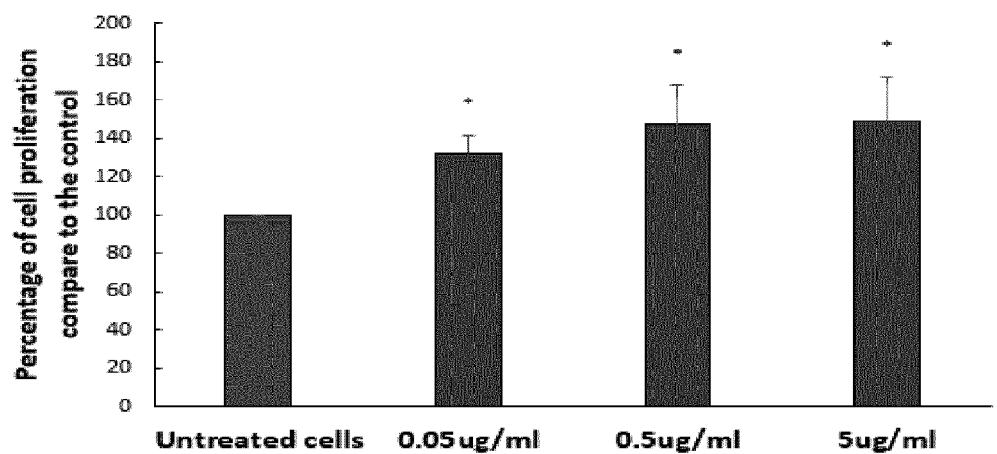

FIG. 29 shows an increase in HGF cell proliferation of 49% when incubated with SEQ ID 98.

Figure 30:
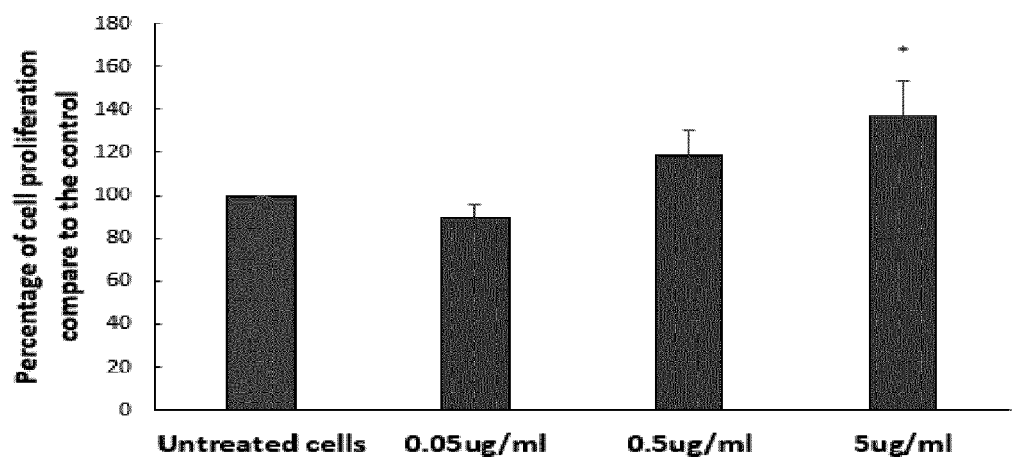

FIG. 30 shows an increase in HGF cell proliferation of 38% when incubated with SEQ ID 454.

Figure 31:
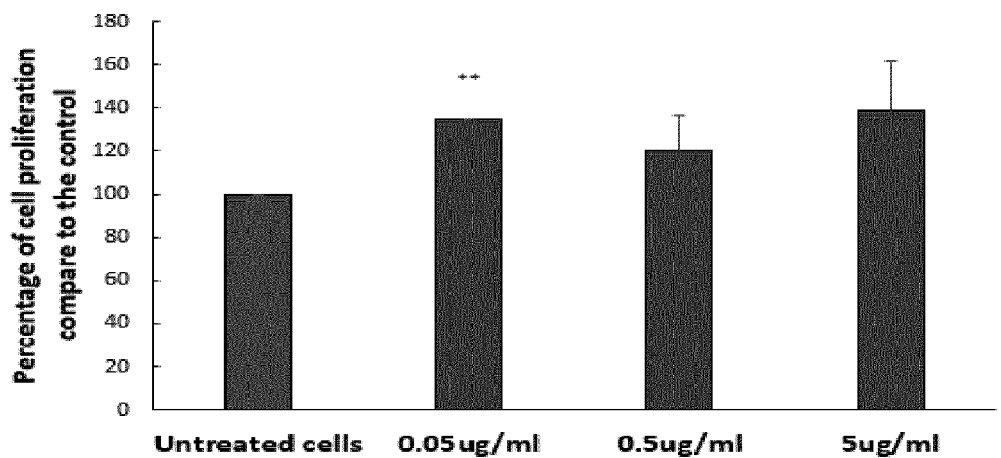

FIG. 31 shows an increase in HGF cell proliferation of 35% when incubated with SEQ ID 85.

Figure 32:
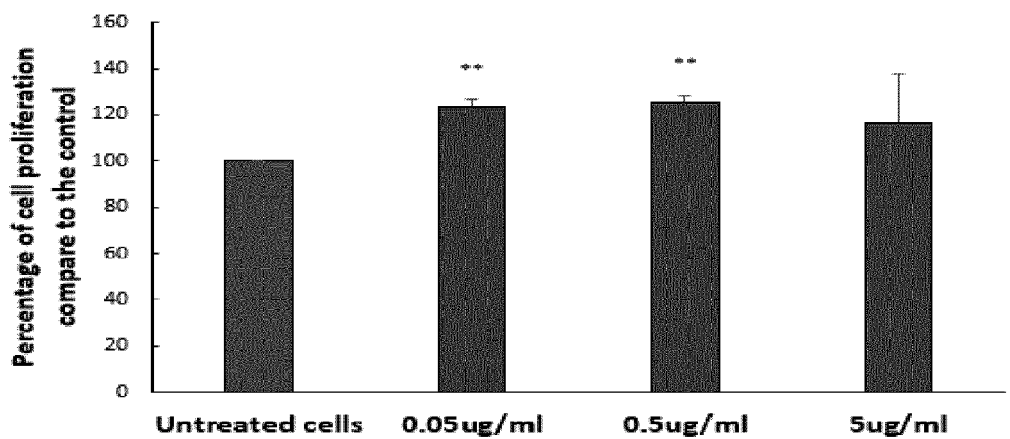

FIG. 32 shows an increase in HGF cell proliferation of 25% when incubated with SEQ ID 453.

Figure 33:
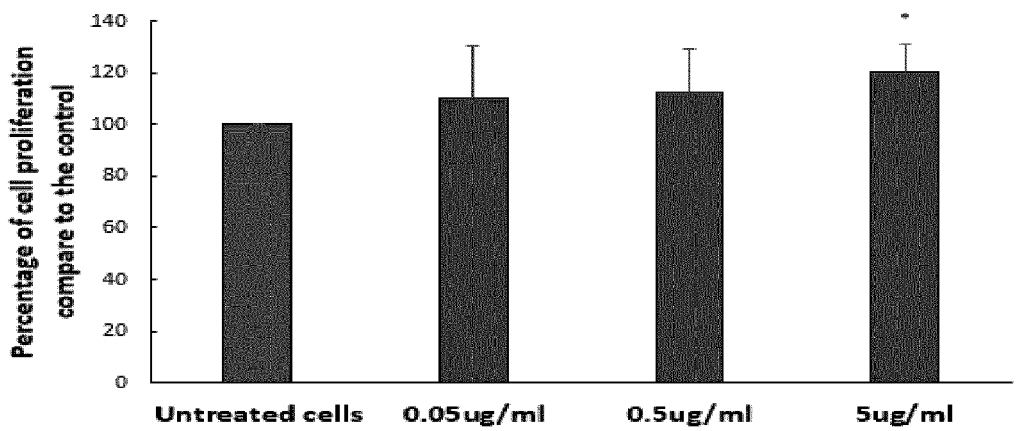

FIG. 33 shows an increase in HGF cell proliferation of 21% when incubated with SEQ ID 158.

Figure 34:
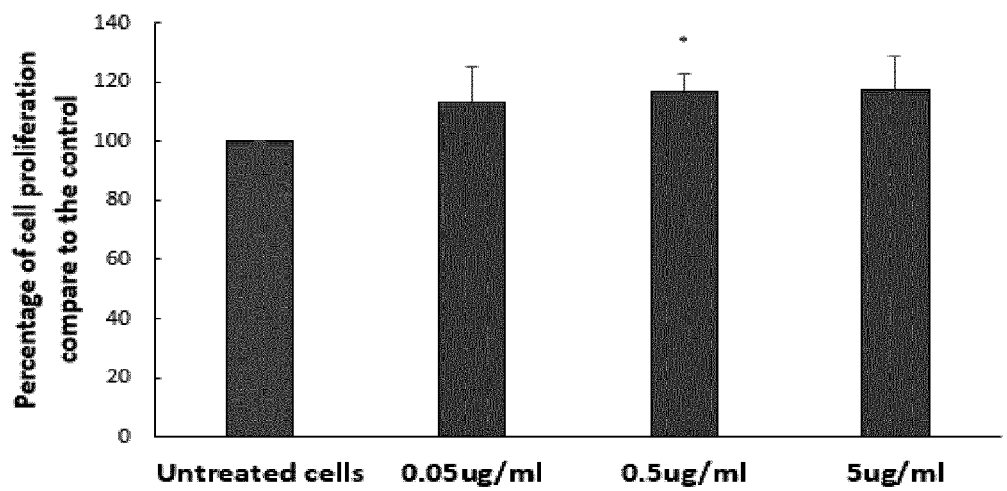

FIG. 34 shows an increase in HGF cell proliferation of 18% when incubated with SEQ ID 464.

Figure 35:
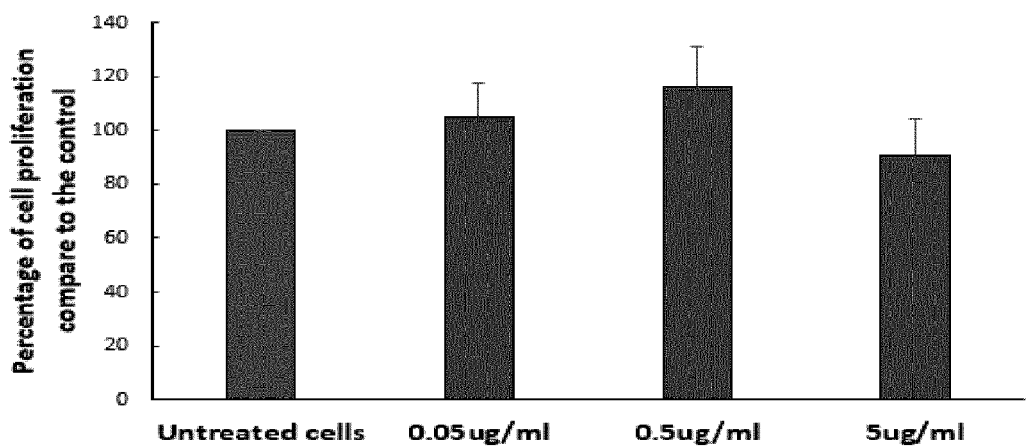

FIG. 35 shows an increase in HGF cell proliferation of 16% when incubated with SEQ ID 73.

Figure 36:
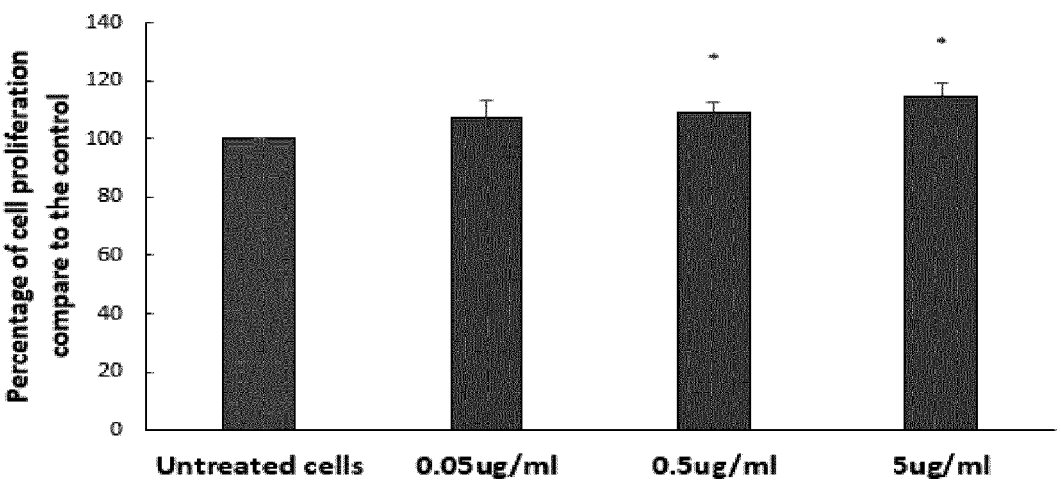

FIG. 36 shows an increase in HGF cell proliferation of 15% when incubated with SEQ ID 359.

Figure 37:
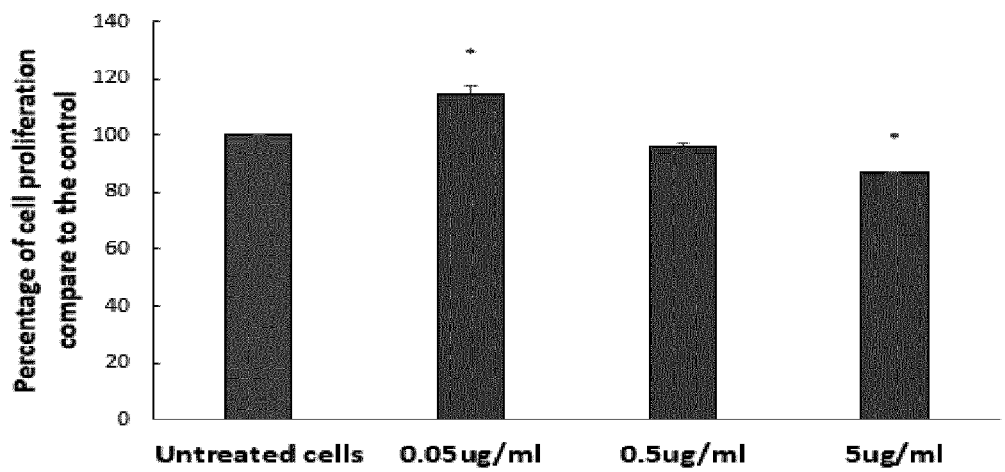

FIG. 37 shows an increase in HGF cell proliferation of 15% when incubated with SEQ ID 124.

Figure 38:
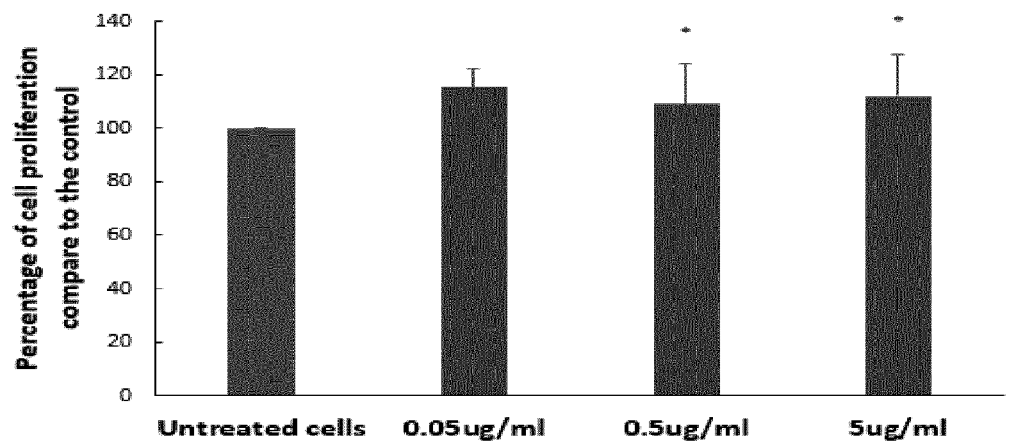
Figure 39:
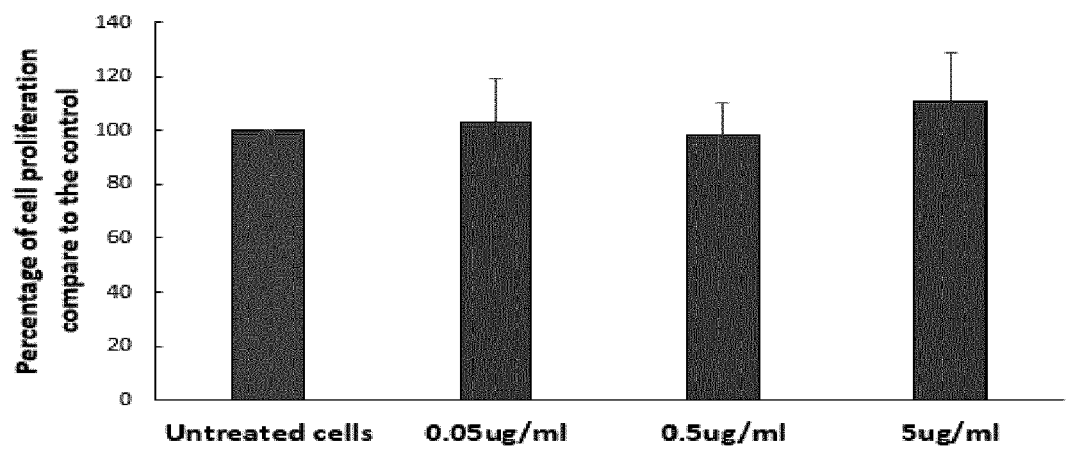
Figure 40:
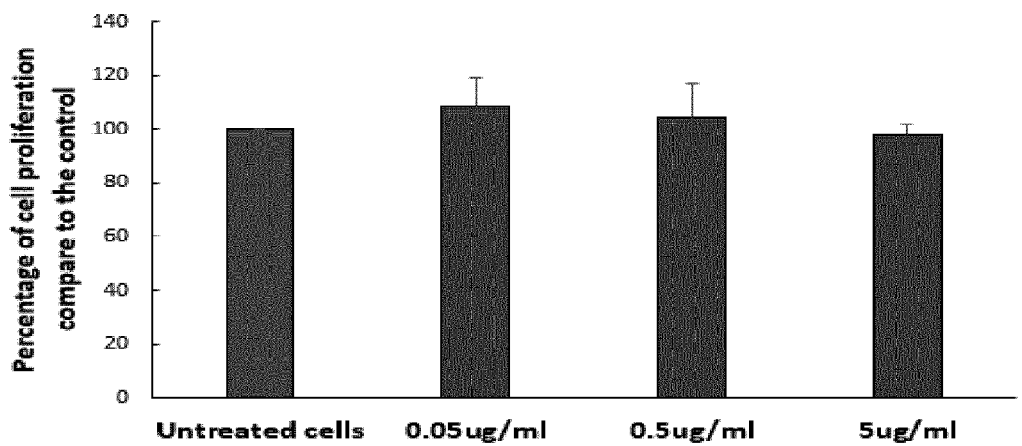
Figure 41:
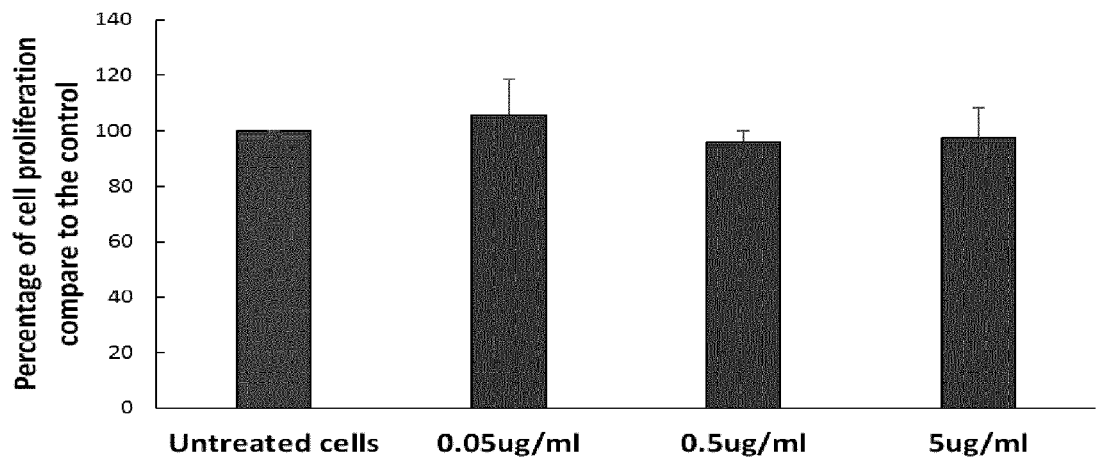
Figure 42:
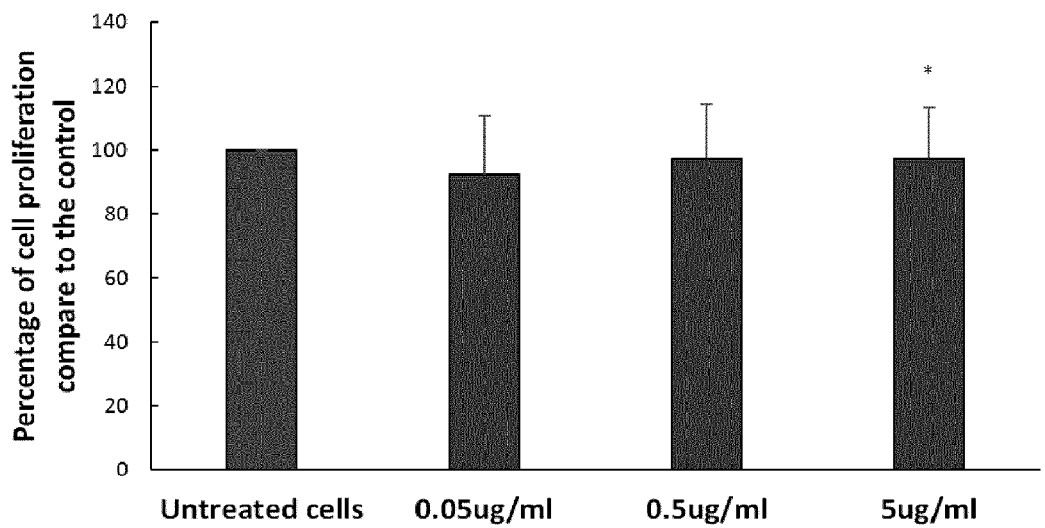
Figure 43:
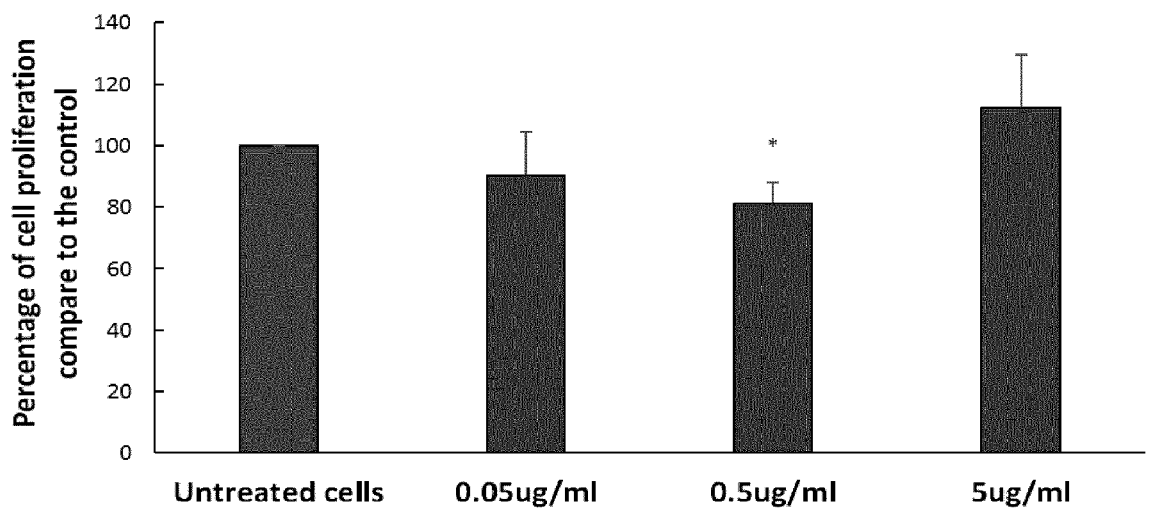
Figure 44:
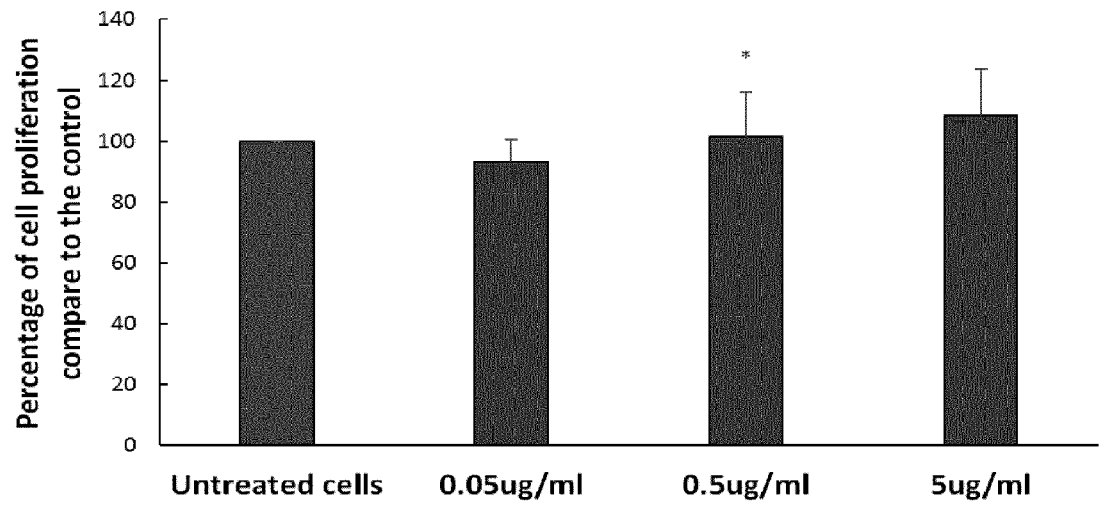
Figure 45:
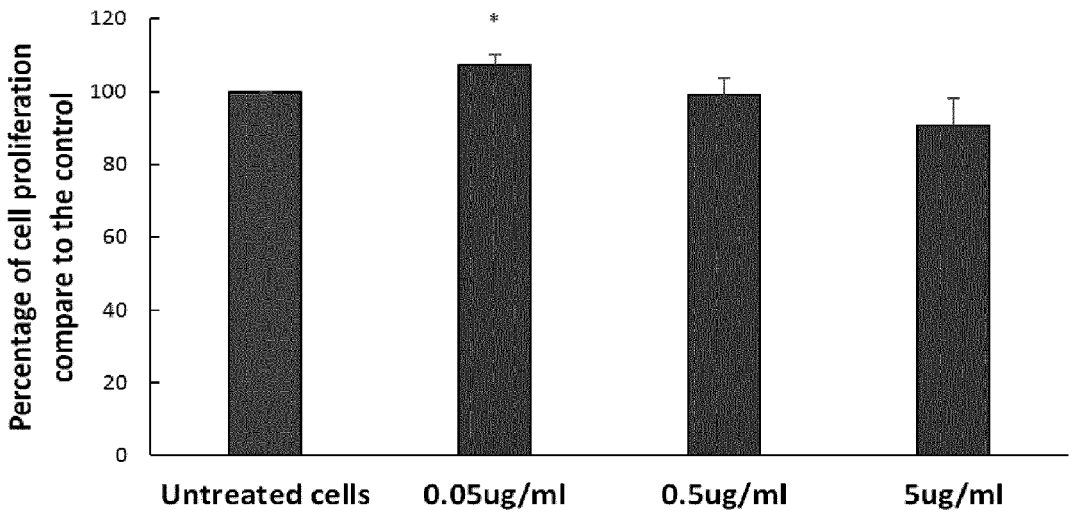
Figure 46:
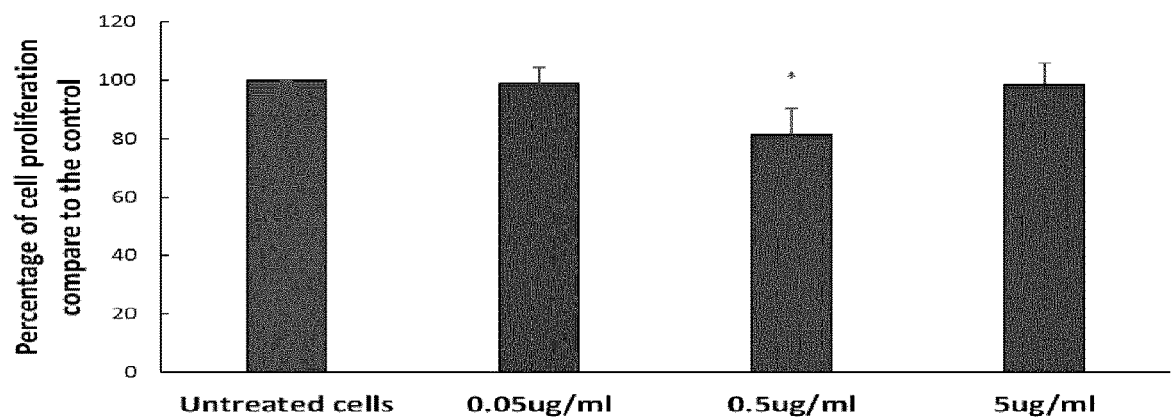
Figure 47:
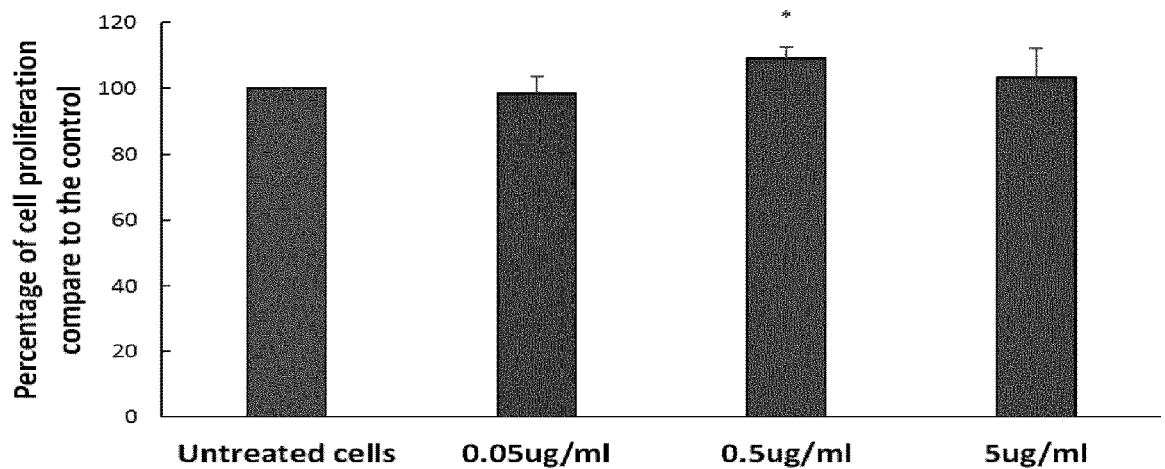
Figure 48:
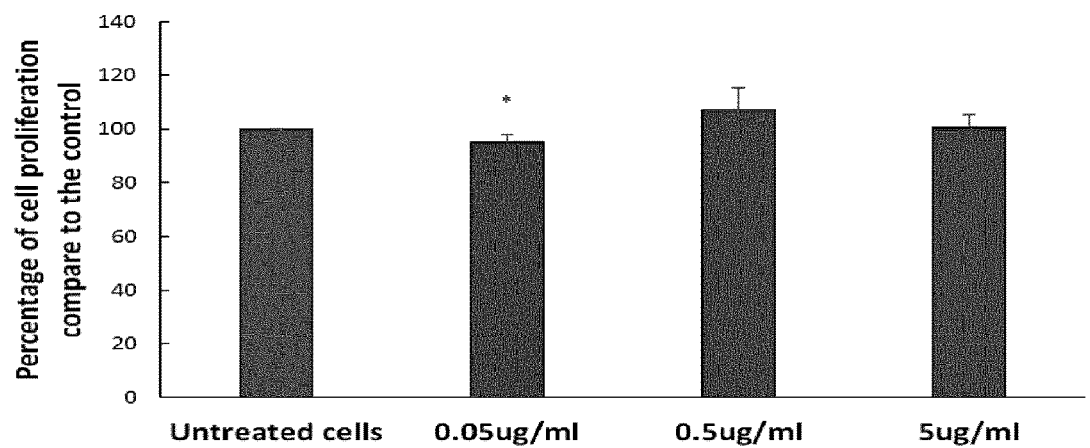
Figure 49:
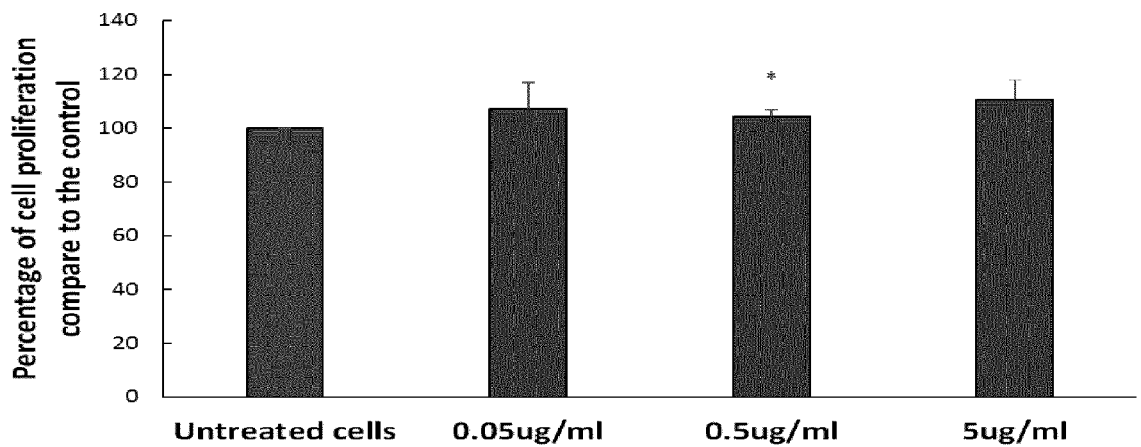
Figure 50:
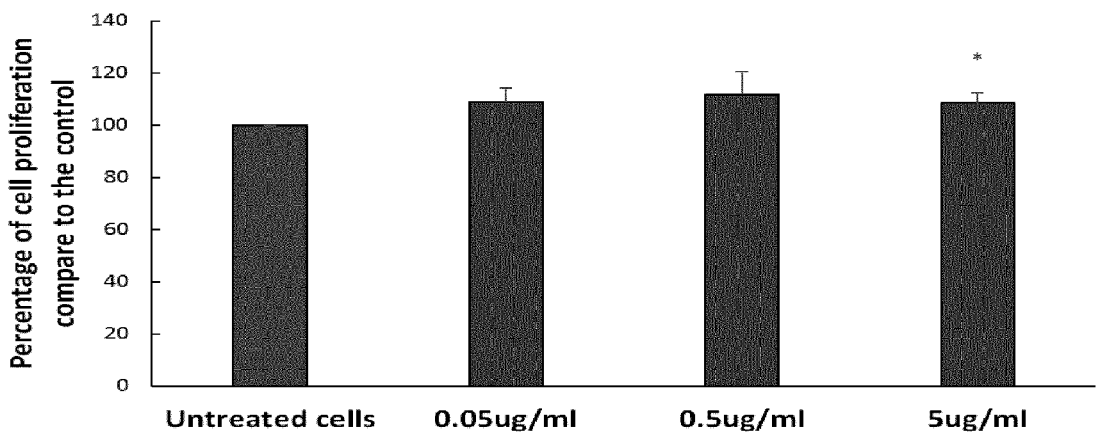
Figure 51:
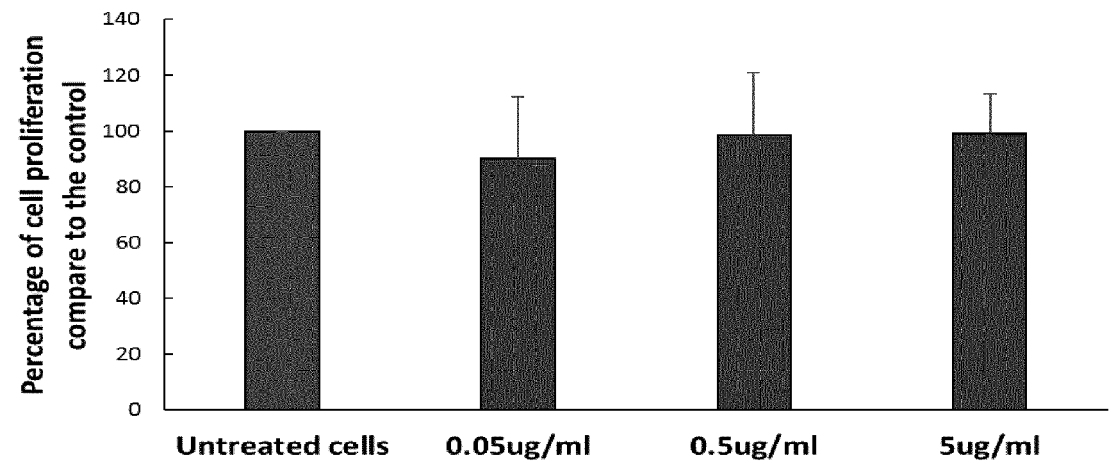
Figure 52:
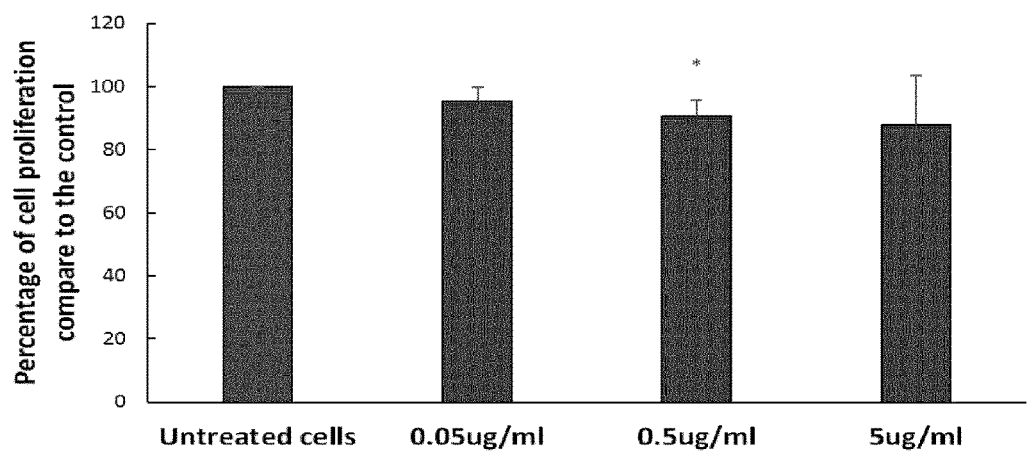
Figure 53:
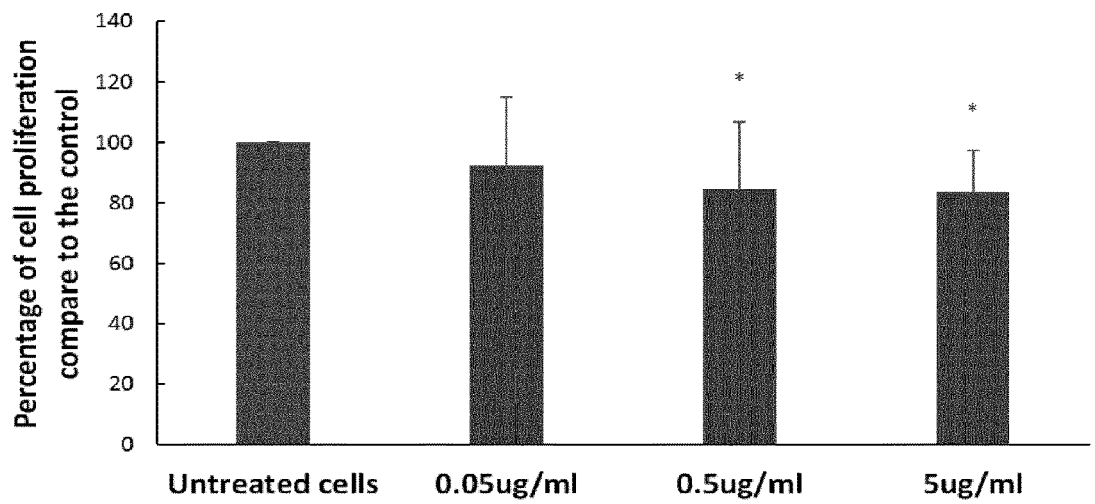

FIG. 38 shows an increase in HGF cell proliferation of 15% when incubated with SEQ ID 112.

Figure 54:
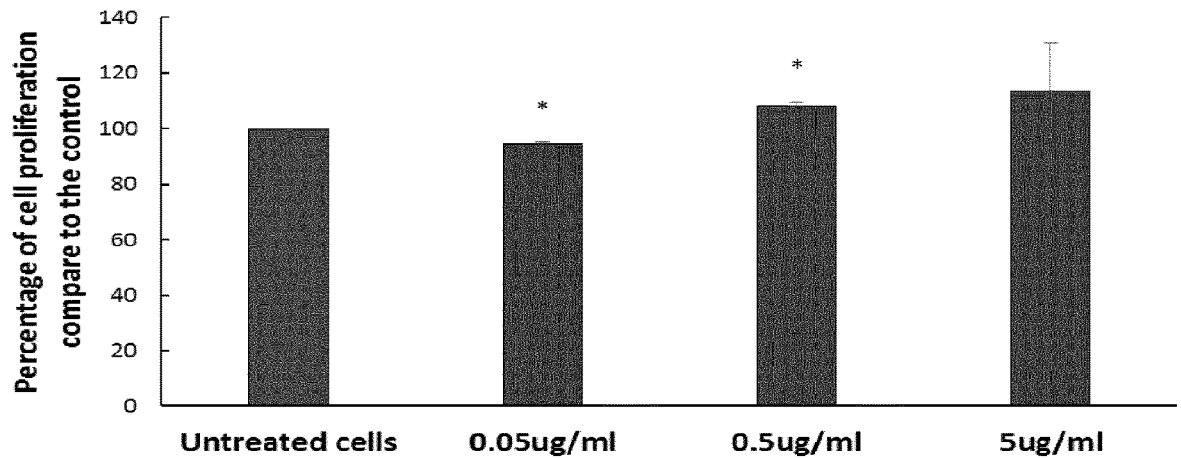
Figure 55:
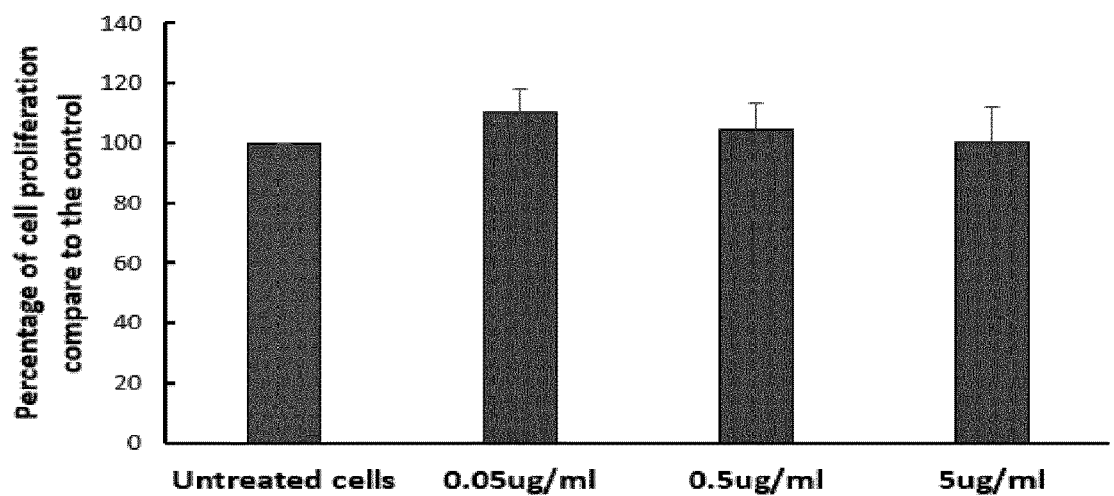

FIG. 54 shows an increase in HGF cell proliferation of 13% when incubated with SEQ ID 475.

Figure 56:
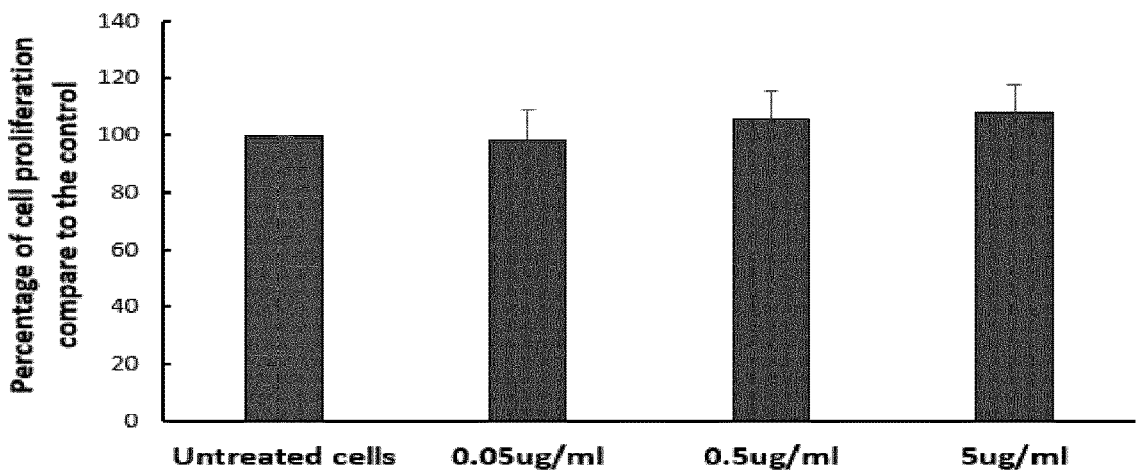

FIG. 56 shows an increase in HGF cell proliferation of 8% when incubated with SEQ ID 337.

Figure 57:
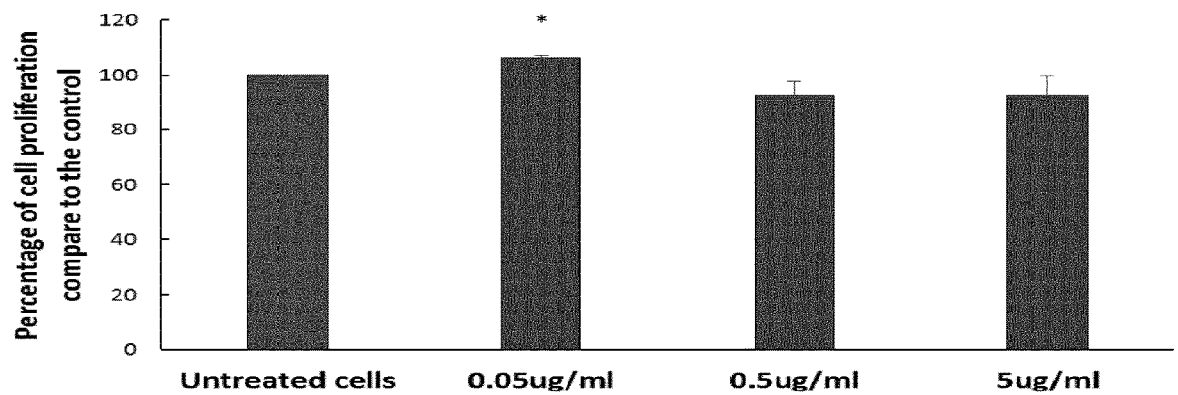
Figure 58:
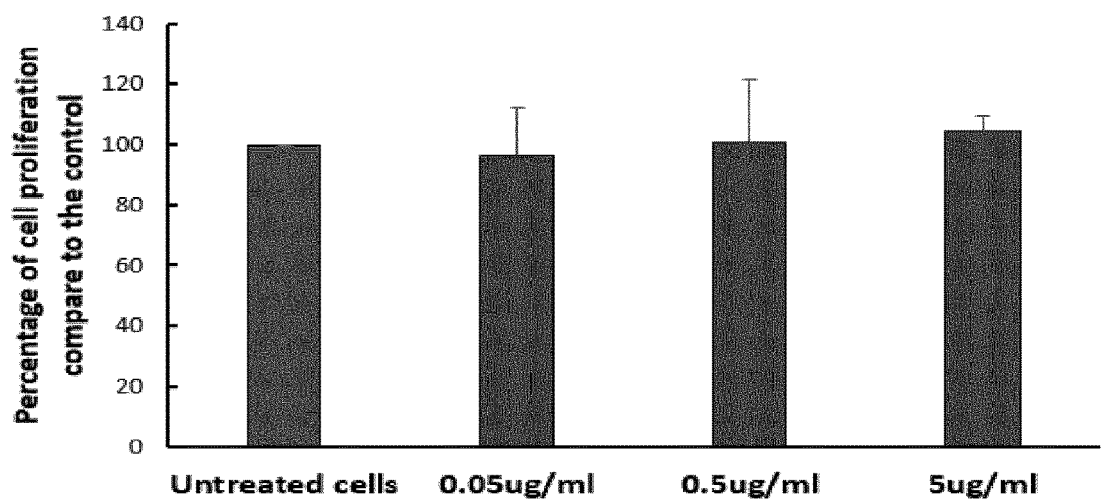
Figure 59:
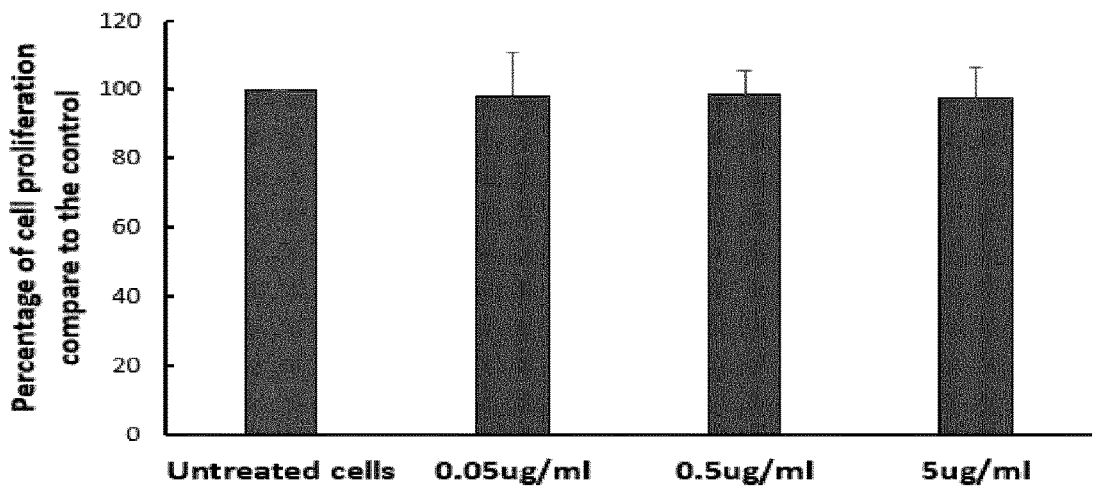
Figure 60:
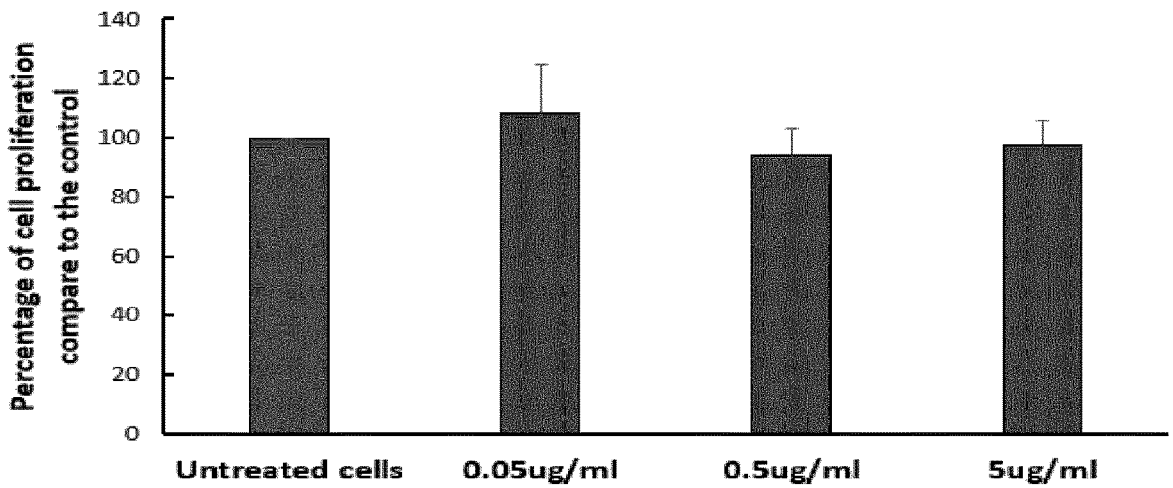
Figure 61:
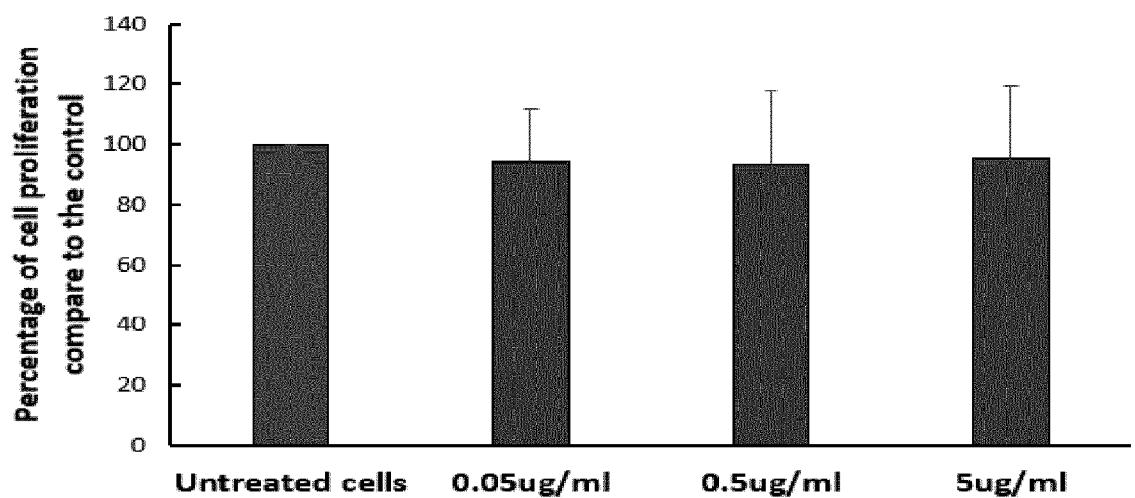
Figure 62:
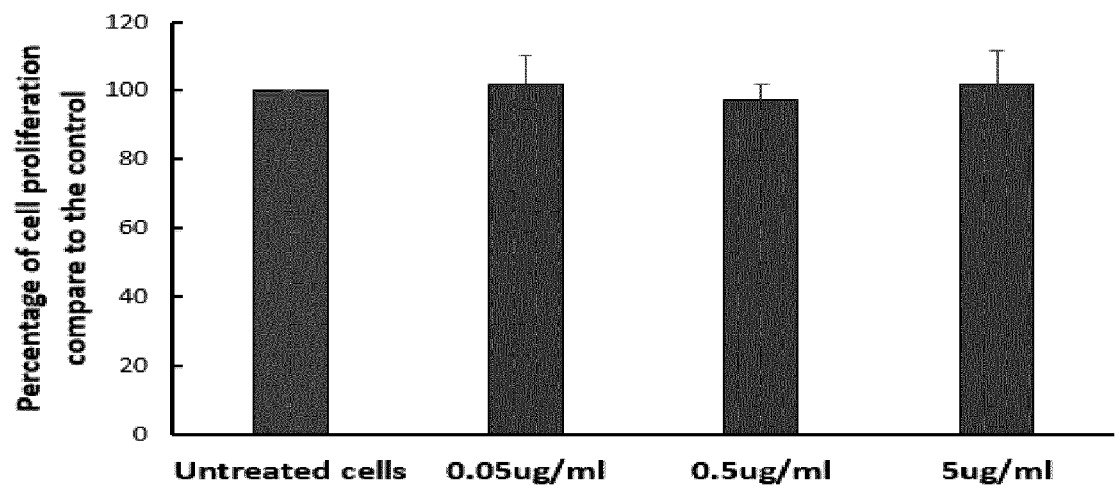
Figure 63:
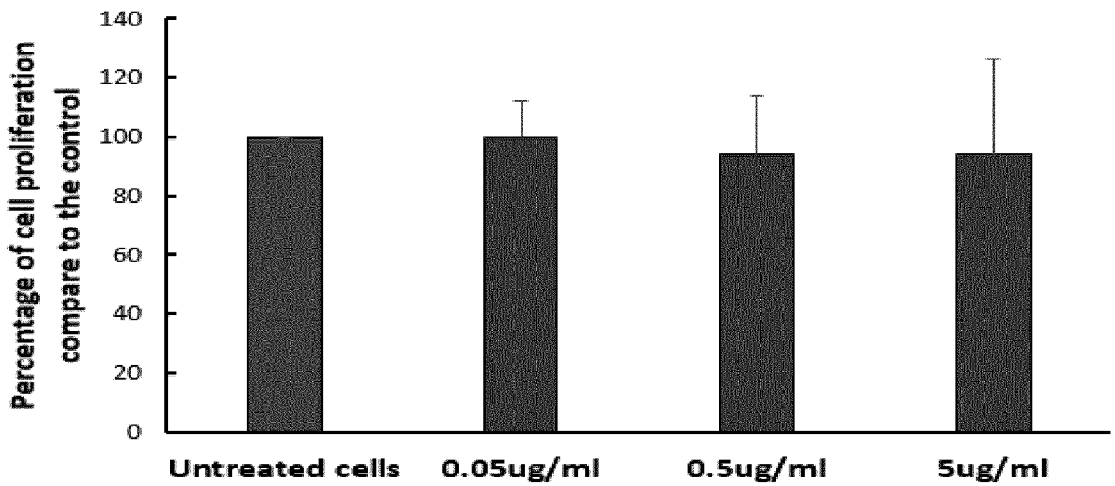
Figure 64:
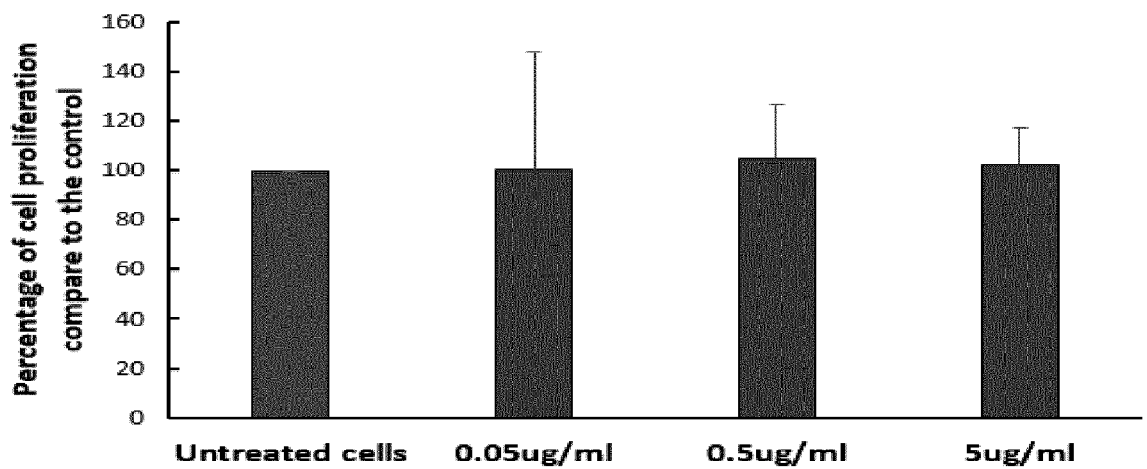
Figure 65:
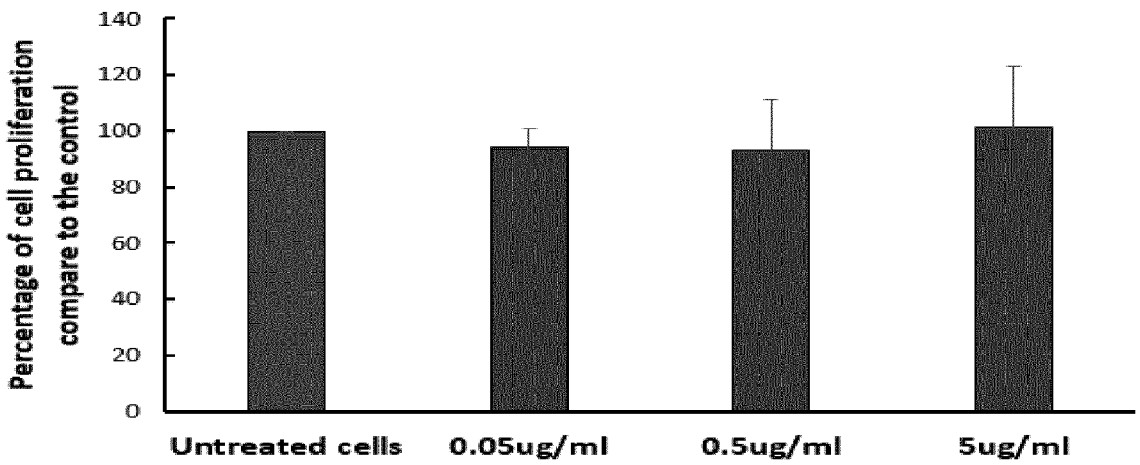
Figure 66:
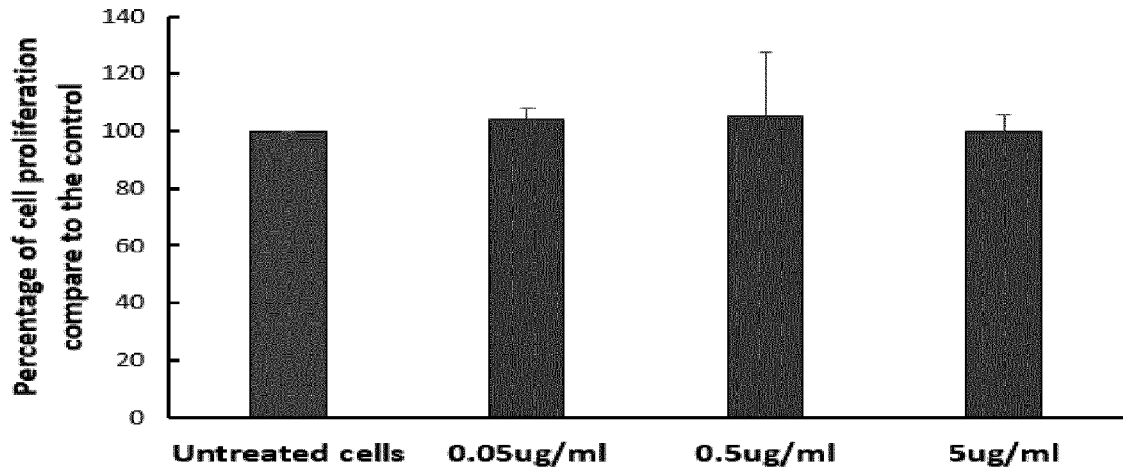

FIG. 57 shows an increase in HGF cell proliferation of 6% when incubated with SEQ ID 500.

Figure 67:
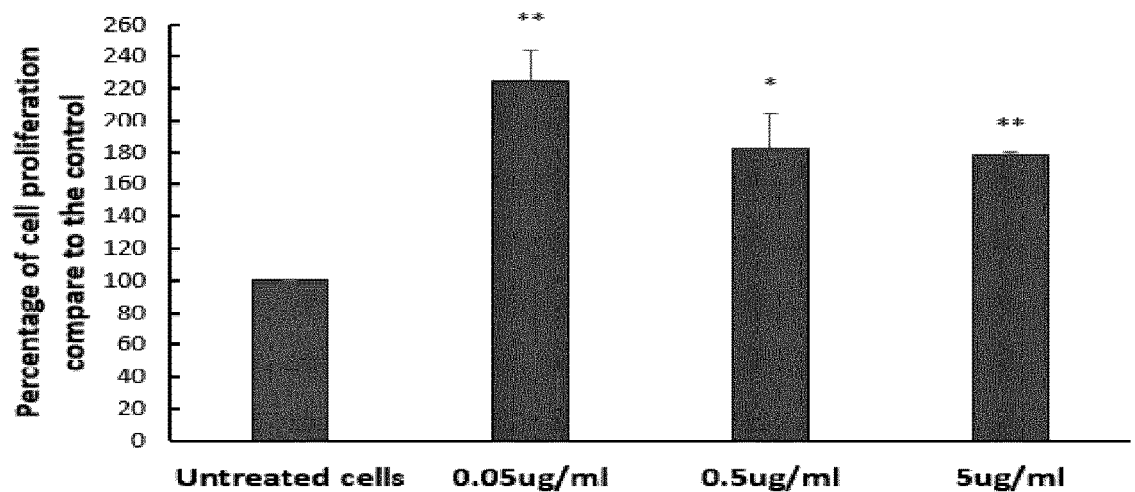

FIG. 67 shows an increase in HGF cell proliferation of 125% when incubated with SEQ ID 503.

Figure 68:
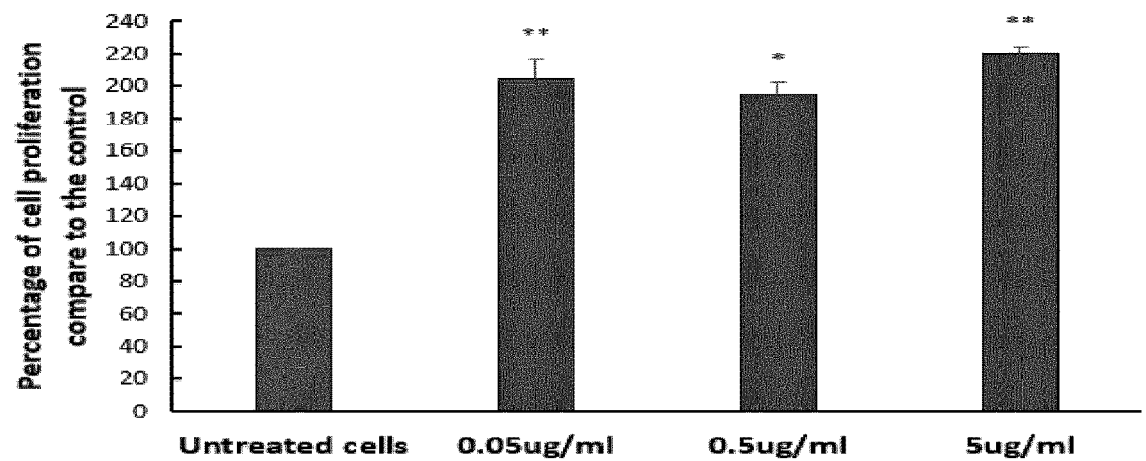

FIG. 68 shows an increase in HGF cell proliferation of 121% when incubated with SEQ ID 474.

Figure 69:
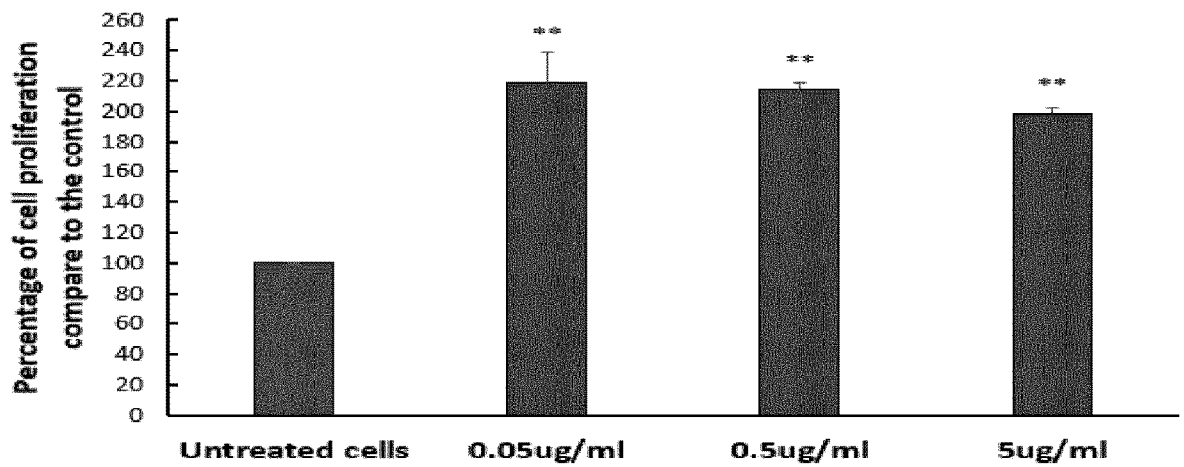

FIG. 69 shows an increase in HGF cell proliferation of 119% when incubated with SEQ ID 504.

Figure 70:
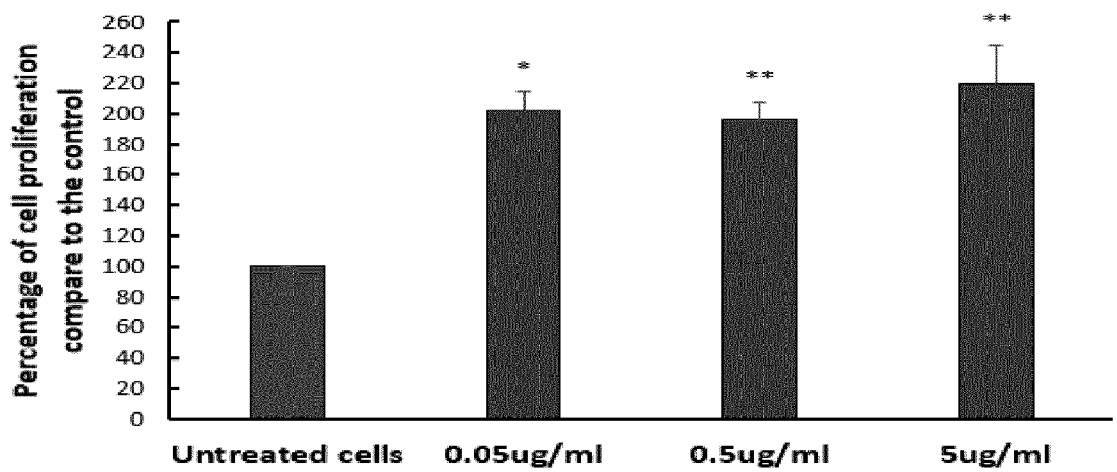

FIG. 70 shows an increase in HGF cell proliferation of 119% when incubated with SEQ ID 114.

Figure 71:
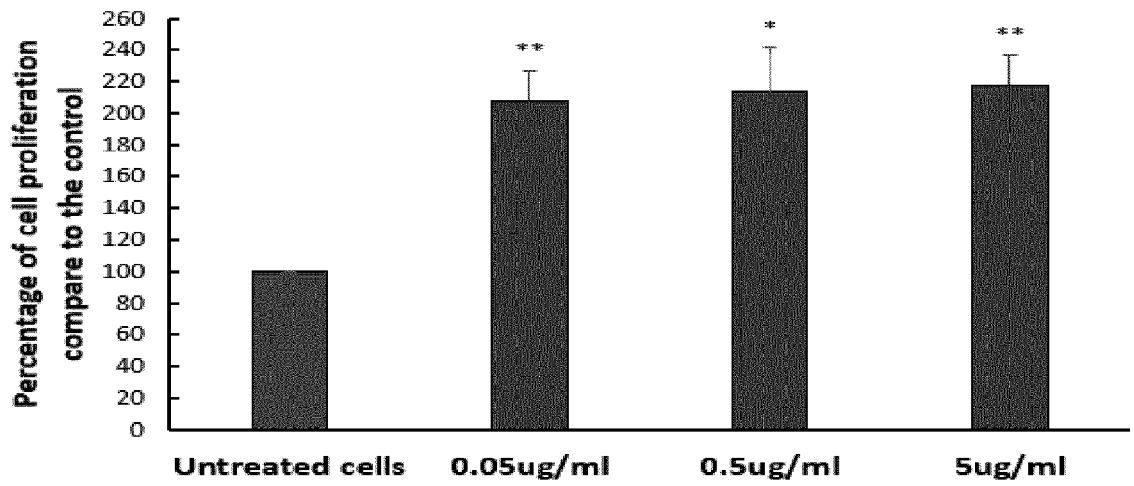

FIG. 71 shows an increase in HGF cell proliferation of 118% when incubated with SEQ ID 505.

Figure 72:
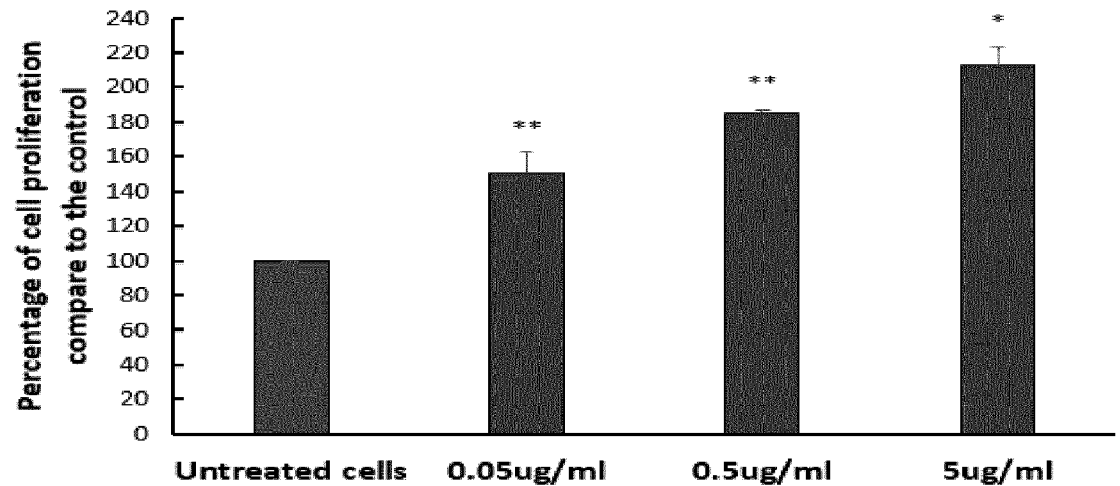

FIG. 72 shows an increase in HGF cell proliferation of 113% when incubated with SEQ ID 482.

Figure 73:
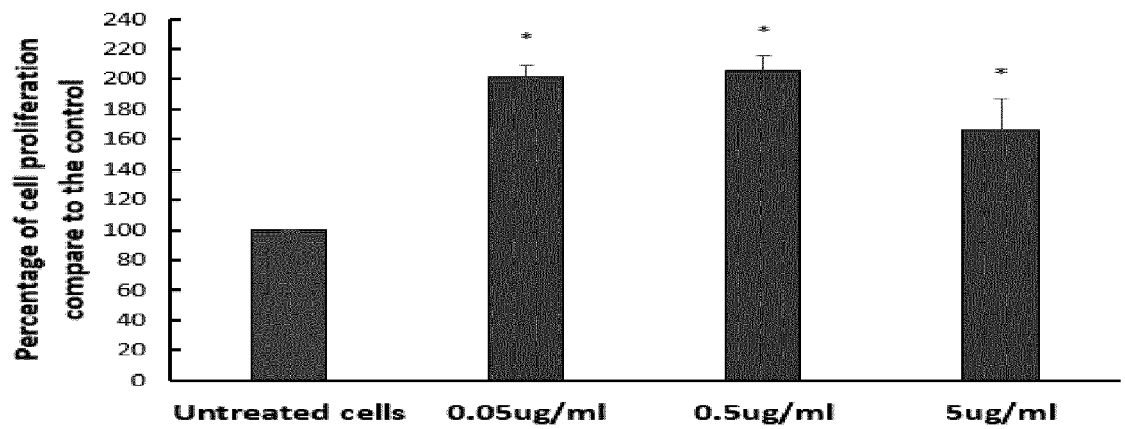

FIG. 73 shows an increase in HGF cell proliferation of 106% when incubated with SEQ ID 479.

Figure 74:
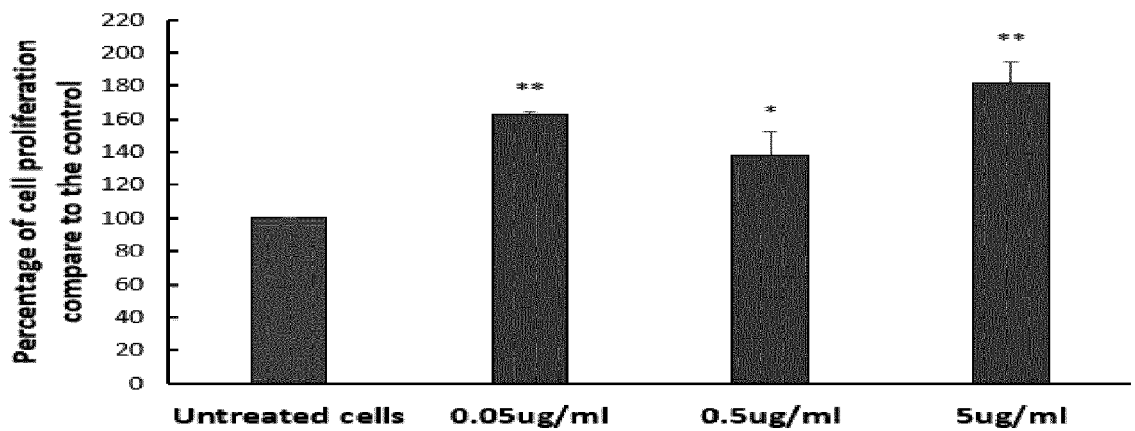

FIG. 74 shows an increase in HGF cell proliferation of 81% when incubated with SEQ ID 477.

Figure 75:
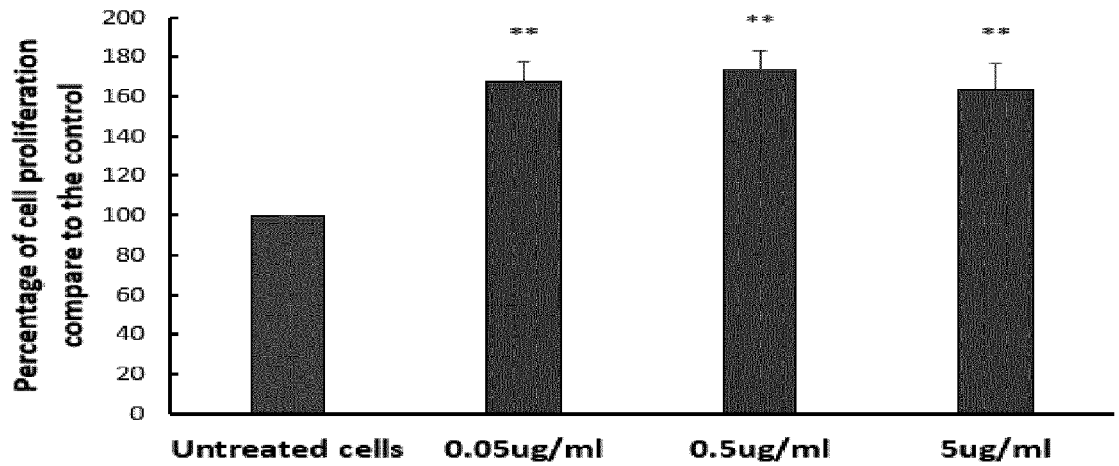

FIG. 75 shows an increase in HGF cell proliferation of 73% when incubated with SEQ ID 410.

Figure 76:
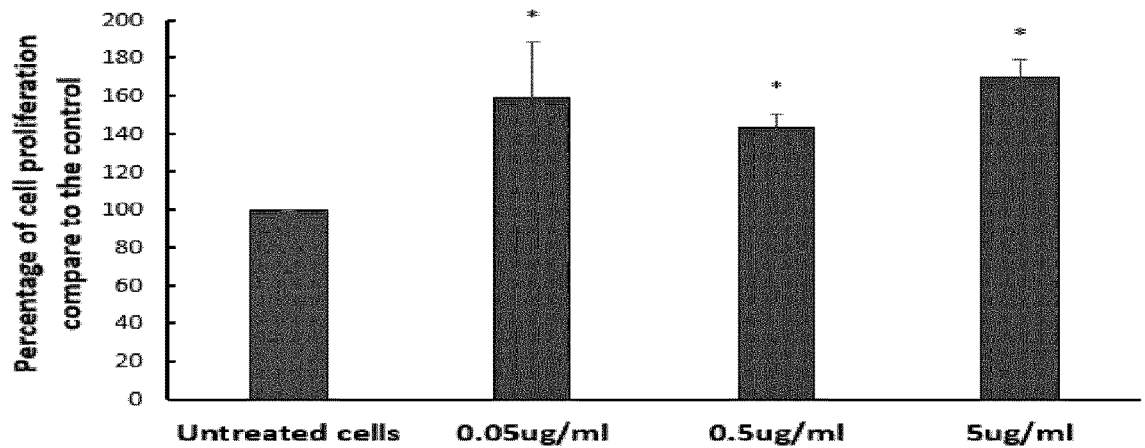

FIG. 76 shows an increase in HGF cell proliferation of 69% when incubated with SEQ ID 475.

Figure 77:
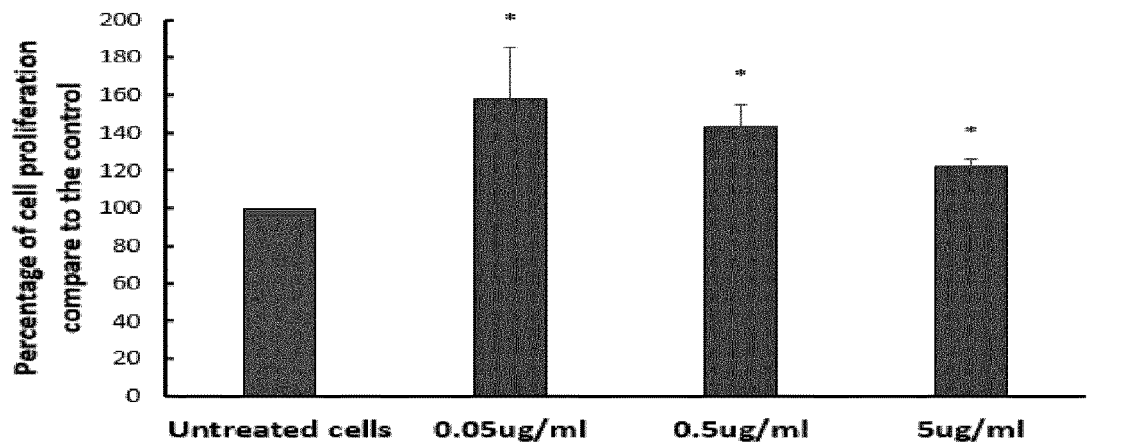

FIG. 77 shows an increase in HGF cell proliferation of 58% when incubated with SEQ ID 497.

Figure 78:
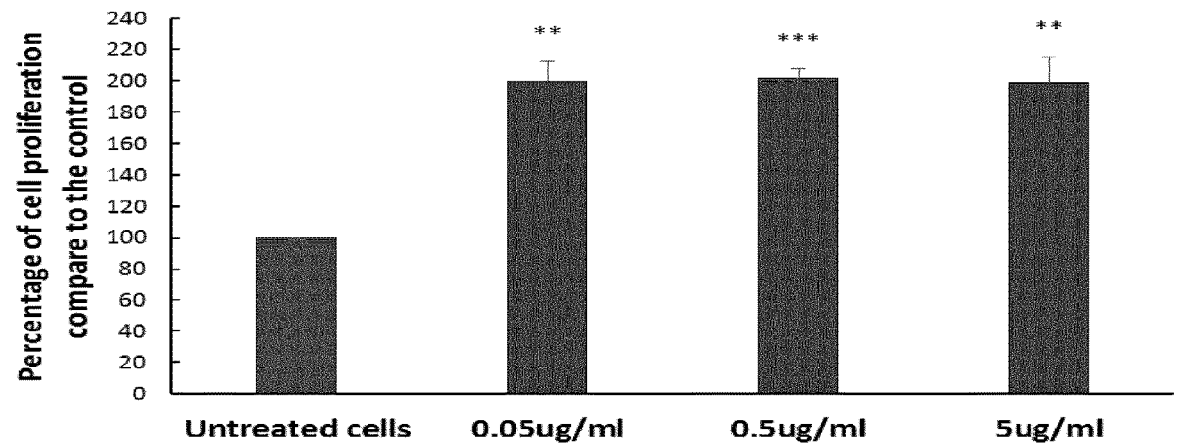

FIG. 78 shows an increase in HGF cell proliferation of 102% when incubated with SEQ ID 480.

Figure 79:
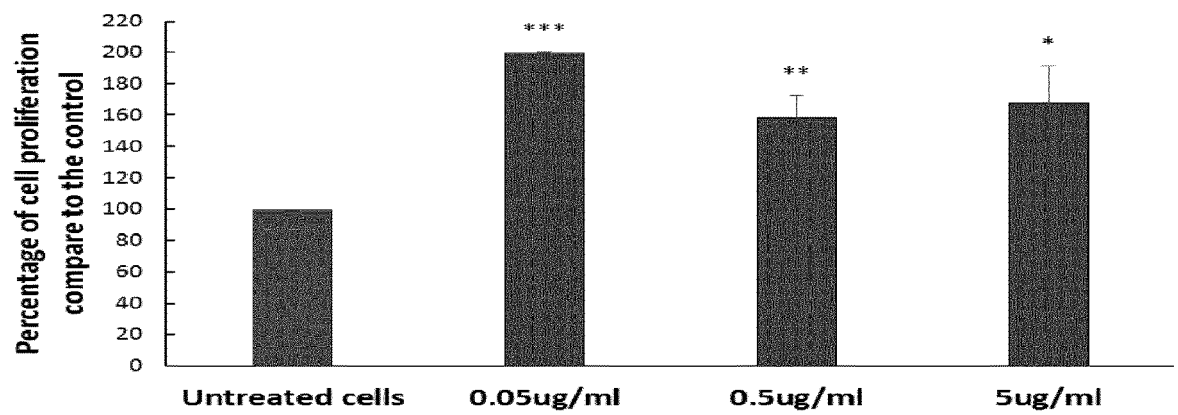

FIG. 79 shows an increase in HGF cell proliferation of 100% when incubated with SEQ ID 463.

Figure 80:
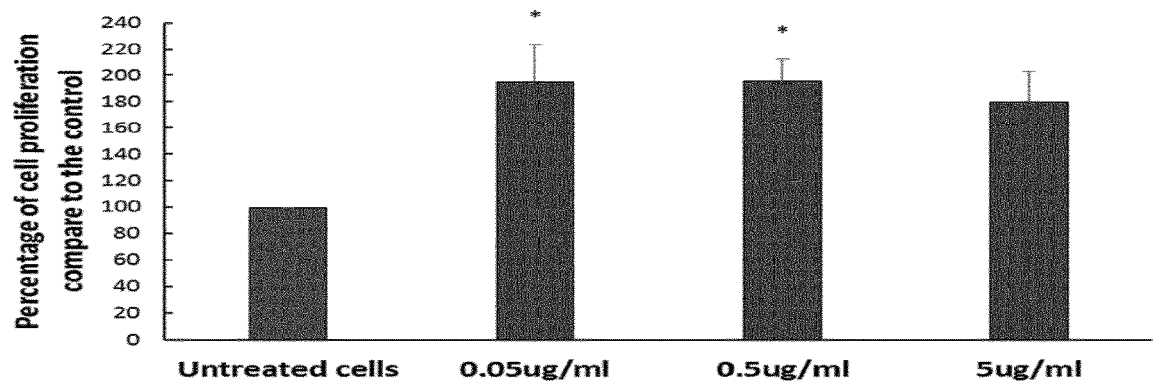

FIG. 80 shows an increase in HGF cell proliferation of 96% when incubated with SEQ ID 465.

Figure 81:
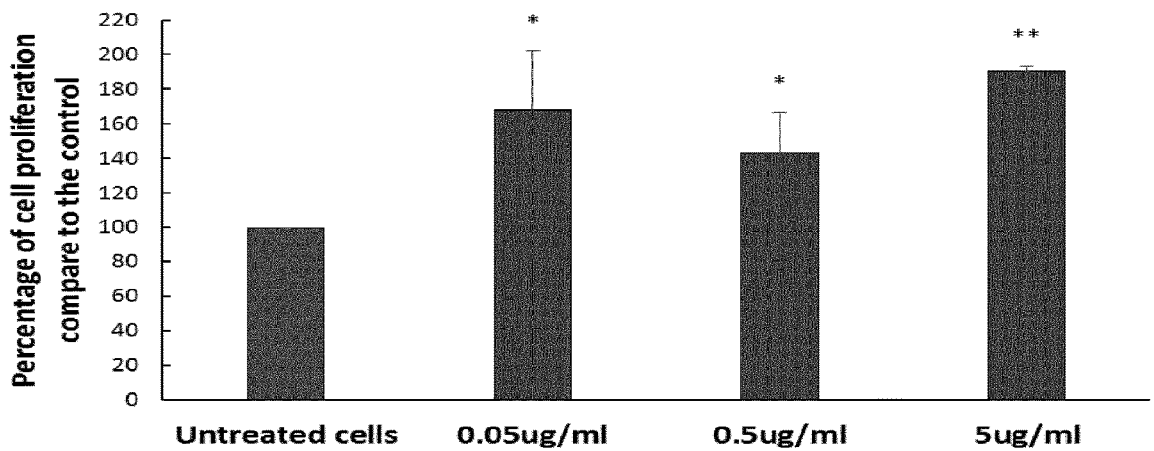

FIG. 81 shows an increase in HGF cell proliferation of 90% when incubated with SEQ ID 467.

Figure 82:
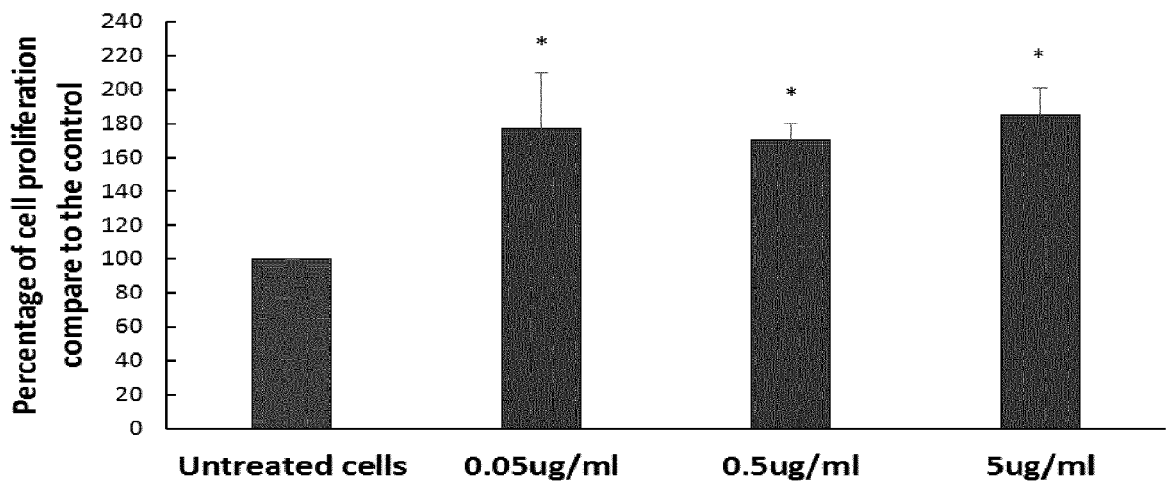

FIG. 82 shows an increase in HGF cell proliferation of 85% when incubated with SEQ ID 461.

Figure 83:
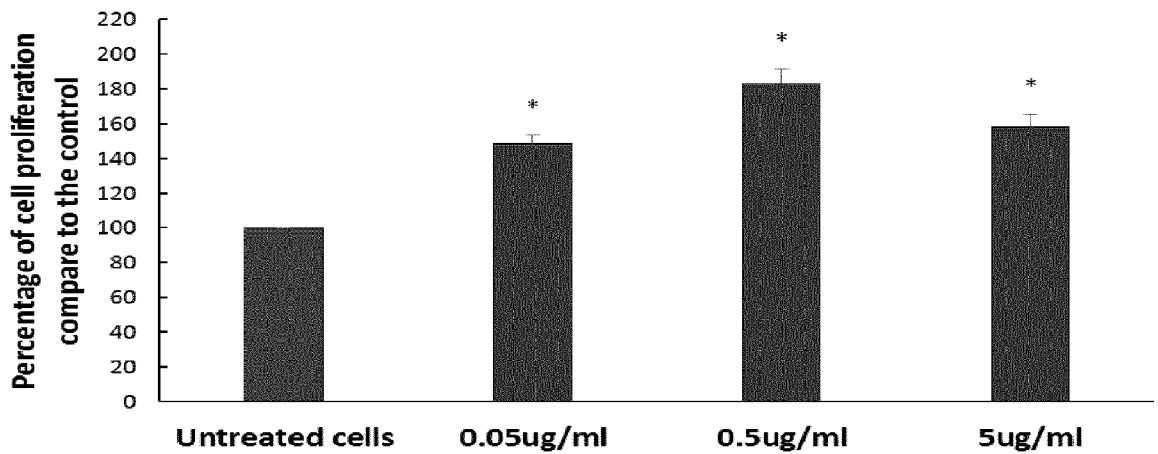

FIG. 83 shows an increase in HGF cell proliferation of 83% when incubated with SEQ ID 341.

Figure 84:
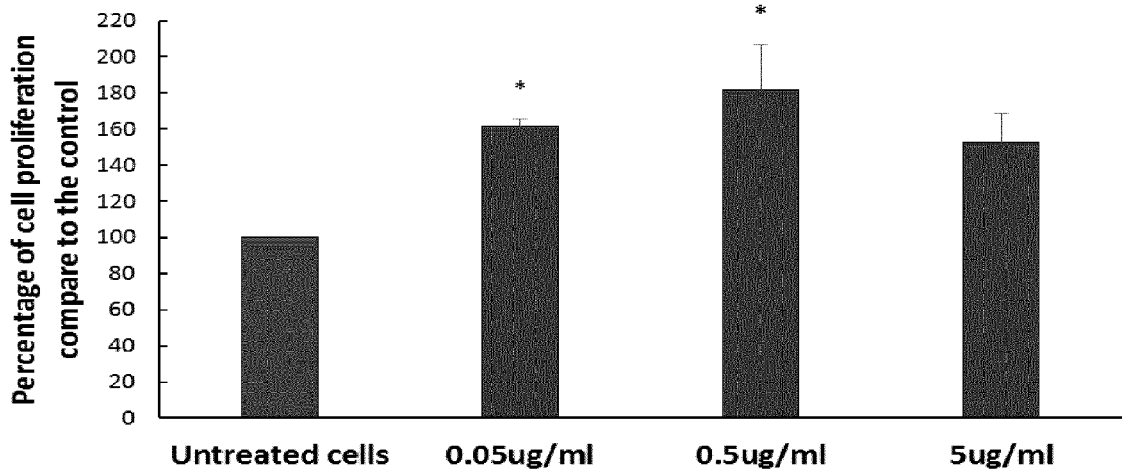

FIG. 84 shows an increase in HGF cell proliferation of 82% when incubated with SEQ ID 468.

Figure 85:
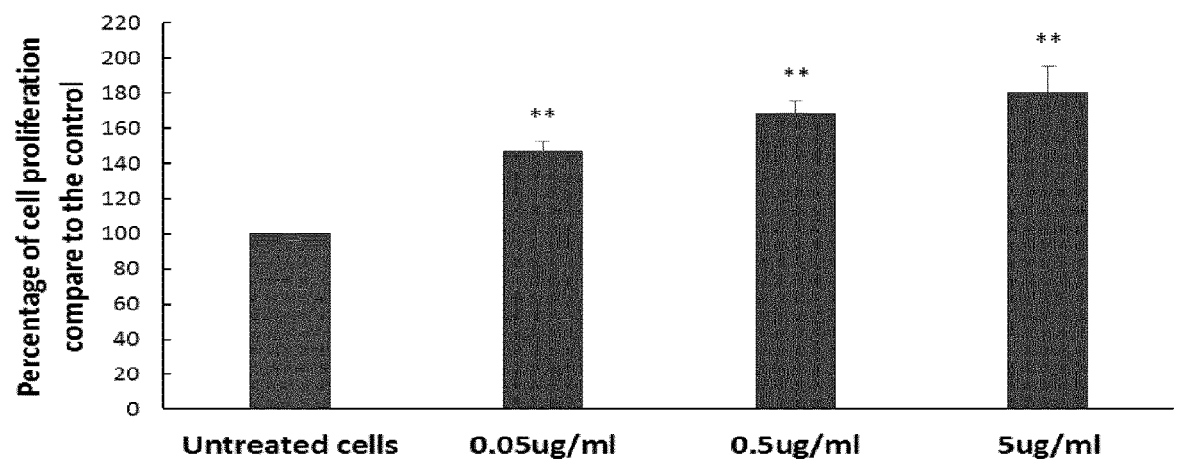

FIG. 85 shows an increase in HGF cell proliferation of 81% when incubated with SEQ ID 485.

Figure 86:
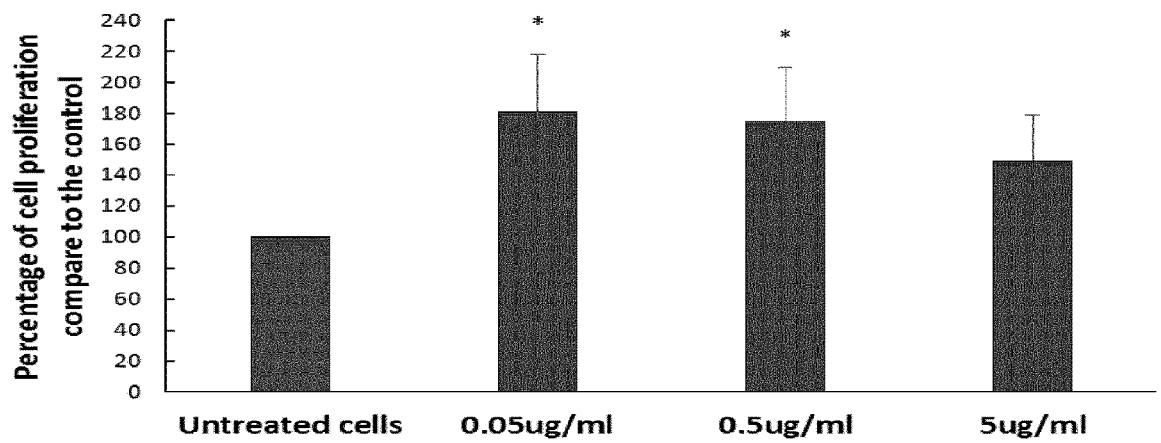

FIG. 86 shows an increase in HGF cell proliferation of 81% when incubated with SEQ ID 496.

Figure 87:
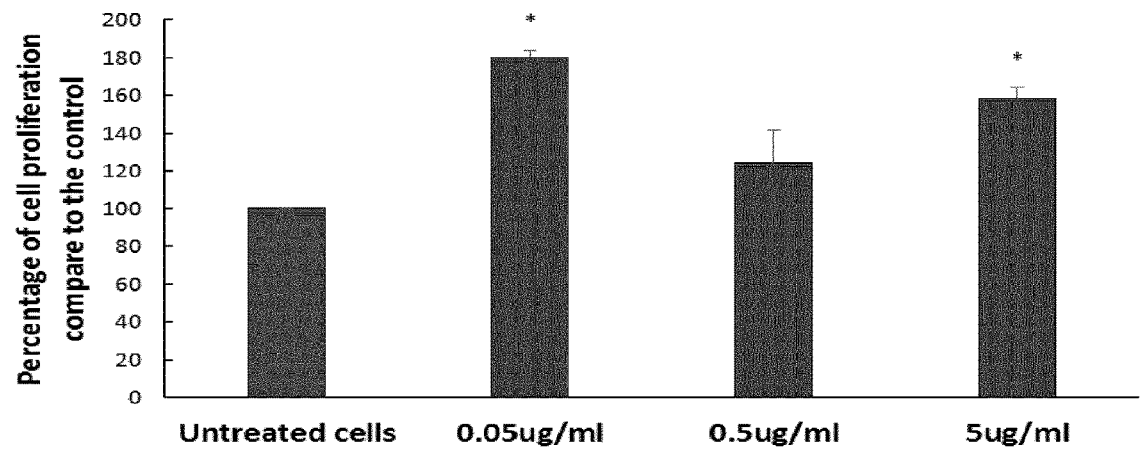

FIG. 87 shows an increase in HGF cell proliferation of 80% when incubated with SEQ ID 146.

Figure 88:
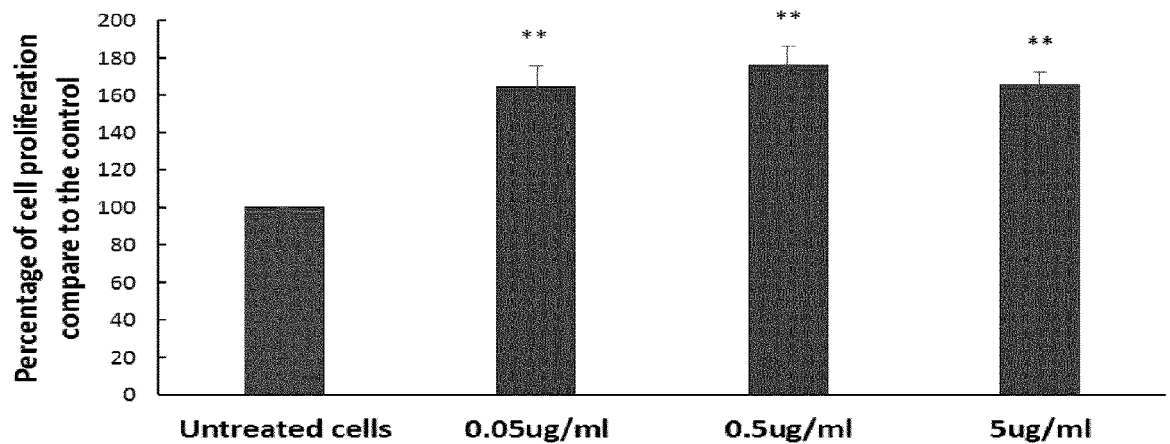

FIG. 88 shows an increase in HGF cell proliferation of 76% when incubated with SEQ ID 478.

Figure 89:
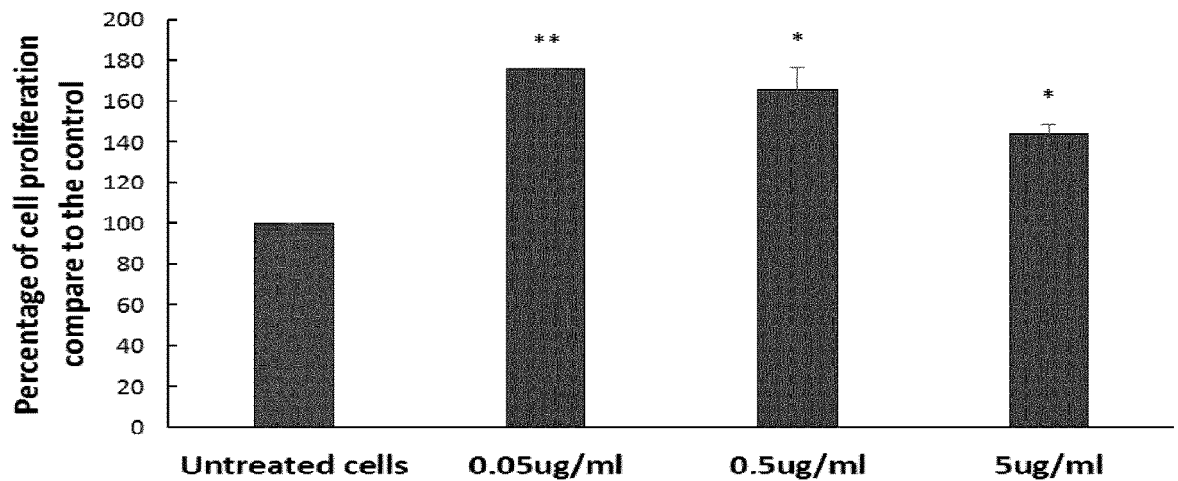

FIG. 89 shows an increase in HGF cell proliferation of 76% when incubated with SEQ ID 452.

Figure 90:
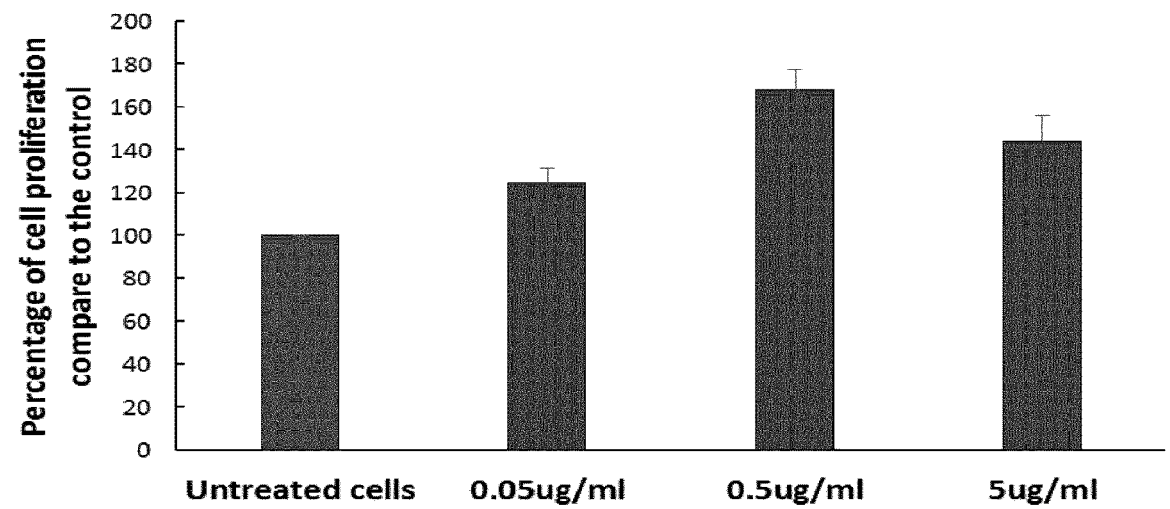

FIG. 90 shows an increase in HGF cell proliferation of 68% when incubated with SEQ ID 495.

Figure 91:
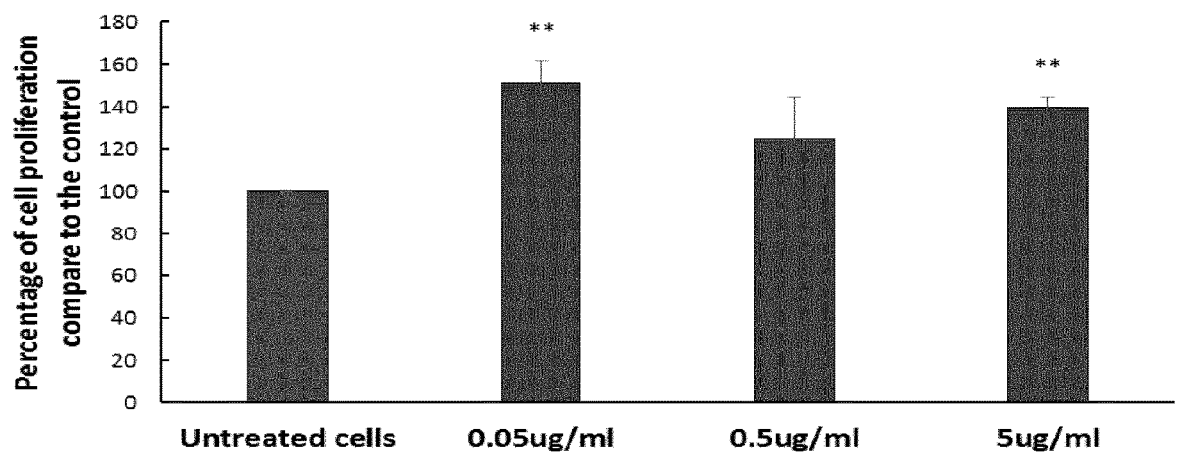

FIG. 91 shows an increase in HGF cell proliferation of 51% when incubated with SEQ ID 403.

Figure 92:
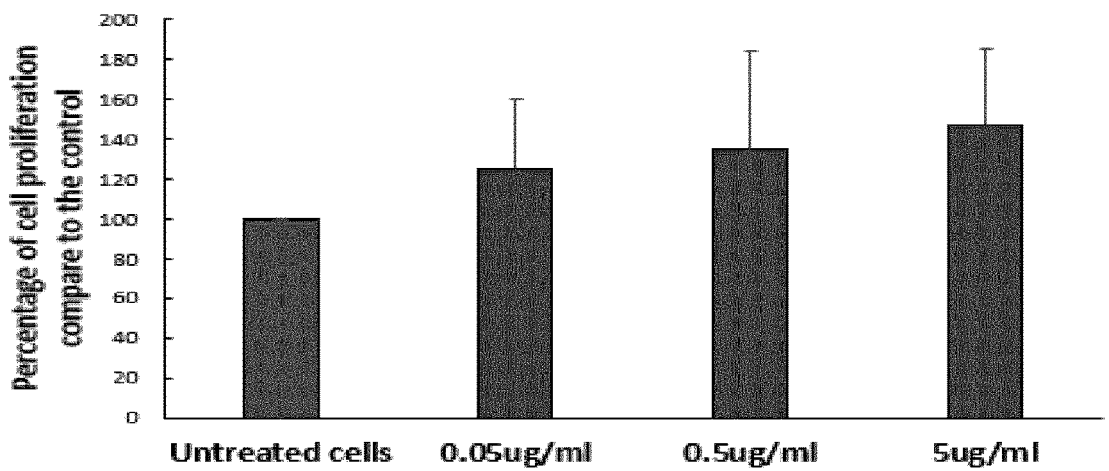

FIG. 92 shows an increase in HGF cell proliferation of 47% when incubated with SEQ ID 455.

Figure 93:
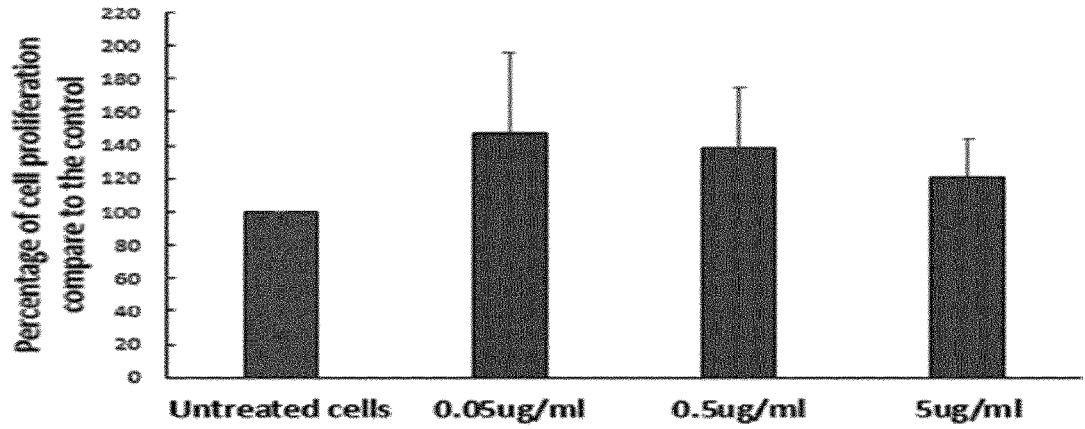

FIG. 93 shows an increase in HGF cell proliferation of 47% when incubated with SEQ ID 270.

Figure 94:
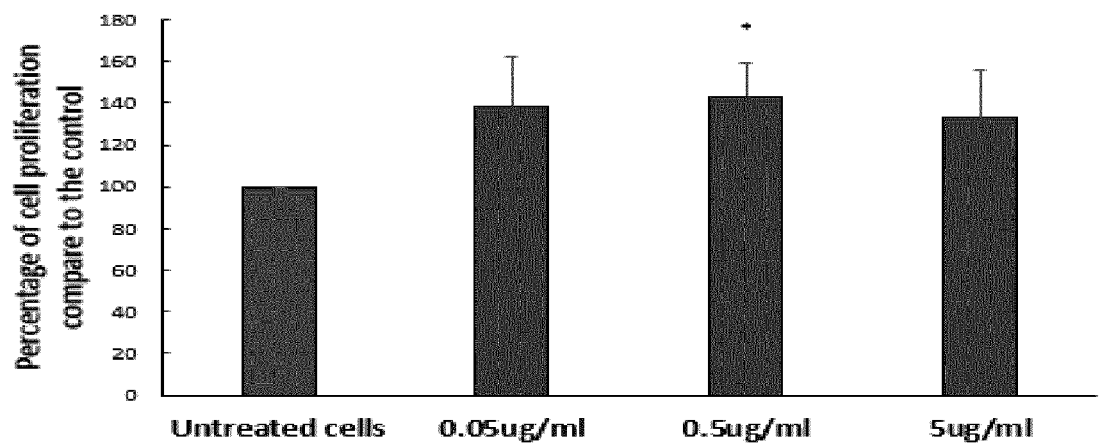

FIG. 94 shows an increase in HGF cell proliferation of 43% when incubated with SEQ ID 501.

Figure 95:
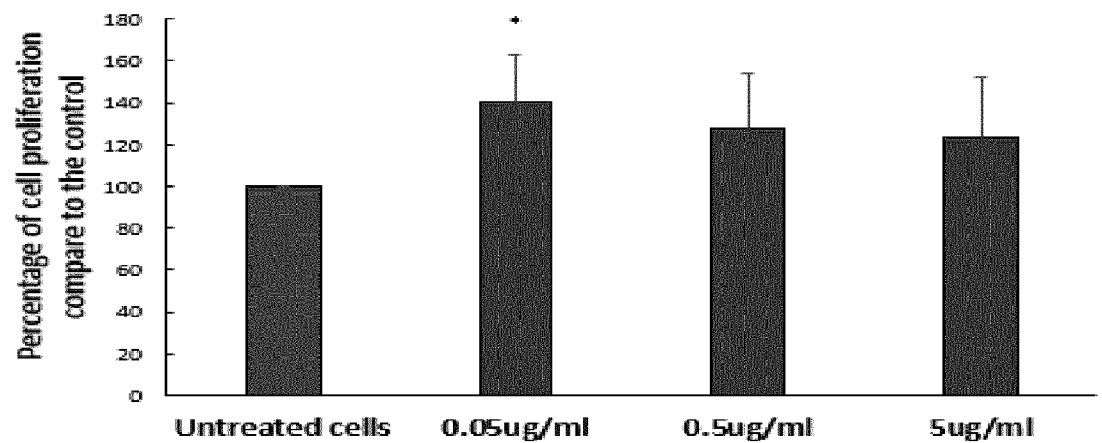
Figure 96:
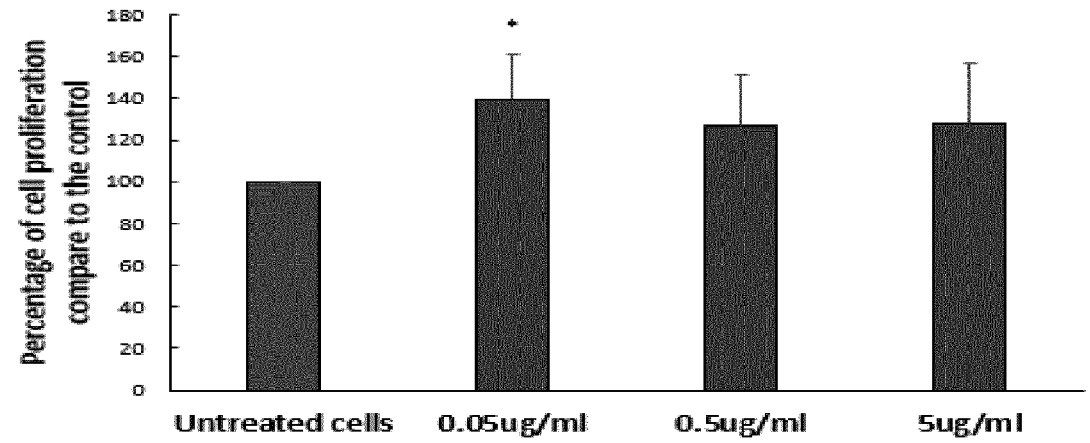

FIG. 95 shows an increase in HGF cell proliferation of 41% when incubated with SEQ ID 473.

Figure 97:
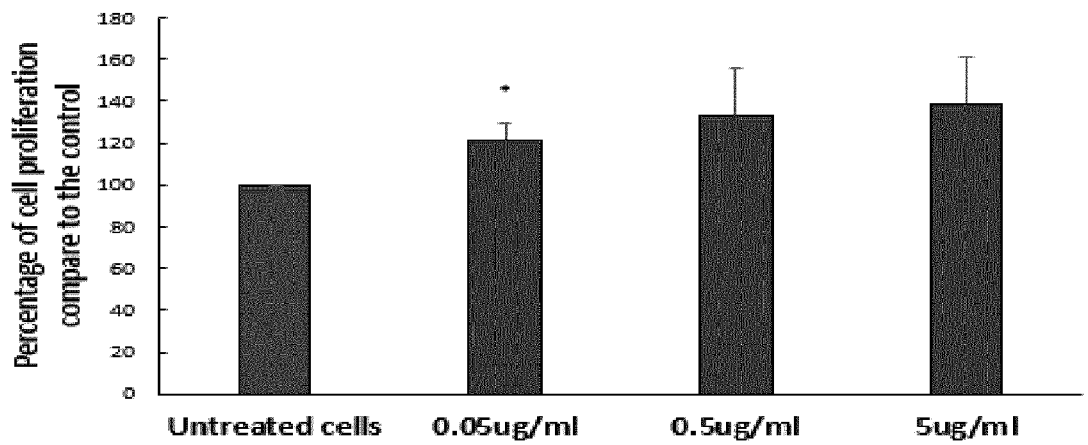

FIG. 97 shows an increase in HGF cell proliferation of 38% when incubated with SEQ ID 471.

Figure 98:
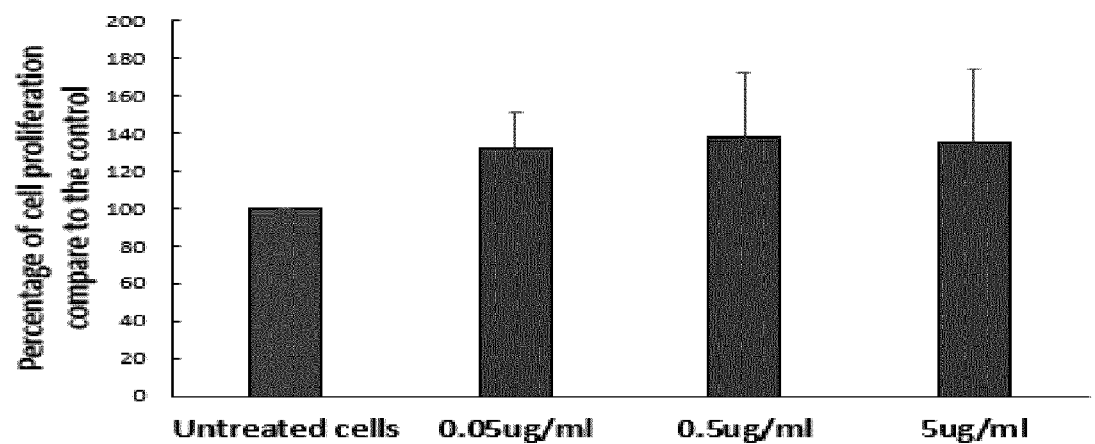

FIG. 98 shows an increase in HGF cell proliferation of 38% when incubated with SEQ ID 460.

Figure 99:
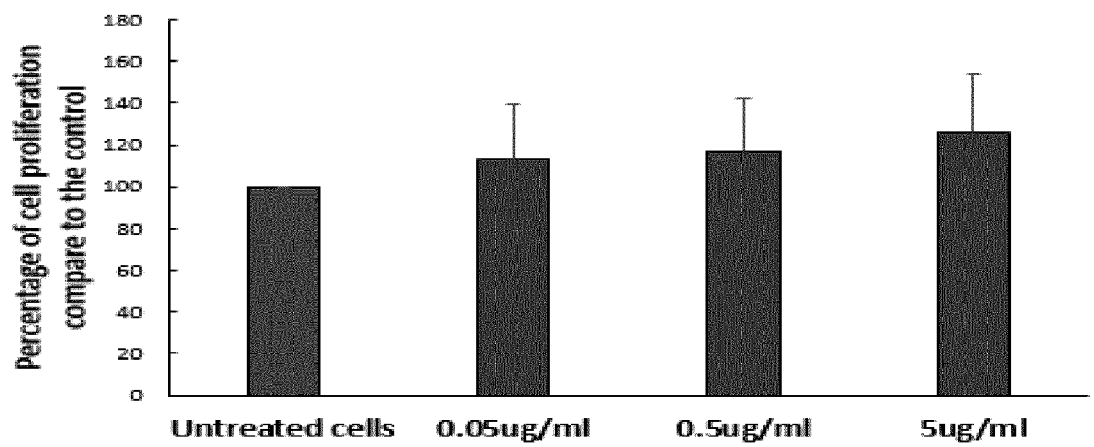

FIG. 99 shows an increase in HGF cell proliferation of 26% when incubated with SEQ ID 93.

FIG. 100 shows an increase in HGF cell proliferation of 15% when incubated with SEQ ID 462.

Example 2—Collagen Production Assay

Hydroxyproline in tissue preparations is a direct measure of the amount of collagen present. FIRELISA Human Hydroxyproline ELISA kit assay is designed to measure hydroxyproline in tissue or peptide compositions.

Human Dermal Fibroblasts (HDF Sigma 10605a) were seeded in 24 well plates at 50,000 cells per well in DMEM containing 10% fetal calf serum (FCS), 1% Pen/strep, 1% L-glutamine and allowed to adhere for 24 h.

Following the initial 24 h incubation the cells were incubated with 5 µg/ml, 1 µg/ml or 0.1 µg/ml synthetic peptide for 96 h respectively.

After treatment the cells were lysed using 4 freeze thaw cycles in liquid nitrogen. The lysed cells were centrifuged and 50 µl/ml of each supernatant was assayed using the FIRELISA Human Hydroxyproline ELISA kit. All steps were carried out according to the manufacturer's instructions.

Results were calculated as a percentage of the untreated control. An increase in optical density reading indicates an increase collagen content.

The results are shown in FIGS. 102, 104, 106 and 109

Example 3—Elastin Production Assay

Elastin is a highly elastic protein in connective tissue and allows many tissues in the body to resume their shape after stretching or contracting. FIRELISA Human Elastin ELISA kit assay is designed to measure Elastin in tissue or protein/peptide compositions.

Human Dermal Fibroblasts (HDF) were seeded in 24 well plates at 50,000 cells per well in DMEM containing 10% fetal calf serum (FCS), 1% Pen/strep, 1% L-glutamine and allowed to adhere for 24 h.

Following the initial 24 h incubation the cells were incubated with 5 μg/ml, 1 μg/ml or 0.1 μg/ml synthetic peptide for 96 h respectively.

After treatment the cells were lysed using 4 freeze thaw cycles in liquid nitrogen. The lysed cells were centrifuged and 50 μl/ml of each supernatant was assayed using the FIRELISA Human Elastin ELISA kit. All steps were carried out according to the manufacturer's instructions.

Results were calculated as a percentage of the untreated control. An increase in optical density reading indicates an increase collagen content.

The results are shown in FIGS. 101, 103, 105, 107, 108 and 109.

Example 4—Elastin and Cell Proliferation Assays

TABLE 2

Test items. Orange bands correspond to samples dissolved into DMSO 0.3% instead of water.

| Item | Denomination | Concentration | Provider | Nature | Intertek reference | Solubility | Storage |
|---|---|---|---|---|---|---|---|
| Peptide 1 | E_280_PJ | 20 μM | Nuritas | Peptide 0723-01 | 14-CHL- | Water | −80° C. |
| Peptide 2 | I_222two_IN | 20 μM | Nuritas | Peptide 0723-02 | 14-CHL- | Water | Ambient |
| Peptide 3 | E_134_two_IN | 20 μM | Nuritas | Peptide 0723-03 | 14-CHL- | Water | −80° C. |
| Peptide 4 | E_30two_IN | 20 μM | Nuritas | Peptide 0723-04 | 14-CHL- | Water | −80° C. |
| Peptide 5 | E_121two_IN | 20 μM | Nuritas | Peptide 0723-05 | 14-CHL- | Water | −80° C. |
| Peptide 6 | I_10two_IN | 20 μM | Nuritas | Peptide 0723-06 | 14-CHL- 0.3% | DMSO | −80° C. |
| Peptide 7 | I_41two_IN | 20 μM | Nuritas | Peptide 0723-07 | 14-CHL- 0.3% | DMSO | −80° C. |
| Peptide 8 | E_41_PJ | 10 μM* | Nuritas | Peptide 0723-08 | 14-CHL- | Water | −80° C. |
| Composition P9 | E_2_IN | 500 μg/mL | Nuritas | Composition of peptides 0723-09 | 14-CHL- | Water | −80° C. |
| Composition P10 | I_2_IN | 500 μg/mL | Nuritas | Composition of peptides 0723-10 | 14-CHL- | Water | −80° C. |

Equipment

Incubator, Flow Laminar Chamber, Sterile Polished Plastic Rod, Pipettor, Maintenance medium, Plate 6 well, Plate 24 well.

Reagents

MTT, PBS, SDS, Formaldehyde, Xylene, Ethanol absolute, Dulbecco's phosphate-buffered saline (DPBS), Metal Enhanced DAB substrate kit, ABC peroxidase staining kit, Citric acid, Sodium hydroxide 2N, Hydrogen peroxide 30%, Anti-Filaggrin, Anti-rabbit IgG-Biotin, Tween 20.

Test System

Nature: Human skin tissue 5 mm diameter

Batch number: EXP004050B009 and EXP004050B011

Provider: Laboratoire Biopredic International—8-18 rue Jean Pecker—35000 Rennes—France. Tel: +33 (0)2.99.14.36.14—Fax: +33 (0)2.99.54.44.72.

Certificates of analysis are present in Annex 1.

Two batches are used for the assay. Batch EXP004050B005 is used for experiment day 1, and Batch EXP004050B006 is used for experiment day 5.

Maintenance Medium

Maintenance Medium: Batch No: MIL 218C

Provider: Laboratoire Biopredic International—8-18 rue Jean Pecker—35000 Rennes—France.

Peptides Tested

P1:
SEQ ID NO: 283

P2:
SEQ ID NO: 246

P3:
SEQ ID NO: 284

P4:
(SEQ ID NO: 776)
RPYYSNAPQEIF

P5:
(SEQ ID NO: 777)
VLLEQQEQEPQH

P6:
SEQ ID NO: 245

P7:
(SEQ ID NO: 778)
QQYGIAASPFLQSAA

P8:
SEQ ID NO: 42

Compositions Tested

P9 (14-CHL-0723-09) is the Pea composition (SEQ ID Numbers: 50, 85, 74, 140, 82, 136, 189, 77, 169, 149, 171, 178, 143, 127, 190, 141, 147, 133, 186, 125, 122, 119, 87, 90, 86, 89, 138, 129, 123, 120, 117, 113, 110, 121, 105, 98, 55, 161, 19, 317, 135, 130, 146, 177, 160, 170, 188, 83, 78, 36, 96, 159, 26, 330, 168, 148, 184, 151, 151, 165, 114, 284)

P10 (14-CHL-0723-010) is the Rice composition (SEQ ID Numbers: 245, 246, 263, 250, 257, 259, 276, 255, 251, 264, 256, 266, 274, 270, 269, 356, 245, 380, 262, 258, 356, 218, 252, 358, 271, 253, 344, 275, 272, 226, 224, 220, 248, 261, 265, 373, 375, 247, 249, 363, 273, 343, 273, 362)

Application Method

Skin explants were prepared from abdominal plastic surgery. Some explants were delipidated with alcohol to obtain a dehydrated skin.

These explants were maintained in maintenance medium supplied by the provider Bioprédic International for 5 days. Test items are applied twice per day with 5 µL per explant.

At the end of the test, viabilities controls are realized with the MTT on two explants, the third explant is fixed in the formaldehyde 4% for histology and cell staining.

For each time of analysis (D1 and D5), histologies on delipidated explants, treated explants with test items, the DMSO 0.3% control and water control, are performed.

After receipt in the laboratory, each skin explant in the maintenance medium is delipidated with 5 µL alcohol during 3 hours.

After 3 hours, all skin explants are treated two per day with test items, and they are incubated at 37° C.+/−2° C., 5% CO2 for 1 day or 5 days.

Integrity of the system is realized at day 1 and day 5 with a viability control with MTT.

Immunostaining

Histology is realized by the laboratory Gredeco and the immunostaining to elastin and Ki67 are realized by the same laboratory. Immunostaining to filaggrin is realized by the laboratory Intertek.

The detection of elastin (rabbit monoclonal antibody, clone P15502, LSBio) is performed using an immunoperoxidase technique two layers (ABC kit, Vector Laboratories) and revealed by AEC (3-amino-9-ethylcarbazole). The immunohistochemical staining intensity in the elastic fibers is evaluated using a semi-quantitative histological score.

Epithelial proliferation was analyzed by immunohistochemistry using anti-Ki67 antibody. Immunodetection was performed using an indirect immunoperoxidase technique three layers, amplified (DAKO kit) and revealed by AEC (3-Amino-9-ethylcarbazole). Counting the number of labeled cells (keratinocytes of the basal layer of the epidermis) is performed and provides the total number of basal cells to calculate the % of labeled cells.

The specific staining of filaggrin is performed with an immunoperoxidase staining (ABC kit, Fisher). The intensity of immunohistochemical marker in the epidermis is evaluated relative to the negative control of the solvent (Water or DMSO 0.3%).

C: Results

Viability Control

The integrity control and the viability control are present in FIG. 1. These controls do allow to validate the assay system. The viability is >50% for test items, and they do not show a cytotoxicity according to the test.

Immunostaining

Elastin Expression

The elastic fibers of the dermis were revealed by staining with the catechin and morphometrically quantified by analysis by computer-assisted image. The percentage area taken up by elastic fibers in the dermis was calculated in the dermis and the average superficial dermis. Results are presented in FIGS. 101, 105, 107, and 108.

TABLE 3

Morphometric quantification of elastic fibers in the superficial dermis (%) and middle dermis. All samples dissolved in water except where indicated.

| Conditions | Morphometric quantification of elastic fibers in the superficial dermis (%) | | Morphometric quantification of elastic fibers in the middle dermis (%) | |
|---|---|---|---|---|
| | D1 | D5 | D1 | D5 |
| Dehydrated with alcohol and hydrated with water | 4.31 | 4.9 | 5 | 5.83 |
| Dehydrated | 2.38 | 7.26 | 4.39 | 9.59 |
| EGF (Epidermal Growth Factor) 10 ng/mL | 3.64 | 5.61 | 5.68 | 6.61 |
| Dehydrated with alcohol and hydrated with DMSO 0.3% | 3.76 | 7.24 | 6 | 10.36 |
| 0723.01 | 4.45 | 10.21 | 7.59 | 10.17 |
| 0723.02 | 6.09 | 7.59 | 11.75 | 9.08 |
| 0723.03 | 3 | 11.68 | 4.9 | 9 |
| 0723.04 | 3.28 | 8.94 | 5.22 | 9 |
| 0723.05 | 6.34 | 6.26 | 8.8 | 6.61 |
| 0723.06 (dissolved in DMSO 0.3% instead of water) | 3.8 | 4.03 | 4.54 | 8.67 |
| 0723.07 (dissoved in DMSO 0.3% instead of water) | 4 | 5.15 | 6.46 | 5.33 |
| 0723.08 | 2.7 | 5.32 | 3.52 | 7.27 |
| 0723.09 | 3.26 | 8.26 | 5.75 | 7.92 |
| 0723.10 | 4.1 | 8 | 5.73 | 8.34 |

Under the experimental conditions of the study, 0723-1 and 0723-3 samples show an increase by twice of elastic fibers in the superficial dermis compared to control water (Figure), and an increase in the middle dermis compared to the water control at D5.

The 0723-2 sample shows an increase doubled in the middle dermis at day 1 compared to control water and an increase at day 5.

Ki67 Expression

Figure 115:
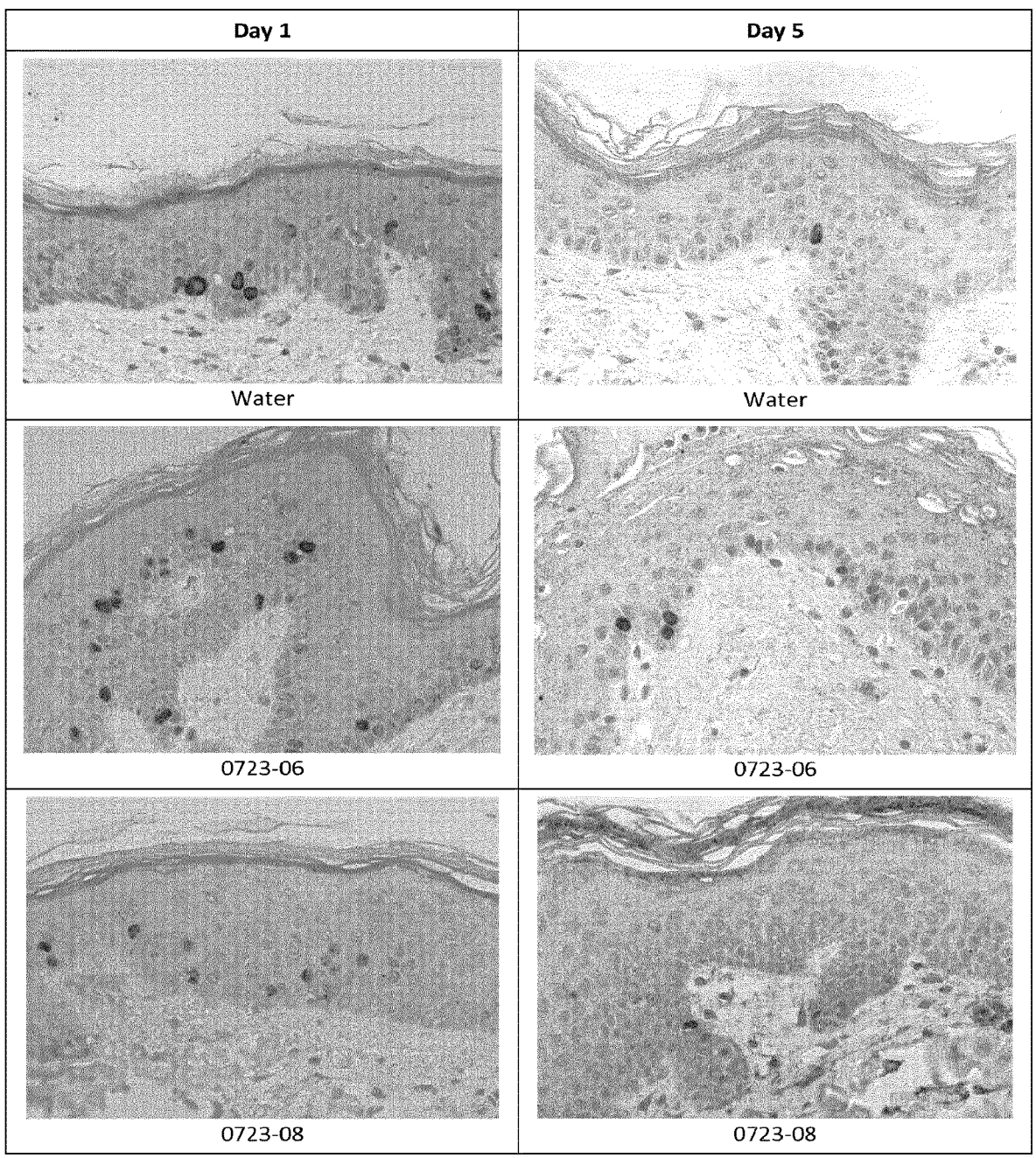

The results of the immunohistochemical analysis of Ki67 are reported in Table 4 and expressed as % of labelled at the basal layer of the epidermis. The FIG. 115 shows the percentage of Ki 67 cells compared to negative controls (water or DMSO). Immunohistochemical analysis of mitotic activity is shown in annex 4 with a reminder of the average for each analysed conditions.

TABLE 4

% of Ki67 positive cells in the basal layer of the epidermis. All samples dissolved in water except where indicated.

| Conditions | D1 | D5 |
|---|---|---|
| Dehydrated with alcohol and hydrated with water | 19.09 | 3.53 |
| Dehydrated | 17.05 | 1.76 |
| EGF (Epidermal Growth Factor) 10 ng/mL | 25.11 | 4.2 |
| Dehydrated with alcohol and hydrated with DMSO 0.3% | 17.2 | 2.61 |
| 0723.01 | 18.57 | 3.92 |
| 0723.02 | 19.61 | 6.73 |
| 0723.03 | 22.01 | 10.04 |
| 0723.04 | 14.97 | 11.36 |
| 0723.05 | 9.48 | 3.08 |
| 0723.06 (dissolved in DMSO 0.3% instead of water) | 31.97 | 5.04 |

TABLE 4-continued

% of Ki67 positive cells in the basal layer of the epidermis.
All samples dissolved in water except where indicated.

| Conditions | D1 | D5 |
|---|---|---|
| 0723.07 (dissoved in DMSO 0.3% instead of water) | 22.22 | 5.26 |
| 0723.08 | 27.83 | 5.72 |
| 0723.09 | 31.02 | 2.4 |
| 0723.10 | 31.94 | 3.57 |

Under the experimental conditions of the study, test item 0723-06, 0723-08, 0723-09 and 0723-010 show an increase in the number of mitotic cells compared to EGF at day 1. A decrease in the mitotic index was observed on day 5 compared to day 1 for all analysed conditions.

The decrease in this cell staining on day 5 is caused by the model. Indeed, after approximately 3 days cell turnover is exhausted on this model.

The invention is not limited to the embodiments hereinbefore described which may be varied in construction and detail without departing from the spirit of the invention.

What is claimed is:

1. A composition formulated for topical application to the skin of a human comprising a peptide and a cosmetically acceptable excipient, wherein the peptide is up to 50 amino acids in length and comprises the amino acid sequence of SEQ ID NO: 283.

2. The composition according to claim 1, wherein the peptide consists of the amino acid sequence of SEQ ID NO: 283.

3. The composition according to claim 1, wherein the composition is in the form of a gel, cream, lotion or ointment.

4. The composition according to claim 1, wherein the composition is in the form of a cream, lotion or ointment, and wherein the cosmetically acceptable excipient is selected from an emollient or an emulsifying agent.

5. The composition according to claim 1, comprising 0.1 to 5000 ppm of the peptide.

6. The composition according to claim 1, comprising 0.5 to 500 ppm of the peptide.

7. The composition according to claim 1, wherein the composition is in the form of an emulsion.

8. The composition according to claim 1, wherein the cosmetically acceptable excipient is selected from the group consisting of: a diluent, carrier, binder, lubricant, suspending agent, coating agent, preservative, stabilisers, dyes, vehicle, solubilising agent, base, emollient, emulsifying agent, fragrance, humectant, and surfactants.

9. The composition according to claim 1, wherein the cosmetically acceptable excipient is an emollient or an emulsifying agent.

10. A composition comprising a peptide, wherein the peptide is up to 50 amino acids in length and comprises the amino acid sequence of SEQ ID NO: 283, and wherein the composition is a powder.

11. The composition according to claim 10, wherein the powder is free of un-hydrolysed protein.

* * * * *